US012758640B2

(12) United States Patent
Kley et al.

(10) Patent No.: US 12,758,640 B2
(45) Date of Patent: Oct. 13, 2026

(54) BIFUNCTIONAL AGENTS FOR PROTEIN RECRUITMENT AND/OR DEGRADATION

(71) Applicant: Orionis Biosciences, Inc., Waltham, MA (US)

(72) Inventors: Nikolai Kley, Waltham, MA (US); Riccardo Sabatini, Waltham, MA (US); Edward Suh, Waltham, MA (US)

(73) Assignee: Orionis Biosciences, Inc., Waltham, MA (US)

( * ) Notice: Subject to any disclaimer, the term of this patent is extended or adjusted under 35 U.S.C. 154(b) by 909 days.

(21) Appl. No.: 17/786,162

(22) PCT Filed: Dec. 16, 2020

(86) PCT No.: PCT/US2020/065304

§ 371 (c)(1),
(2) Date: Jun. 16, 2022

(87) PCT Pub. No.: WO2021/126974

PCT Pub. Date: Jun. 24, 2021

(65) Prior Publication Data

US 2023/0099031 A1 Mar. 30, 2023

Related U.S. Application Data

(60) Provisional application No. 62/949,028, filed on Dec. 17, 2019.

(51) Int. Cl.

| | |
|---|---|
| ***A61K 47/55*** | (2017.01) |
| ***A61K 47/54*** | (2017.01) |
| ***A61P 35/00*** | (2006.01) |

(52) U.S. Cl.

CPC ............ *A61K 47/55* (2017.08); *A61K 47/545* (2017.08); *A61P 35/00* (2018.01)

(58) Field of Classification Search

CPC ........ A61K 47/66; A61K 47/545; A61P 35/00
See application file for complete search history.

(56) References Cited

U.S. PATENT DOCUMENTS

| | | | | |
|---|---|---|---|---|
| 9,993,514 | B2 * | 6/2018 | Campos | C07K 5/06043 |
| 2016/0058872 | A1 * | 3/2016 | Crew | A61K 47/545 544/323 |
| 2016/0176916 | A1 | 6/2016 | Bradner et al. | |
| 2016/0328159 | A1 | 11/2016 | Coddington et al. | |
| 2018/0155322 | A1 * | 6/2018 | Crew | A61K 31/501 |
| 2018/0179183 | A1 | 6/2018 | Crew et al. | |
| 2018/0224435 | A1 | 8/2018 | Chamberlain et al. | |
| 2019/0076539 | A1 | 3/2019 | Phillips et al. | |
| 2020/0157078 | A1 * | 5/2020 | Fan | C07D 401/14 |
| 2022/0306659 | A1 * | 9/2022 | Zhao | C07D 401/14 |

FOREIGN PATENT DOCUMENTS

| | | | | |
|---|---|---|---|---|
| CA | 3090417 | A1 | 8/2019 | |
| CA | 3096790 | A1 | 10/2019 | |
| CN | 103396397 | A | 11/2013 | |
| CN | 106458993 | A | 2/2017 | |
| CN | 107739389 | A | 2/2018 | |
| CN | 110545853 | A | 12/2019 | |
| JP | 2018-502097 | A | 1/2018 | |
| JP | 2018-526429 | A | 9/2018 | |
| JP | 2019-526616 | A | 9/2019 | |
| WO | WO 2010/053732 | A1 | 5/2010 | |
| WO | WO 2015/038649 | A1 | 3/2015 | |
| WO | 2016105518 | A1 | 6/2016 | |
| WO | 2016197032 | A1 | 12/2016 | |
| WO | WO 2017/059062 | A1 | 4/2017 | |
| WO | WO 2017/184995 | A1 | 10/2017 | |
| WO | 2017/197051 | A1 | 11/2017 | |
| WO | WO-2017197056 | A1 * | 11/2017 | C07D 519/00 |
| WO | 2018052949 | A1 | 3/2018 | |
| WO | WO 2018/052945 | A1 | 3/2018 | |
| WO | WO 2018/071606 | A1 | 4/2018 | |
| WO | 2018/106870 | A1 | 6/2018 | |
| WO | 2018/119448 | A1 | 6/2018 | |
| WO | WO 2018/102725 | A1 | 6/2018 | |
| WO | 2018/144832 | A1 | 8/2018 | |
| WO | 2018/200981 | A1 | 11/2018 | |
| WO | 2018237026 | A1 | 12/2018 | |
| WO | 2019043214 | A1 | 3/2019 | |
| WO | WO 2019/078522 | A1 | 4/2019 | |
| WO | 2019/196812 | A1 | 10/2019 | |
| WO | 2019/199816 | A1 | 10/2019 | |
| WO | WO-2020038415 | A1 * | 2/2020 | A61K 47/55 |
| WO | WO 2020/051564 | A1 | 3/2020 | |
| WO | WO-2020160196 | A1 * | 8/2020 | C07D 519/00 |
| WO | WO-2020200291 | A1 * | 10/2020 | A61P 35/00 |

OTHER PUBLICATIONS

Ammouri, European Medical Journal Reviews, 2020; 1: 71-80 (Year: 2020).*
Ferguson, Journal of Central Nervous System Disease, May 21, 2022 (Year: 2022).*
Zheng, International Journal of Molecular Sciences, 2024, 25, 4969 (Year: 2024).*
International Search Report & Written Opinion, PCT Application No. PCT/US22/65304, dated Apr. 23, 2021, 11 pages.
Pubmed Compound Record for CID 141341744, '3-[7-(4-Heptoxyphenyl)-3-oxo-1H-isoindol-2-yl]piperidine-2,6-dione', U.S. National library of Medicine, Dec. 6, 2019 (Dec. 6, 2019). pp. 1-8 (https://pubchem.ncbi.nlm.nih.gov/compound/141341744); p. 2.
Stewart, et al., "New thalidomide analogues derived through Sonogashira or Suzuki reactions and their TNF expression inhibition profiles," Bioorganic & Medicinal Chemistry, vol. 18, pp. 650-662, 2010.
Yang, et al., "A Cell-Based Target Engagement Assay for the Identification of Cereblon E3 Ubiquitin Ligase Ligands and Their Application in HDAC6 Degraders," Cell Chemical Biology, vol. 27, pp. 866-876, Jul. 16, 2020.
Ito, T. et al., Science, 2010, 327: 1345.
Lu, G. et al., Science, 2014, 343:305-309.
Kronke, J. et al., Science, 2014, 343:301-305.

(Continued)

*Primary Examiner* — Andrew D Kosar
*Assistant Examiner* — Phillip Matthew Rzeczycki
(74) *Attorney, Agent, or Firm* — Morgan, Lewis & Bockius LLP

(57) ABSTRACT

The disclosure relates to new compounds, including bifunctional compounds, to be used as modulators of ubiquitination for targeted protein degradation.

10 Claims, 3 Drawing Sheets

(56) References Cited

OTHER PUBLICATIONS

Ramachandran, et al., Current Opinion in Structural Biology 2021, 67:110-119.
Rana et al. Cancers 2021, 13, 5506.
Luh et al, Angew. Chem. Int. Ed. 2020, 59, 15448-15466.
Gerry et al., Nat Chem Biol. Apr. 2020; 16(4): 369-378.
Front. Chem., Dec. 10, 2019 (7) 849.
Tweedie, et al., A cellular model of inflammation for identifying TNF-α synthesis inhibitors, J Neurosci Methods, vol. 183, No. 2, pp. 182-187, Oct. 15, 2010.
Ruch Elman Alexander L, et al., "Isosteric analogs of lenalidomide and pomalidomide: Synthesis and biological activity", Bioorganic & Medicinal Chemistry Letters, vol. 23, No. 1, pp. 360-365, XP028961553, ISSN: 0960-894X, DOI: 10.1016/J.BMCL.2012.10.071.
Solomon, et al., "Targeted degradation of IKZF2 for cancer immunotherapy", Research Square, Novartis Institutes for BioMedical Research, Apr. 8, 2022, 29 pages.
Zhang et al. Clinical Handbook of Tumor Markers, People's Military Medical Press, Beijing, China, Jul. 2008, pp. 58-59 with machine-generated English translation (7 pages total).

* cited by examiner

Peak List for "220 from Sample TMP-Lenalidomide

| | Time (min) | Area (counts) | % Area | Height (%) | % Height | Width (min) | Baseline Type |
|---|---|---|---|---|---|---|---|
| 1 | 0,2996 | 1,3111 | 0,2132 | 0,4013 | 0,6798 | 0,1100 | Base to Base |
| 2 | 1,2953 | 613,6739 | 99,7868 | 58,6347 | 99,3202 | 0,5800 | Base to Base |

BIFUNCTIONAL AGENTS FOR PROTEIN RECRUITMENT AND/OR DEGRADATION

CROSS-REFERENCE TO RELATED APPLICATIONS

This application is a 371 national stage filing of International Application No. PCT/US20/65304, filed Dec. 16, 2020, which claims the benefit of U.S. Provisional Application No. 62/949,028, filed on Dec. 17, 2019, the entire contents of which are incorporated herein.

FIELD OF THE INVENTION

The invention provides new compounds, including bifunctional compounds, for the degradation of a target protein by the ubiquitin proteasome pathway for therapeutic applications as described further herein.

BACKGROUND OF THE INVENTION

Protein degradation is a highly regulated and essential process that maintains cellular homeostasis. The selective identification and removal of damaged, misfolded, or excess proteins is achieved via the ubiquitin-proteasome pathway (UPP). The UPP is essential to the regulation of almost all cellular processes.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins.

Thalidomide and its analogues have been found to bind to the ubiquitin ligase cereblon and redirect its ubiquitination activity (Ito, T. et al., Science, 2010, 327: 1345).

Cereblon forms part of an E3 ubiquitin ligase complex which interacts with damaged DNA binding protein, forming an E3 ubiquitin ligase complex with Cullin 4 and the E2-binding protein ROC1 (known as RBX1) where it functions as a substrate receptor to select proteins for ubiquitination. The binding of lenalidomide to cereblon facilitates subsequent binding of cereblon to Ikaros and Aiolos, leading to their ubiquitination and degradation by the proteasome (Lu, G. et al., Science, 2014, 343:305-309; Kronke, J. et al., Science, 2014, 343:301-305).

It is an object of the present invention to provide new compounds binding to cereblon and the use thereof for the treatment of various diseases and disorders, e.g. by modulating protein degradation.

SUMMARY OF THE INVENTION

The present invention relates to new compounds and their uses and manufacture thereof. The compounds have general formula $(A)_k$-$L_1$ or $(A)_k$-L-Q. Moiety A of the compounds binds to cereblon. L or $L_1$ is a linker. Moiety Q is a moiety that binds to a target protein which is sequestered to the E3 ubiquitin ligase and/or degraded upon interaction with the E3 ubiquitin ligase.

In one aspect, the present invention relates to a compound having the general formula $(A)_k$-$L_1$, or a salt, enantiomer, stereoisomer, polymorph, or N-oxide thereof, wherein:

A is a moiety that binds to an E3 ubiquitin ligase and has the structure selected from the group consisting of Formula I, Formula II, Formula III, Formula IV, Formula V, Formula VI, Formula VII, Formula VIII, Formula IX, and Formula X;

I

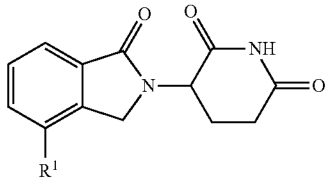

II

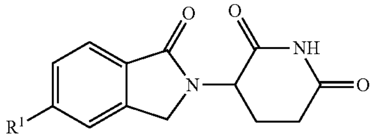

III

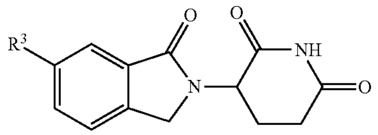

IV

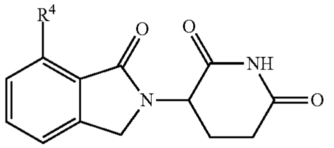

V

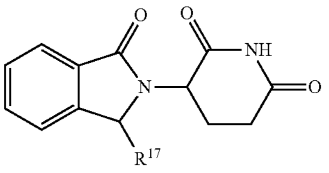

VI

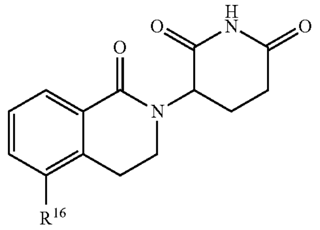

VII

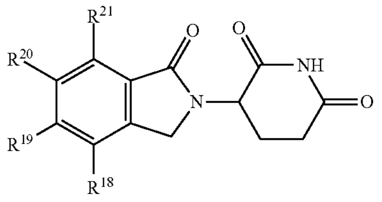

VIII

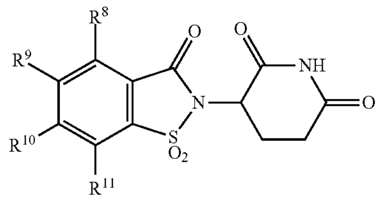

-continued

IX

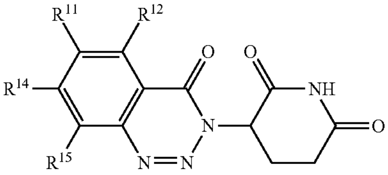

X

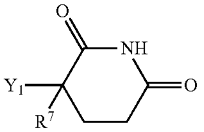

$L_1$ is a linker;

each A is covalently linked to the $L_1$ as allowed by valence;

$R^1$ is aryl, —$N(R^5)$—X—$R^6$, —$SO_2R^5$, or —$O(CH_2)_mR^5$, any of which may be optionally substituted with 1 or more $R^w$ groups as allowed by valence;

$R^2$ is aryl, —NH—($C_3$-$C_{10}$) heteroaryl, or —$N(R^5)$—$(CH_2)_m$—X—$(CH_2)_n$—$R^6$, any of which may be optionally substituted with 1 or more $R^w$ groups as allowed by valence;

$R^3$ is cyano, aryl, —NH—($C_3$-$C_{10}$) heteroaryl, ($C_3$-$C_{10}$) heterocyclo, or —$N(R^5)$—$(CH_2)_m$—X—$(CH_2)_n$—$R^6$, any of which may be optionally substituted with 1 or more $R^w$ groups as allowed by valence;

$R^4$ is halo, cyano, aryl, $OR^5$, or —$N(R^5)$—$(CH_2)_m$—X—$(CH_2)_n$—$R^6$, any of which may be optionally substituted with 1 or more $R^w$ groups as allowed by valence;

$R^5$ at each occurrence is independently H, ($C_1$-$C_3$)alkyl, ($C_3$-$C_{10}$)heterocyclo, ($C_3$-$C_{10}$)cycloalkyl, —$(CH_2)_n$—($C_3$-$C_{10}$) cycloalkyl, —$(CH_2)_n$—($C_3$-$C_{10}$)heterocyclo, —$(CH_2)_n$-aryl, —$(CH_2)_n$-heteroaryl, aryl, or heteroaryl, any of which may be optionally substituted with 1 or more $R^w$ groups as allowed by valence;

$R^6$ at each occurrence is independently OH, ($C_1$-$C_3$)alkyl, —($C_1$-$C_3$)alkoxy, ($C_3$-$C_{10}$)heterocyclo, ($C_3$-$C_{10}$)cycloalkyl, —$(CH_2)_n$—($C_3$-$C_{10}$) cycloalkyl, —$(CH_2)_n$—($C_3$-$C_{10}$)heterocyclo, —$(CH_2)_n$-aryl, —$(CH_2)_n$-heteroaryl, aryl, heteroaryl, or $R^5$ and $R^6$ taken together with the atoms they are attached to forming a nitrogen containing ($C_3$-$C_{10}$)heterocyclic ring, any of which may be optionally substituted with 1 or more $R^w$ groups as allowed by valence;

$R^7$ is H, ($C_1$-$C_3$)alkyl, or $R^7$ and $R^{26}$ taken together with the carbons they are attached to forming a carbon carbon double bond;

$R^8$, $R^9$, $R^{10}$, $R^{11}$ each independently is H, halo, OH, cyano, ($C_1$-$C_3$)alkyl, ($C_1$-$C_3$)alkoxy, aryl, or heteroaryl, any of which may be optionally substituted with 1 or more $R^w$ groups as allowed by valence;

$R^{12}$, $R^{13}$, $R^{14}$, $R^{15}$ each is independently H, $NH_2$, ($C_1$-$C_3$)alkyl, —$N(R^5)$—$(CH_2)_m$—$N(R^5)$—X—$R^6$, with proviso that no more than three substituents out of $R^{12}$, $R^{13}$, $R^{14}$, and $R^{15}$ are H, any of which may be optionally substituted with 1 or more $R^w$ groups as allowed by valence;

$R^{16}$ is $NH_2$ or —$N(R^5)$—$(CH_2)_m$—X—$(CH_2)_n$—$R^6$, any of which may be optionally substituted with 1 or more $R^w$ groups as allowed by valence;

$R^{17}$ is cyano, heteroaryl, —$(CH_2)_m$—C(O)O—$R^6$, or —$N(R^5)$—$(CH_2)_m$—X—$(CH_2)_n$—$R^6$, any of which may be optionally substituted with 1 or more $R^w$ groups as allowed by valence;

$R^{18}$, $R^{19}$, $R^{20}$, $R^{21}$ each independently is H, halo, ($C_1$-$C_3$) alkyl, ($C_1$-$C_3$)alkoxy, or —$N(R^5)$—X—$R^6$, with the proviso that no more than two substituents of $R^{18}$, $R^{19}$, $R^{20}$, $R^{21}$ are H; or $R^{18}$, $R^{19}$ taken together with the carbons they are attached to forming a ($C_3$-$C_{10}$)cycloalkyl or a ($C_3$-$C_{10}$)heterocyclo, or $R^{19}$, $R^{20}$ taken together with the carbons they are attached to forming a ($C_3$-$C_{10}$)cycloalkyl or a ($C_3$-$C_{10}$)heterocyclo, or $R^{20}$, $R^{21}$ taken together with the carbons they are attached to forming a ($C_3$-$C_{10}$) cycloalkyl or a ($C_3$-$C_{10}$)heterocyclo, any of which may be optionally substituted with 1 or more $R^w$ groups as allowed by valence;

$R^{25}$ is aryl, heteroaryl, or ($C_3$-$C_{10}$)heterocyclo, any of which may be optionally substituted with 1 or more $R^w$ groups as allowed by valence;

$R^w$ at each occurrence is independently H, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more groups selected from the group consisting of halo, cyano, oxo($C_3$-$C_{10}$)heterocyclo, ($C_3$-$C_{10}$)cycloalkyl, —$(CH_2)_n$—($C_3$-$C_{10}$) cycloalkyl, —$(CH_2)_n$—($C_3$-$C_{10}$)heterocyclo, —$(CH_2)_n$-aryl, —$(CH_2)_n$-heteroaryl, aryl, and heteroaryl;

X is a bond, —$SO_2$—, —$(CH_2)_nC(O)(CH_2)_m$—, —C(O)NH—, —C(O)N($R^w$)—, —NHC(O)NH—, or —$(CH_2)_n$—;

$Y_1$ is —$NHR^{21}$, —NHC(O)$R^{25}$, or —$CHR^{25}R^{26}$;

m is 0, 1, 2, 3, or 4;

k is 1, 2, 3, 4, 5, 6, 7, 8, 9, or 10;

n is 0, 1, 2, 3, or 4.

In an embodiment, $L_1$ is -$L_b$-$(L_a)_r$-H; wherein $L_a$ at each occurrence is independently selected from the group consisting of a bond, $CR^5R^6$, $C(R^5R^6)O$, $C(R^5R^6)C(R^5R^6)O$, $SO_2$, $NR^5$, $C(R^5R^6)NR^5$, $SO_2NR^5$, $SONR^5$, $CONR^5$, $NR^5CONR^6$, $NR^5SO_2NR^6$, CO, $CR^5$=$CR^6$, C≡C, $SiR^5R^6$, $P(O)R^5$, $P(O)OR^5$, $NR^5C$(=NCN)$NR^6$, $NR^5C$(=NCN), and $NR^5C(=CNO_2)NR^6$, any of which may be optionally substituted with 1 or more $R^w$ groups as allowed by valence;

H is hydrogen.

$L_b$ is selected from the group consisting of:

a bond,

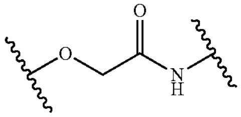
,
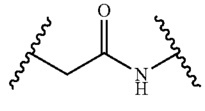
,

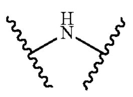
,
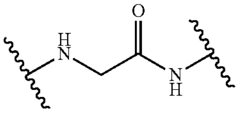
,

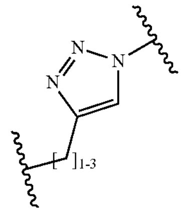
,
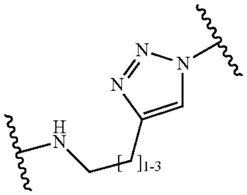
,

-continued

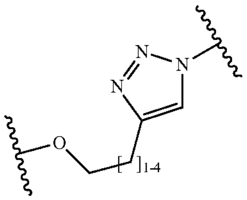, 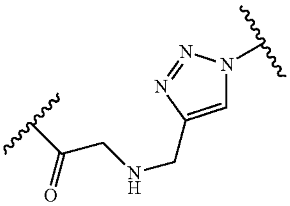,

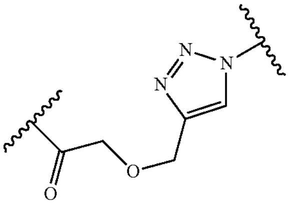, 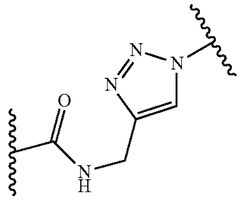,

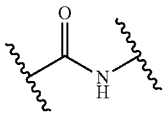, 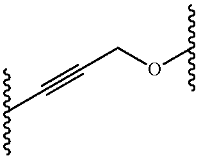 and 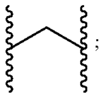;

t is 0, 1, 2, 3, 4, 5, 6, 7, 8, 9, 10, 11, 12, 13, 14, 15, 16, 17, 18, 19, or 20.

In one aspect, the present invention relates to a compound of the general formula $(A)_k$-L-Q, or a salt, enantiomer, stereoisomer, polymorph, or N-oxide thereof, wherein:

A is a compound that binds to an E3 ubiquitin ligase and has the structure selected from the group consisting of Formula I, Formula II, Formula III, Formula IV, Formula V, Formula VI, Formula VII, Formula VIII, Formula IX, and Formula X;

I

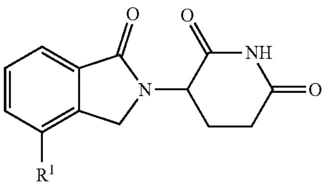

II

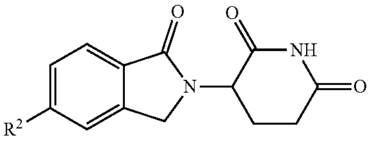

III

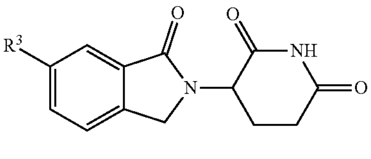

IV

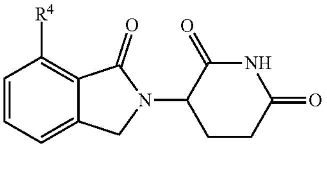

-continued

V

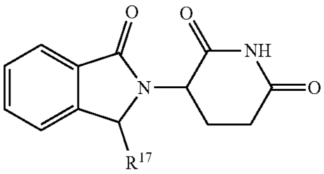

VI

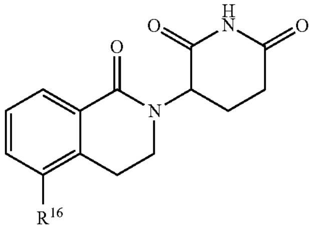

VII

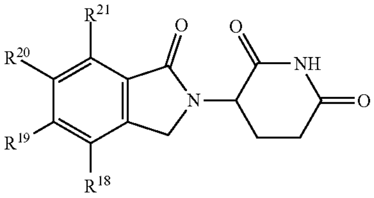

VIII

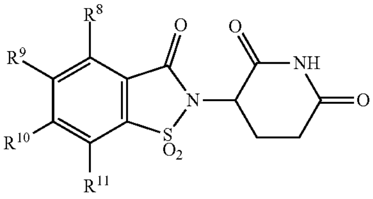

IX

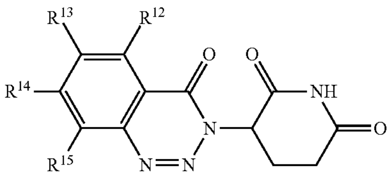

X

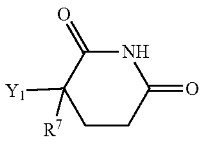

Q is a moiety that binds to a target protein which is sequestered to the E3 ubiquitin ligase and/or degraded upon interaction with the E3 ubiquitin ligase;

L is a linker;

each A is covalently linked to the L as allowed by valence;

$R^1$ is aryl, —$N(R^5)$—X—$R^6$, —$SO_2R^5$, or —$O(CH_2)_mR^5$, any of which may be optionally substituted with 1 or more $R^w$ groups as allowed by valence;

$R^2$ is aryl, —NH—($C_3$-$C_{10}$) heteroaryl, or —$N(R^5)$—$(CH_2)_m$—X—$(CH_2)_n$—$R^6$, any of which may be optionally substituted with 1 or more $R^w$ groups as allowed by valence;

$R^3$ is cyano, aryl, —NH—($C_3$-$C_{10}$)heteroaryl, ($C_3$-$C_{10}$) heterocyclo, or —$N(R^5)$—$(CH_2)_m$—X—$(CH_2)_n$—$R^6$, any of which may be optionally substituted with 1 or more $R^w$ groups as allowed by valence;

$R^4$ is halo, cyano, aryl, $OR^5$, or —$N(R^5)$—$(CH_2)_m$—X—$(CH_2)_n$—$R^6$, any of which may be optionally substituted with 1 or more $R^w$ groups as allowed by valence;

$R^5$ at each occurrence is independently H, $(C_1-C_3)$alkyl, $(C_3-C_{10})$heterocyclo, $(C_3-C_{10})$cycloalkyl, $—(CH_2)_n—(C_3-C_{10})$ cycloalkyl, $—(CH_2)_n—(C_3-C_{10})$heterocyclo, $—(CH_2)_n$-aryl, $—(CH_2)_n$-heteroaryl, aryl, or heteroaryl, any of which may be optionally substituted with 1 or more $R^w$ groups as allowed by valence;

$R^6$ at each occurrence is independently OH, $(C_1-C_3)$alkyl, $—(C_1-C_3)$alkoxy, $(C_3-C_{10})$heterocyclo, $(C_3-C_{10})$cycloalkyl, $—(CH_2)_n—(C_3-C_{10})$cycloalkyl, $—(CH_2)_n—(C_3-C_{10})$heterocyclo, $—(CH_2)_n$-aryl, $—(CH_2)_n—$ heteroaryl, aryl, heteroaryl, or $R^5$ and $R^6$ taken together with the atoms they are attached to forming a nitrogen containing $(C_3-C_{10})$heterocyclic ring, any of which may be optionally substituted with 1 or more $R^w$ groups as allowed by valence;

$R^7$ is H, $(C_1-C_3)$alkyl, or $R^7$ and $R^{26}$ taken together with the carbons they are attached to forming a carbon carbon double bond;

$R^8$, $R^9$, $R^{10}$, $R^{11}$ each independently is H, halo, OH, cyano, $(C_1-C_3)$alkyl, $(C_1-C_3)$alkoxy, aryl, or heteroaryl, any of which may be optionally substituted with 1 or more $R^w$ groups as allowed by valence;

$R^{12}$, $R^{13}$, $R^{14}$, $R^{15}$ each is independently H, $NH_2$, $(C_1-C_3)$alkyl, $—N(R^5)—(CH_2)$m-$N(R^5)—X—R^6$, with proviso that no more than three substituents out of $R^{12}$, $R^{13}$, $R^{14}$, and $R^{15}$ are H, any of which may be optionally substituted with 1 or more $R^w$ groups as allowed by valence;

$R^{16}$ is $NH_2$ or $—N(R^5)—(CH_2)_m—X—(CH_2)_n—R^6$, any of which may be optionally substituted with 1 or more $R^w$ groups as allowed by valence;

$R^{17}$ is cyano, heteroaryl, $—(CH_2)_m—C(O)O—R^6$, or $—N(R^5)—(CH_2)_m—X—(CH_2)_n—R^6$, any of which may be optionally substituted with 1 or more $R^w$ groups as allowed by valence;

$R^{18}$, $R^{19}$, $R^{20}$, $R^{21}$ each independently is H, halo, $(C_1-C_3)$ alkyl, $(C_1-C_3)$alkoxy, or $—N(R^5)—X—R^6$, with the proviso that no more than two substituents of $R^{18}$, $R^{19}$, $R^{20}$, $R^{21}$ are H; or $R^{18}$, $R^{19}$ taken together with the carbons they are attached to forming a $(C_3-C_{10})$cycloalkyl or a $(C_3-C_{10})$heterocyclo, or $R^{19}$, $R^{20}$ taken together with the carbons they are attached to forming a $(C_3-C_{10})$cycloalkyl or a $(C_3-C_{10})$heterocyclo, or $R^{20}$, $R^{21}$ taken together with the carbons they are attached to forming a $(C_3-C_{10})$ cycloalkyl or a $(C_3-C_{10})$heterocyclo, any of which may be optionally substituted with 1 or more $R^w$ groups as allowed by valence;

$R^{25}$ is aryl, heteroaryl, or $(C_3-C_{10})$heterocyclo, any of which may be optionally substituted with 1 or more $R^w$ groups as allowed by valence;

$R^w$ at each occurrence is independently H, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more groups selected from the group consisting of halo, cyano, oxo$(C_3-C_{10})$heterocyclo, $(C_3-C_{10})$cycloalkyl, $—(CH_2)_n—(C_3-C_{10})$cycloalkyl, $—(CH_2)_n—(C_3-C_{10})$heterocyclo, $—(CH_2)_n$-aryl, $—(CH_2)_n$-heteroaryl, aryl, and heteroaryl;

X is a bond, $—SO_2—$, $—(CH_2)_nC(O)(CH_2)_m—$, $—C(O)NH—$, $—C(O)N(R^w)—$, $—NHC(O)NH—$, or $—(CH_2)_n—$;

$Y_1$ is $—NHR^{25}$, $—NHC(O)R^{25}$, or $—CHR^{25}R^{26}$;

m is 0, 1, 2, 3, or 4;

k is 1, 2, 3, 4, 5, 6, 7, 8, 9, or 10;

n is 0, 1, 2, 3, or 4.

In an embodiment, L is $-L_b-(L_a)_t-$; wherein La at each occurrence is independently selected from the group consisting of a bond, $CR^5R^6$, $C(R^5R^6)O$, $C(R^5R^6)C(R^5R^6)O$, $SO_2$, $NR^5$, $C(R^5R^6)$ $NR^5$, $SO_2NR^5$, $SONR^5$, $CONR^5$, $NR^5CONR^6$, $NR^5SO_2NR^6$, CO, $CR^5{=}CR^6$, C≡C, $SiR^5R^6$, $P(O)R^5$, $P(O)OR^5$, $NR^5C({=}NCN)NR^6$, $NR^5C({=}NCN)$, and $NR^5C({=}CNO_2)NR^6$, any of which may be optionally substituted with 1 or more $R^w$ groups as allowed by valence;

$L_b$ is selected from the group consisting of:

a bond,

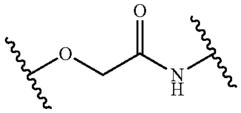,
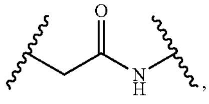,

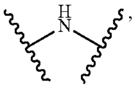,
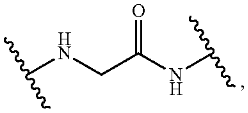,

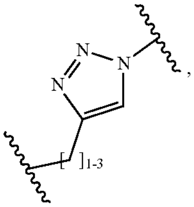,
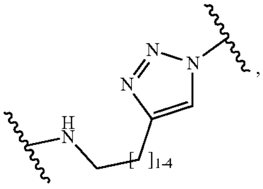,

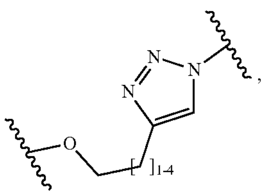,
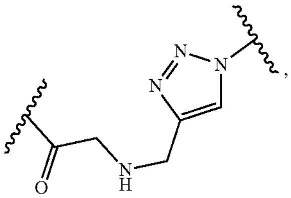,

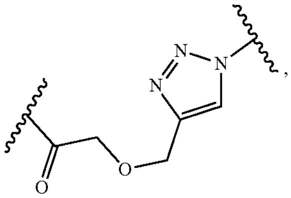,
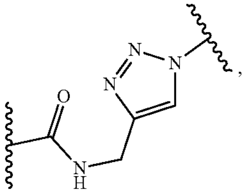,

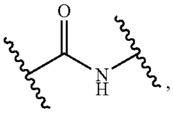,
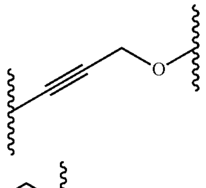 and

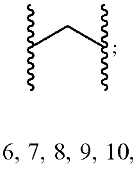;

t is 0, 1, 2, 3, 4, 5, 6, 7, 8, 9, 10, 11, 12, 13, 14, 15, 16, 17, 18, 19, or 20.

In an embodiment, L is $—(CH_2CH_2)_r—$, $—(CH_2O)_r—$ or $—(CH_2CH_2O)_r—$.

In one aspect, moiety A is selected from the group consisting of:

3-[1-oxo-5-(quinazolin-4-ylamino)isoindolin-2-yl]piperidine-2,6-dione;

3-[5-[(4-aminothieno[2,3-d]pyrimidin-2-yl)amino]-1-oxo-isoindolin-2-yl]piperidine-2,6-dione;

N-[2-(2,6-dioxo-3-piperidyl)-1-oxo-isoindolin-5-yl]acetamide;

3-[5-[(2-aminopyrimidin-4-yl)amino]-1-oxo-isoindolin-2-yl]piperidine-2,6-dione;

6-[[2-(2,6-dioxo-3-piperidyl)-1-oxo-isoindolin-5-yl]amino]pyridazine-3-carbonitrile;

3-[[2-[[2-(2,6-dioxo-3-piperidyl)-1-oxo-isoindolin-5-yl]amino]acetyl]amino]benzamide;

2-[[2-(2,6-dioxo-3-piperidyl)-1-oxo-isoindolin-5-yl]amino]acetic acid;

N-[2-(2,6-dioxo-3-piperidyl)-3-oxo-isoindolin-5-yl]quinoline-2-carboxamide;

3-[6-[[2-(2-methyl-1-piperidyl)-2-oxo-ethyl]amino]-1-oxo-isoindolin-2-yl]piperidine-2,6-dione;

3-[6-[(2-isoindolin-2-yl-2-oxo-ethyl)amino]-1-oxo-isoindolin-2-yl]piperidine-2,6-dione;

N-(cyclopropylmethyl)-2-[[2-(2,6-dioxo-3-piperidyl)-3-oxo-isoindolin-5-yl]amino]-N-methyl-acetamide;

acetic acid; 3-[1-oxo-6-(quinazolin-4-ylamino)isoindolin-2-yl]piperidine-2,6-dione;

3-[6-[[2-(3-methyl-1-piperidyl)-2-oxo-ethyl]amino]-1-oxo-isoindolin-2-yl]piperidine-2,6-dione;

3-[6-[(4-methyl-3-oxo-pyrazin-2-yl)amino]-1-oxo-isoindolin-2-yl]piperidine-2,6-dione;

3-[1-oxo-6-(quinoxalin-2-ylamino)isoindolin-2-yl]piperidine-2,6-dione;

3-[6-[(1-methylpyrazolo[3,4-d]pyrimidin-4-yl)amino]-1-oxo-isoindolin-2-yl]piperidine-2,6-dione;

3-[6-(5,7-dihydrofuro[3,4-d]pyrimidin-2-ylamino)-1-oxo-isoindolin-2-yl]piperidine-2,6-dione;

3-[6-[(6-methylpyrimidin-4-yl)amino]-1-oxo-isoindolin-2-yl]piperidine-2,6-dione;

2-[[2-(2,6-dioxo-3-piperidyl)-3-oxo-isoindolin-5-yl]amino]-N-phenyl-acetamide;

3-[6-[[2-(2,4-dimethylpiperazin-1-yl)-2-oxo-ethyl]amino]-1-oxo-isoindolin-2-yl]piperidine-2,6-dione;

3-[6-(dimethylamino)-1-oxo-isoindolin-2-yl]piperidine-2,6-dione;

3-(1-oxo-6-phenyl-isoindolin-2-yl)piperidine-2,6-dione;

2-[[2-(2,6-dioxo-3-piperidyl)-3-oxo-isoindolin-5-yl]amino]-N,N-dimethyl-acetamide;

3-[6-[[2-(2-methylmorpholin-4-yl)-2-oxo-ethyl]amino]-1-oxo-isoindolin-2-yl]piperidine-2,6-dione;

2-[[2-(2,6-dioxo-3-piperidyl)-3-oxo-isoindolin-5-yl]amino]-N-methyl-N-[(1-methylpyrazol-4-yl)methyl]acetamide;

N-benzyl-2-[[2-(2,6-dioxo-3-piperidyl)-3-oxo-isoindolin-5-yl]amino]acetamide;

6-[[2-(2,6-dioxo-3-piperidyl)-3-oxo-isoindolin-5-yl]amino]pyridazine-3-carbonitrile;

3-[6-[(6-methylpyrrolo[3,2-d]pyrimidin-4-yl)amino]-1-oxo-isoindolin-2-yl]piperidine-2,6-dione;

2-(dimethylamino)-N-[2-(2,6-dioxo-3-piperidyl)-3-oxo-isoindolin-5-yl]acetamide;

N-[2-(2,6-dioxo-3-piperidyl)-3-oxo-isoindolin-5-yl]-5H-pyrrolo[2,3-b]pyridine-4-carboxamide;

N-cyclopropyl-2-[[2-(2,6-dioxo-3-piperidyl)-3-oxo-isoindolin-5-yl]amino]acetamide;

3-[1-oxo-6-(2-oxoimidazolidin-1-yl)isoindolin-2-yl]piperidine-2,6-dione;

2-(2,6-dioxo-3-piperidyl)-3-oxo-isoindoline-5-carbonitrile;

2-[[2-(2,6-dioxo-3-piperidyl)-3-oxo-isoindolin-5-yl]amino]propanoic acid;

2-acetamido-N-[2-(2,6-dioxo-3-piperidyl)-3-oxo-isoindolin-5-yl]acetamide;

2-[[2-(2,6-dioxo-3-piperidyl)-3-oxo-isoindolin-5-yl]amino]acetamide;

3-[6-[[2-(3-methyl-5-oxo-piperazin-1-yl)-2-oxo-ethyl]amino]-1-oxo-isoindolin-2-yl]piperidine-2,6-dione;

N-[2-(2,6-dioxo-3-piperidyl)-3-oxo-isoindolin-5-yl]acetamide;

3-[6-[[2-(4-methyl-3-oxo-piperazin-1-yl)-2-oxo-ethyl]amino]-1-oxo-isoindolin-2-yl]piperidine-2,6-dione;

N-[2-(2,6-dioxo-3-piperidyl)-3-oxo-isoindolin-5-yl]-3H-imidazo[4,5-b]pyridine-6-carboxamide;

2-[[2-(2,6-dioxo-3-piperidyl)-3-oxo-isoindolin-5-yl]amino]-N-tetrahydropyran-4-yl-acetamide;

2-[[2-(2,6-dioxo-3-piperidyl)-3-oxo-isoindolin-5-yl]amino]acetic acid;

3-[1-oxo-6-[[2-oxo-2-(1-piperidyl)ethyl]amino]isoindolin-2-yl]piperidine-2,6-dione;

3-(1-oxo-7-phenyl-isoindolin-2-yl)piperidine-2,6-dione;

2-(2,6-dioxo-3-piperidyl)-3-oxo-isoindoline-4-carbonitrile;

2-[[2-(2,6-dioxo-3-piperidyl)-3-oxo-isoindolin-4-yl]amino]acetic acid;

3-(7-fluoro-1-oxo-isoindolin-2-yl)piperidine-2,6-dione;

3-(5-amino-1-oxo-3,4-dihydroisoquinolin-2-yl)piperidine-2,6-dione;

t-butyl 2-[2-(2,6-dioxo-3-piperidyl)-3-oxo-isoindolin-1-yl]acetate;

3-[1-(2H-indol-3-yl)-3-oxo-isoindolin-2-yl]piperidine-2,6-dione;

2-(2,6-dioxo-3-piperidyl)-3-oxo-isoindoline-1-carbonitrile;

3-[1-(dimethylamino)-3-oxo-isoindolin-2-yl]piperidine-2,6-dione;

3-(2-oxopyrrolidin-1-yl)piperidine-2,6-dione;

3-(quinazolin-2-ylamino)piperidine-2,6-dione;

(3Z)-3-benzylidenepiperidine-2,6-dione;

3-(quinoxalin-2-ylamino)piperidine-2,6-dione;

3-(pyrimidin-2-ylamino)piperidine-2,6-dione;

N-(2,6-dioxo-3-piperidyl)-2-oxo-3H-pyridine-6-carboxamide;

3-(4-methyl-1,1,3-trioxo-1,2-benzothiazol-2-yl)piperidine-2,6-dione;

3-(8-amino-4-oxo-1,2,3-benzotriazin-3-yl)piperidine-2,6-dione;

3-(5-amino-4-oxo-1,2,3-benzotriazin-3-yl)piperidine-2,6-dione;

3-(4-oxo-1,2,3-benzotriazin-3-yl)piperidine-2,6-dione;

3-(5-methyl-4-oxo-1,2,3-benzotriazin-3-yl)piperidine-2,6-dione;

3-(6-methyl-4-oxo-1,2,3-benzotriazin-3-yl)piperidine-2,6-dione; and 3-(8-methyl-4-oxo-1,2,3-benzotriazin-3-yl)piperidine-2,6-dione.

In an embodiment, Q is a moiety that binds to a target protein, wherein said target protein is selected from the group consisting of B7.1 and B7, TINFR1m, TNFR2, NADPH oxidase, Bel, C5a receptor, HMG-CoA reductase, PDE V phosphodiesterase type, PDE IV phosphodiesterase type 4, PDE I, PDEII, PDEIII, Squalene-hopene cyclase, CXCR1, CXCR2, nitric oxide (NO) synthase, cyclo-oxygenase 1, cyclo-oxygenase 2, 5HT receptors, dopamine receptors, G Proteins, Gq, histamine receptors, 5-lipoxygenase, tryptase serine protease, thymidylate synthase, purine nucleoside phosphorylase, GAPDH trypanosomal, glycogen phosphorylase, carbonic anhydrase, chemokine receptors, JAW/STAT, retinoid X receptor, HIV 1 protease, HIV 1 integrase, influenza, neuramimidase, hepatitis B reverse transcriptase, sodium channel, protein P-glycoprotein (and MRP), tyrosine kinases, CD23, CD124, tyrosine kinase p56 lck, CD4, CD5, IL-2 receptor, IL-1 receptor, TNF-alpha, ICAM1, Cat+ channels, VCAM, VLA-4 integrin, selectins, CD40/CD40L, newokinins and receptors, inosine monophosphate dehydrogenase, p38 MAP Kinase, Ras/Raf/ME/ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I) protease, cytomegalovirus (CMV) protease, poly (ADP-ribose) polymerase, cyclin dependent kinases, vascular endothelial growth factor, c-Kit, TGFβ activated kinase 1, mammalian target of rapamycin, SHP2, androgen receptor, oxytocin receptor, microsomal transfer protein inhibitor, 5 alpha reductase, angiotensin II, glycine receptor, noradrenaline reuptake receptor, estrogen receptor, estrogen related receptors, focal adhesion kinase, Src, endothelin receptors, neuropeptide Y and receptor, adenosine receptors, adenosine kinase and AMP deaminase, purinergic receptors (P2Y1, P2Y2, P2Y4, P2Y6, P2X1-7), famesyltransferases, geranylgeranyl transferase, TrkA a receptor for NGF, beta-amyloid, tyrosine kinase Flk-1, vitronectin receptor, integrin receptor, Her-2/neu, telomerase, cytosolic phospholipaseA2 and EGF receptor tyrosine kinase, ecdysone 20-monooxygenase, ion channel of the GABA gated chloride channel, acetylcholinesterase, voltage-sensitive sodium channel protein, calcium channel protein, and chloride channel protein, acetyl-CoA carboxylase, adenylosuccinate synthetase, protoporphyrinogen oxidase, and enolpyruvylshikimate-phosphate synthase.

In an embodiment, Q is a moiety that is an Hsp90 inhibitor, a kinase inhibitor, a phosphatase inhibitor, an HDM2/MDM2 inhibitor, a human BET Bromodomain inhibitor, an HDAC inhibitor, a human lysine methyltransferase inhibitor, a RAF receptor inhibitor, a FKBP inhibitor, an angiogenesis inhibitor, an aryl hydrocarbon receptor inhibitor, an androgen receptor inhibitor, an estrogen receptor inhibitor, a thyroid hormone receptor inhibitor, an HIV protease inhibitor, an HIV integrase inhibitor, an acyl protein thioesterase 1 inhibitor, or an acyl protein thioesterase 2 inhibitor.

In an embodiment, Q is a moiety that is a TANK-binding kinase 1 (TBK1) inhibitor, an estrogen receptor α (ERα) inhibitor, a bromodomain-containing protein 4 (BRD4) inhibitor, an androgen receptor (AR) inhibitor, a platelet-derived growth factor receptor inhibitor, a p38 MAPK inhibitor, a Bcr-Abl tyrosine-kinase inhibitor, an Her2 inhibitor, an EGFR inhibitor, an MDM2 inhibitor, a bromodomain-containing protein 2 (BRD2) inhibitor, an HDAC inhibitor, a DHFR inhibitor, or a c-Myc inhibitor.

In an embodiment, Q is a moiety selected from the group consisting of trimethoprim, vorinostat, tamoxifen, JQ1, Nutlin 3, afatinib, chloroalkane, dasatinib, BIRB796, FK-506, simvastatin, rapamycin, and sorafenib.

In one aspect, the present invention relates to a pharmaceutical composition comprising the compound of Formula $(A)_k$-L-Q or $(A)_k$-$L_1$ and a pharmaceutically acceptable carrier, additive, and/or excipient.

In embodiments, the composition is a bivalent inducer of protein degradation (also known as a proteolysis-targeting chimera (PROTAC)). In embodiments, the composition is a CLIckable Proteolysis TArgeting Chimeras (CLIPTACs). Such CLIPTAC, in embodiments, includes (a) a first portion comprising a ligand for a target protein; (b) a second portion comprising a ligand for an E3 ubiquitin ligase; and (c) a linker portion covalently coupling the first and second portions; wherein the linker comprises a covalent bond produced by a bioorthogonal click reaction between a compatible pair of reactive moieties. In embodiments, the composition is an in-cell click-formed proteolysis targeting chimera (CLIPTAC).

In one aspect, the present invention relates to a method for treating a disease in a subject, said method comprising administering an effective amount of a compound having Formula $(A)_k$-L-Q or $(A)_k$-$L_1$.

In one aspect, the present invention relates to a method for treating a disease in a subject wherein dysregulated protein activity is responsible for said disease, said method comprising administering an effective amount of a compound having Formula $(A)_k$-L-Q or $(A)_k$-$L_1$.

In an embodiment, the cancer is selected from the group consisting of squamous-cell carcinoma, basal cell carcinoma, adenocarcinoma, hepatocellular carcinomas, renal cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, uterine cancer, leukemias, lymphomas, Burkitt's lymphoma, Non-Hodgkin's lymphoma, melanomas, myeloproliferative diseases, multiple myeloma, sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, Schwannomas, testicular cancer, thyroid cancer, astrocytoma, Hodgkin's disease, Wilms' tumor, and teratocarcinomas.

In another aspect, the present invention relates to a method of treating or preventing one or more autoimmune diseases or disorders comprising administering a composition comprising a pharmaceutically effective amount of the compound described herein and a pharmaceutically acceptable carrier to a subject in need thereof. In an embodiment, the autoimmune disease or disorder is selected from, such as multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and other autoimmune diseases or disorders.

In an embodiment, the subject is a human.

BRIEF DESCRIPTION OF THE DRAWINGS

The foregoing summary, as well as the following detailed description of the invention, will be better understood when read in conjunction with the appended drawings.

DETAILED DESCRIPTION OF THE INVENTION

Figure 1:
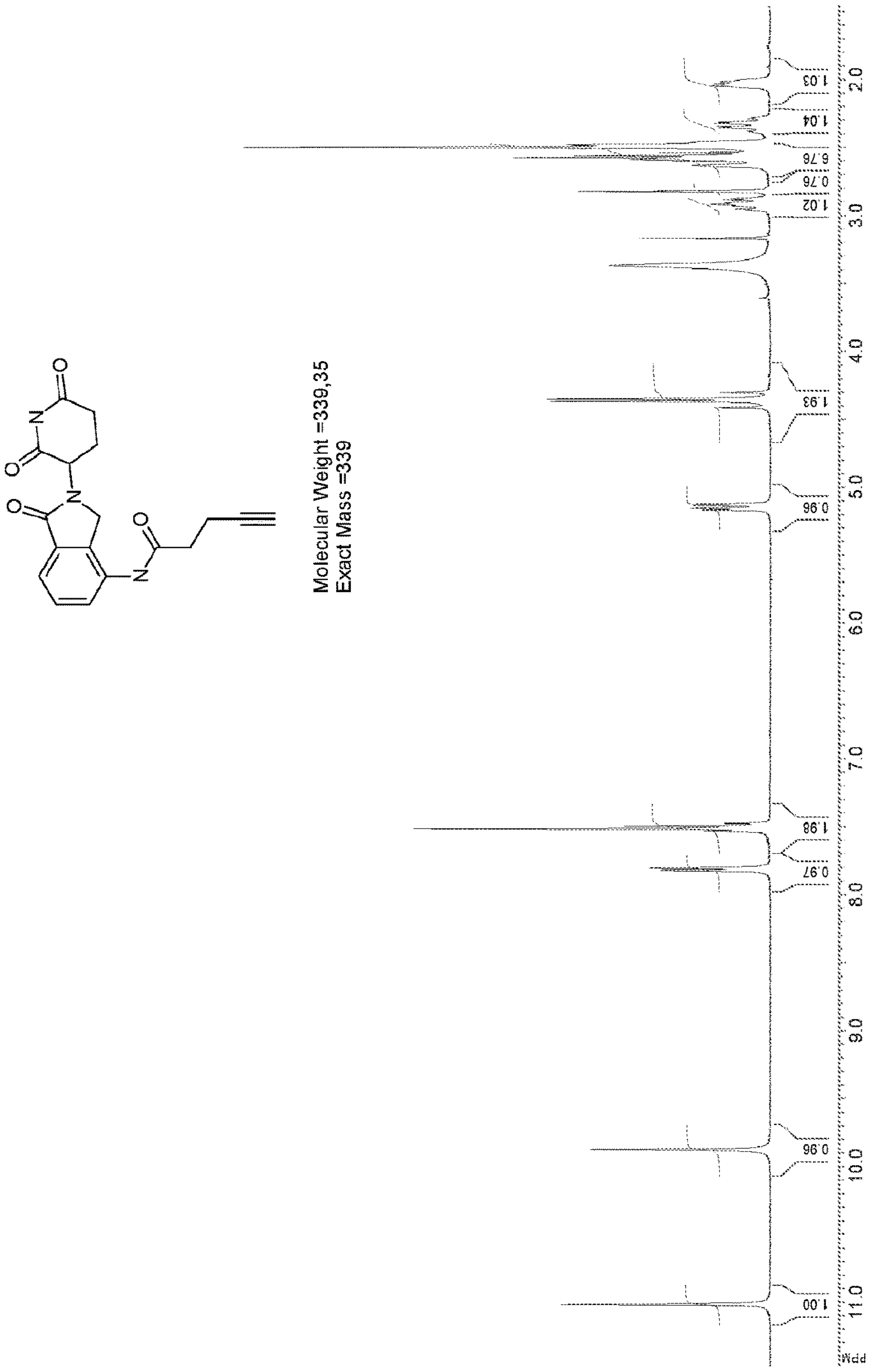
FIG. 1 illustrates the HNMR of the intermediate compound 53 in Example 5.
Figure 2:
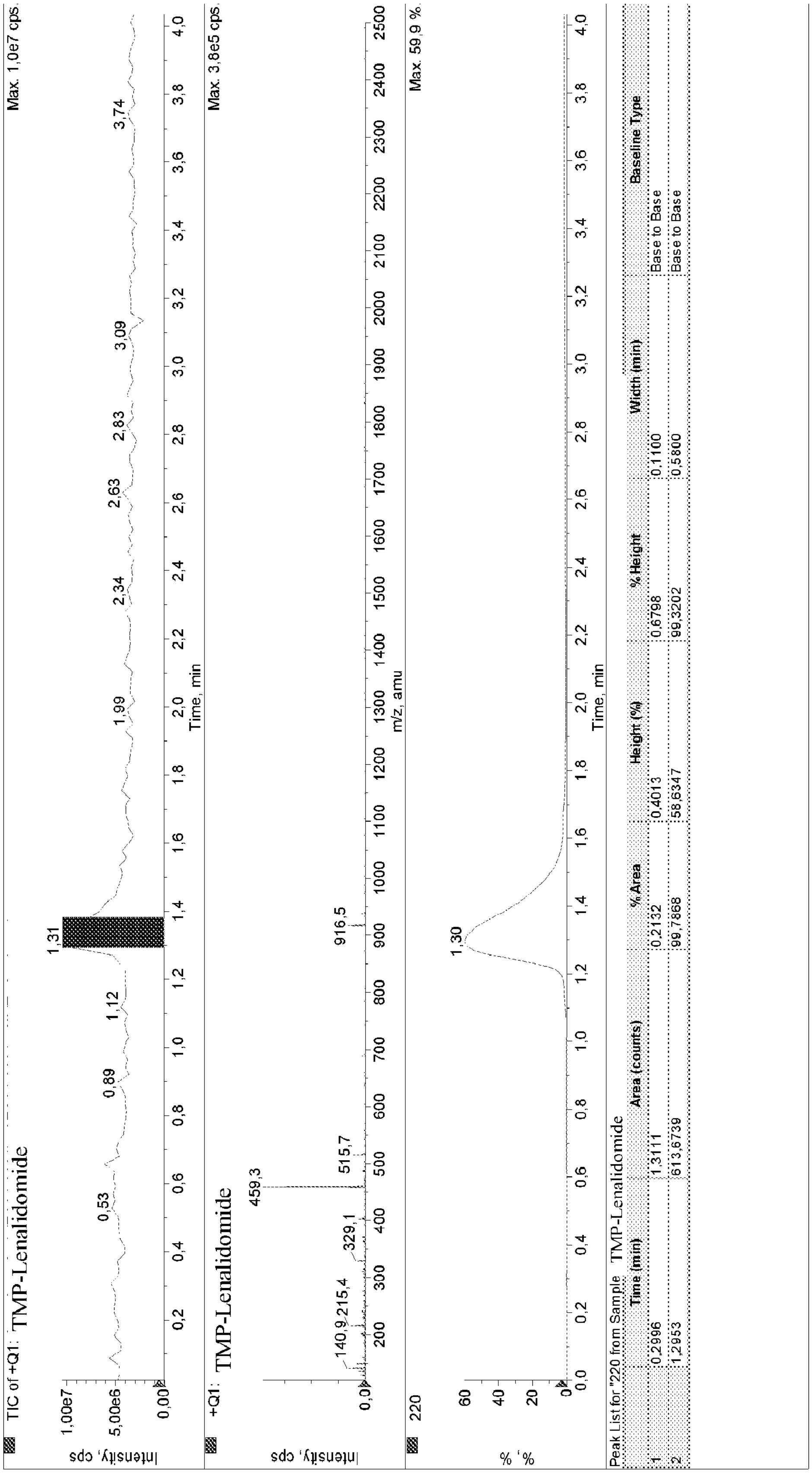
FIG. 2 illustrates the LCMS data of Trimethoprim-lenalidomide (TMP-LEN).

The following is a detailed description of the present invention. Those of ordinary skill in the art may make modifications and variations in the embodiments described herein without departing from the spirit or scope of the present disclosure. All publications, patent applications, patents, and other references mentioned herein are expressly incorporated by reference in their entirety.

Presently described are novel compounds, including bifunctional compounds, compositions and methods that relate to the surprising and unexpected discovery that an E3 ubiquitin ligase protein, e.g., cereblon, ubiquitinates a target protein once it and the target protein are placed in proximity by a bifunctional or chimeric construct that binds the E3 ubiquitin ligase protein and the target protein. Accordingly the present invention provides such compounds having general formula $(A)_k$-$L_1$ or $(A)_k$-L-Q, wherein A is a moiety binding to the E3 ubiquitin ligase protein; L or $L_1$ is a linker; Q is a moiety binding to the target protein.

In an embodiment, compounds disclosed herein, pharmaceutically acceptable salts thereof, or pharmaceutically acceptable compositions thereof can be used to treat a disorder mediated by one or more of cereblon, IKZF1, SALL4, and ASS1, e.g. various cancers and autoimmune diseases or disorders.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

Definition

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

"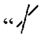" indicates the double bond in E or Z configuration.

The term "H" denotes a single hydrogen atom. This radical may be attached, for example, to an oxygen atom to form a hydroxyl radical.

Where the term "alkyl" is used, either alone or within other terms such as "haloalkyl" or "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" or "alkylene" embraces bridging divalent alkyl radicals such as methylenyl or ethylenyl. The term "lower alkyl substituted with $R^2$" does not include an acetal moiety. The term "alkyl" further includes alkyl radicals wherein one or more carbon atoms in the chain is substituted with a heteroatom selected from oxygen, nitrogen, or sulfur.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, and butynyl, and the like.

Alkyl, alkylenyl, alkenyl, and alkynyl radicals may be optionally substituted with one or more functional groups such as halo, hydroxy, nitro, amino, cyano, haloalkyl, aryl, heteroaryl, and heterocyclo and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1 to 6 carbon atoms.

Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings, wherein such rings may be attached together in a fused manner.

The term "aryl" embraces aromatic radicals such as phenyl, naphthyl, indenyl, tetrahydronaphthyl, and indanyl. More preferred aryl is phenyl. An "aryl" group may have 1 or more substituents such as lower alkyl, hydroxyl, halo, haloalkyl, nitro, cyano, alkoxy, and lower alkylamino, and the like. Phenyl substituted with $—O—CH_2—O—$ forms the aryl benzodioxolyl substituent.

The term "heterocyclyl" (or "heterocyclo") embraces saturated, partially saturated and unsaturated heteroatom-containing ring radicals, where the heteroatoms may be selected from nitrogen, sulfur and oxygen. It does not include rings containing —O—O—, —O—S— or —S—S— portions. The "heterocyclyl" group may have 1 to 4 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g., pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g., morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term heterocyclyl, (or heterocyclo) also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, and benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-TH-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-TH-1λ'-benzo[d]isothiazol-6-yl, dihydropyranyl, dihydrofuryl and dihydrothiazolyl, and the like.

The term "heterocyclo" thus encompasses the following ring systems:

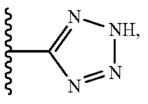
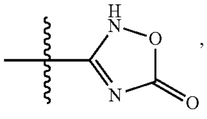
,
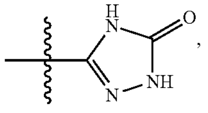
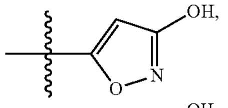
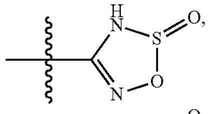
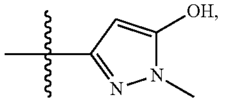
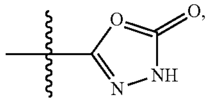

-continued
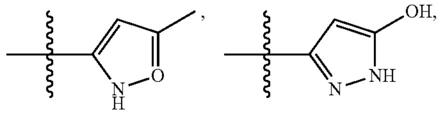
,
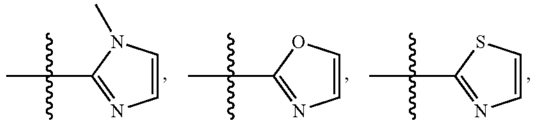
, , ,
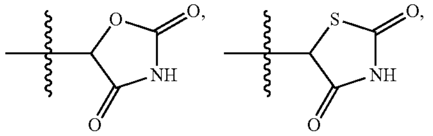
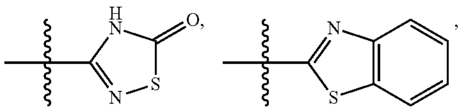
,
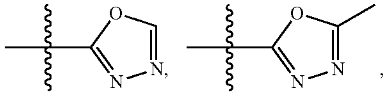
,
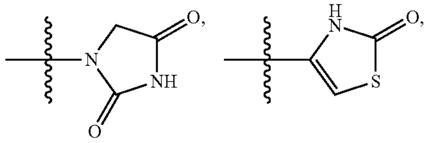
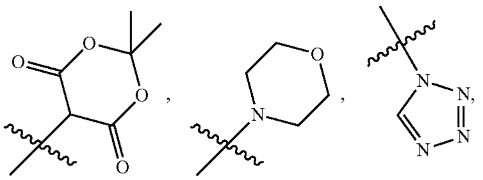
, ,
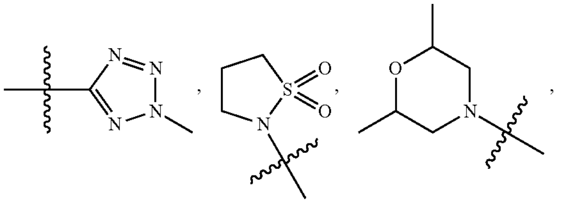
, , ,
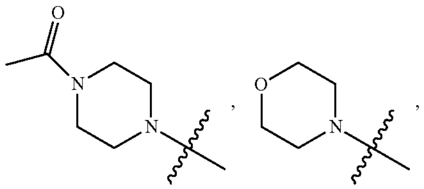
, ,
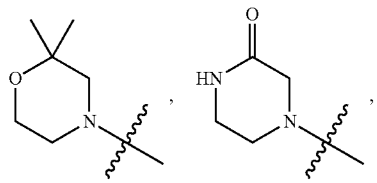
, ,
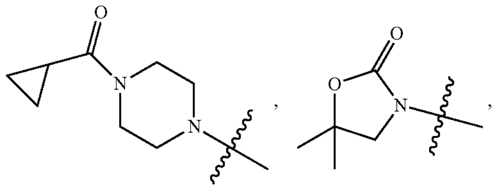
, ,
-continued
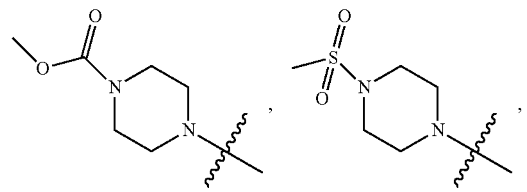
, ,
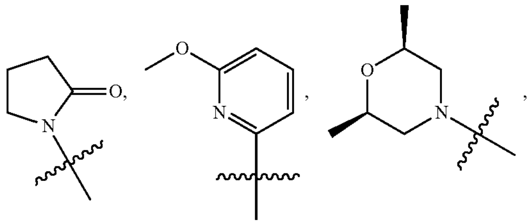
, ,
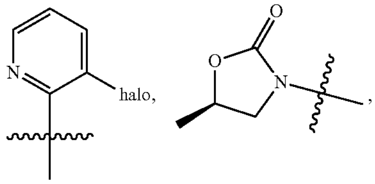
,
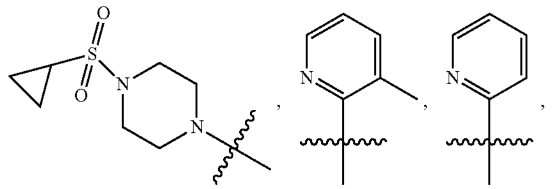
, , ,
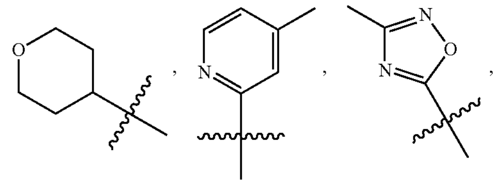
, , ,
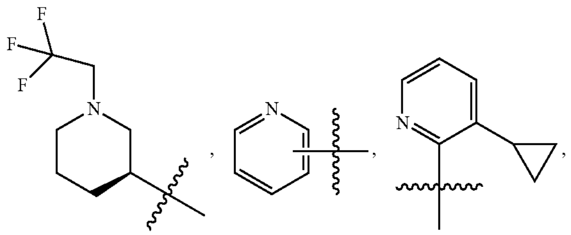
, , ,
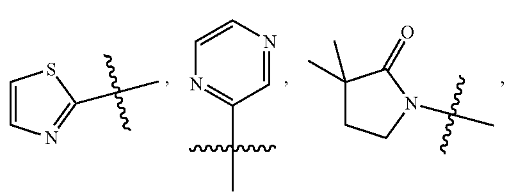
, , ,
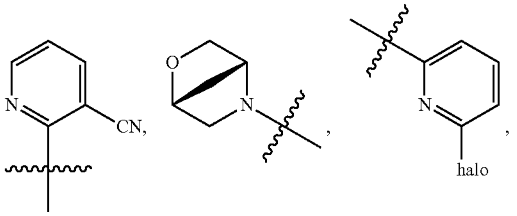
, , -continued

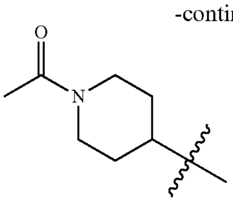
,
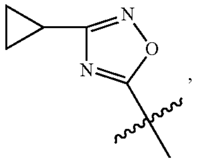
,
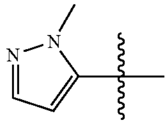
,
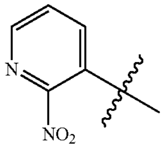
,
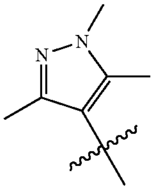
, and the like.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," denotes a sulfonyl radical substituted with an amine radical, forming a sulfonamide (—$SO_2NH_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl," whether used alone or with other terms, such as "carboxyalkyl," denotes —$CO_2H$.

The term "carbonyl," whether used alone or with other terms, such as "aminocarbonyl," denotes —(C═O)—.

The term "aminocarbonyl" denotes an amide group of the formula C(═O)$NH_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, and N,N-diethylamino, and the like.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "aralkylamino" denotes amino groups, which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups, which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, and N,N-diethylaminomethyl, and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, and N,N-diethylaminoethoxy, and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, and N,N-diethylaminomethoxymethoxy, and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, and carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5 to 6-membered cycloalkylalkyl" attached to alkyl portions having one to three carbon atoms.

Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

A group or atom that replaces a hydrogen atom is also called a substituent.

Any particular molecule or group can have one or more substituent depending on the number of hydrogen atoms that can be replaced.

The symbol "-" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptom of a particular disease or condition, or prevents or delays the onset of one of more symptom of a particular disease or condition.

The terms "patient" and "subject" may be used interchangeably and mean animals, such as dogs, cats, cows, horses, sheep and humans. Particular patients are mammals. The term patient includes males and females.

The term "pharmaceutically acceptable" means that the referenced substance, such as a compound of Formula I, or a salt of a compound of Formula I, or a formulation containing a compound of Formula I, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The term "cancer" means a physiological condition in mammals that is characterized by unregulated cell growth. General classes of cancers include carcinomas, lymphomas, sarcomas, and blastomas.

Composition

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

The compounds of the present invention, if desired, can be administered to a patient either orally, rectally, parenterally, (for example, intravenously, intramuscularly, or subcutaneously) intracistemally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)$(OH)_2$, —P(O)(O($C_1$-$C_6$)alkyl$)_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention.

Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{18}$O, $^{31}$P, $^{32}$P, $^{35}$S, $^{18}$F, and $^{36}$Cl. In one aspect, the present invention relates to compounds wherein one or more hydrogen atom is replaced with deuterium ($^2$H) atoms.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

All patents, published patent applications and other publications recited herein are hereby incorporated by reference.

Compounds

In one aspect, the present invention relates to a compound having the general formula $(A)_k$-$L_1$, or a salt, enantiomer, stereoisomer, polymorph, or N-oxide thereof, wherein:

A is a moiety that binds to an E3 ubiquitin ligase and has the structure selected from the group consisting of Formula I, Formula II, Formula III, Formula IV, Formula V, Formula VI, Formula VII, Formula VIII, Formula IX, and Formula X;

I

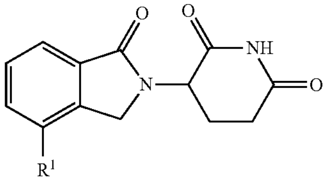

II

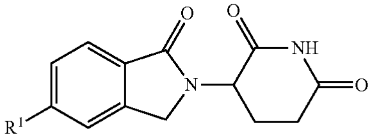

III

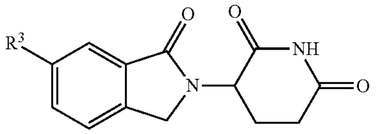

IV

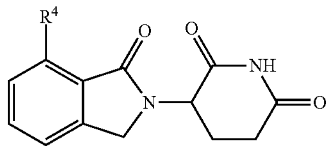

V

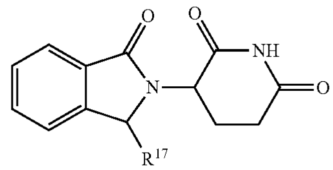

VI

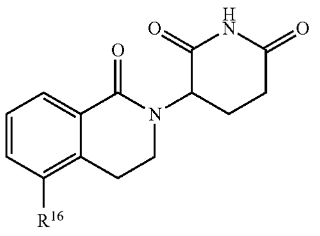

VII

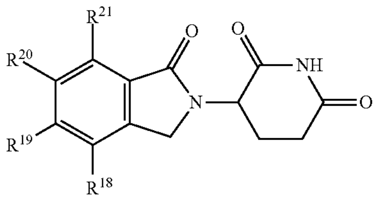

VIII

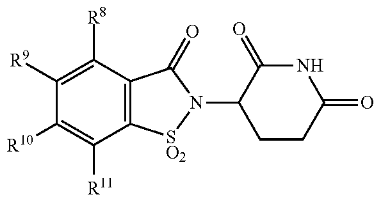

-continued

IX

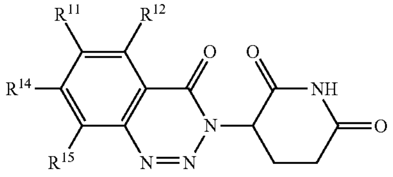

X

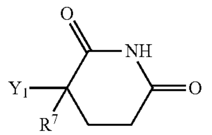

$L_1$ is a linker;

each A is covalently linked to the $L_1$ as allowed by valence;

$R^1$ is aryl, —N($R^5$)—X—$R^6$, —$SO_2R^5$, or —O$(CH_2)_m R^5$, any of which may be optionally substituted with 1 or more $R^w$ groups as allowed by valence;

$R^2$ is aryl, —NH—($C_3$-$C_{10}$) heteroaryl, or —N($R^5$)—$(CH_2)_m$—X—$(CH_2)_n$—$R^6$, any of which may be optionally substituted with 1 or more $R^w$ groups as allowed by valence;

$R^3$ is cyano, aryl, —NH—($C_3$-$C_{10}$) heteroaryl, ($C_3$-$C_{10}$) heterocyclo, or —N($R^5$)—$(CH_2)_m$—X—$(CH_2)_n$—$R^6$, any of which may be optionally substituted with 1 or more $R^w$ groups as allowed by valence;

$R^4$ is halo, cyano, aryl, $OR^5$, or —N($R^5$)—$(CH_2)_m$—X—$(CH_2)_n$—$R^6$, any of which may be optionally substituted with 1 or more $R^w$ groups as allowed by valence;

$R^5$ at each occurrence is independently H, ($C_1$-$C_3$)alkyl, ($C_3$-$C_{10}$)heterocyclo, ($C_3$-$C_{10}$)cycloalkyl, —$(CH_2)_n$—($C_3$-$C_{10}$) cycloalkyl, —$(CH_2)_n$—($C_3$-$C_{10}$)heterocyclo, —$(CH_2)_n$-aryl, —$(CH_2)_n$-heteroaryl, aryl, or heteroaryl, any of which may be optionally substituted with 1 or more $R^w$ groups as allowed by valence;

$R^6$ at each occurrence is independently OH, ($C_1$-$C_3$)alkyl, —($C_1$-$C_3$)alkoxy, ($C_3$-$C_{10}$)heterocyclo, ($C_3$-$C_{10}$)cycloalkyl, —$(CH_2)_n$—($C_3$-$C_{10}$) cycloalkyl, —$(CH_2)_n$—($C_3$-$C_{10}$)heterocyclo, —$(CH_2)_n$-aryl, —$(CH_2)_n$-heteroaryl, aryl, heteroaryl, or $R^5$ and $R^6$ taken together with the atoms they are attached to forming a nitrogen containing ($C_3$-$C_{10}$)heterocyclic ring, any of which may be optionally substituted with 1 or more $R^w$ groups as allowed by valence;

$R^7$ is H, ($C_1$-$C_3$)alkyl, or $R^7$ and $R^{26}$ taken together with the carbons they are attached to forming a carbon carbon double bond;

$R^8$, $R^9$, $R^{10}$, $R^{11}$ each independently is H, halo, OH, cyano, ($C_1$-$C_3$)alkyl, ($C_1$-$C_3$)alkoxy, aryl, or heteroaryl, any of which may be optionally substituted with 1 or more $R^w$ groups as allowed by valence;

$R^{12}$, $R^{13}$, $R^{14}$, $R^{15}$ each is independently H, $NH_2$, ($C_1$-$C_3$)alkyl, —N($R^5$)—$(CH_2)_m$—N($R^5$)—X—$R^6$, with proviso that no more than three substituents out of $R^1$, $R^{13}$, $R^{14}$, and $R^{15}$ are H, any of which may be optionally substituted with 1 or more $R^w$ groups as allowed by valence;

$R^{16}$ is $NH_2$ or —N($R^5$)—$(CH_2)_m$—X—$(CH_2)_n$—$R^6$, any of which may be optionally substituted with 1 or more $R^w$ groups as allowed by valence;

$R^{17}$ is cyano, heteroaryl, —$(CH_2)_m$—C(O)O—$R^6$, or —N($R^5$)—$(CH_2)_m$—X—$(CH_2)_n$—$R^6$, any of which may be optionally substituted with 1 or more $R^w$ groups as allowed by valence;

$R^{18}$, $R^{19}$, $R^{20}$, $R^{21}$ each independently is H, halo, $(C_1\text{-}C_3)$ alkyl, $(C_1\text{-}C_3)$alkoxy, or —$N(R^5)$—X—$R^6$, with the proviso that no more than two substituents of $R^{18}$, $R^{19}$, $R^{20}$, $R^{21}$ are H; or $R^{18}$, $R^{19}$ taken together with the carbons they are attached to forming a $(C_3\text{-}C_{10})$cycloalkyl or a $(C_3\text{-}C_{10})$heterocyclo, or $R^{19}$, $R^{20}$ taken together with the carbons they are attached to forming a $(C_3\text{-}C_{10})$cycloalkyl or a $(C_3\text{-}C_{10})$heterocyclo, or $R^{20}$, $R^{21}$ taken together with the carbons they are attached to forming a $(C_3\text{-}C_{10})$ cycloalkyl or a $(C_3\text{-}C_{10})$heterocyclo, any of which may be optionally substituted with 1 or more $R^w$ groups as allowed by valence;

$R^{25}$ is aryl, heteroaryl, or $(C_3\text{-}C_{10})$heterocyclo, any of which may be optionally substituted with 1 or more $R^w$ groups as allowed by valence;

$R^w$ at each occurrence is independently H, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more groups selected from the group consisting of halo, cyano, oxo$(C_3\text{-}C_{10})$heterocyclo, $(C_3\text{-}C_{10})$cycloalkyl, —$(CH_2)_n$—$(C_3\text{-}C_{10})$ cycloalkyl, —$(CH_2)_n$—$(C_3\text{-}C_{10})$heterocyclo, —$(CH_2)_n$-aryl, —$(CH_2)_n$-heteroaryl, aryl, and heteroaryl;

X is a bond, —$SO_2$—, —$(CH_2)_nC(O)(CH_2)_m$—, —C(O)NH—, —C(O)N($R^w$)—, —NHC(O)NH—, or —$(CH_2)_n$—;

$Y_1$ is —$NHR^{25}$, —$NHC(O)R^{25}$, or —$CHR^{25}R^{26}$;

m is 0, 1, 2, 3, or 4;

k is 1, 2, 3, 4, 5, 6, 7, 8, 9, or 10;

n is 0, 1, 2, 3, or 4.

In an embodiment, $L_1$ is -$L_b$-$(L_a)_t$-H; wherein $L_a$ at each occurrence is independently selected from the group consisting of a bond, $CR^5R^6$, $C(R^5R^6)O$, $C(R^5R^6)C(R^5R^6)O$, $SO_2$, $NR^5$, $C(R^5R^6)$ $NR^5$, $SO_2NR^5$, $SONR^5$, $CONR^5$, $NR^5CONR^6$, $NR^5SO_2NR^6$, CO, $CR^5$═$CR^6$, C≡C, $SiR^5R^6$, $P(O)R^5$, $P(O)OR^5$, $NR^5C$(═NCN)$NR^6$, $NR^5C$(═NCN), and $NR^5C(═CNO_2)NR^6$, any of which may be optionally substituted with 1 or more $R^w$ groups as allowed by valence;

H is hydrogen.

$L_b$ is selected from the group consisting of:

a bond,

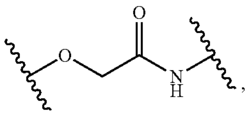,
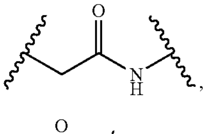,

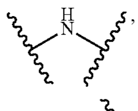,
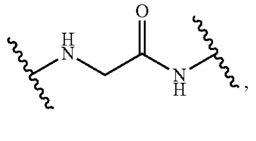,

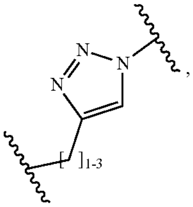,
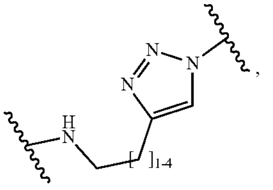,

-continued

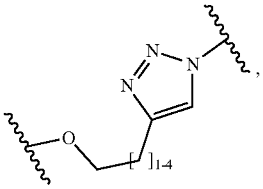,
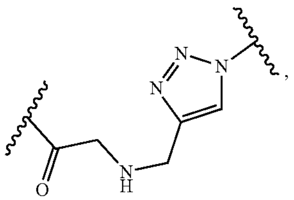,

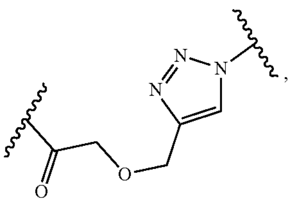,
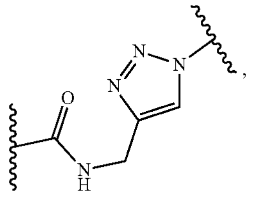,

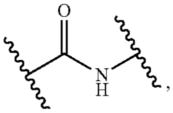,
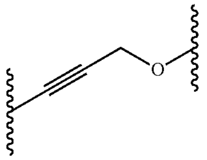 and

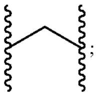;

t is 0, 1, 2, 3, 4, 5, 6, 7, 8, 9, 10, 11, 12, 13, 14, 15, 16, 17, 18, 19, or 20.

In an embodiment, moiety A is selected from the compounds listed in Table 6 in Example 6.

In one aspect, the present invention relates to a compound of the general formula $(A)_k$-L-Q, or a salt, enantiomer, stereoisomer, polymorph, or N-oxide thereof, wherein:

A is a compound that binds to an E3 ubiquitin ligase and has the structure selected from the group consisting of Formula I, Formula II, Formula III, Formula IV, Formula V, Formula VI, Formula VII, Formula VIII, Formula IX, and Formula X;

I

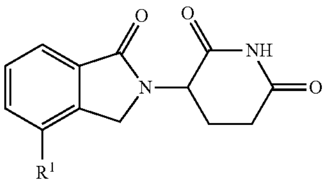

II

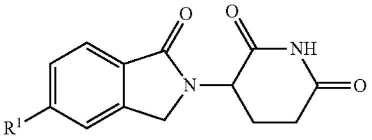

III

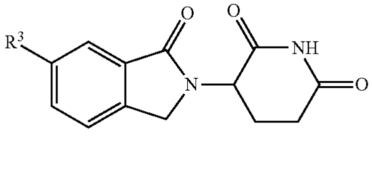

-continued

IV
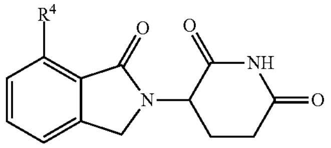

V
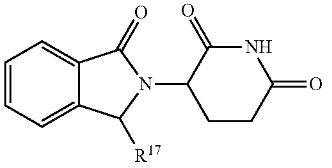

VI
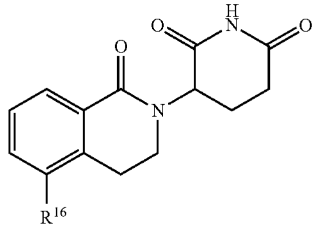

VII
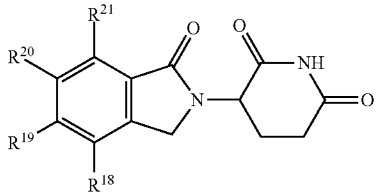

VIII
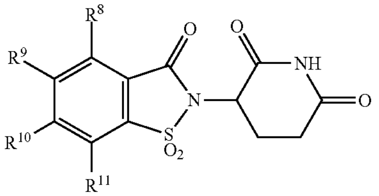

IX
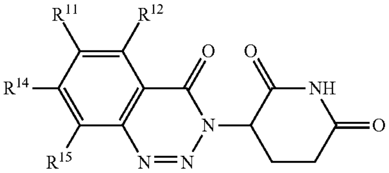

X
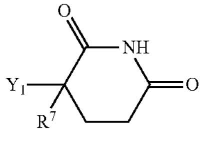

Q is a moiety that binds to a target protein which is sequestered to the E3 ubiquitin ligase and/or degraded upon interaction with the E3 ubiquitin ligase;

L is a linker;

each A is covalently linked to the L as allowed by valence;

$R^1$ is aryl, —N($R^5$)—X—$R^6$, —$SO_2R^5$, or —O$(CH_2)_m R^5$, any of which may be optionally substituted with 1 or more $R^w$ groups as allowed by valence;

$R^2$ is aryl, —NH—($C_3$-$C_{10}$) heteroaryl, or —N($R^5$)—$(CH_2)_m$—X—$(CH_2)_n$—$R^6$, any of which may be optionally substituted with 1 or more $R^w$ groups as allowed by valence;

$R^3$ is cyano, aryl, —NH—($C_3$-$C_{10}$) heteroaryl, ($C_3$-$C_{10}$) heterocyclo, or —N($R^5$)—$(CH_2)_m$—X—$(CH_2)_n$—$R^6$, any of which may be optionally substituted with 1 or more $R^w$ groups as allowed by valence;

$R^4$ is halo, cyano, aryl, $OR^5$, or —N($R^5$)—$(CH_2)_m$—X—$(CH_2)_n$—$R^6$, any of which may be optionally substituted with 1 or more $R^w$ groups as allowed by valence;

$R^5$ at each occurrence is independently H, ($C_1$-$C_3$)alkyl, ($C_3$-$C_{10}$)heterocyclo, ($C_3$-$C_{10}$)cycloalkyl, —$(CH_2)_n$—($C_3$-$C_{10}$) cycloalkyl, —$(CH_2)_n$—($C_3$-$C_{10}$)heterocyclo, —$(CH_2)_n$-aryl, —$(CH_2)_n$-heteroaryl, aryl, or heteroaryl, any of which may be optionally substituted with 1 or more $R^w$ groups as allowed by valence;

$R^6$ at each occurrence is independently OH, ($C_1$-$C_3$)alkyl, —($C_1$-$C_3$)alkoxy, ($C_3$-$C_{10}$)heterocyclo, ($C_3$-$C_{10}$)cycloalkyl, —$(CH_2)_n$—($C_3$-$C_{10}$) cycloalkyl, —$(CH_2)_n$—($C_3$-$C_{10}$)heterocyclo, —$(CH_2)_n$-aryl, —$(CH_2)_n$-heteroaryl, aryl, heteroaryl, or $R^5$ and $R^6$ taken together with the atoms they are attached to forming a nitrogen containing ($C_3$-$C_{10}$)heterocyclic ring, any of which may be optionally substituted with 1 or more $R^w$ groups as allowed by valence;

$R^7$ is H, ($C_1$-$C_3$)alkyl, or $R^7$ and $R^{26}$ taken together with the carbons they are attached to forming a carbon carbon double bond;

$R^8$, $R^9$, $R^{10}$, $R^{11}$ each independently is H, halo, OH, cyano, ($C_1$-$C_3$)alkyl, ($C_1$-$C_3$)alkoxy, aryl, or heteroaryl, any of which may be optionally substituted with 1 or more $R^w$ groups as allowed by valence;

$R^{12}$, $R^{13}$, $R^{14}$, $R^{15}$ each is independently H, $NH_2$, ($C_1$-$C_3$)alkyl, —N($R^5$)—$(CH_2)_m$—N($R^5$)—X—$R^6$, with proviso that no more than three substituents out of $R^1$, $R^{13}$, $R^{14}$, and $R^{15}$ are H, any of which may be optionally substituted with 1 or more $R^w$ groups as allowed by valence;

$R^{16}$ is $NH_2$ or —N($R^5$)—$(CH_2)_m$—X—$(CH_2)_n$—$R^6$, any of which may be optionally substituted with 1 or more $R^w$ groups as allowed by valence;

$R^{17}$ is cyano, heteroaryl, —$(CH_2)_m$—C(O)O—$R^6$, or —N($R^5$)—$(CH_2)_m$—X—$(CH_2)_n$—$R^6$, any of which may be optionally substituted with 1 or more $R^w$ groups as allowed by valence;

$R^{18}$, $R^{19}$, $R^{20}$, $R^{21}$ each independently is H, halo, ($C_1$-$C_3$) alkyl, ($C_1$-$C_3$)alkoxy, or —N($R^5$)—X—$R^6$, with the proviso that no more than two substituents of $R^{18}$, $R^{19}$, $R^{20}$, $R^{21}$ are H; or $R^{18}$, $R^{19}$ taken together with the carbons they are attached to forming a ($C_3$-$C_{10}$)cycloalkyl or a ($C_3$-$C_{10}$)heterocyclo, or $R^{19}$, $R^{20}$ taken together with the carbons they are attached to forming a ($C_3$-$C_{10}$)cycloalkyl or a ($C_3$-$C_{10}$)heterocyclo, or $R^{20}$, $R^{21}$ taken together with the carbons they are attached to forming a ($C_3$-$C_{10}$) cycloalkyl or a ($C_3$-$C_{10}$)heterocyclo, any of which may be optionally substituted with 1 or more $R^w$ groups as allowed by valence;

$R^{25}$ is aryl, heteroaryl, or ($C_3$-$C_{10}$)heterocyclo, any of which may be optionally substituted with 1 or more $R^w$ groups as allowed by valence;

$R^w$ at each occurrence is independently H, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more groups selected from the group consisting of halo, cyano, oxo$(C_3-C_{10})$heterocyclo, $(C_3-C_{10})$cycloalkyl, $-(CH_2)_n-(C_3-C_{10})$ cycloalkyl, $-(CH_2)_n-(C_3-C_{10})$heterocyclo, $-(CH_2)_n$-aryl, $-(CH_2)_n$-heteroaryl, aryl, and heteroaryl;

X is a bond, $-SO_2-$, $-(CH_2)_nC(O)(CH_2)_m-$, $-C(O)NH-$, $-C(O)N(R^w)-$, $-NHC(O)NH-$, or $-(CH_2)_n-$;

$Y_1$ is $-NHR^{25}$, $-NHC(O)R^{21}$, or $-CHR^{25}R^{26}$;

m is 0, 1, 2, 3, or 4;

k is 1, 2, 3, 4, 5, 6, 7, 8, 9, or 10;

n is 0, 1, 2, 3, or 4.

In an embodiment, L is $-L_b-(L_a)_t-$; wherein $L_a$ at each occurrence is independently selected from the group consisting of a bond, $CR^5R^6$, $C(R^5R^6)O$, $C(R^5R^6)C(R^5R^6)O$, $SO_2$, $NR^5$, $C(R^5R^6)$ $NR^5$, $SO_2NR^5$, $SONR^5$, $CONR^5$, $NR^5CONR^6$, $NR^5SO_2NR^6$, CO, $CR^5{=}CR^6$, C≡C, $SiR^5R^6$, $P(O)R^5$, $P(O)OR^5$, $NR^5C({=}NCN)NR^6$, $NR^5C({=}NCN)$, and $NR^5C({=}CNO_2)NR^6$, any of which may be optionally substituted with 1 or more $R^w$ groups as allowed by valence;

$L_b$ is selected from the group consisting of:

a bond,

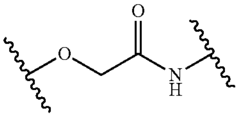, 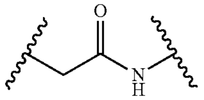,

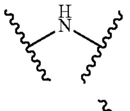, 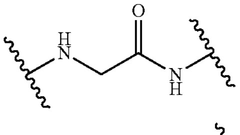,

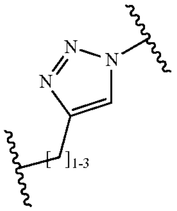, 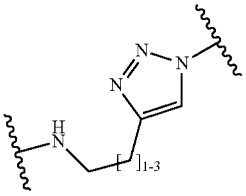,

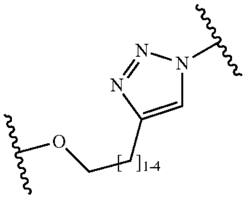, 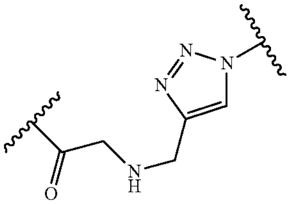,

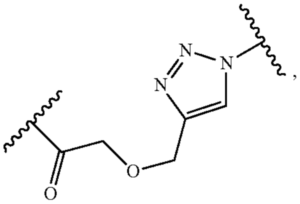, 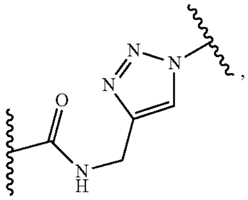,

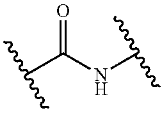, 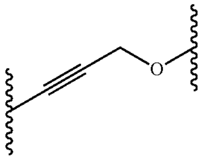 and 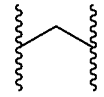;

t is 0, 1, 2, 3, 4, 5, 6, 7, 8, 9, 10, 11, 12, 13, 14, 15, 16, 17, 18, 19, or 20.

In an embodiment, L is $-(CH_2CH_2)_t-$, $-(CH_2O)_t-$ or $-(CH_2CH_2O)_t-$.

In an embodiment, A is a moiety of Formula XI

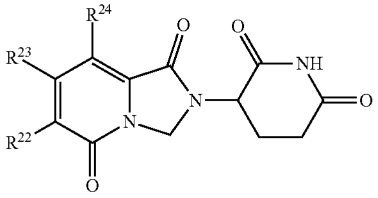

XI or a pharmaceutically acceptable salt thereof, wherein:

$R^{22}$ is H, halo, OH, $-NR^5R^5$, $(C_1-C_3)$alkyl, $(C_1-C_3)$alkoxy, (hydroxy)$(C_1-C_3)$alkyl, cyano, $-N(R^5)-X-R^6$, $-N(R^5)-(CH_2)_m-N(R^5)-X-R^6$, aryl, or heteroaryl, any of which may be optionally substituted with 1 or more $R^w$ groups as allowed by valence;

$R^{23}$ is H, halo, OH, $-NR^5R^5$, $-(CH_2)_n-NR^5R^5$, $(C_1-C_3)$alkyl, $(C_1-C_3)$alkoxy, $-C(O)NR^5R^6$, (hydroxy)$(C_1-C_3)$alkyl, cyano, $-N(R^5)-X-R^6$, $-N(R^5)-(CHR^5)_m-X-R^6$, $-N(R^5)-(CH_2)_m-N(R^5)-X-R^6$, aryl, heteroaryl, or $R^{22}$ and $R^{23}$ taken together with the carbons they are attached to forming a $(C_3-C_{10})$cycloalkyl ring or a $(C_3-C_{10})$heterocyclic ring, any of which may be optionally substituted with 1 or more $R^w$ groups as allowed by valence;

$R^{24}$ is H, halo, OH, $-NR^5R^5$, $-(CH_2)_n-NR^5R^5$, $(C_1-C_3)$alkyl, $(C_1-C_3)$alkoxy, (halo)$(C_1-C_3)$alkyl, (hydroxy)$(C_1-C_3)$alkyl, cyano, $-NO_2$, $-N(R^5)-X-R^6$, $-N(R^5)-(CH_2)_m-N(R^5)-X-R^6$, aryl, heteroaryl, or $R^{23}$ and $R^{24}$ taken together with the carbons they are attached to forming a $(C_3-C_{10})$cycloalkyl ring or a $(C_3-C_{10})$heterocyclic ring, any of which may be optionally substituted with 1 or more $R^w$ groups as allowed by valence;

$R^5$ at each occurrence is independently H, $(C_1-C_3)$alkyl, $(C_3-C_{10})$heterocyclo, $(C_3-C_{10})$cycloalkyl, $-(CH_2)_n-(C_3-C_{10})$ cycloalkyl, $-(CH_2)_n-(C_3-C_{10})$heterocyclo, $-(CH_2)_n$-aryl, $-(CH_2)_n$-heteroaryl, aryl, or heteroaryl, any of which may be optionally substituted with 1 or more $R^w$ groups as allowed by valence;

$R^6$ at each occurrence is independently OH, $(C_1-C_3)$alkyl, $-(C_1-C_3)$alkoxy, $(C_3-C_{10})$heterocyclo, $(C_3-C_{10})$cycloalkyl, $-(CH_2)_n-(C_3-C_{10})$ cycloalkyl, $-(CH_2)_n-(C_3-C_{10})$heterocyclo, $-(CH_2)_n$-aryl, $-(CH_2)_n$-heteroaryl, aryl, heteroaryl, or $R^5$ and $R^6$ taken together with the atoms they are attached to forming a nitrogen containing $(C_3-C_{10})$heterocyclic ring, any of which may be optionally substituted with 1 or more $R^w$ groups as allowed by valence;

$R^w$ at each occurrence is independently H, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more groups selected from the group consisting of halo, cyano, oxo$(C_3-C_{10})$heterocyclo, $(C_3-C_{10})$cycloalkyl, $-(CH_2)_n-(C_3-C_{10})$ cycloalkyl, $-(CH_2)_n-(C_3-C_{10})$heterocyclo, $-(CH_2)_n$-aryl, $-(CH_2)_n$-heteroaryl, aryl, and heteroaryl;

X is a bond, $—SO_2—$, $—(CH_2)_nC(O)(CH_2)_m—$, —C(O)NH—, $—C(O)N(R^w)—$, —NHC(O)NH—, or $—(CH_2)_n—$;

m is 0, 1, 2, 3, or 4;

n is 0, 1, 2, 3, or 4.

In an embodiment, $R^{22}$ is H; $R^{23}$ is H; $R^{24}$ is halo.

In an embodiment, A is a moiety of Formula XII, XIII, XIV, XV, XVI, XVII, or XVIII,

XII

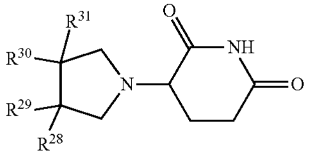

XIII

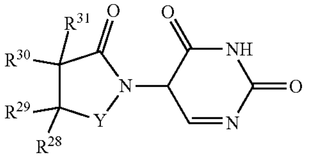

XIV

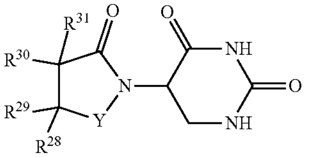

XV

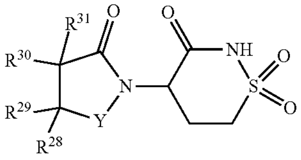

XVI

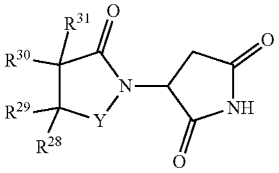

XVII

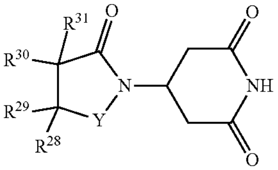

XVIII

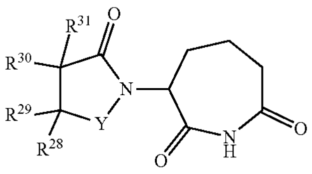

or a pharmaceutically acceptable salt thereof, wherein:

$R^{28}$, $R^{29}$, $R^{30}$, $R^{31}$ is independently H, halo, OH, $—NR^5R^5$, $—(CH_2)_n—NR^5R^5$, $(C_1\text{-}C_3)$alkyl, $(C_1\text{-}C_3)$alkoxy, (halo)$(C_1\text{-}C_3)$alkyl, (hydroxy)$(C_1\text{-}C_3)$alkyl, cyano, $—NO_2$, $—N(R^5)—X—R^6$, $—N(R^5)—(CH_2)_m—N(R^5)—X—R^6$, aryl, heteroaryl, or $R^{28}$, $R^{29}$ taken together with the carbons to which they are attached to form a $(C_3\text{-}C_{10})$cycloalkyl or a $(C_3\text{-}C_{10})$heterocyclo, or $R^{30}$, $R^{31}$ taken together with the carbons to which they are attached to form a $(C_3\text{-}C_{10})$cycloalkyl or a $(C_3\text{-}C_{10})$heterocyclo, or $R^{29}$, $R^{30}$ taken together to form a bond, or $R^{29}$, $R^{30}$ taken together with the carbons to which they are attached to form a $(C_3\text{-}C_{10})$cycloalkyl or a $(C_3\text{-}C_{10})$heterocyclo or an aryl or a heteroaryl, any of which may be optionally substituted with 1 or more $R^w$ groups as allowed by valence;

$R^5$ at each occurrence is independently H, $(C_1\text{-}C_3)$alkyl, $(C_3\text{-}C_{10})$heterocyclo, $(C_3\text{-}C_{10})$cycloalkyl, $—(CH_2)_n—(C_3\text{-}C_{10})$cycloalkyl, $—(CH_2)_n—(C_3\text{-}C_{10})$heterocyclo, $—(CH_2)_n$-aryl, $—(CH_2)_n$-heteroaryl, aryl, or heteroaryl, any of which may be optionally substituted with 1 or more $R^w$ groups as allowed by valence;

$R^6$ at each occurrence is independently OH, $(C_1\text{-}C_3)$alkyl, $—(C_1\text{-}C_3)$alkoxy, $(C_3\text{-}C_{10})$heterocyclo, $(C_3\text{-}C_{10})$cycloalkyl, $—(CH_2)_n—(C_3\text{-}C_{10})$ cycloalkyl, $—(CH_2)_n—(C_3\text{-}C_{10})$heterocyclo, $—(CH_2)_n$-aryl, $—(CH_2)_n$-heteroaryl, aryl, heteroaryl, or $R^5$ and $R^6$ taken together with the atoms they are attached to forming a nitrogen containing $(C_3\text{-}C_{10})$heterocyclic ring, any of which may be optionally substituted with 1 or more $R^w$ groups as allowed by valence;

$R^w$ at each occurrence is independently H, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more groups selected from the group consisting of halo, cyano, oxo$(C_3\text{-}C_{10})$heterocyclo, $(C_3\text{-}C_{10})$cycloalkyl, $—(CH_2)_n—(C_3\text{-}C_{10})$ cycloalkyl, $—(CH_2)_n—(C_3\text{-}C_{10})$heterocyclo, $—(CH_2)_n$-aryl, $—(CH_2)_n$-heteroaryl, aryl, and heteroaryl;

X is a bond, $—SO_2—$, $—(CH_2)_nC(O)(CH_2)_m—$, —C(O)NH—, $—C(O)N(R^w)—$, —NHC(O)NH—, or $—(CH_2)_n—$;

m is 0, 1, 2, 3, or 4;

n is 0, 1, 2, 3, or 4.

Linker $L_1$ and L

The linker $L_1$ and L each is independently covalently bound to the E3 ubiquitin ligase binding moiety A. The linker L is also independently covalently bound to the target protein binding moiety Q. The covalent bond of linking is preferably through an amide, ester, thioester, keto group, carbamate (urethane), carbon or ether, each of which groups may be inserted anywhere on A moiety or Q moiety as allowed by valence, including any substituent or functional group in A moiety or Q moiety. In certain preferred aspects, the linker may be optionally substituted with $(C_1\text{-}C_6)$alkyl, $(C_1\text{-}C_6)$alkylene, $(C_1\text{-}C_6)$ alkyne, aryl, heteroaryl, $(C_3\text{-}C_8)$cycloalkyl, or $(C_3\text{-}C_8)$heterocyclo. In an embodiment, the linker $L_1$ or L is linked to A moiety via $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, or $R^{31}$, as defined above.

In an embodiment, $L_1$ is $\text{-}L_b\text{-}(L_a)_t\text{-}H$, wherein H is hydrogen.

In an embodiment, L is $\text{-}L_b\text{-}(L_a)_t\text{-}$.

In an embodiment, t is 0, 1, 2, 3, 4, 5, 6, 7, 8, 9, 10, 11, 12, 13, 14, 15, 16, 17, 18, 19, or 20.

In an embodiment, $L_a$ is selected from the group consisting of
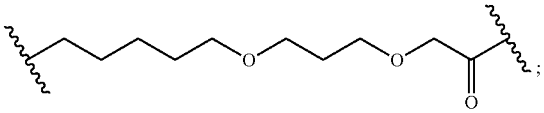
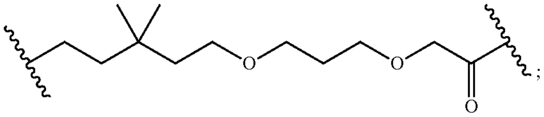
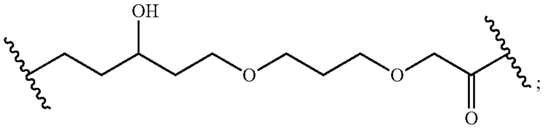
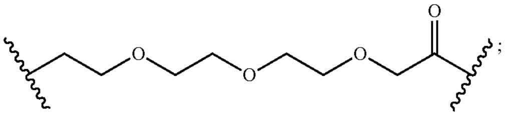
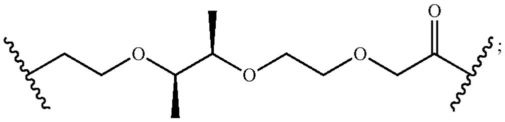
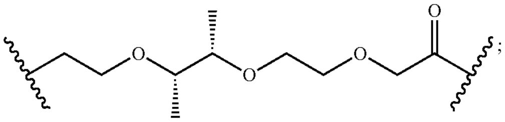
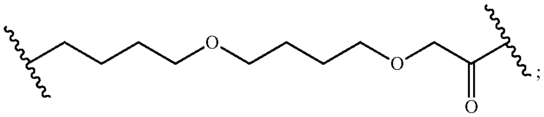
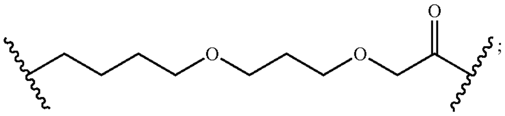
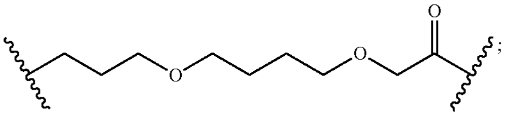
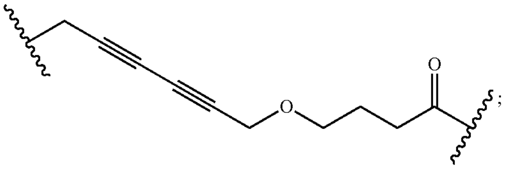
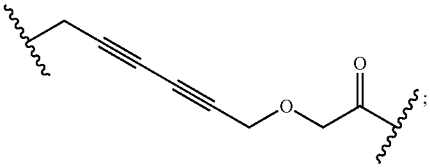
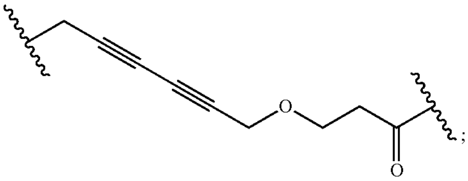
-continued
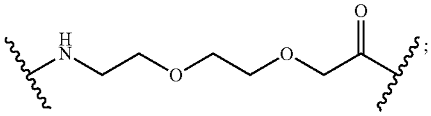
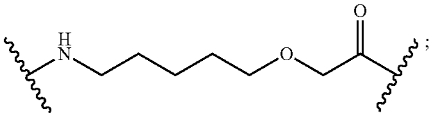
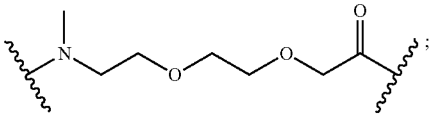
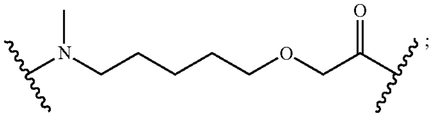
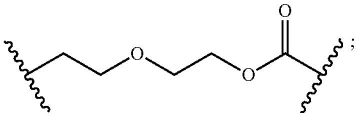
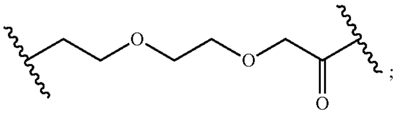
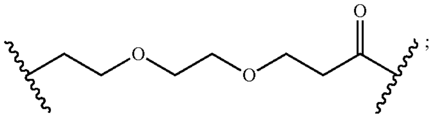
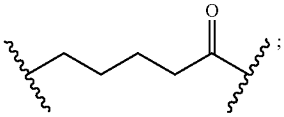
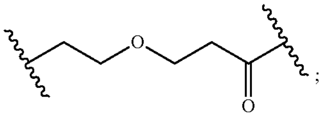
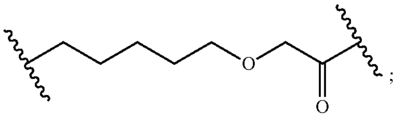
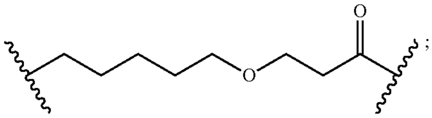
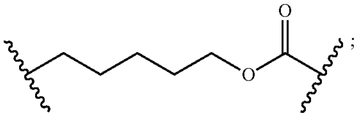
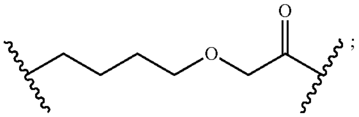
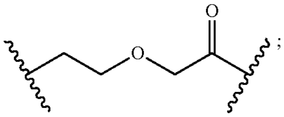

-continued
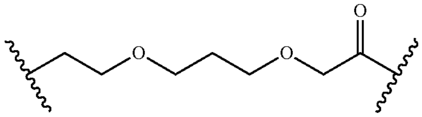
;
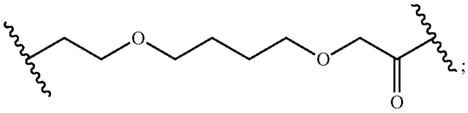
;
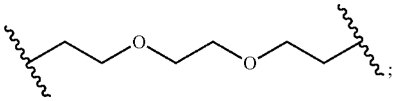
;
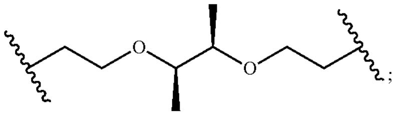
;
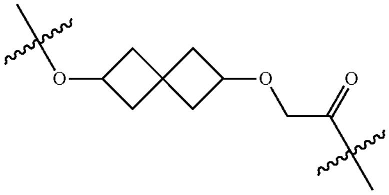
;
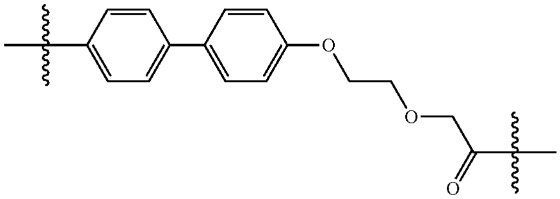
;
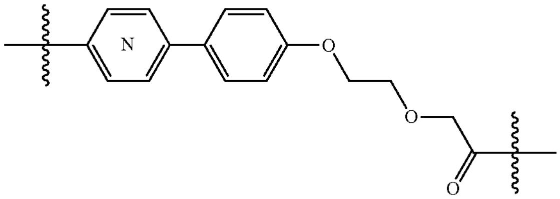
;
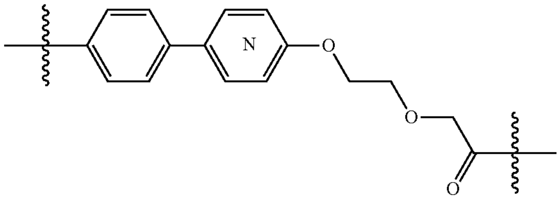
;
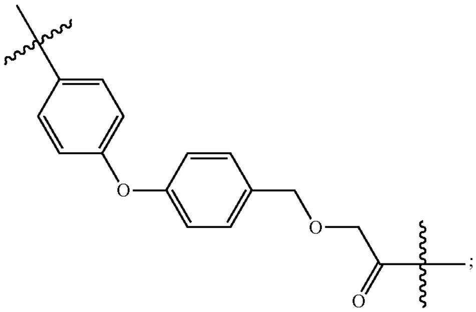
; and
-continued
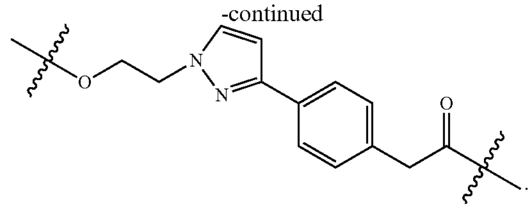
.
$L_b$ is selected from the group consisting of:
a bond,
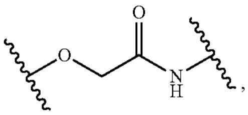
,
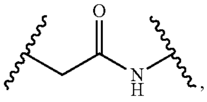
,
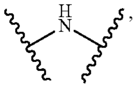
,
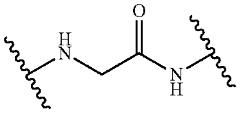
,
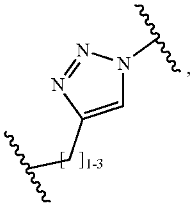
,
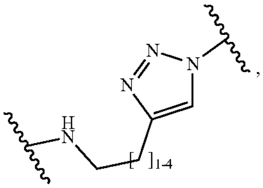
,
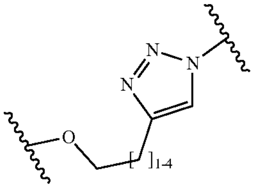
,
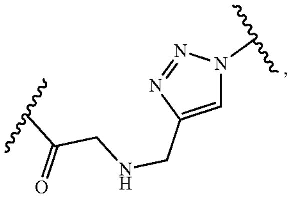
,
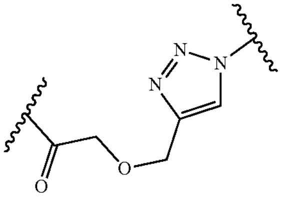
,
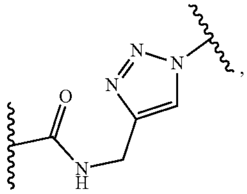
,
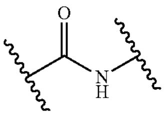
,
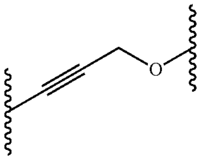
and
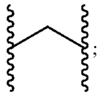
;
t is 0, 1, 2, 3, 4, 5, 6, 7, 8, 9, 10, 11, 12, 13, 14, 15, 16, 17, 18, 19, or 20.
Embodiments of A-$L_1$
In an embodiment, the compound having general formula A-$L_1$ is selected from the compounds listed in Table 1.

TABLE 1
| Embodiments of general formula A-$L_1$ |
| --- |
| 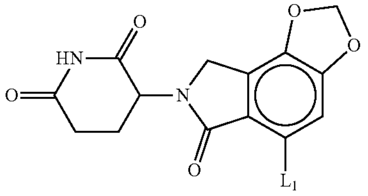 |
| 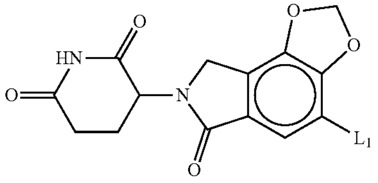 |
| 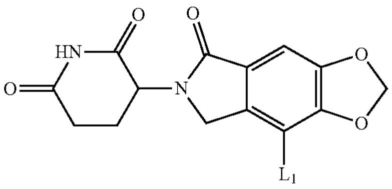 |
| 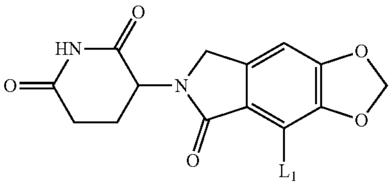 |
| 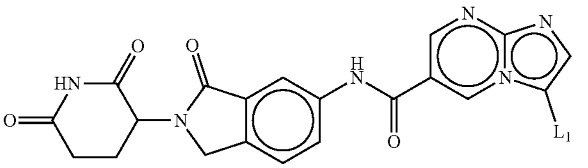 |
| 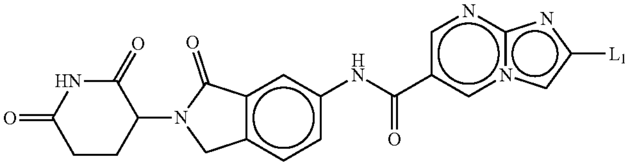 |
| 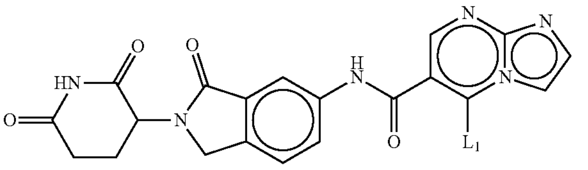 |
| 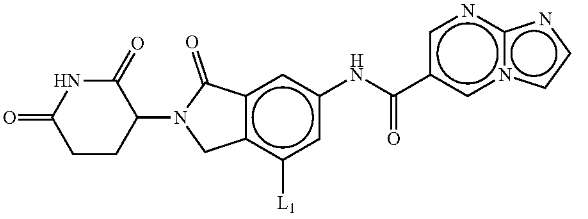 |

TABLE 1-continued
| Embodiments of general formula A-$L_1$ |
| --- |
| 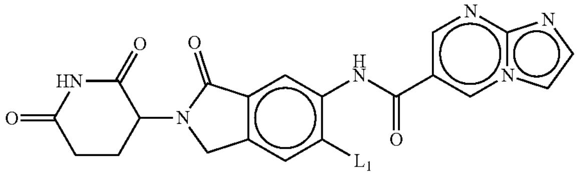 |
| 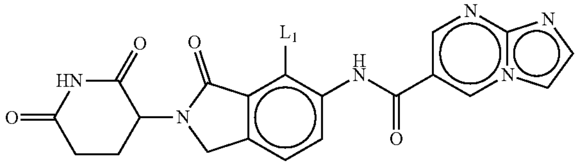 |
| 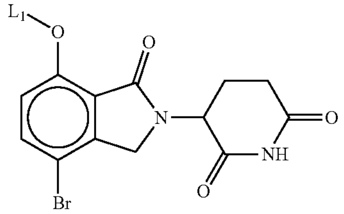 |
| 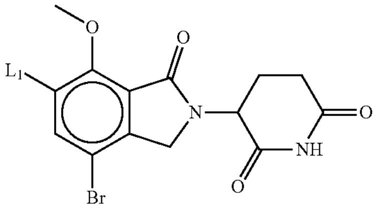 |
| 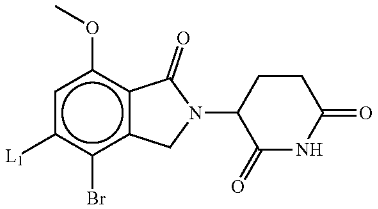 |
| 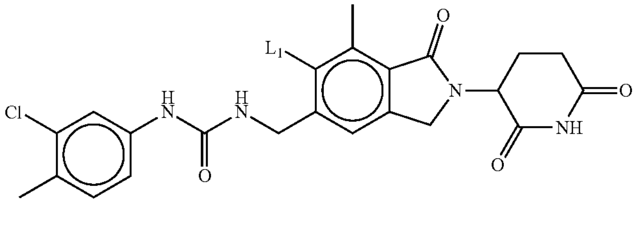 |
| 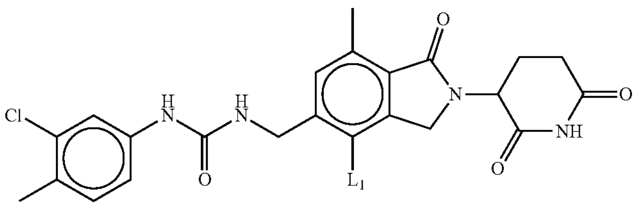 |

TABLE 1-continued
| Embodiments of general formula A-$L_1$ |
| --- |
| 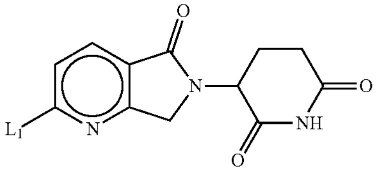 |
| 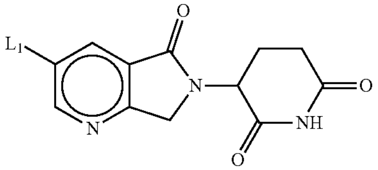 |
| 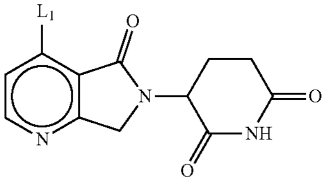 |
| 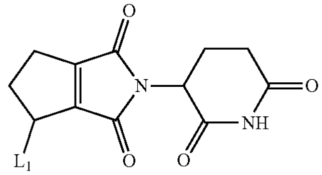 |
| 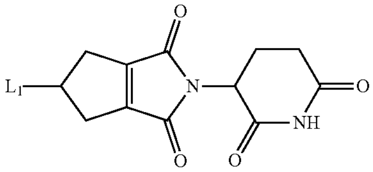 |
| 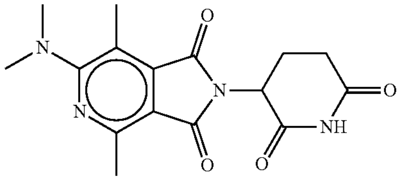 |
| 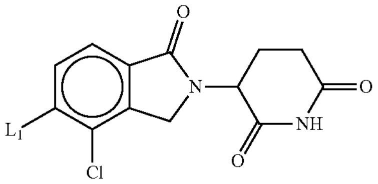 |
| 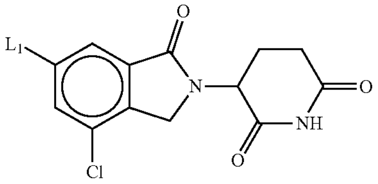 |

TABLE 1-continued
| Embodiments of general formula A-$L_1$ |
| --- |
| 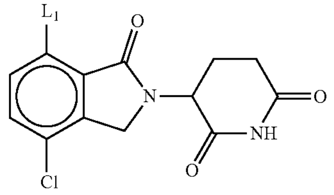 |
| 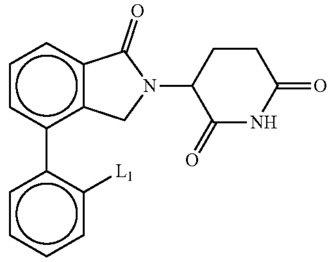 |
| 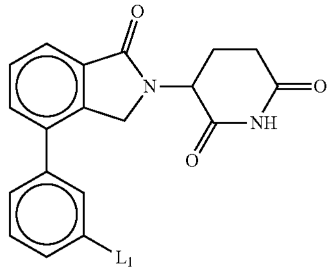 |
| 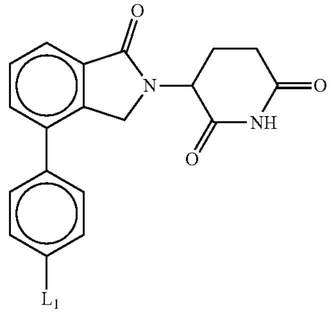 |
| 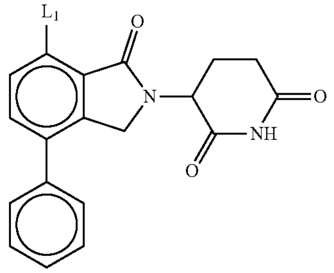 |
| 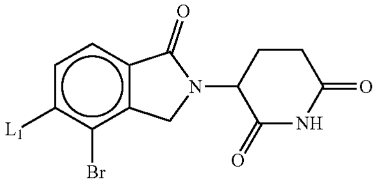 |

TABLE 1-continued
| Embodiments of general formula A-$L_1$ |
| --- |
| 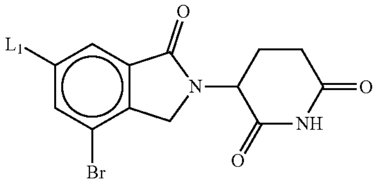 |
| 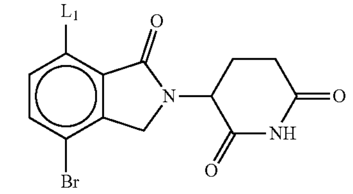 |
| 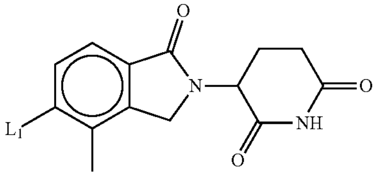 |
| 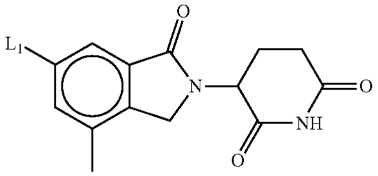 |
| 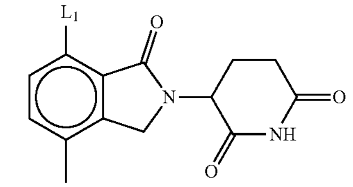 |
| 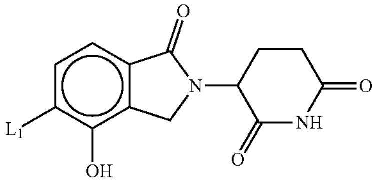 |
| 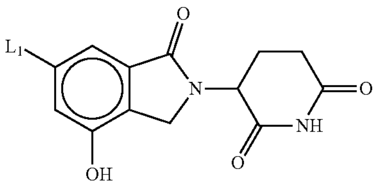 |
| 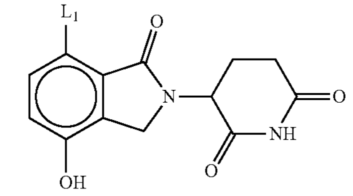 |

TABLE 1-continued
| Embodiments of general formula A-$L_1$ |
| --- |
| 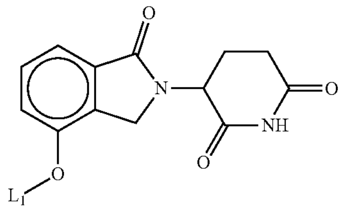 |
| 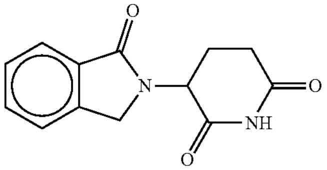 |
| 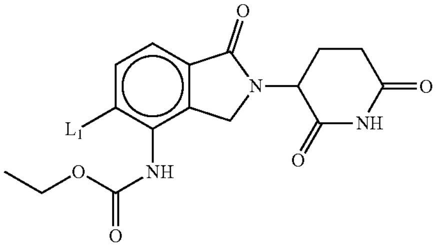 |
| 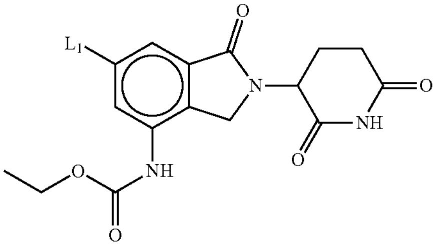 |
| 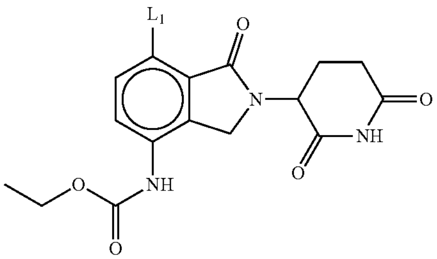 |

TABLE 1-continued
| Embodiments of general formula A-$L_1$ |
|---|
| 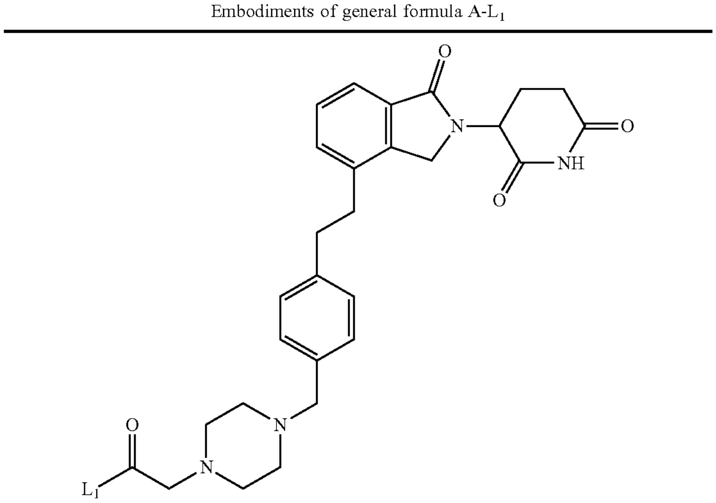 |
| 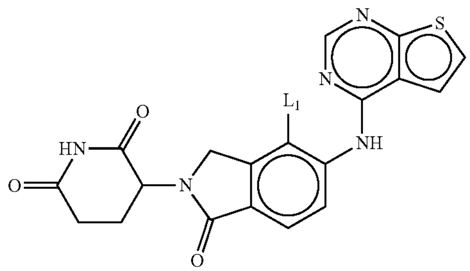 |
| 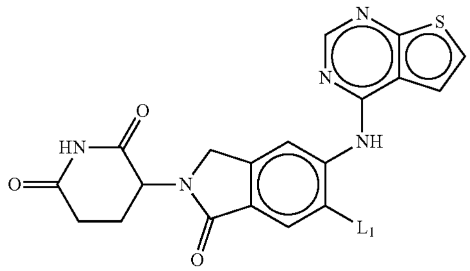 |
| 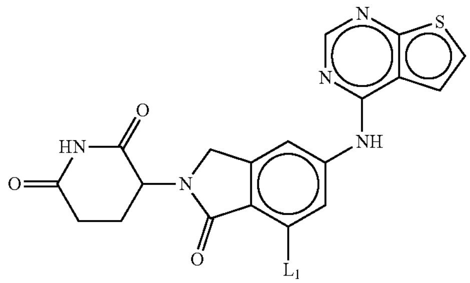 |
| 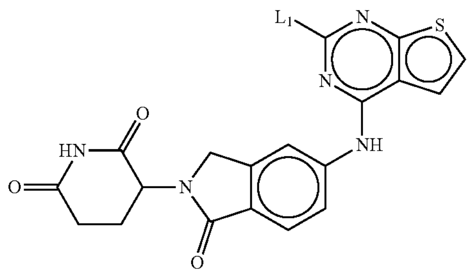 |

TABLE 1-continued
| Embodiments of general formula A-$L_1$ |
|---|
| 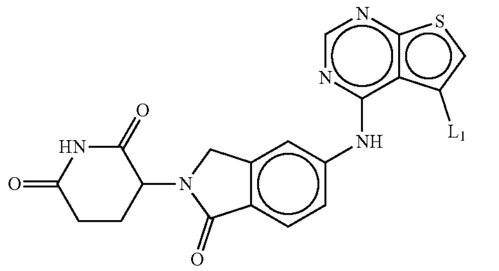 |
| 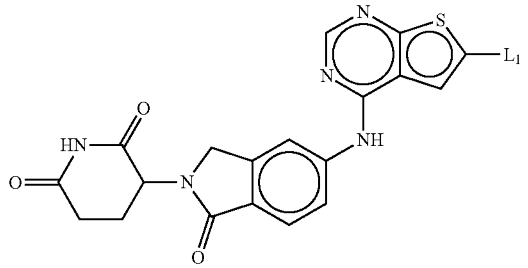 |
| 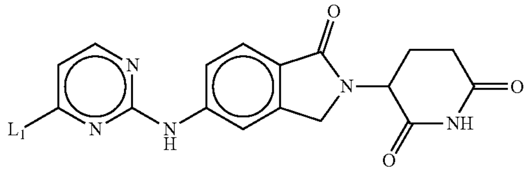 |
| 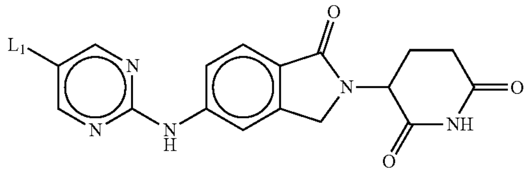 |
| 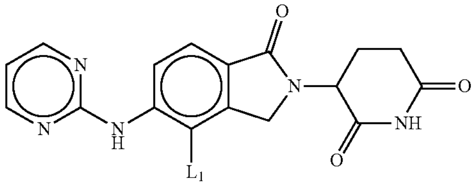 |
| 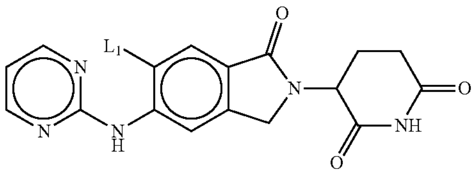 |
| 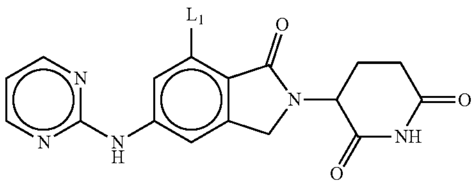 |

TABLE 1-continued
| Embodiments of general formula A-$L_1$ |
| --- |
| 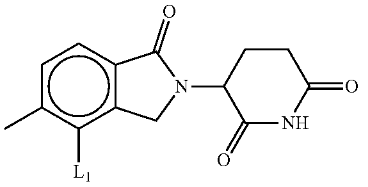 |
| 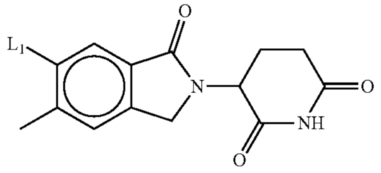 |
| 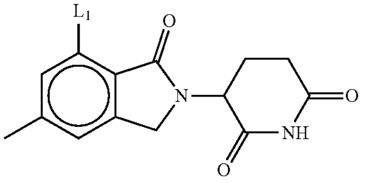 |
| 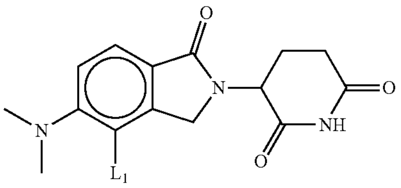 |
| 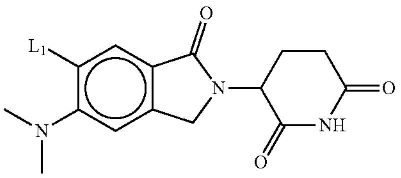 |
| 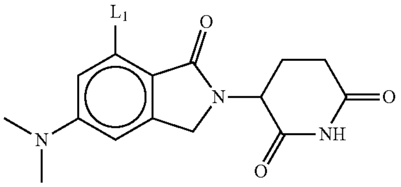 |
| 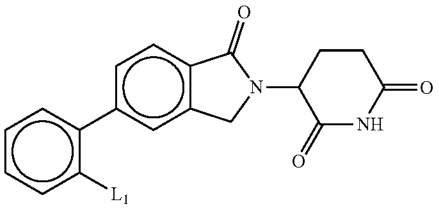 |
| 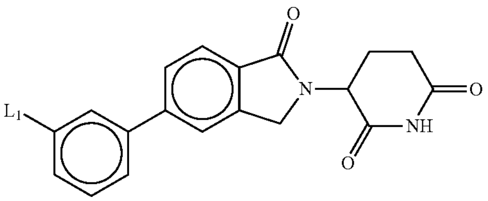 |

TABLE 1-continued
| Embodiments of general formula A-$L_1$ |
| --- |
| 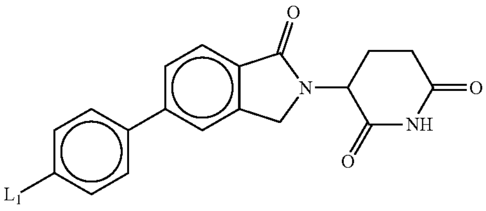 |
| 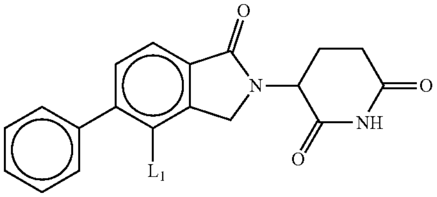 |
| 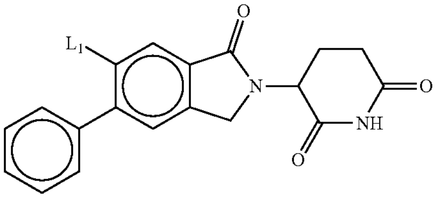 |
| 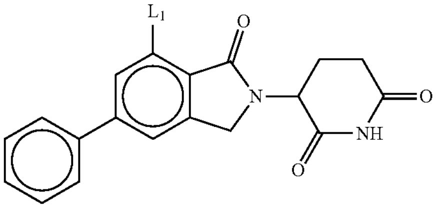 |
| 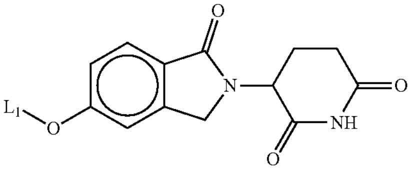 |
| 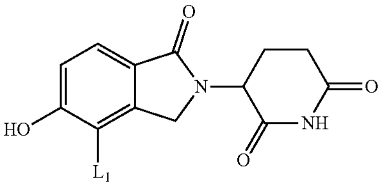 |
| 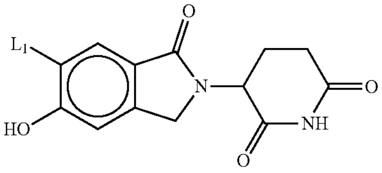 |
| 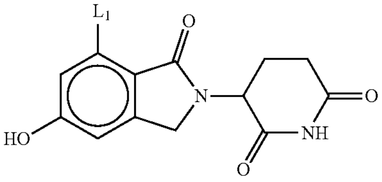 |

TABLE 1-continued
| Embodiments of general formula A-$L_1$ |
|---|
| 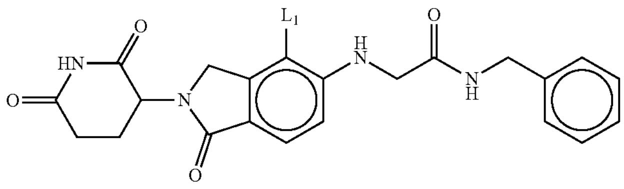 |
| 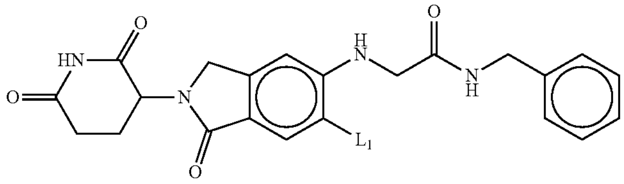 |
| 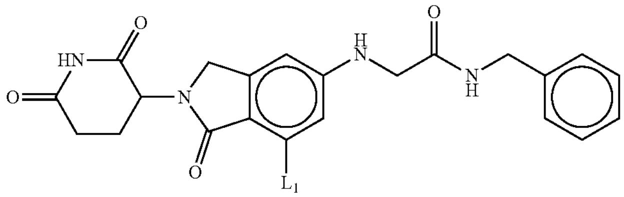 |
| 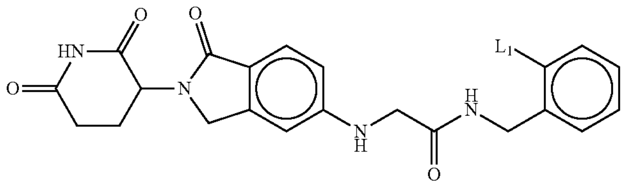 |
| 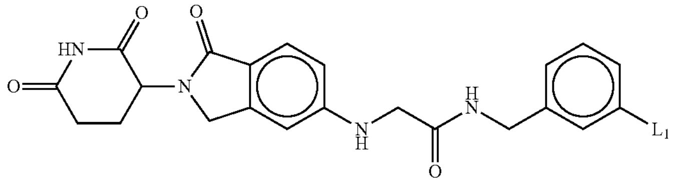 |
| 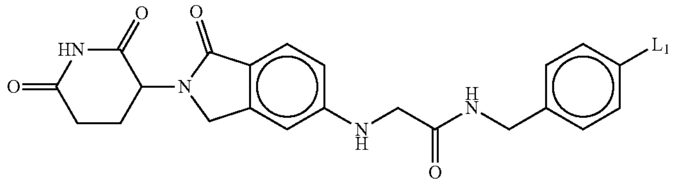 |
| 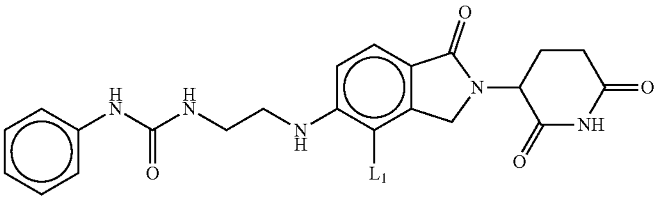 |
| 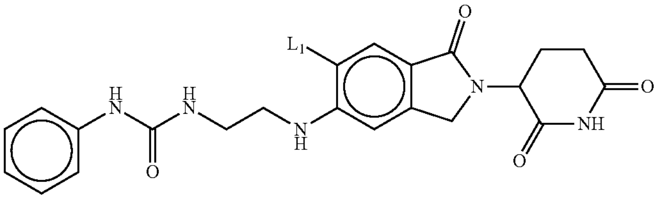 |

TABLE 1-continued
| Embodiments of general formula A-$L_1$ |
| --- |
| 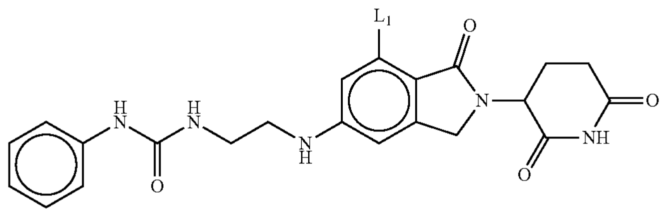 |
| 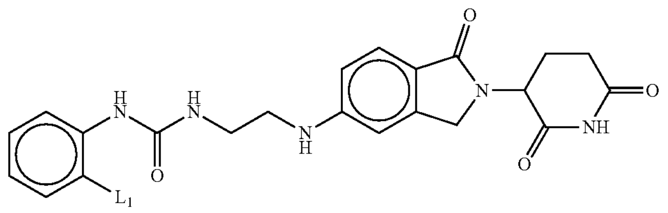 |
| 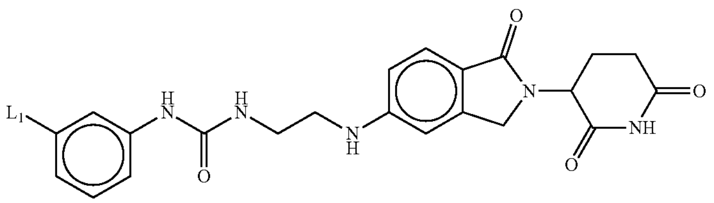 |
| 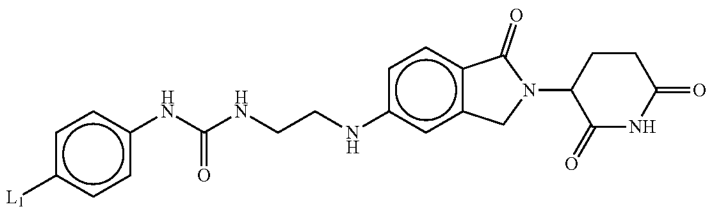 |
| 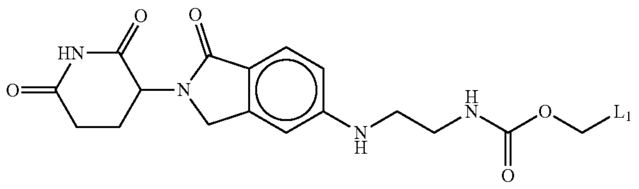 |
| 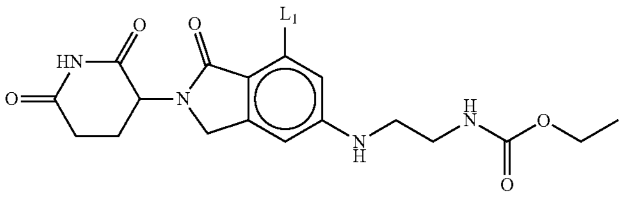 |
| 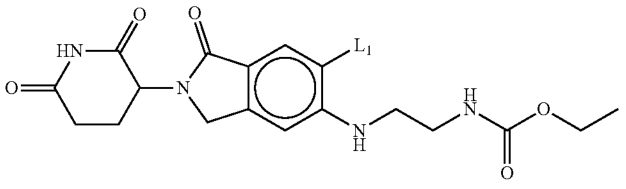 |

TABLE 1-continued
| Embodiments of general formula A-$L_1$ |
|---|
| 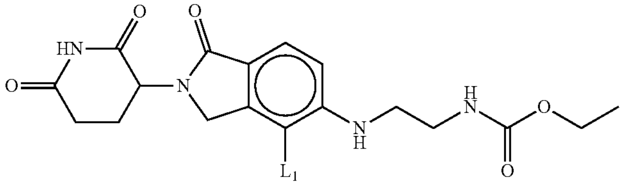 |
| 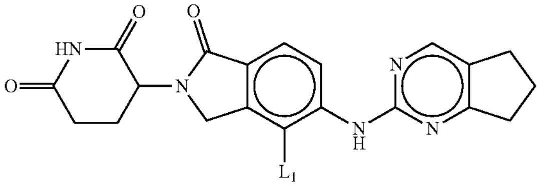 |
| 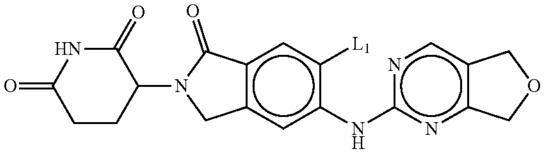 |
| 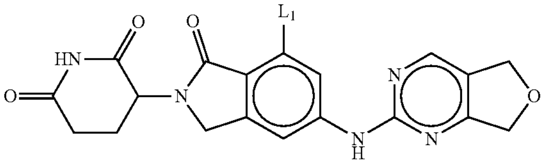 |
| 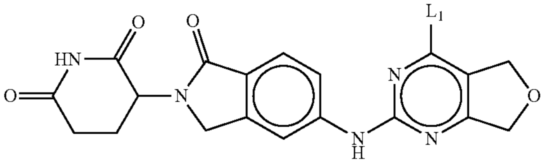 |
| 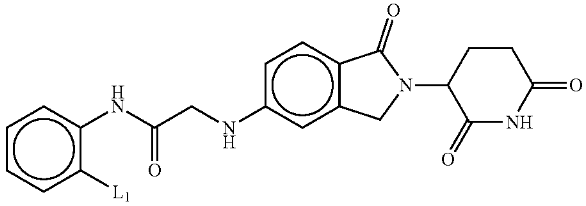 |
| 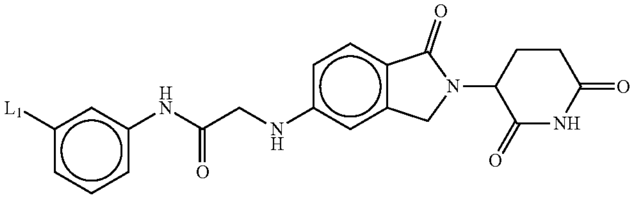 |
| 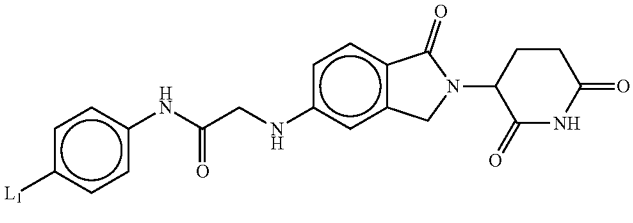 |

TABLE 1-continued
| Embodiments of general formula A-$L_1$ |
| --- |
| 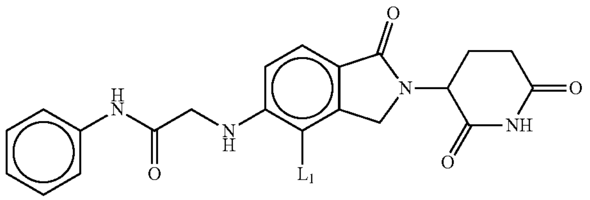 |
| 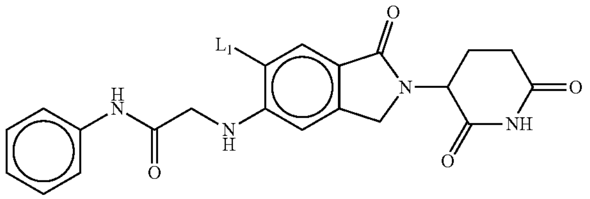 |
| 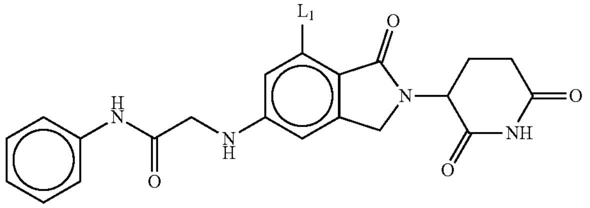 |
| 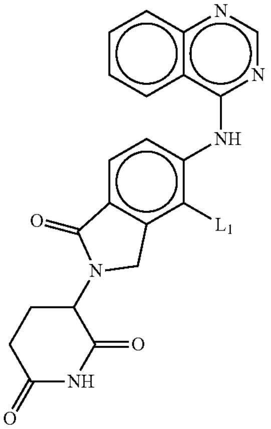 |
| 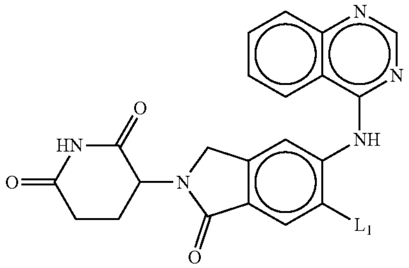 |

TABLE 1-continued
| Embodiments of general formula A-$L_1$ |
| --- |
| 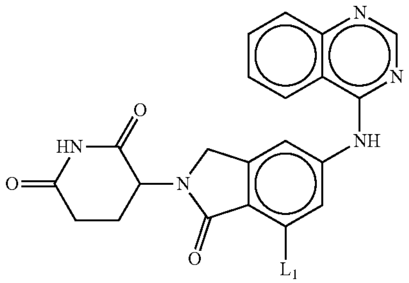 |
| 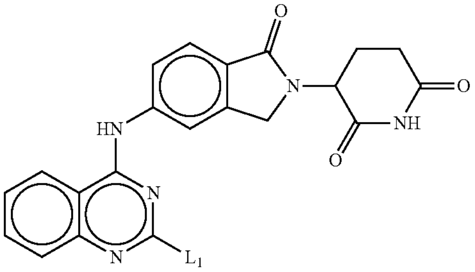 |
| 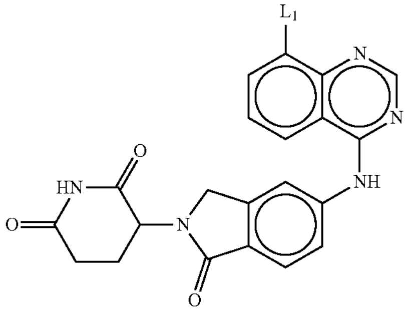 |
| 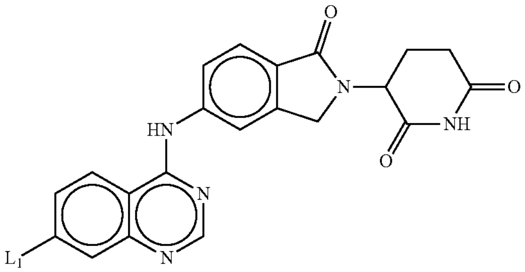 |
| 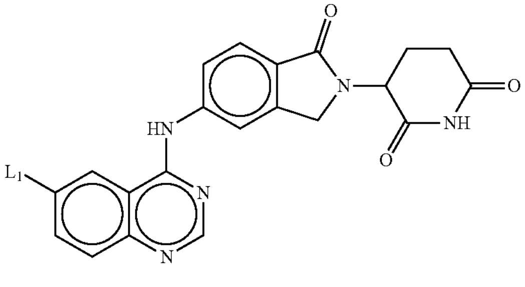 |

TABLE 1-continued
| Embodiments of general formula A-$L_1$ |
| --- |
| 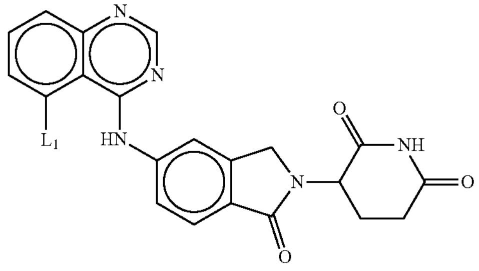 |
| 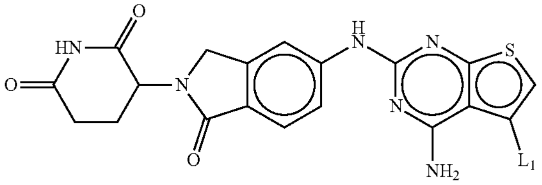 |
| 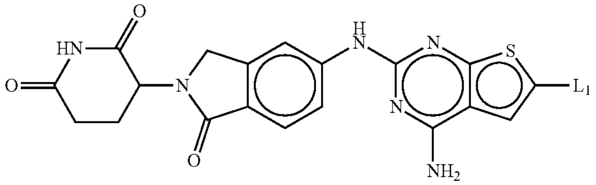 |
| 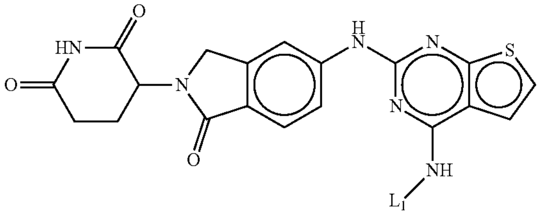 |
| 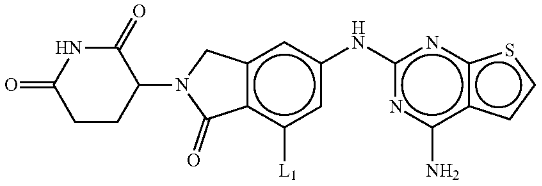 |
| 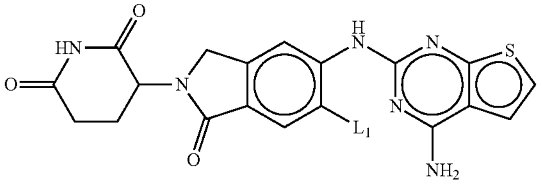 |
| 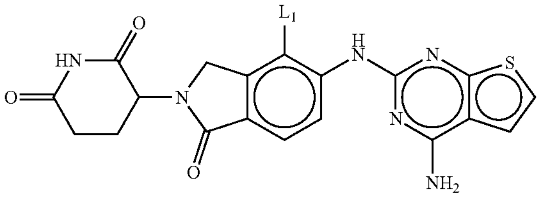 |

TABLE 1-continued
| Embodiments of general formula A-$L_1$ |
| --- |
| 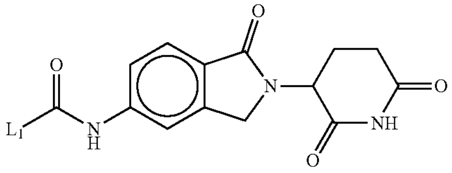 |
| 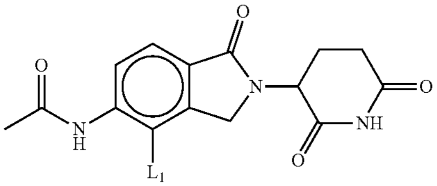 |
| 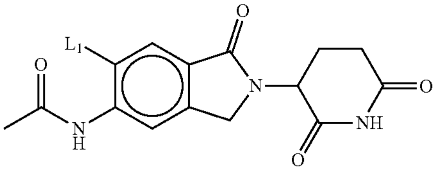 |
| 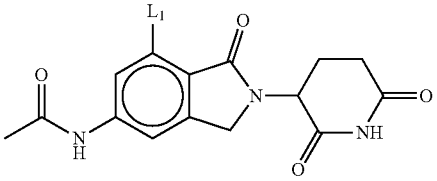 |
| 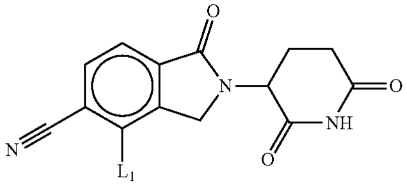 |
| 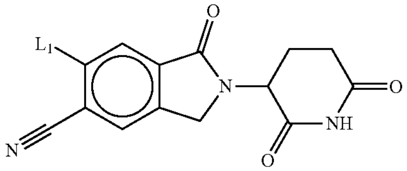 |
| 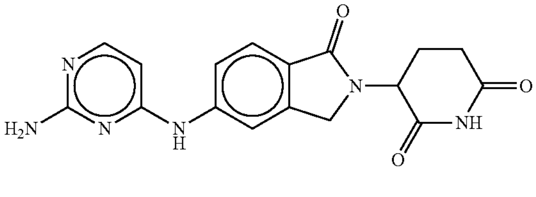 |
| 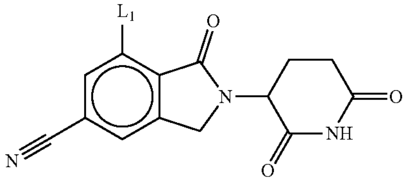 |

TABLE 1-continued
| Embodiments of general formula A-$L_1$ |
|---|
| 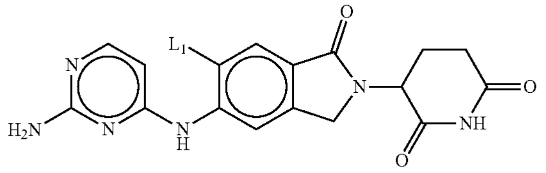 |
| 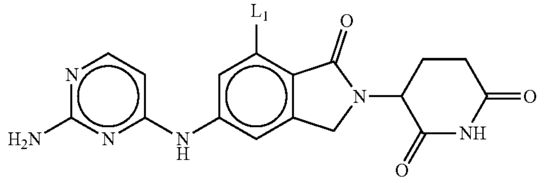 |
| 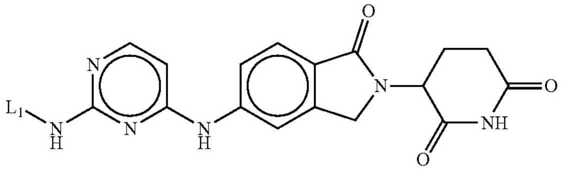 |
| 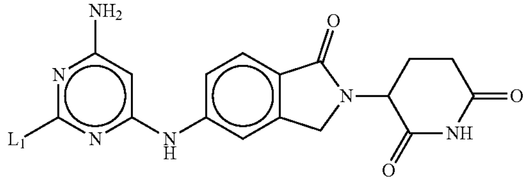 |
| 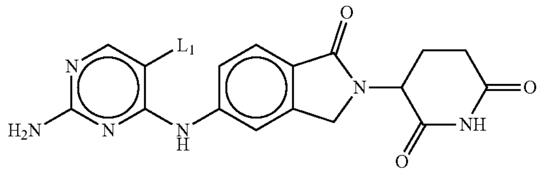 |
| 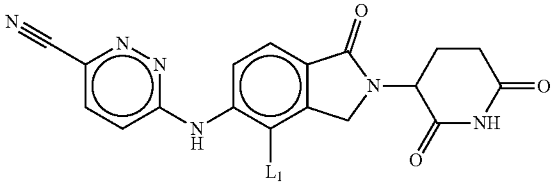 |
| 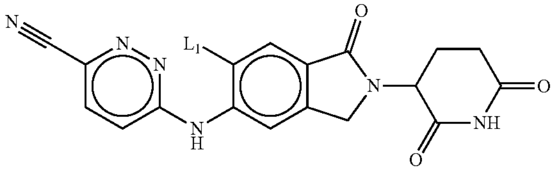 |
| 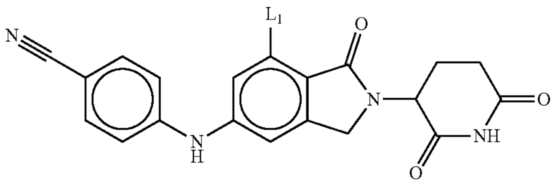 |

TABLE 1-continued
| Embodiments of general formula A-$L_1$ |
|---|
| 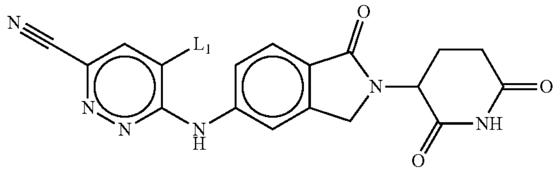 |
| 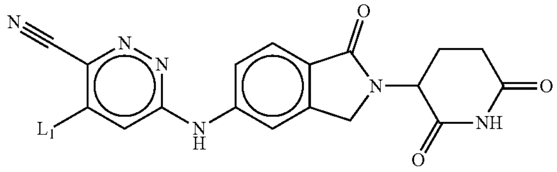 |
| 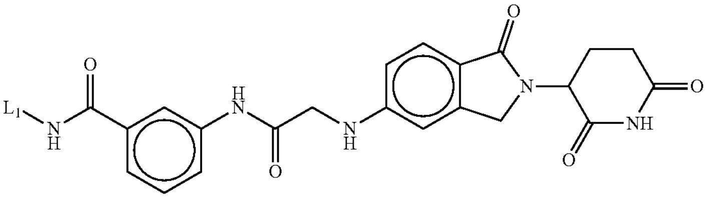 |
| 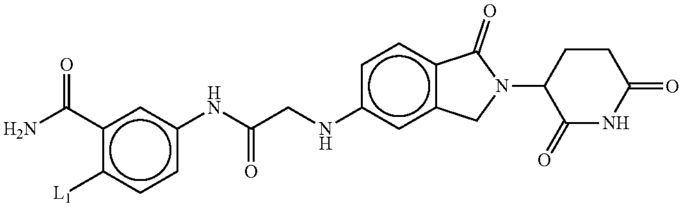 |
| 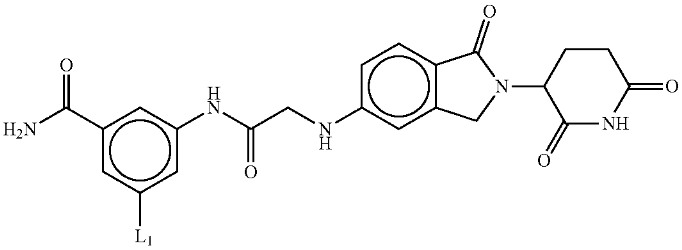 |
| 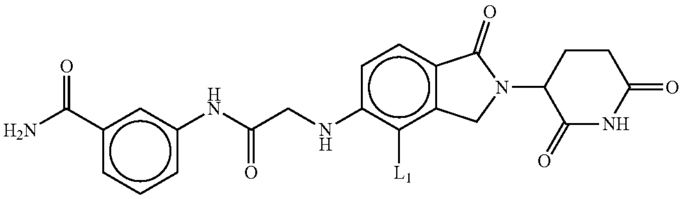 |
| 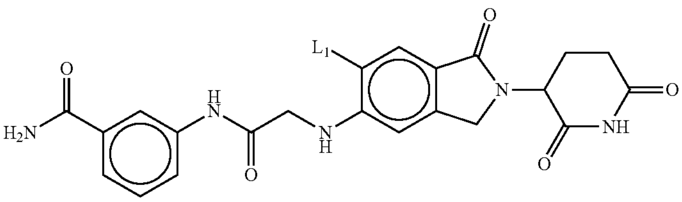 |

TABLE 1-continued
| Embodiments of general formula A-$L_1$ |
|---|
| 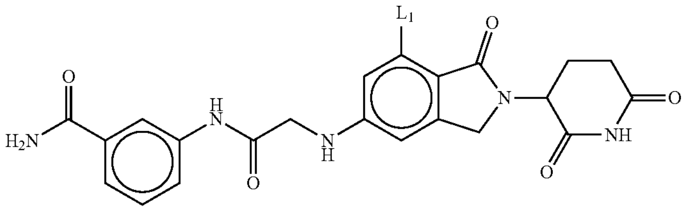 |
| 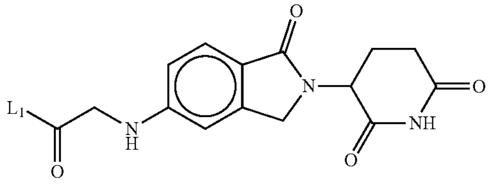 |
| 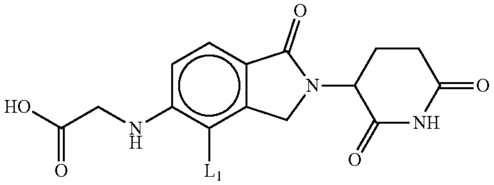 |
| 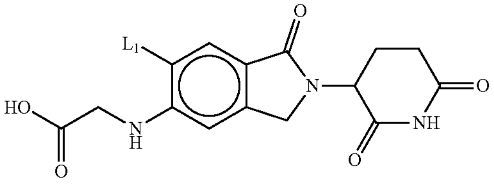 |
| 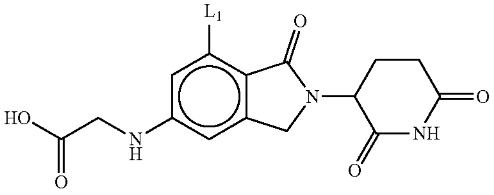 |
| 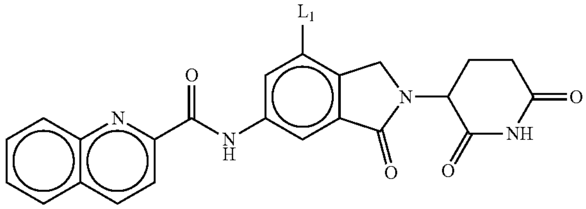 |
| 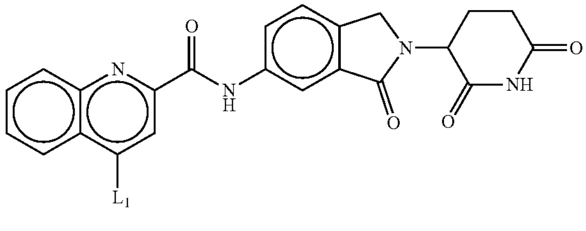 |

TABLE 1-continued
| Embodiments of general formula A-$L_1$ |
| --- |
| 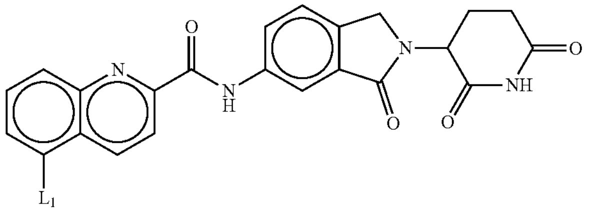 |
| 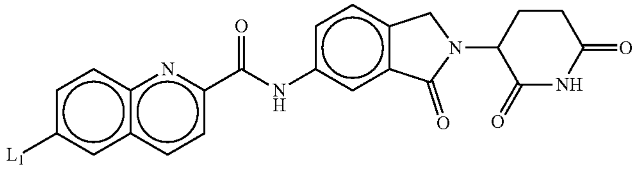 |
| 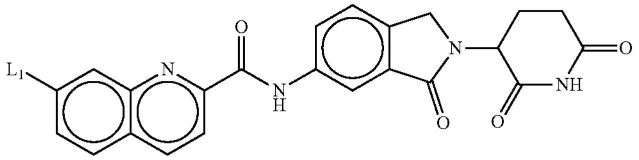 |
| 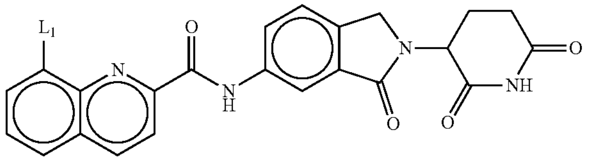 |
| 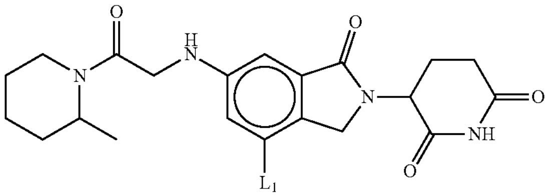 |
| 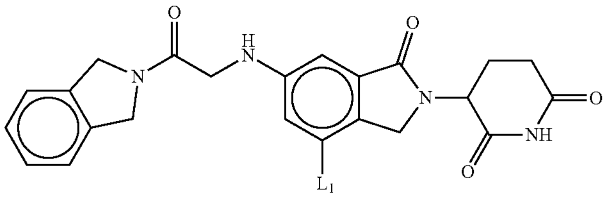 |
| 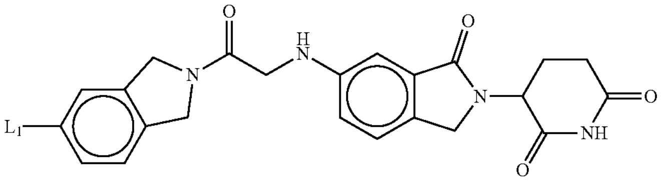 |
| 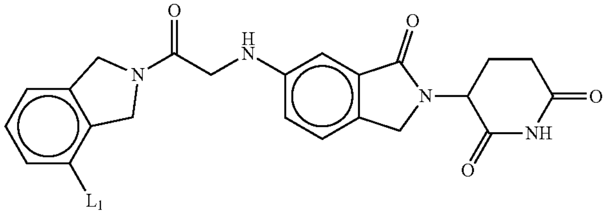 |

TABLE 1-continued
| Embodiments of general formula A-$L_1$ |
| --- |
| 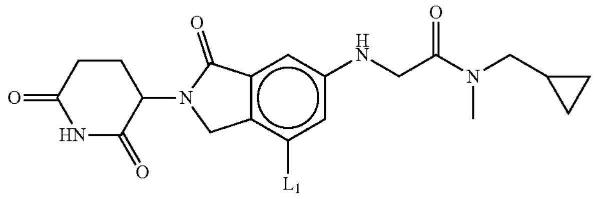 |
| 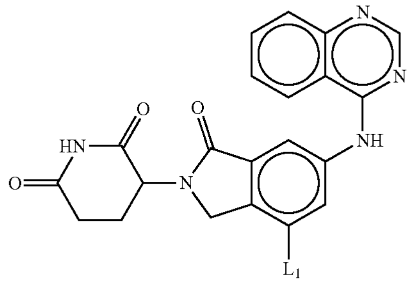 |
| 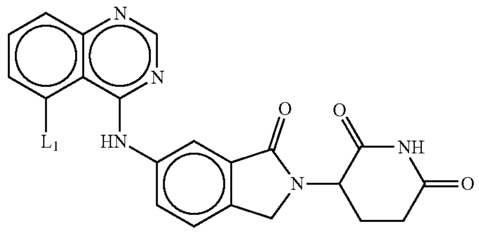 |
| 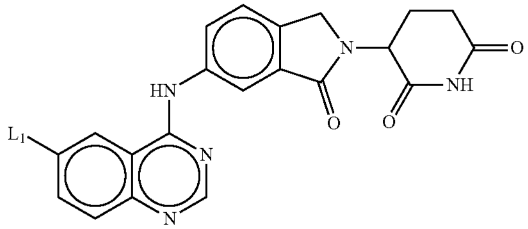 |
| 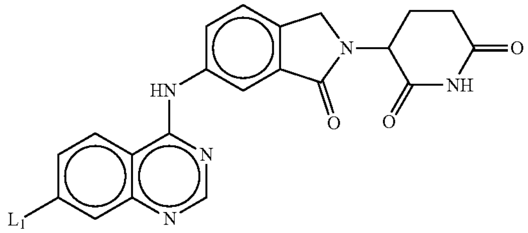 |
| 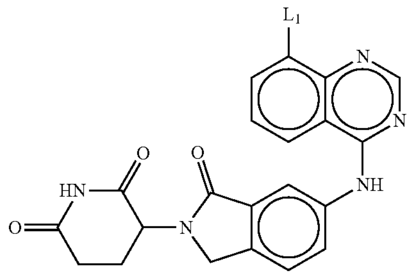 |

TABLE 1-continued
| Embodiments of general formula A-$L_1$ |
|---|
| 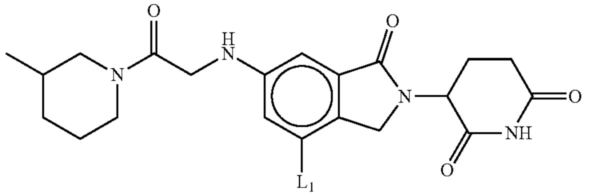 |
| 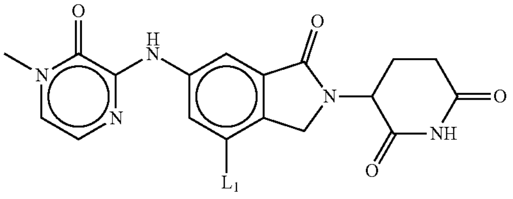 |
| 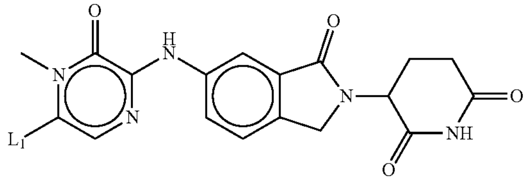 |
| 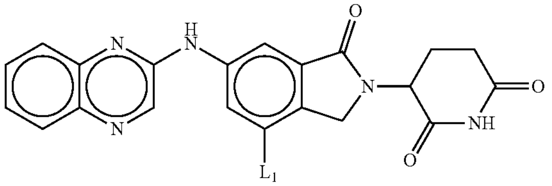 |
| 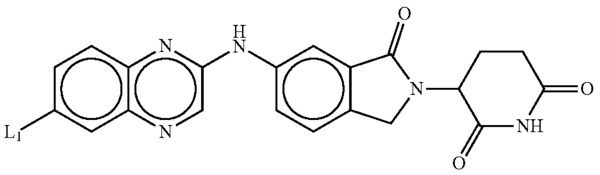 |
| 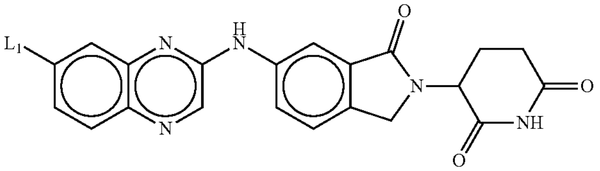 |
| 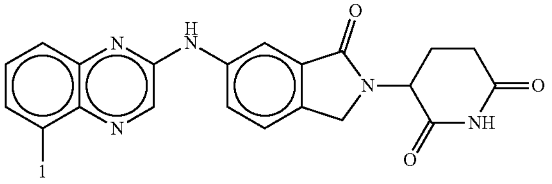 |
| 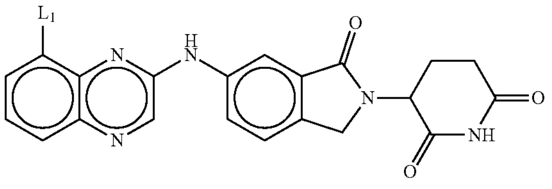 |

TABLE 1-continued
| Embodiments of general formula A-$L_1$ |
|---|
| 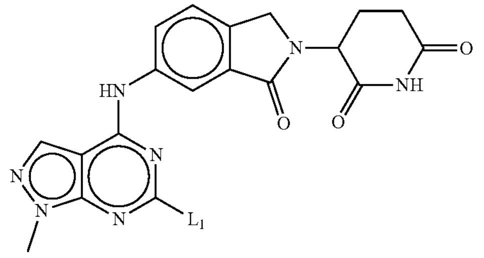 |
| 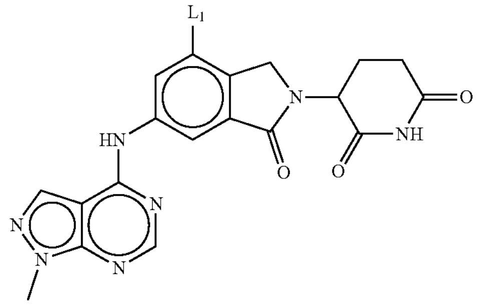 |
| 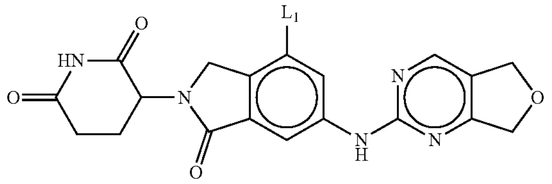 |
| 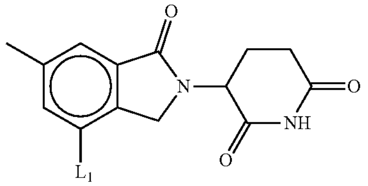 |
| 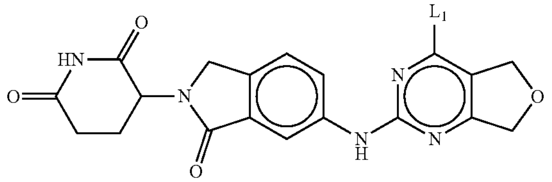 |
| 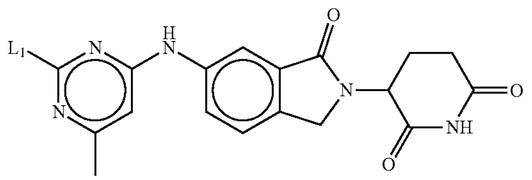 |
| 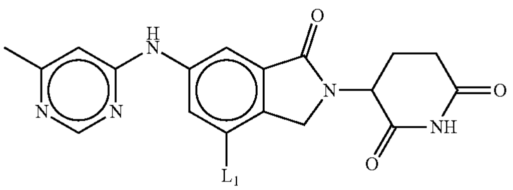 |

TABLE 1-continued
| Embodiments of general formula A-$L_1$ |
| --- |
| 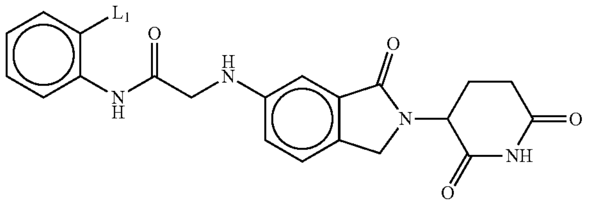 |
| 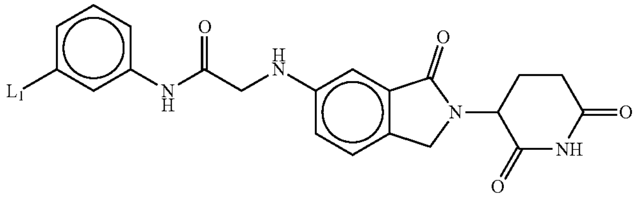 |
| 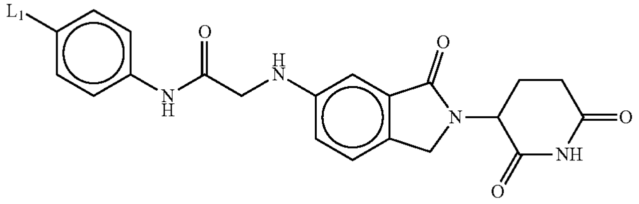 |
| 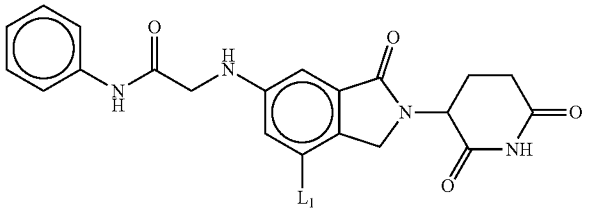 |
| 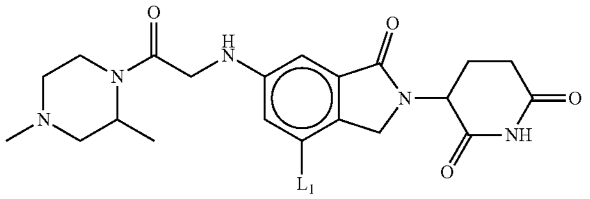 |
| 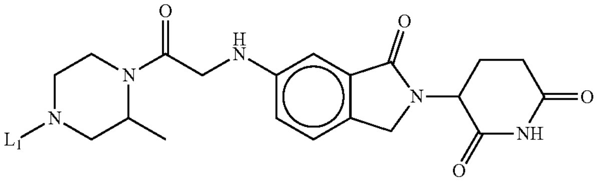 |
| 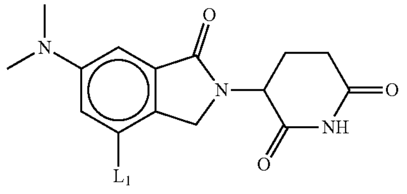 |

TABLE 1-continued
| Embodiments of general formula A-$L_1$ |
|---|
| 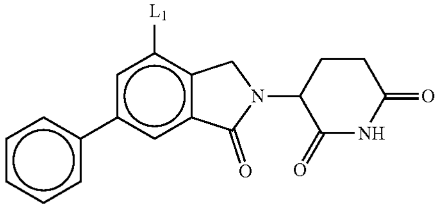 |
| 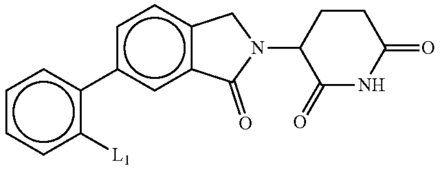 |
| 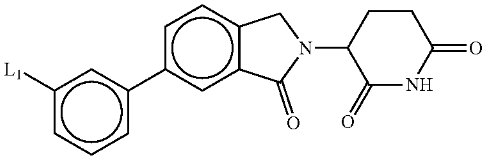 |
| 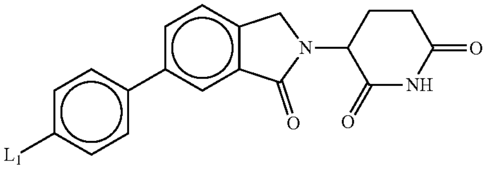 |
| 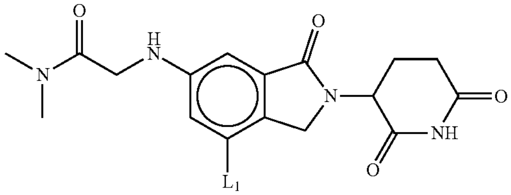 |
| 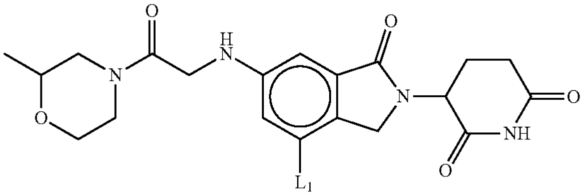 |
| 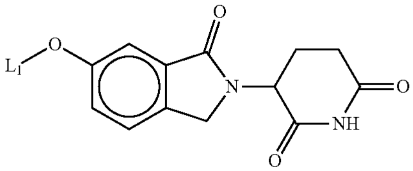 |
| 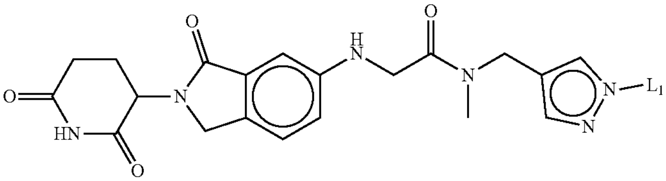 |

TABLE 1-continued
| Embodiments of general formula A-$L_1$ |
|---|
| 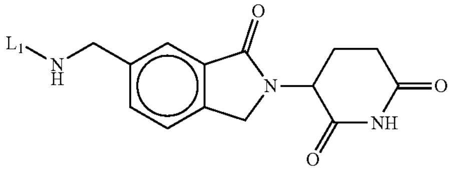 |
| 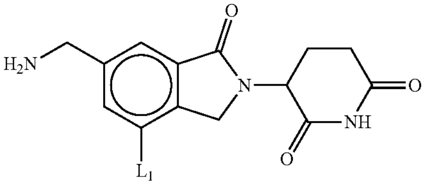 |
| 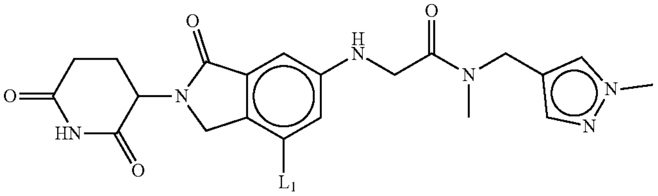 |
| 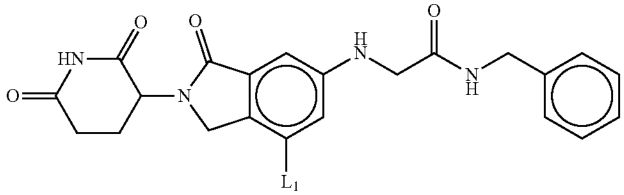 |
| 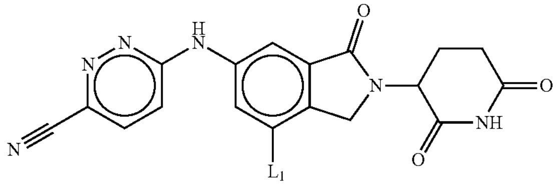 |
| 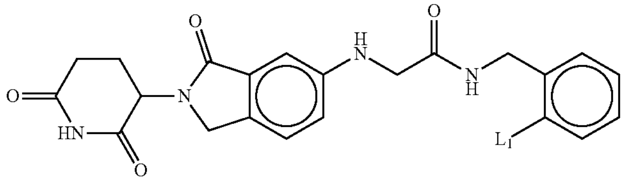 |
| 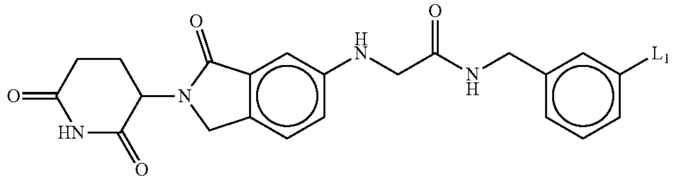 |
| 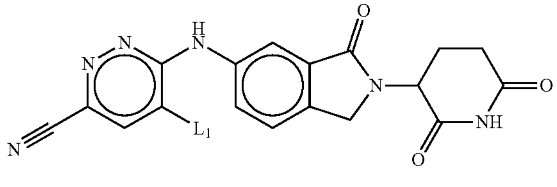 |

TABLE 1-continued
| Embodiments of general formula A-$L_1$ |
|---|
| 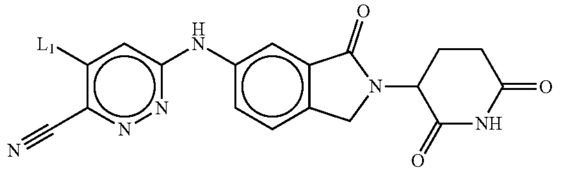 |
| 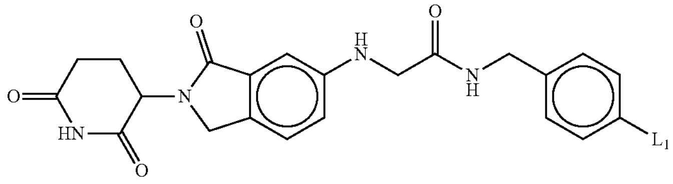 |
| 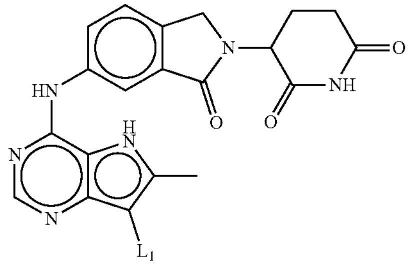 |
| 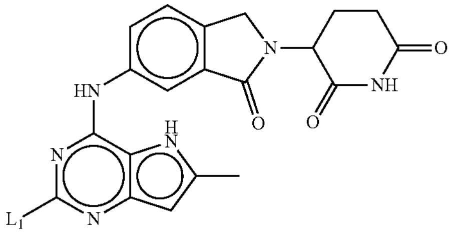 |
| 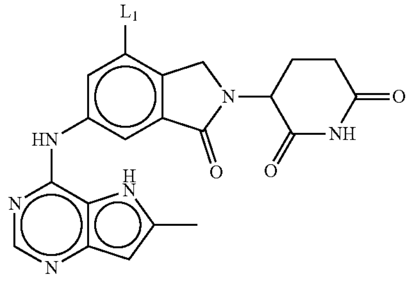 |
| 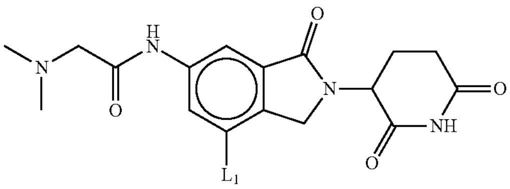 |

TABLE 1-continued
| Embodiments of general formula A-$L_1$ |
|---|
| 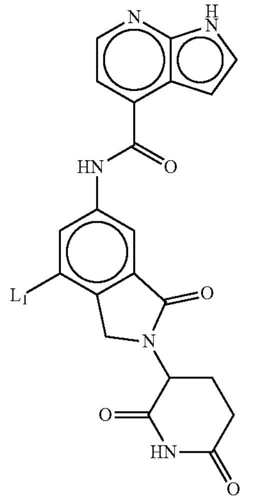 |
| 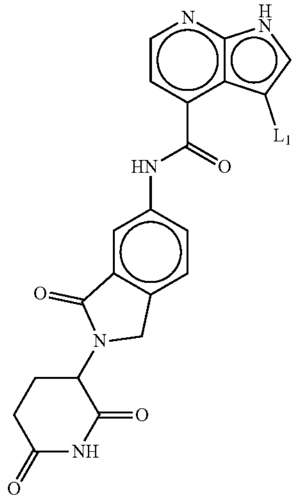 |
| 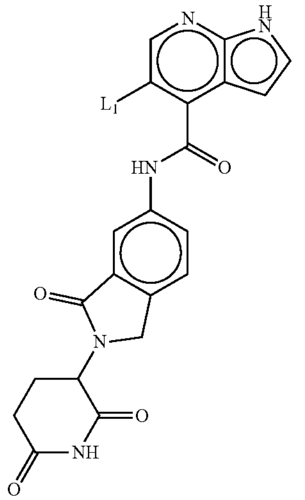 |

TABLE 1-continued
| Embodiments of general formula A-$L_1$ |
|---|
| 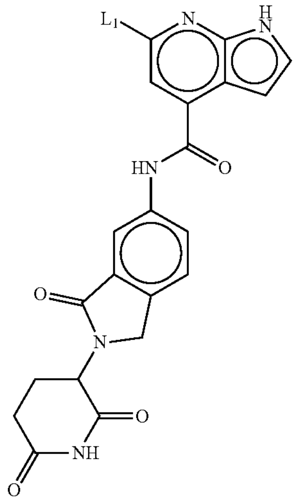 |
| 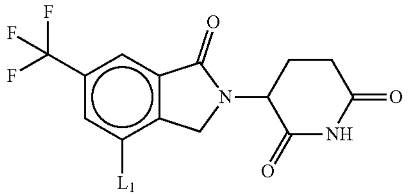 |
| 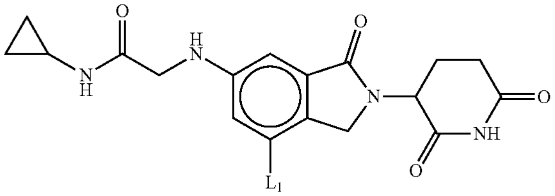 |
| 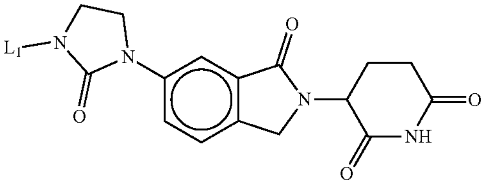 |
| 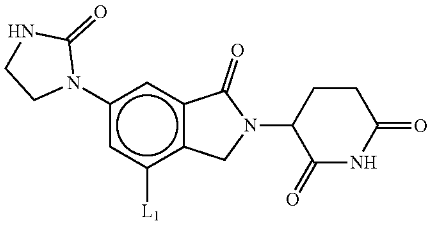 |
| 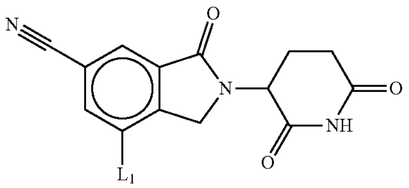 |

TABLE 1-continued
| Embodiments of general formula A-$L_1$ |
| --- |
| 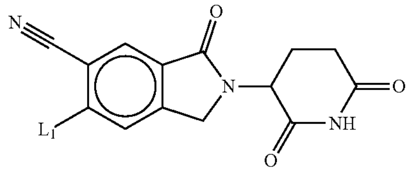 |
| 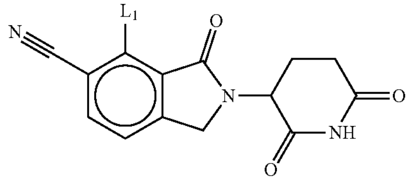 |
| 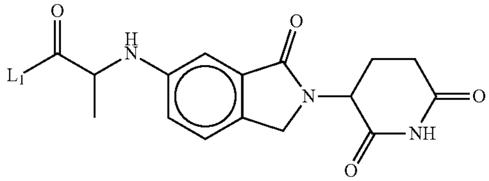 |
| 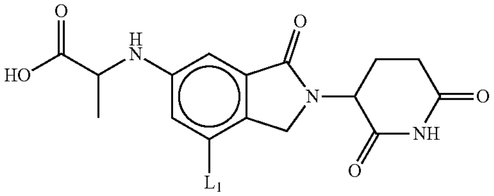 |
| 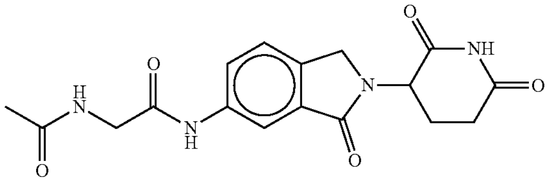 |
| 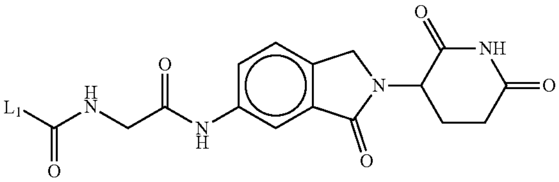 |
| 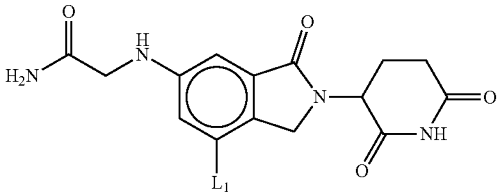 |
| 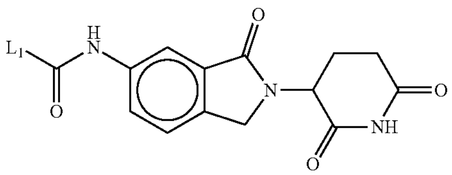 |

TABLE 1-continued
| Embodiments of general formula A-$L_1$ |
|---|
| 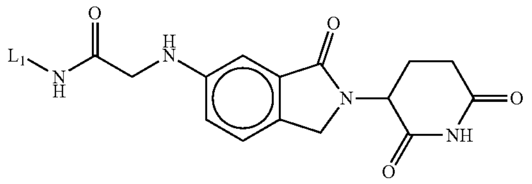 |
| 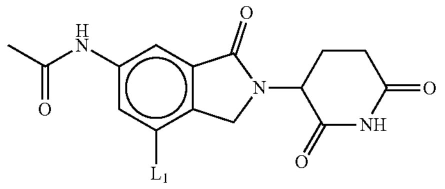 |
| 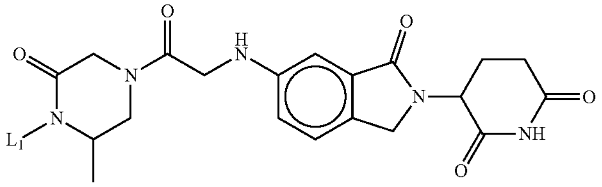 |
| 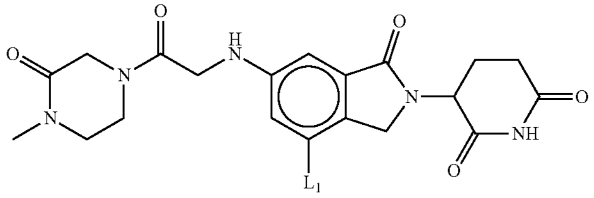 |
| 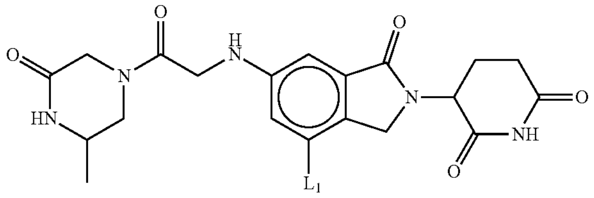 |
| 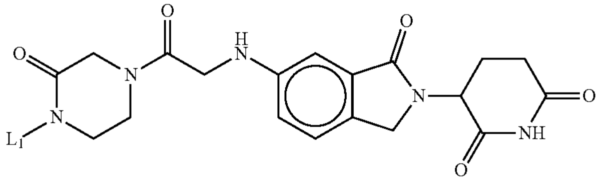 |
| 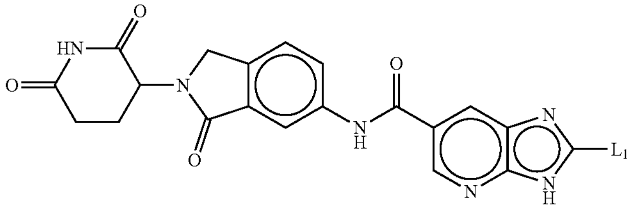 |

TABLE 1-continued
| Embodiments of general formula A-$L_1$ |
|---|
| 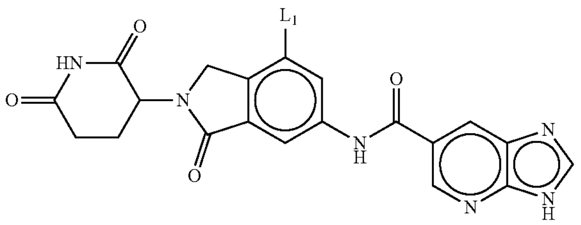 |
| 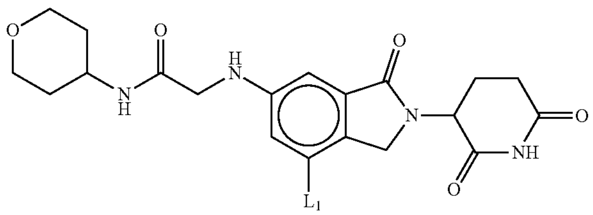 |
| 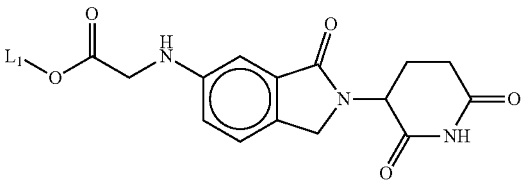 |
| 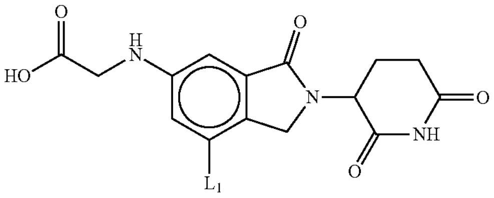 |
| 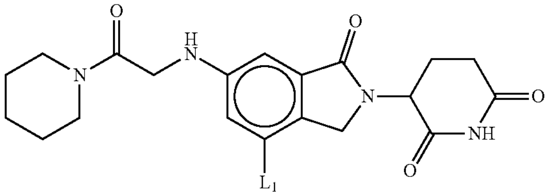 |
| 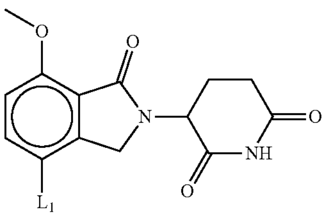 |
| 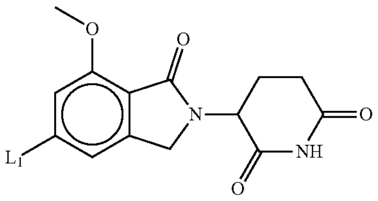 |

TABLE 1-continued
| Embodiments of general formula A-$L_1$ |
|---|
| 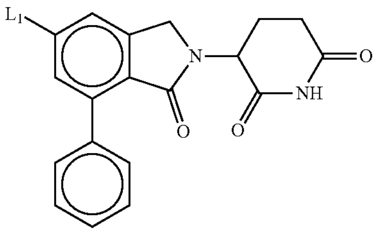 |
| 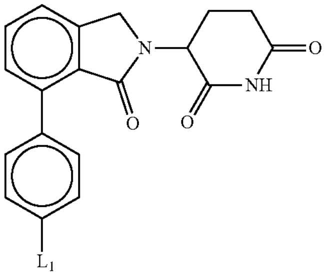 |
| 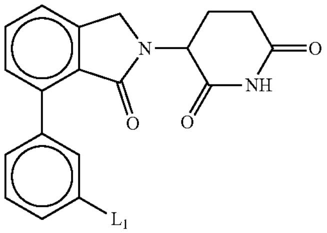 |
| 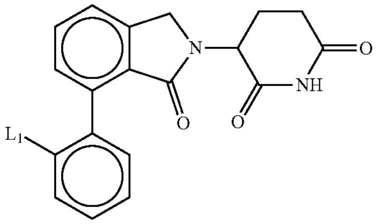 |
| 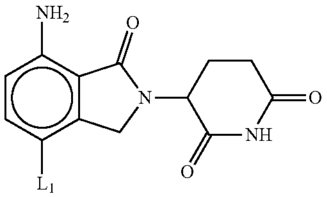 |
| 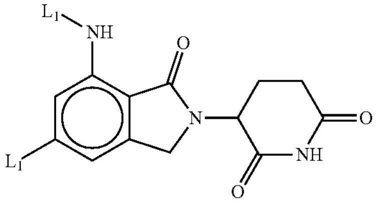 |
| 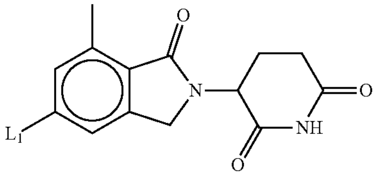 |

TABLE 1-continued
| Embodiments of general formula A-$L_1$ |
|---|
| 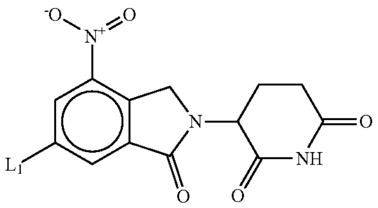 |
| 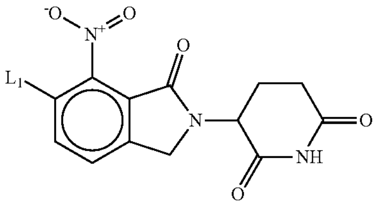 |
| 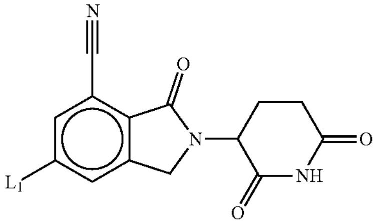 |
| 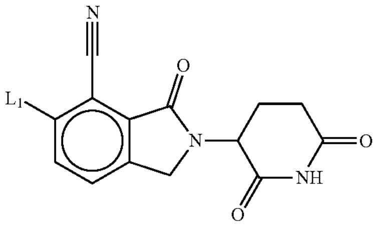 |
| 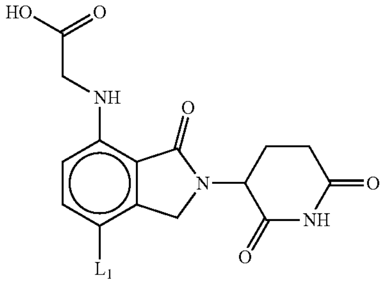 |
| 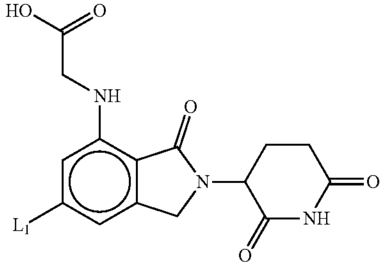 |

TABLE 1-continued
| Embodiments of general formula A-$L_1$ |
| --- |
| 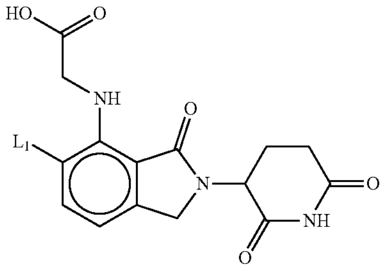 |
| 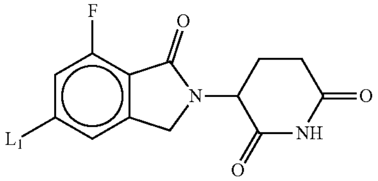 |
| 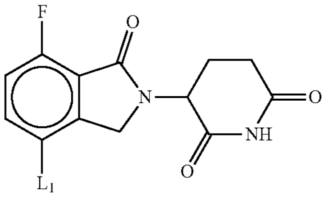 |
| 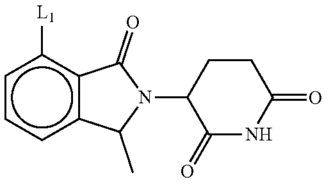 |
| 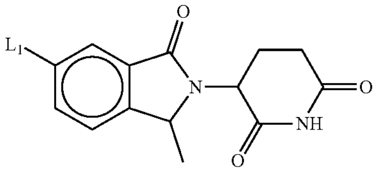 |
| 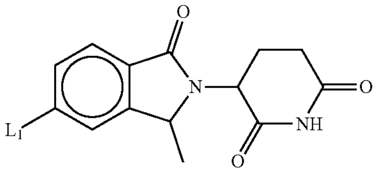 |
| 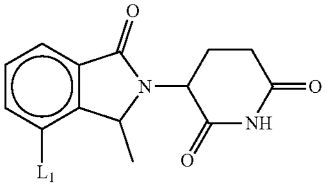 |

TABLE 1-continued
| Embodiments of general formula A-$L_1$ |
| --- |
| 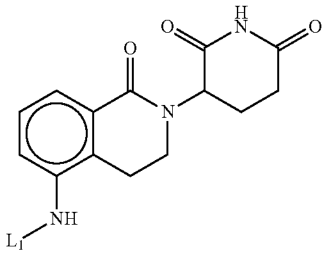 |
| 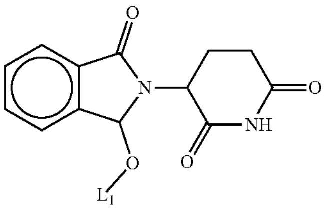 |
| 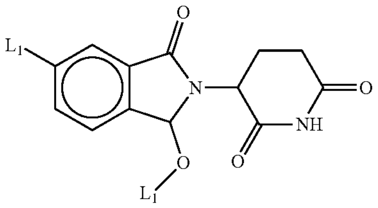 |
| 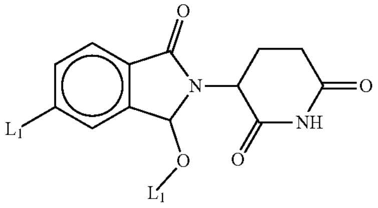 |
| 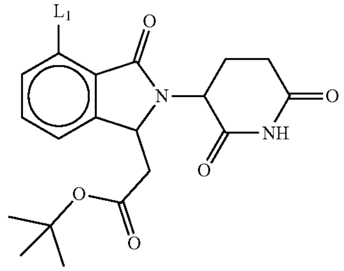 |
| 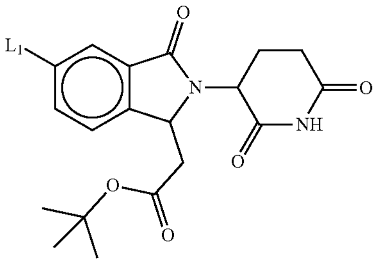 |

TABLE 1-continued
| Embodiments of general formula A-$L_1$ |
| --- |
| 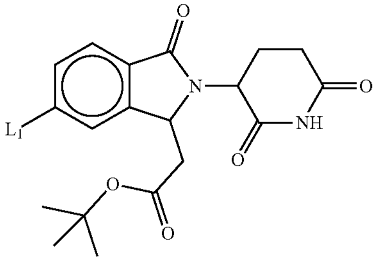 |
| 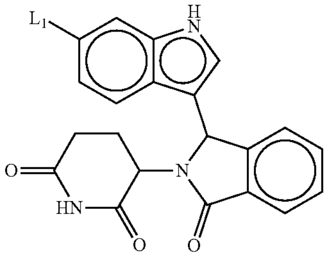 |
| 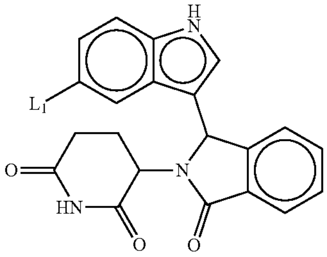 |
| 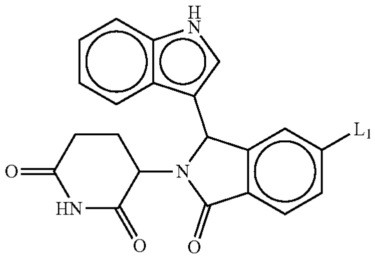 |
| 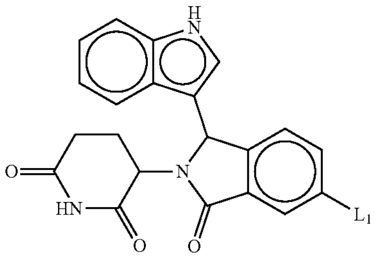 |
| 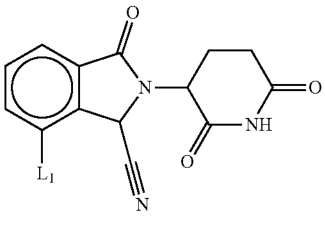 |

TABLE 1-continued
| Embodiments of general formula A-$L_1$ |
|---|
| 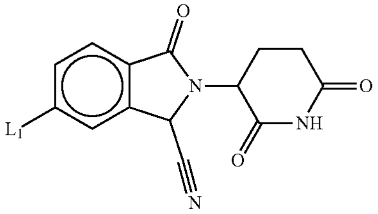 |
| 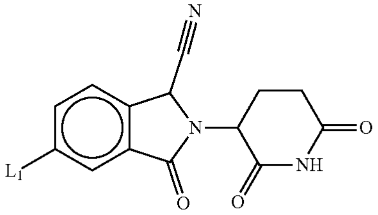 |
| 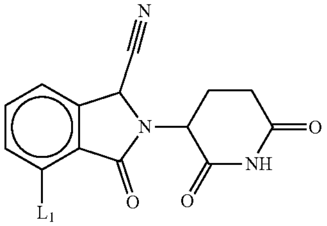 |
| 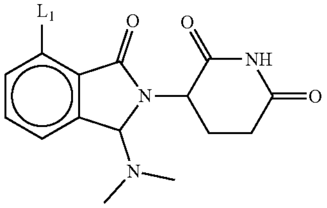 |
| 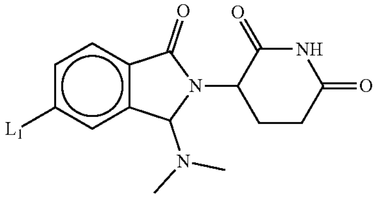 |
| 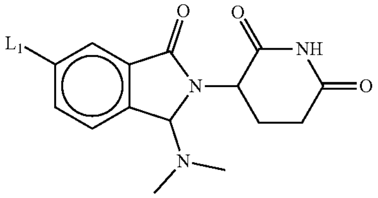 |
| 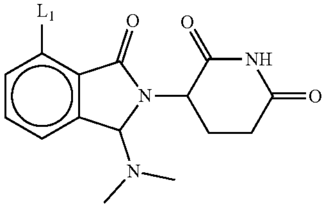 |

TABLE 1-continued
Embodiments of general formula A-$L_1$
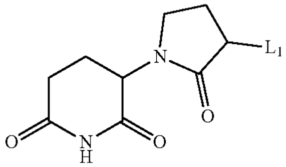
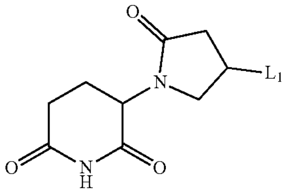
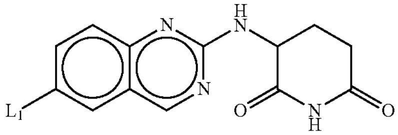
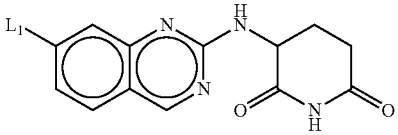
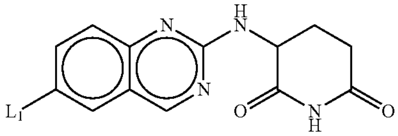
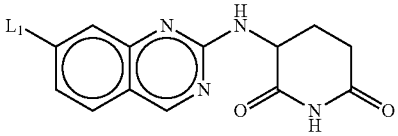
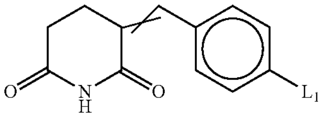
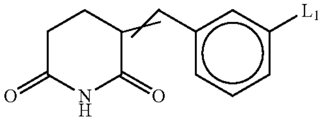
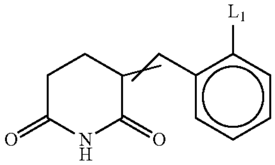
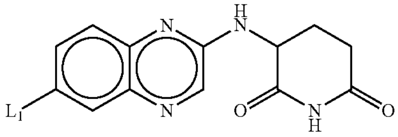

TABLE 1-continued
| Embodiments of general formula A-$L_1$ |
|---|
| 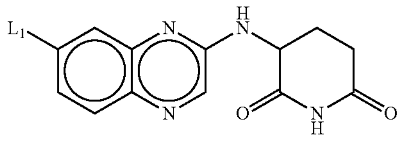 |
| 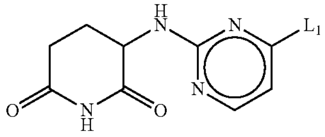 |
| 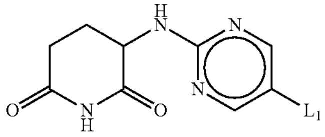 |
| 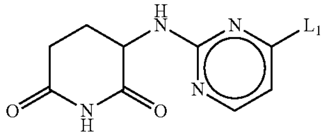 |
| 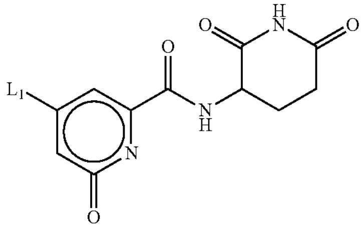 |
| 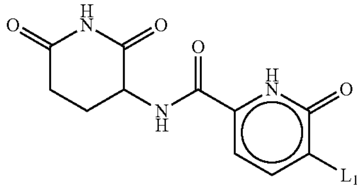 |
| 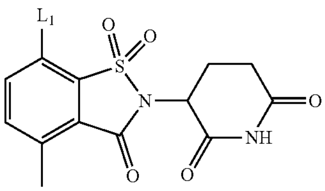 |
| 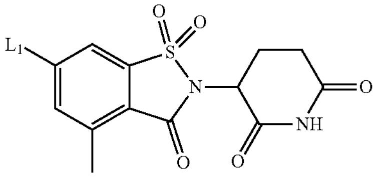 |
| 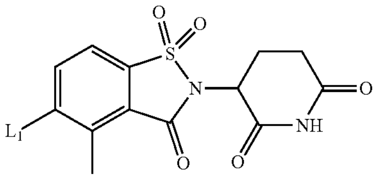 |

TABLE 1-continued
| Embodiments of general formula A-$L_1$ |
| --- |
| 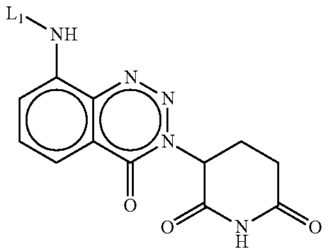 |
| 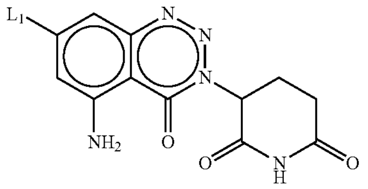 |
| 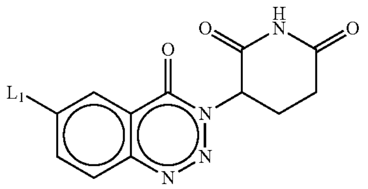 |
| 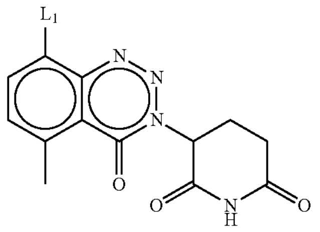 |
| 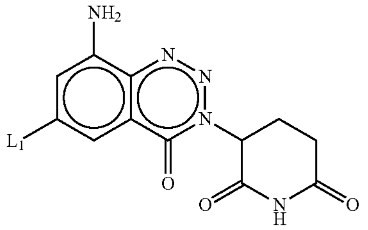 |
| 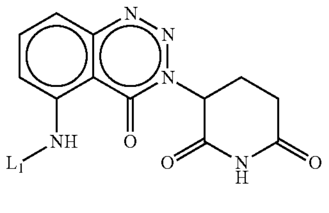 |
| 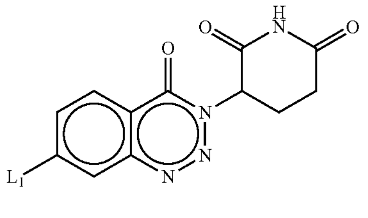 |

TABLE 1-continued
| Embodiments of general formula A-$L_1$ |
| --- |
| 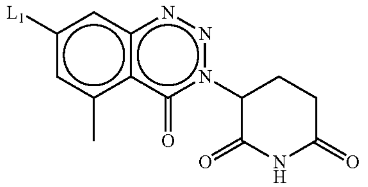 |
| 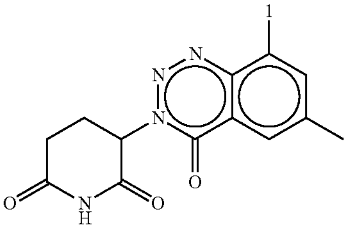 |
| 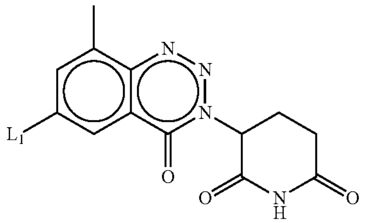 |
| 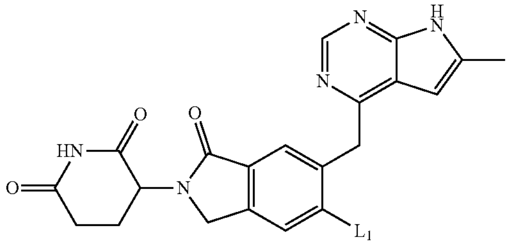 |
Embodiments of $(A)_k$-L-Q
In an embodiment, the compound having general formula $(A)_k$-L-Q is selected from the compounds listed in Table 2, Table 3, or Table 4.
TABLE 2
| Embodiments of general formula $(A)_k$-L-Q, having L-Q moiety. |
| --- |
| 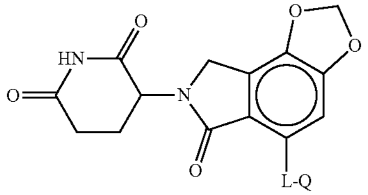 |
| 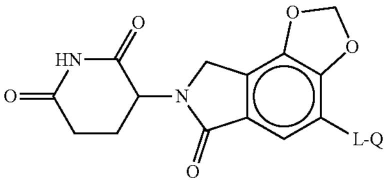 |
TABLE 2-continued
| Embodiments of general formula $(A)_k$-L-Q, having L-Q moiety. |
| --- |
| 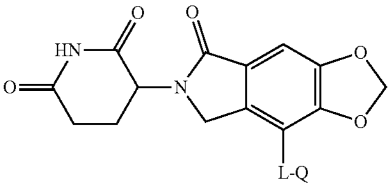 |
| 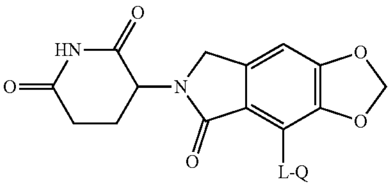 |
| 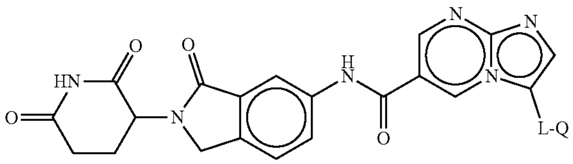 |

TABLE 2-continued
Embodiments of general formula $(A)_k$-L-Q, having L-Q moiety.
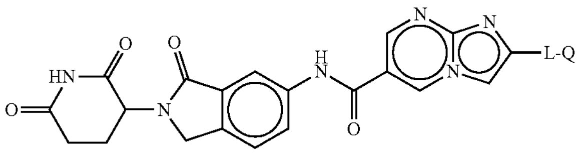
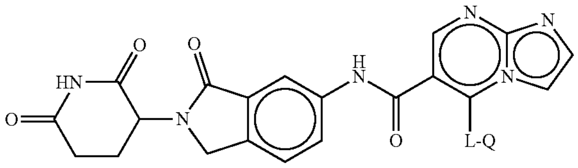
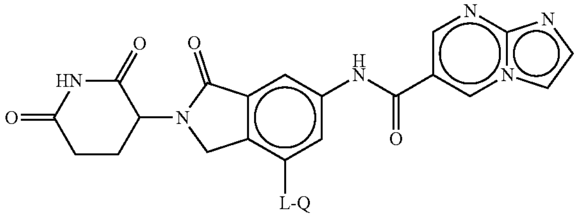
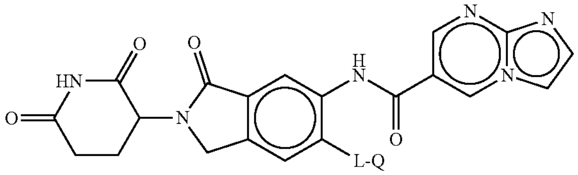
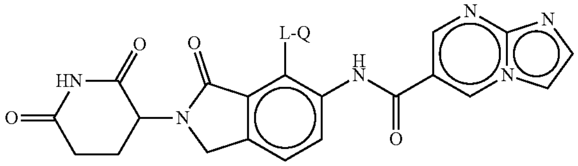
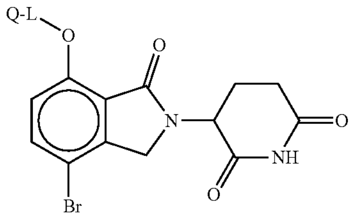
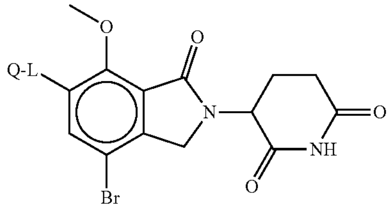
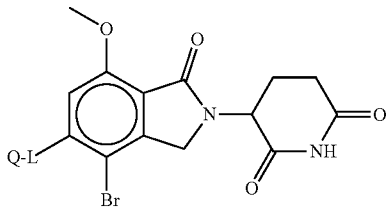
TABLE 2-continued
Embodiments of general formula $(A)_k$-L-Q, having L-Q moiety.
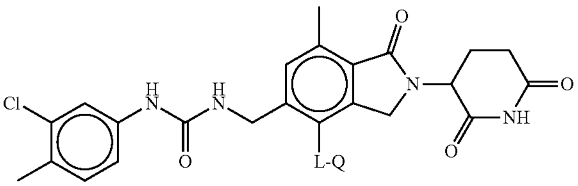
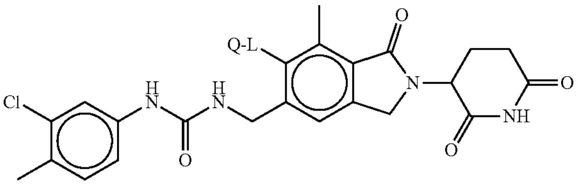
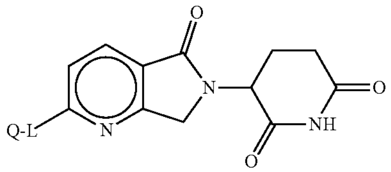
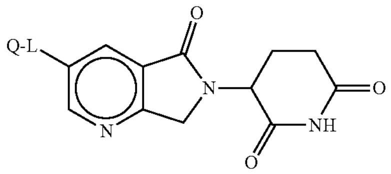
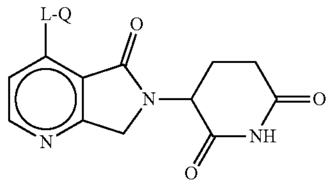
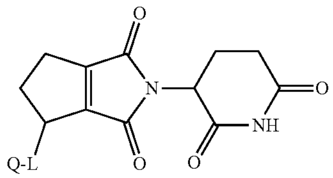
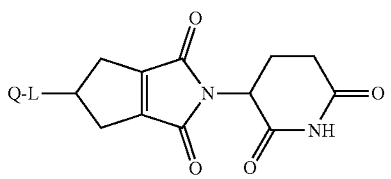
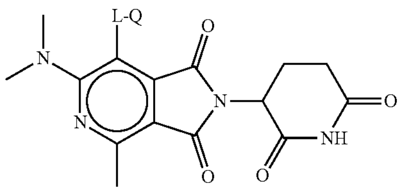

TABLE 2-continued
| Embodiments of general formula $(A)_k$-L-Q, having L-Q moiety. |
|---|
| 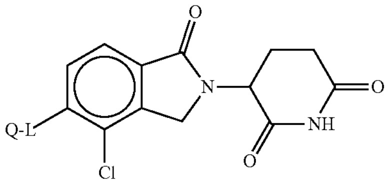 |
| 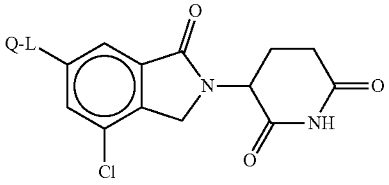 |
| 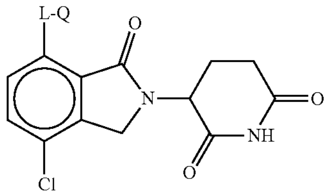 |
| 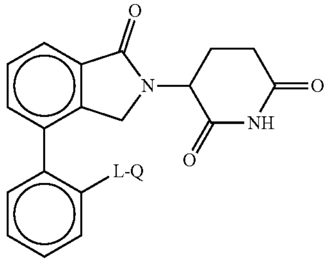 |
| 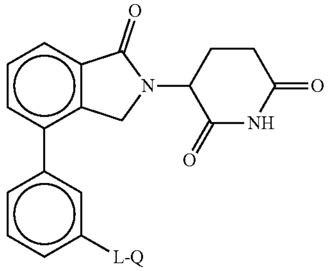 |
| 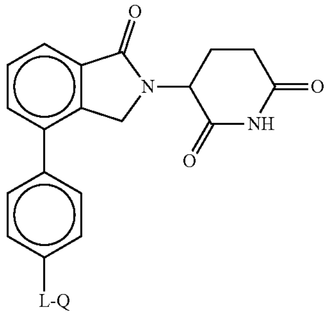 |
TABLE 2-continued
| Embodiments of general formula $(A)_k$-L-Q, having L-Q moiety. |
|---|
| 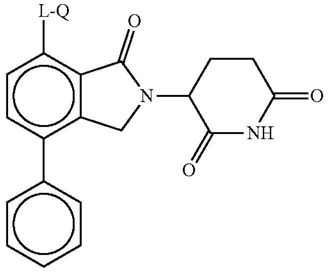 |
| 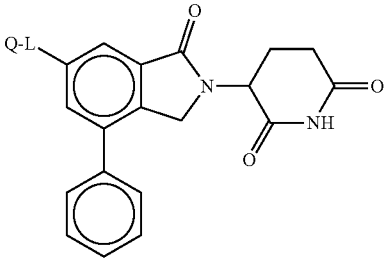 |
| 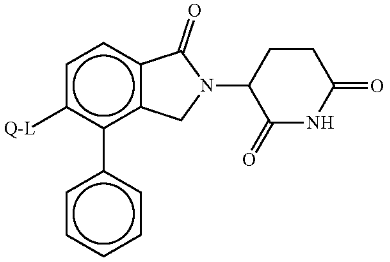 |
| 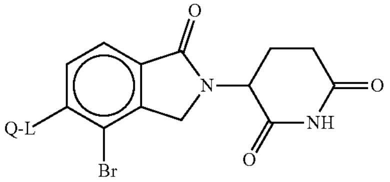 |
| 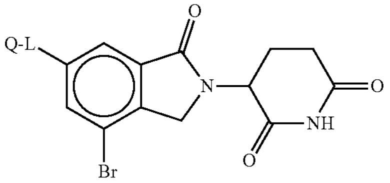 |
| 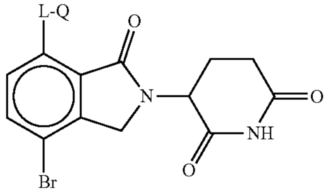 |
| 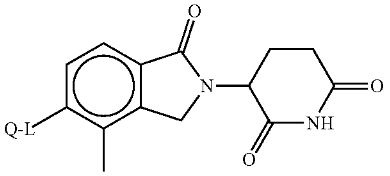 |

TABLE 2-continued
| Embodiments of general formula $(A)_k$-L-Q, having L-Q moiety. |
| --- |
| 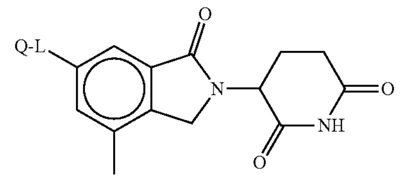 |
| 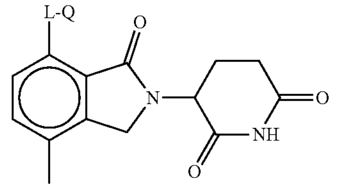 |
| 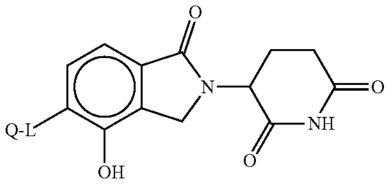 |
| 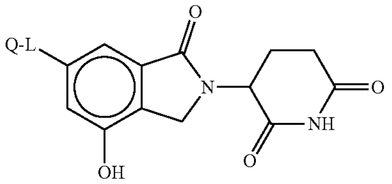 |
| 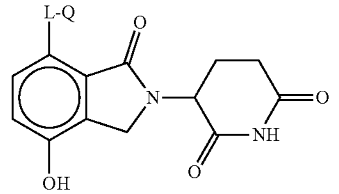 |
| 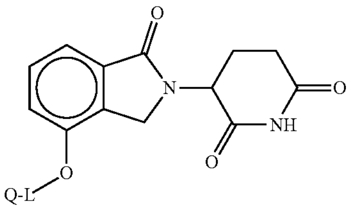 |
| 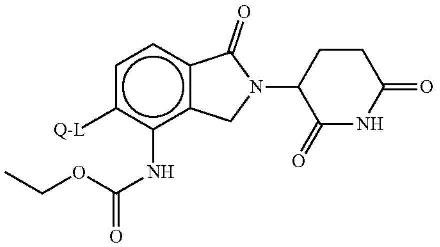 |
TABLE 2-continued
| Embodiments of general formula $(A)_k$-L-Q, having L-Q moiety. |
| --- |
| 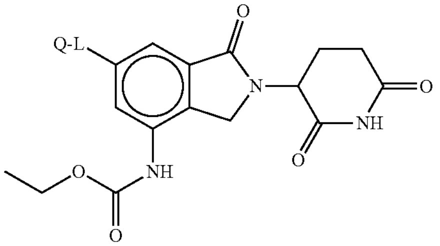 |
| 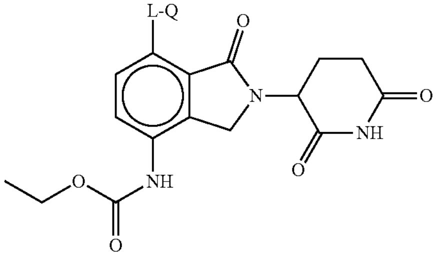 |
| 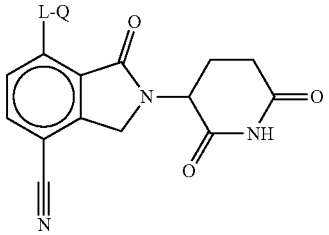 |
| 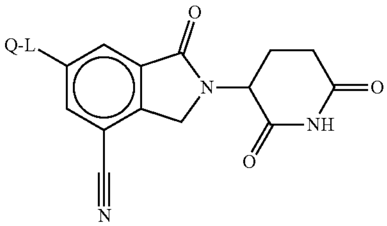 |
| 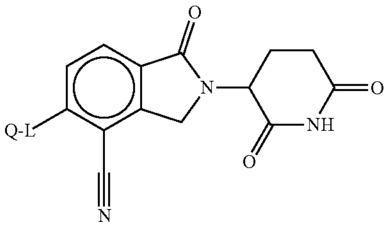 |
| 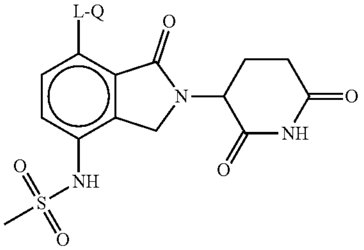 |

TABLE 2-continued
Embodiments of general formula $(A)_k$-L-Q, having L-Q moiety.
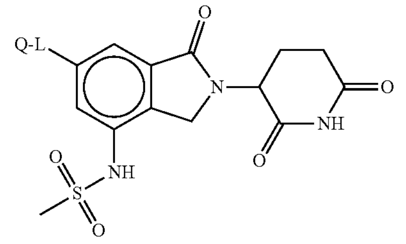
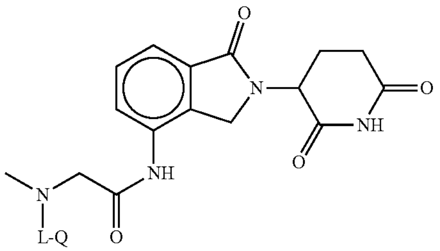
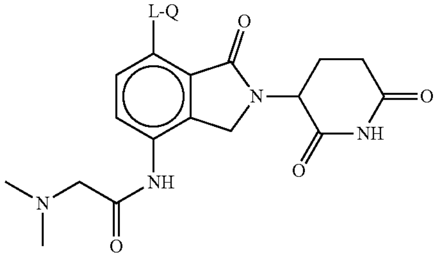
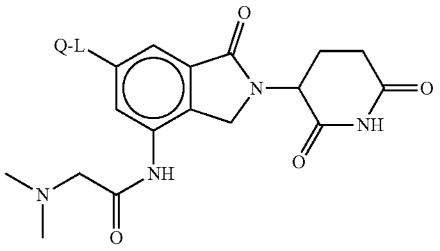
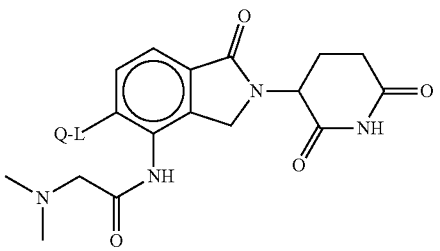
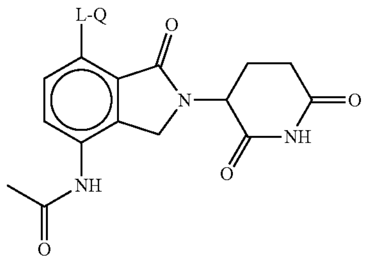
TABLE 2-continued
Embodiments of general formula $(A)_k$-L-Q, having L-Q moiety.
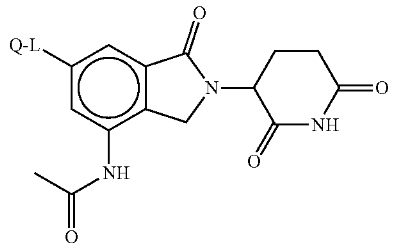
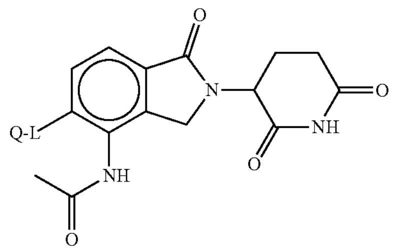
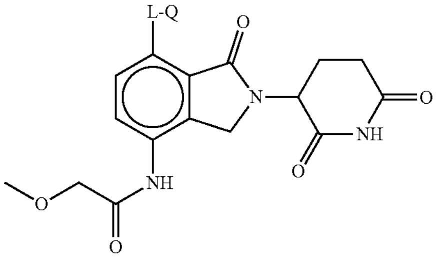
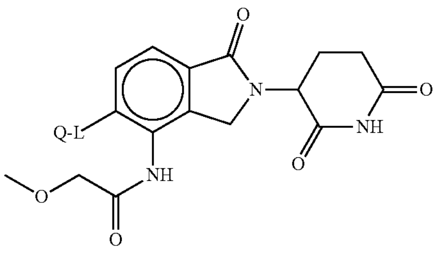
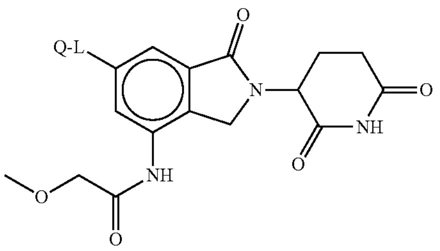
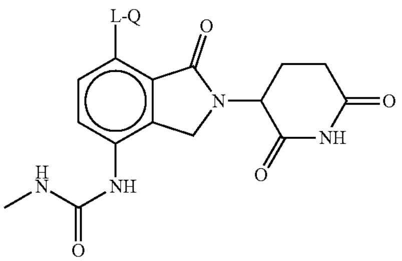

TABLE 2-continued
Embodiments of general formula $(A)_k$-L-Q, having L-Q moiety.
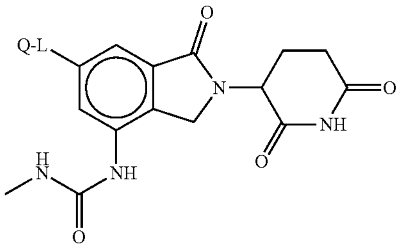
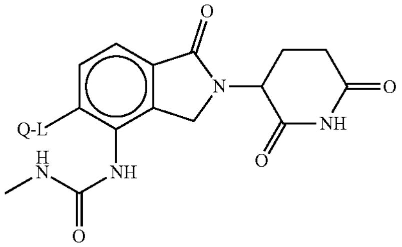
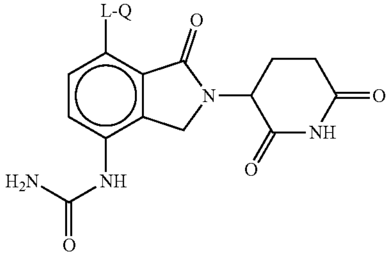
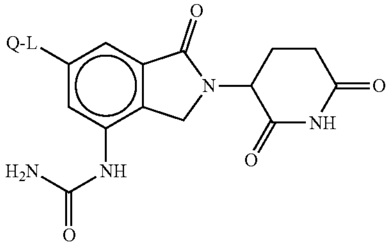
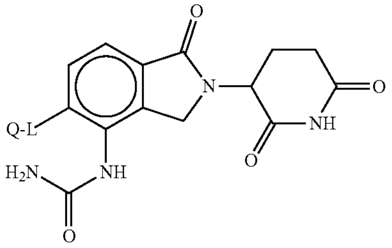
TABLE 2-continued
Embodiments of general formula $(A)_k$-L-Q, having L-Q moiety.
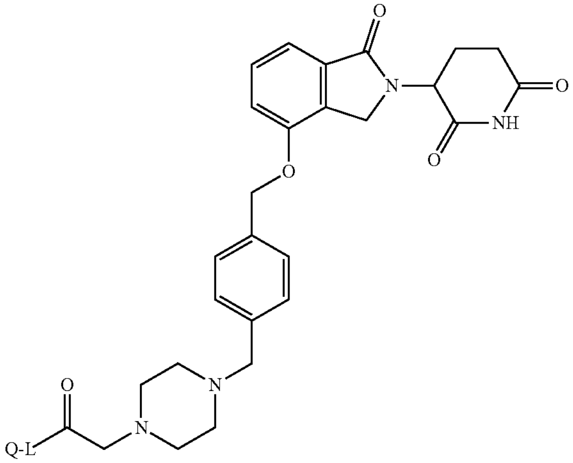
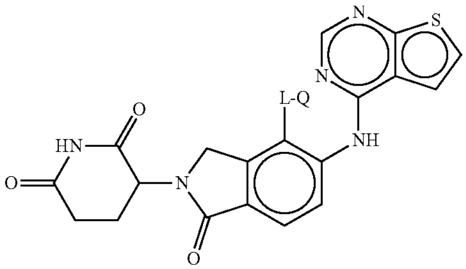
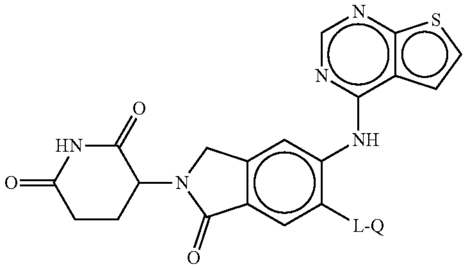
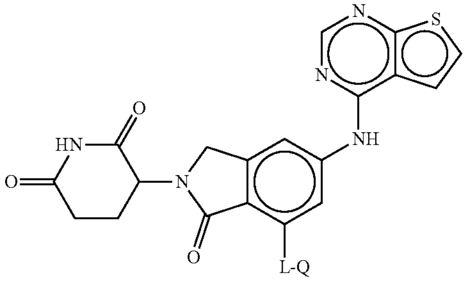
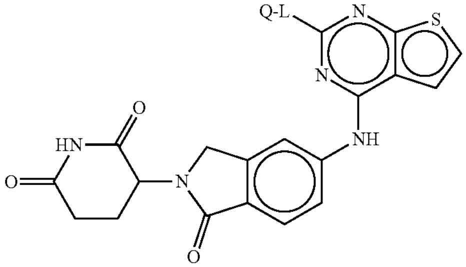

TABLE 2-continued
| Embodiments of general formula $(A)_k$-L-Q, having L-Q moiety. |
| --- |
| 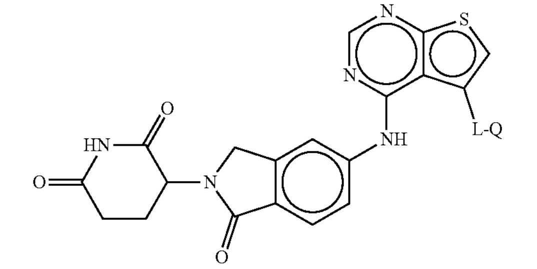 |
| 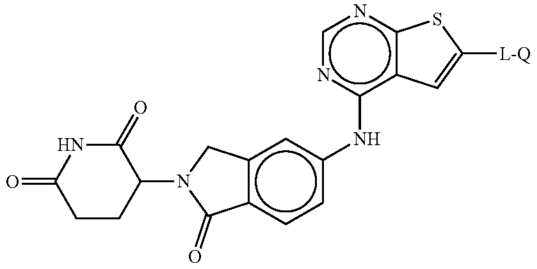 |
| 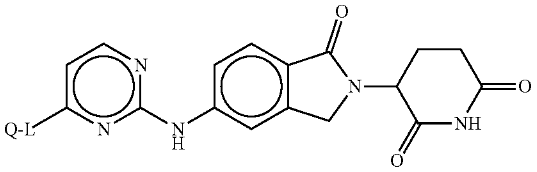 |
| 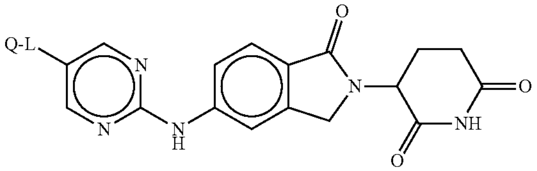 |
| 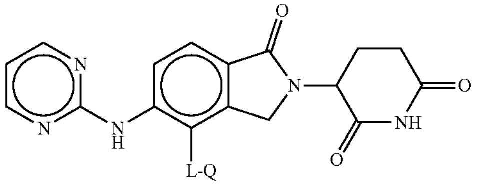 |
| 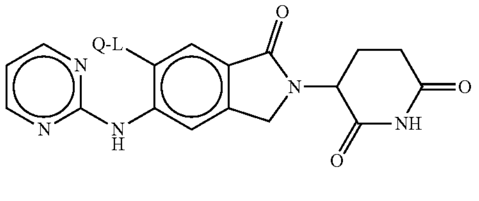 |
| 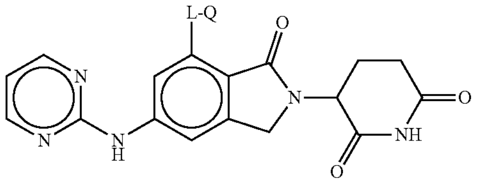 |
TABLE 2-continued
| Embodiments of general formula $(A)_k$-L-Q, having L-Q moiety. |
| --- |
| 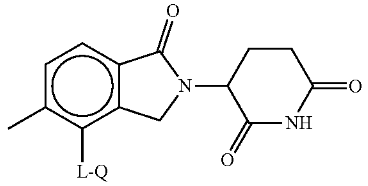 |
| 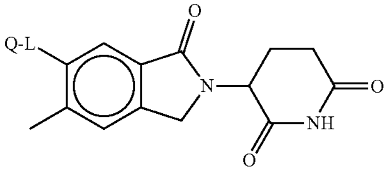 |
| 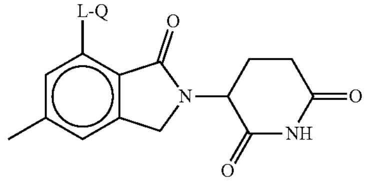 |
| 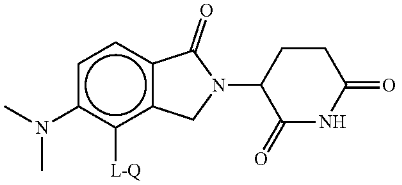 |
| 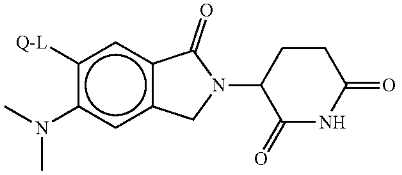 |
| 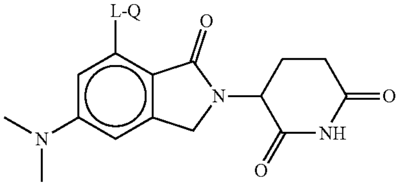 |
| 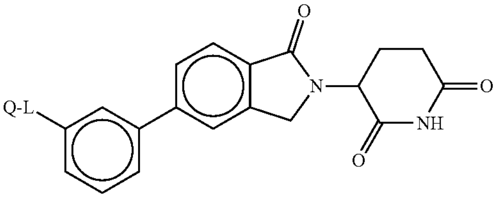 |
| 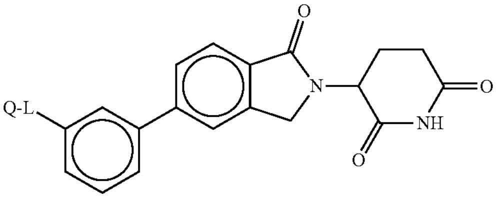 |

TABLE 2-continued
Embodiments of general formula $(A)_k$-L-Q, having L-Q moiety.
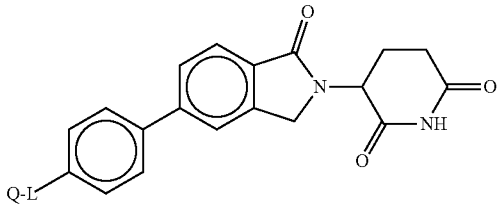
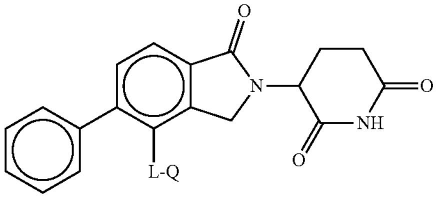
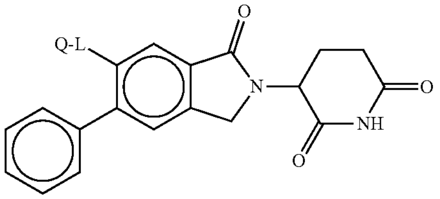
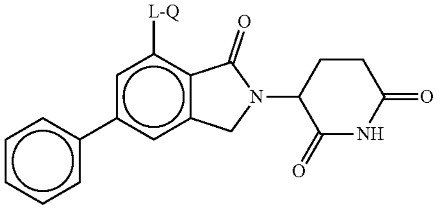
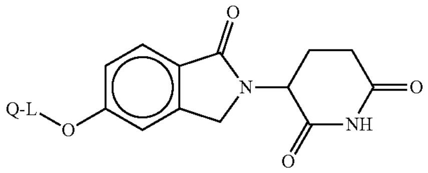
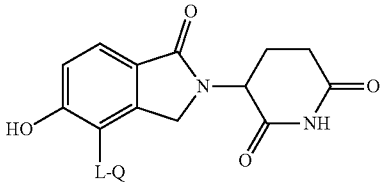
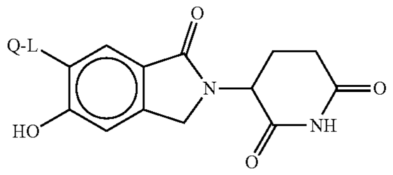
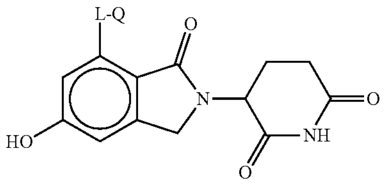
TABLE 2-continued
Embodiments of general formula $(A)_k$-L-Q, having L-Q moiety.
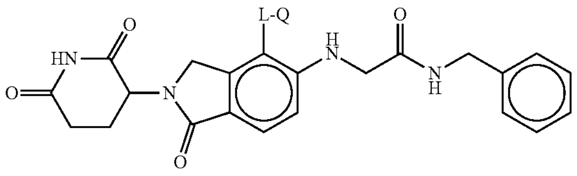
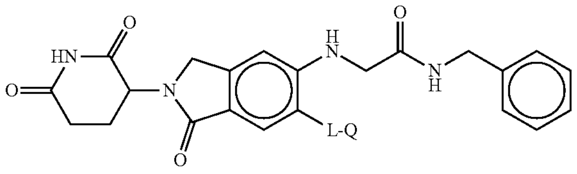
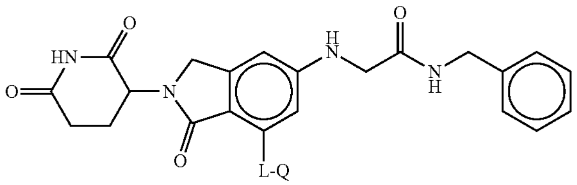
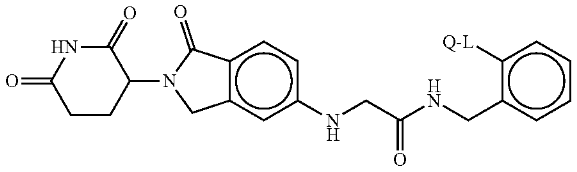
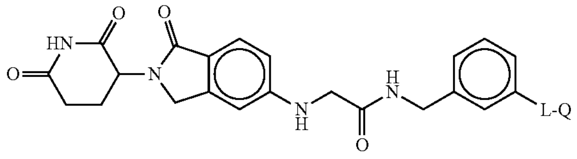
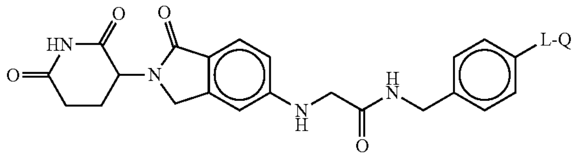
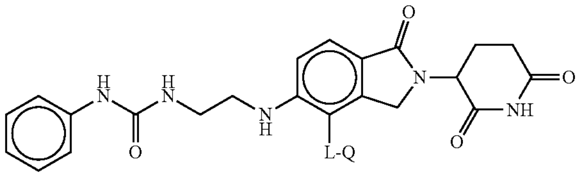
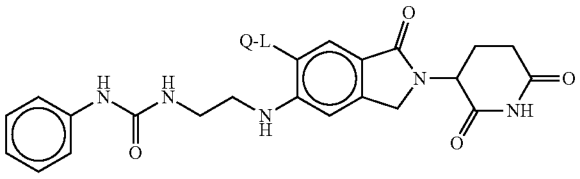

TABLE 2-continued
| Embodiments of general formula $(A)_k$-L-Q, having L-Q moiety. |
| --- |
| 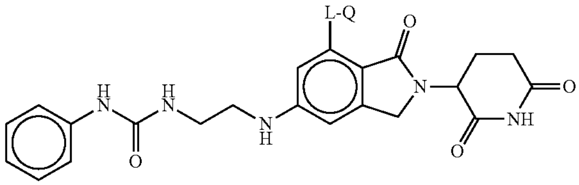 |
| 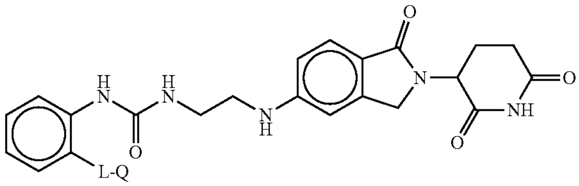 |
| 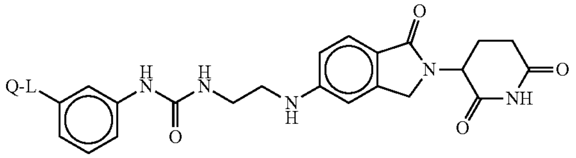 |
| 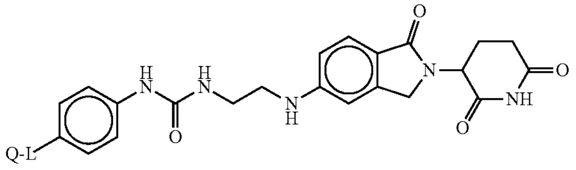 |
| 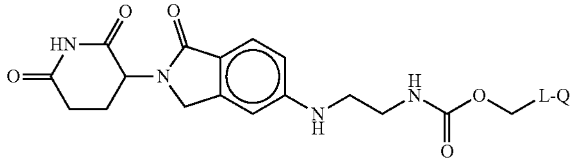 |
| 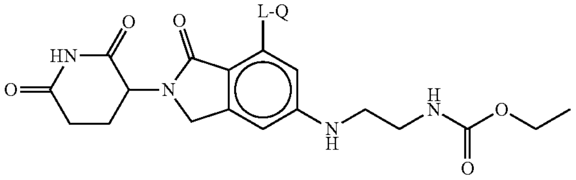 |
| 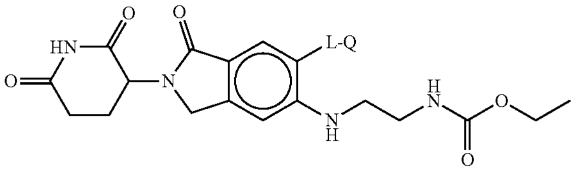 |
| 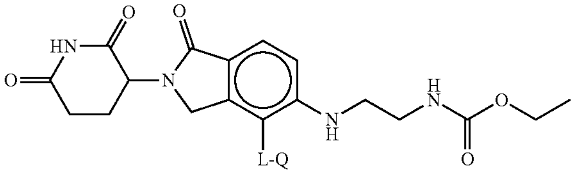 |
TABLE 2-continued
| Embodiments of general formula $(A)_k$-L-Q, having L-Q moiety. |
| --- |
| 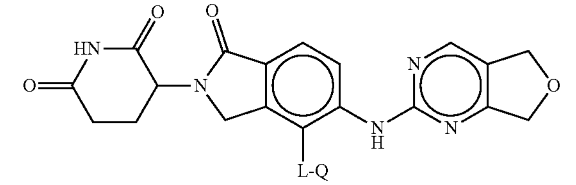 |
| 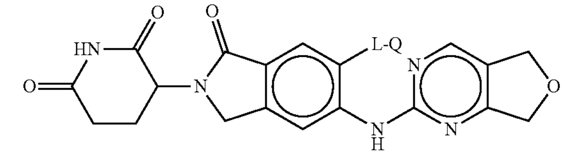 |
| 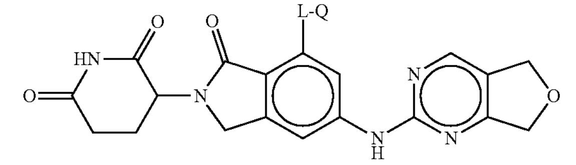 |
| 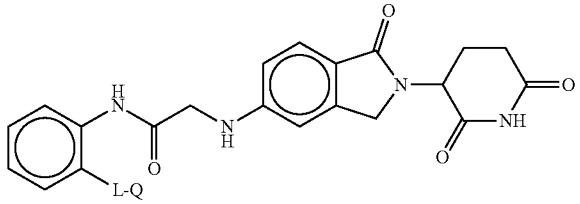 |
| 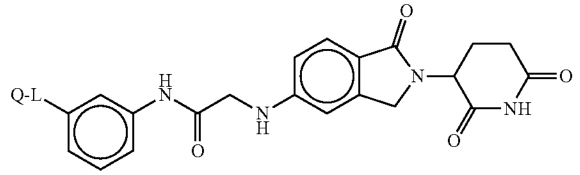 |
| 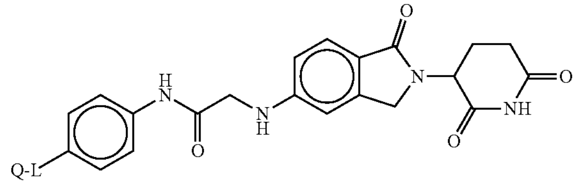 |
| 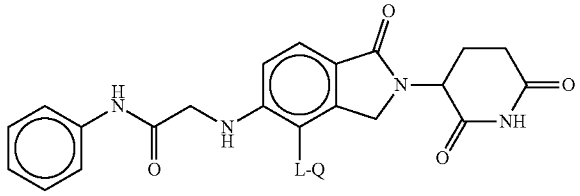 |
| 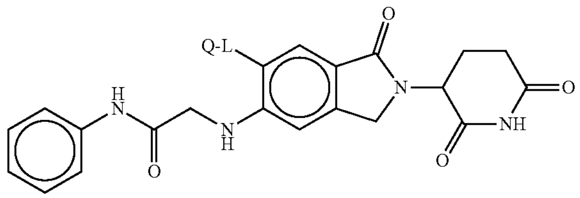 |

TABLE 2-continued
| Embodiments of general formula $(A)_k$-L-Q, having L-Q moiety. |
|---|
| 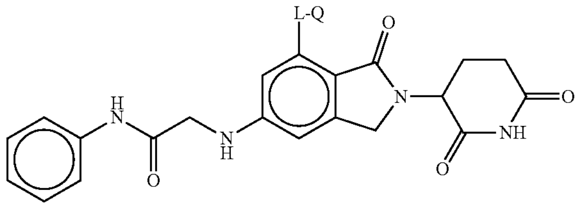 |
| 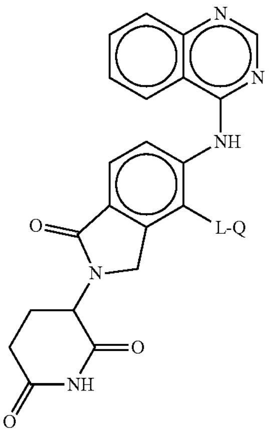 |
| 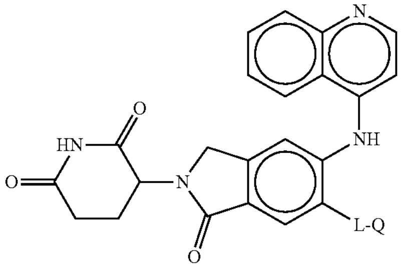 |
| 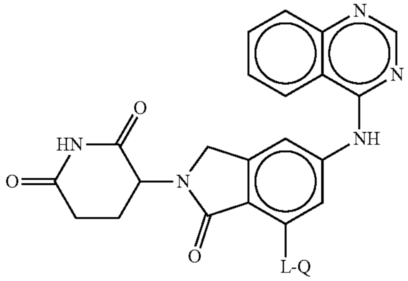 |
| 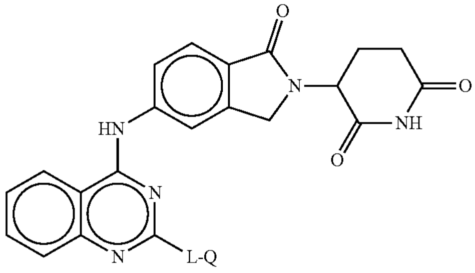 |
TABLE 2-continued
| Embodiments of general formula $(A)_k$-L-Q, having L-Q moiety. |
|---|
| 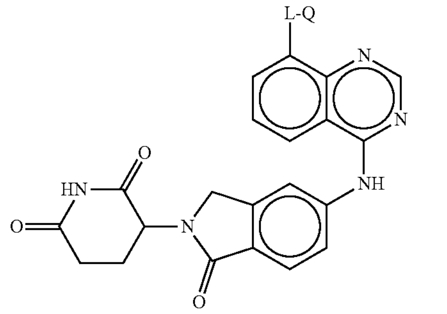 |
| 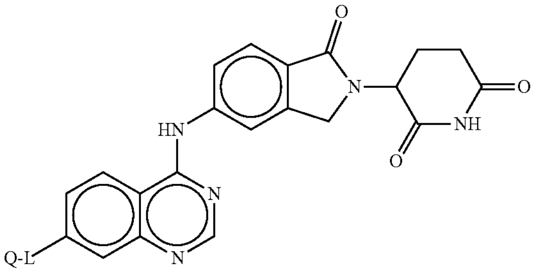 |
| 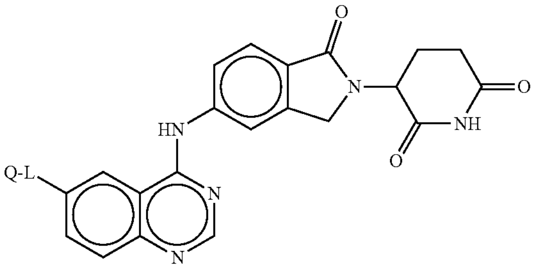 |
| 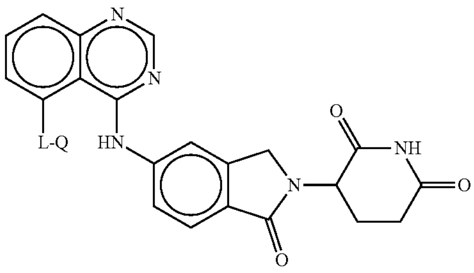 |
| 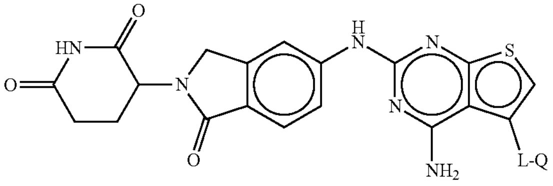 |
| 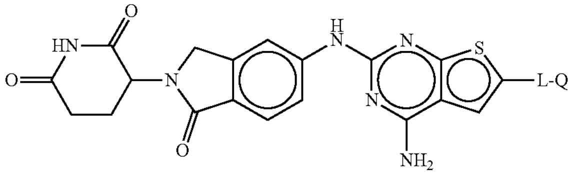 |

TABLE 2-continued
Embodiments of general formula $(A)_k$-L-Q, having L-Q moiety.
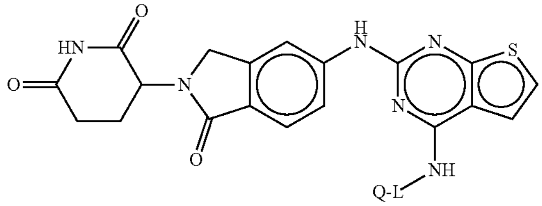
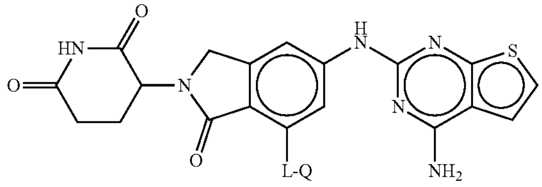
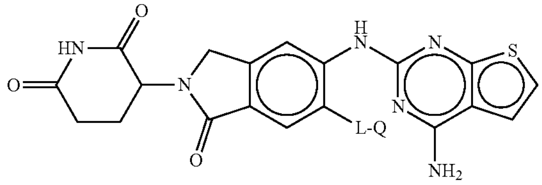
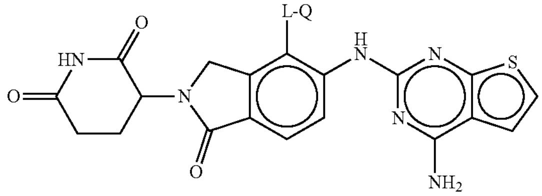
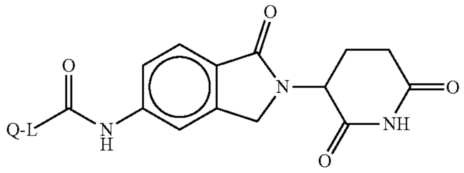
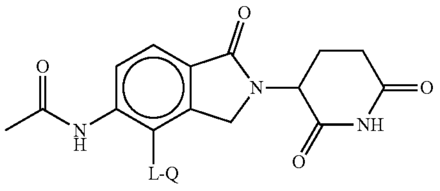
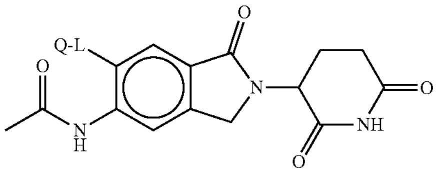
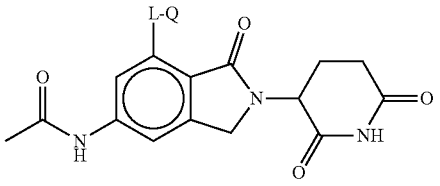
TABLE 2-continued
Embodiments of general formula $(A)_k$-L-Q, having L-Q moiety.
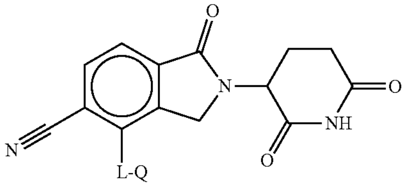
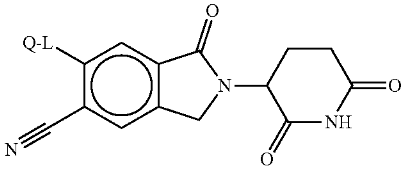
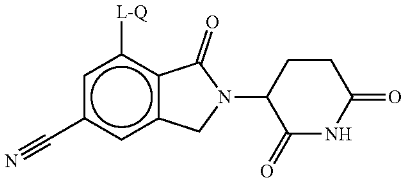
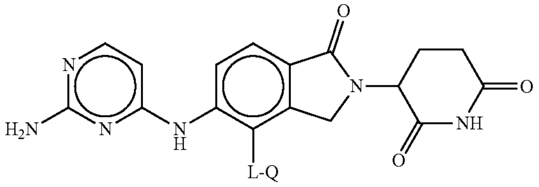
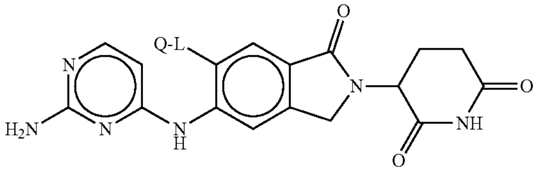
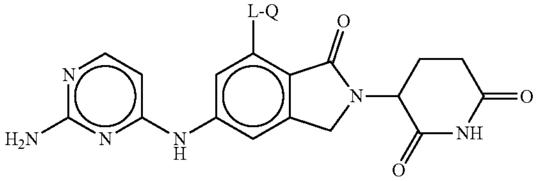
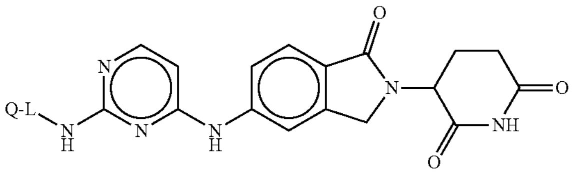
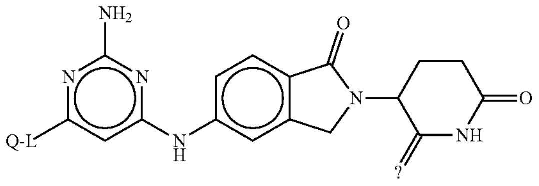

TABLE 2-continued
| Embodiments of general formula $(A)_k$-L-Q, having L-Q moiety. |
|---|
| 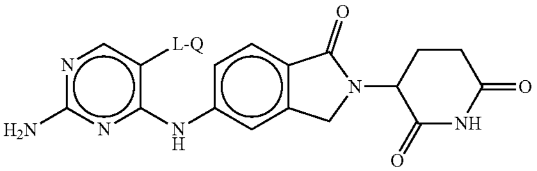 |
| 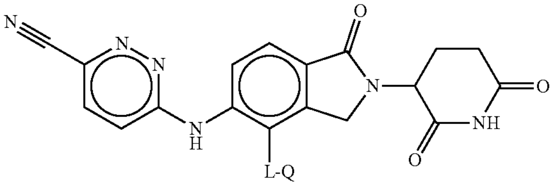 |
| 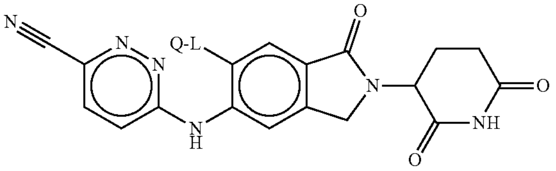 |
| 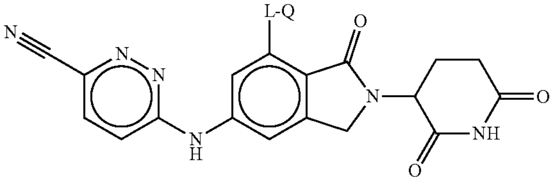 |
| 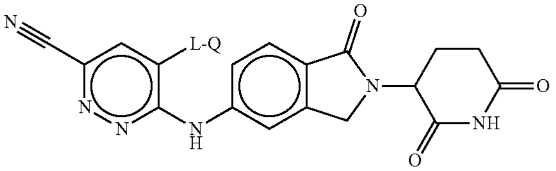 |
| 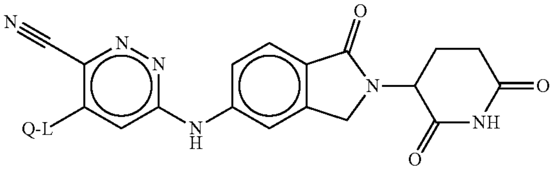 |
| 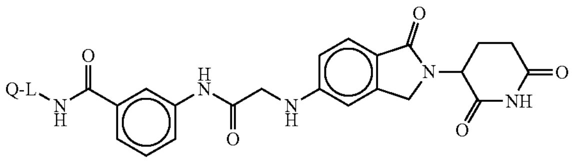 |
| 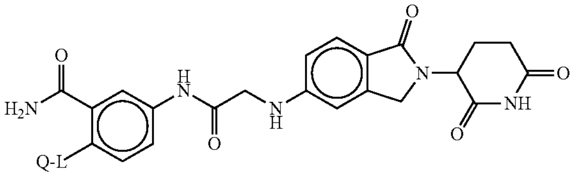 |
TABLE 2-continued
| Embodiments of general formula $(A)_k$-L-Q, having L-Q moiety. |
|---|
| 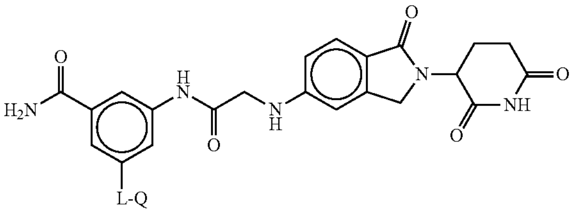 |
| 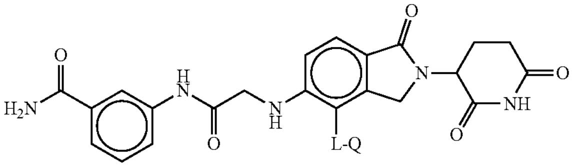 |
| 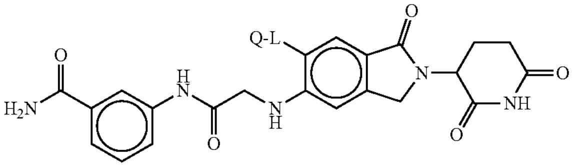 |
| 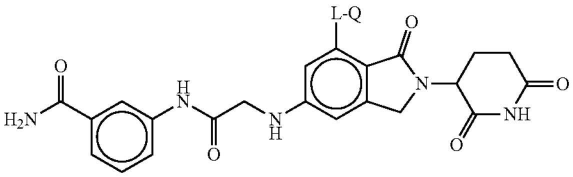 |
| 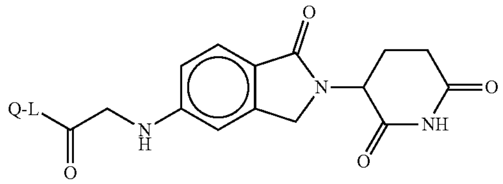 |
| 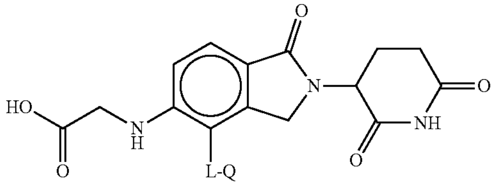 |
| 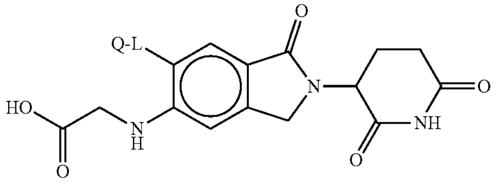 |
| 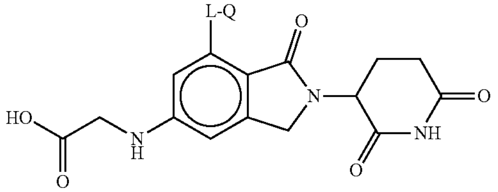 |

TABLE 2-continued
| Embodiments of general formula $(A)_k$-L-Q, having L-Q moiety. |
|---|
| 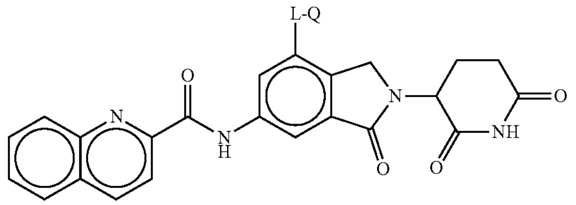 |
| 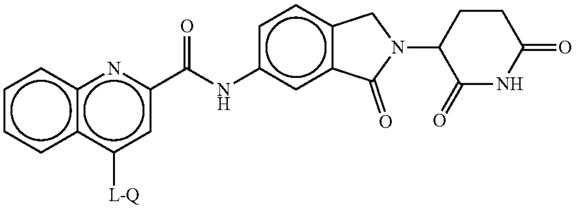 |
| 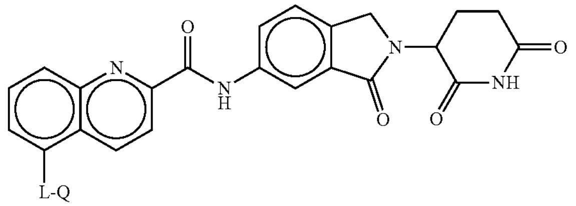 |
| 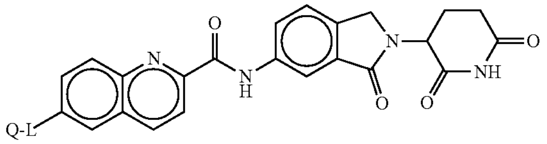 |
| 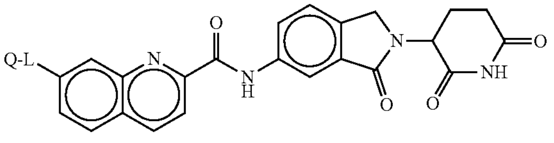 |
| 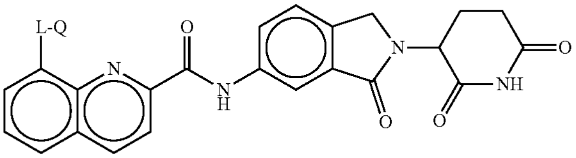 |
| 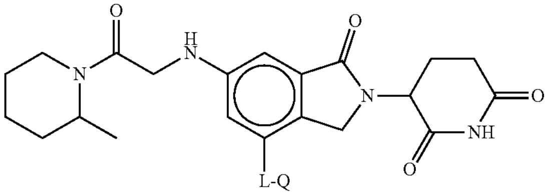 |
| 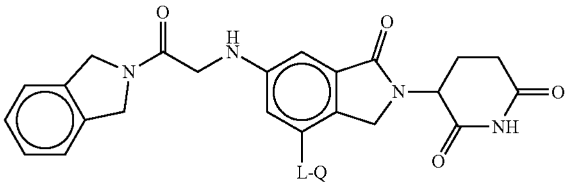 |
TABLE 2-continued
| Embodiments of general formula $(A)_k$-L-Q, having L-Q moiety. |
|---|
| 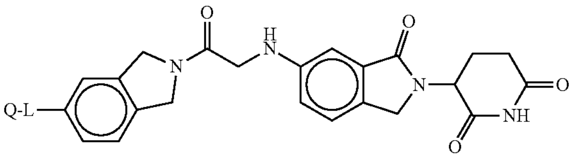 |
| 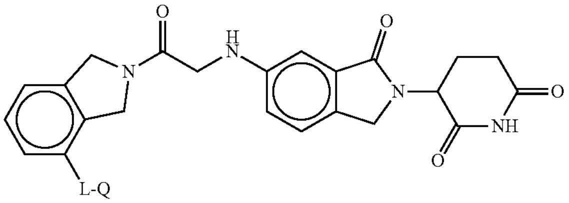 |
| 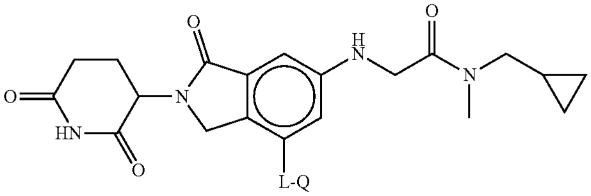 |
| 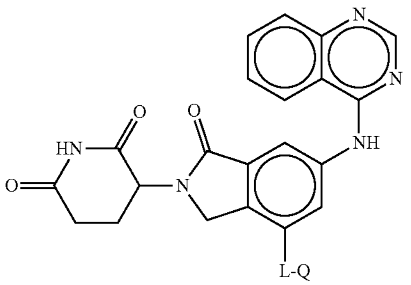 |
| 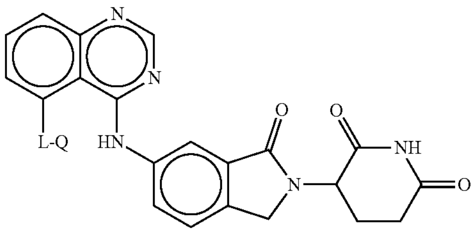 |
| 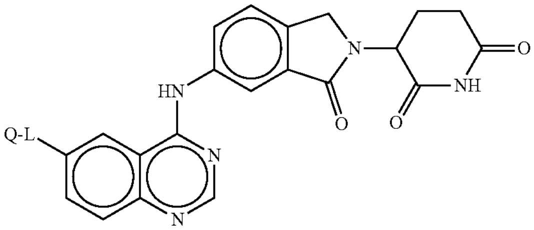 |
| 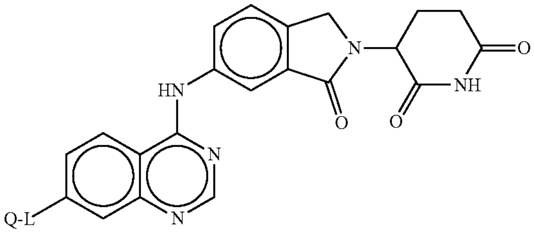 |

TABLE 2-continued
| Embodiments of general formula $(A)_k$-L-Q, having L-Q moiety. |
|---|
| 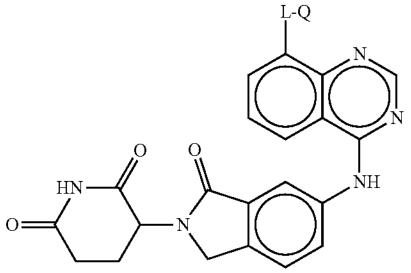 |
| 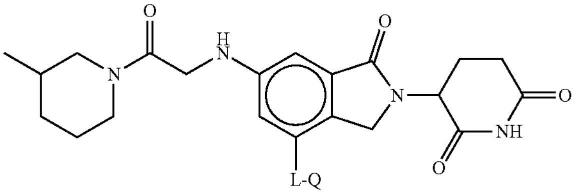 |
| 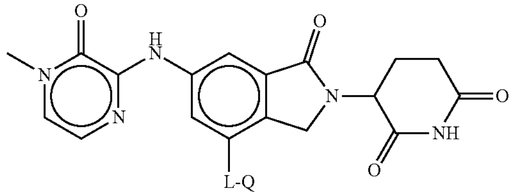 |
| 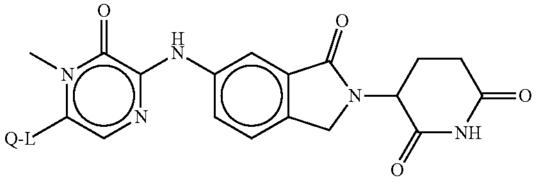 |
| 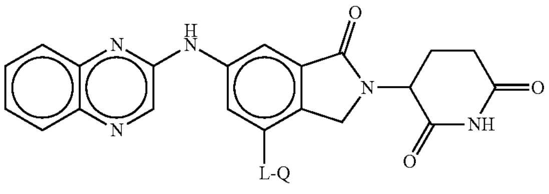 |
| 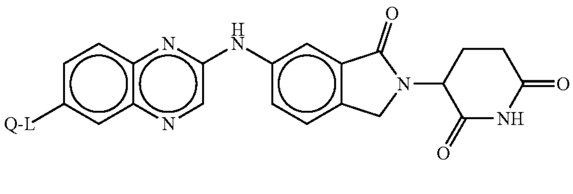 |
| 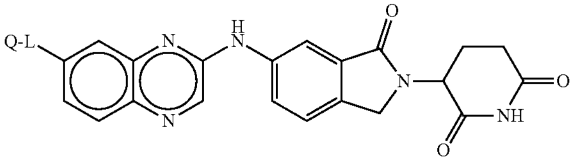 |
TABLE 2-continued
| Embodiments of general formula $(A)_k$-L-Q, having L-Q moiety. |
|---|
| 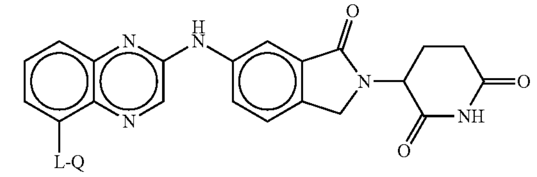 |
| 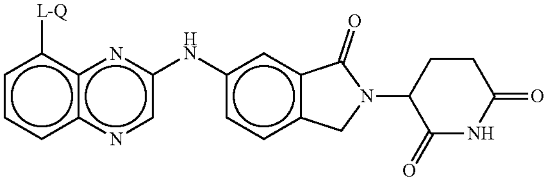 |
| 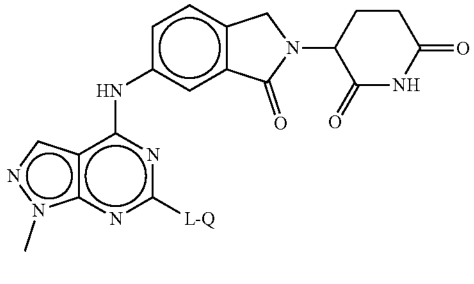 |
| 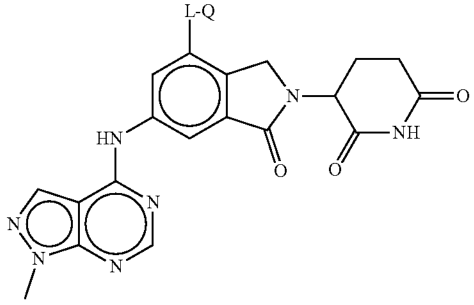 |
| 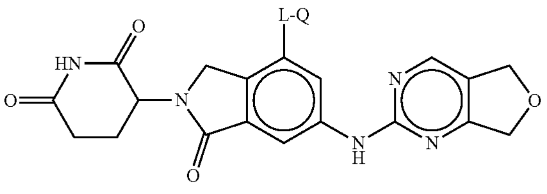 |
| 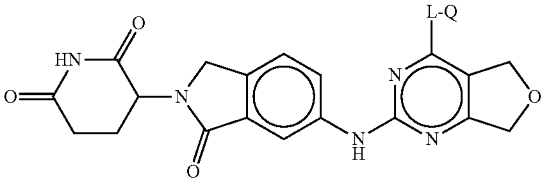 |
| 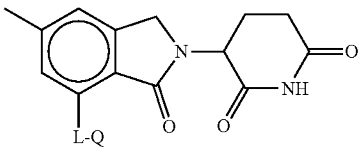 |

TABLE 2-continued
| Embodiments of general formula $(A)_k$-L-Q, having L-Q moiety. |
|---|
| 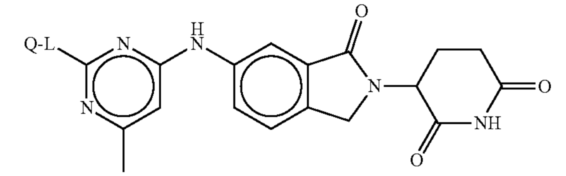 |
| 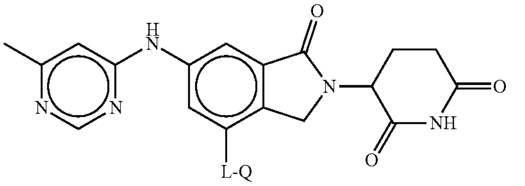 |
| 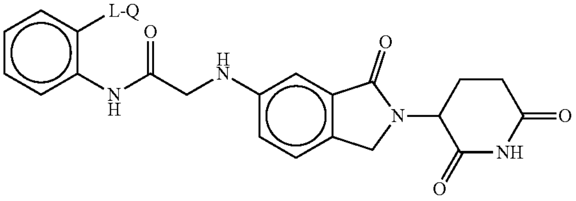 |
| 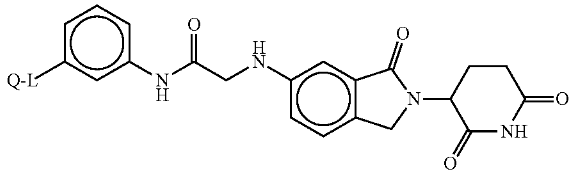 |
| 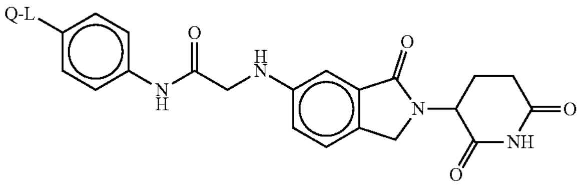 |
| 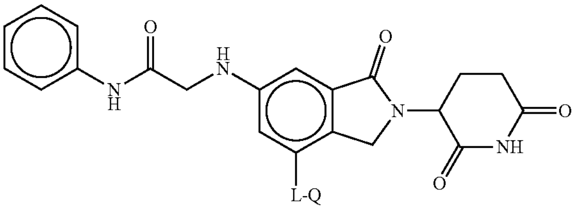 |
| 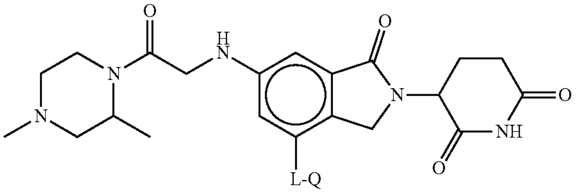 |
| 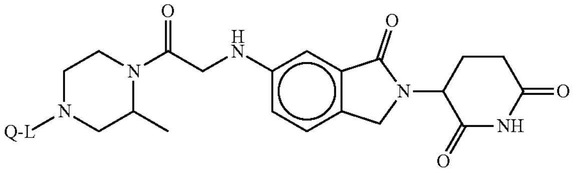 |
TABLE 2-continued
| Embodiments of general formula $(A)_k$-L-Q, having L-Q moiety. |
|---|
| 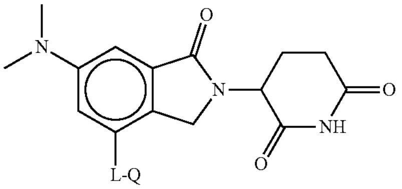 |
| 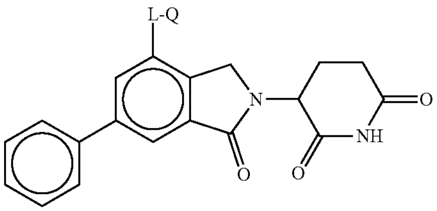 |
| 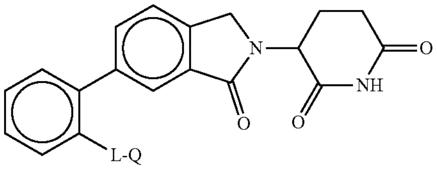 |
| 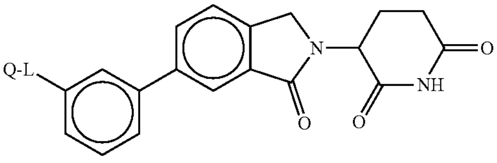 |
| 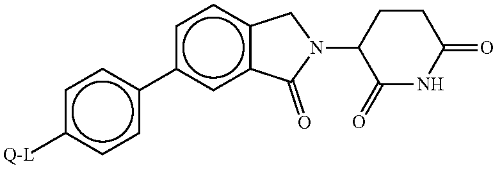 |
| 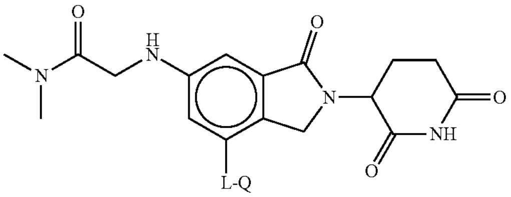 |
| 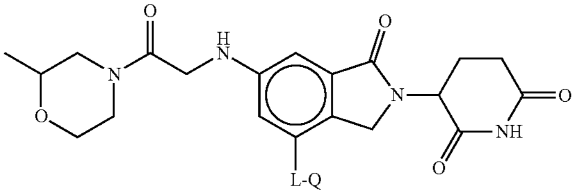 |
| 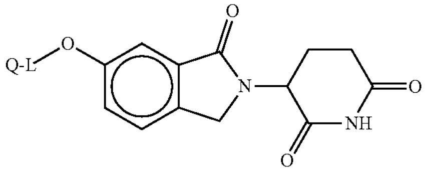 |

TABLE 2-continued
| Embodiments of general formula $(A)_k$-L-Q, having L-Q moiety. |
|---|
| 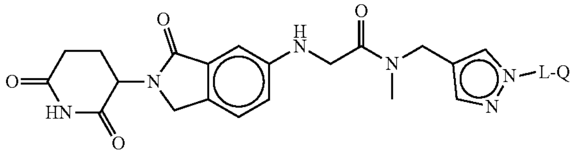 |
| 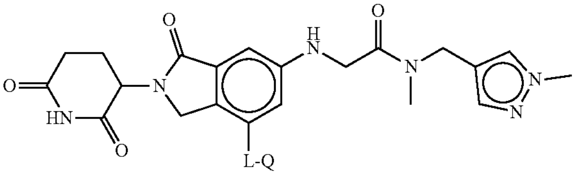 |
| 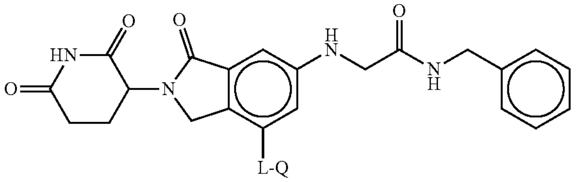 |
| 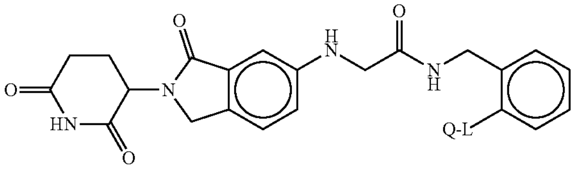 |
| 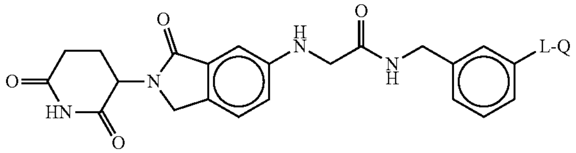 |
| 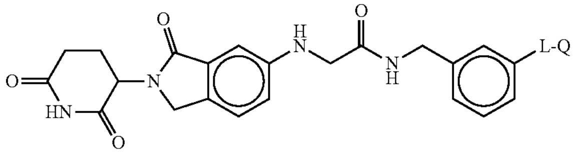 |
| 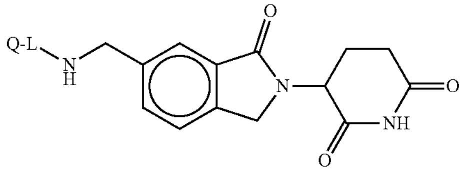 |
| 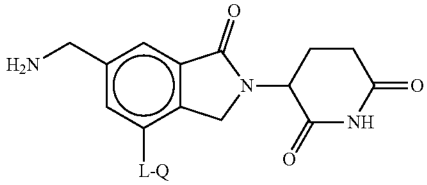 |
TABLE 2-continued
| Embodiments of general formula $(A)_k$-L-Q, having L-Q moiety. |
|---|
| 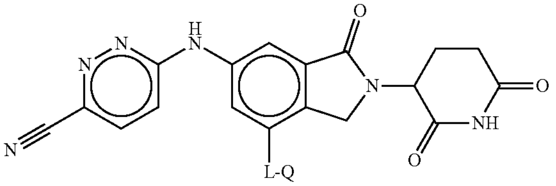 |
| 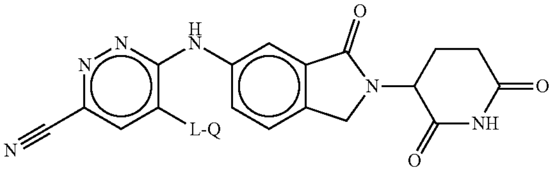 |
| 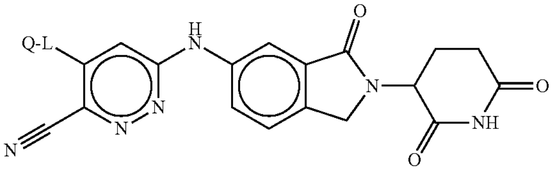 |
| 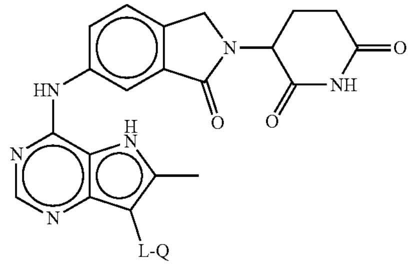 |
| 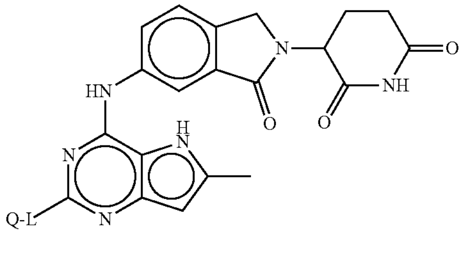 |
| 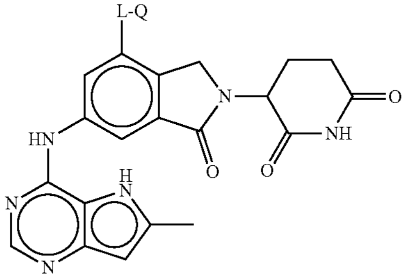 |
| 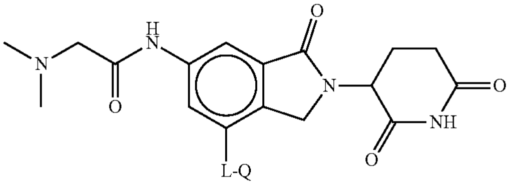 |

TABLE 2-continued
| Embodiments of general formula $(A)_k$-L-Q, having L-Q moiety. |
| --- |
| 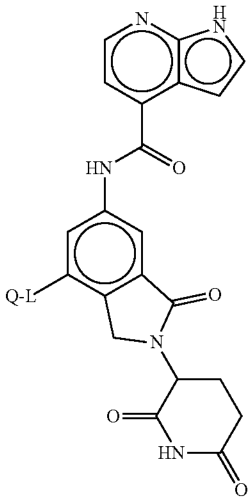 |
| 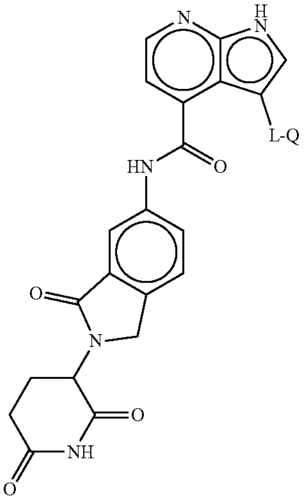 |
| 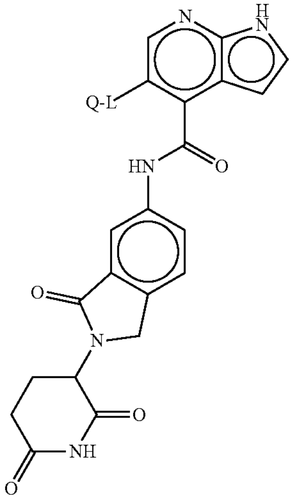 |
TABLE 2-continued
| Embodiments of general formula $(A)_k$-L-Q, having L-Q moiety. |
| --- |
| 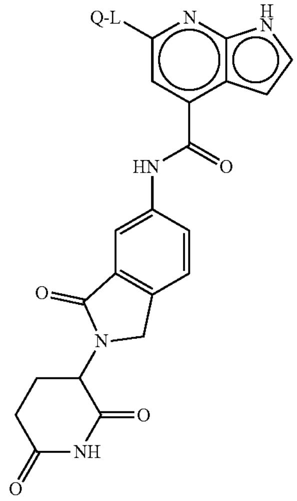 |
| 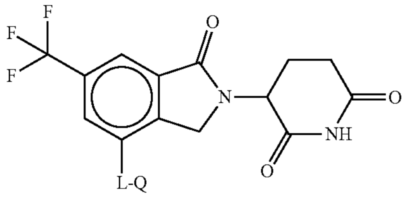 |
| 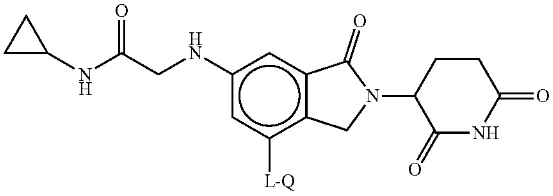 |
| 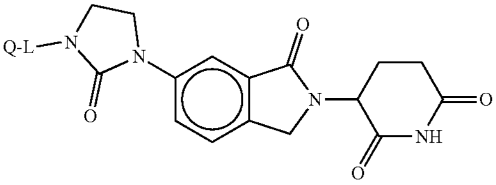 |
| 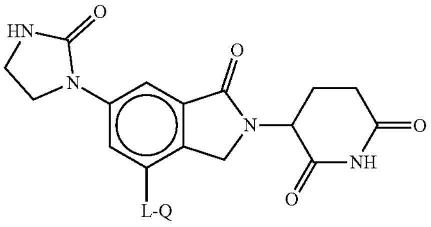 |
| 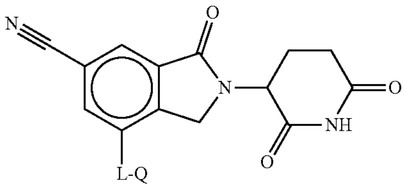

TABLE 2-continued
| Embodiments of general formula $(A)_k$-L-Q, having L-Q moiety. |
|---|
| 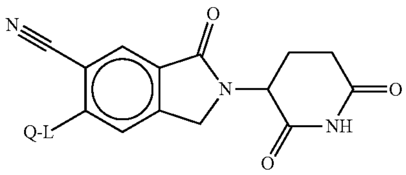 |
| 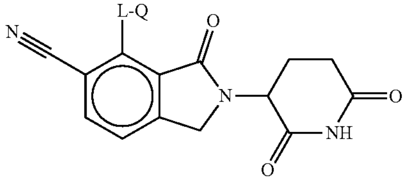 |
| 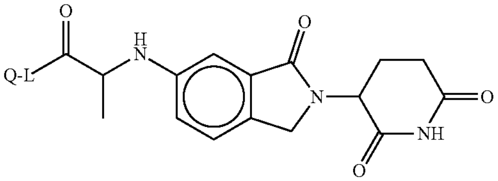 |
| 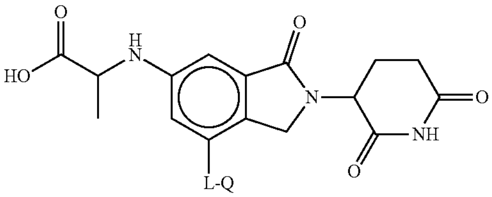 |
| 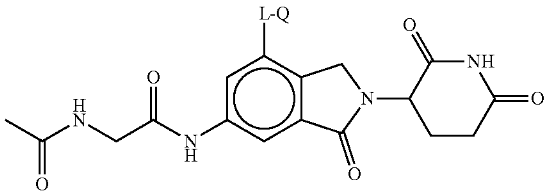 |
| 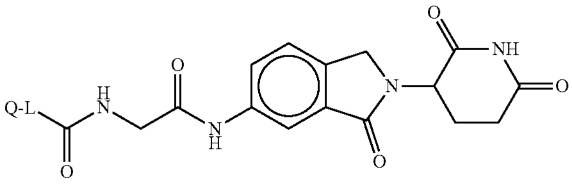 |
| 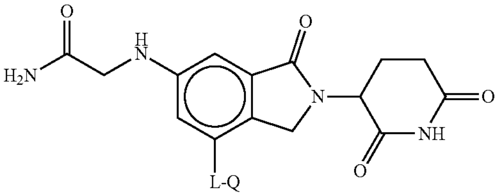 |
| 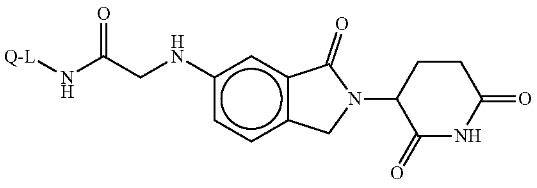 |
TABLE 2-continued
| Embodiments of general formula $(A)_k$-L-Q, having L-Q moiety. |
|---|
| 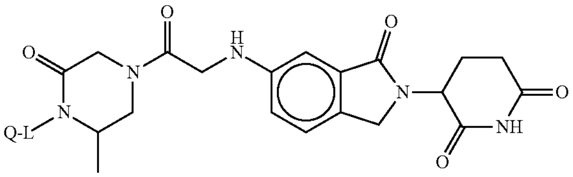 |
| 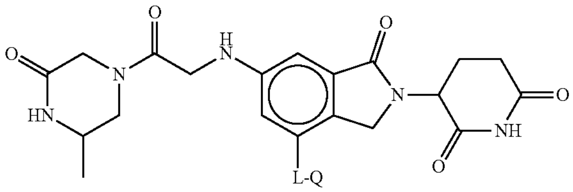 |
| 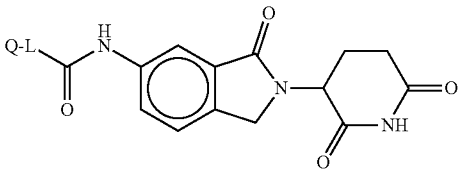 |
| 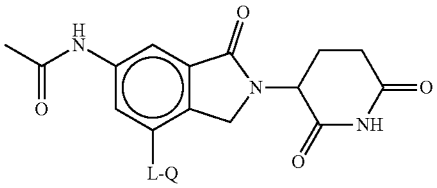 |
| 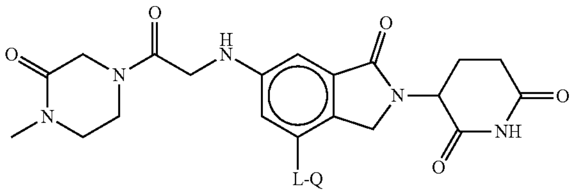 |
| 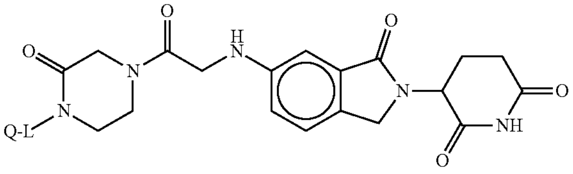 |
| 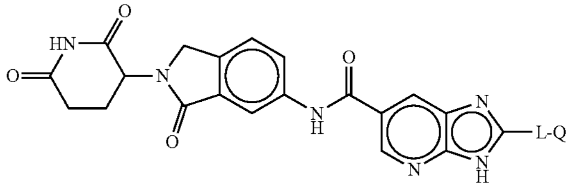 |
| 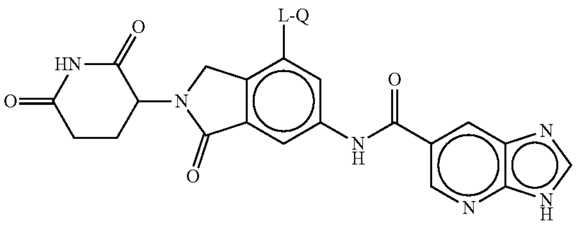 |

TABLE 2-continued
Embodiments of general formula $(A)_k$-L-Q, having L-Q moiety.
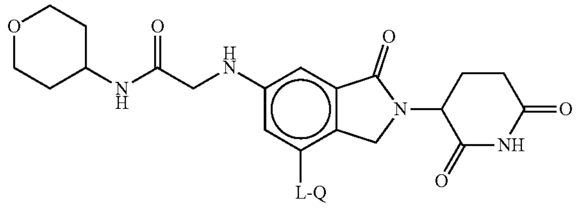
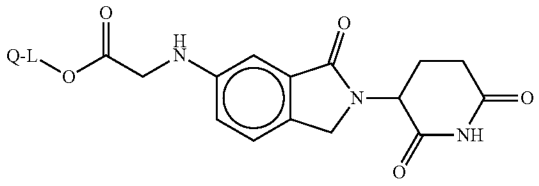
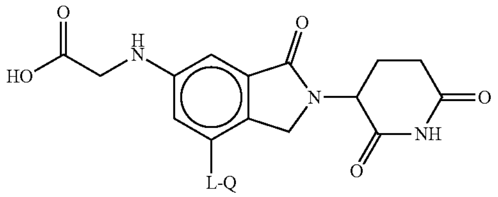
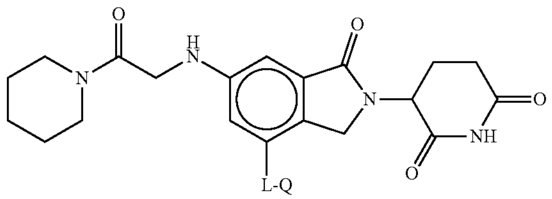
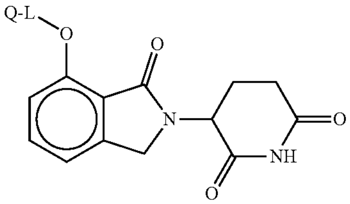
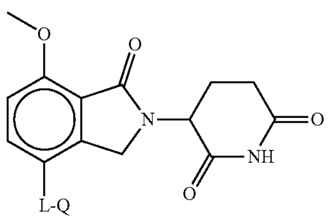
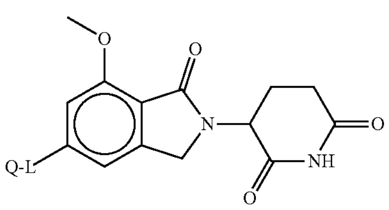
TABLE 2-continued
Embodiments of general formula $(A)_k$-L-Q, having L-Q moiety.
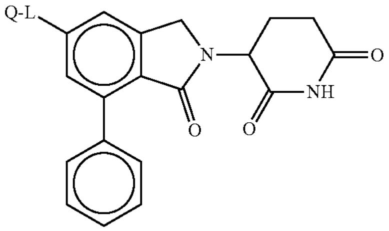
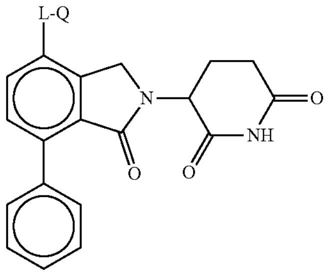
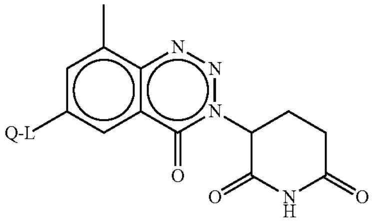
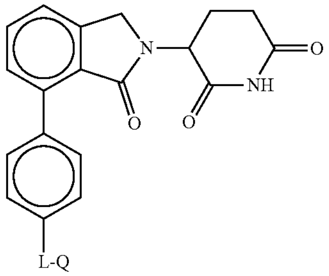
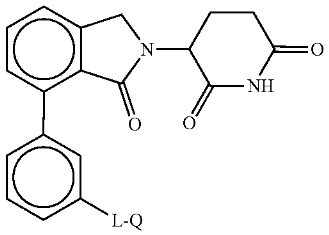
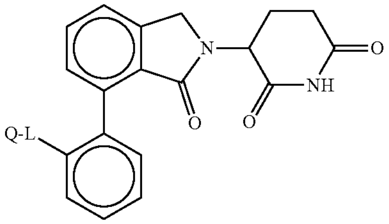

TABLE 2-continued
| Embodiments of general formula $(A)_k$-L-Q, having L-Q moiety. |
|---|
| 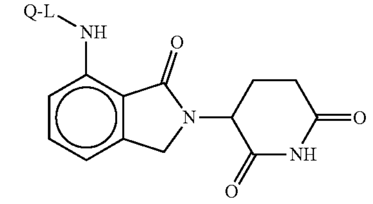 |
| 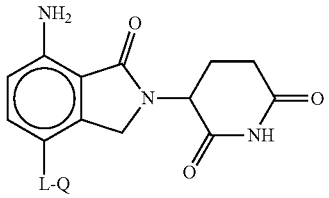 |
| 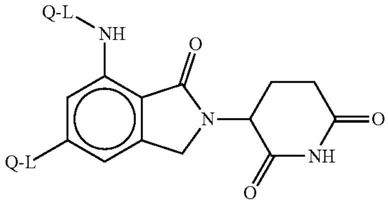 |
| 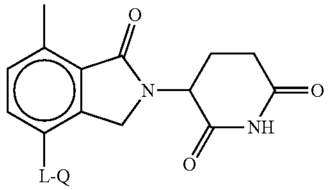 |
| 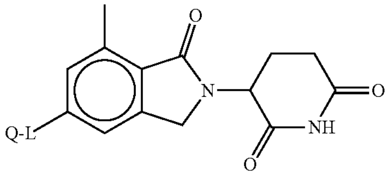 |
| 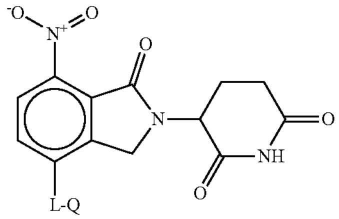 |
| 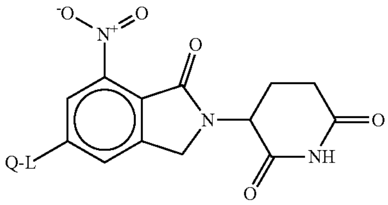 |
TABLE 2-continued
| Embodiments of general formula $(A)_k$-L-Q, having L-Q moiety. |
|---|
| 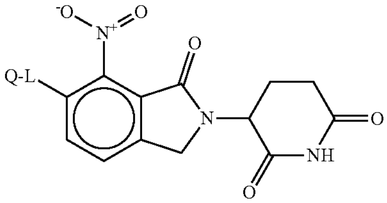 |
| 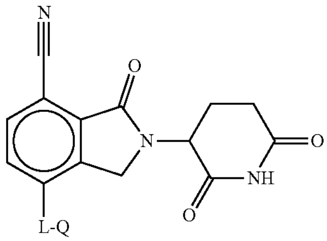 |
| 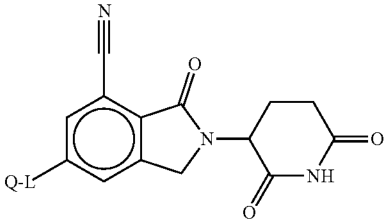 |
| 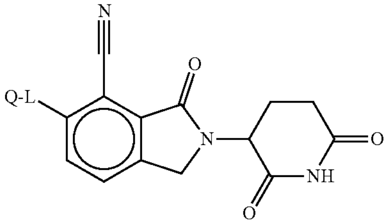 |
| 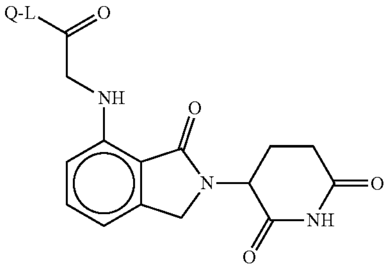 |
| 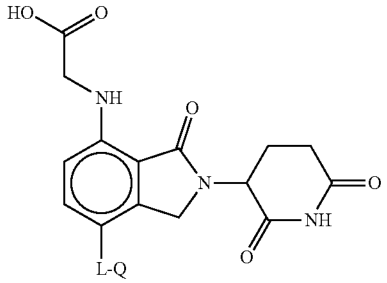 |

TABLE 2-continued
Embodiments of general formula $(A)_k$-L-Q, having L-Q moiety.
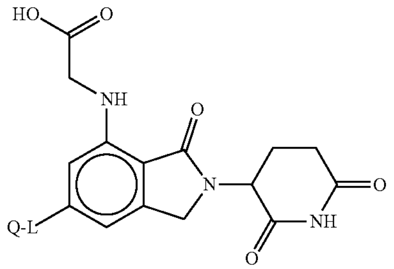
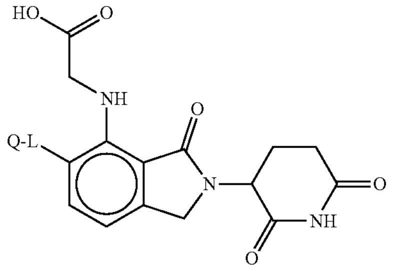
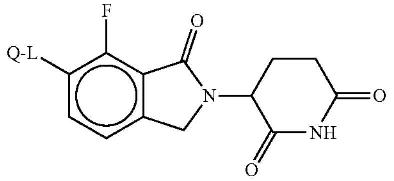
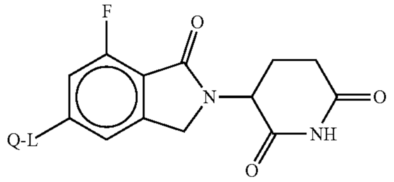
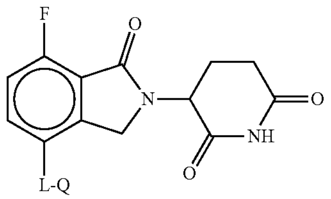
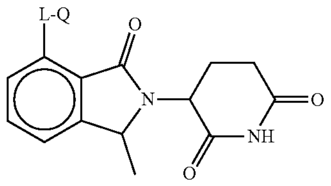
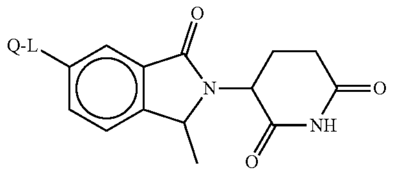
TABLE 2-continued
Embodiments of general formula $(A)_k$-L-Q, having L-Q moiety.
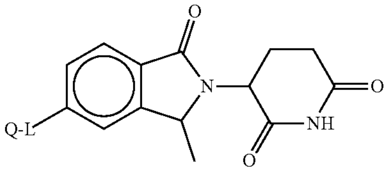
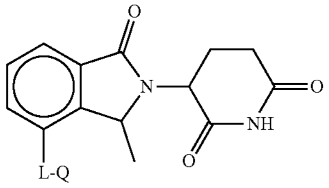
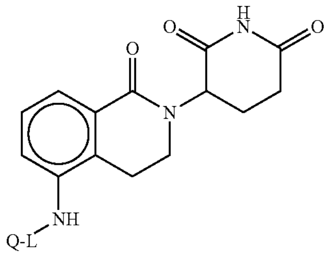
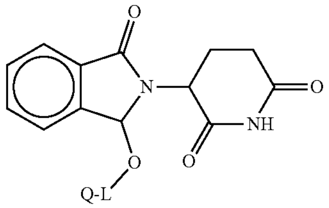
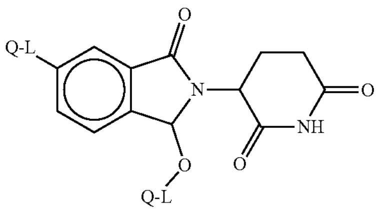
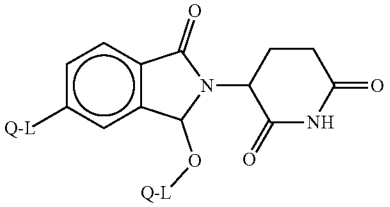
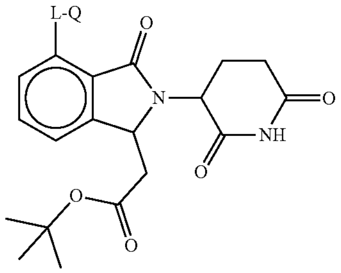

TABLE 2-continued
| Embodiments of general formula $(A)_k$-L-Q, having L-Q moiety. |
|---|
| 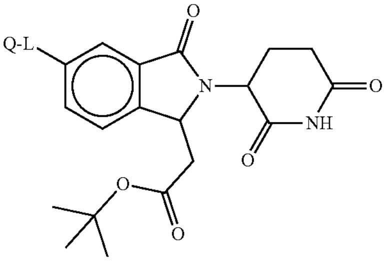 |
| 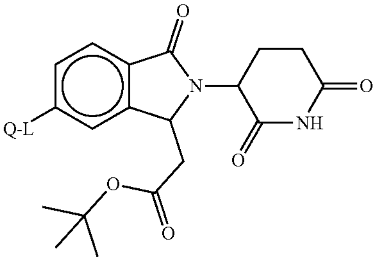 |
| 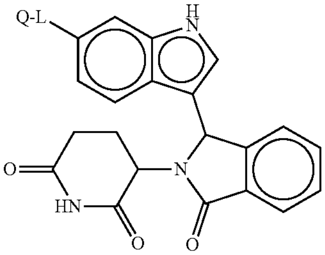 |
| 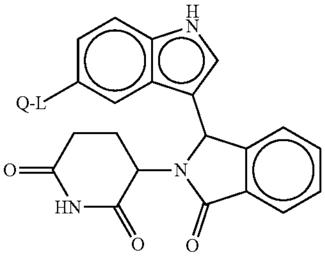 |
| 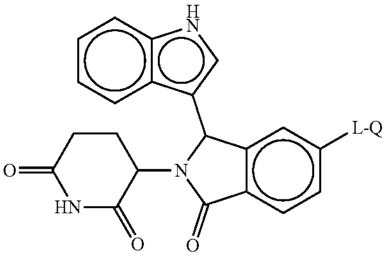 |
| 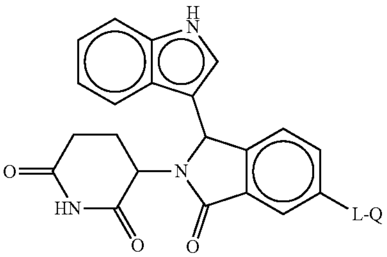 |
TABLE 2-continued
| Embodiments of general formula $(A)_k$-L-Q, having L-Q moiety. |
|---|
| 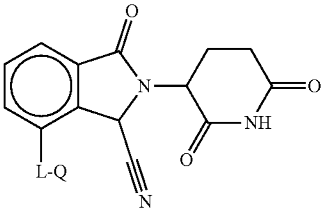 |
| 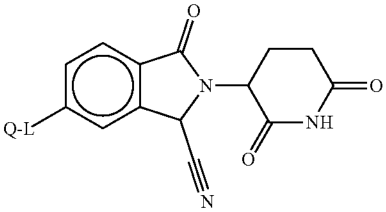 |
| 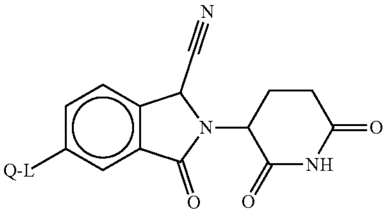 |
| 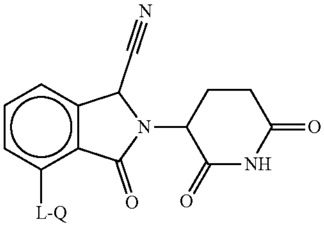 |
| 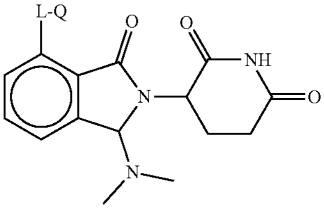 |
| 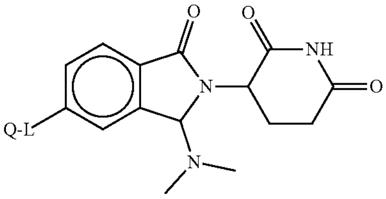 |
| 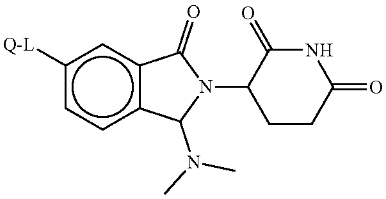 |

TABLE 2-continued
| Embodiments of general formula $(A)_k$-L-Q, having L-Q moiety. |
|---|
| 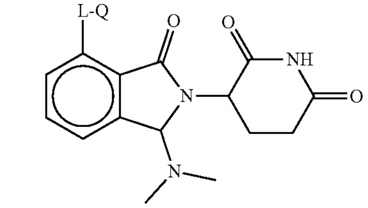 |
| 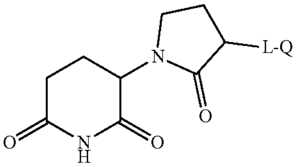 |
| 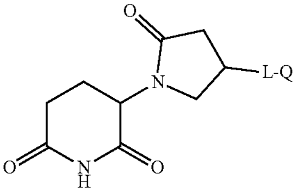 |
| 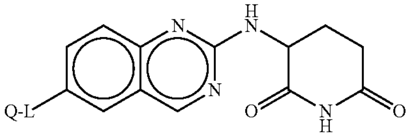 |
| 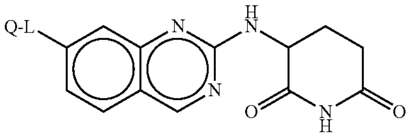 |
| 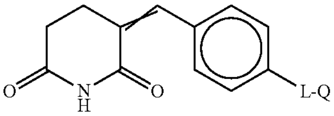 |
| 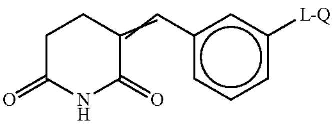 |
| 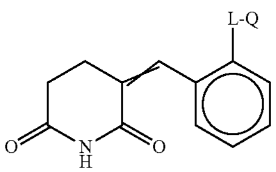 |
| 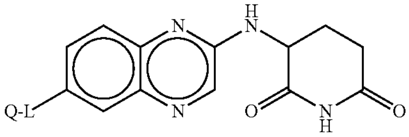 |
TABLE 2-continued
| Embodiments of general formula $(A)_k$-L-Q, having L-Q moiety. |
|---|
| 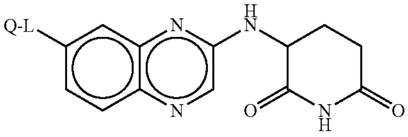 |
| 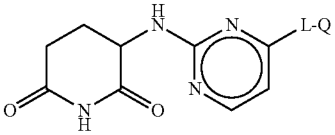 |
| 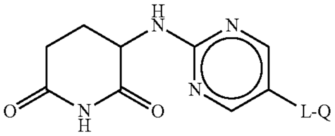 |
| 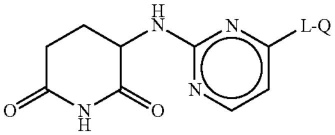 |
| 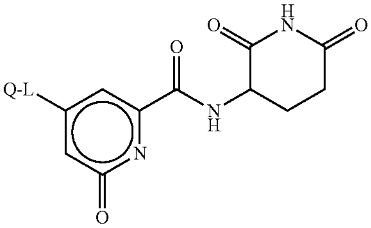 |
| 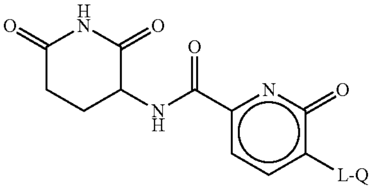 |
| 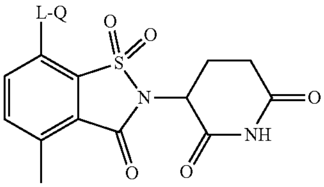 |
| 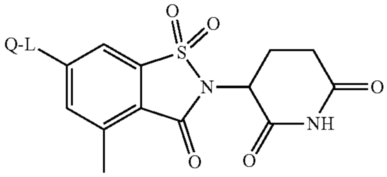 |
| 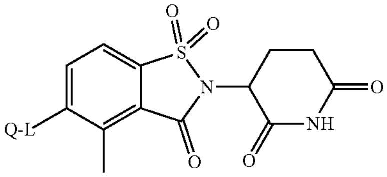 |

TABLE 2-continued
| Embodiments of general formula $(A)_k$-L-Q, having L-Q moiety. |
| --- |
| 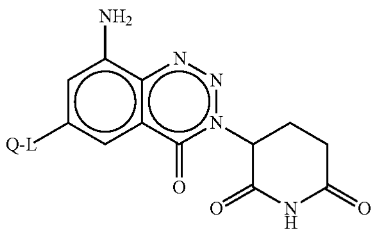 |
| 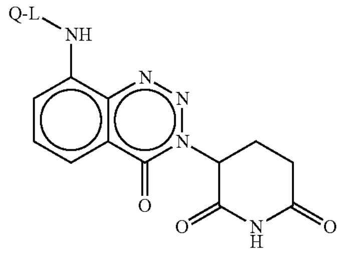 |
| 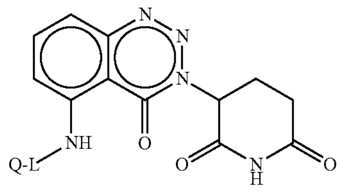 |
| 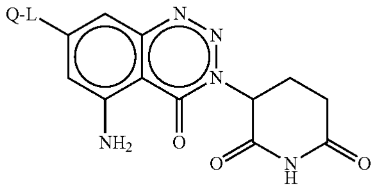 |
| 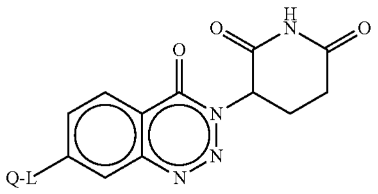 |
| 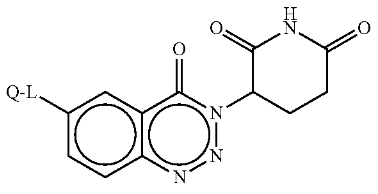 |
TABLE 2-continued
| Embodiments of general formula $(A)_k$-L-Q, having L-Q moiety. |
| --- |
| 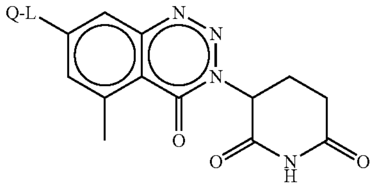 |
| 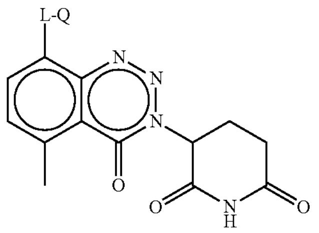 |
| 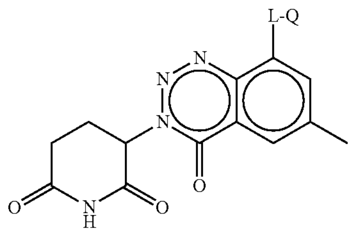 |
| 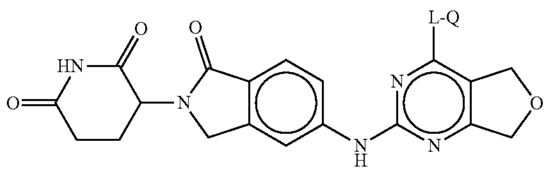 |
| 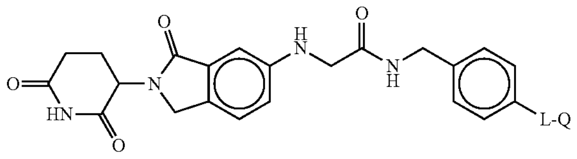 |
| 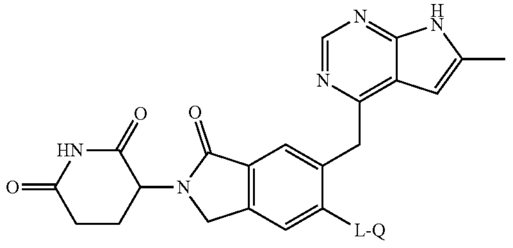 |

TABLE 3
| Embodiments of general formula $(A)_k$-L-Q, having Q moiety. | |
|---|---|
| 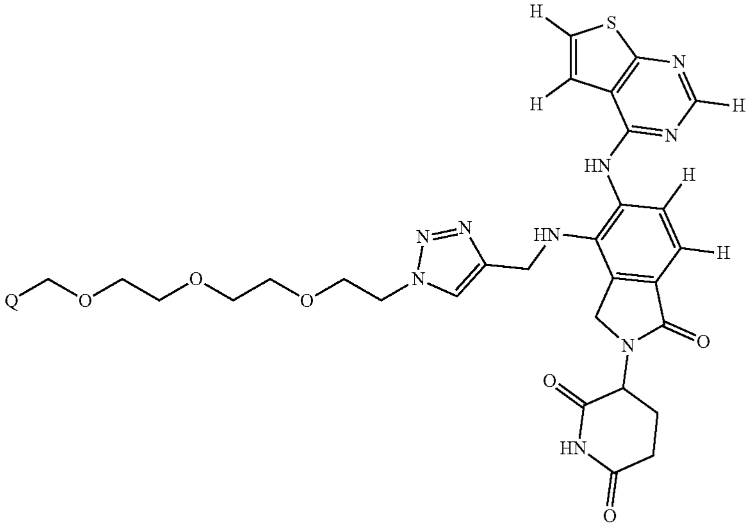 | 3.001 |
| 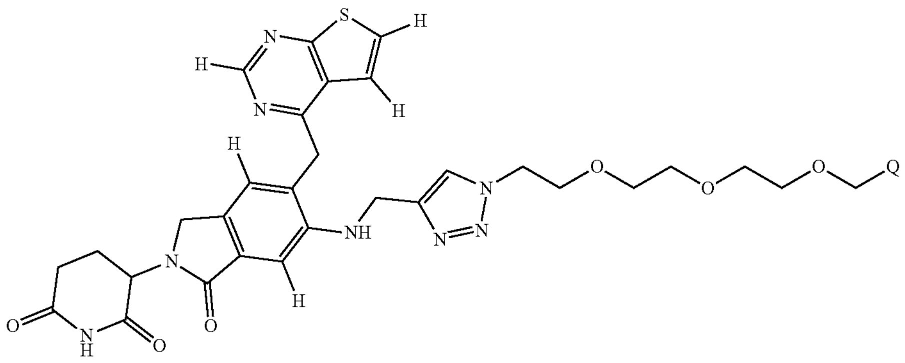 | 3.002 |
| 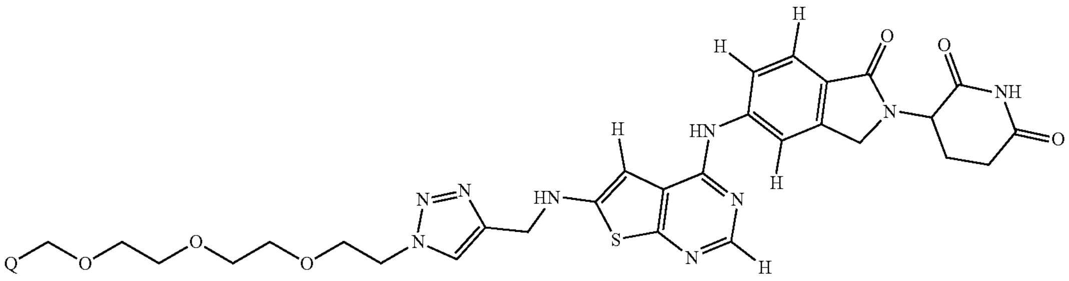 | 3.003 |

TABLE 3-continued
| Embodiments of general formula $(A)_k$-L-Q, having Q moiety. | |
|---|---|
| 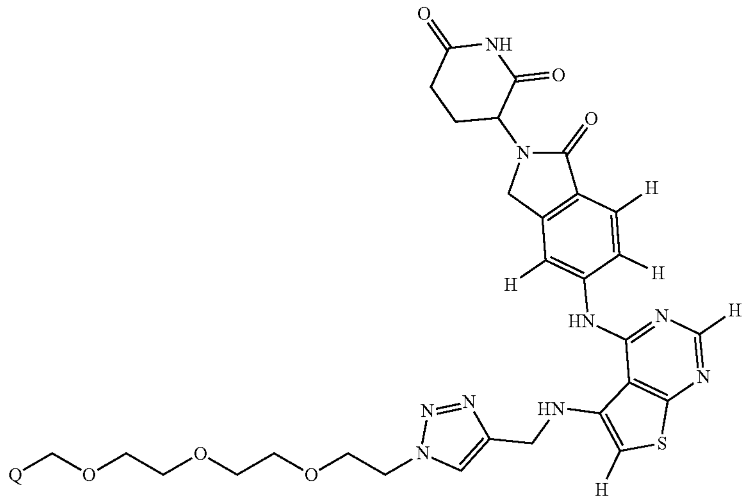 | 3.004 |
| 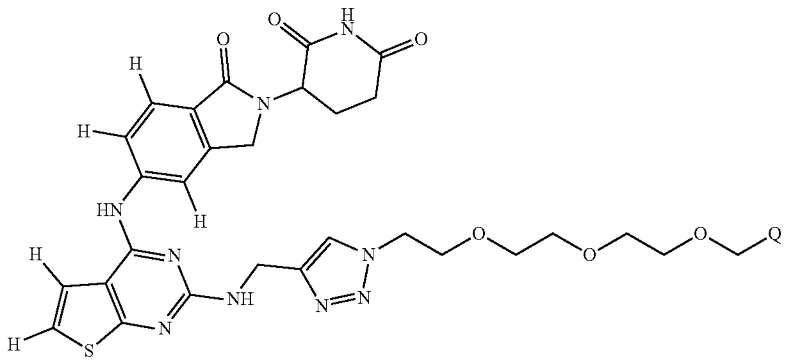 | 3.005 |
| 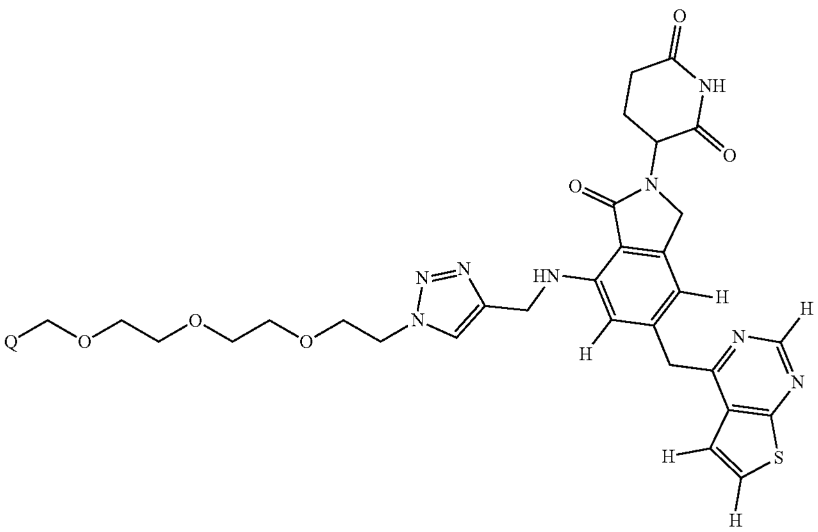 | 3.006 |

TABLE 3-continued
Embodiments of general formula $(A)_k$-L-Q, having Q moiety.
3.007
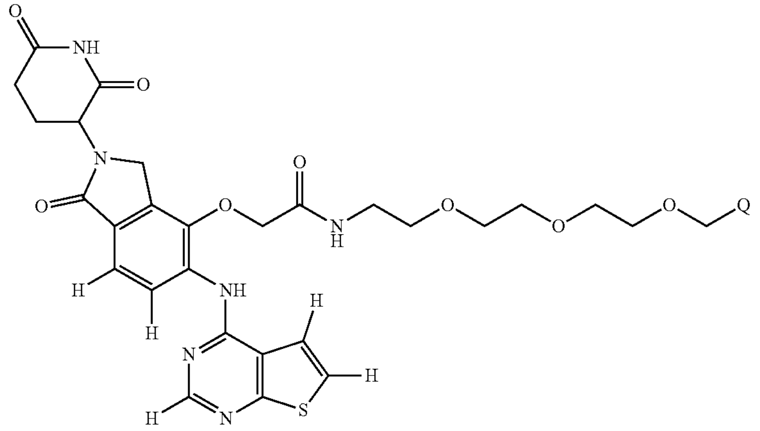
3.008
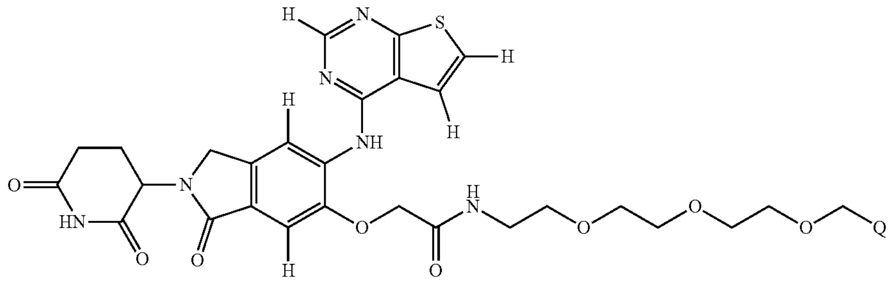
3.009
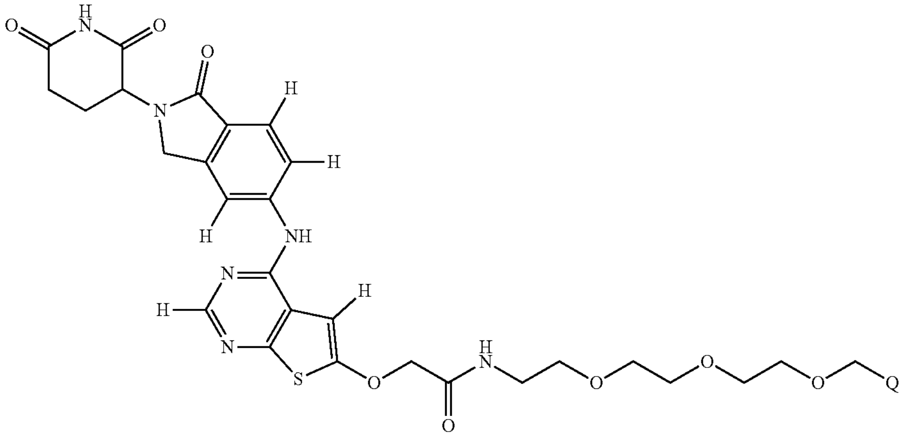

TABLE 3-continued
Embodiments of general formula $(A)_k$-L-Q, having Q moiety.
3.010
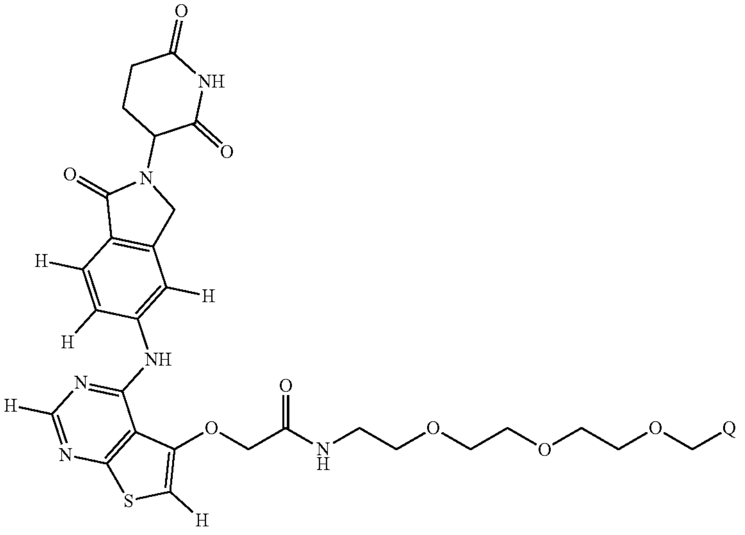
3.011
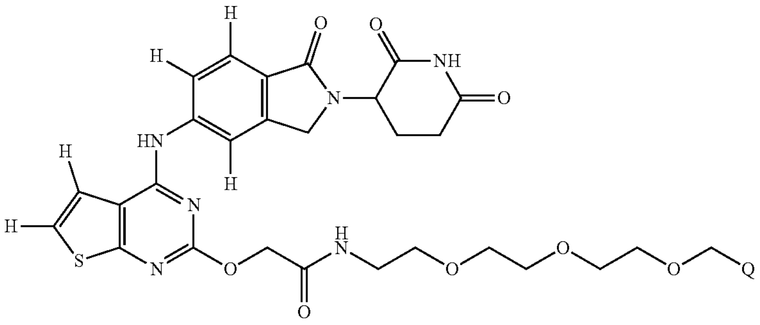
3.012
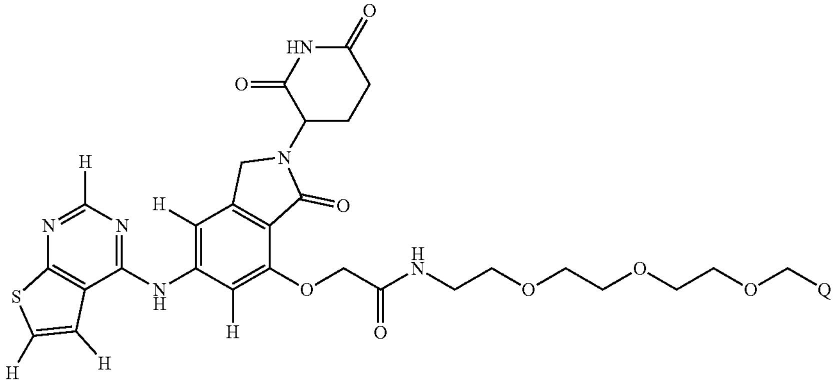

TABLE 3-continued
Embodiments of general formula $(A)_k$-L-Q, having Q moiety.
3.013
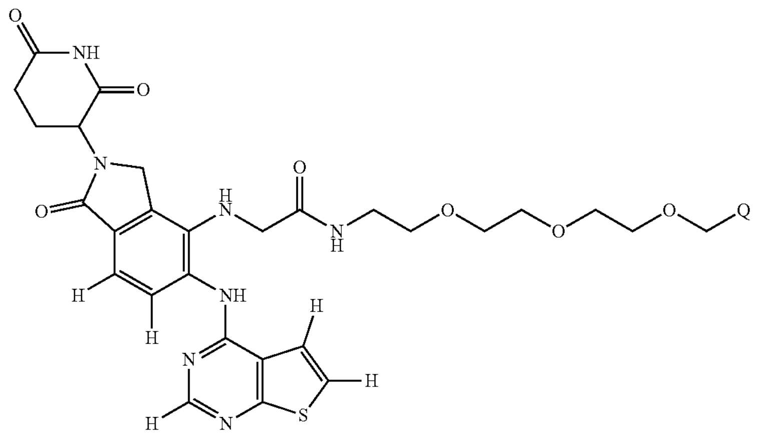
3.014
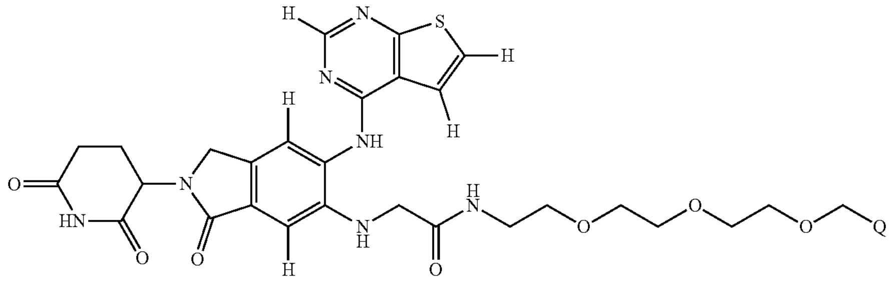
3.015
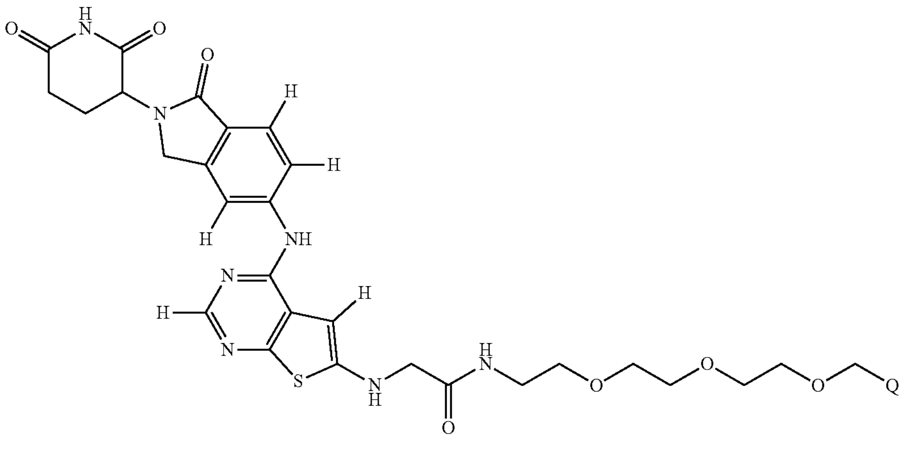

TABLE 3-continued
| Embodiments of general formula $(A)_k$-L-Q, having Q moiety. |
|---|
| 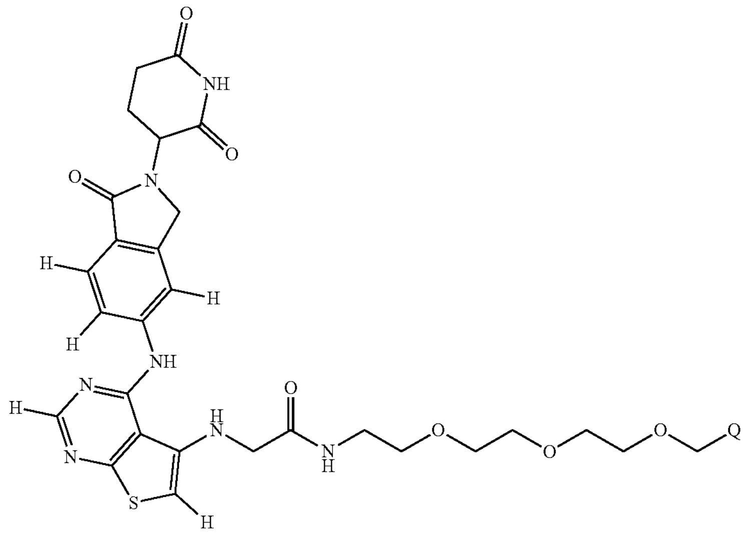 3.016 |
| 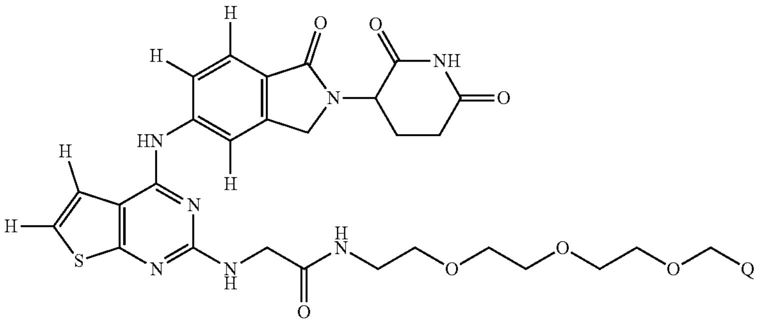 3.017 |
| 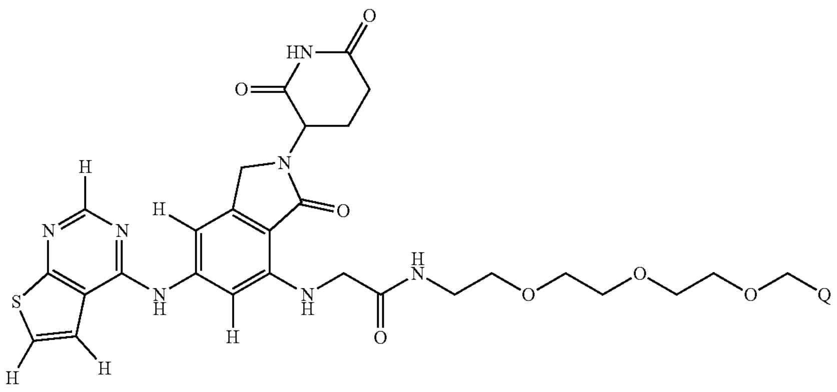 3.018 |

TABLE 3-continued
| Embodiments of general formula $(A)_k$-L-Q, having Q moiety. | |
|---|---|
| 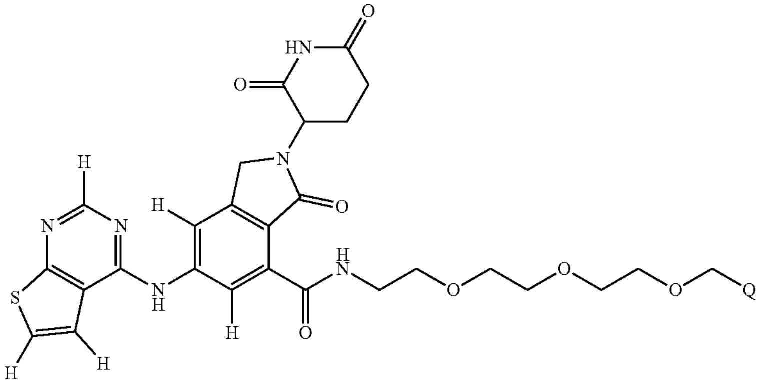 | 3.019 |
| 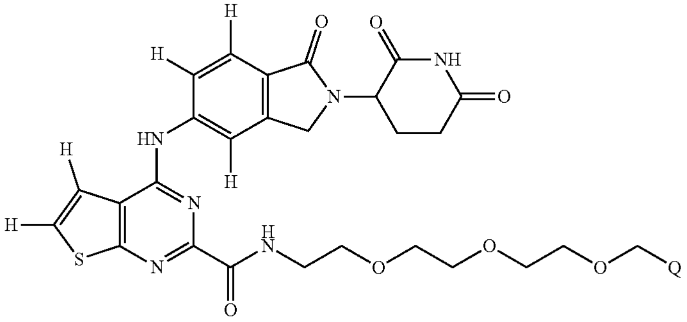 | 3.020 |
| 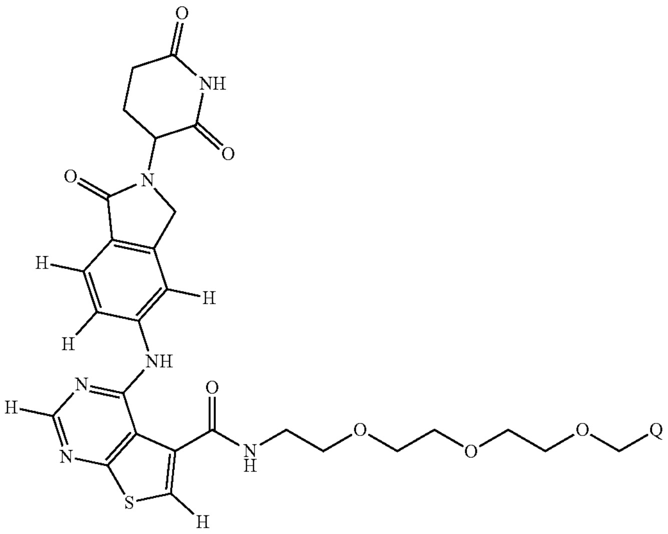 | 3.021 |

TABLE 3-continued
| Embodiments of general formula $(A)_k$-L-Q, having Q moiety. | |
|---|---|
| 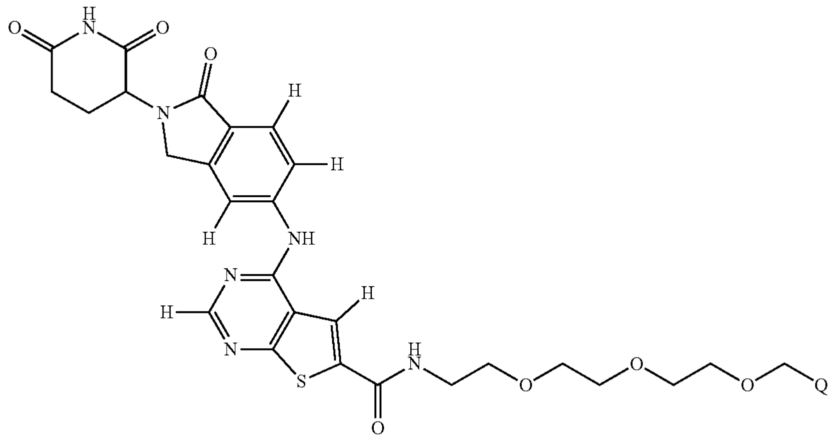 | 3.022 |
| 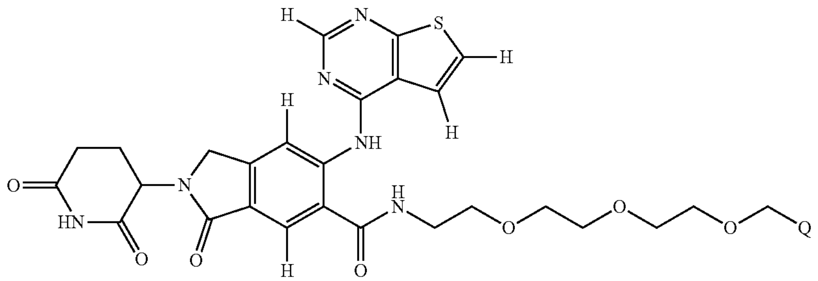 | 3.023 |
| 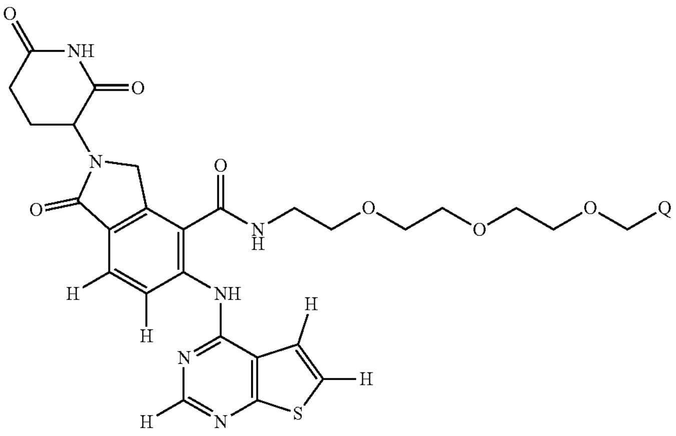 | 3.024 |
| 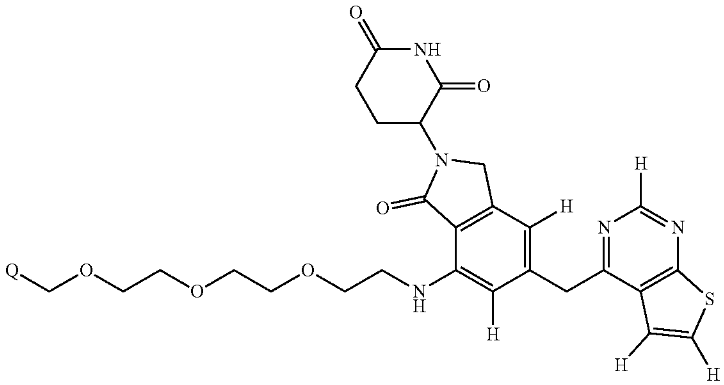 | 3.025 |

TABLE 3-continued
| Embodiments of general formula $(A)_k$-L-Q, having Q moiety. | |
|---|---|
| 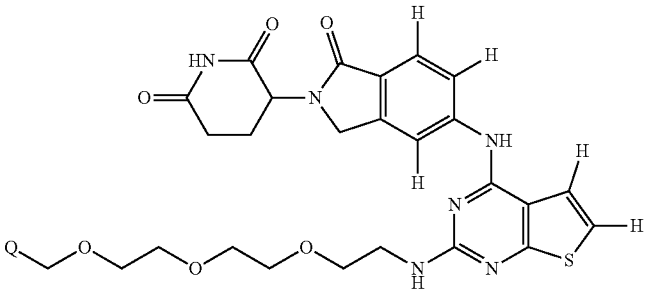 | 3.026 |
| 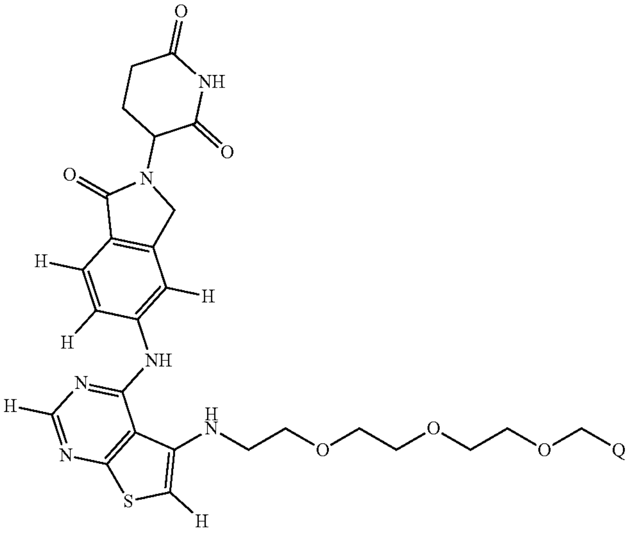 | 3.027 |
| 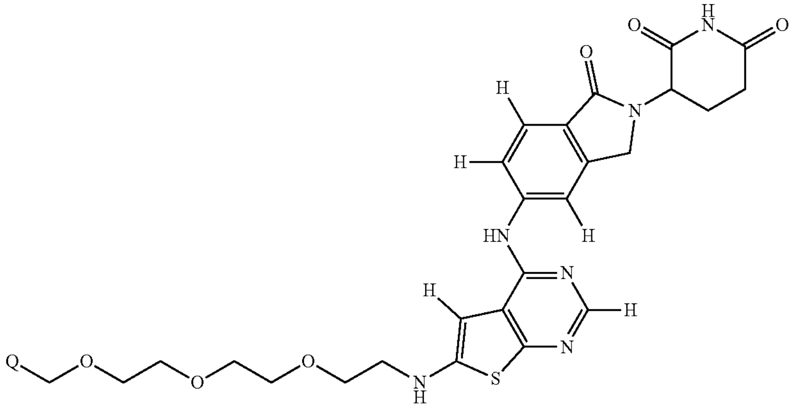 | 3.028 |
| 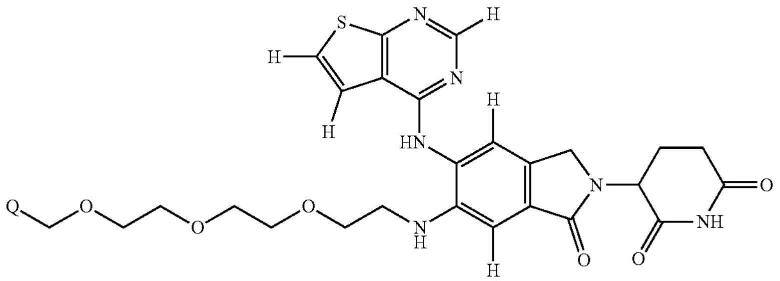 | 3.029 |

TABLE 3-continued
| Embodiments of general formula $(A)_k$-L-Q, having Q moiety. | |
|---|---|
| 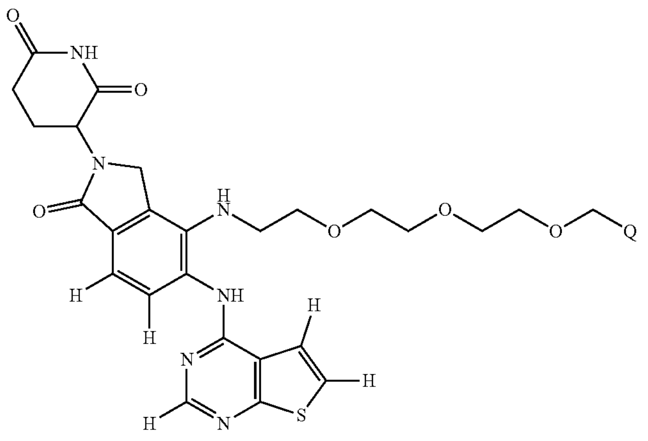 | 3.030 |
| 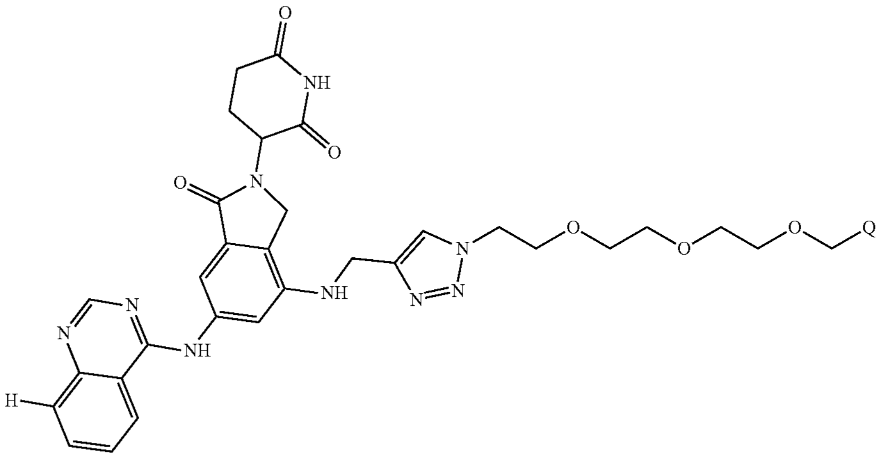 | 3.031 |
| 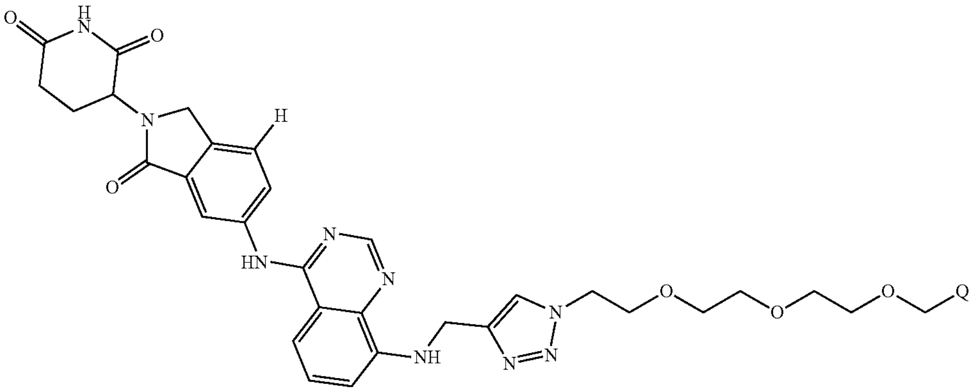 | 3.032 |

TABLE 3-continued
| Embodiments of general formula $(A)_k$-L-Q, having Q moiety. |
|---|
3.033
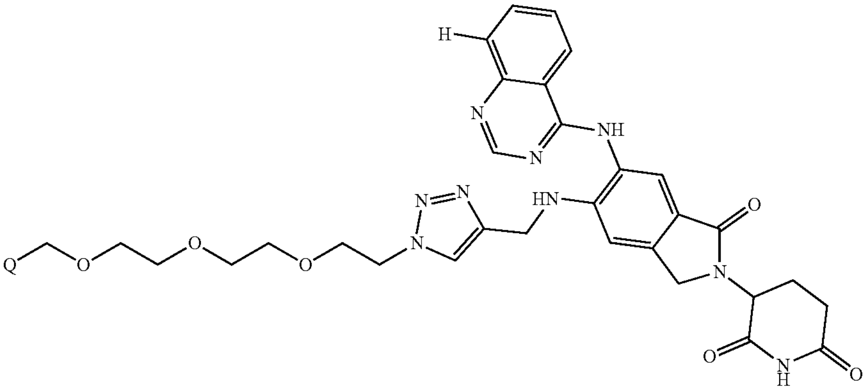
3.034
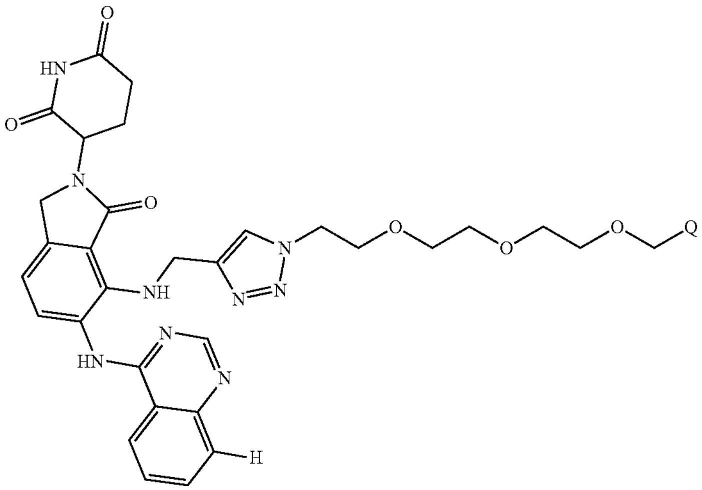
3.035
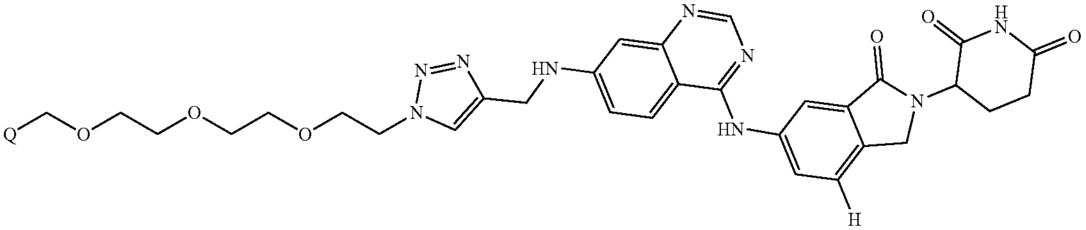
3.036
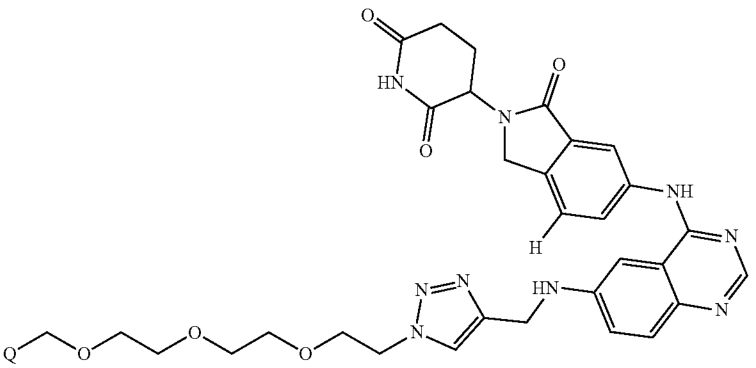

TABLE 3-continued
| Embodiments of general formula $(A)_k$-L-Q, having Q moiety. |
|---|
| 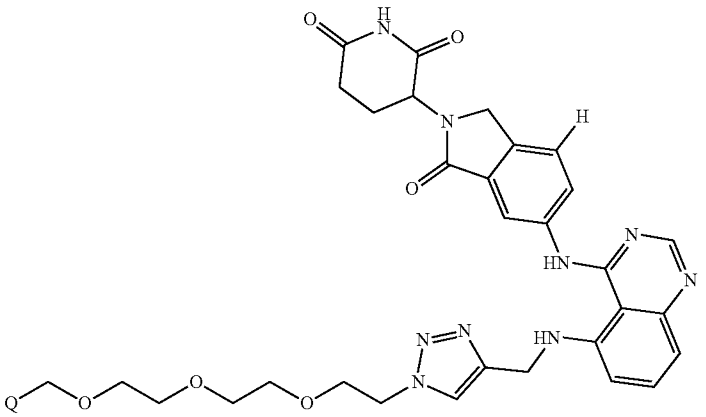 3.037 |
| 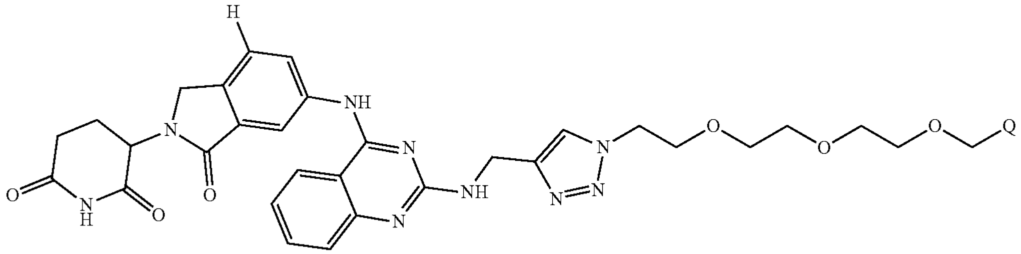 3.038 |
| 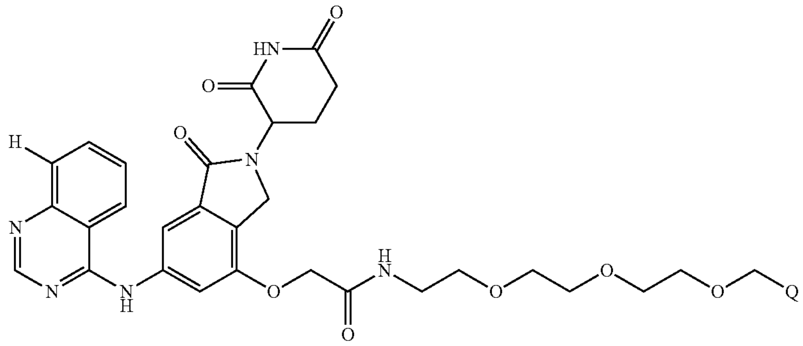 3.039 |
| 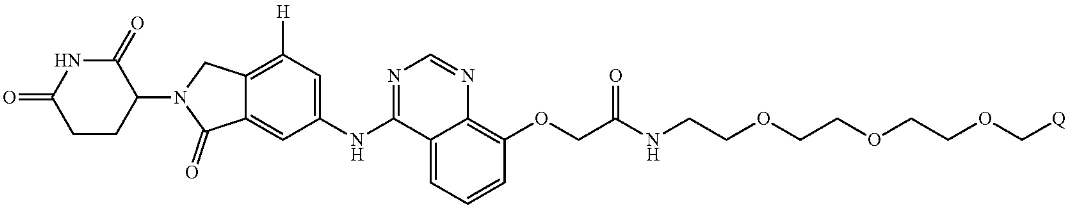 3.040 |
| 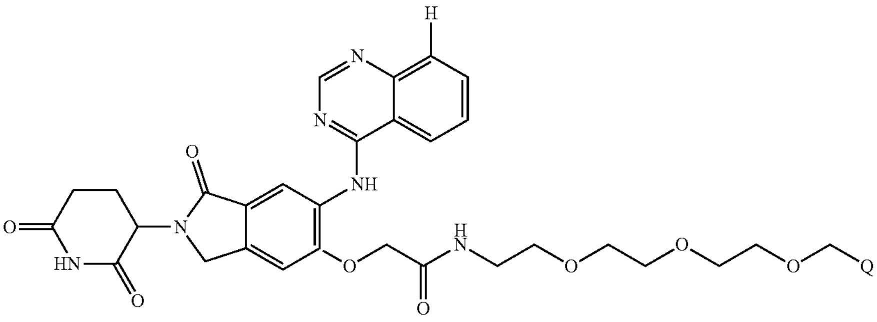 3.041 |

TABLE 3-continued
Embodiments of general formula $(A)_k$-L-Q, having Q moiety.
3.042
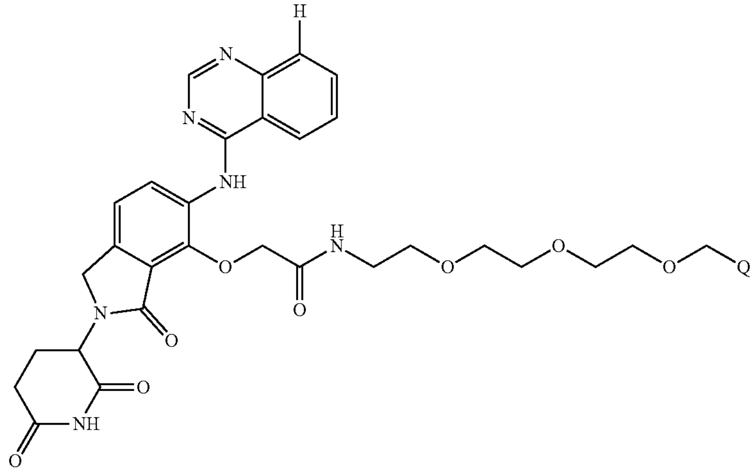
3.043
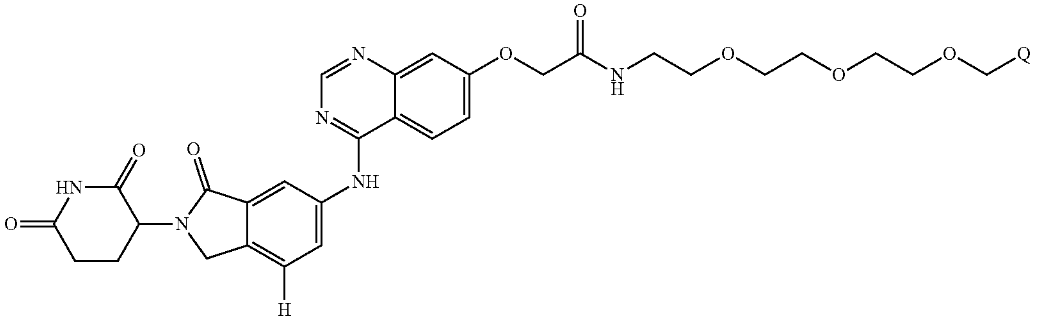
3.044
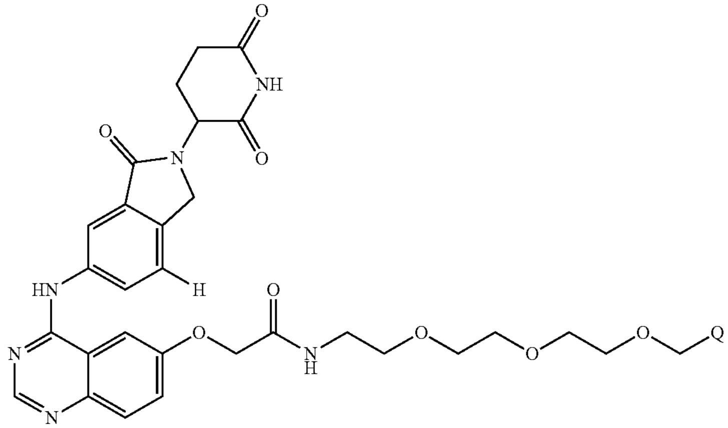

TABLE 3-continued
Embodiments of general formula $(A)_k$-L-Q, having Q moiety.
3.045
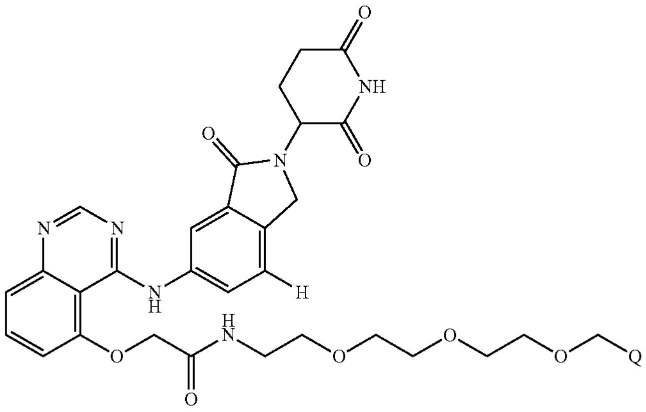
3.046
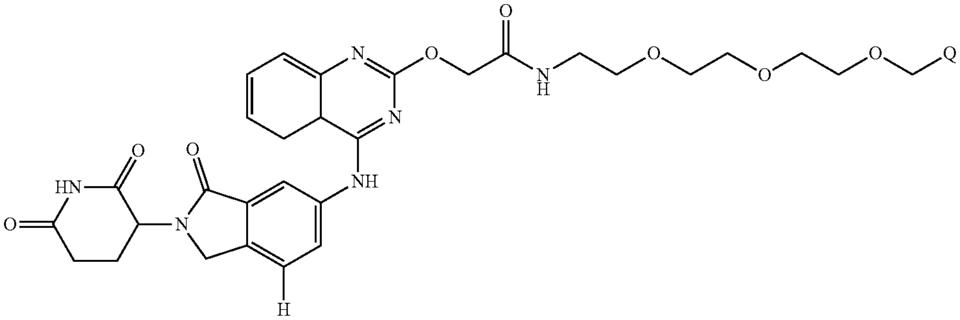
3.047
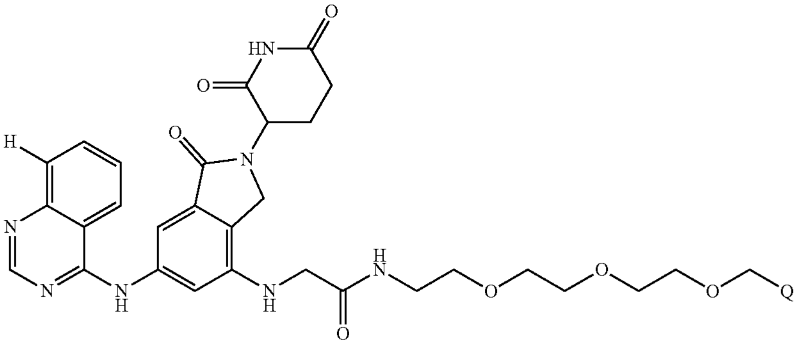
3.048
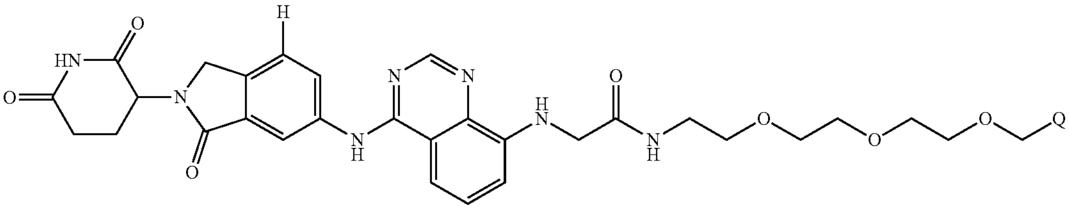

TABLE 3-continued
| Embodiments of general formula $(A)_k$-L-Q, having Q moiety. |
| --- |
| 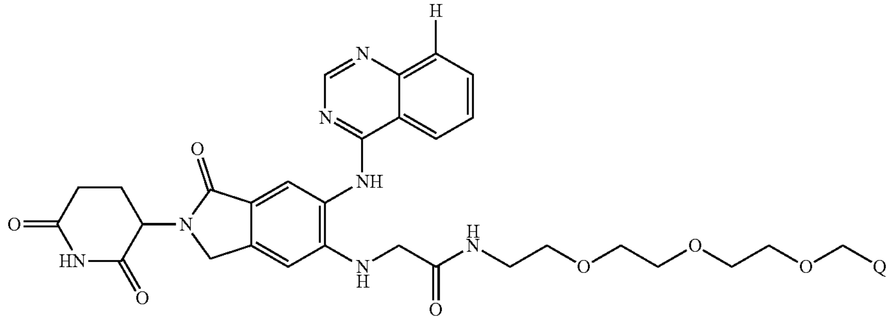 3.049 |
| 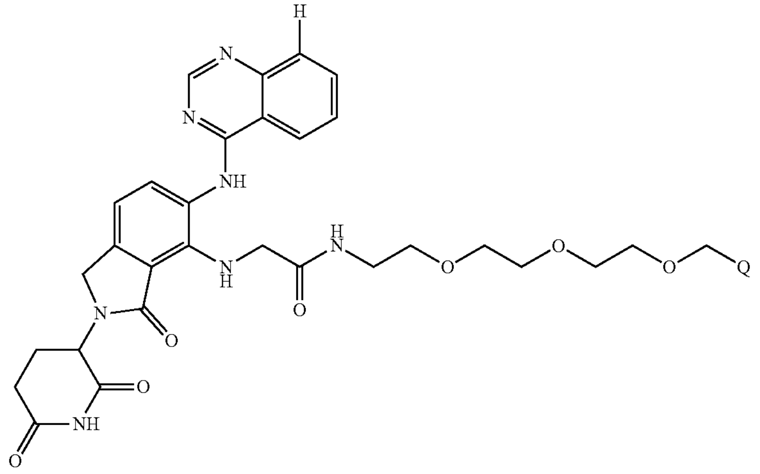 3.050 |
| 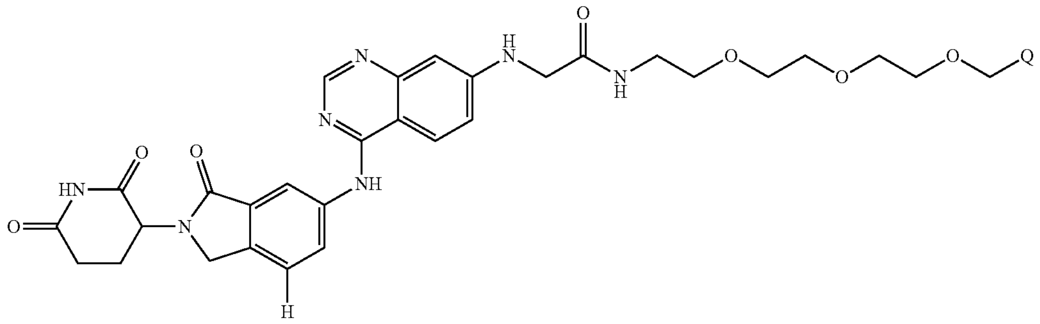 3.051 |
| 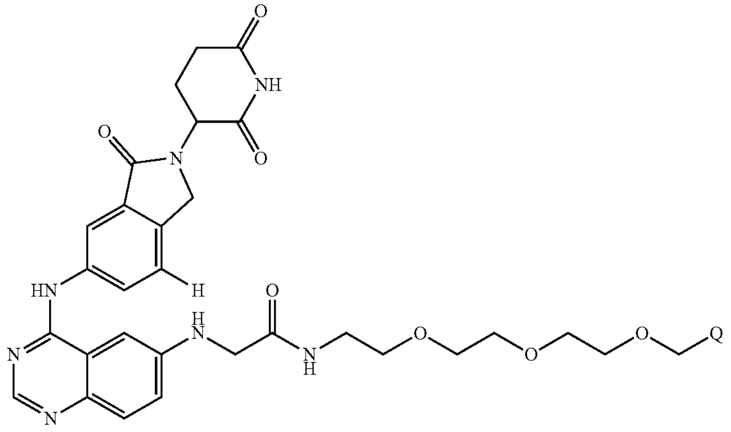 3.052 |

TABLE 3-continued
Embodiments of general formula $(A)_k$-L-Q, having Q moiety.
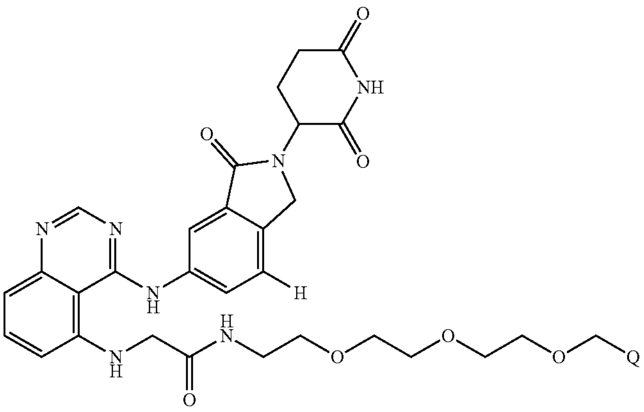
3.053
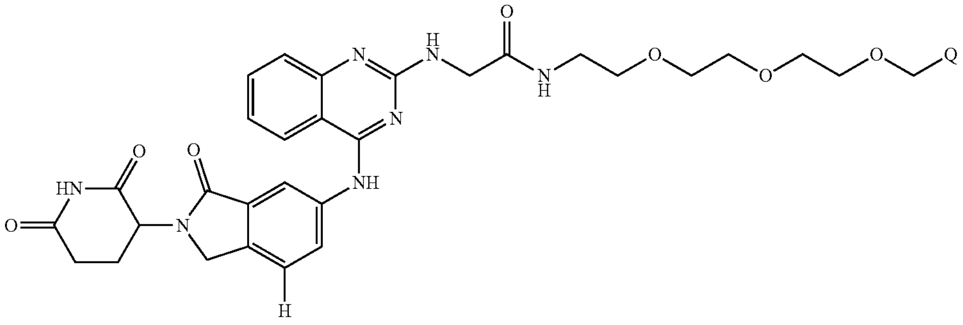
3.054
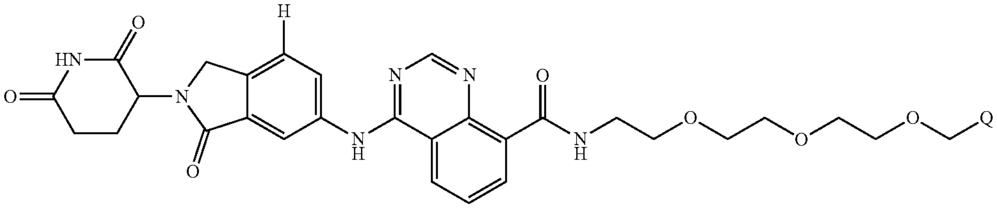
3.055
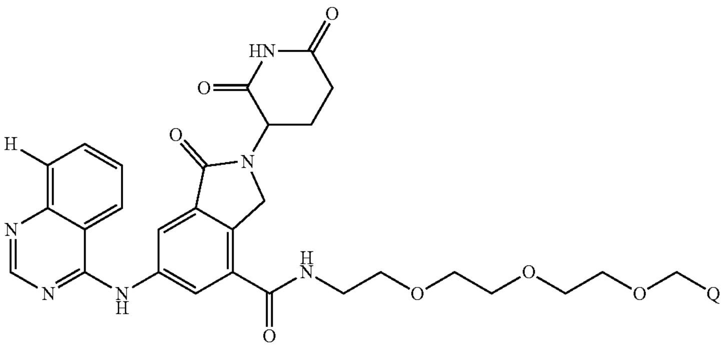
3.056

TABLE 3-continued
Embodiments of general formula $(A)_k$-L-Q, having Q moiety.
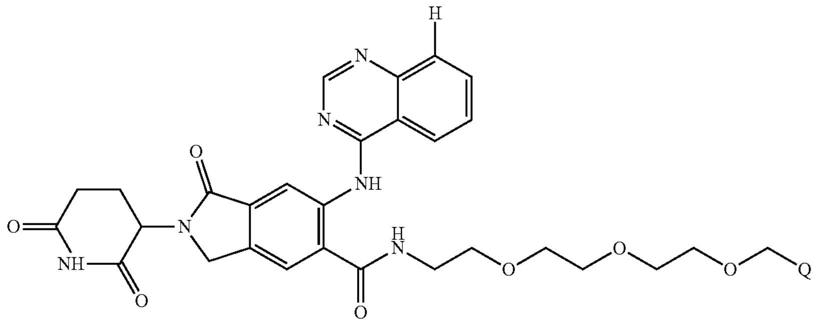
3.057
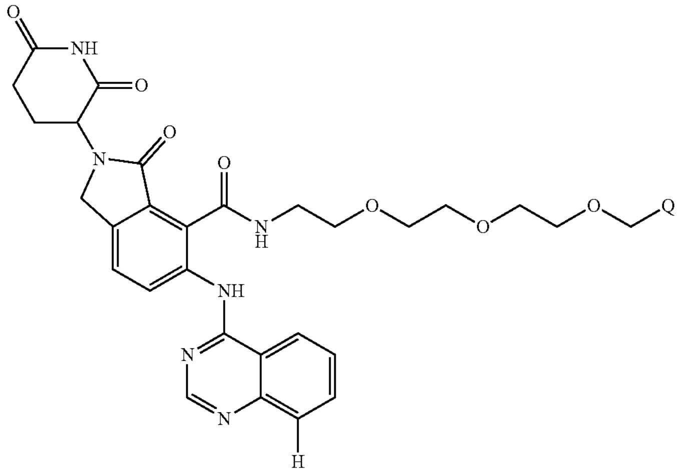
3.058
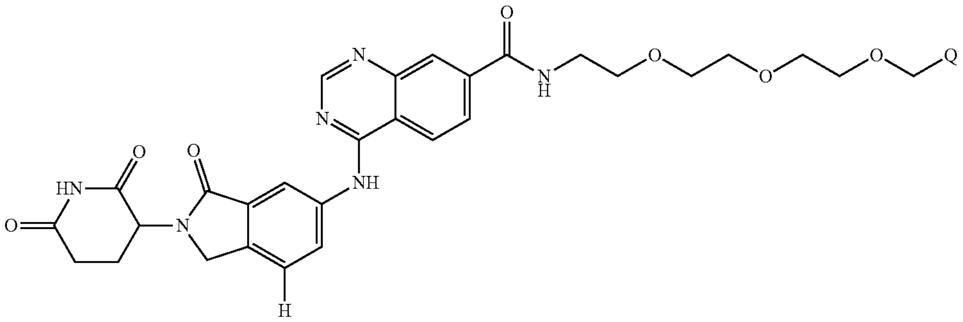
3.059
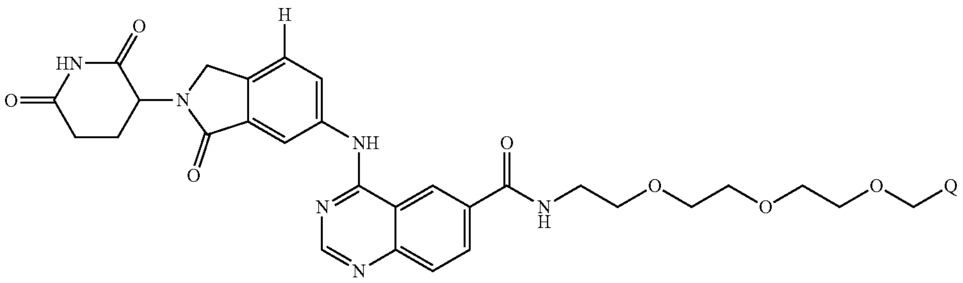
3.060

TABLE 3-continued
Embodiments of general formula $(A)_k$-L-Q, having Q moiety.
3.061
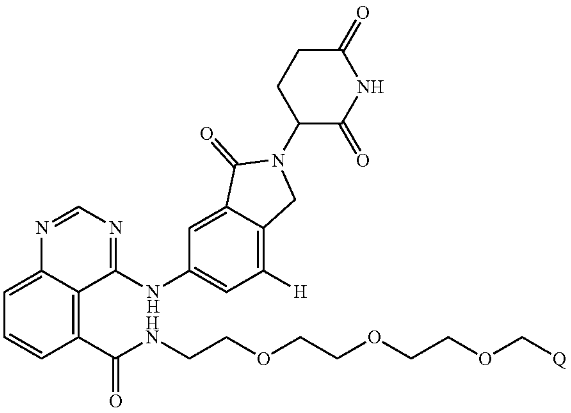
3.062
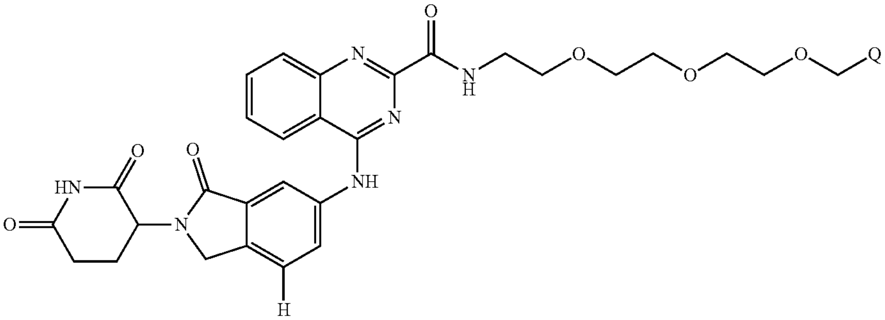
3.063
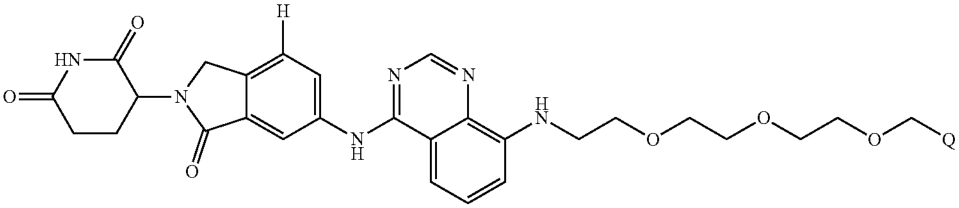
3.064
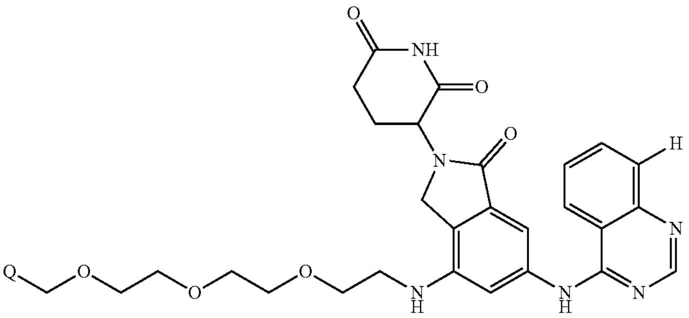
3.065
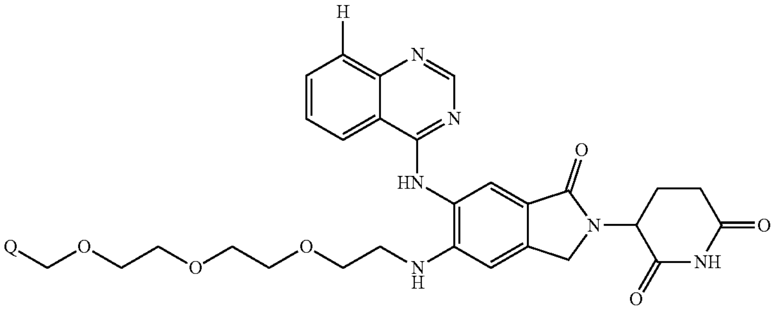

TABLE 3-continued
Embodiments of general formula $(A)_k$-L-Q, having Q moiety.
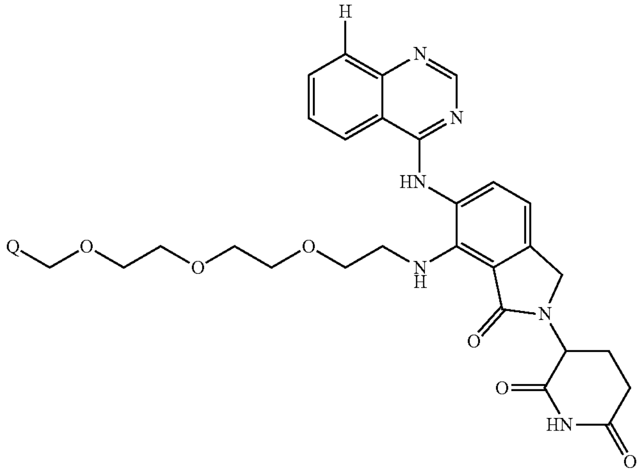
3.066
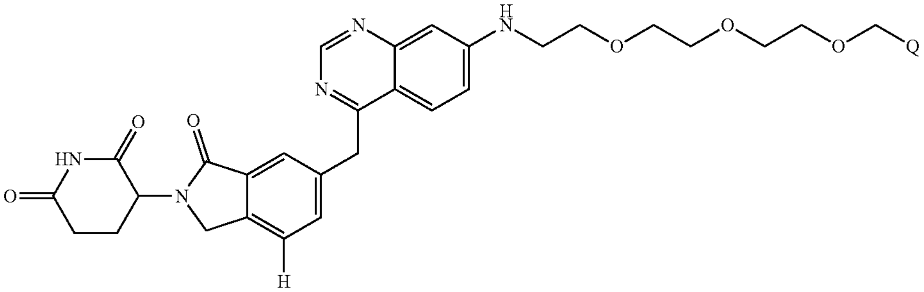
3.067
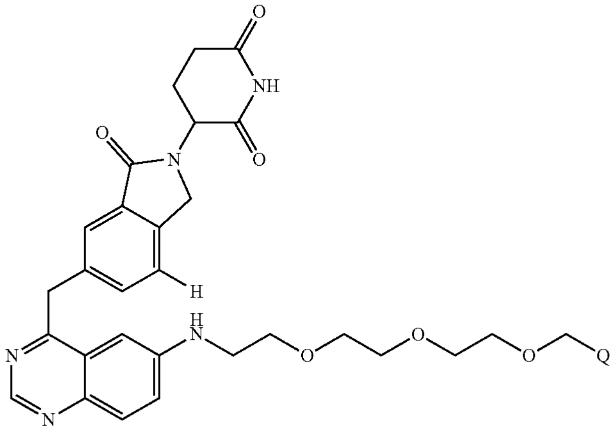
3.068
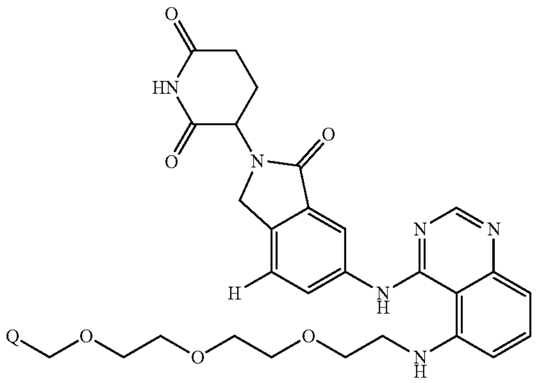
3.069

TABLE 3-continued
Embodiments of general formula $(A)_k$-L-Q, having Q moiety.
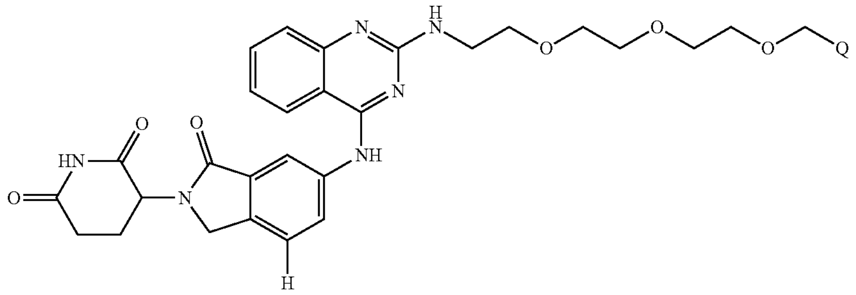
3.070
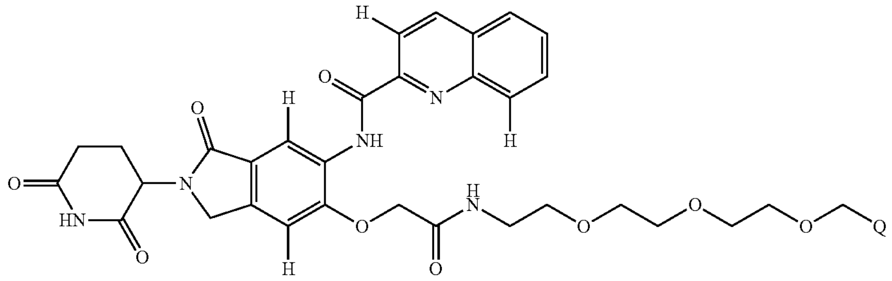
3.071
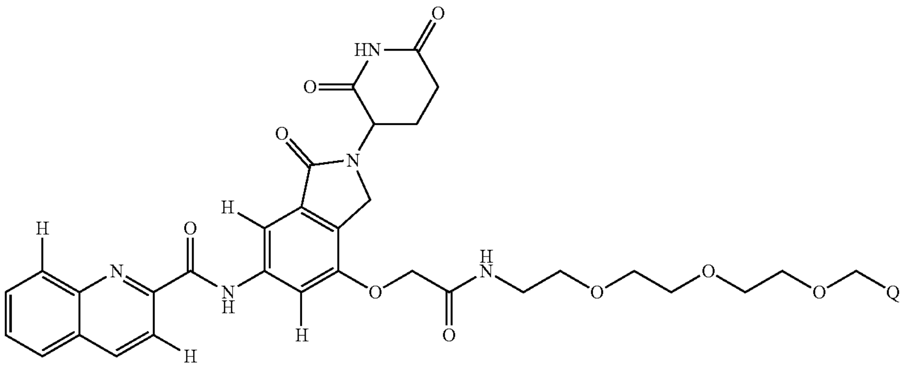
3.072
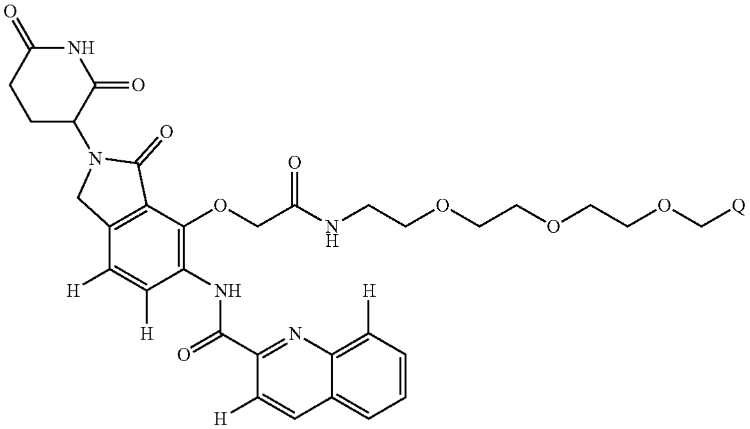
3.073

TABLE 3-continued
Embodiments of general formula $(A)_k$-L-Q, having Q moiety.
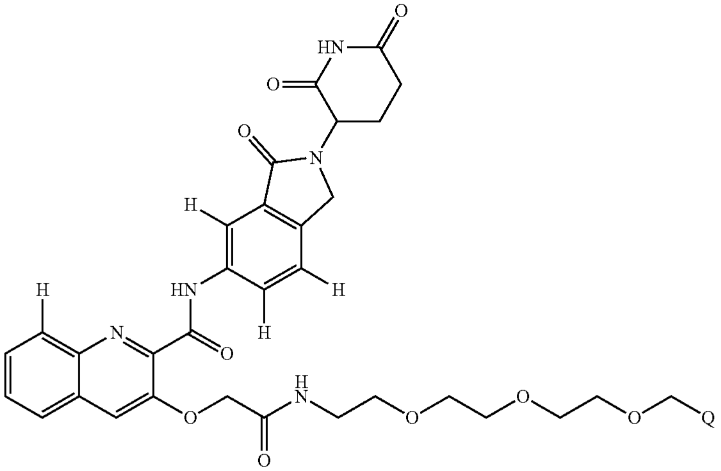
3.074
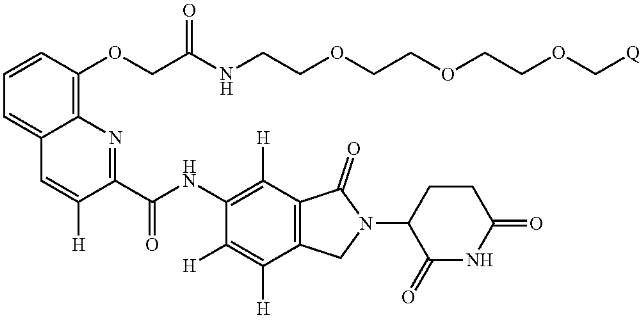
3.075
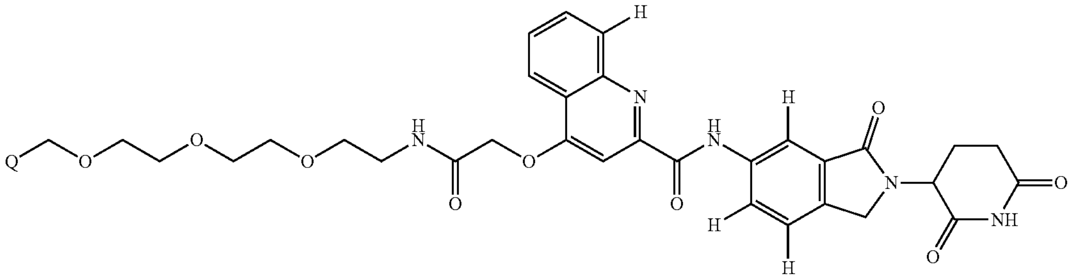
3.076
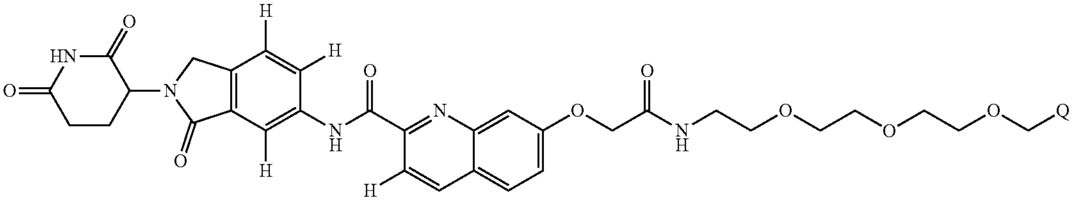
3.077
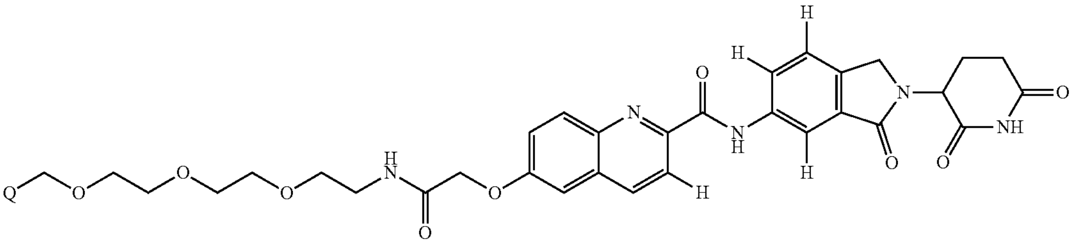
3.078

TABLE 3-continued
| Embodiments of general formula $(A)_k$-L-Q, having Q moiety. |
| --- |
3.079
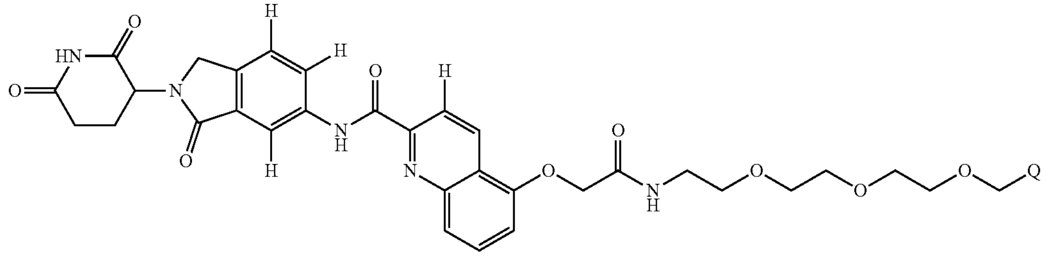
3.080
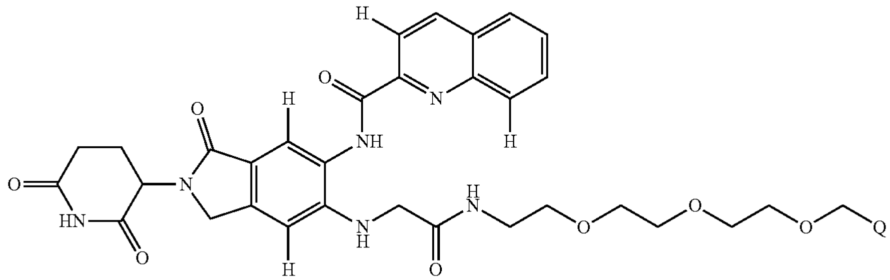
3.081
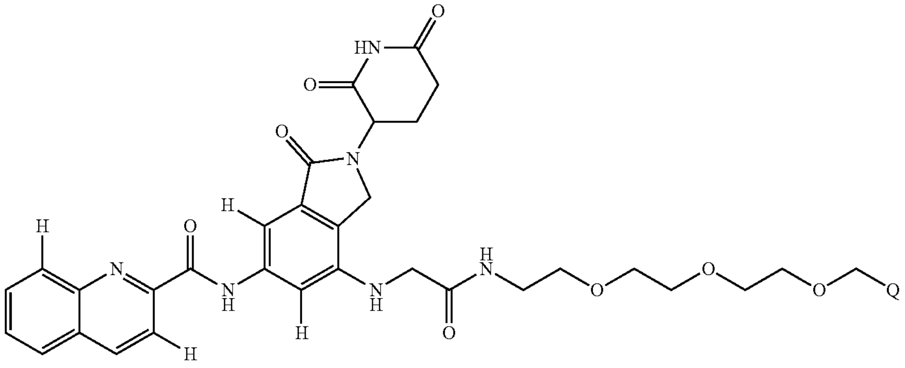
3.082
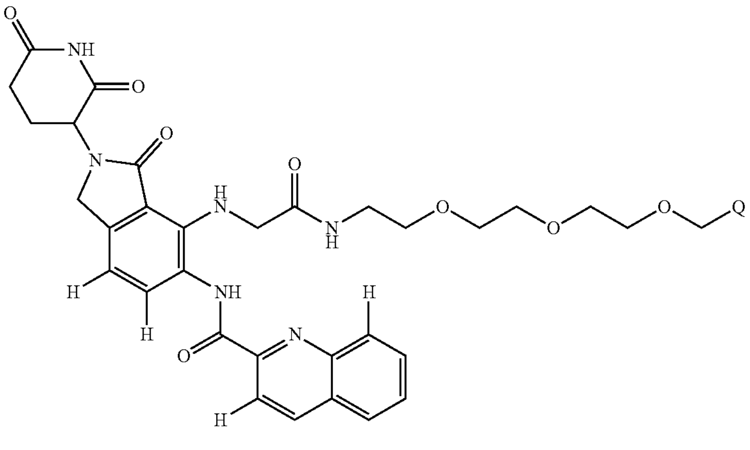

TABLE 3-continued
Embodiments of general formula $(A)_k$-L-Q, having Q moiety.
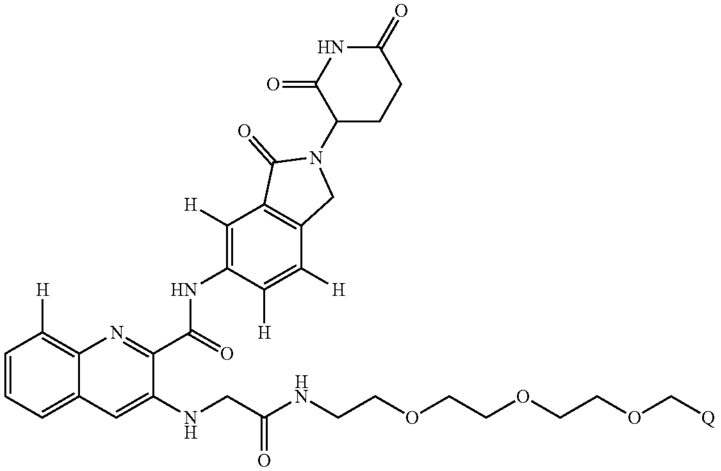
3.083
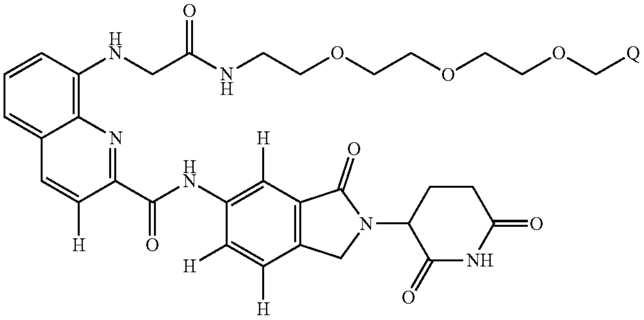
3.084
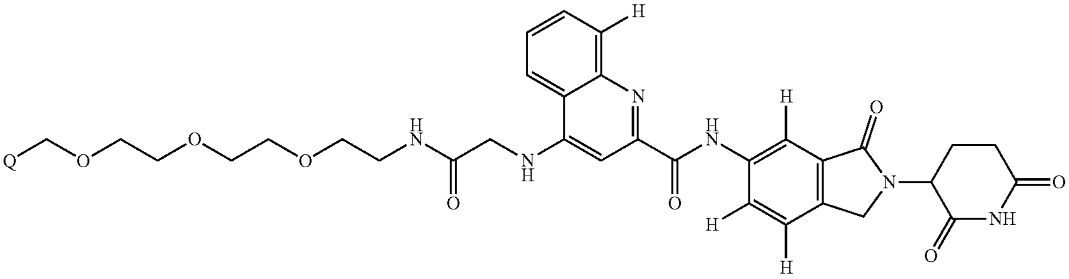
3.085
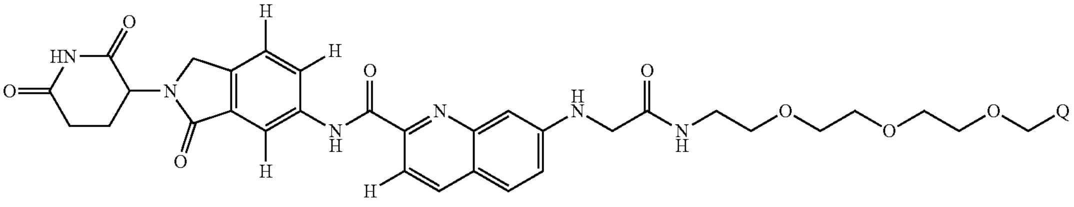
3.086
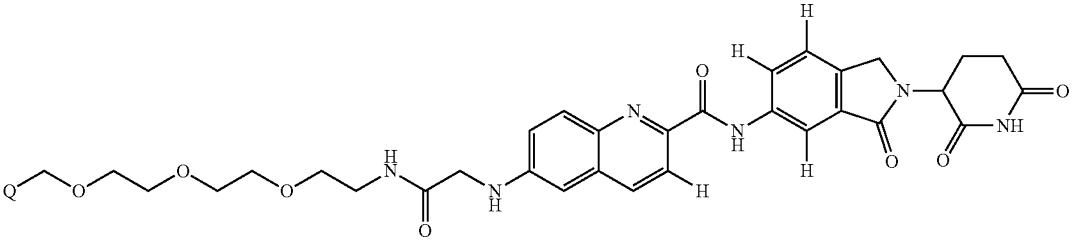
3.087

TABLE 3-continued
| Embodiments of general formula $(A)_k$-L-Q, having Q moiety. |
|---|
| 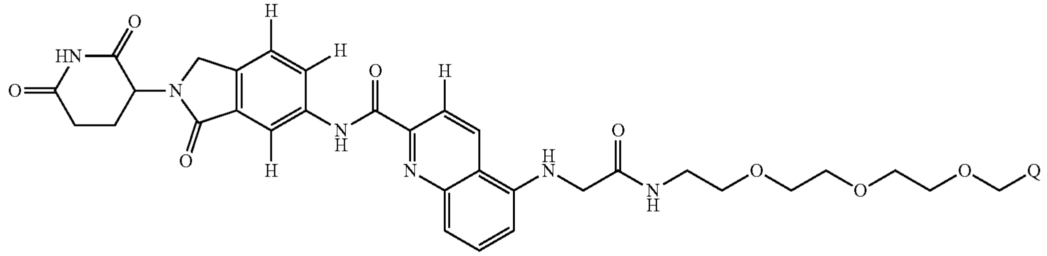 3.088 |
| 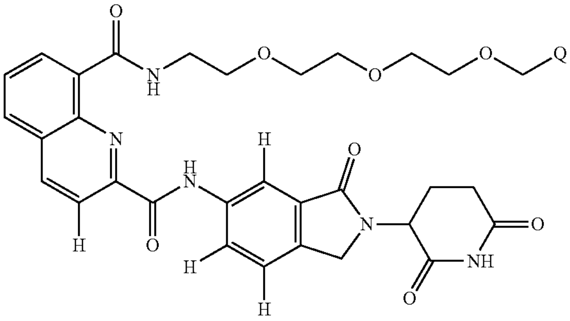 3.089 |
| 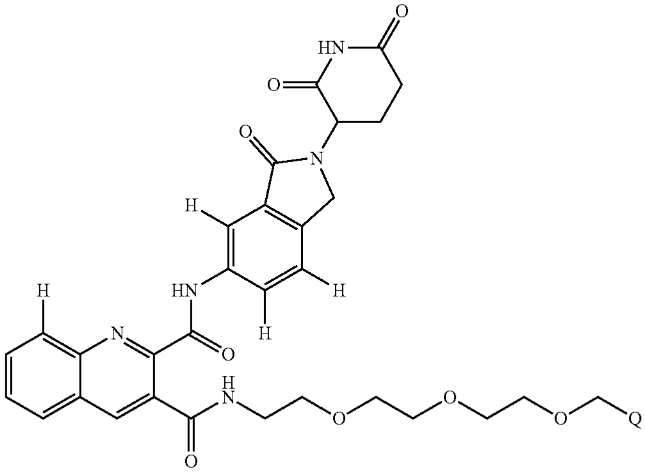 3.090 |
| 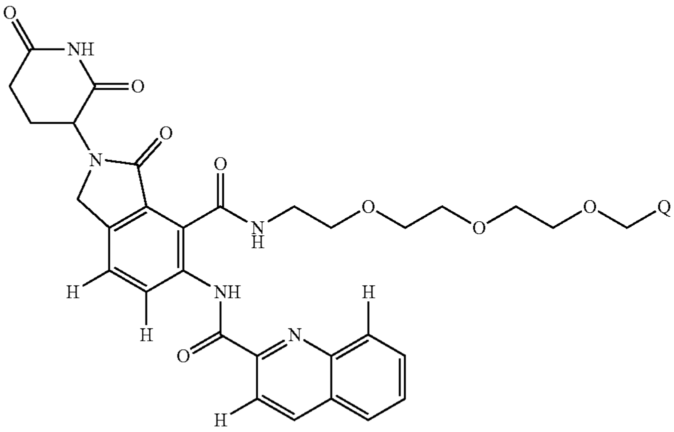 3.091 |

TABLE 3-continued
| Embodiments of general formula $(A)_k$-L-Q, having Q moiety. |
| --- |
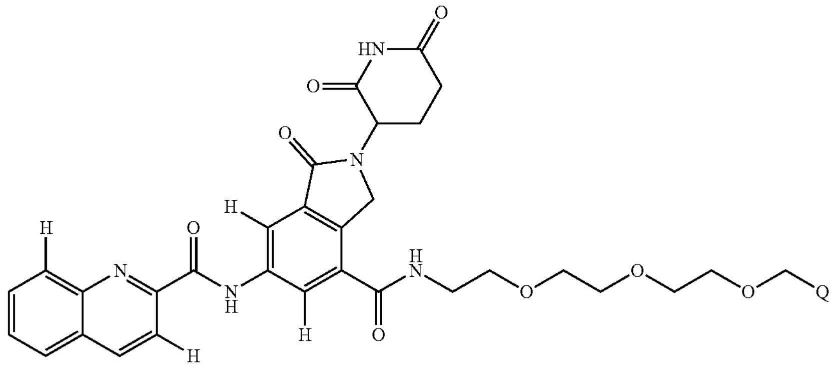
3.092
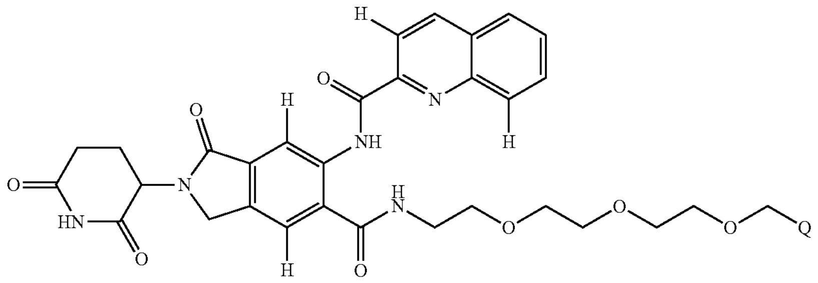
3.093
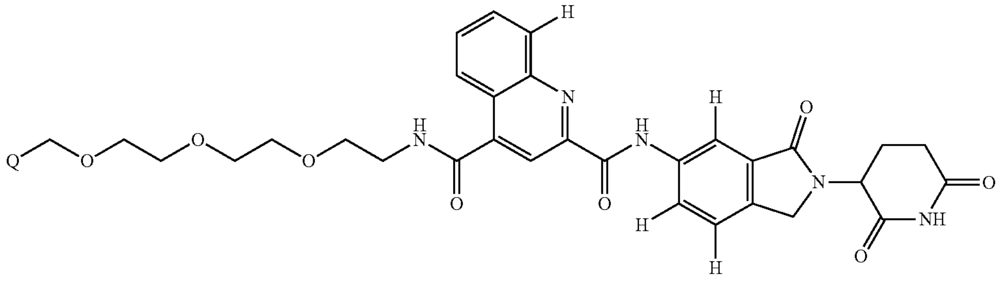
3.094
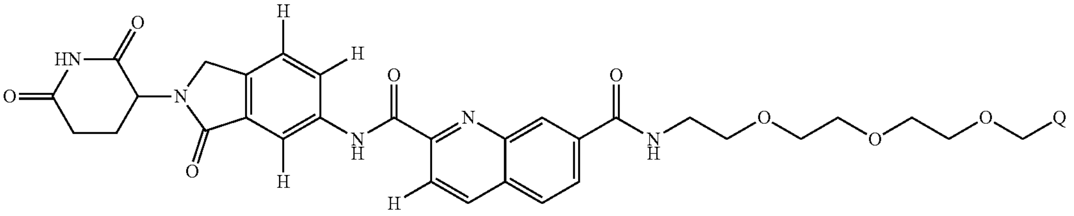
3.095
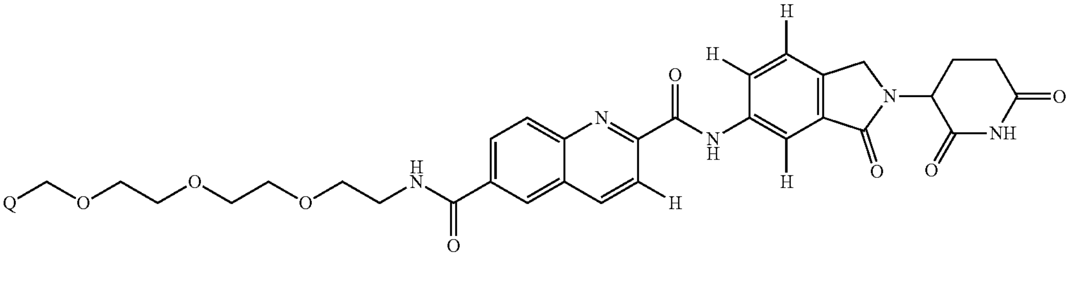
3.096

TABLE 3-continued
Embodiments of general formula $(A)_k$-L-Q, having Q moiety.
3.097
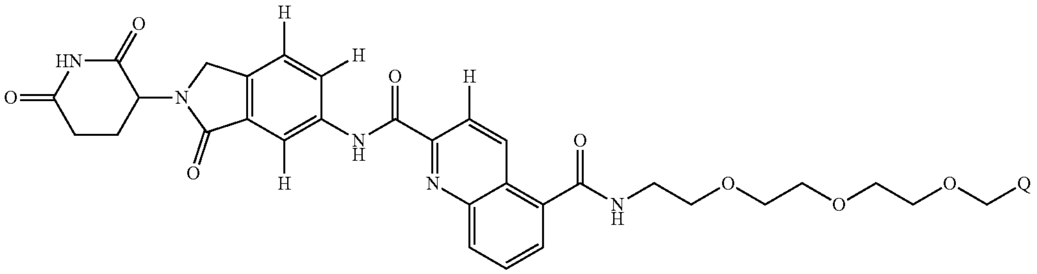
3.098
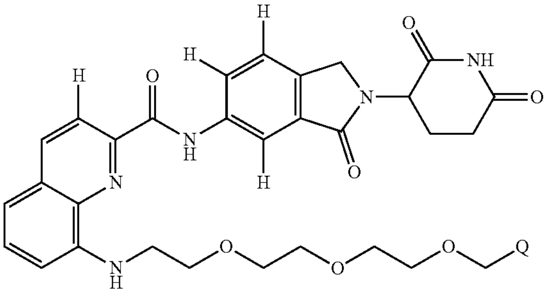
3.099
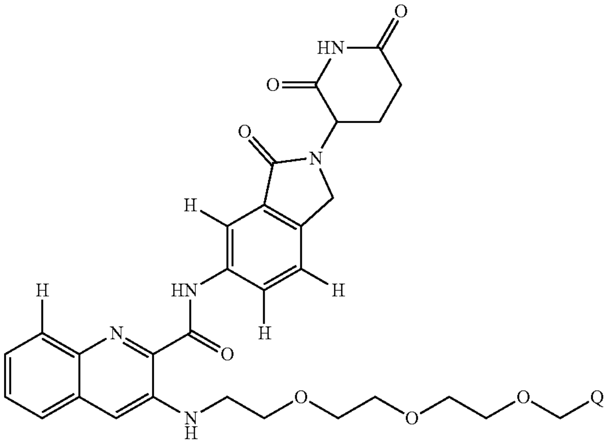
3.100
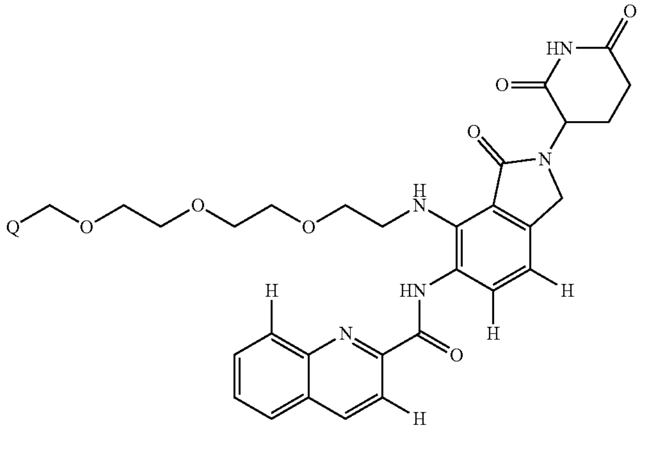

TABLE 3-continued
Embodiments of general formula $(A)_k$-L-Q, having Q moiety.
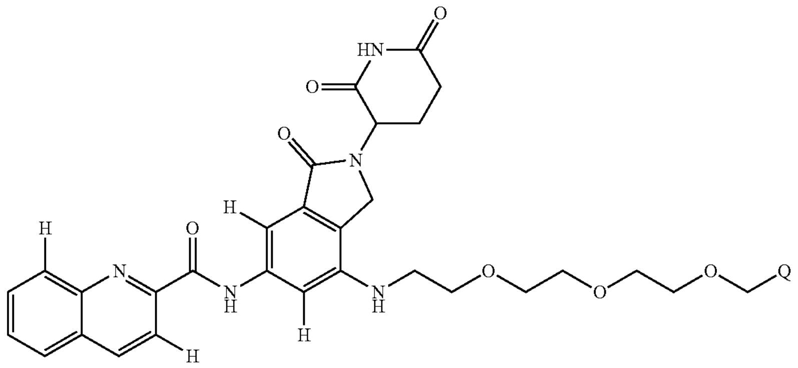
3.101
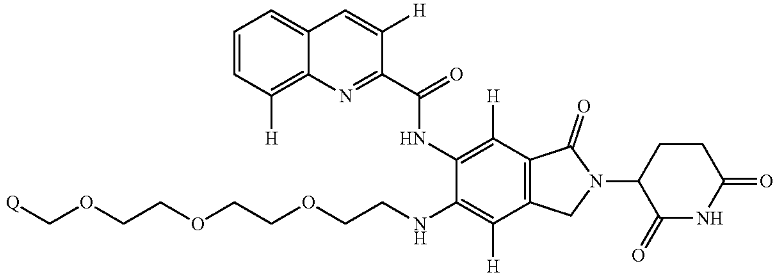
3.102
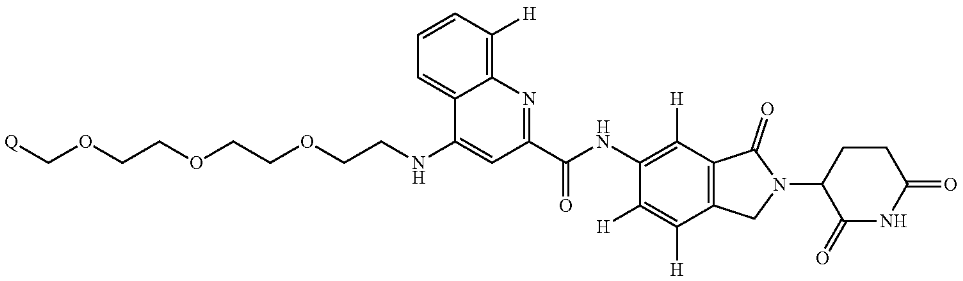
3.103
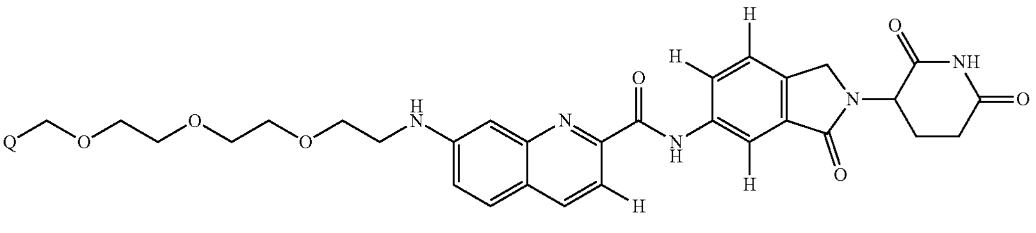
3.104
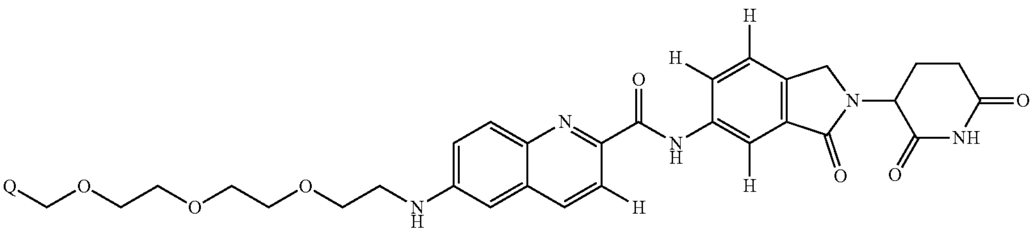
3.105

TABLE 3-continued
Embodiments of general formula $(A)_k$-L-Q, having Q moiety.
3.106
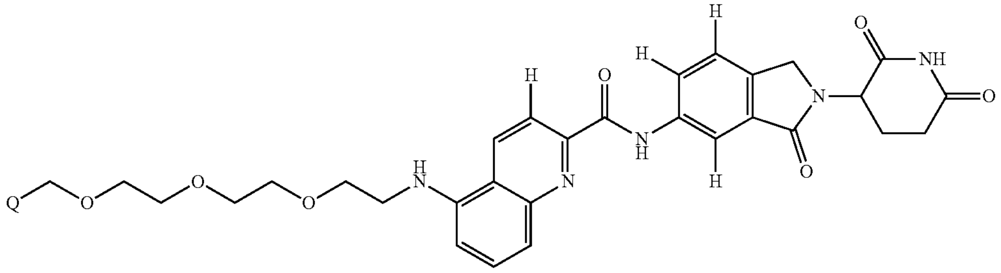
3.107
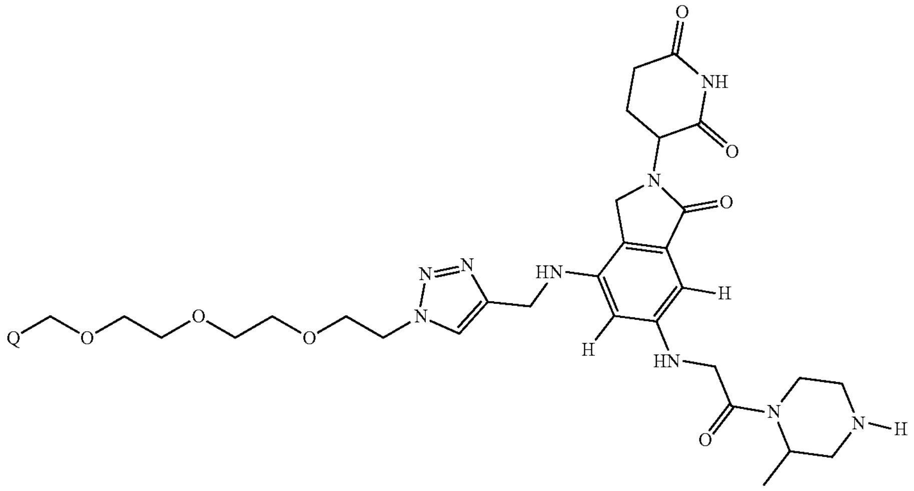
3.108
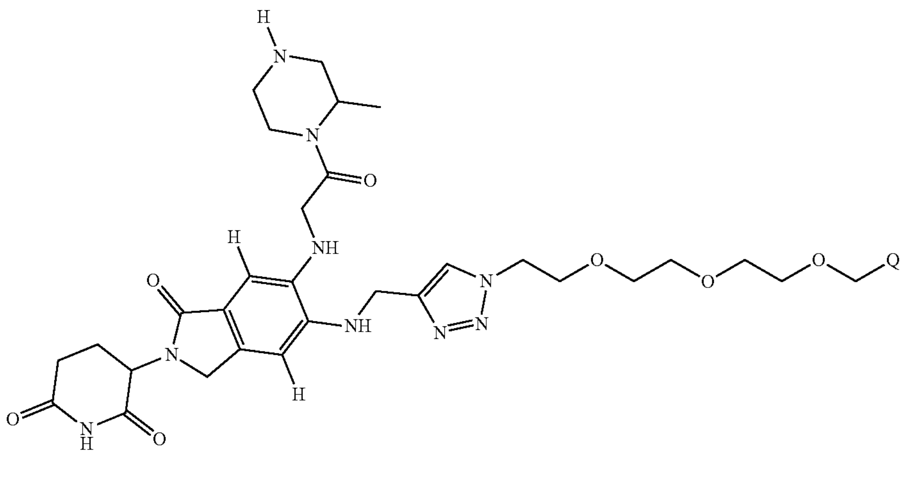

TABLE 3-continued
Embodiments of general formula $(A)_k$-L-Q, having Q moiety.
3.109
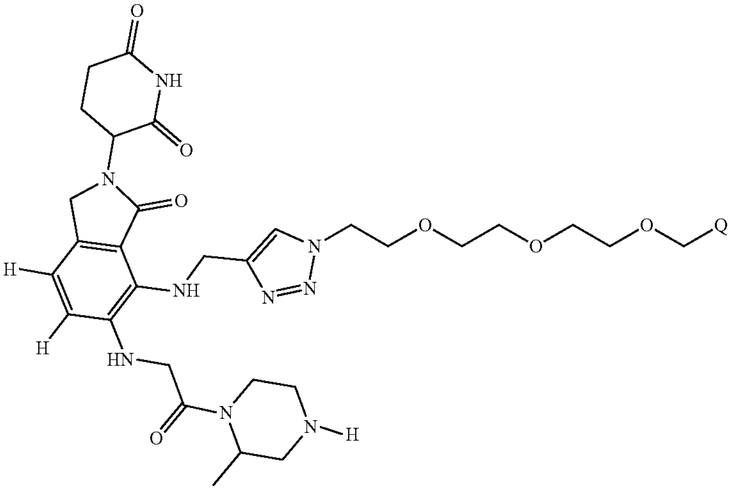
3.110
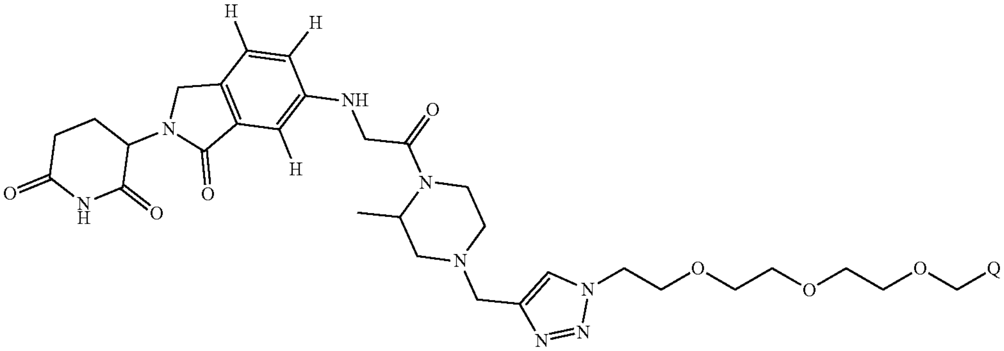
3.111
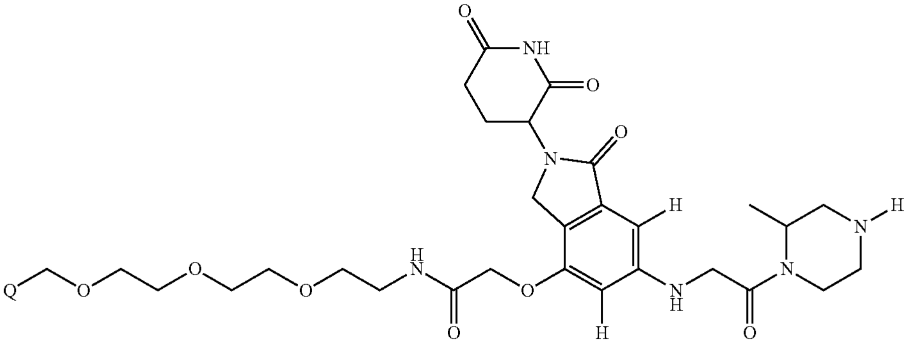
3.112
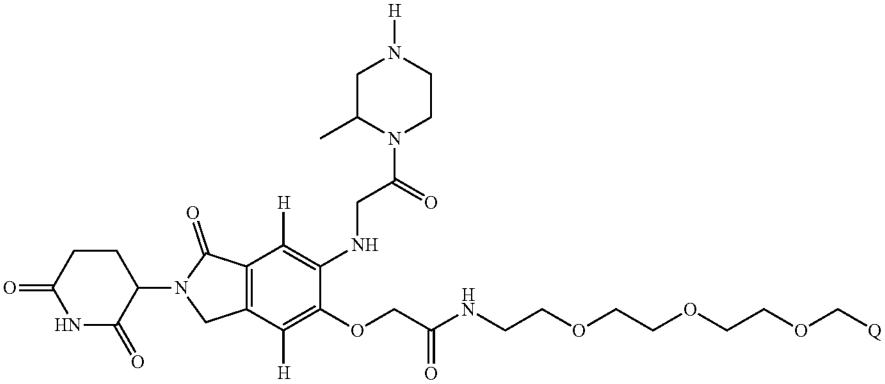

TABLE 3-continued
Embodiments of general formula $(A)_k$-L-Q, having Q moiety.
3.113
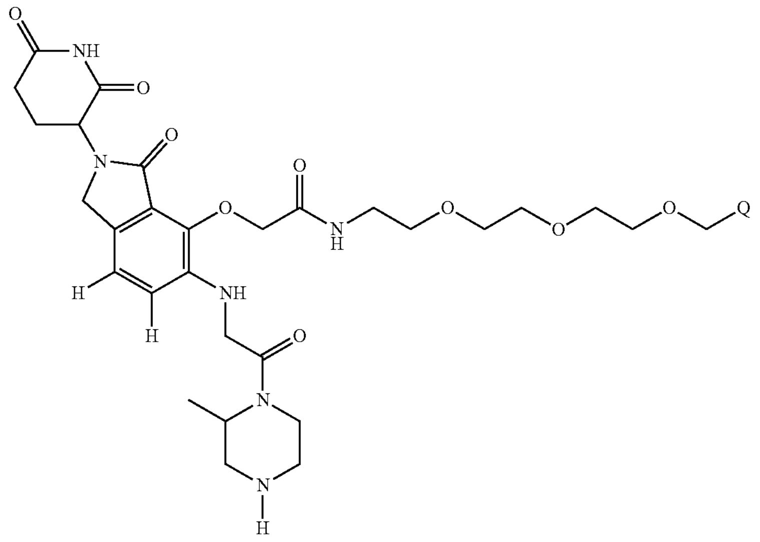
3.114
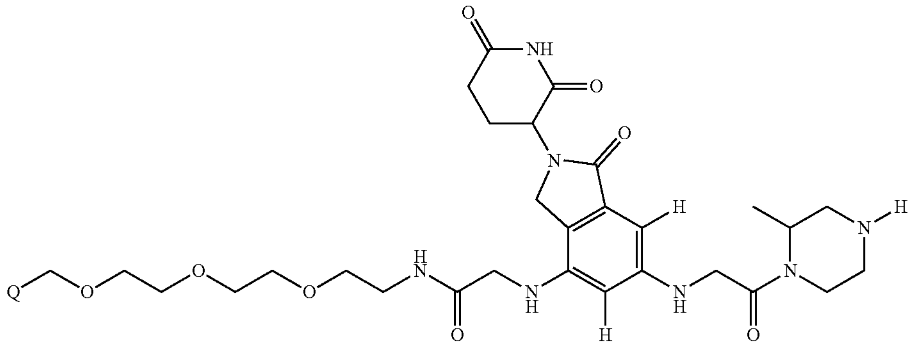
3.115
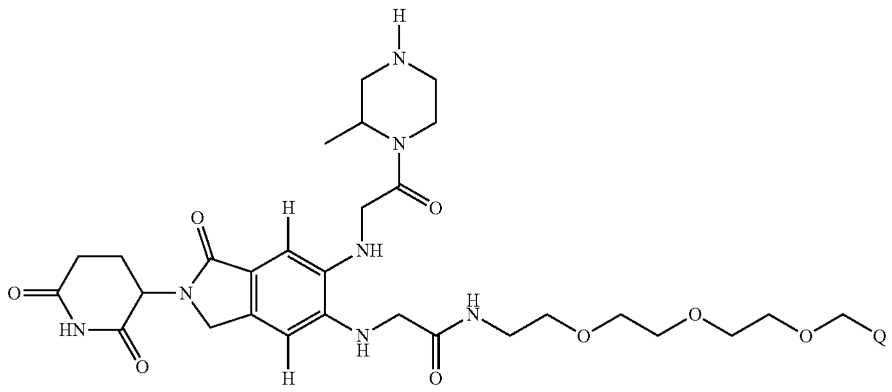

TABLE 3-continued
Embodiments of general formula $(A)_k$-L-Q, having Q moiety.
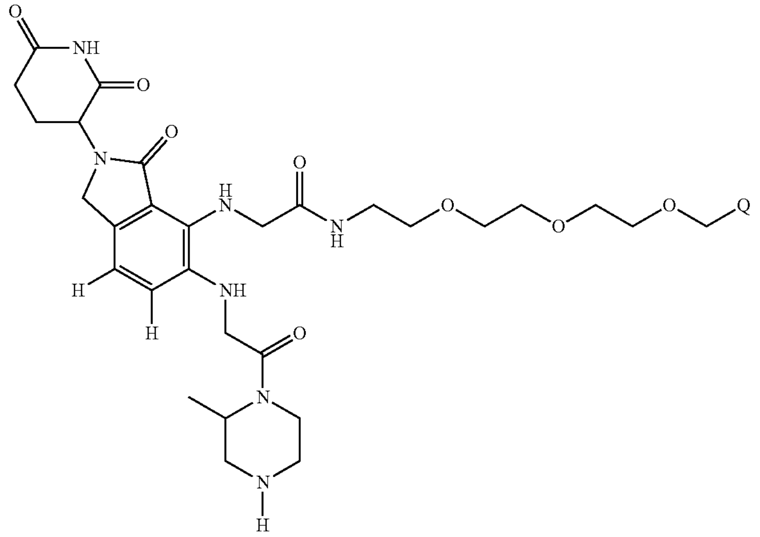
3.116
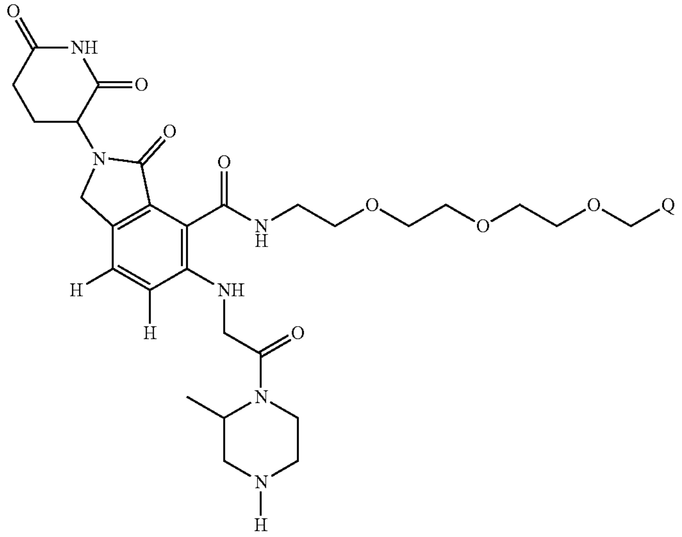
3.117
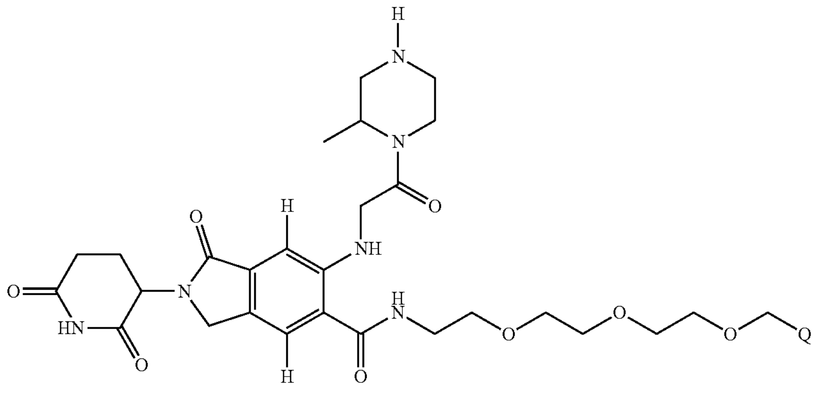
3.118

TABLE 3-continued
| Embodiments of general formula $(A)_k$-L-Q, having Q moiety. |
| --- |
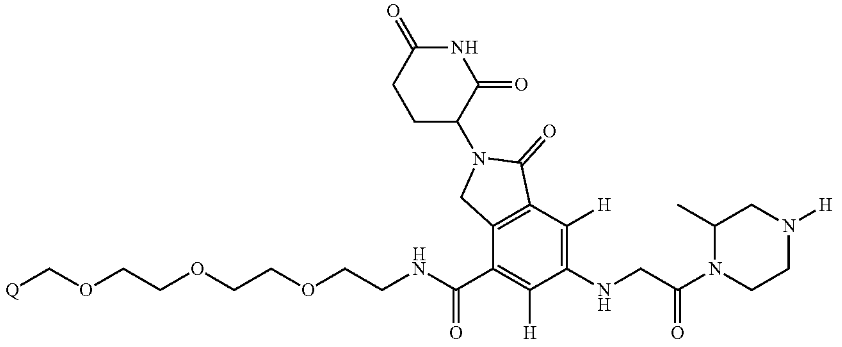
3.119
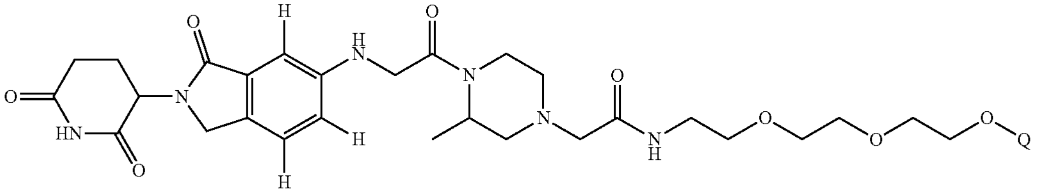
3.120
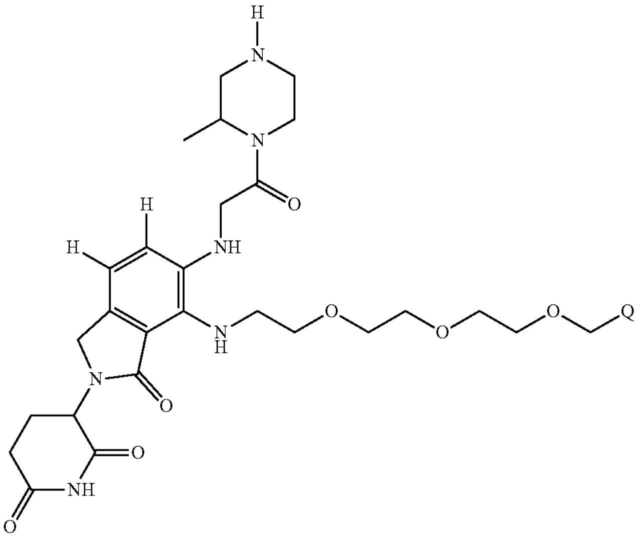
3.121
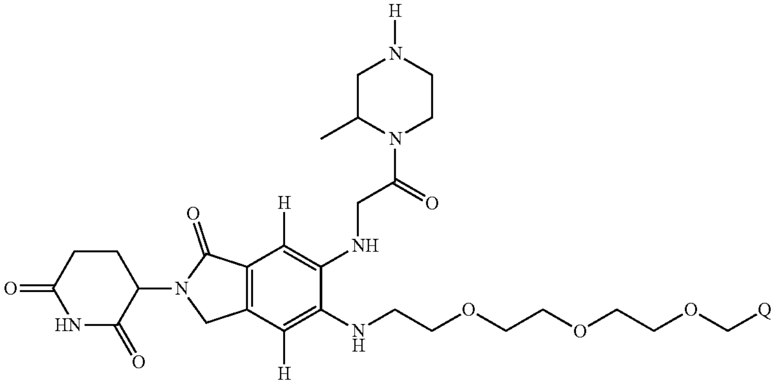
3.122

TABLE 3-continued
Embodiments of general formula $(A)_k$-L-Q, having Q moiety.
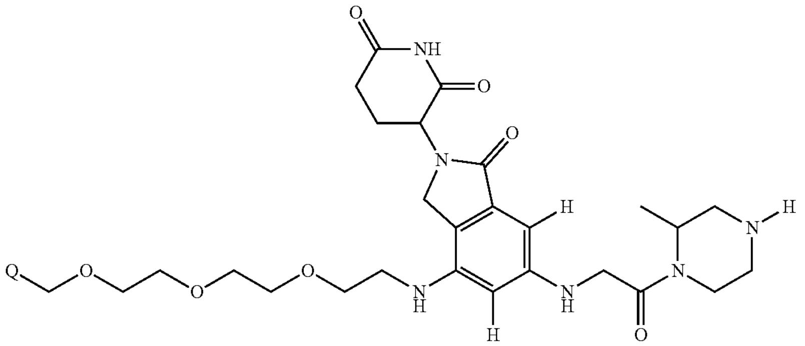
3.123
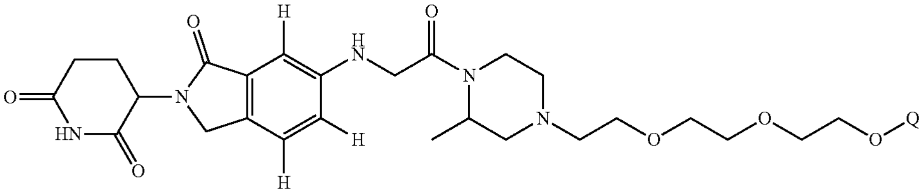
3.124
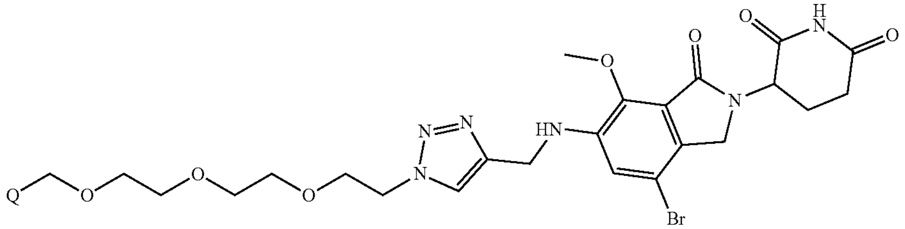
3.125
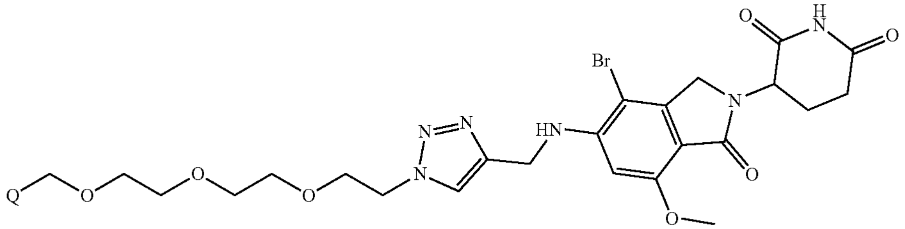
3.126
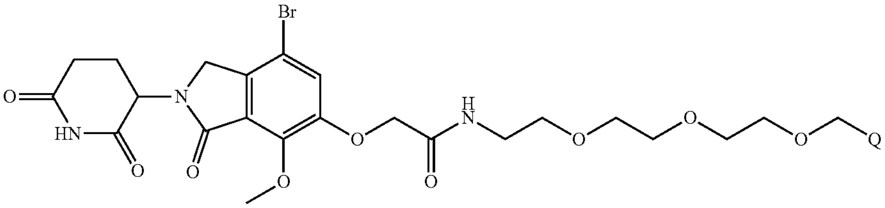
3.127
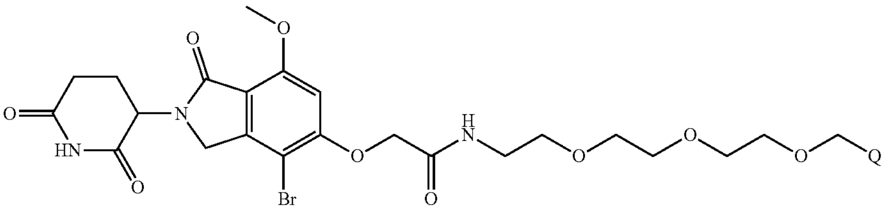
3.128

TABLE 3-continued
Embodiments of general formula $(A)_k$-L-Q, having Q moiety.
3.129
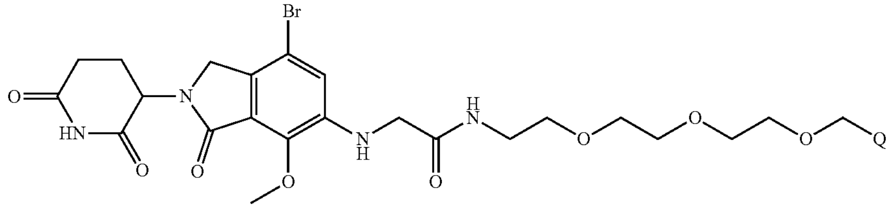
3.130
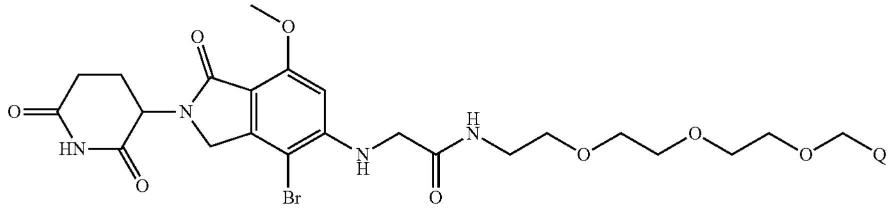
3.131
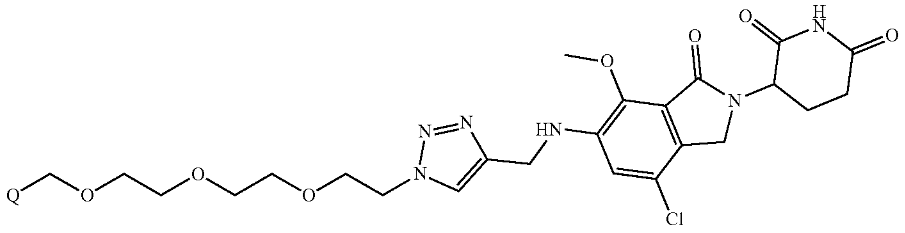
3.132
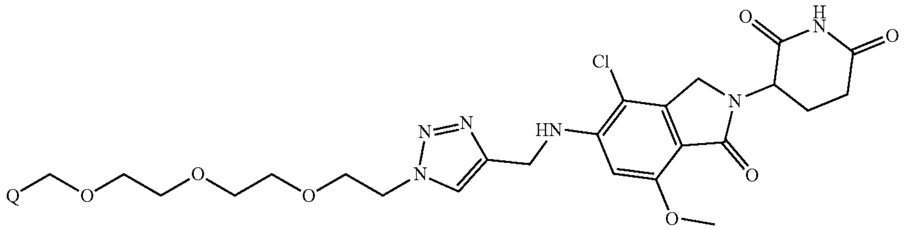
3.133
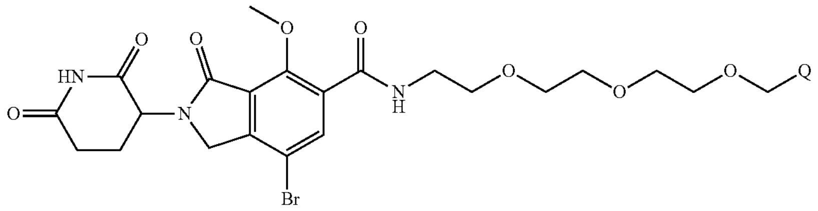
3.134
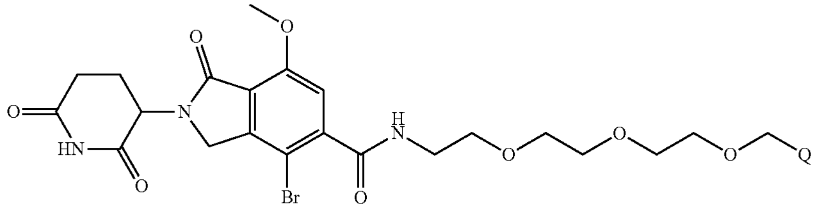
3.135
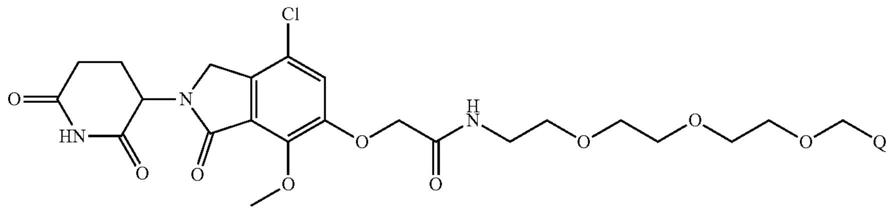

TABLE 3-continued
Embodiments of general formula $(A)_k$-L-Q, having Q moiety.
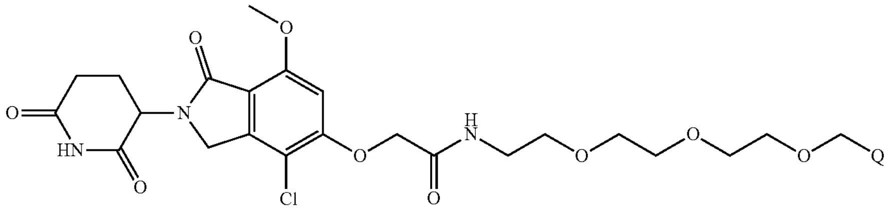
3.136
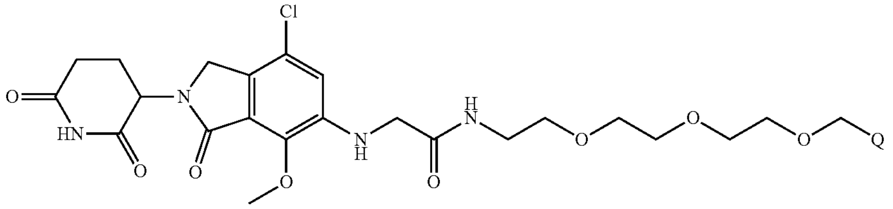
3.137
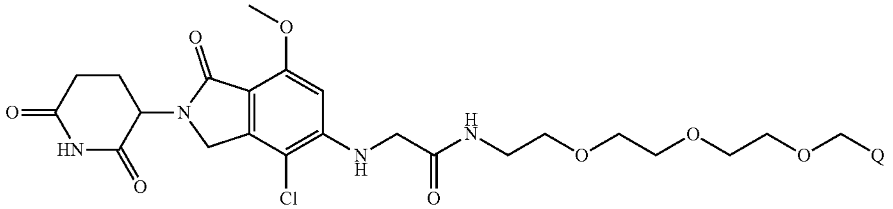
3.138
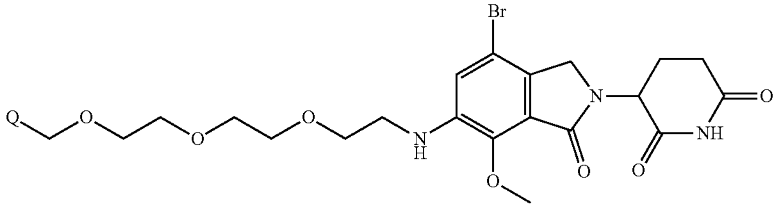
3.139
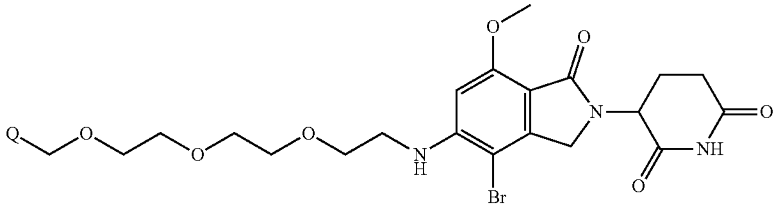
3.140
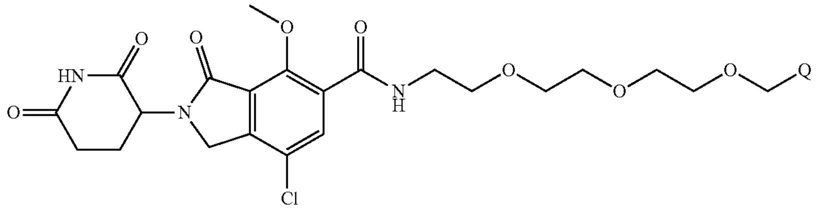
3.141
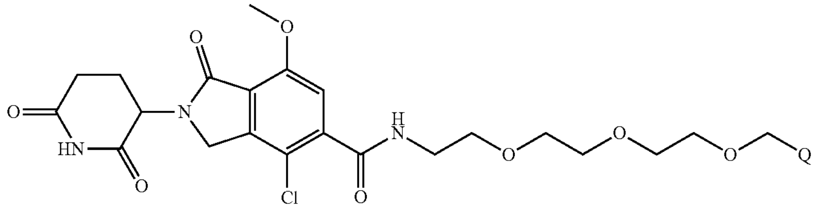
3.142

TABLE 3-continued
Embodiments of general formula $(A)_k$-L-Q, having Q moiety.
3.143
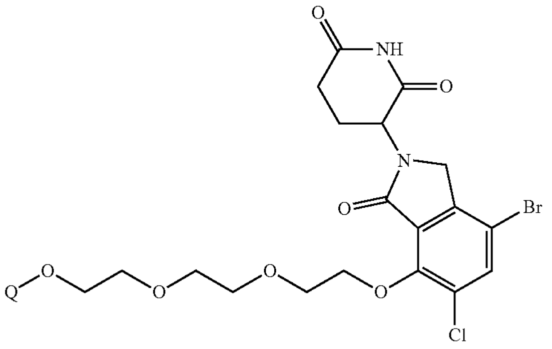
3.144
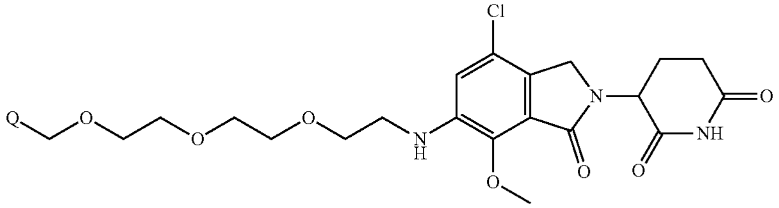
3.145
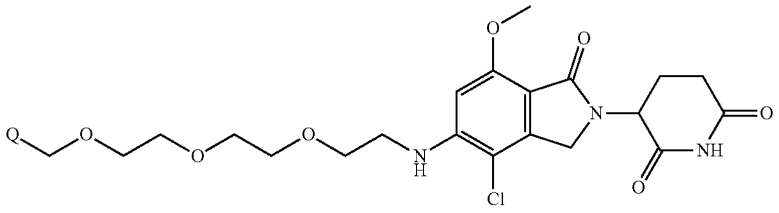
3.146
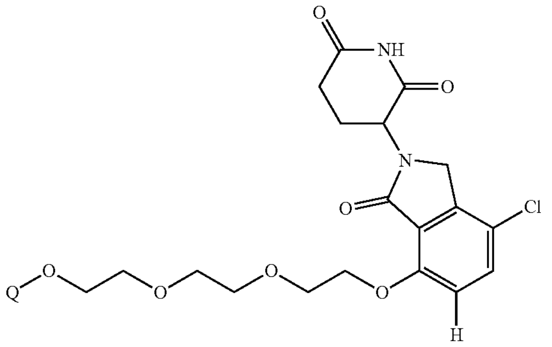
3.147
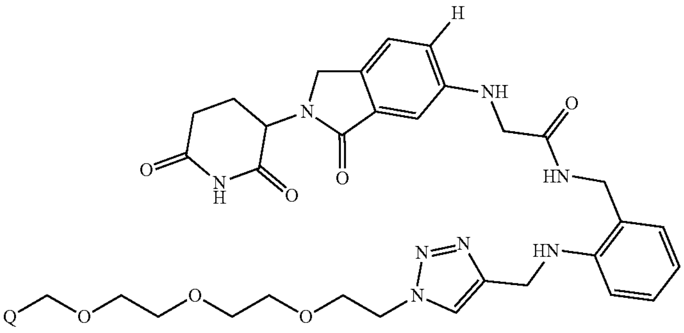

TABLE 3-continued
| Embodiments of general formula $(A)_k$-L-Q, having Q moiety. | |
|---|---|
| 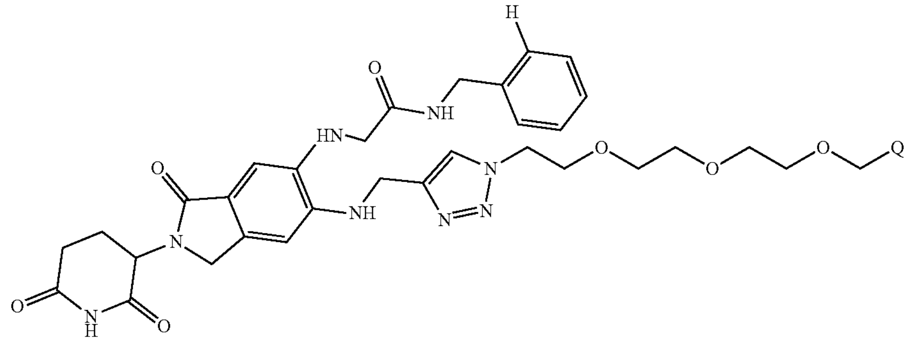 | 3.148 |
| 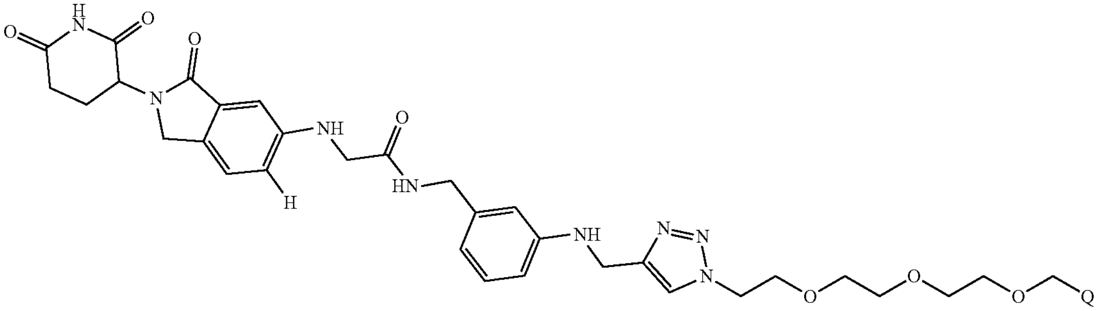 | 3.149 |
| 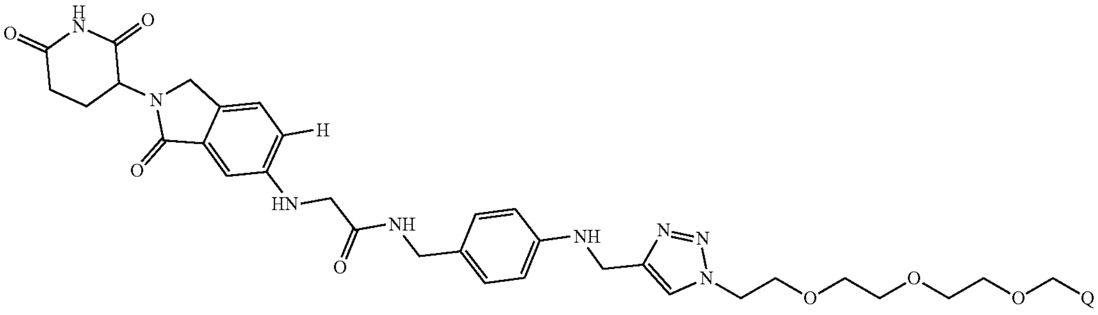 | 3.150 |
| 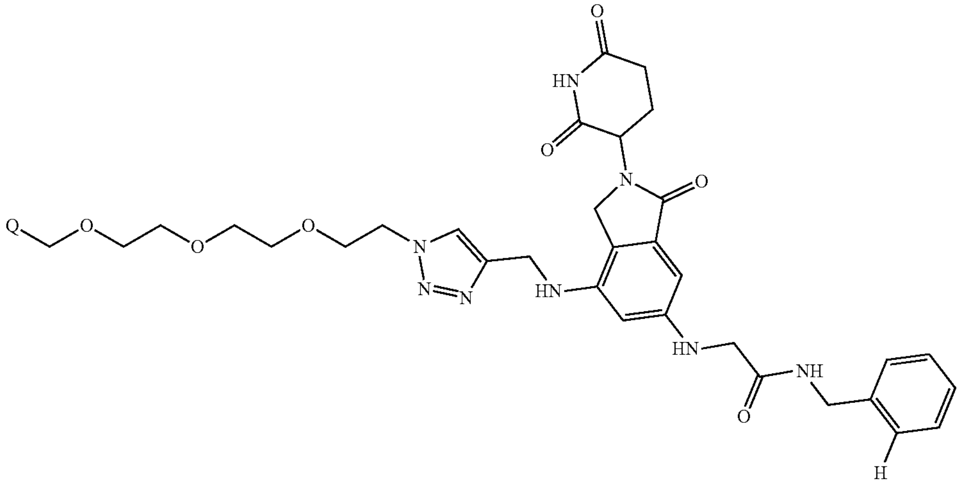 | 3.151 |

TABLE 3-continued
Embodiments of general formula $(A)_k$-L-Q, having Q moiety.
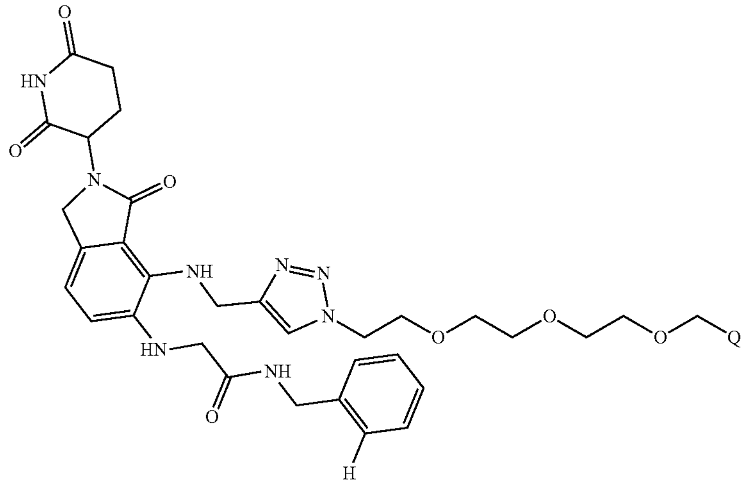
3.152
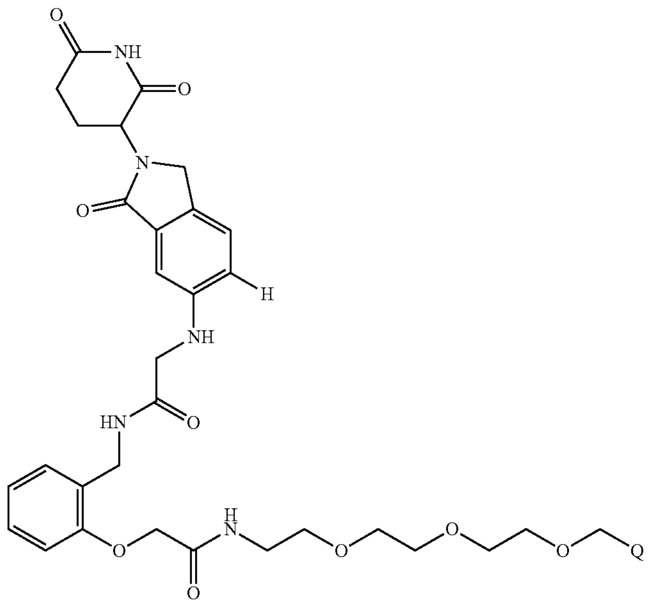
3.153
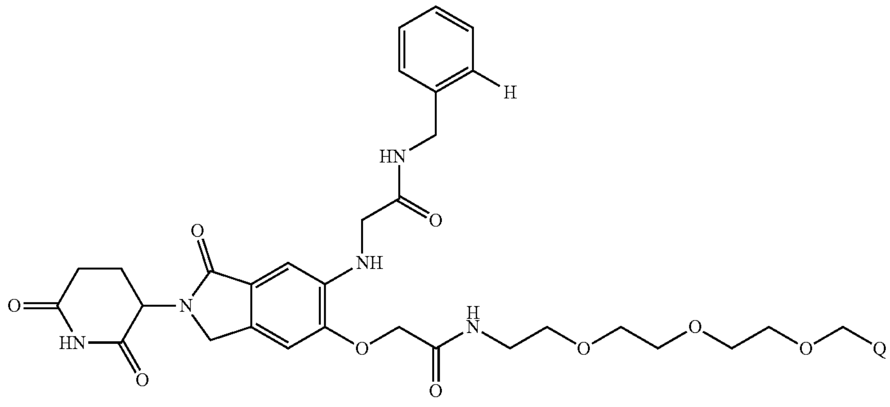
3.154

TABLE 3-continued
| Embodiments of general formula $(A)_k$-L-Q, having Q moiety. | |
|---|---|
| 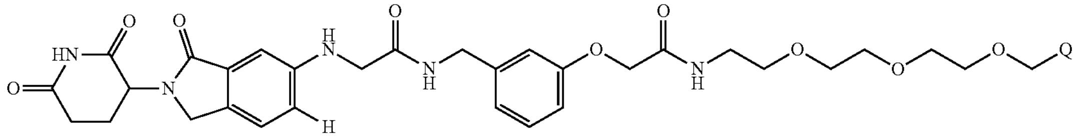 | 3.155 |
| 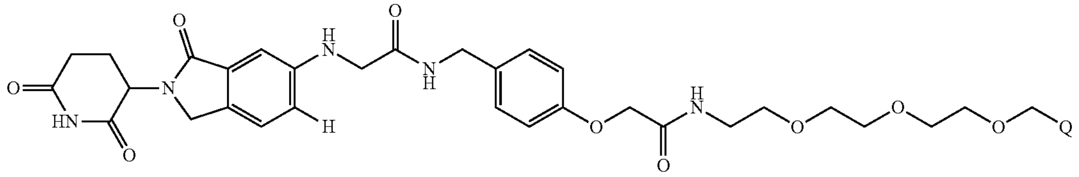 | 3.156 |
| 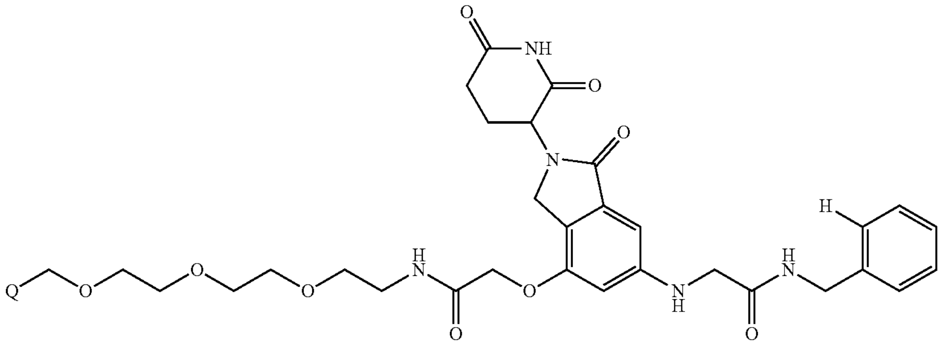 | 3.157 |
| 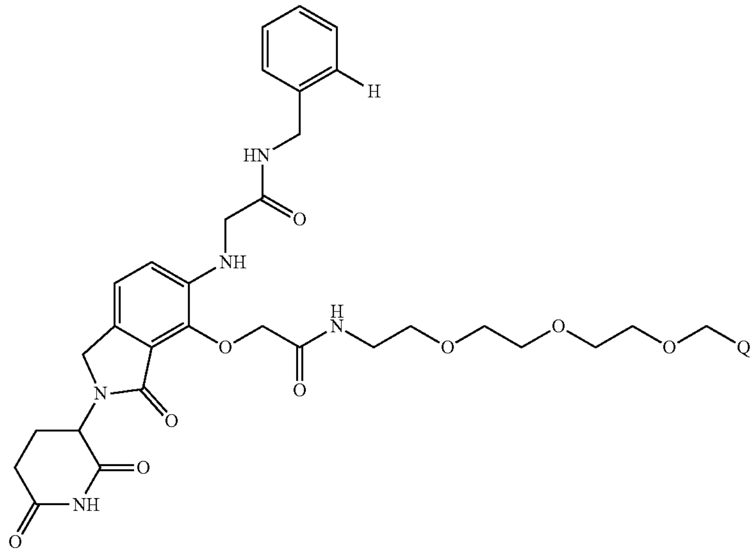 | 3.158 |

TABLE 3-continued
Embodiments of general formula $(A)_k$-L-Q, having Q moiety.
3.159
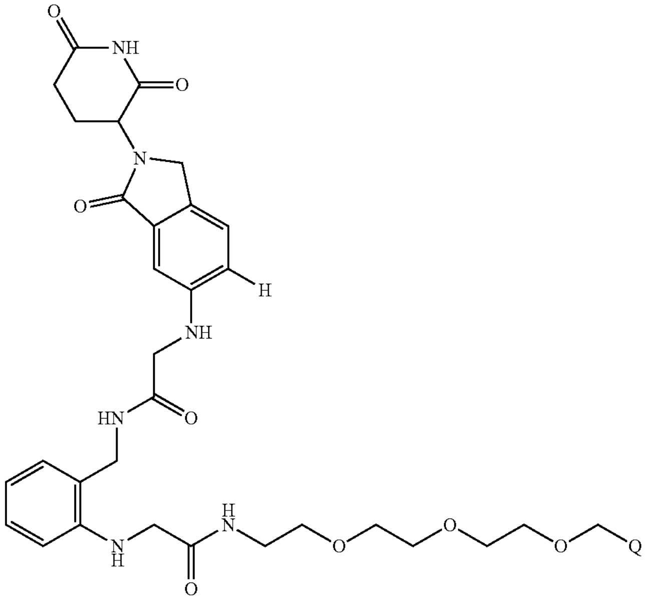
3.160
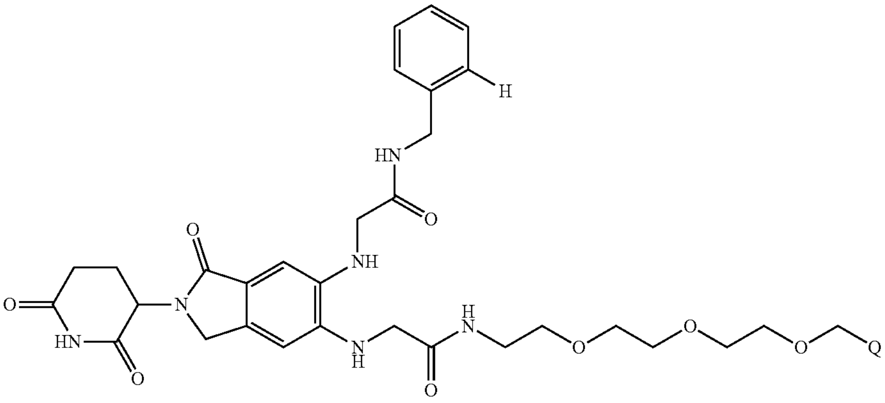
3.161
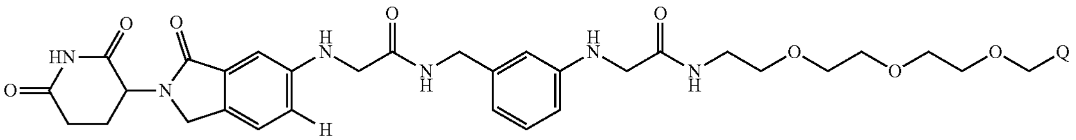
3.162
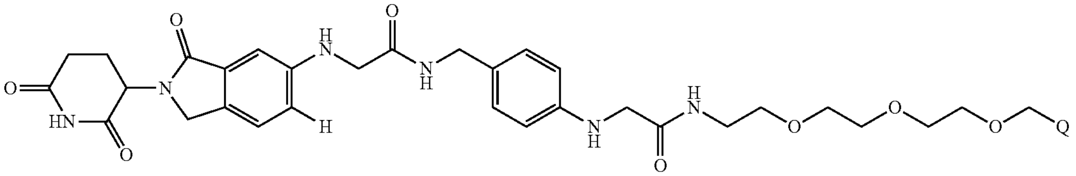

TABLE 3-continued
Embodiments of general formula $(A)_k$-L-Q, having Q moiety.
3.163
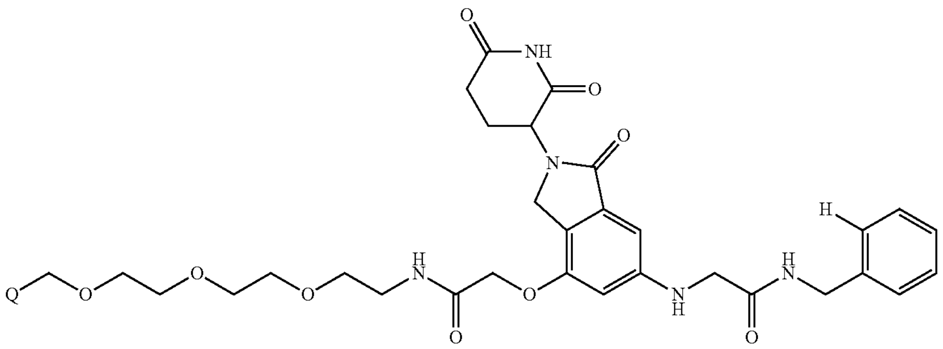
3.164
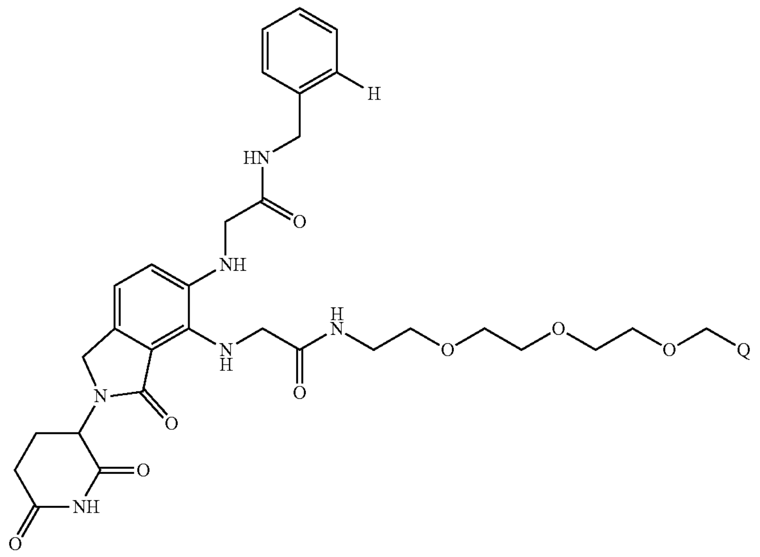
3.165
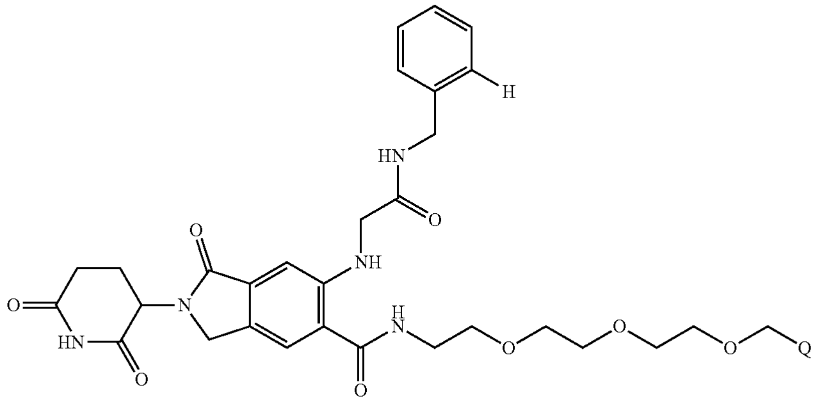

TABLE 3-continued
| Embodiments of general formula $(A)_k$-L-Q, having Q moiety. |
| --- |
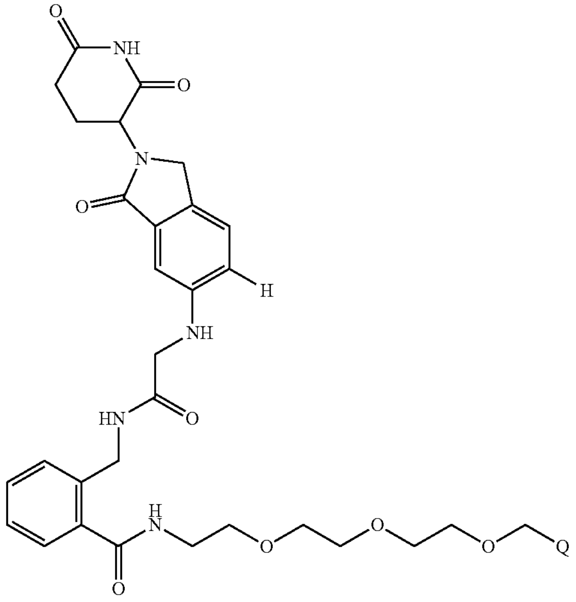
3.166
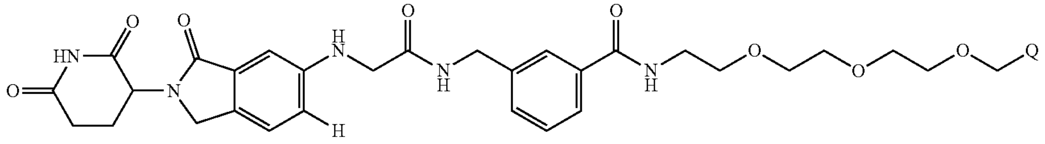
3.167
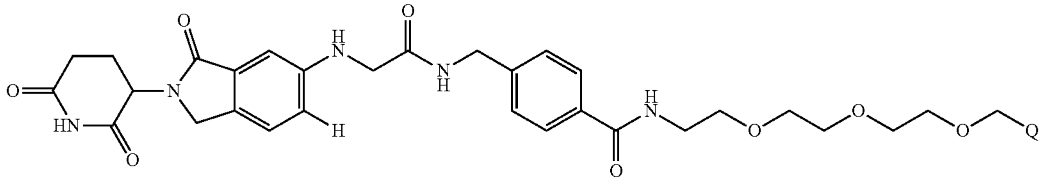
3.168
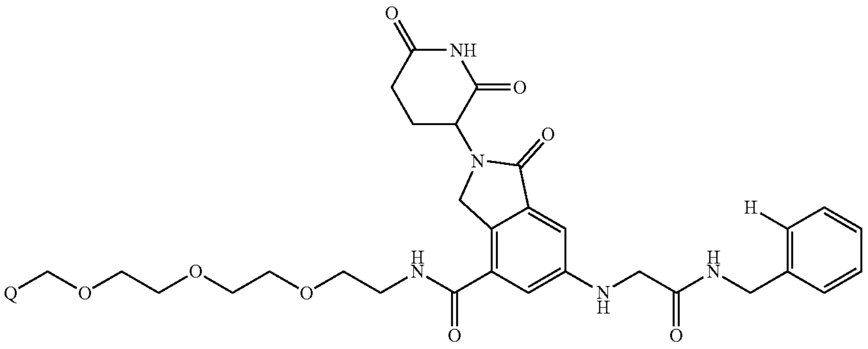
3.169

TABLE 3-continued
| Embodiments of general formula $(A)_k$-L-Q, having Q moiety. |
| --- |
3.170
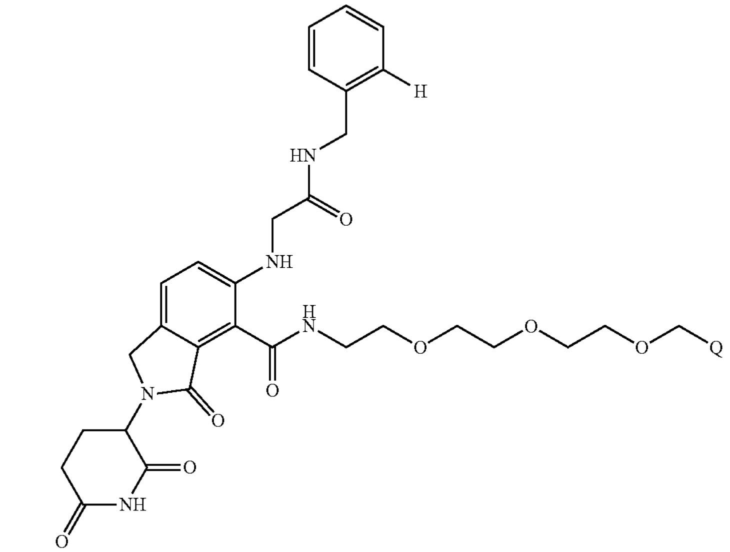
3.171
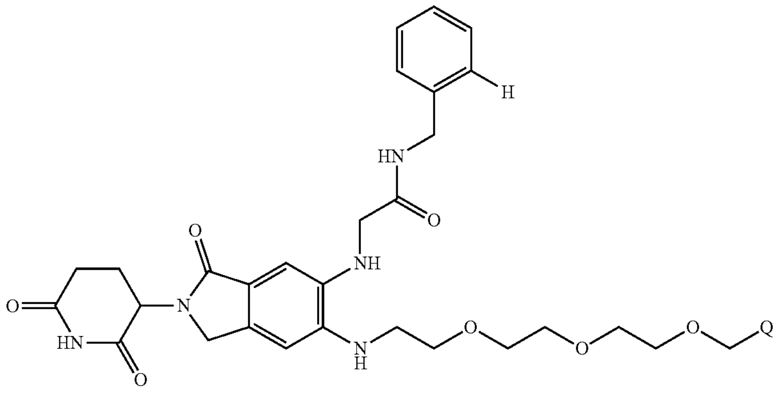
3.172
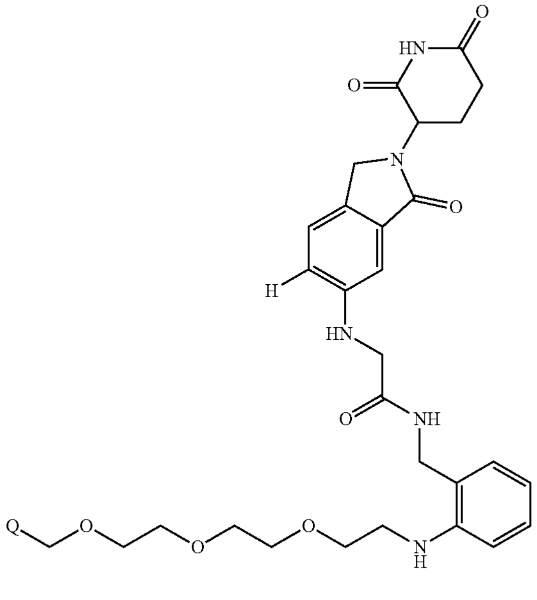

TABLE 3-continued
Embodiments of general formula $(A)_k$-L-Q, having Q moiety.
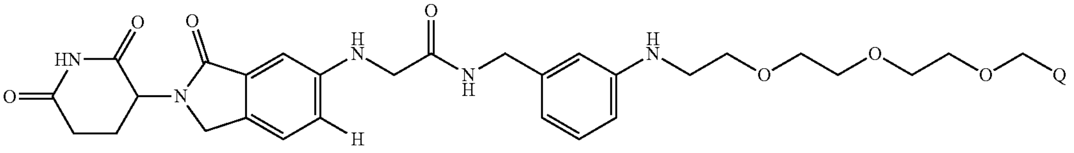
3.173
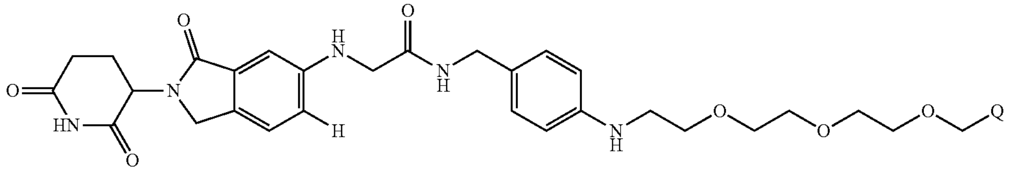
3.174
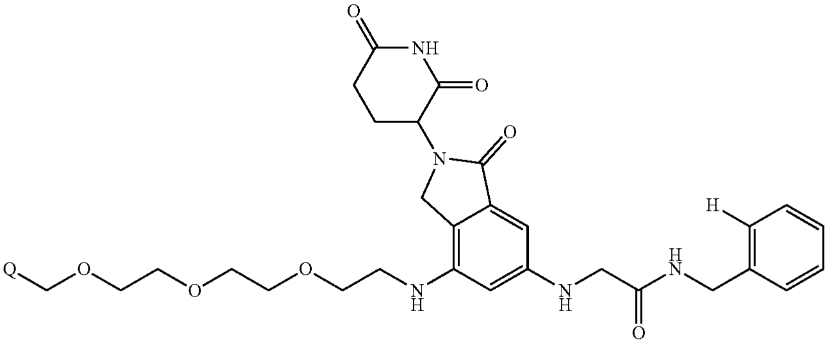
3.175
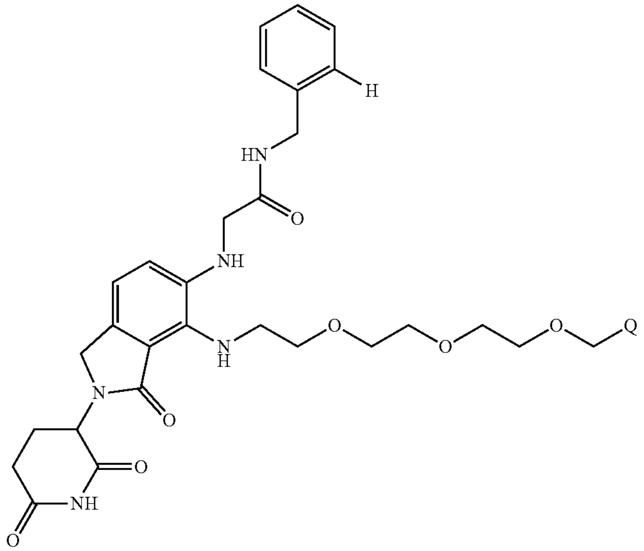
3.176
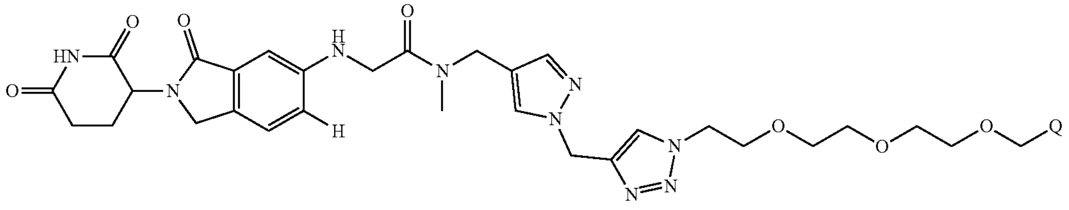
3.177

TABLE 3-continued
| Embodiments of general formula $(A)_k$-L-Q, having Q moiety. |
| --- |
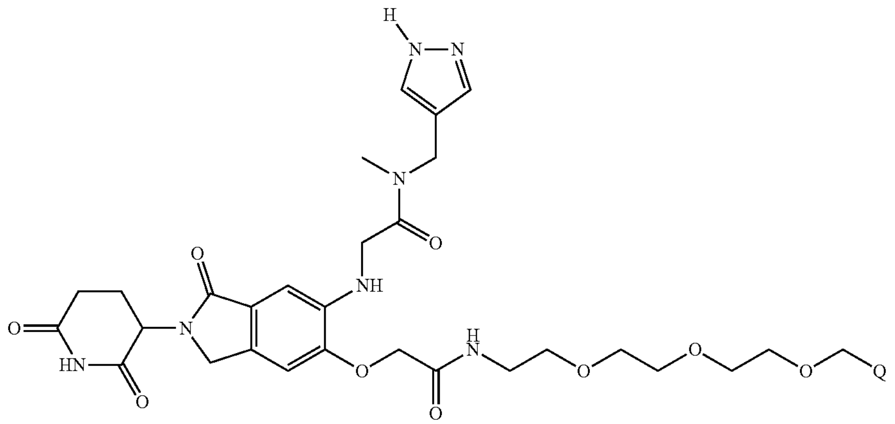
3.178
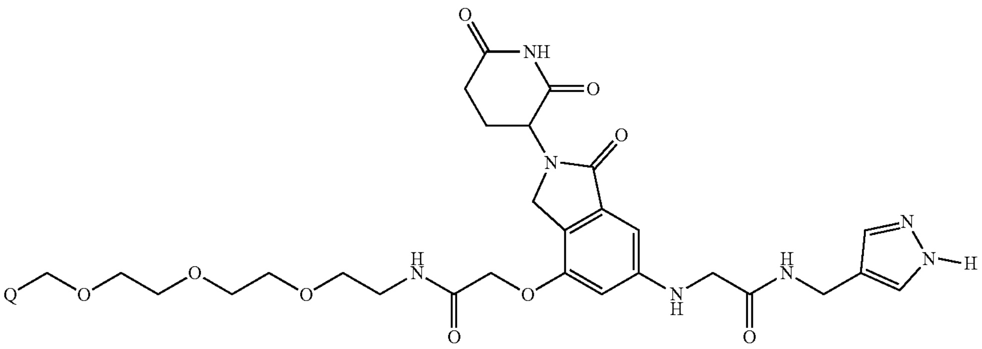
3.179
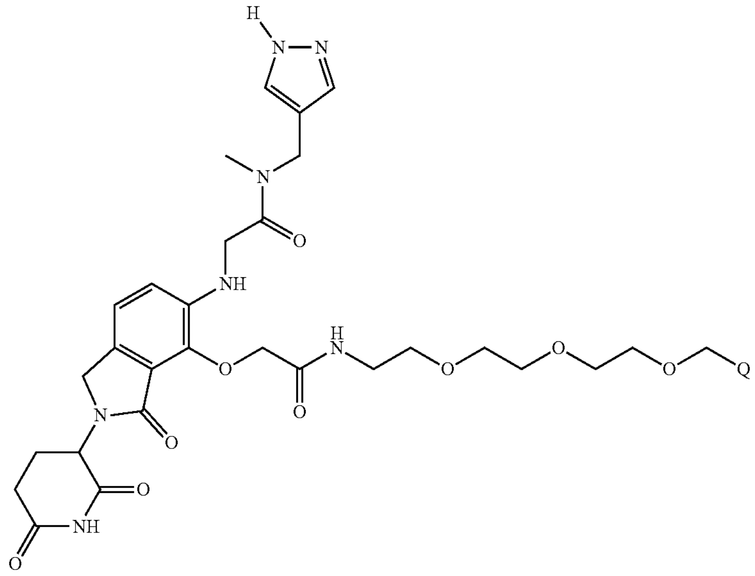
3.180

TABLE 3-continued
| Embodiments of general formula $(A)_k$-L-Q, having Q moiety. | |
|---|---|
| 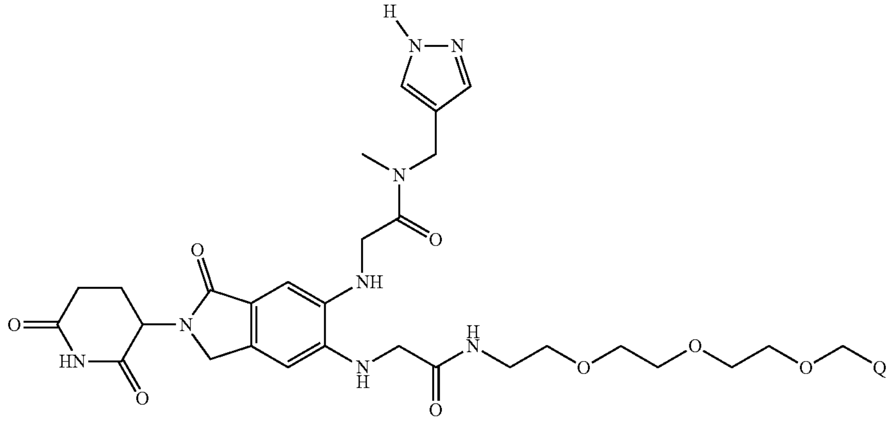 | 3.181 |
| 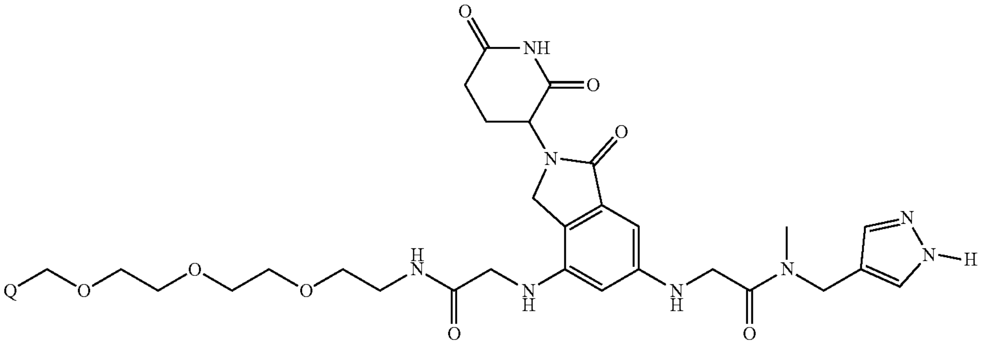 | 3.182 |
| 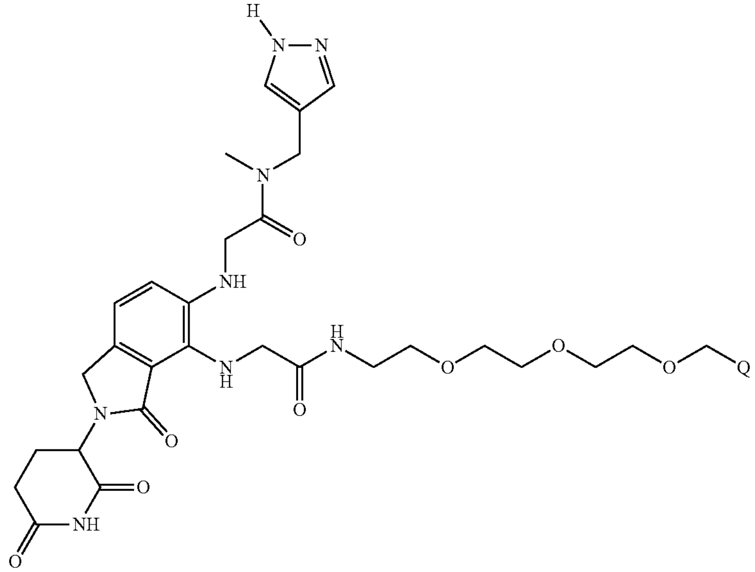 | 3.183 |

TABLE 3-continued
Embodiments of general formula $(A)_k$-L-Q, having Q moiety.
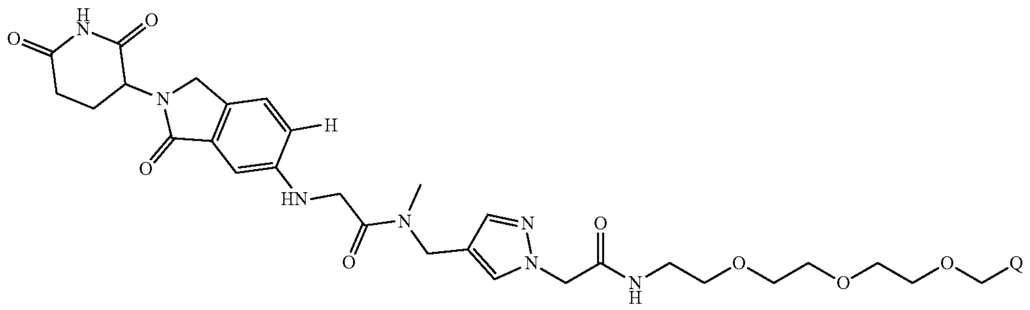
3.184
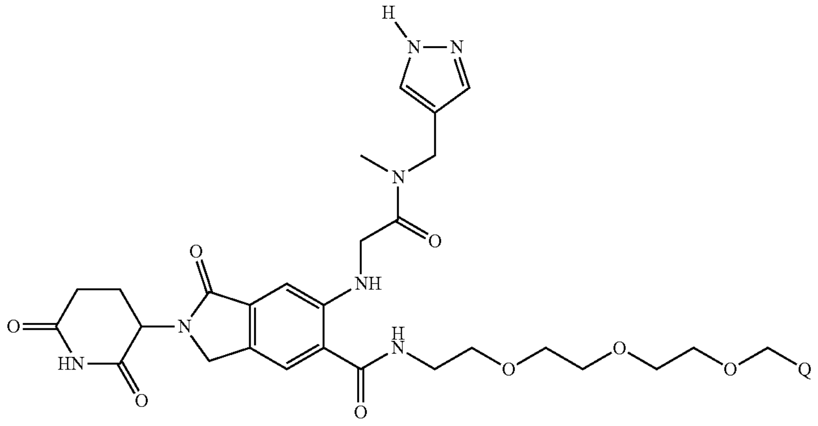
3.185
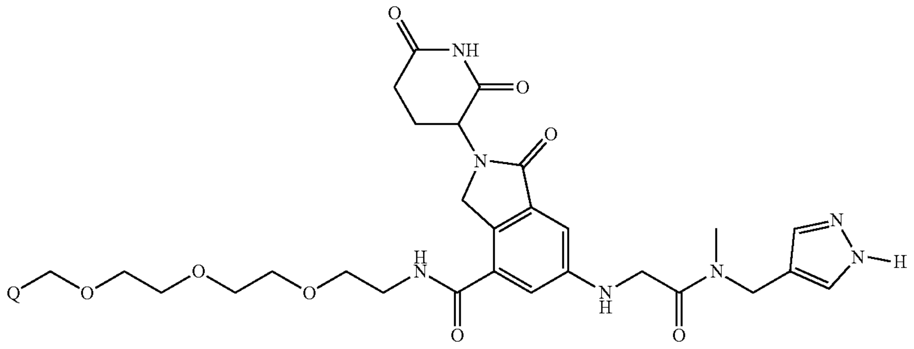
3.186

TABLE 3-continued
| Embodiments of general formula $(A)_k$-L-Q, having Q moiety. |
|---|
| 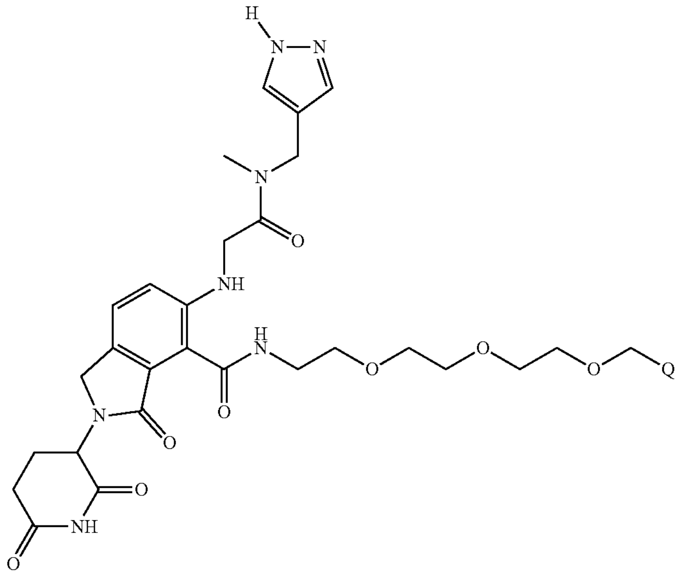 3.187 |
| 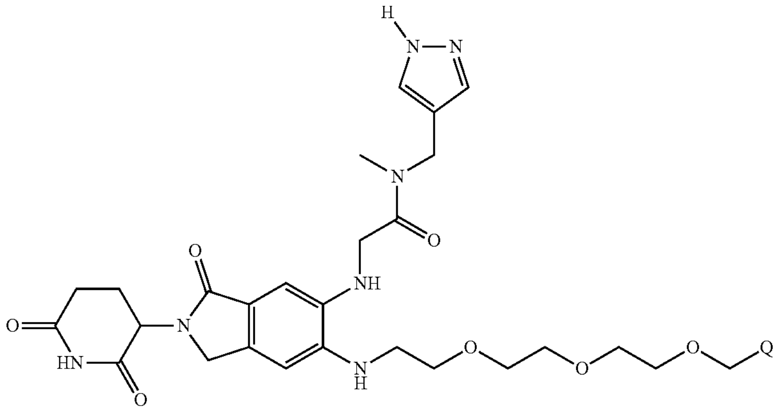 3.188 |
| 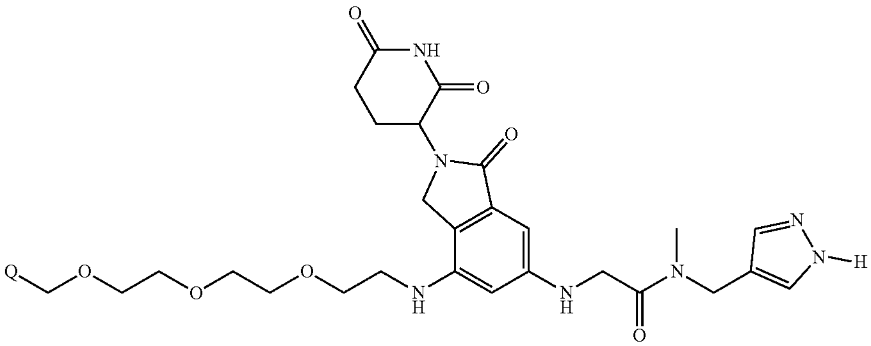 3.189 |

TABLE 3-continued
| Embodiments of general formula $(A)_k$-L-Q, having Q moiety. | |
|---|---|
| 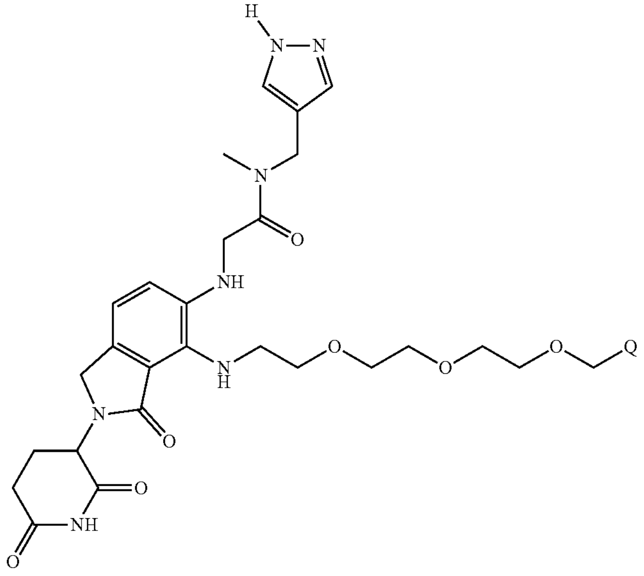 | 3.190 |
| 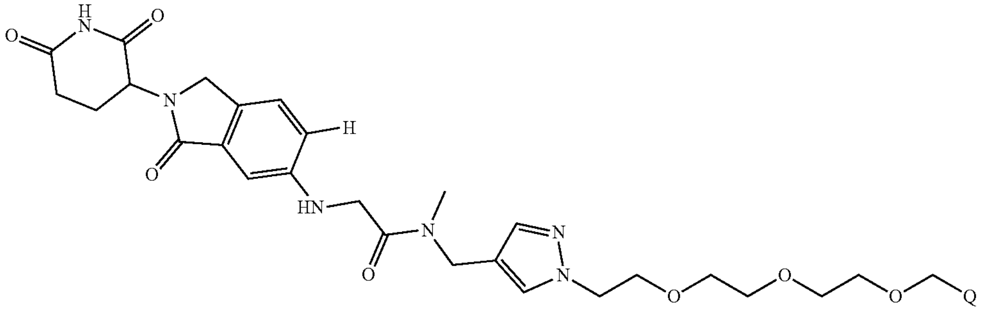 | 3.191 |
| 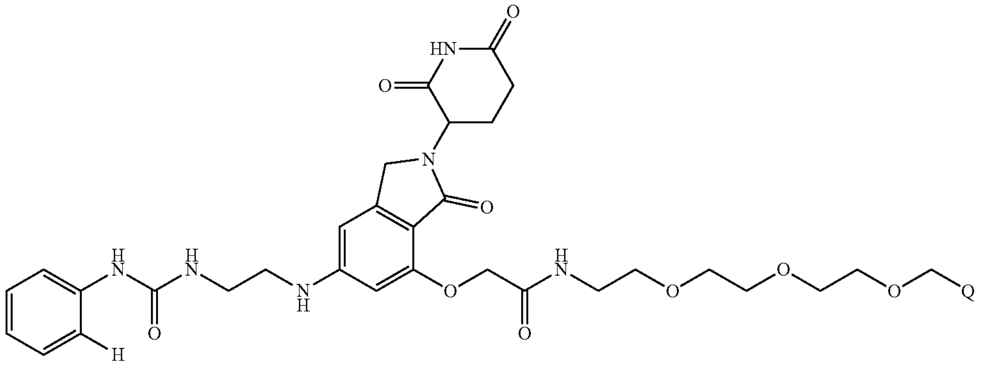 | 3.192 |

TABLE 3-continued
| Embodiments of general formula $(A)_k$-L-Q, having Q moiety. |
| --- |
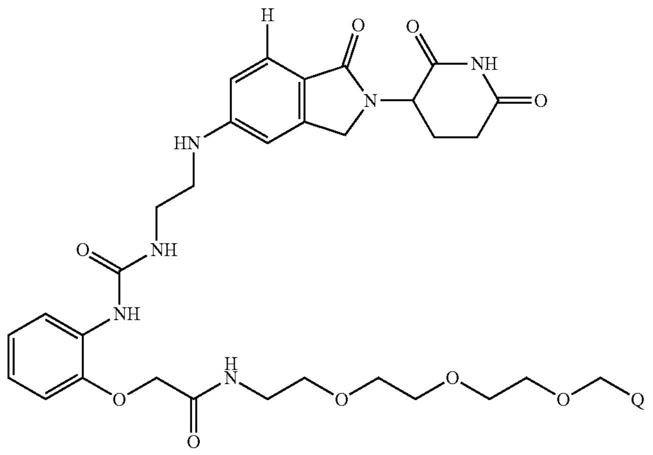
3.193
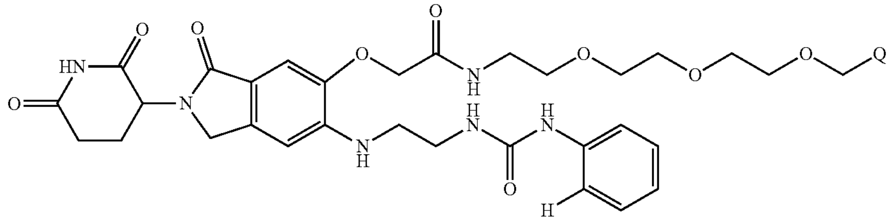
3.194
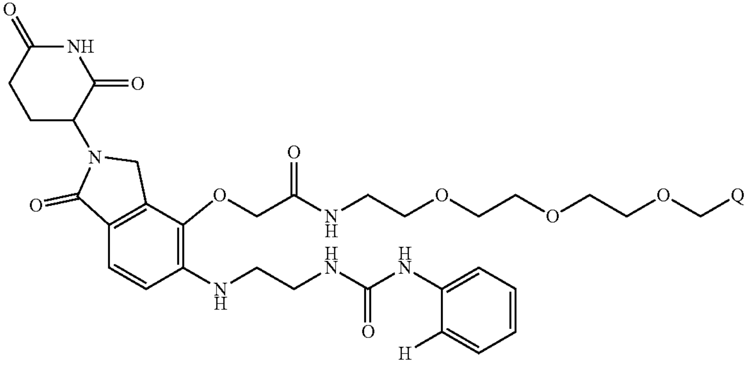
3.195
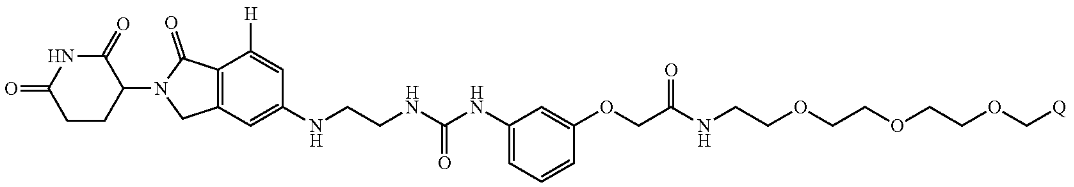
3.196
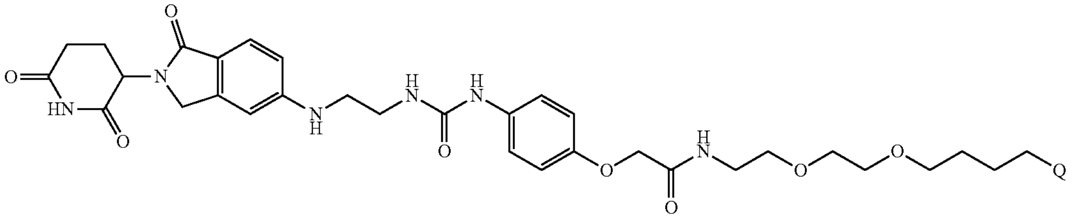
3.197

TABLE 3-continued
Embodiments of general formula $(A)_k$-L-Q, having Q moiety.
3.198
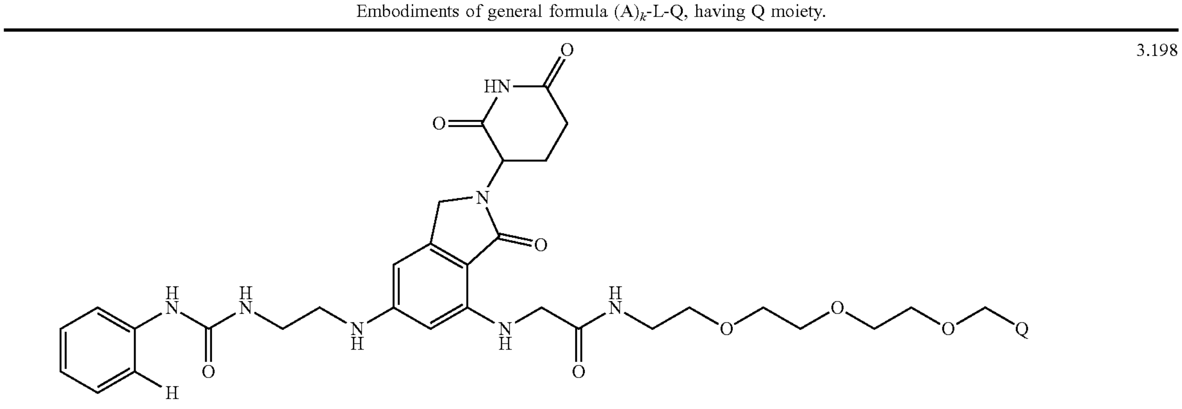
3.199
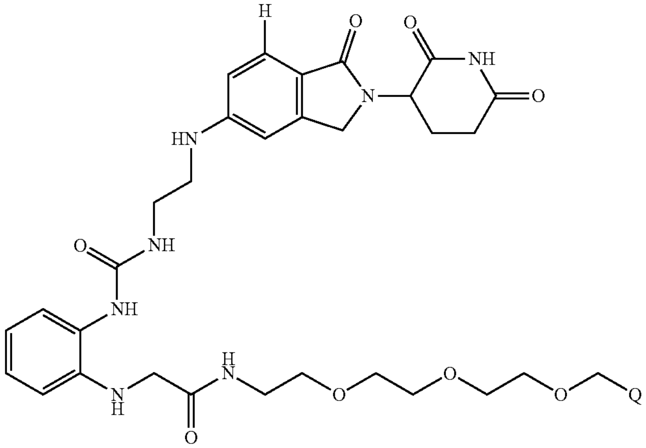
3.200
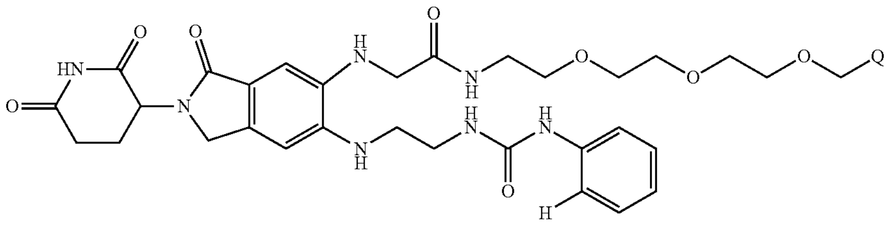
3.201
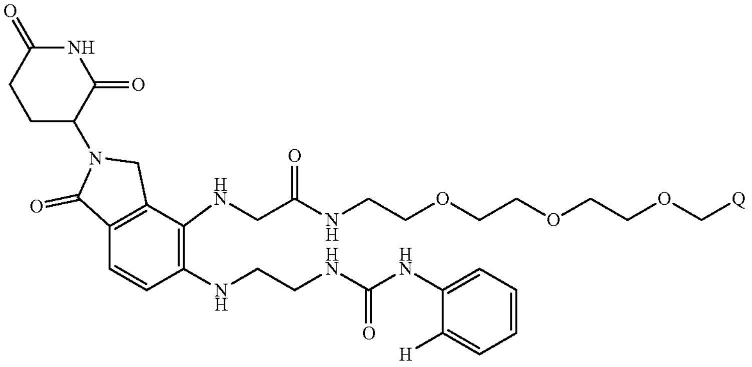
3.202
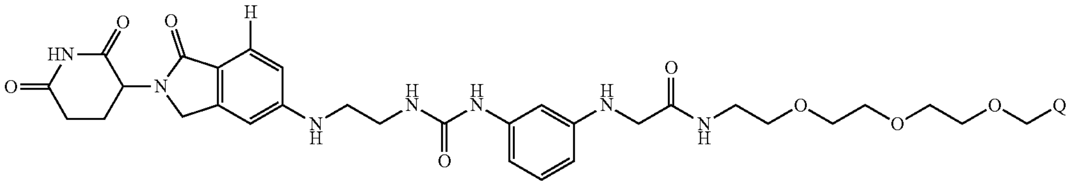

TABLE 3-continued
| Embodiments of general formula $(A)_k$-L-Q, having Q moiety. |
| --- |
3.203
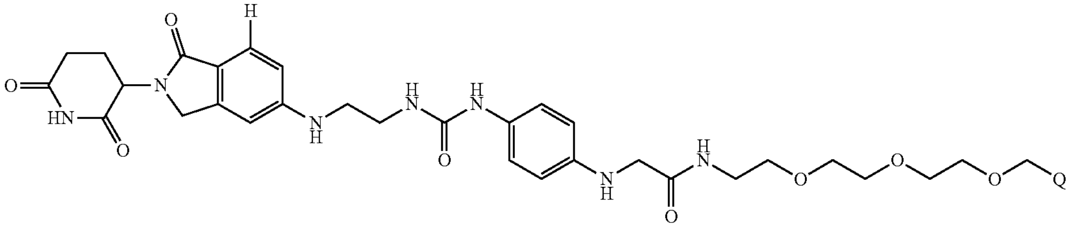
3.204
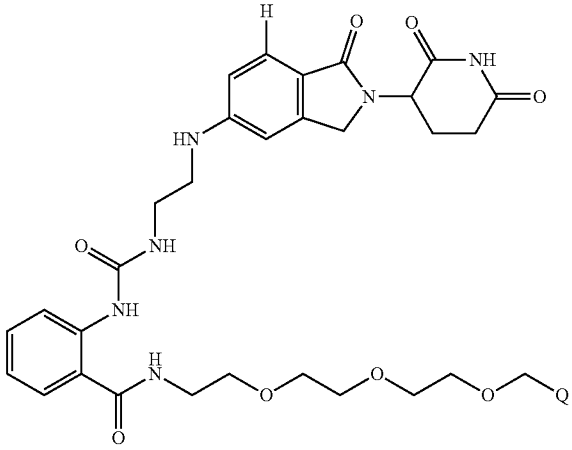
3.205
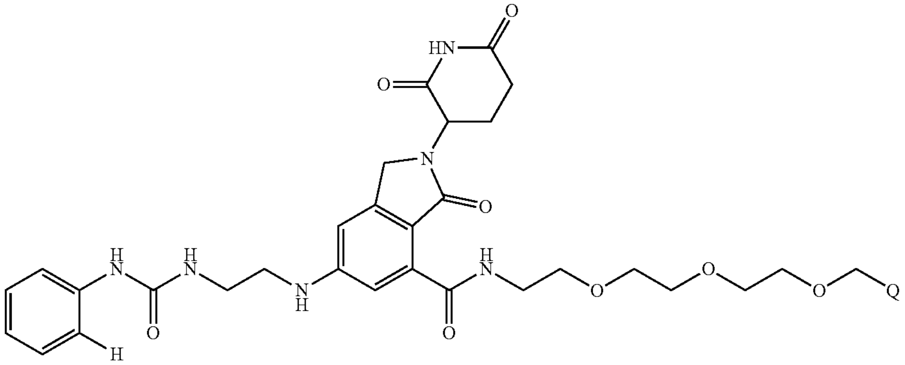
3.206
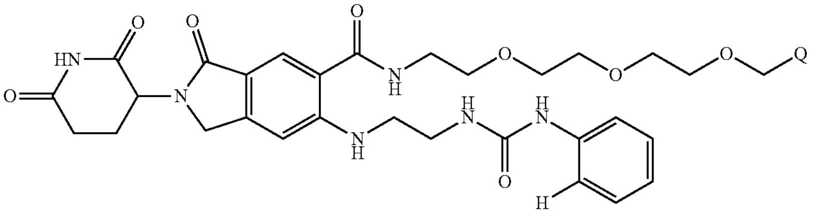

TABLE 3-continued
Embodiments of general formula $(A)_k$-L-Q, having Q moiety.
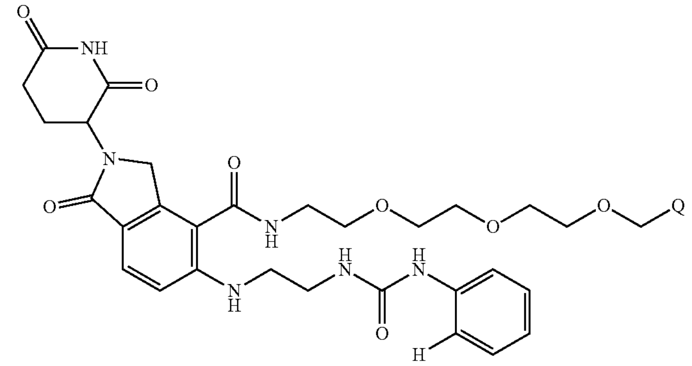
3.207
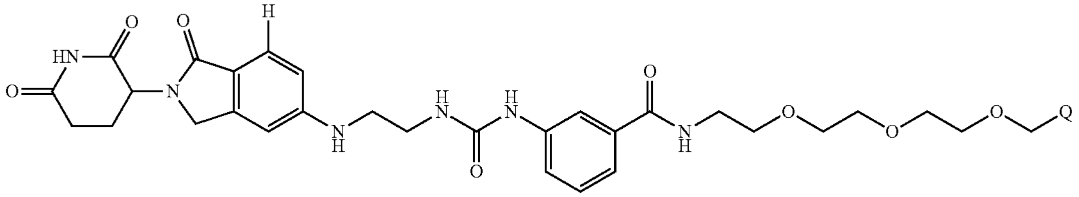
3.208
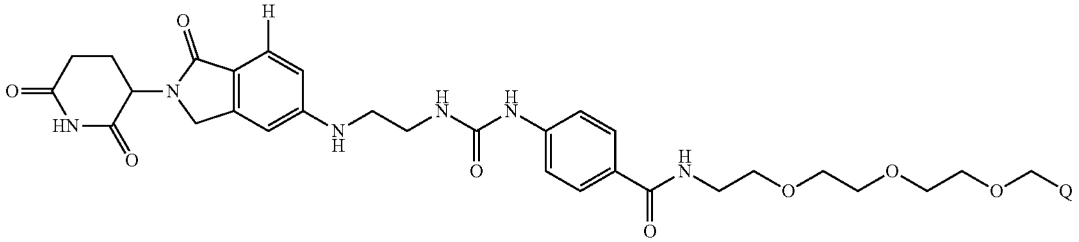
3.209
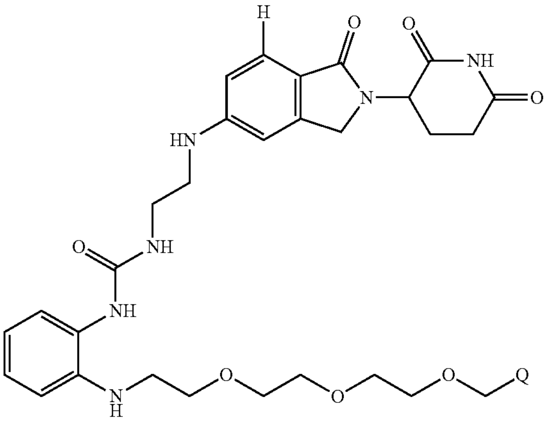
3.210

TABLE 3-continued
| Embodiments of general formula $(A)_k$-L-Q, having Q moiety. |
|---|
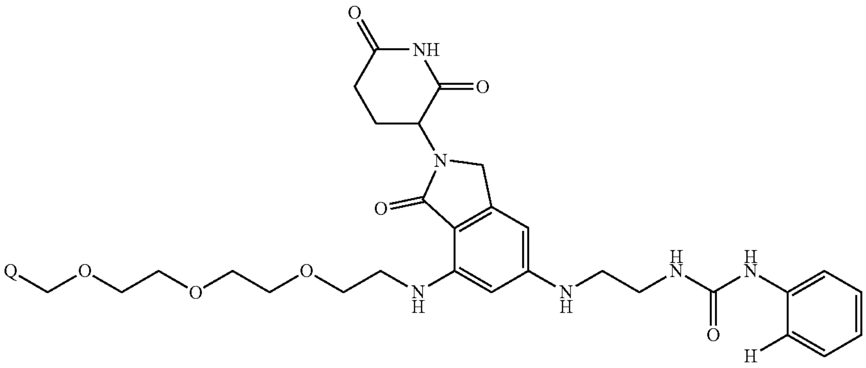
3.211
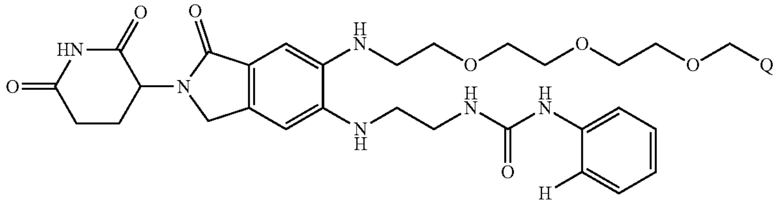
3.212
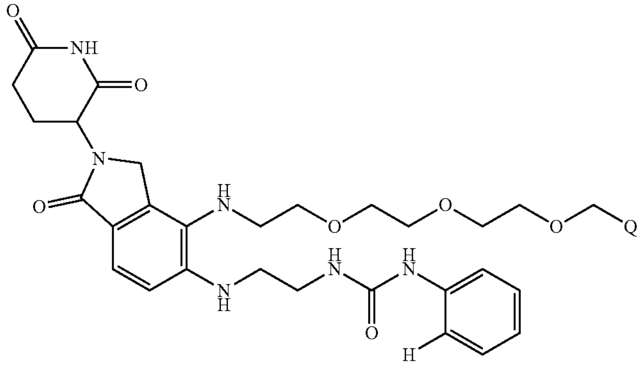
3.213
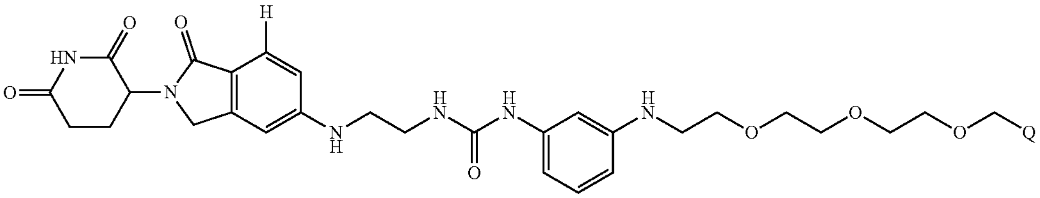
3.214
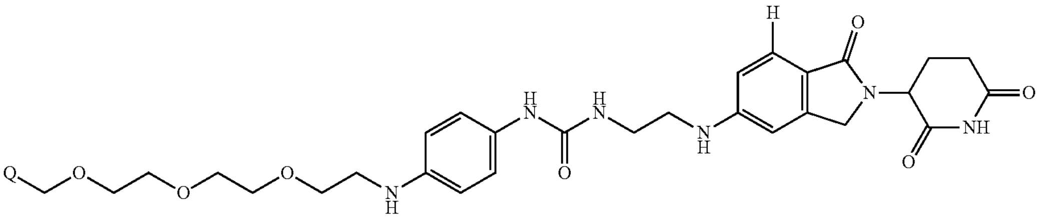
3.215

TABLE 3-continued
| Embodiments of general formula $(A)_k$-L-Q, having Q moiety. | |
|---|---|
| 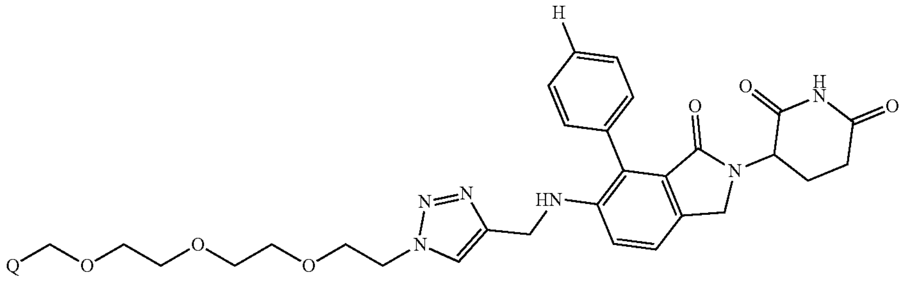 | 3.216 |
| 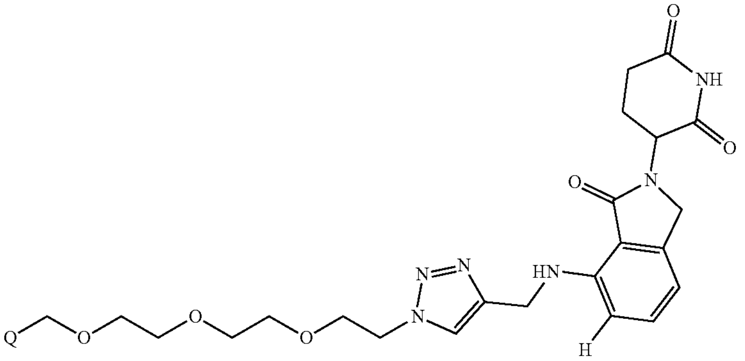 | 3.217 |
| 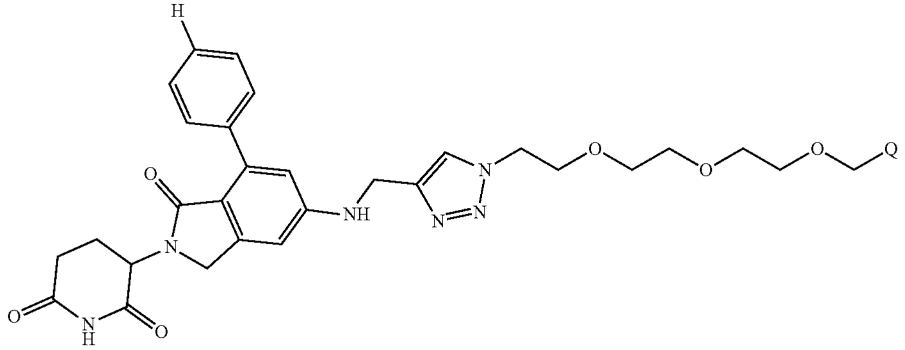 | 3.218 |
| 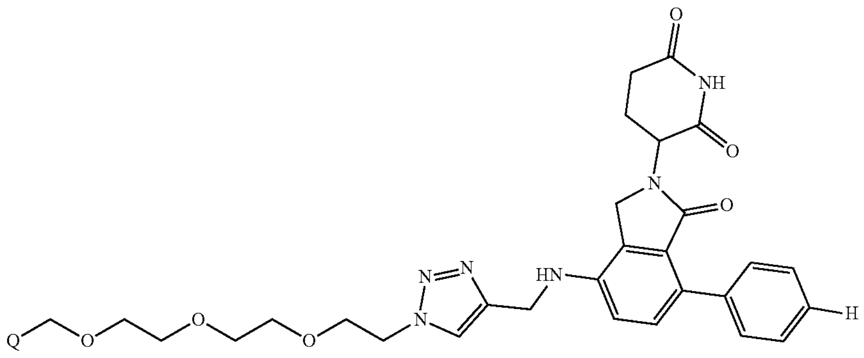 | 3.219 |

TABLE 3-continued
Embodiments of general formula $(A)_k$-L-Q, having Q moiety.
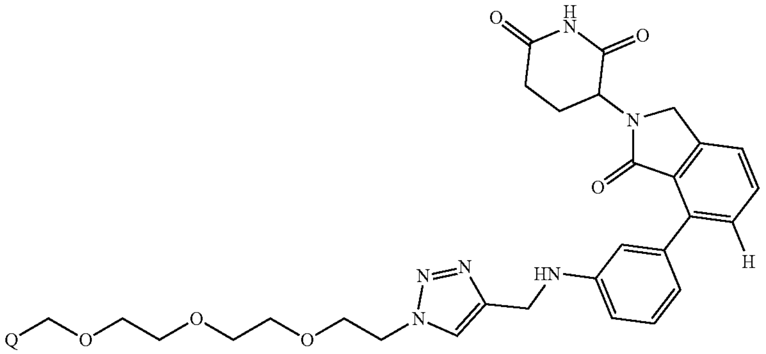
3.220
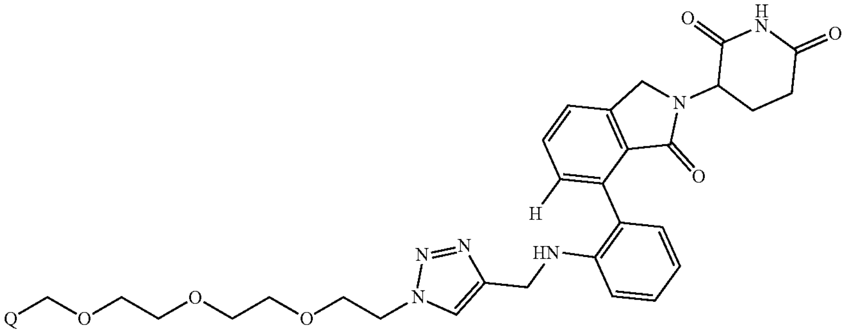
3.221
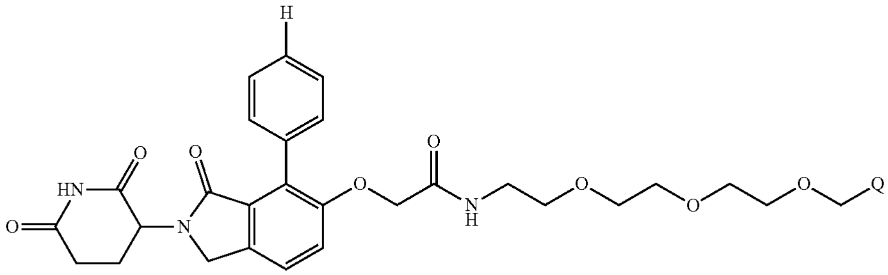
3.222
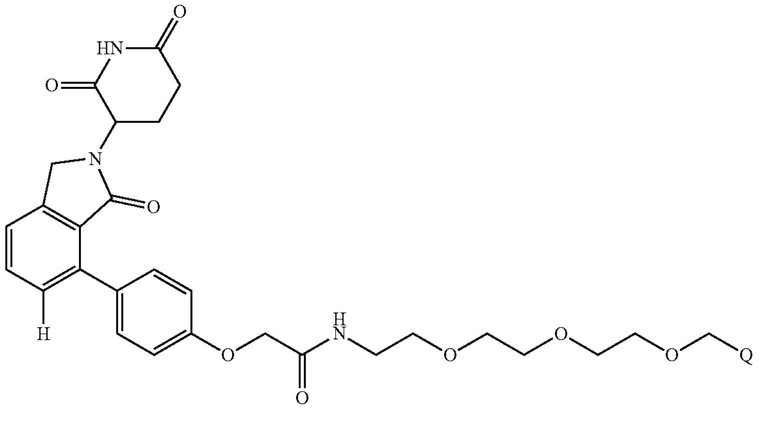
3.223

TABLE 3-continued
Embodiments of general formula $(A)_k$-L-Q, having Q moiety.
3.224
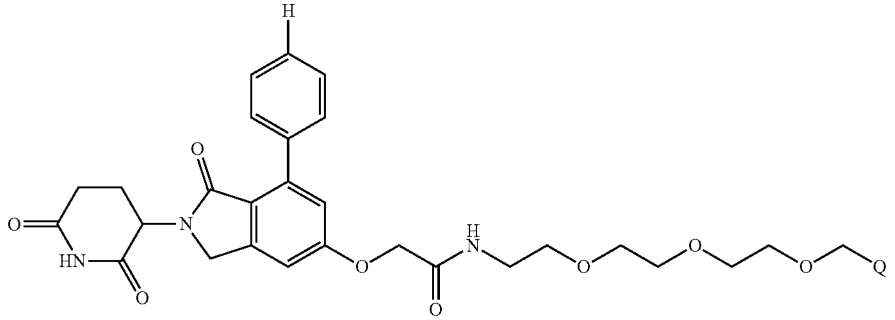
3.225
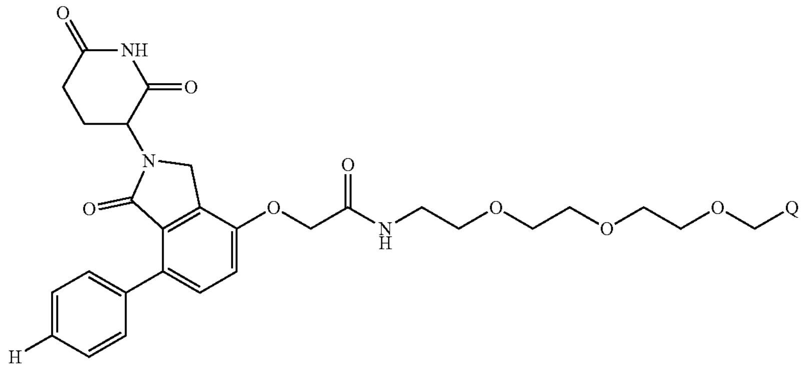
3.226
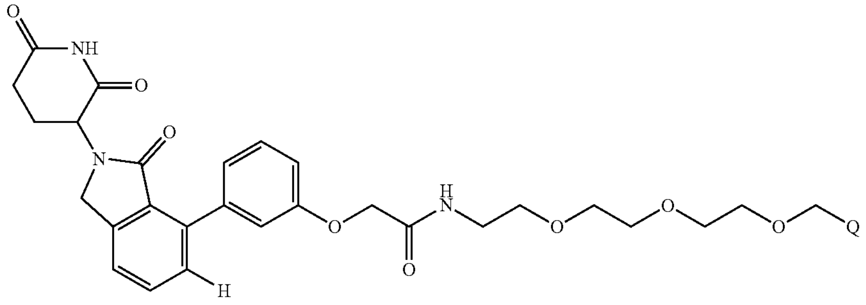
3.227
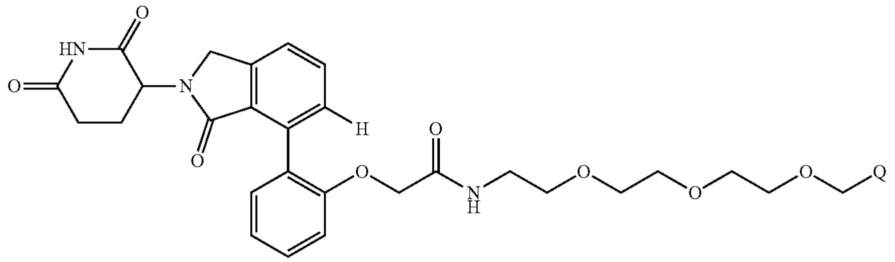
3.228
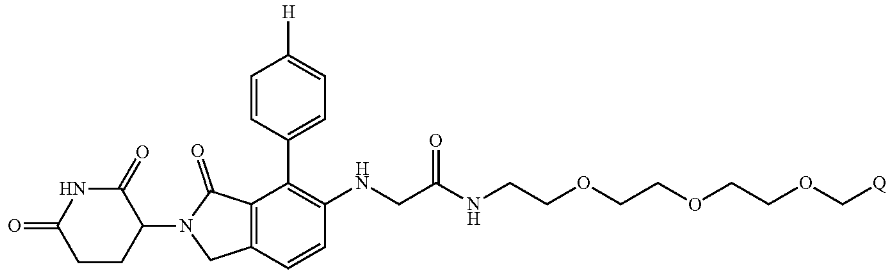

TABLE 3-continued
| Embodiments of general formula $(A)_k$-L-Q, having Q moiety. |
|---|
| 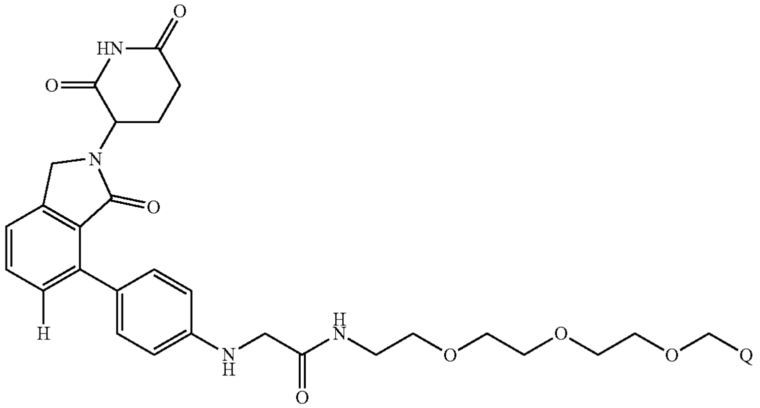 3.229 |
| 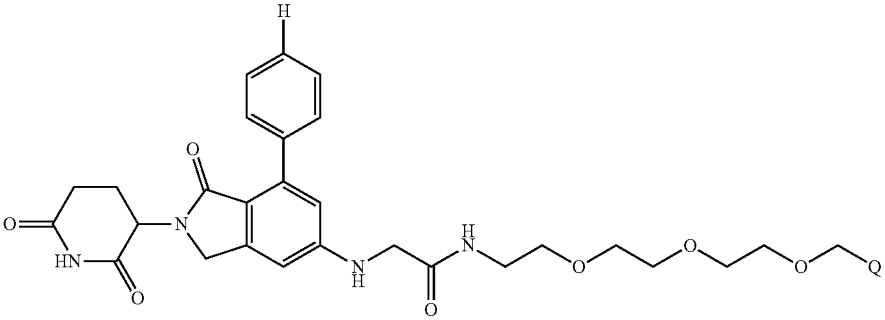 3.230 |
| 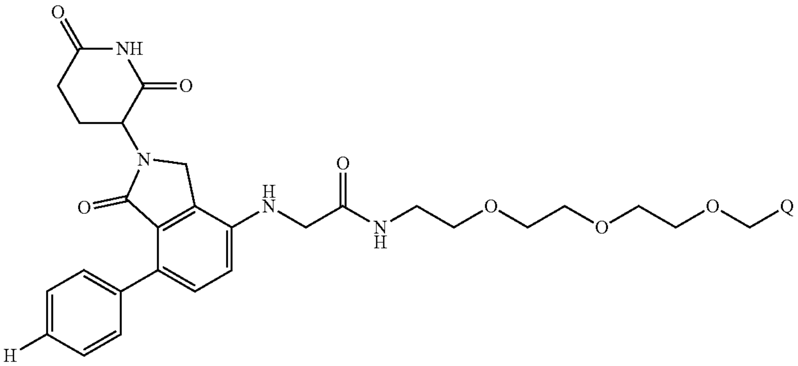 3.231 |
| 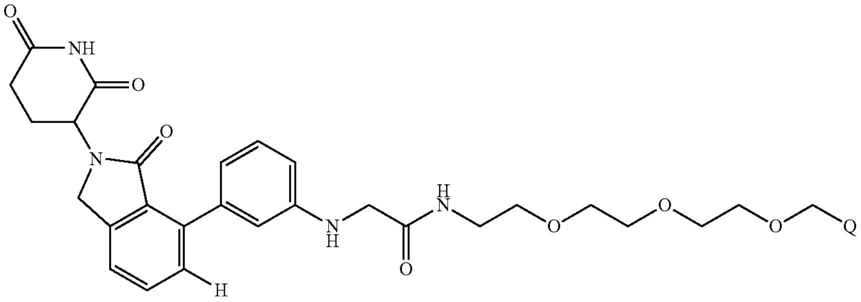 3.232 |

TABLE 3-continued
Embodiments of general formula $(A)_k$-L-Q, having Q moiety.
3.233
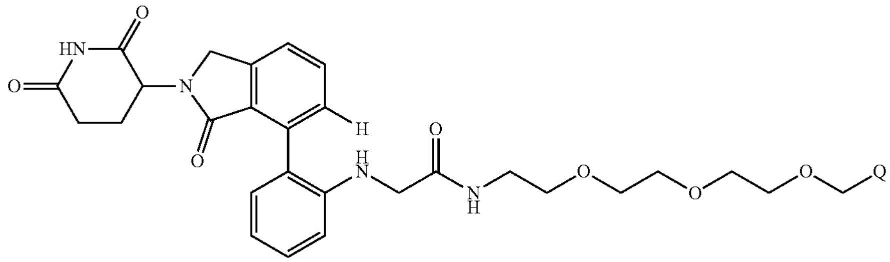
3.234
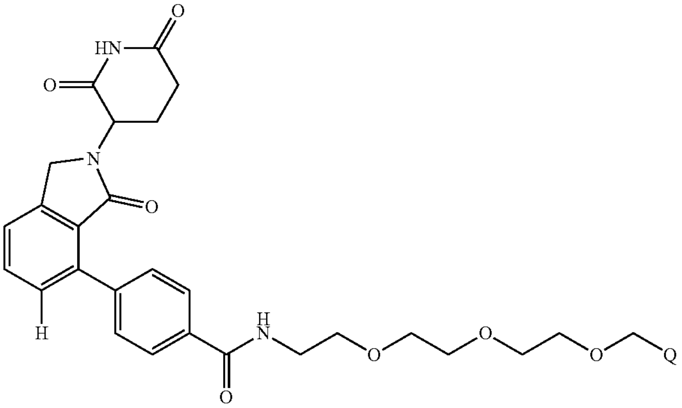
3.235
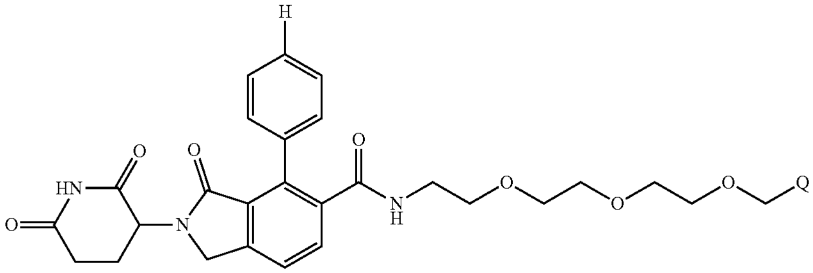
3.236
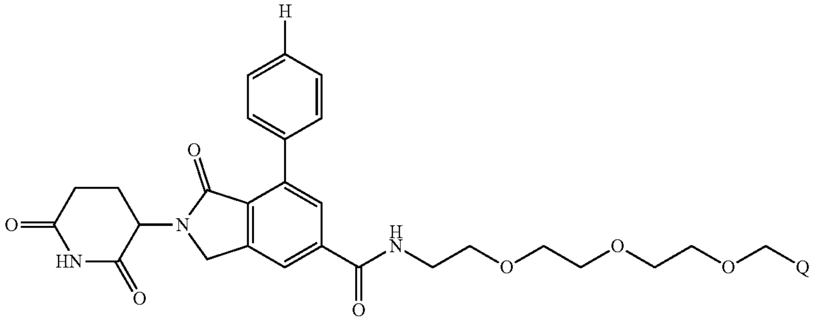

TABLE 3-continued
| Embodiments of general formula $(A)_k$-L-Q, having Q moiety. |
| --- |
| 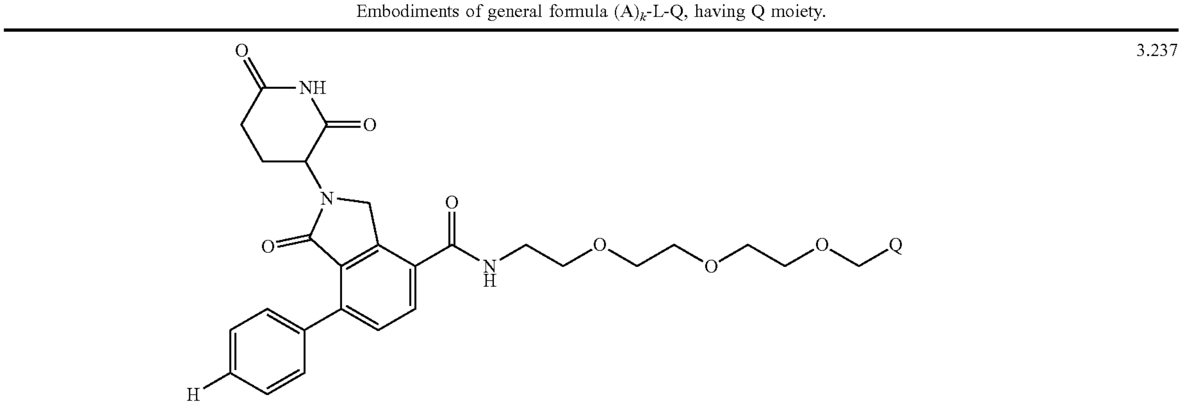 3.237 |
| 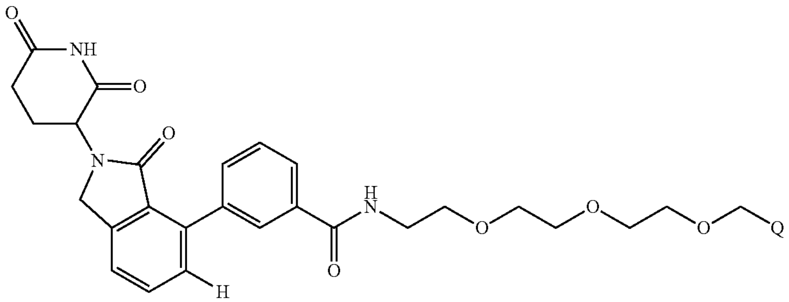 3.238 |
| 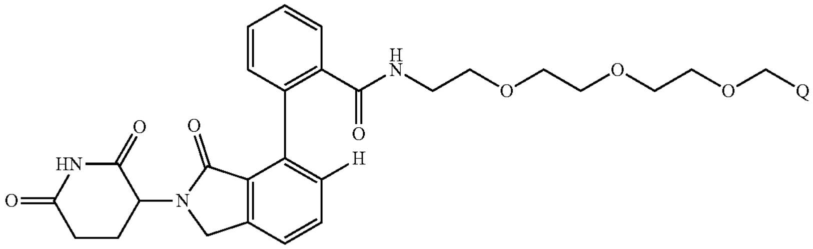 3.239 |
| 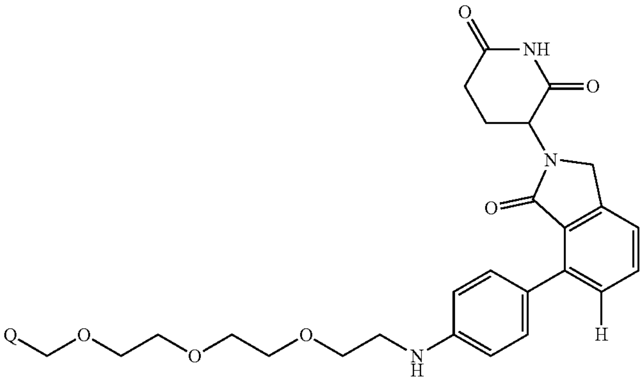 3.240 |
| 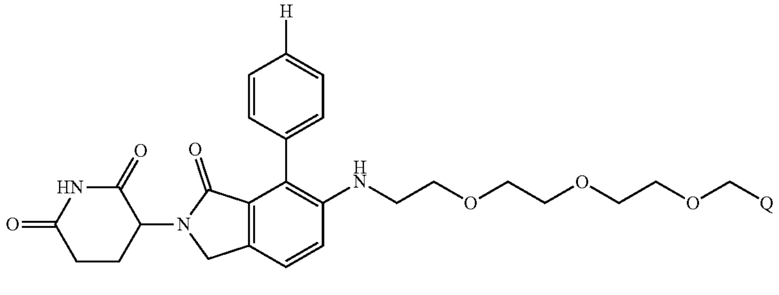 3.241 |

TABLE 3-continued
| Embodiments of general formula $(A)_k$-L-Q, having Q moiety. | |
|---|---|
| 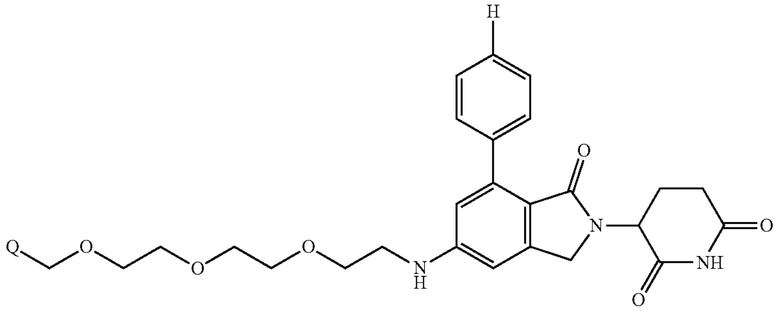 | 3.242 |
| 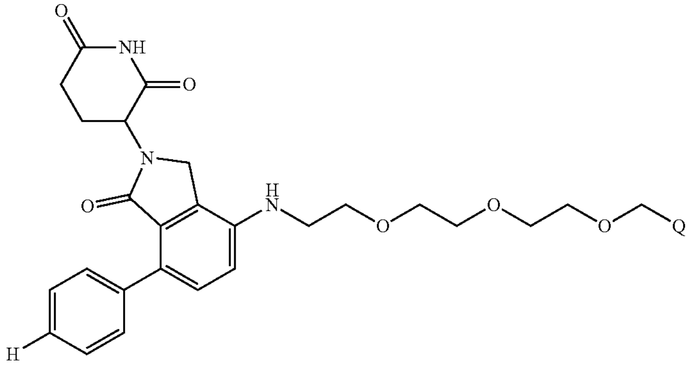 | 3.243 |
| 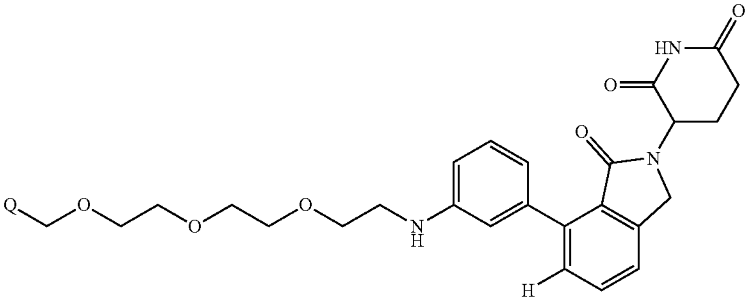 | 3.244 |
| 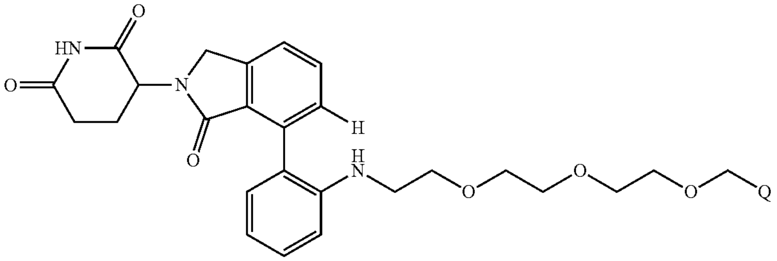 | 3.245 |

TABLE 4
| Embodiments of general formula A-$L_b$-$L_a$-Q | | |
|---|---|---|
| A | $L_b$ | $L_a$-Q |
| 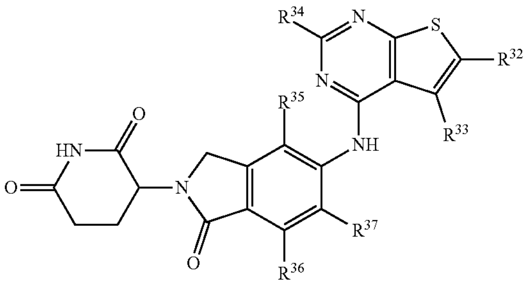<br>4.001 | 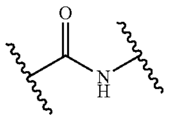<br>$L_b$1 | 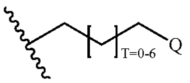<br>$L_a$1.0-6 |
| 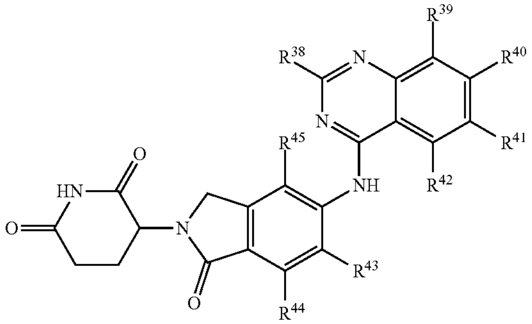<br>4.002 | 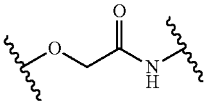<br>$L_b$2 | 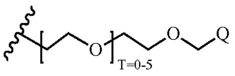<br>$L_a$2.0-5 |
| 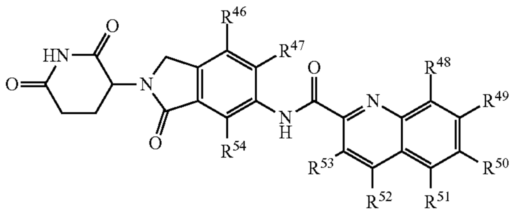<br>4.003 | 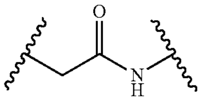<br>$L_b$3 | |
| 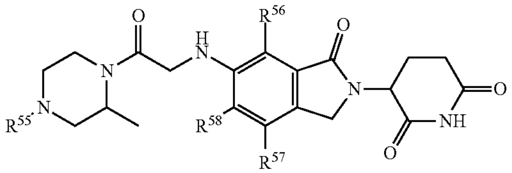<br>4.004 | 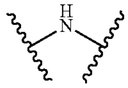<br>$L_b$4 | |
| 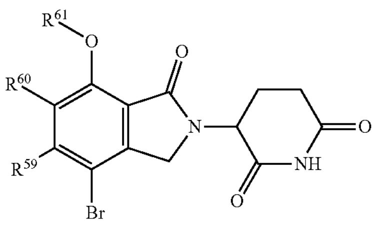<br>4.005 | 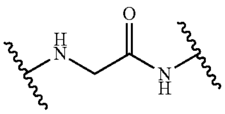<br>$L_b$5 | |

TABLE 4-continued
| Embodiments of general formula A-$L_b$-$L_a$-Q | | |
|---|---|---|
| A | $L_b$ | $L_a$-Q |
| 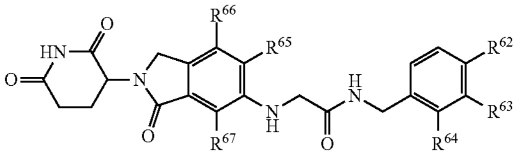<br>4.006 | 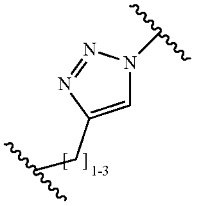<br>$L_b$6.1-3 | |
| 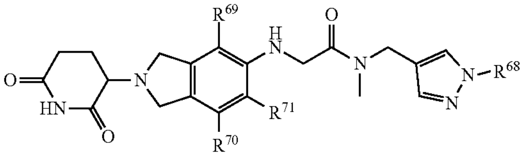<br>4.007 | 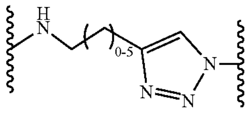<br>$L_b$7.0-5 | |
| 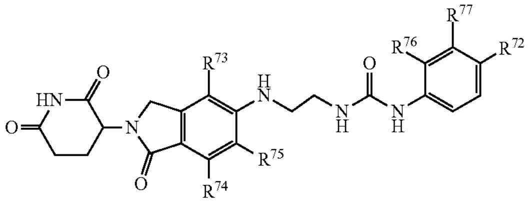<br>4.008 | 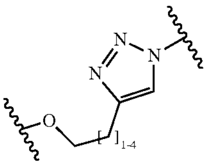<br>$L_b$8.1-4 | |
| 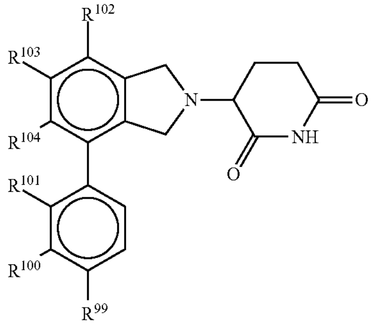<br>4.009 | 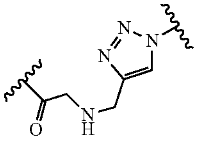<br>$L_b$9 | |
| 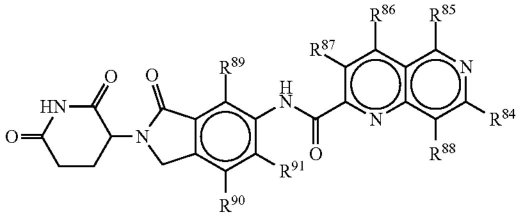<br>4.010 | 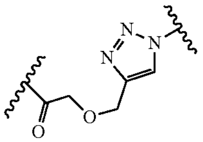<br>$L_b$10 | |
| 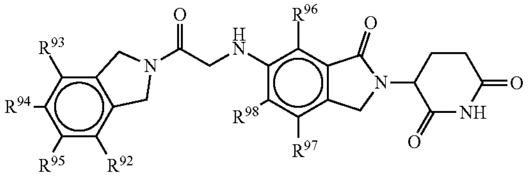<br>4.011 | 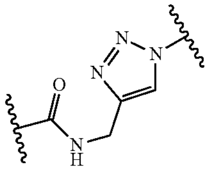<br>$L_b$11 | |

TABLE 4-continued

| Embodiments of general formula A-$L_b$-$L_a$-Q | | |
|---|---|---|
| A | $L_b$ | $L_a$-Q |
| 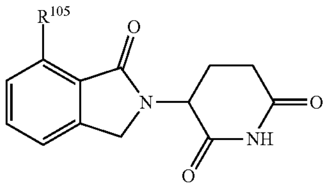 4.012 | $L_b$12 = a bond | |
| | 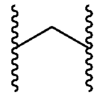 $L_b$13 | |
| | 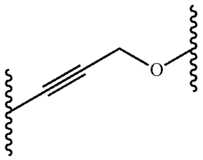 $L_b$14 | |

In some embodiments, the compounds of the present invention have the general formula A-$L_b$-$L_a$-Q, wherein the moiety A, $L_b$, and $L_a$-Q are independently selected from Table 4. Any combination of the A, $L_b$, and $L_a$-Q listed in Table 4 are contemplated as the compound of the present invention. $L_b$ is connected to the moiety A via a covalent bond at any position of A as allowed by valence. For clarity, $L_a$1.0-6 includes seven Lal moieties, wherein T is 0, 1, 2, 3, 4, 5, or 6 respectively. Likewise, $L_a$2.0-5 includes six $L_a$2 moieties, wherein T is 0, 1, 2, 3, 4, or 5 respectively; $L_b$6.1-3 includes three $L_b$6 moieties, having 1, 2, or 3 methylene chain respectively; $L_b$7.0-5 includes six $L_b$7 moieties, having 0, 1, 2, 3, 4, or 5 methylene chain respectively; $L_b$8.1-4 includes four $L_b$8 moieties, having 1, 2, 3, or 4 methylene chain respectively. $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$, $R^{80}$, $R^{81}$, $R^{82}$, $R^{83}$, $R^{84}$, $R^{85}$, $R^{86}$, $R^{87}$, $R^{88}$, $R^{89}$, $R^{90}$, $R^{91}$, $R^{92}$, $R^{93}$, $R^{94}$, $R^{95}$, $R^{96}$, $R^{97}$, $R^{98}$, $R^{99}$, $R^{100}$, $R^{101}$, $R^{102}$, $R^{103}$, $R^{104}$, and $R^{105}$ are each independently selected from the group consisting of H, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl, wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more groups selected from the group consisting of halo, cyano, oxo($C_3$-$C_{10}$)heterocyclo, ($C_3$-$C_{10}$)cycloalkyl, —$(CH_2)_n$—($C_3$-$C_{10}$) cycloalkyl, —$(CH_2)_n$—($C_3$-$C_{10}$)heterocyclo, —$(CH_2)_n$-aryl, —$(CH_2)_n$-heteroaryl, aryl, and heteroaryl. In an embodiment, $L_b$ is covalently connected to A moiety via $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$, $R^{80}$, $R^{81}$, $R^{82}$, $R^{83}$, $R^{84}$, $R^{85}$, $R^{86}$, $R^{87}$, $R^{88}$, $R^{89}$, $R^{90}$, $R^{91}$, $R^{92}$, $R^{93}$, $R^{94}$, $R^{95}$, $R^{96}$, $R^{97}$, $R^{98}$, $R^{99}$, $R^{100}$, $R^{101}$, $R^{102}$, $R^{103}$, $R^{104}$, or $R^{105}$.

In an embodiment, the compound has the structure of 4.001-$L_b$1-$L_a$1.0-6, 4.001-$L_b$1-$L_a$2.0-5, 4.002-$L_b$1-$L_a$1.0-6, 4.002-$L_b$1-$L_a$2.0-5, 4.003-$L_b$1-$L_a$1.0-6, 4.003-$L_b$1-$L_a$2.0-5, 4.004-$L_b$1-$L_a$1.0-6, 4.004-$L_b$1-$L_a$2.0-5, 4.005-$L_b$1-$L_a$1.0-6, 4.005-$L_b$1-$L_a$2.0-5, 4.006-$L_b$1-$L_a$1.0-6, 4.006-$L_b$1-$L_a$2.0-5, 4.007-$L_b$1-$L_a$1.0-6, 4.007-$L_b$1-$L_a$2.0-5, 4.008-$L_b$1-$L_a$1.0-6, 4.008-$L_b$1-$L_a$2.0-5, 4.009-$L_b$1-$L_a$1.0-6, 4.009-$L_b$1-$L_a$2.0-5, 4.010-$L_b$1-$L_a$1.0-6, 4.010-$L_b$1-$L_a$2.0-5, 4.011-$L_b$1-$L_a$1.0-6, 4.011-$L_b$1-$L_a$2.0-5, or 4.012-$L_b$1-$L_a$2.0-5.

In an embodiment, the compound has the structure of 4.001-$L_b$2-$L_a$1.0-6, 4.001-$L_b$2-$L_a$2.0-5, 4.002-$L_b$2-$L_a$1.0-6, 4.002-$L_b$2-$L_a$2.0-5, 4.003-$L_b$2-$L_a$1.0-6, 4.003-$L_b$2-$L_a$2.0-5, 4.004-$L_b$2-$L_a$1.0-6, 4.004-$L_b$2-$L_a$2.0-5, 4.005-$L_b$2-$L_a$1.0-6, 4.005-$L_b$2-$L_a$2.0-5, 4.006-$L_b$2-$L_a$1.0-6, 4.006-$L_b$2-$L_a$2.0-5, 4.007-$L_b$2-$L_a$1.0-6, 4.007-$L_b$2-$L_a$2.0-5, 4.008-$L_b$2-$L_a$1.0-6, 4.008-$L_b$2-$L_a$2.0-5, 4.009-$L_b$2-$L_a$1.0-6, 4.009-$L_b$2-$L_a$2.0-5, 4.010-$L_b$2-$L_a$1.0-6, 4.010-$L_b$2-$L_a$2.0-5, 4.011-$L_b$2-$L_a$1.0-6, 4.011-$L_b$2-$L_a$2.0-5, or 4.012-$L_b$2-$L_a$2.0-5.

In an embodiment, the compound has the structure of 4.001-$L_b$3-$L_a$1.0-6, 4.001-$L_b$3-$L_a$2.0-5, 4.002-$L_b$3-$L_a$1.0-6, 4.002-$L_b$3-$L_a$2.0-5, 4.003-$L_b$3-$L_a$1.0-6, 4.003-$L_b$3-$L_a$2.0-5, 4.004-$L_b$3-$L_a$1.0-6, 4.004-$L_b$3-$L_a$2.0-5, 4.005-$L_b$3-$L_a$1.0-6, 4.005-$L_b$3-$L_a$2.0-5, 4.006-$L_b$3-$L_a$1.0-6, 4.006-$L_b$3-$L_a$2.0-5, 4.007-$L_b$3-$L_a$1.0-6, 4.007-$L_b$3-$L_a$2.0-5, 4.008-$L_b$3-$L_a$1.0-6, 4.008-$L_b$3-$L_a$2.0-5, 4.009-$L_b$3-$L_a$1.0-6, 4.009-$L_b$3-$L_a$2.0-5, 4.010-$L_b$3-$L_a$1.0-6, 4.010-$L_b$3-$L_a$2.0-5, 4.011-$L_b$3-$L_a$1.0-6, 4.011-$L_b$3-$L_a$2.0-5, or 4.012-$L_b$3-$L_a$2.0-5.

In an embodiment, the compound has the structure of 4.001-$L_b$4-$L_a$1.0-6, 4.001-$L_b$4-$L_a$2.0-5, 4.002-$L_b$4-$L_a$1.0-6, 4.002-$L_b$4-$L_a$2.0-5, 4.003-$L_b$4-$L_a$1.0-6, 4.003-$L_b$4-$L_a$2.0-5, 4.004-$L_b$4-$L_a$1.0-6, 4.004-$L_b$4-$L_a$2.0-5, 4.005-$L_b$4-$L_a$1.0-6, 4.005-$L_b$4-$L_a$2.0-5, 4.006-$L_b$4-$L_a$1.0-6, 4.006-$L_b$4-$L_a$2.0-5, 4.007-$L_b$4-$L_a$1.0-6, 4.007-$L_b$4-$L_a$2.0-5, 4.008-$L_b$4-$L_a$1.0-6, 4.008-$L_b$4-$L_a$2.0-5, 4.009-$L_b$4-$L_a$1.0-6, 4.009-$L_b$4-$L_a$2.0-5, 4.010-$L_b$4-$L_a$1.0-6, 4.010-$L_b$4-$L_a$2.0-5, 4.011-$L_b$4-$L_a$1.0-6, 4.011-$L_b$4-$L_a$2.0-5, or 4.012-$L_b$4-$L_a$2.0-5.

In an embodiment, the compound has the structure of 4.001-$L_b$5-$L_a$1.0-6, 4.001-$L_b$5-$L_a$2.0-5, 4.002-$L_b$5-$L_a$1.0-6, 4.002-$L_b$5-$L_a$2.0-5, 4.003-$L_b$5-$L_a$1.0-6, 4.003-$L_b$5-$L_a$2.0-5, 4.004-$L_b$5-$L_a$1.0-6, 4.004-$L_b$5-$L_a$2.0-5, 4.005-$L_b$5-$L_a$1.0-6, 4.005-$L_b$5-$L_a$2.0-5, 4.006-$L_b$5-$L_a$1.0-6, 4.006-$L_b$5-$L_a$2.0-5, 4.007-$L_b$5-$L_a$1.0-6, 4.007-$L_b$5-$L_a$2.0-5, 4.008-$L_b$5-$L_a$1.0-6, 4.008-$L_b$5-$L_a$2.0-5, 4.009-$L_b$5-$L_a$1.0-6, 4.009-$L_b$5-$L_a$2.0-5, 4.010-$L_b$5-$L_a$1.0-6, 4.010-$L_b$5-$L_a$2.0-5, 4.011-$L_b$5-$L_a$1.0-6, 4.011-$L_b$5-$L_a$2.0-5, or 4.012-$L_b$5-$L_a$2.0-5.

In an embodiment, the compound has the structure of 4.001-$L_b$6-$L_a$1.0-6, 4.001-$L_b$6-$L_a$2.0-5, 4.002-$L_b$6-$L_a$1.0-6, 4.002-$L_b$6-$L_a$2.0-5, 4.003-$L_b$6-$L_a$1.0-6, 4.003-$L_b$6-$L_a$2.0-5, 4.004-$L_b$6-$L_a$1.0-6, 4.004-$L_b$6-$L_a$2.0-5, 4.005-$L_b$6-$L_a$1.0-6, 4.005-$L_b$6-$L_a$2.0-5, 4.006-$L_b$6-$L_a$1.0-6, 4.006-$L_b$6-$L_a$2.0-5, 4.007-$L_b$6-$L_a$1.0-6, 4.007-$L_b$6-$L_a$2.0-5, 4.008-$L_b$6-$L_a$1.0-6, 4.008-$L_b$6-$L_a$2.0-5, 4.009-$L_b$6-$L_a$1.0-6, 4.009-$L_b$6-$L_a$2.0-5, 4.010-$L_b$6-$L_a$1.0-6, 4.010-$L_b$6-$L_a$2.0-5, 4.011-$L_b$6-$L_a$1.0-6, 4.011-$L_b$6-$L_a$2.0-5, or 4.012-$L_b$6-$L_a$2.0-5.

In an embodiment, the compound has the structure of 4.001-$L_b$7-$L_a$1.0-6, 4.001-$L_b$7-$L_a$2.0-5, 4.002-$L_b$7-$L_a$1.0-6, 4.002-$L_b$7-$L_a$2.0-5, 4.003-$L_b$7-$L_a$1.0-6, 4.003-$L_b$7-$L_a$2.0-5, 4.004-$L_b$7-$L_a$1.0-6, 4.004-$L_b$7-$L_a$2.0-5, 4.005-$L_b$7-$L_a$1.0-6, 4.005-$L_b$7-$L_a$2.0-5, 4.006-$L_b$7-$L_a$1.0-6, 4.006-$L_b$7-$L_a$2.0-5, 4.007-$L_b$7-$L_a$1.0-6, 4.007-$L_b$7-$L_a$2.0-5, 4.008-$L_b$7-$L_a$1.0-6, 4.008-$L_b$7-$L_a$2.0-5, 4.009-$L_b$7-$L_a$1.0-6, 4.009-$L_b$7-$L_a$2.0-5, 4.010-$L_b$7-$L_a$1.0-6, 4.010-$L_b$7-$L_a$2.0-5, 4.011-$L_b$7-$L_a$1.0-6, 4.011-$L_b$7-$L_a$2.0-5, or 4.012-$L_b$7-$L_a$2.0-5.

In an embodiment, the compound has the structure of 4.001-$L_b$8-$L_a$1.0-6, 4.001-$L_b$8-$L_a$2.0-5, 4.002-$L_b$8-$L_a$1.0-6, 4.002-$L_b$8-$L_a$2.0-5, 4.003-$L_b$8-$L_a$1.0-6, 4.003-$L_b$8-$L_a$2.0-5, 4.004-$L_b$8-$L_a$1.0-6, 4.004-$L_b$8-$L_a$2.0-5, 4.005-$L_b$8-$L_a$1.0-6, 4.005-$L_b$8-$L_a$2.0-5, 4.006-$L_b$8-$L_a$1.0-6, 4.006-$L_b$8-$L_a$2.0-5, 4.007-$L_b$8-$L_a$1.0-6, 4.007-$L_b$8-$L_a$2.0-5, 4.008-$L_b$8-$L_a$1.0-6, 4.008-$L_b$8-$L_a$2.0-5, 4.009-$L_b$8-$L_a$1.0-6, 4.009-$L_b$8-$L_a$2.0-5, 4.010-$L_b$8-$L_a$1.0-6, 4.010-$L_b$8-$L_a$2.0-5, 4.011-$L_b$8-$L_a$1.0-6, 4.011-$L_b$8-$L_a$2.0-5, or 4.012-$L_b$8-$L_a$2.0-5.

In an embodiment, the compound has the structure of 4.001-$L_b$9-$L_a$1.0-6, 4.001-$L_b$9-$L_a$2.0-5, 4.002-$L_b$9-$L_a$1.0-6, 4.002-$L_b$9-$L_a$2.0-5, 4.003-$L_b$9-$L_a$1.0-6, 4.003-$L_b$9-$L_a$2.0-5, 4.004-$L_b$9-$L_a$1.0-6, 4.004-$L_b$9-$L_a$2.0-5, 4.005-$L_b$9-$L_a$1.0-6, 4.005-$L_b$9-$L_a$2.0-5, 4.006-$L_b$9-$L_a$1.0-6, 4.006-$L_b$9-$L_a$2.0-5, 4.007-$L_b$9-$L_a$1.0-6, 4.007-$L_b$9-$L_a$2.0-5, 4.008-$L_b$9-$L_a$1.0-6, 4.008-$L_b$9-$L_a$2.0-5, 4.009-$L_b$9-$L_a$1.0-6, 4.009-$L_b$9-$L_a$2.0-5, 4.010-$L_b$9-$L_a$1.0-6, 4.010-$L_b$9-$L_a$2.0-5, 4.011-$L_b$9-$L_a$1.0-6, 4.011-$L_b$9-$L_a$2.0-5, or 4.012-$L_b$9-$L_a$2.0-5.

In an embodiment, the compound has the structure of 4.001-$L_b$10-$L_a$1.0-6, 4.001-$L_b$10-$L_a$2.0-5, 4.002-$L_b$10-$L_a$1.0-6, 4.002-$L_b$10-$L_a$2.0-5, 4.003-$L_b$10-$L_a$1.0-6, 4.003-$L_b$10-$L_a$2.0-5, 4.004-$L_b$10-$L_a$1.0-6, 4.004-$L_b$10-$L_a$2.0-5, 4.005-$L_b$10-$L_a$1.0-6, 4.005-$L_b$10-$L_a$2.0-5, 4.006-$L_b$10-$L_a$1.0-6, 4.006-$L_b$10-$L_a$2.0-5, 4.007-$L_b$10-$L_a$1.0-6, 4.007-$L_b$10-$L_a$2.0-5, 4.008-$L_b$10-$L_a$1.0-6, 4.008-$L_b$10-$L_a$2.0-5, 4.009-$L_b$10-$L_a$1.0-6, 4.009-$L_b$10-$L_a$2.0-5, 4.010-$L_b$10-$L_a$1.0-6, 4.010-$L_b$10-$L_a$2.0-5, 4.011-$L_b$10-$L_a$1.0-6, 4.011-$L_b$10-$L_a$2.0-5, or 4.012-$L_b$10-$L_a$2.0-5.

In an embodiment, the compound has the structure of 4.001-$L_b$11-$L_a$1.0-6, 4.001-$L_b$11-$L_a$2.0-5, 4.002-$L_b$11-$L_a$1.0-6, 4.002-$L_b$11-$L_a$2.0-5, 4.003-$L_b$11-$L_a$1.0-6, 4.003-$L_b$11-$L_a$2.0-5, 4.004-$L_b$11-$L_a$1.0-6, 4.004-$L_b$11-$L_a$2.0-5, 4.005-$L_b$11-$L_a$1.0-6, 4.005-$L_b$11-$L_a$2.0-5, 4.006-$L_b$11-$L_a$1.0-6, 4.006-$L_b$11-$L_a$2.0-5, 4.007-$L_b$11-$L_a$1.0-6, 4.007-$L_b$11-$L_a$2.0-5, 4.008-$L_b$11-$L_a$1.0-6, 4.008-$L_b$11-$L_a$2.0-5, 4.009-$L_b$11-$L_a$1.0-6, 4.009-$L_b$11-$L_a$2.0-5, 4.010-$L_b$11-$L_a$1.0-6, 4.010-$L_b$11-$L_a$2.0-5, 4.011-$L_b$11-$L_a$1.0-6, 4.011-$L_b$11-$L_a$2.0-5, or 4.012-$L_b$11-$L_a$2.0-5.

In an embodiment, the compound has the structure of 4.001-$L_b$12-$L_a$1.0-6, 4.001-$L_b$12-$L_a$2.0-5, 4.002-$L_b$12-$L_a$1.0-6, 4.002-$L_b$12-$L_a$2.0-5, 4.003-$L_b$12-$L_a$1.0-6, 4.003-$L_b$12-$L_a$2.0-5, 4.004-$L_b$12-$L_a$1.0-6, 4.004-$L_b$12-$L_a$2.0-5, 4.005-$L_b$12-$L_a$1.0-6, 4.005-$L_b$12-$L_a$2.0-5, 4.006-$L_b$12-$L_a$1.0-6, 4.006-$L_b$12-$L_a$2.0-5, 4.007-$L_b$12-$L_a$1.0-6, 4.007-$L_b$12-$L_a$2.0-5, 4.008-$L_b$12-$L_a$1.0-6, 4.008-$L_b$12-$L_a$2.0-5, 4.009-$L_b$12-$L_a$1.0-6, 4.009-$L_b$12-$L_a$2.0-5, 4.010-$L_b$12-$L_a$1.0-6, 4.010-$L_b$12-$L_a$2.0-5, 4.011-$L_b$12-$L_a$1.0-6, 4.011-$L_b$12-$L_a$2.0-5, or 4.012-$L_b$12-$L_a$2.0-5.

In an embodiment, the compound has the structure of 4.001-$L_b$13-$L_a$1.0-6, 4.001-$L_b$13-$L_a$2.0-5, 4.002-$L_b$13-$L_a$1.0-6, 4.002-$L_b$13-$L_a$2.0-5, 4.003-$L_b$13-$L_a$1.0-6, 4.003-$L_b$13-$L_a$2.0-5, 4.004-$L_b$13-$L_a$1.0-6, 4.004-$L_b$13-$L_a$2.0-5, 4.005-$L_b$13-$L_a$1.0-6, 4.005-$L_b$13-$L_a$2.0-5, 4.006-$L_b$13-$L_a$1.0-6, 4.006-$L_b$13-$L_a$2.0-5, 4.007-$L_b$13-$L_a$1.0-6, 4.007-$L_b$13-$L_a$2.0-5, 4.008-$L_b$13-$L_a$1.0-6, 4.008-$L_b$13-$L_a$2.0-5, 4.009-$L_b$13-$L_a$1.0-6, 4.009-$L_b$13-$L_a$2.0-5, 4.010-$L_b$13-$L_a$1.0-6, 4.010-$L_b$13-$L_a$2.0-5, 4.011-$L_b$13-$L_a$1.0-6, 4.011-$L_b$13-$L_a$2.0-5, or 4.012-$L_b$13-$L_a$2.0-5.

In an embodiment, the compound has the structure of 4.001-$L_b$14-$L_a$1.0-6, 4.001-$L_b$14-$L_a$2.0-5, 4.002-$L_b$14-$L_a$1.0-6, 4.002-$L_b$14-$L_a$2.0-5, 4.003-$L_b$14-$L_a$1.0-6, 4.003-$L_b$14-$L_a$2.0-5, 4.004-$L_b$14-$L_a$1.0-6, 4.004-$L_b$14-$L_a$2.0-5, 4.005-$L_b$14-$L_a$1.0-6, 4.005-$L_b$14-$L_a$2.0-5, 4.006-$L_b$14-$L_a$1.0-6, 4.006-$L_b$14-$L_a$2.0-5, 4.007-$L_b$14-$L_a$1.0-6, 4.007-$L_b$14-$L_a$2.0-5, 4.008-$L_b$14-$L_a$1.0-6, 4.008-$L_b$14-$L_a$2.0-5, 4.009-$L_b$14-$L_a$1.0-6, 4.009-$L_b$14-$L_a$2.0-5, 4.010-$L_b$14-$L_a$1.0-6, 4.010-$L_b$14-$L_a$2.0-5, 4.011-$L_b$14-$L_a$1.0-6, 4.011-$L_b$14-$L_a$2.0-5, or 4.012-$L_b$14-$L_a$2.0-5.

TABLE 5
| Specific Embodiments of general formula $(A)_k$-L-Q. | |
|---|---|
| Compound No. | Structure |
| 5.01 | 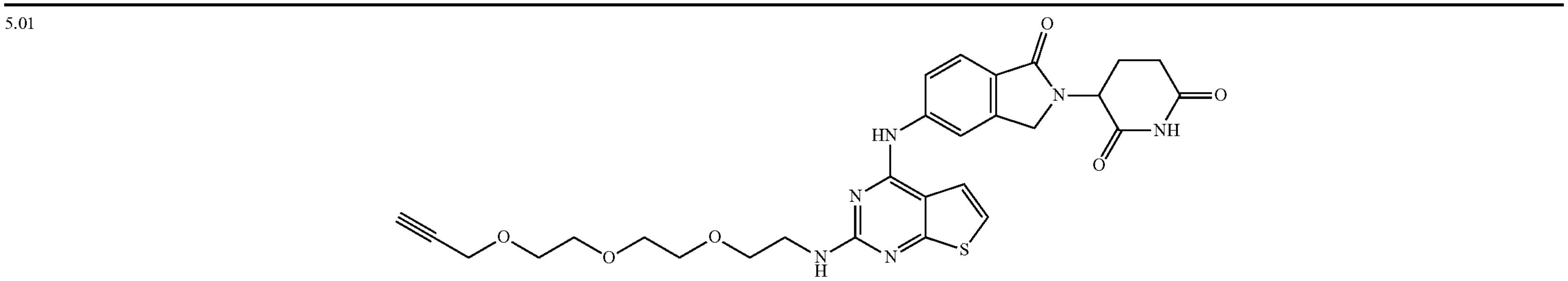 |
| 5.02 | 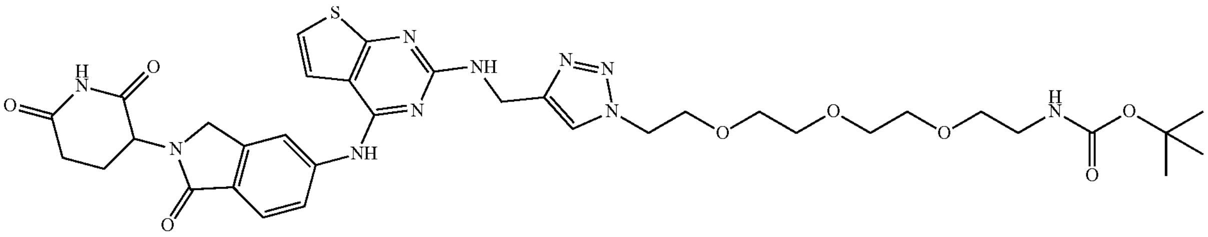 [SMILES: CC(C)(C)OC(=O)NCCOCCOCCOCCn1cc(CNc2nc(Nc3ccc4c(c3)CN(C3CCC(=O)NC3=O)C4=O)c3ccsc3n2)nn1] |
| 5.03 | 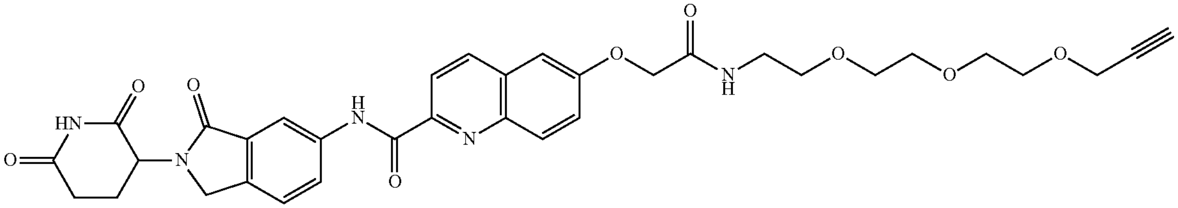 [SMILES: C#CCOCCOCCOCCNC(=O)COc1ccc2nc(C(=O)Nc3ccc4c(c3)C(=O)N(C3CCC(=O)NC3=O)C4)ccc2c1] |

TABLE 5-continued
| Specific Embodiments of general formula $(A)_k$-L-Q. | |
|---|---|
| Compound No. | Structure |
| 5.04 | 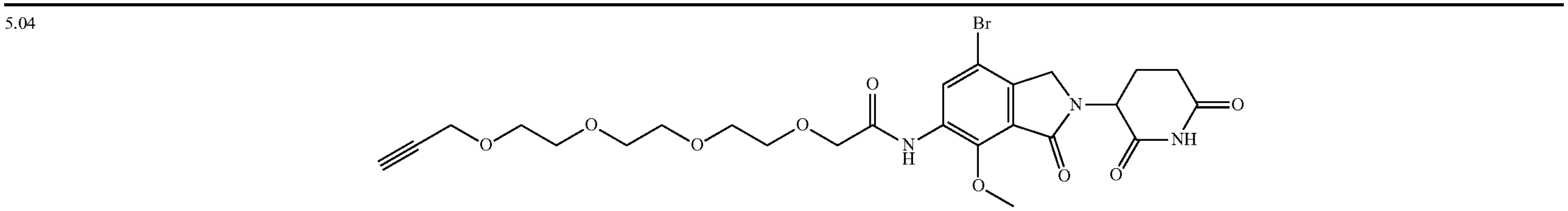 |
| 5.05 | 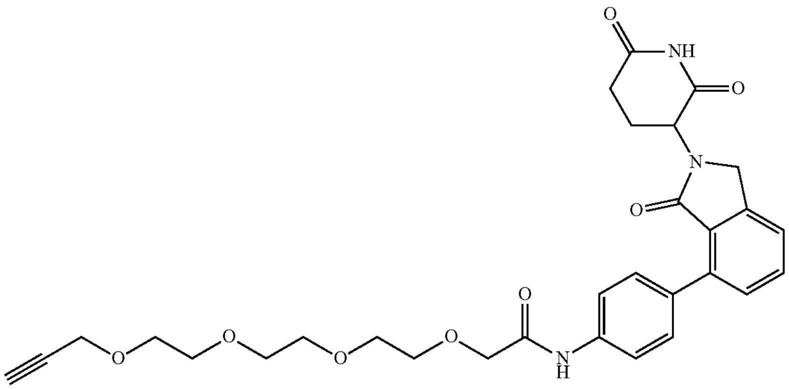 [SMILES: C#CCOCCOCCOCCOCC(=O)Nc1ccc(-c2cccc3c2C(=O)N(C2CCC(=O)NC2=O)C3)cc1] |
| 5.06 | 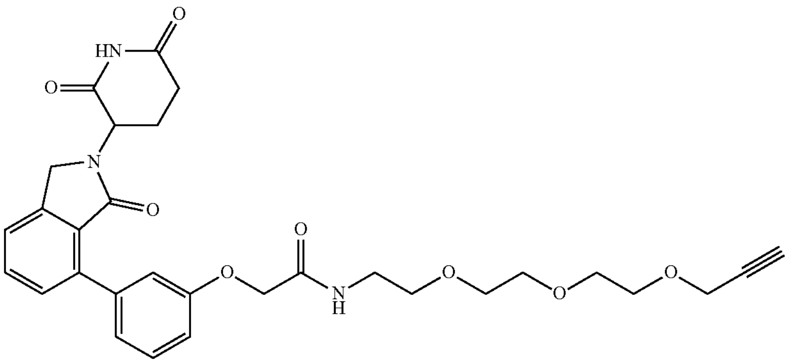 [SMILES: C#CCOCCOCCOCCNC(=O)COc1cccc(-c2cccc3c2C(=O)N(C2CCC(=O)NC2=O)C3)c1] |

TABLE 5-continued
| Specific Embodiments of general formula $(A)_k$-L-Q. | |
|---|---|
| Compound No. | Structure |
| 5.07 | 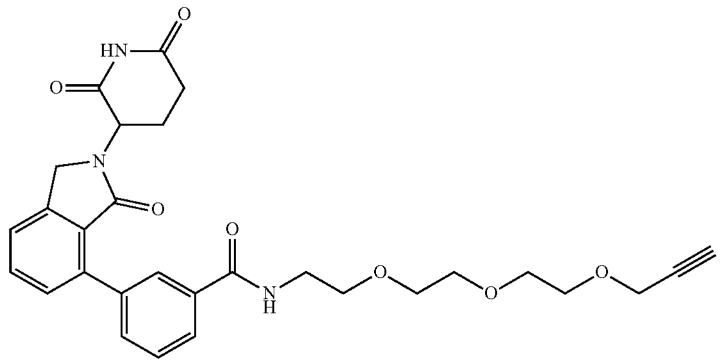 [SMILES: C#CCOCCOCCOCCNC(=O)c1cccc(-c2cccc3c2C(=O)N(C2CCC(=O)NC2=O)C3)c1] |
| 5.08 | 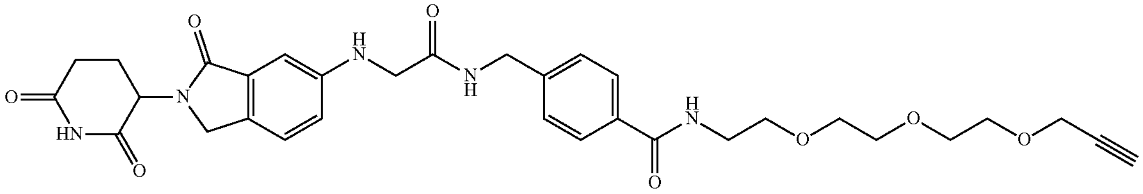 [SMILES: C#CCOCCOCCOCCNC(=O)c1ccc(CNC(=O)CNc2ccc3c(c2)C(=O)N(C2CCC(=O)NC2=O)C3)cc1] |
| 5.09 | 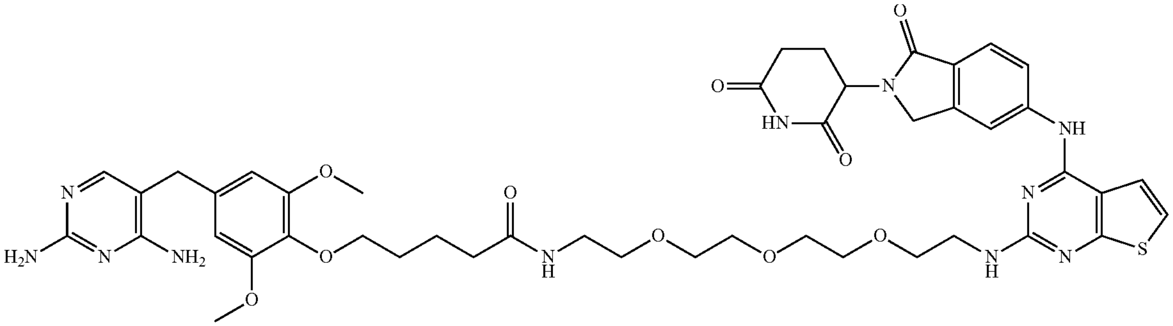 [SMILES: COc1cc(Cc2cnc(N)nc2N)cc(OC)c1OCCCCC(=O)NCCOCCOCCOCCNc1nc(Nc2ccc3c(c2)CN(C2CCC(=O)NC2=O)C3=O)c2ccsc2n1] |

TABLE 5-continued
Specific Embodiments of general formula $(A)_k$-L-Q.
| Compound No. | Structure |
| --- | --- |
| 5.10 | 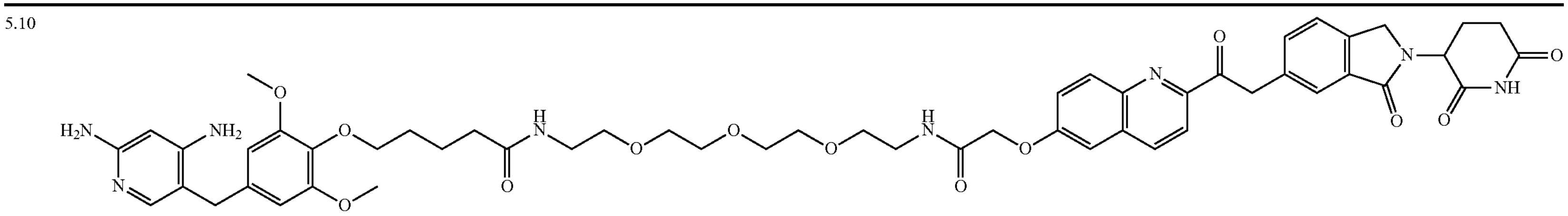 |
| 5.11 | 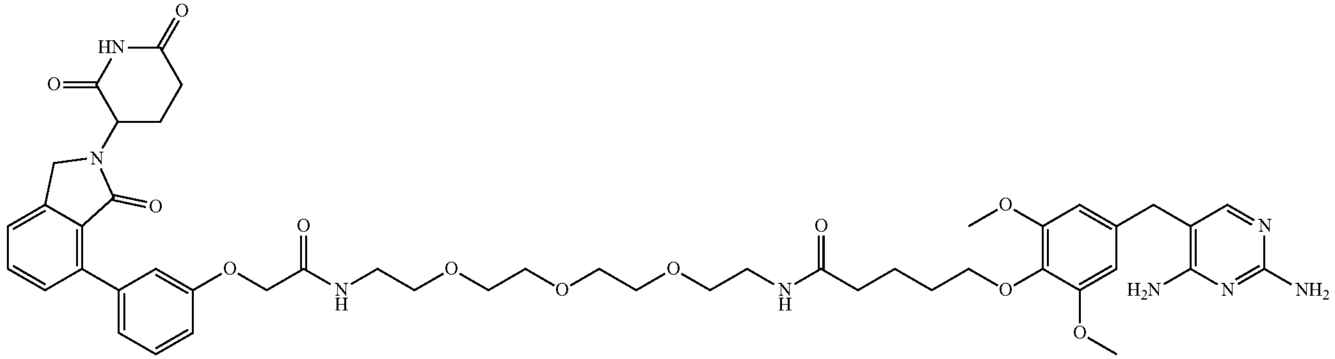 [SMILES: COc1cc(Cc2cnc(N)nc2N)cc(OC)c1OCCCCC(=O)NCCOCCOCCOCCNC(=O)COc1cccc(-c2cccc3c2C(=O)N(C2CCC(=O)NC2=O)C3)c1] |
| 5.12 | 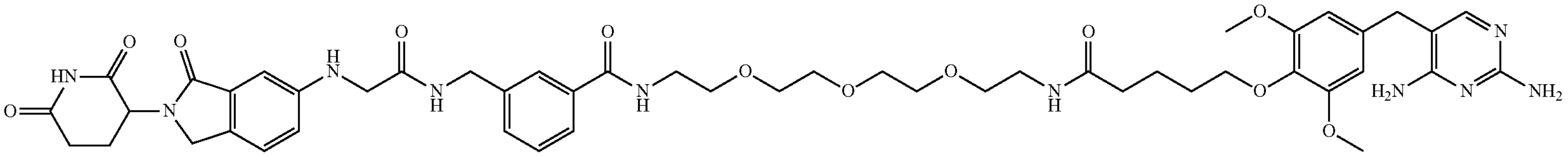 [SMILES: COc1cc(Cc2cnc(N)nc2N)cc(OC)c1OCCCCC(=O)NCCOCCOCCOCCNC(=O)c1cccc(CNC(=O)CNc2ccc3c(c2)C(=O)N(C2CCC(=O)NC2=O)C3)c1] |

TABLE 5-continued
Specific Embodiments of general formula $(A)_k$-L-Q.
| Compound No. | Structure |
|---|---|
| 5.13 | 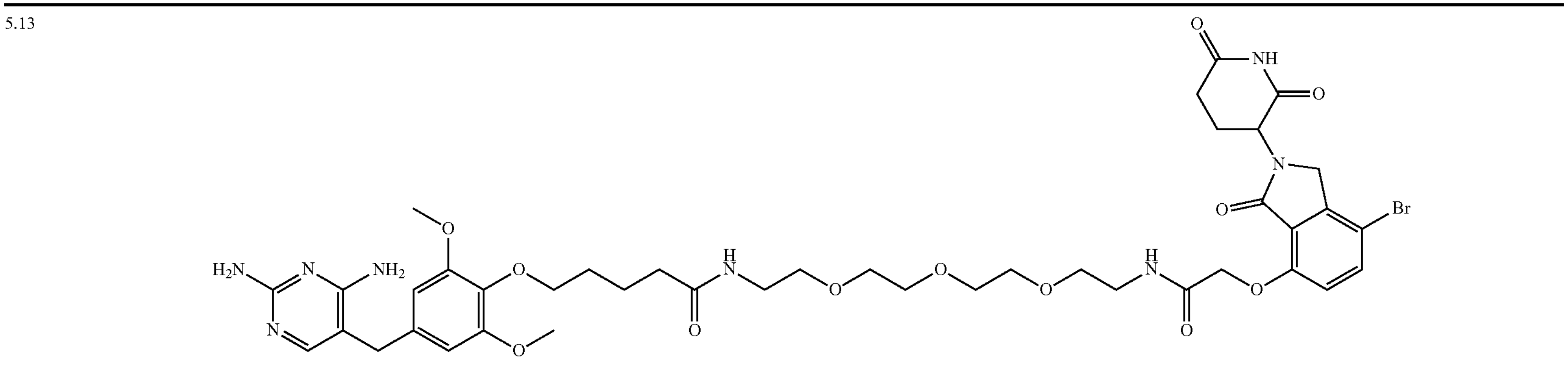 |
| 5.14 | 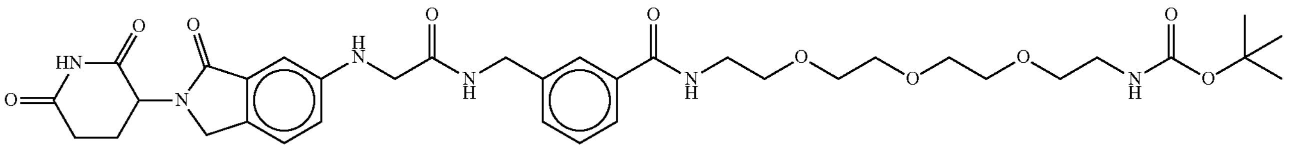 |
| 5.15 | 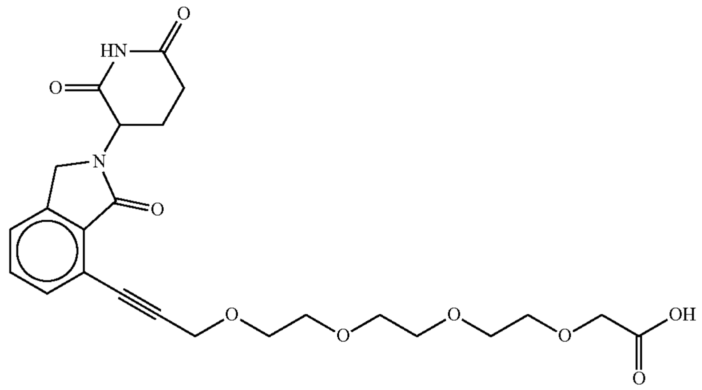 |

TABLE 5-continued
| Specific Embodiments of general formula $(A)_k$-L-Q. | |
| --- | --- |
| Compound No. | Structure |
| 5.16 | 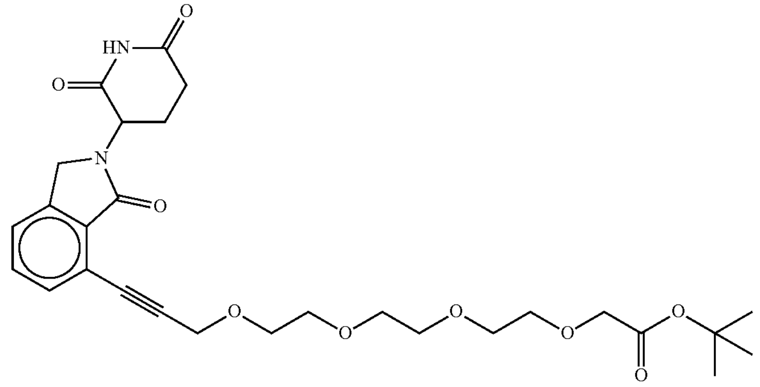 |
| 5.17 | 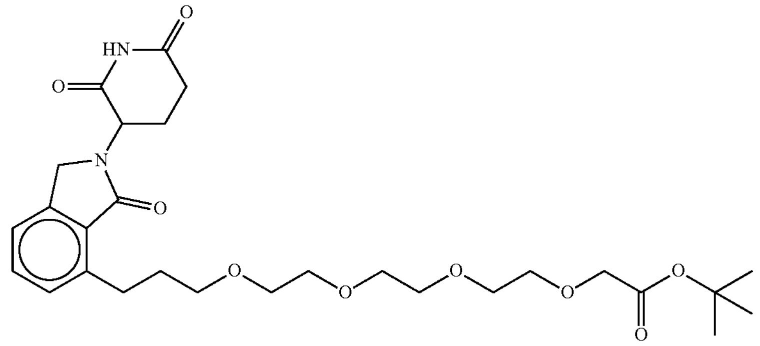 |

TABLE 5-continued
| Specific Embodiments of general formula $(A)_k$-L-Q. | |
|---|---|
| Compound No. | Structure |
| 5.18 | 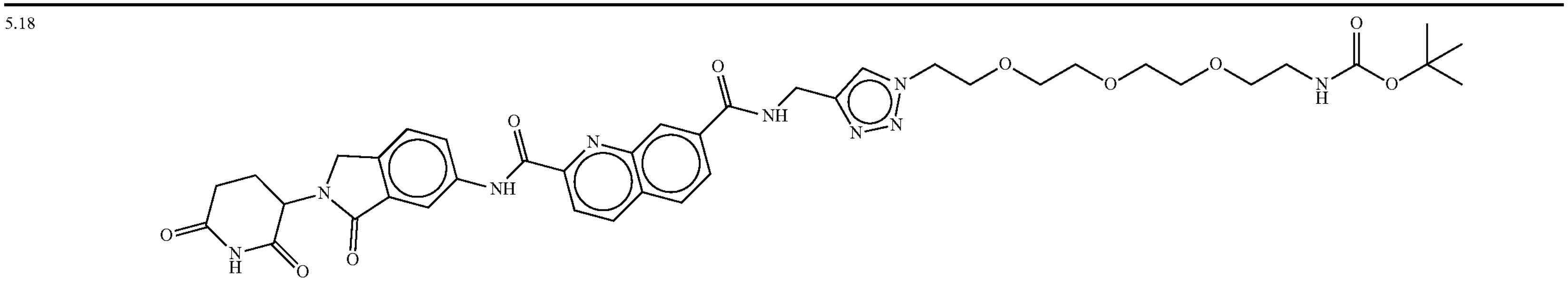 |
| 5.19 | 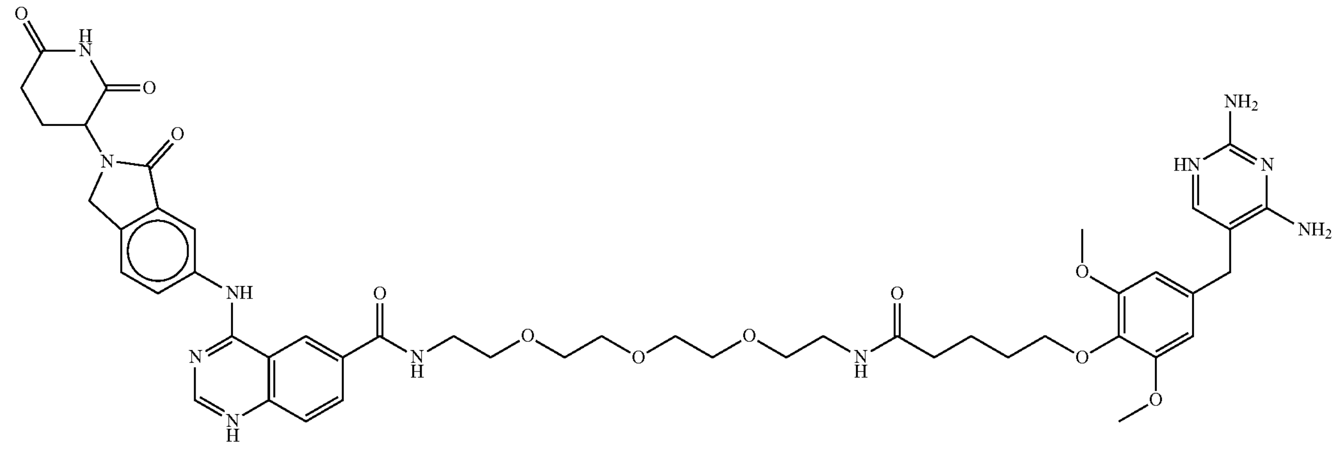 |

TABLE 5-continued
| Specific Embodiments of general formula $(A)_k$-L-Q. | |
|---|---|
| Compound No. | Structure |
| 5.20 | 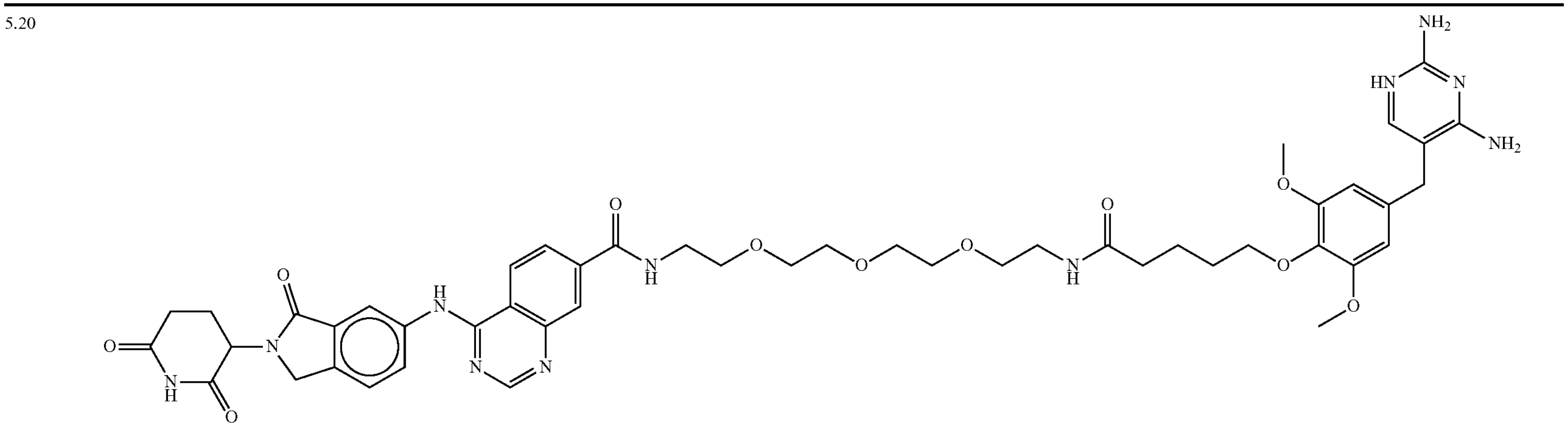 |
| 5.21 | 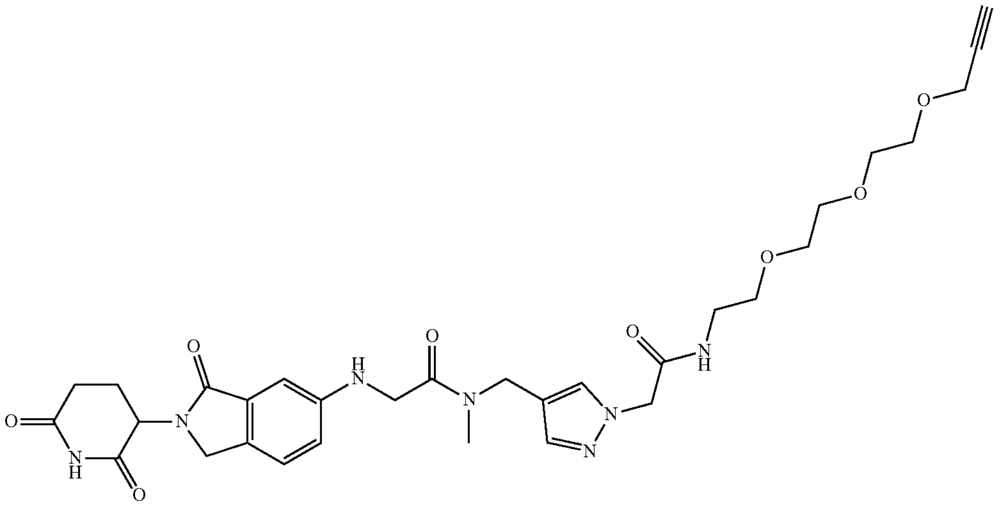 [SMILES: C#CCOCCOCCOCCNC(=O)Cn1cc(CN(C)C(=O)CNc2ccc3c(c2)C(=O)N(C2CCC(=O)NC2=O)C3)cn1] |

TABLE 5-continued
| Specific Embodiments of general formula $(A)_k$-L-Q. | |
|---|---|
| Compound No. | Structure |
| 5.22 | 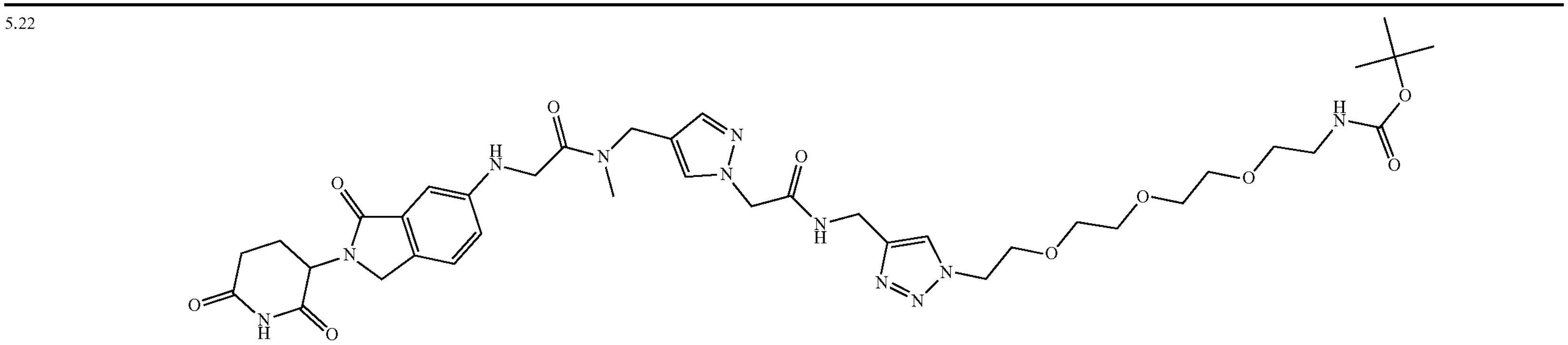 |
| 5.23 | 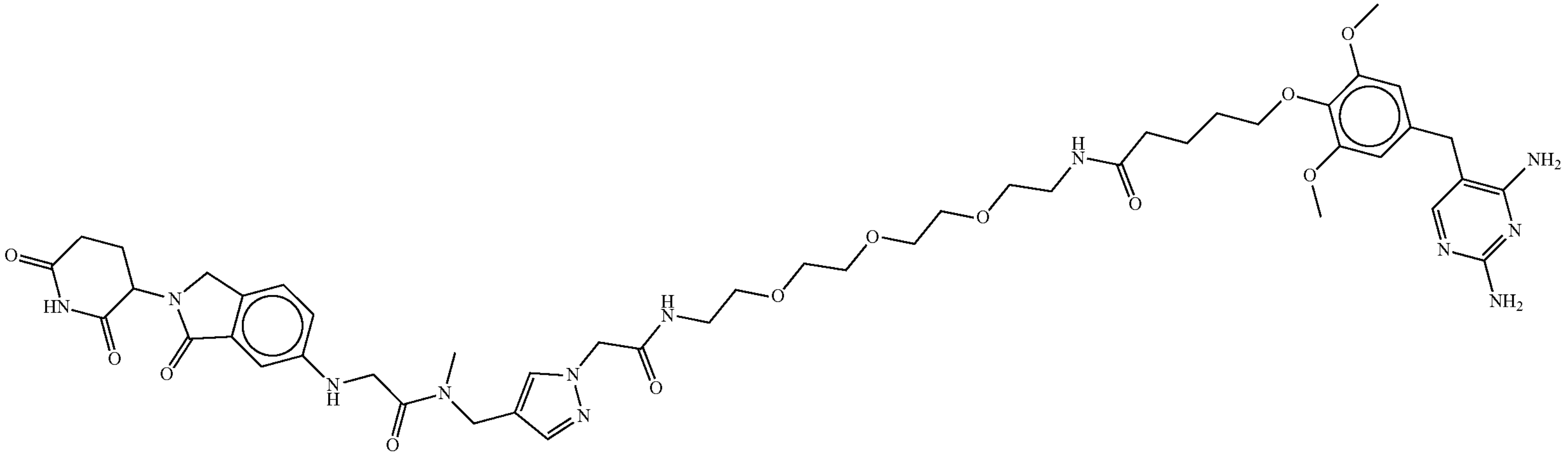 |

TABLE 5-continued
| Specific Embodiments of general formula $(A)_k$-L-Q. | |
|---|---|
| Compound No. | Structure |
| 5.24 | 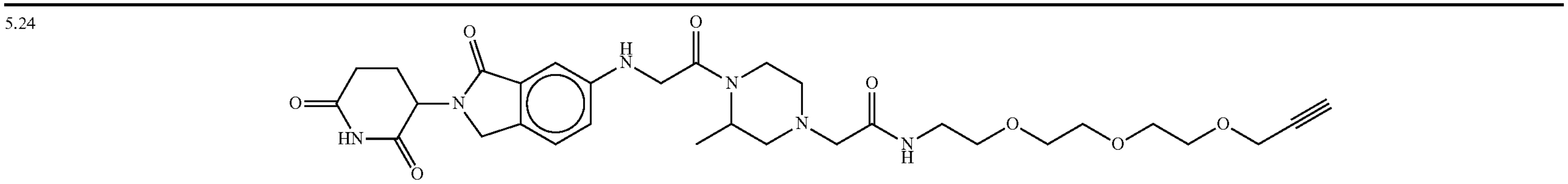 |
| 5.25 | 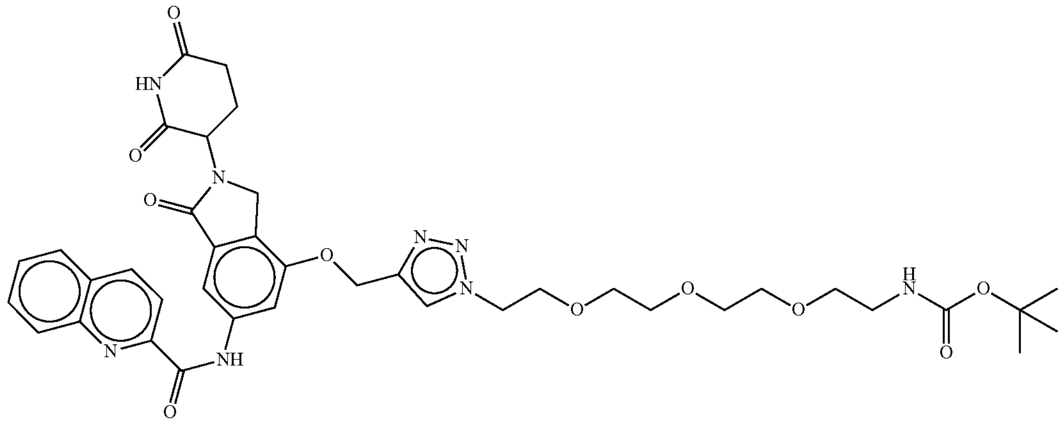 |
| 5.26 | 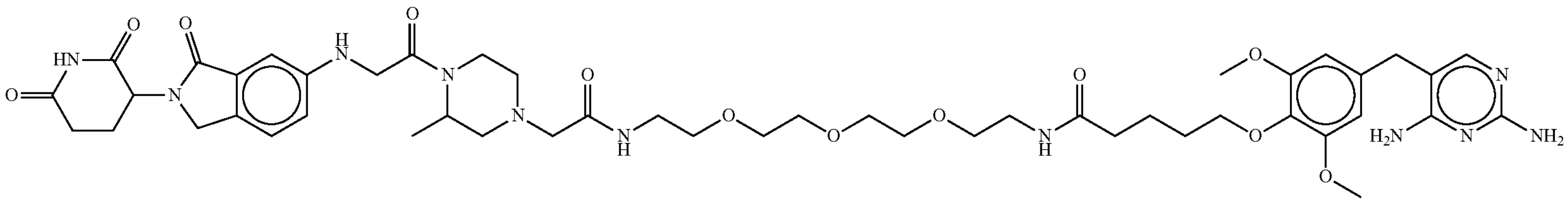 |

TABLE 5-continued
| Specific Embodiments of general formula $(A)_k$-L-Q. | |
|---|---|
| Compound No. | Structure |
| 5.27 | 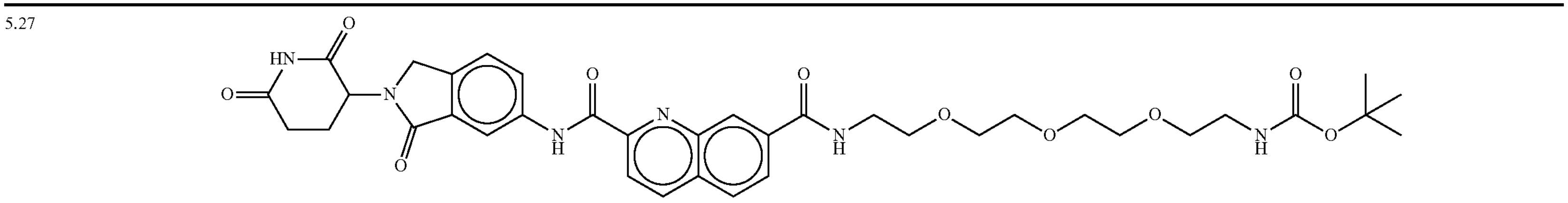 |
| 5.28 | 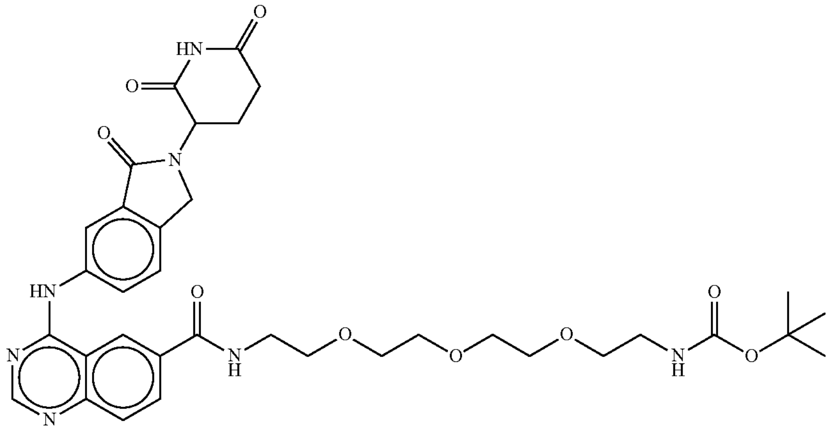 |
| 5.29 | 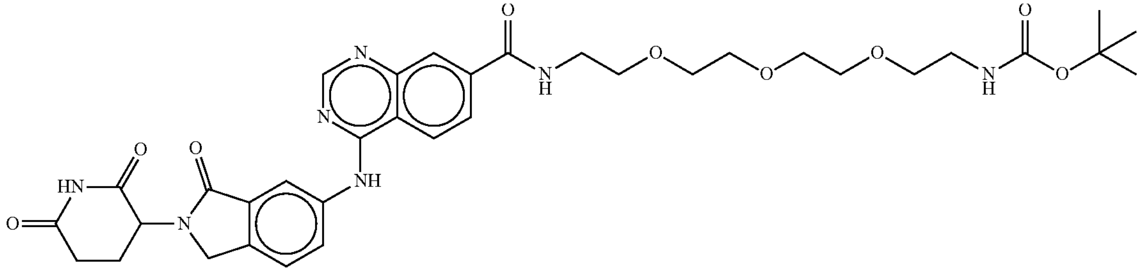 |

TABLE 5-continued
| Specific Embodiments of general formula $(A)_k$-L-Q. | |
|---|---|
| Compound No. | Structure |
| 5.30 | 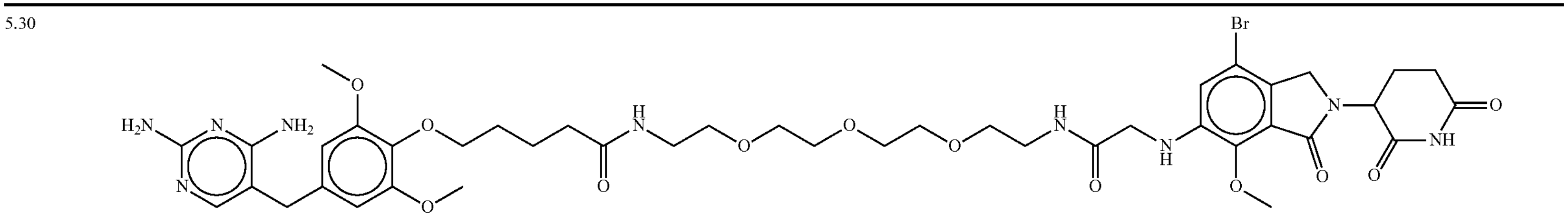 |
| 5.31 | 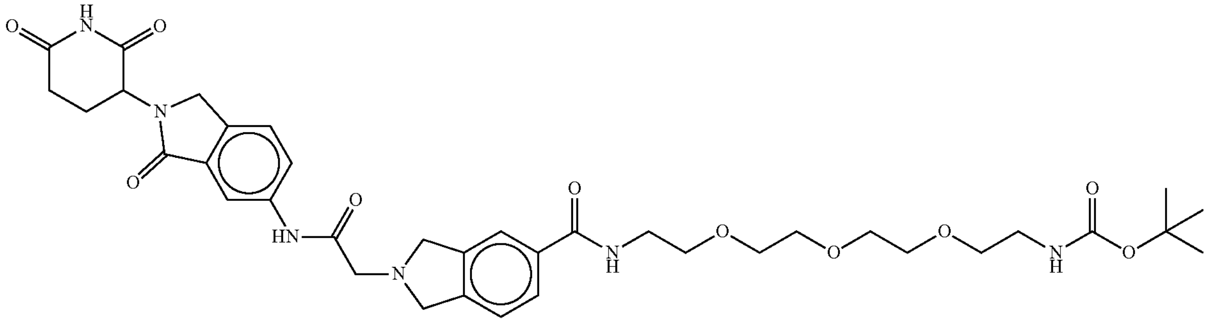 |
| 5.32 | 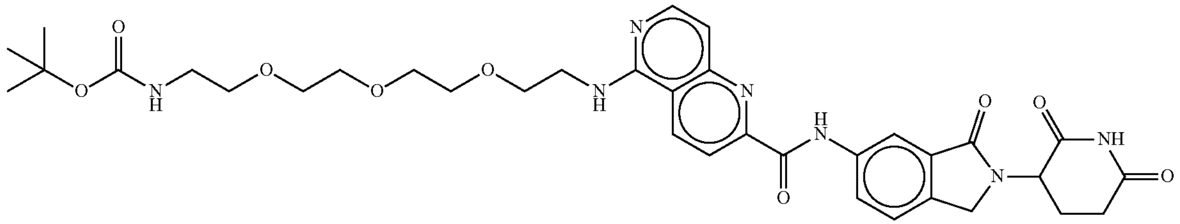 |

TABLE 5-continued
Specific Embodiments of general formula $(A)_k$-L-Q.
| Compound No. | Structure |
| --- | --- |
| 5.33 | 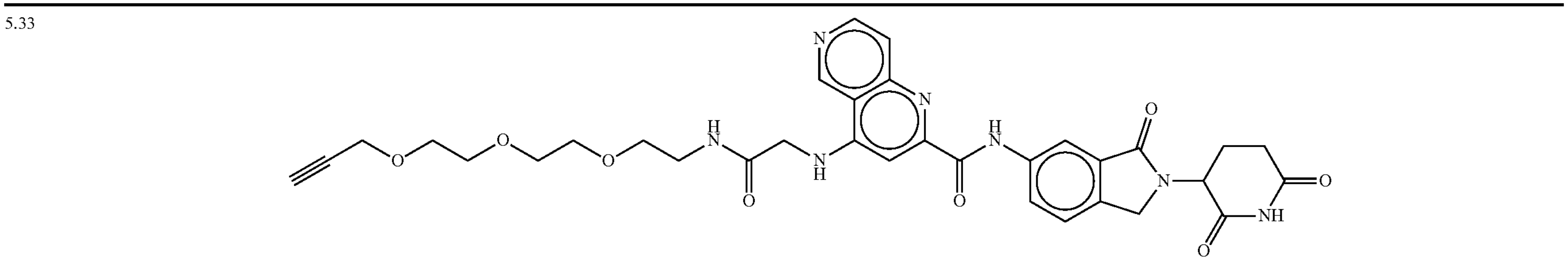 |
| 5.34 | 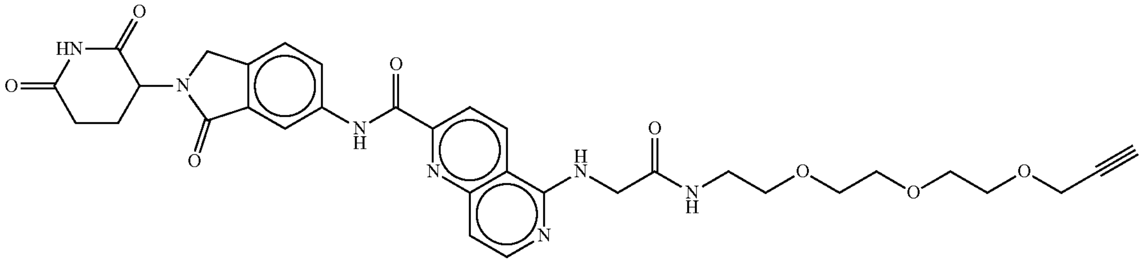 |
| 5.35 | 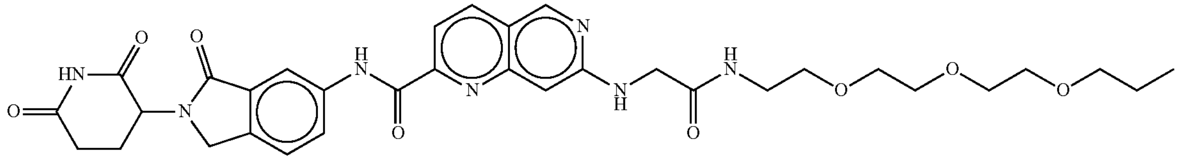 |
| 5.36 | 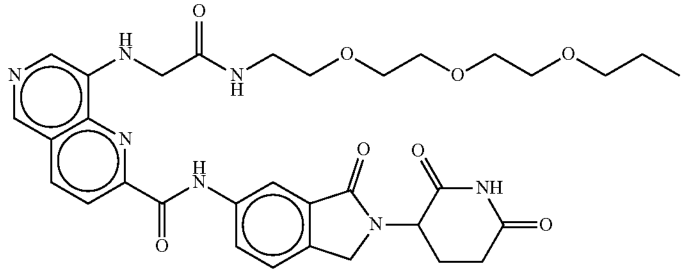 |

TABLE 5-continued
| Specific Embodiments of general formula $(A)_k$-L-Q. | |
|---|---|
| Compound No. | Structure |
| 5.37 | 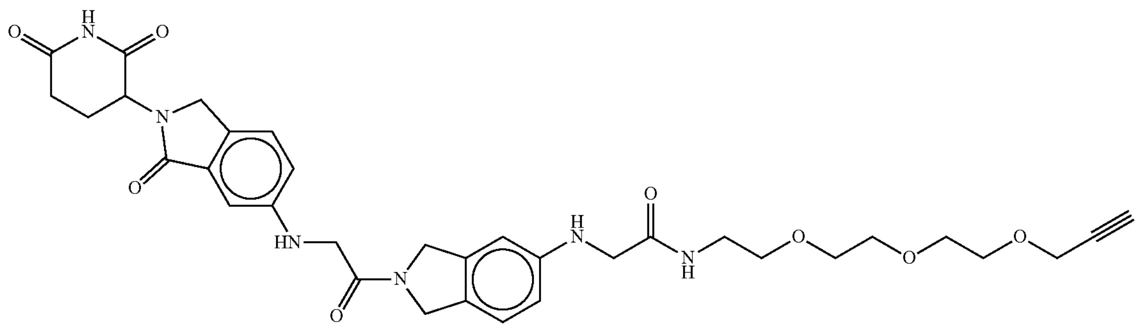 |
| 5.38 | 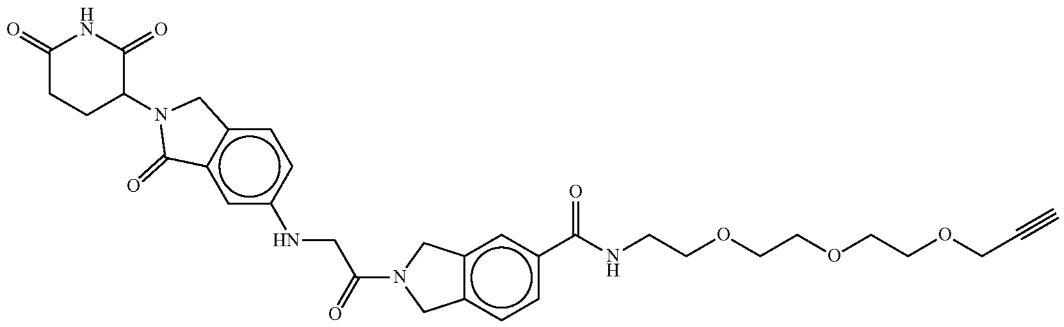 |

TABLE 5-continued
| Specific Embodiments of general formula $(A)_k$-L-Q. | |
|---|---|
| Compound No. | Structure |
| 5.39 | 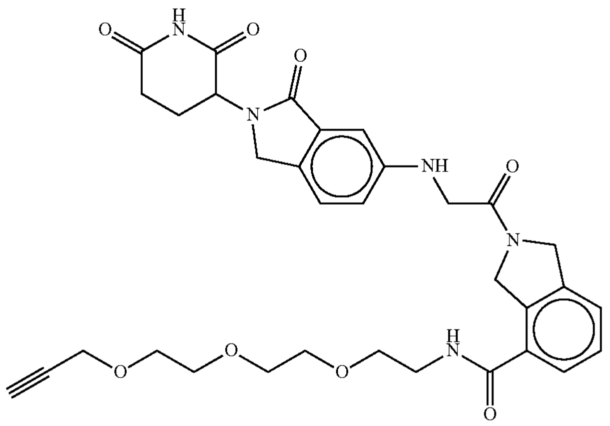 |
| 5.40 | 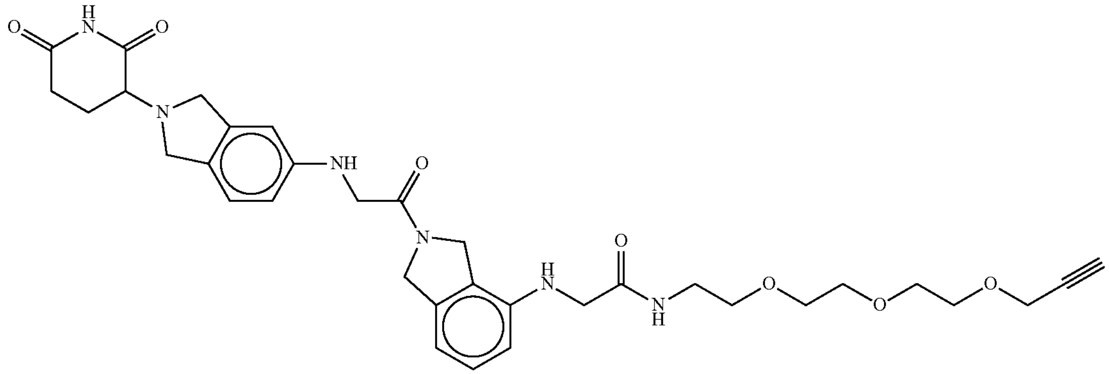 |

TABLE 5-continued
| Specific Embodiments of general formula $(A)_k$-L-Q. | |
|---|---|
| Compound No. | Structure |
| 5.41 | 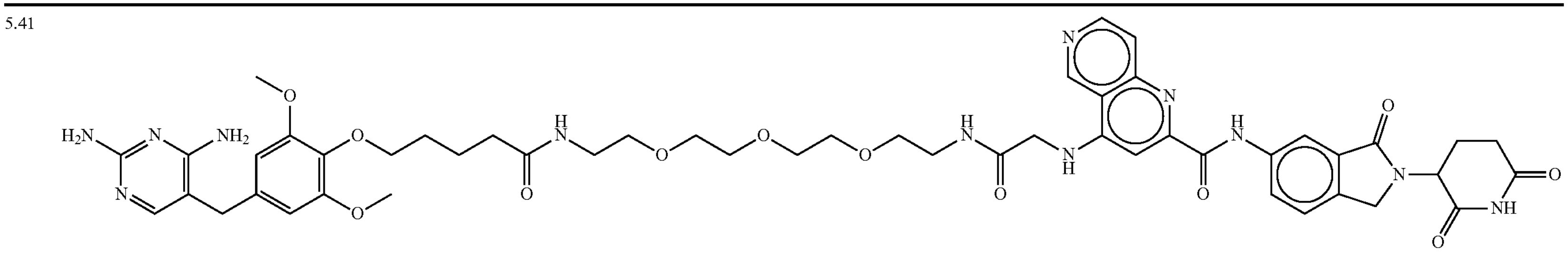 |
| 5.42 | 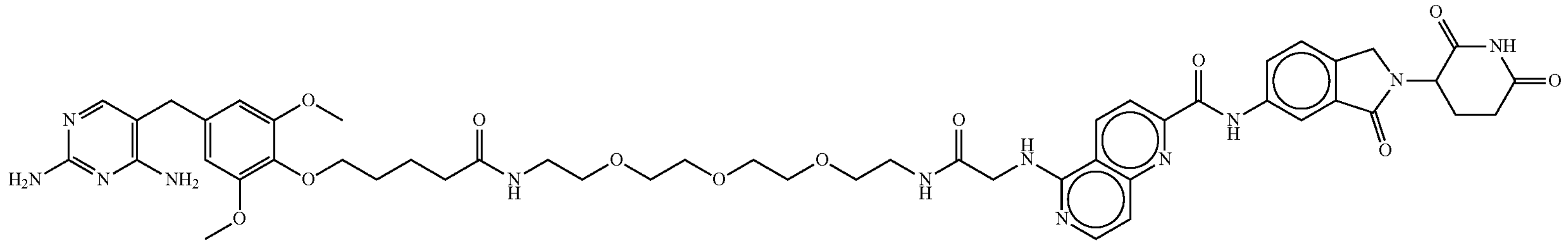 |
| 5.43 | 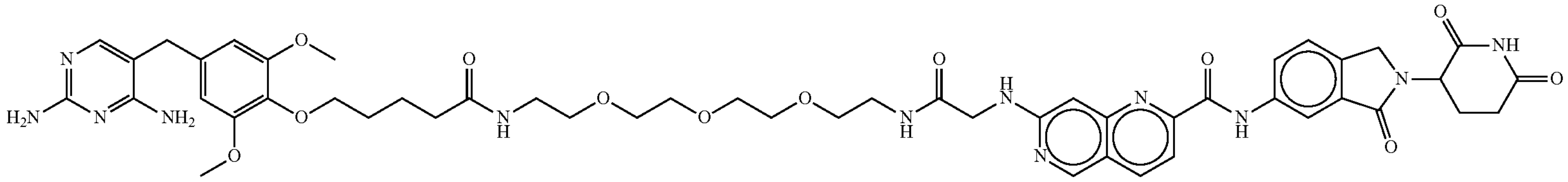 |

TABLE 5-continued
| Specific Embodiments of general formula $(A)_k$-L-Q. | |
|---|---|
| Compound No. | Structure |
| 5.44 | 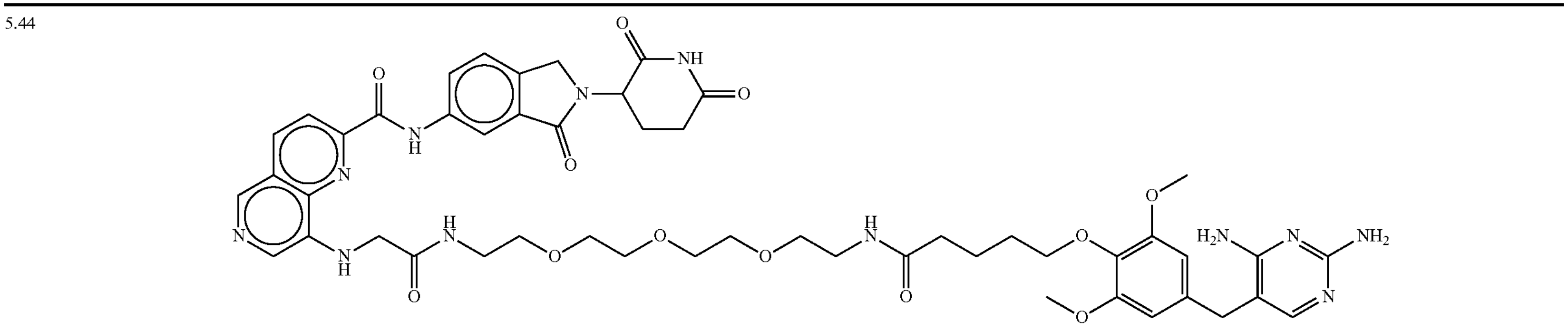 |
| 5.45 | 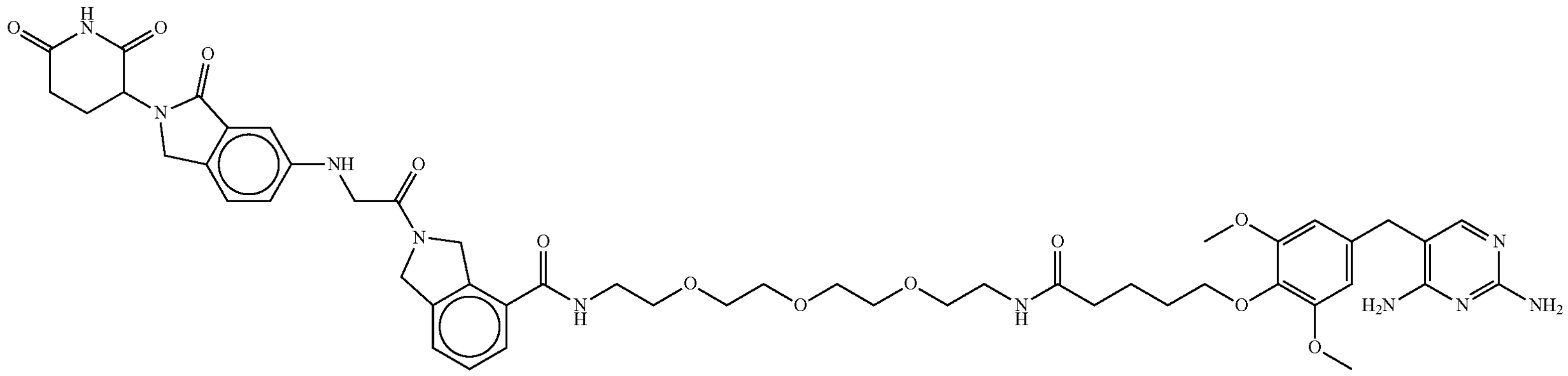 |

TABLE 5-continued
Specific Embodiments of general formula $(A)_k$-L-Q.
| Compound No. | Structure |
| --- | --- |
| 5.46 | 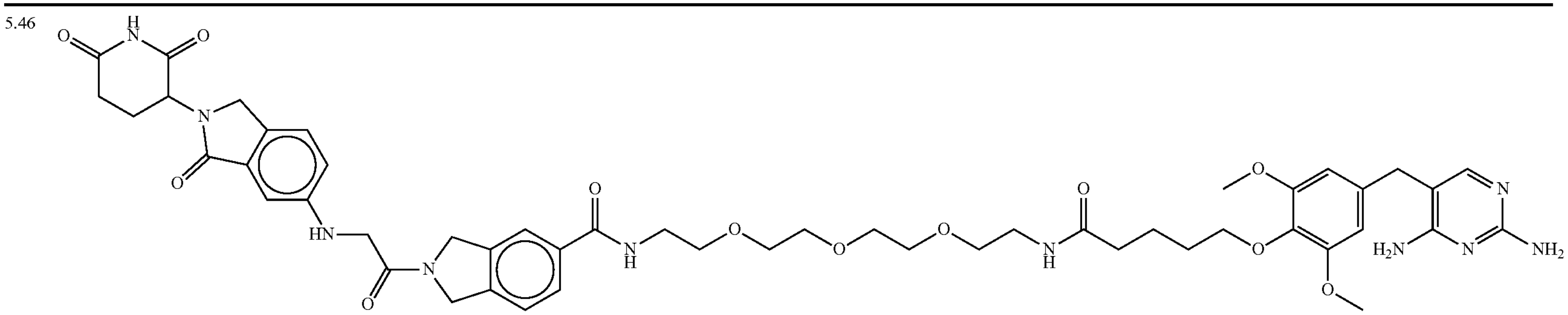 |
| 5.47 | 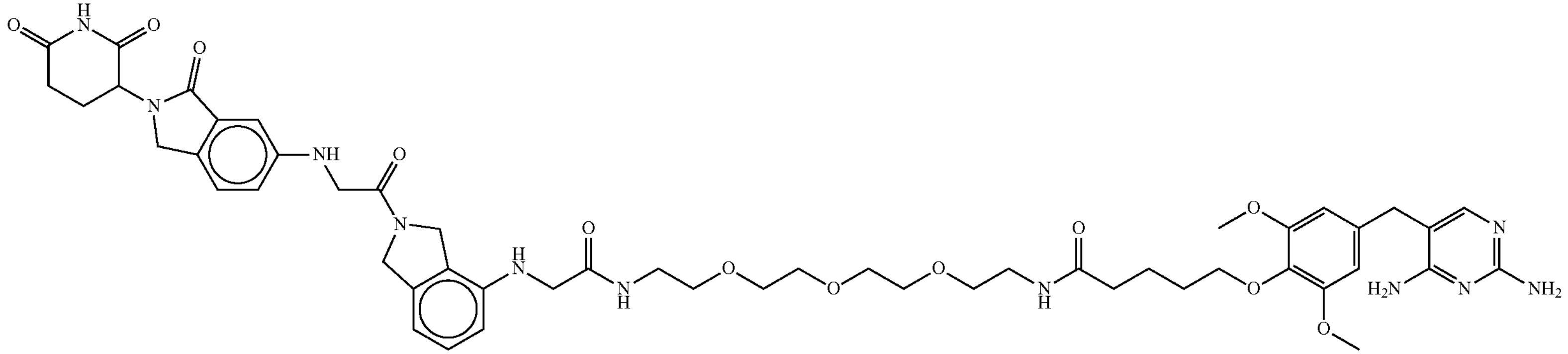 |

TABLE 5-continued
| Specific Embodiments of general formula $(A)_k$-L-Q. | |
|---|---|
| Compound No. | Structure |
| 5.48 | 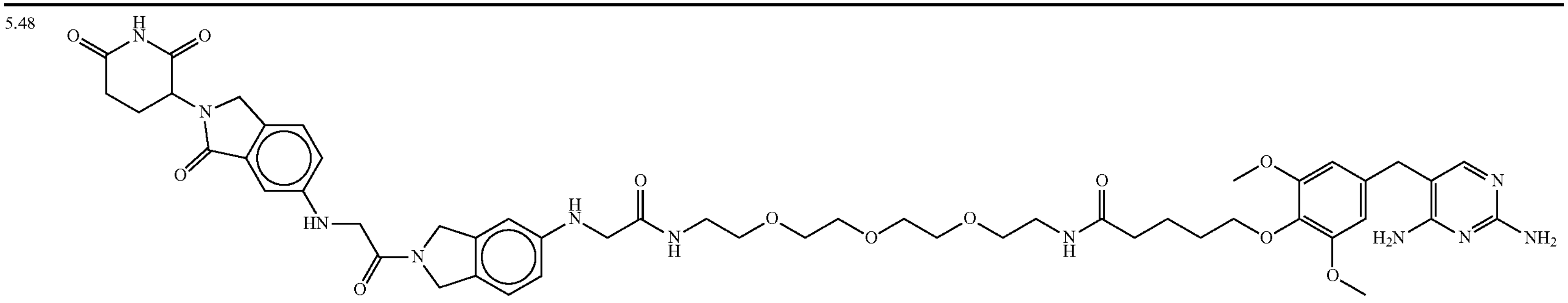 |
| 5.49 | 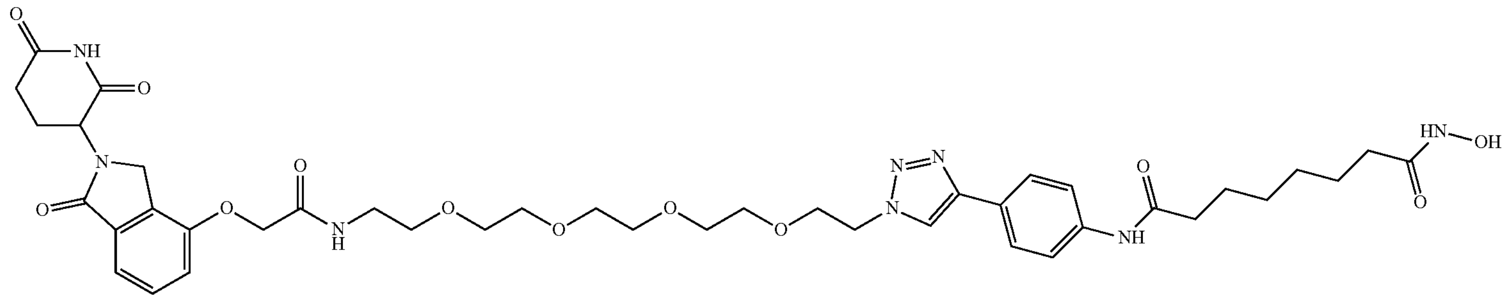 [SMILES: O=C(CCCCCCC(=O)Nc1ccc(-c2cn(CCOCCOCCOCCOCCNC(=O)COc3cccc4c3CN(C3CCC(=O)NC3=O)C4=O)nn2)cc1)NO] |
| 5.50 | 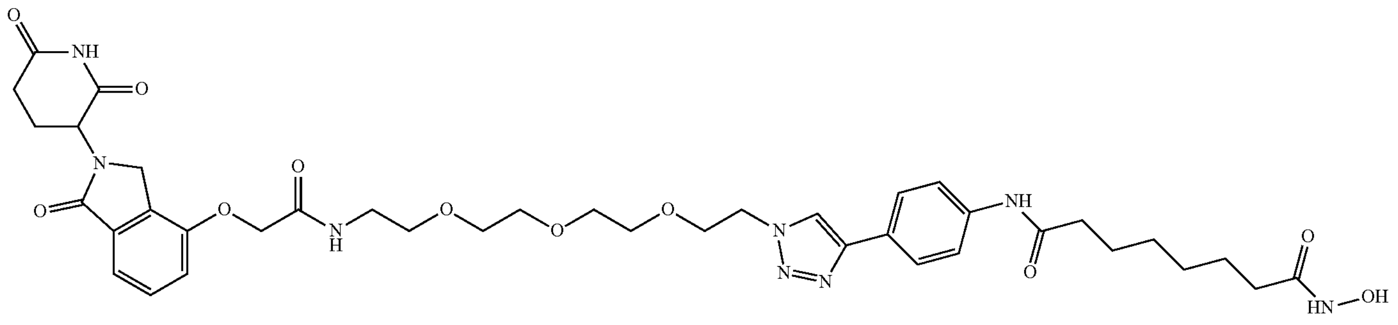 [SMILES: O=C(CCCCCCC(=O)Nc1ccc(-c2cn(CCOCCOCCOCCNC(=O)COc3cccc4c3CN(C3CCC(=O)NC3=O)C4=O)nn2)cc1)NO] |

TABLE 5-continued
| Specific Embodiments of general formula $(A)_k$-L-Q. | |
|---|---|
| Compound No. | Structure |
| 5.51 | 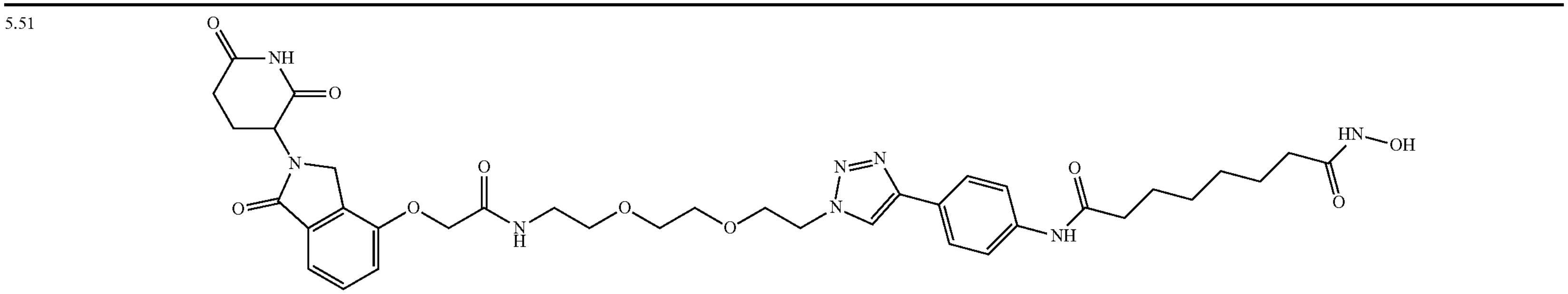 |
| 5.52 | 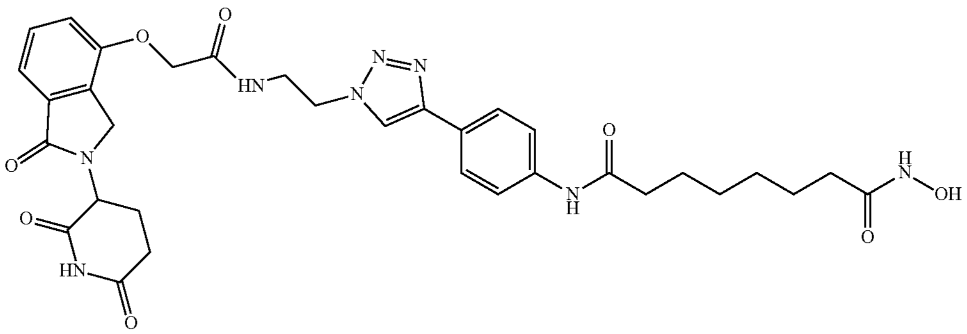 [SMILES: O=C(CCCCCCC(=O)Nc1ccc(-c2cn(CCNC(=O)COc3cccc4c3CN(C3CCC(=O)NC3=O)C4=O)nn2)cc1)NO] |

TABLE 5-continued
| Specific Embodiments of general formula (A)$_k$-L-Q. | |
|---|---|
| Compound No. | Structure |
| 5.53 | 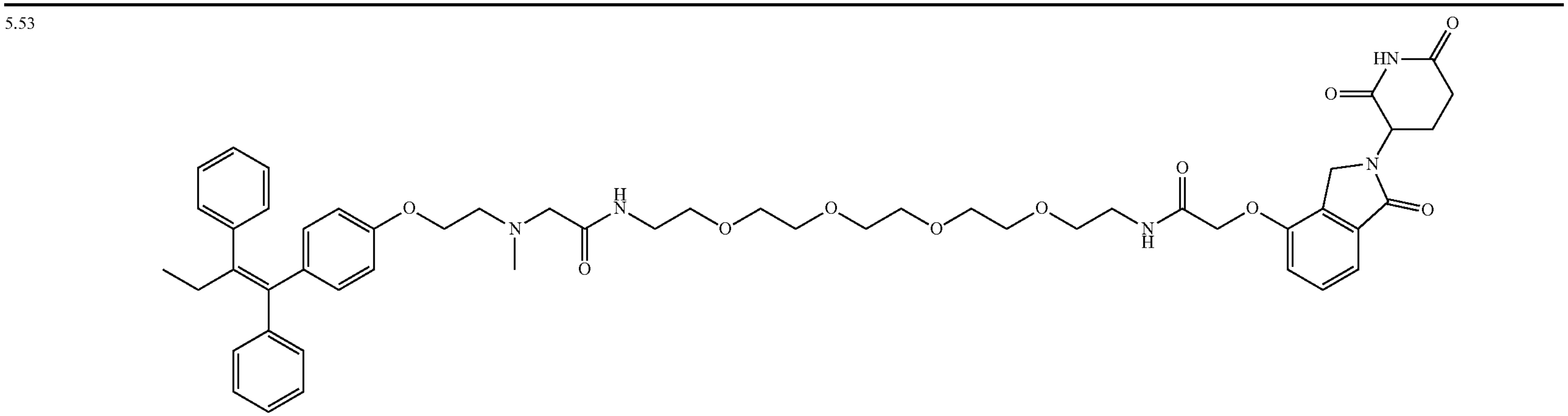 |
| 5.54 | 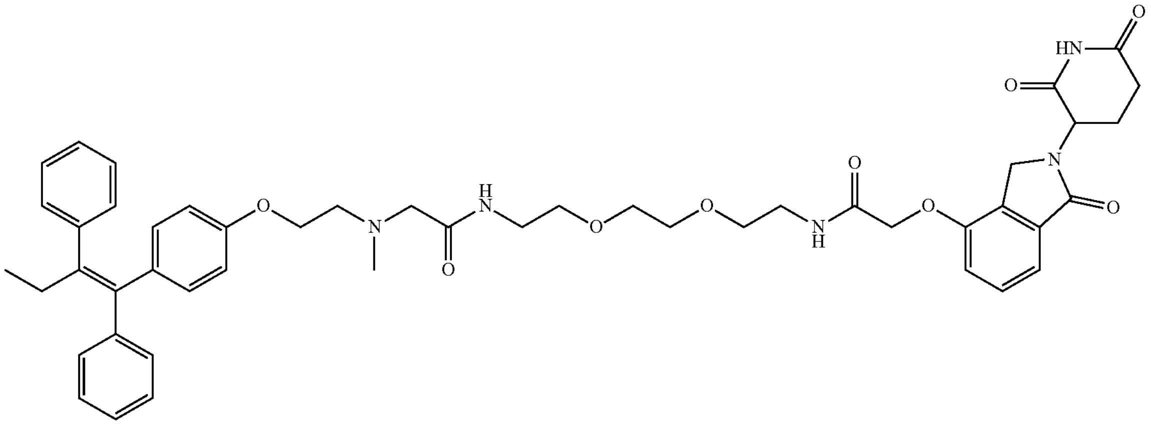 [SMILES: CC/C(=C(\c1ccccc1)c1ccc(OCCN(C)CC(=O)NCCOCCOCCNC(=O)COc2cccc3c2CN(C2CCC(=O)NC2=O)C3=O)cc1)c1ccccc1] |

TABLE 5-continued
| Specific Embodiments of general formula $(A)_k$-L-Q. | |
|---|---|
| Compound No. | Structure |
| 5.55 | 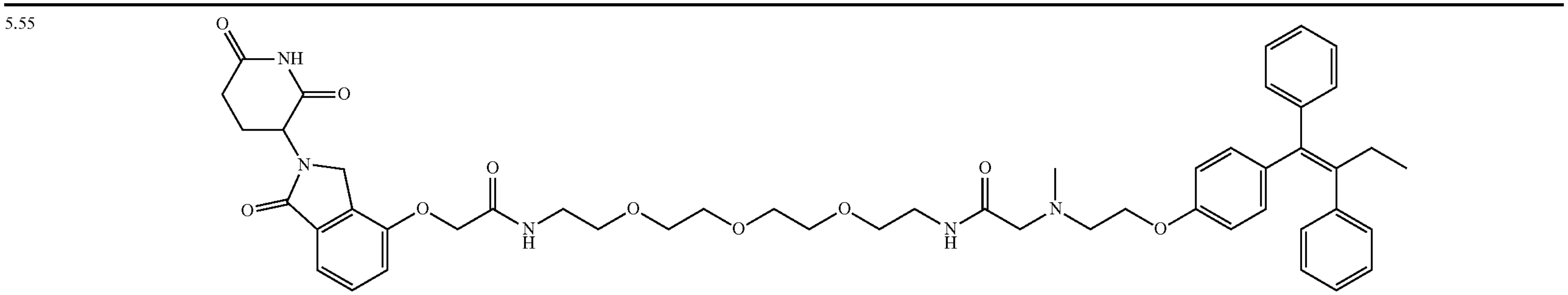 |
| 5.56 | 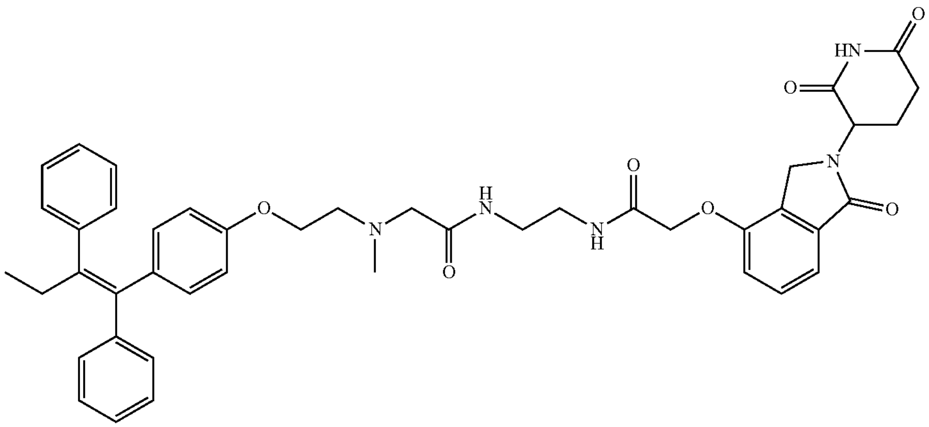 [SMILES: CC/C(=C(\c1ccccc1)c1ccc(OCCN(C)CC(=O)NCCNC(=O)COc2cccc3c2CN(C2CCC(=O)NC2=O)C3=O)cc1)c1ccccc1] |

TABLE 5-continued
| Specific Embodiments of general formula $(A)_k$-L-Q. | |
|---|---|
| Compound No. | Structure |
| 5.57 | 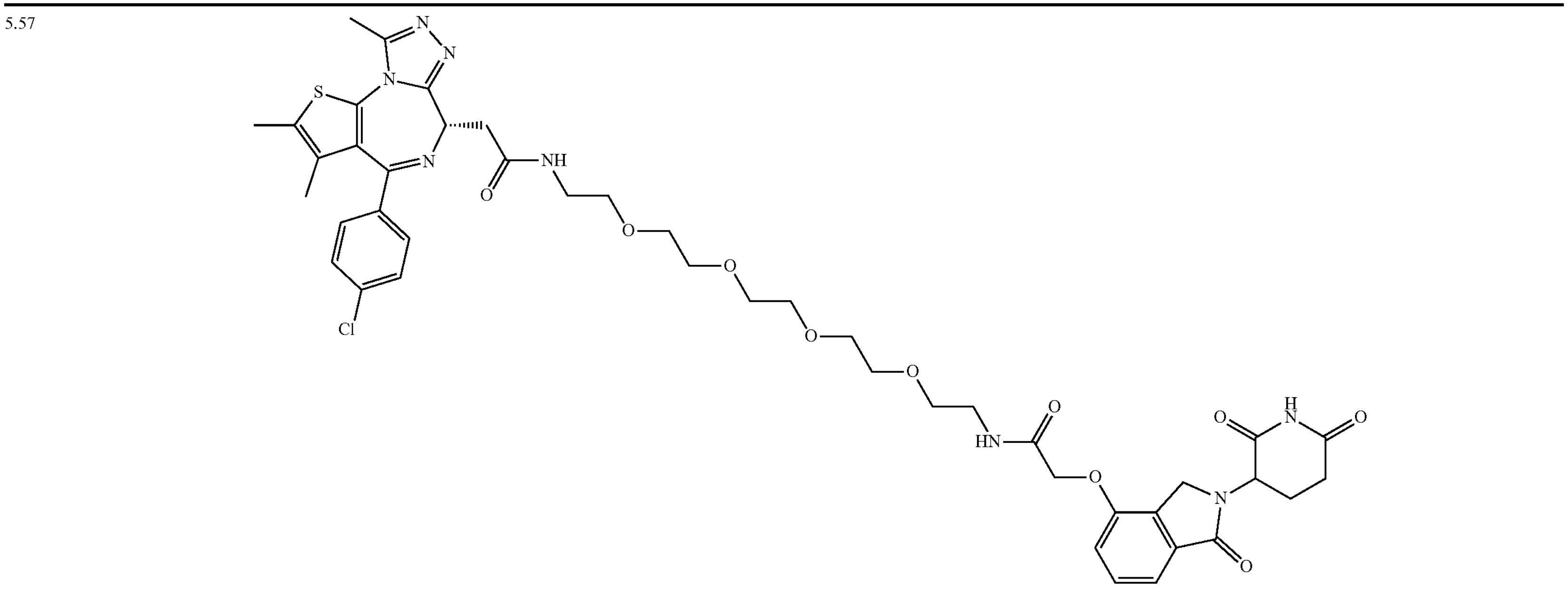 |

TABLE 5-continued
| Specific Embodiments of general formula $(A)_k$-L-Q. | |
|---|---|
| Compound No. | Structure |
| 5.58 | 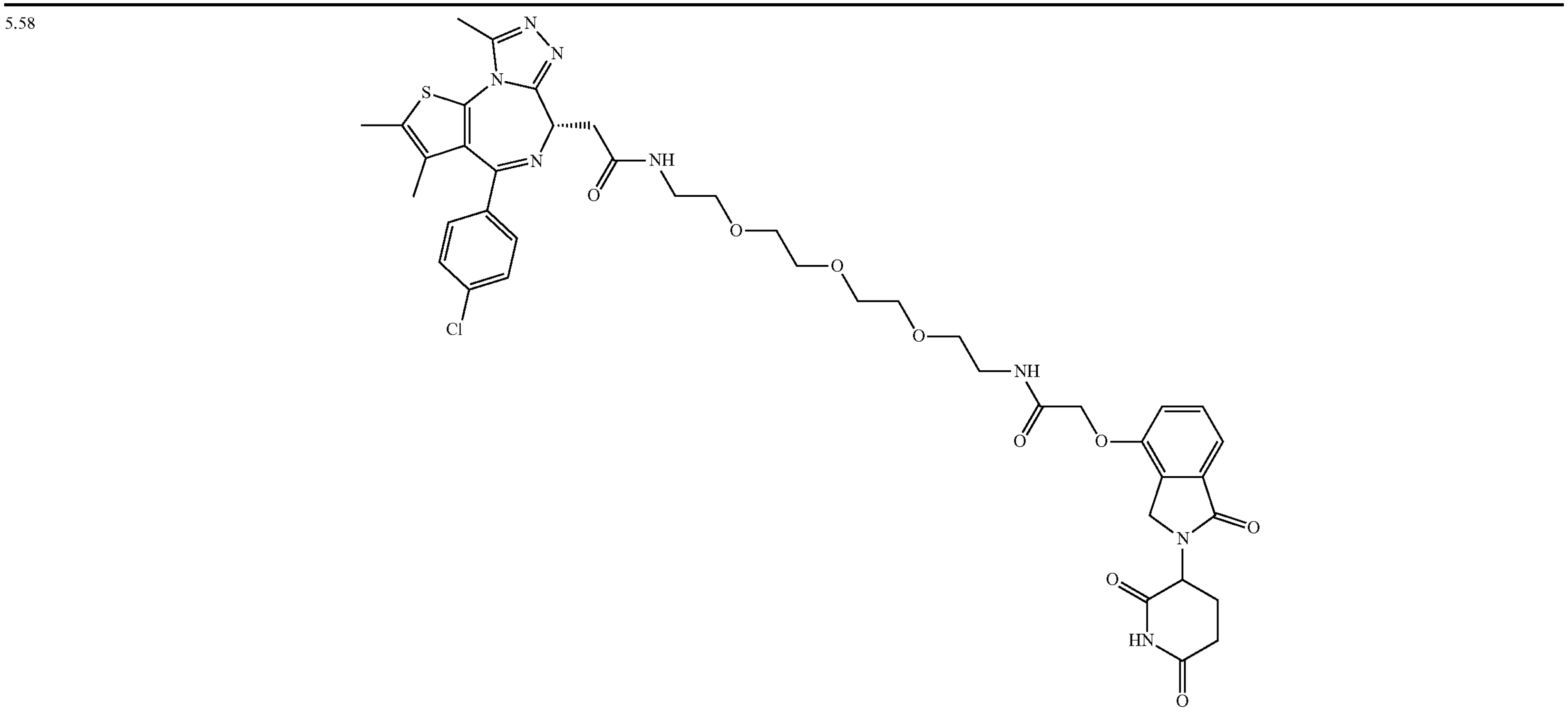 |

TABLE 5-continued
| Specific Embodiments of general formula $(A)_k$-L-Q. | |
|---|---|
| Compound No. | Structure |
| 5.59 | 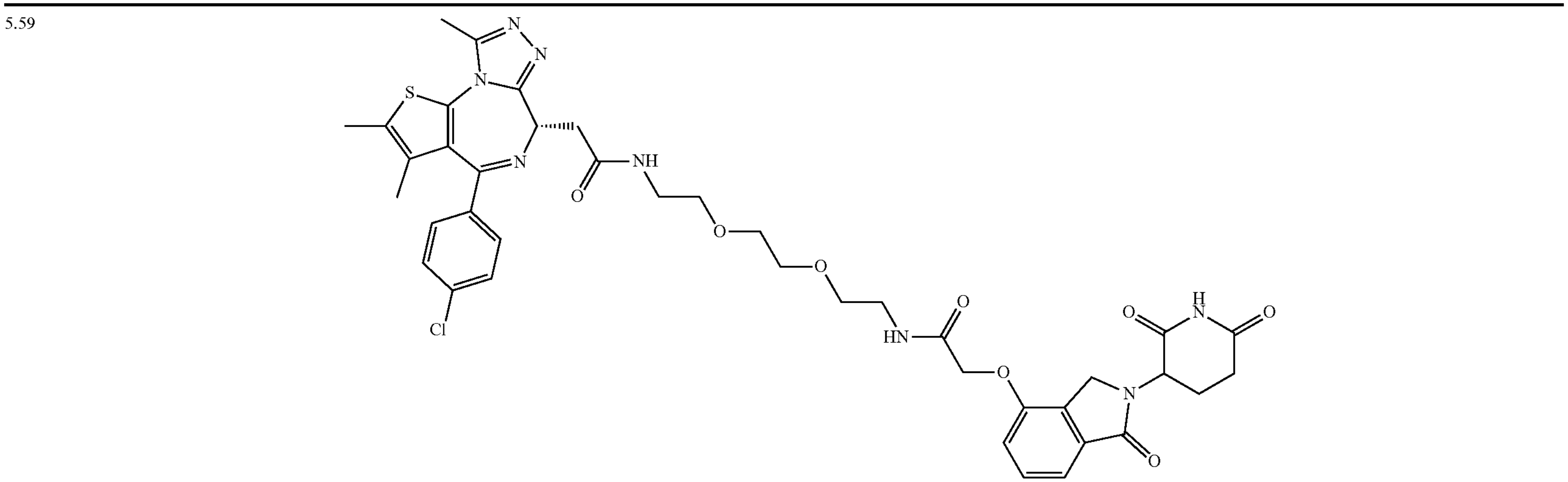 |
| 5.60 | 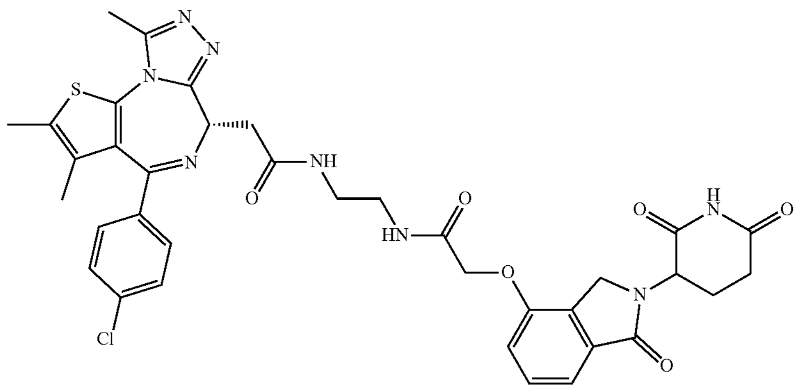 [SMILES: Cc1sc2c(c1C)C(c1ccc(Cl)cc1)=N[C@@H](CC(=O)NCCNC(=O)COc1cccc3c1CN(C1CCC(=O)NC1=O)C3=O)c1nnc(C)n1-2] |

TABLE 5-continued
| Specific Embodiments of general formula $(A)_k$-L-Q. | |
|---|---|
| Compound No. | Structure |
| 5.61 | 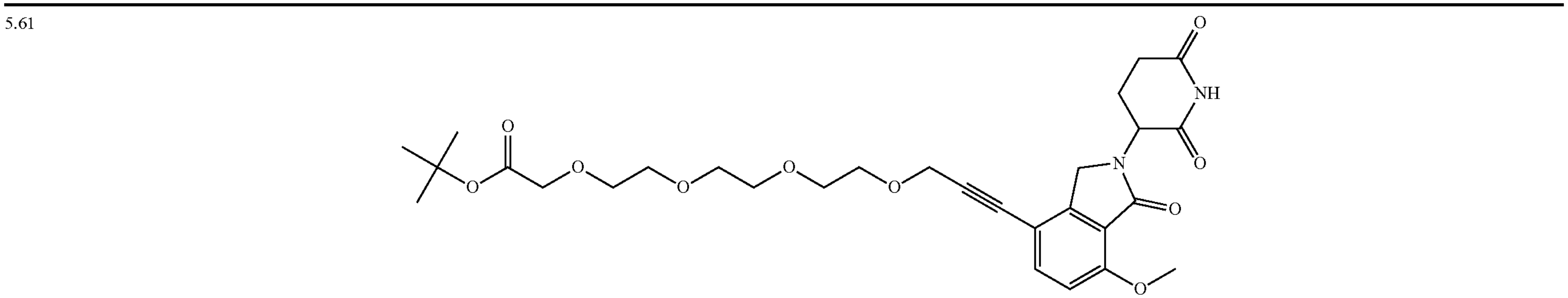 |
| 5.62 | 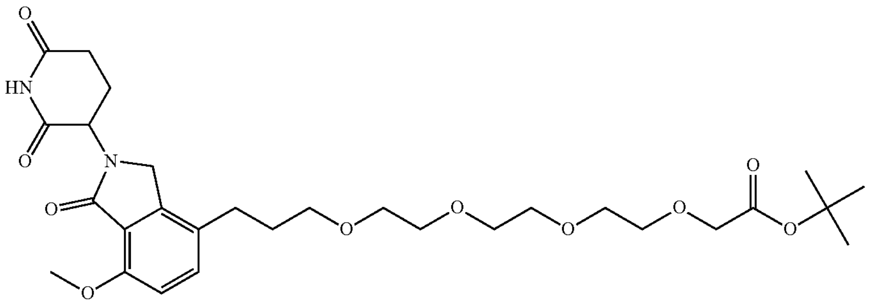 [SMILES: COc1ccc(CCCOCCOCCOCCOCC(=O)OC(C)(C)C)c2c1C(=O)N(C1CCC(=O)NC1=O)C2] |

In an embodiment, moiety A is selected from the compounds listed in Table 6 in Example 6.

In one aspect, moiety A is selected from the group consisting of:

3-[1-oxo-5-(quinazolin-4-ylamino)isoindolin-2-yl]piperidine-2,6-dione;

3-[5-[(4-aminothieno[2,3-d]pyrimidin-2-yl)amino]-1-oxo-isoindolin-2-yl]piperidine-2,6-dione;

N-[2-(2,6-dioxo-3-piperidyl)-1-oxo-isoindolin-5-yl]acetamide;

3-[5-[(2-aminopyrimidin-4-yl)amino]-1-oxo-isoindolin-2-yl]piperidine-2,6-dione;

6-[[2-(2,6-dioxo-3-piperidyl)-1-oxo-isoindolin-5-yl]amino]pyridazine-3-carbonitrile;

3-[[2-[[2-(2,6-dioxo-3-piperidyl)-1-oxo-isoindolin-5-yl]amino]acetyl]amino]benzamide;

2-[[2-(2,6-dioxo-3-piperidyl)-1-oxo-isoindolin-5-yl]amino]acetic acid;

N-[2-(2,6-dioxo-3-piperidyl)-3-oxo-isoindolin-5-yl]quinoline-2-carboxamide;

3-[6-[[2-(2-methyl-1-piperidyl)-2-oxo-ethyl]amino]-1-oxo-isoindolin-2-yl]piperidine-2,6-dione;

3-[6-[(2-isoindolin-2-yl-2-oxo-ethyl)amino]-1-oxo-isoindolin-2-yl]piperidine-2,6-dione;

N-(cyclopropylmethyl)-2-[[2-(2,6-dioxo-3-piperidyl)-3-oxo-isoindolin-5-yl]amino]-N-methyl-acetamide;

acetic acid; 3-[1-oxo-6-(quinazolin-4-ylamino)isoindolin-2-yl]piperidine-2,6-dione;

3-[6-[[2-(3-methyl-1-piperidyl)-2-oxo-ethyl]amino]-1-oxo-isoindolin-2-yl]piperidine-2,6-dione;

3-[6-[(4-methyl-3-oxo-pyrazin-2-yl)amino]-1-oxo-isoindolin-2-yl]piperidine-2,6-dione;

3-[1-oxo-6-(quinoxalin-2-ylamino)isoindolin-2-yl]piperidine-2,6-dione;

3-[6-[(1-methylpyrazolo[3,4-d]pyrimidin-4-yl)amino]-1-oxo-isoindolin-2-yl]piperidine-2,6-dione;

3-[6-(5,7-dihydrofuro[3,4-d]pyrimidin-2-ylamino)-1-oxo-isoindolin-2-yl]piperidine-2,6-dione;

3-[6-[(6-methylpyrimidin-4-yl)amino]-1-oxo-isoindolin-2-yl]piperidine-2,6-dione;

2-[[2-(2,6-dioxo-3-piperidyl)-3-oxo-isoindolin-5-yl]amino]-N-phenyl-acetamide;

3-[6-[[2-(2,4-dimethylpiperazin-1-yl)-2-oxo-ethyl]amino]-1-oxo-isoindolin-2-yl]piperidine-2,6-dione;

3-[6-(dimethylamino)-1-oxo-isoindolin-2-yl]piperidine-2,6-dione;

3-(1-oxo-6-phenyl-isoindolin-2-yl)piperidine-2,6-dione;

2-[[2-(2,6-dioxo-3-piperidyl)-3-oxo-isoindolin-5-yl]amino]-N,N-dimethyl-acetamide;

3-[6-[[2-(2-methylmorpholin-4-yl)-2-oxo-ethyl]amino]-1-oxo-isoindolin-2-yl]piperidine-2,6-dione;

2-[[2-(2,6-dioxo-3-piperidyl)-3-oxo-isoindolin-5-yl]amino]-N-methyl-N-[(1-methylpyrazol-4-yl)methyl]acetamide;

N-benzyl-2-[[2-(2,6-dioxo-3-piperidyl)-3-oxo-isoindolin-5-yl]amino]acetamide;

6-[[2-(2,6-dioxo-3-piperidyl)-3-oxo-isoindolin-5-yl]amino]pyridazine-3-carbonitrile;

3-[6-[(6-methylpyrrolo[3,2-d]pyrimidin-4-yl)amino]-1-oxo-isoindolin-2-yl]piperidine-2,6-dione;

2-(dimethylamino)-N-[2-(2,6-dioxo-3-piperidyl)-3-oxo-isoindolin-5-yl]acetamide;

N-[2-(2,6-dioxo-3-piperidyl)-3-oxo-isoindolin-5-yl]-5H-pyrrolo[2,3-b]pyridine-4-carboxamide;

N-cyclopropyl-2-[[2-(2,6-dioxo-3-piperidyl)-3-oxo-isoindolin-5-yl]amino]acetamide;

3-[1-oxo-6-(2-oxoimidazolidin-1-yl)isoindolin-2-yl]piperidine-2,6-dione;

2-(2,6-dioxo-3-piperidyl)-3-oxo-isoindoline-5-carbonitrile;

2-[[2-(2,6-dioxo-3-piperidyl)-3-oxo-isoindolin-5-yl]amino]propanoic acid;

2-acetamido-N-[2-(2,6-dioxo-3-piperidyl)-3-oxo-isoindolin-5-yl]acetamide;

2-[[2-(2,6-dioxo-3-piperidyl)-3-oxo-isoindolin-5-yl]amino]acetamide;

3-[6-[[2-(3-methyl-5-oxo-piperazin-1-yl)-2-oxo-ethyl]amino]-1-oxo-isoindolin-2-yl]piperidine-2,6-dione;

N-[2-(2,6-dioxo-3-piperidyl)-3-oxo-isoindolin-5-yl]acetamide;

3-[6-[[2-(4-methyl-3-oxo-piperazin-1-yl)-2-oxo-ethyl]amino]-1-oxo-isoindolin-2-yl]piperidine-2,6-dione;

N-[2-(2,6-dioxo-3-piperidyl)-3-oxo-isoindolin-5-yl]-3H-imidazo[4,5-b]pyridine-6-carboxamide;

2-[[2-(2,6-dioxo-3-piperidyl)-3-oxo-isoindolin-5-yl]amino]-N-tetrahydropyran-4-yl-acetamide;

2-[[2-(2,6-dioxo-3-piperidyl)-3-oxo-isoindolin-5-yl]amino]acetic acid;

3-[1-oxo-6-[[2-oxo-2-(1-piperidyl)ethyl]amino]isoindolin-2-yl]piperidine-2,6-dione;

3-(1-oxo-7-phenyl-isoindolin-2-yl)piperidine-2,6-dione;

2-(2,6-dioxo-3-piperidyl)-3-oxo-isoindoline-4-carbonitrile;

2-[[2-(2,6-dioxo-3-piperidyl)-3-oxo-isoindolin-4-yl]amino]acetic acid;

3-(7-fluoro-1-oxo-isoindolin-2-yl)piperidine-2,6-dione;

3-(5-amino-1-oxo-3,4-dihydroisoquinolin-2-yl)piperidine-2,6-dione;

t-butyl 2-[2-(2,6-dioxo-3-piperidyl)-3-oxo-isoindolin-1-yl]acetate;

3-[1-(2H-indol-3-yl)-3-oxo-isoindolin-2-yl]piperidine-2,6-dione;

2-(2,6-dioxo-3-piperidyl)-3-oxo-isoindoline-1-carbonitrile;

3-[1-(dimethylamino)-3-oxo-isoindolin-2-yl]piperidine-2,6-dione;

3-(2-oxopyrrolidin-1-yl)piperidine-2,6-dione;

3-(quinazolin-2-ylamino)piperidine-2,6-dione;

(3Z)-3-benzylidenepiperidine-2,6-dione;

3-(quinoxalin-2-ylamino)piperidine-2,6-dione;

3-(pyrimidin-2-ylamino)piperidine-2,6-dione;

N-(2,6-dioxo-3-piperidyl)-2-oxo-3H-pyridine-6-carboxamide;

3-(4-methyl-1,1,3-trioxo-1,2-benzothiazol-2-yl)piperidine-2,6-dione;

3-(8-amino-4-oxo-1,2,3-benzotriazin-3-yl)piperidine-2,6-dione;

3-(5-amino-4-oxo-1,2,3-benzotriazin-3-yl)piperidine-2,6-dione;

3-(4-oxo-1,2,3-benzotriazin-3-yl)piperidine-2,6-dione;

3-(5-methyl-4-oxo-1,2,3-benzotriazin-3-yl)piperidine-2,6-dione;

3-(6-methyl-4-oxo-1,2,3-benzotriazin-3-yl)piperidine-2,6-dione; and 3-(8-methyl-4-oxo-1,2,3-benzotriazin-3-yl)piperidine-2,6-dione.

Target Protein Binding Moiety Q

The target proteins to be bound by moiety Q are numerous in kind and are selected from proteins that are expressed in a cell such that at least a portion of the sequences is found in the cell. The term "protein" includes oligopeptides and polypeptide sequences of sufficient length that they can bind to a Q moiety according to the present invention. Any protein in a eukaryotic system or a microbial system, including a virus, bacteria or fungus, as otherwise described herein, are targets for ubiquitination mediated by the compounds according to the present invention. Preferably, the target protein is a eukaryotic protein.

The Q moiety according to the present invention include, for example, includes any moiety which binds to a protein specifically (binds to a target protein) and includes the following non-limiting examples of small molecule target protein moieties: Hsp90 inhibitors, kinase inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. Some of the members of these types of small molecule target protein binding moieties are exemplified below. Such small molecule target protein binding moieties also include pharmaceutically acceptable salts, enantiomers, solvates and polymorphs thereof. These binding moieties are linked to the ubiquitin ligase binding moiety through a linker in order to present a target protein (to which the protein target moiety is bound) in proximity to the ubiquitin ligase for ubiquitination and degradation. In an embodiment, the ubiquitin ligase is cereblon.

Any protein, which can bind to moiety Q and acted on or degraded by an ubiquitin ligase is a target protein according to the present invention. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eukaryotes and prokaryotes including humans as targets for drug therapy, other animals, including domesticated animals, microbials for the determination of targets for antibiotics and other antimicrobials and plants, and even viruses, among numerous others.

In an embodiment, the target protein is selected from the group consisting of B7.1 and B7, TINFR1m, TNFR2, NADPH oxidase, Bcl, C5a receptor, HMG-CoA reductase, PDE V phosphodiesterase type, PDE IV phosphodiesterase type 4, PDE I, PDEII, PDEIII, Squalene-hopene cyclase, CXCR1, CXCR2, nitric oxide (NO) synthase, cyclo-oxygenase 1, cyclo-oxygenase 2, 5HT receptors, dopamine receptors, G Proteins, Gq, histamine receptors, 5-lipoxygenase, tryptase serine protease, thymidylate synthase, purine nucleoside phosphorylase, GAPDH trypanosomal, glycogen phosphorylase, carbonic anhydrase, chemokine receptors, JAW/STAT, retinoid X receptor, HIV 1 protease, HIV 1 integrase, influenza, neuramimidase, hepatitis B reverse transcriptase, sodium channel, protein P-glycoprotein (and MRP), tyrosine kinases, CD23, CD124, tyrosine kinase p56 lck, CD4, CD5, IL-2 receptor, IL-1 receptor, TNF-alpha, ICAM1, Cat+ channels, VCAM, VLA-4 integrin, selectins, CD40/CD40L, newokinins and receptors, inosine monophosphate dehydrogenase, p38 MAP Kinase, Ras/Raf/ME/ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I) protease, cytomegalovirus (CMV) protease, poly (ADP-ribose) polymerase, cyclin dependent kinases, vascular endothelial growth factor, c-Kit, TGFβ activated kinase 1, mammalian target of rapamycin, SHP2, androgen receptor, oxytocin receptor, microsomal transfer protein inhibitor, 5 alpha reductase, angiotensin II, glycine receptor, noradrenaline reuptake receptor, estrogen receptor, estrogen related receptors, focal adhesion kinase, Src, endothelin receptors, neuropeptide Y and receptor, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-1, vitronectin receptor, integrin receptor, Her-2/neu, telomerase, cytosolic phospholipaseA2 and EGF receptor tyrosine kinase, ecdysone 20-monooxygenase, ion channel of the GABA gated chloride channel, acetylcholinesterase, voltage-sensitive sodium channel protein, calcium channel protein, and chloride channel protein, acetyl-CoA carboxylase, adenylosuccinate synthetase, protoporphyrinogen oxidase, and enolpyruvylshikimate-phosphate synthase.

In an embodiment, Q is a moiety that is an Hsp90 inhibitor, a kinase inhibitor, a phosphatase inhibitor, an HDM2/MDM2 inhibitor, a human BET Bromodomain inhibitor, an HDAC inhibitor, a human lysine methyltransferase inhibitor, a RAF receptor inhibitor, a FKBP inhibitor, an angiogenesis inhibitor, an aryl hydrocarbon receptor inhibitor, an androgen receptor inhibitor, an estrogen receptor inhibitor, a thyroid hormone receptor inhibitor, an HIV protease inhibitor, an HIV integrase inhibitor, an acyl protein thioesterase 1 inhibitor, or an acyl protein thioesterase 2 inhibitor.

In an embodiment, Q is a moiety that is a TANK-binding kinase 1 (TBK1) inhibitor, an estrogen receptor α (ERα) inhibitor, a bromodomain-containing protein 4 (BRD4) inhibitor, an androgen receptor (AR) inhibitor, a platelet-derived growth factor receptor inhibitor, a p38 MAPK inhibitor, a Bcr-Abl tyrosine-kinase inhibitor, an Her2 inhibitor, an EGFR inhibitor, an MDM2 inhibitor, a bromodomain-containing protein 2 (BRD2) inhibitor, an HDAC inhibitor, a DHFR inhibitor, or a c-Myc inhibitor.

In an embodiment, Q is a moiety selected from the group consisting of trimethoprim, vorinostat, tamoxifen, JQ1, Nutlin 3, afatinib, chloroalkane, dasatinib, BIRB796, FK-506, simvastatin, rapamycin, and sorafenib.

In an embodiment, Q is a moiety binding to a target protein. Such target protein can be degraded or sequestrated by an E3 ubiquitin ligase, wherein the E3 ubiquitin ligase is selected from cereblon (CRBN), damaged DNA binding protein 1 (DDB1), Cullin-4A (CUL4A), regulator of cullins 1 (ROC1), and Von Hippel Lindau (VHL).

In an embodiment, the E3 ubiquitin ligase is CRBN.

In an embodiment, the compound having the general formula $(A)_k$-$L_1$ or $(A)_k$-L-Q described herein is capable of simultaneously binding to the target protein and the E3 ubiquitin ligase. In an embodiment, the binding causes ubiquitination of the target protein by the E3 ubiquitin ligase. In an embodiment, the binding causes degradation of the target protein by the proteasome.

| Name | Structure |
|---|---|
| trimethoprim | 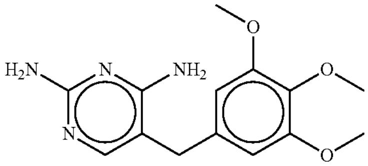 |
| vorinostat | 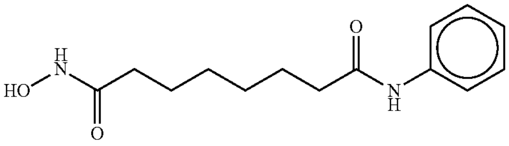 |
| tamoxifen | 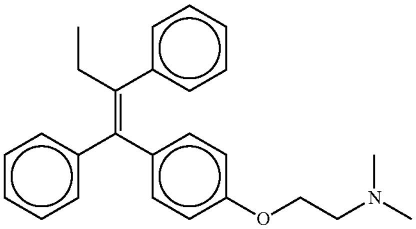 |
| JQ1 | 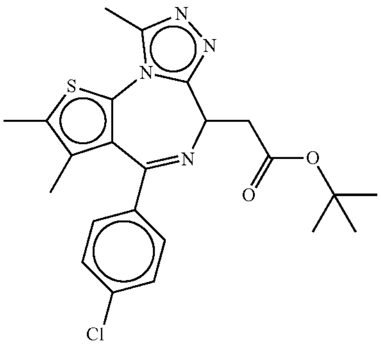 |
| Nutlin 3 | 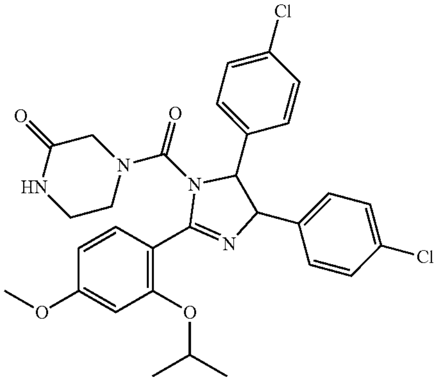 [SMILES: COc1ccc(C2=NC(c3ccc(Cl)cc3)C(c3ccc(Cl)cc3)N2C(=O)N2CCNC(=O)C2)c(OC(C)C)c1] |

-continued
| Name | Structure |
|---|---|
| afatinib | 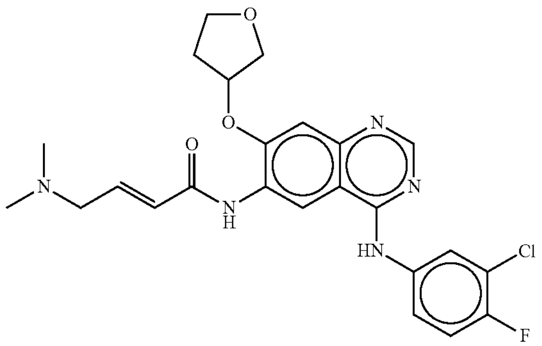 |
| chloroalkane | 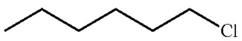 |
| dasatinib | 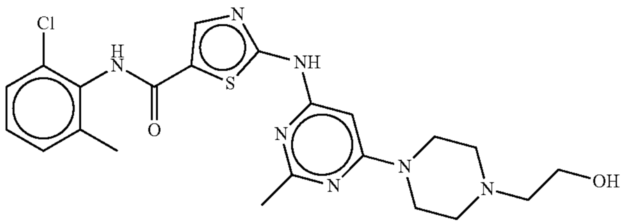 |
| BIRB796 | 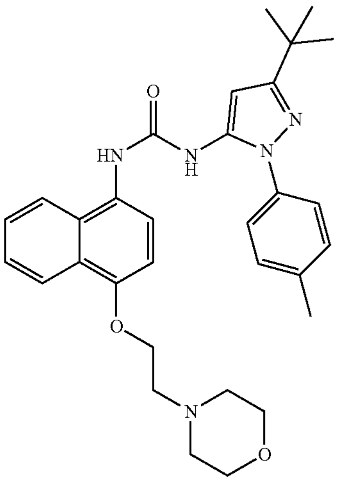 [SMILES: Cc1ccc(-n2nc(C(C)(C)C)cc2NC(=O)Nc2ccc(OCCN3CCOCC3)c3ccccc23)cc1] |
| sorafenib | 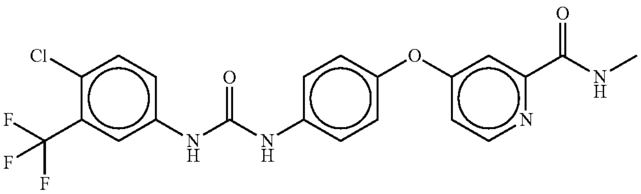 |

-continued
| Name | Structure |
| --- | --- |
| FK-506 | 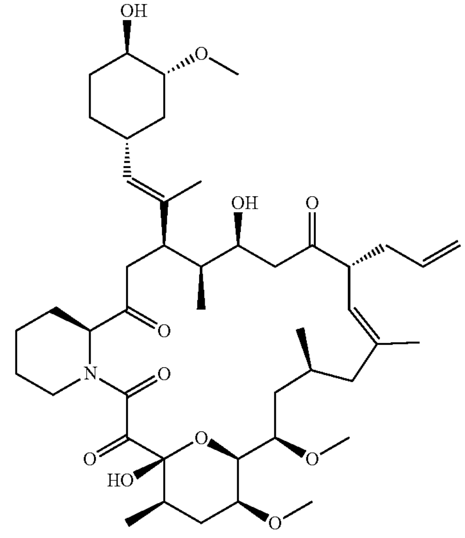 [SMILES: C=CC[C@@H]1/C=C(\C)C[C@H](C)C[C@@H](OC)[C@@H]2O[C@@](O)(C(=O)C(=O)N3CCCC[C@H]3C(=O)C[C@@H](/C(C)=C/[C@@H]3CC[C@@H](O)[C@H](OC)C3)[C@H](C)[C@@H](O)CC1=O)[C@H](C)C[C@@H]2OC] |
| simvastatin | 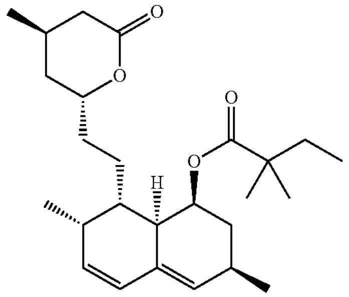 [SMILES: CCC(C)(C)C(=O)O[C@H]1C[C@@H](C)C=C2C=C[C@H](C)[C@H](CC[C@@H]3C[C@@H](C)CC(=O)O3)[C@H]21] |
| rapamycin | 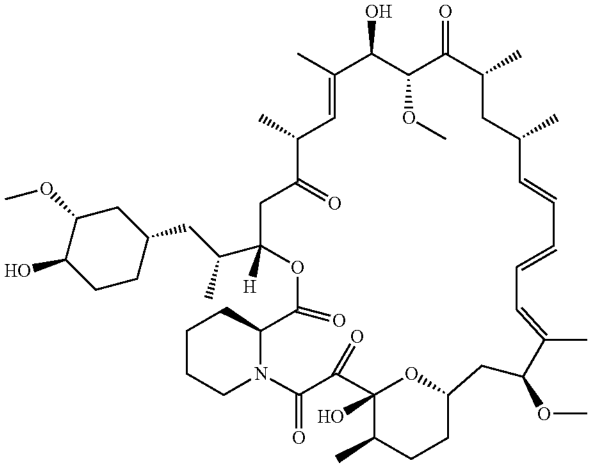 |
The linker L can be covalently connected to Q moiety at any position allowed by valence. In an embodiment, the linker L is covalently connected to Q moiety via the specific position indicated as , shown in the table below.

| Q moiety | Example of linking position |
|---|---|
| FK-506 | 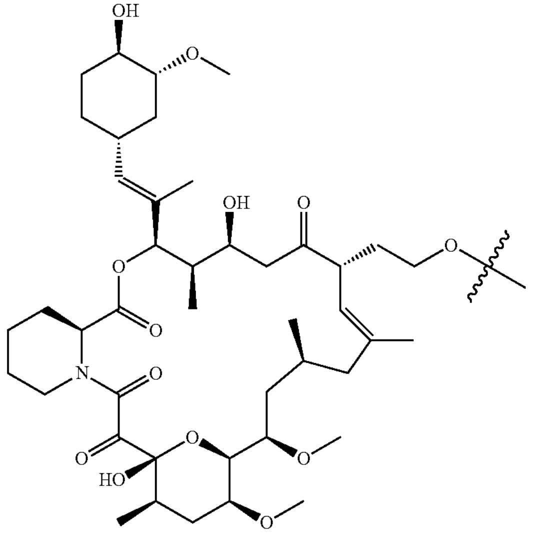 [SMILES: *OCC[C@@H]1/C=C(\C)C[C@H](C)C[C@@H](OC)[C@@H]2O[C@@](O)(C(=O)C(=O)N3CCCC[C@H]3C(=O)O[C@@H](/C(C)=C/[C@@H]3CC[C@@H](O)[C@H](OC)C3)[C@H](C)[C@@H](O)CC1=O)[C@H](C)C[C@@H]2OC] |
| afatinib | 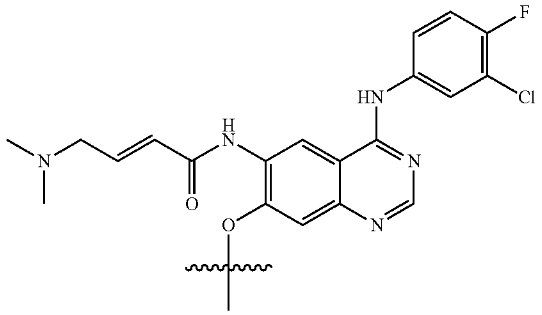 [SMILES: *Oc1cc2ncnc(Nc3ccc(F)c(Cl)c3)c2cc1NC(=O)/C=C/CN(C)C] |
| tamoxifen | 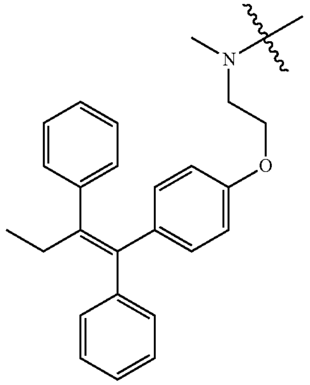 [SMILES: *N(C)CCOc1ccc(/C(=C(/CC)c2ccccc2)c2ccccc2)cc1] |
| simvastatin | 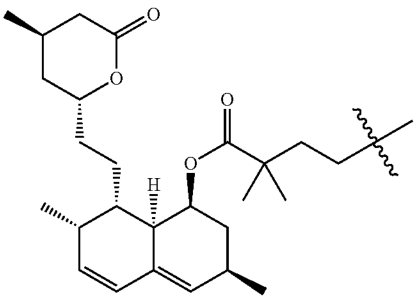 [SMILES: *CCC(C)(C)C(=O)O[C@H]1C[C@@H](C)C=C2C=C[C@H](C)[C@H](CC[C@@H]3C[C@@H](C)CC(=O)O3)[C@H]21] |

-continued

| Q moiety | Example of linking position |
|---|---|
| trimethoprim | 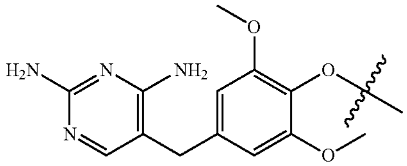 [SMILES: *Oc1c(OC)cc(Cc2cnc(N)nc2N)cc1OC] |
| rapamycin | 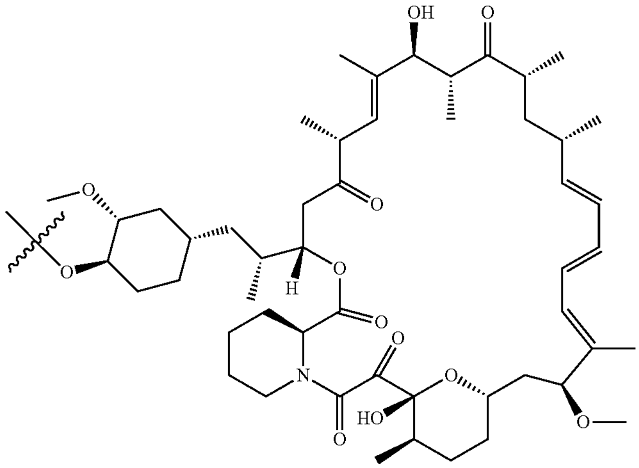 [SMILES: *O[C@@H]1CC[C@@H](C[C@@H](C)[C@@H]2CC(=O)[C@H](C)/C=C(\C)[C@@H](O)[C@@H](C)C(=O)[C@H](C)C[C@H](C)/C=C/C=C/C=C(\C)[C@@H](OC)C[C@@H]3CC[C@@H](C)[C@@](O)(O3)C(=O)C(=O)N3CCCC[C@H]3C(=O)O2)C[C@H]1OC] |
| JQ1 | 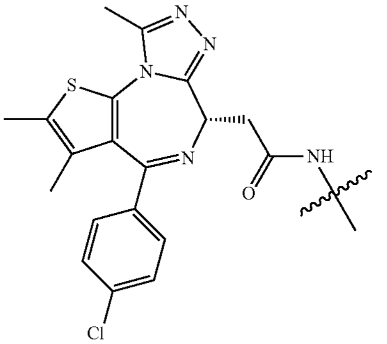 [SMILES: *NC(=O)C[C@@H]1N=C(c2ccc(Cl)cc2)c2c(sc(C)c2C)-n2c(C)nnc21] |
| vorinostat | 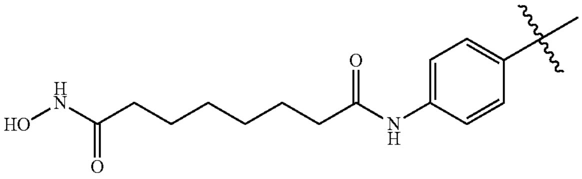 [SMILES: *c1ccc(NC(=O)CCCCCCC(=O)NO)cc1] |

In one aspect, the present invention relates to a pharmaceutical composition comprising the compound of Formula $(A)_k$-L-Q or $(A)_k$-$L_1$ and a pharmaceutically acceptable carrier, additive, and/or excipient.

In one aspect, the present invention relates to a method for treating a disease in a subject, said method comprising administering an effective amount of a compound having Formula $(A)_k$-L-Q or $(A)_k$-$L_1$.

In one aspect, the present invention relates to a method for treating a disease in a subject wherein dysregulated protein activity is responsible for said disease, said method comprising administering an effective amount of a compound having Formula $(A)_k$-L-Q or $(A)_k$-$L_1$.

In an embodiment, the cancer is selected from the group consisting of squamous-cell carcinoma, basal cell carcinoma, adenocarcinoma, hepatocellular carcinomas, renal cell carcinomas, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, uterine cancer, leukemias, lymphomas, Burkitt's lymphoma, Non-Hodgkin's lymphoma, melanomas, myeloproliferative diseases, multiple myeloma, sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, Schwannomas, testicular cancer, thyroid cancer, astrocytoma, Hodgkin's disease, Wilms' tumor, and teratocarcinomas.

In another aspect, the present invention relates to a method of treating or preventing one or more autoimmune diseases or disorders comprising administering a composition comprising a pharmaceutically effective amount of the compound described herein and a pharmaceutically acceptable carrier to a subject in need thereof. In an embodiment, the autoimmune disease or disorder is selected from, such as multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and other autoimmune diseases or disorders In an embodiment, the subject is a human.

In another aspect, the present invention relates to a method of modulating cereblon comprising administering the composition comprising the compounds having the general formula $(A)_k$-$L_1$ or $(A)_k$-L-Q described herein, or a salt, enantiomer, stereoisomer, polymorph, or N-oxide thereof, to a subject in need thereof.

In another aspect, the present invention relates to a method of modulating proteasomal degradation of a protein comprising administering the composition comprising the compounds having the general formula $(A)_k$-$L_1$ or $(A)_k$-L-Q described herein, or a salt, enantiomer, stereoisomer, polymorph, or N-oxide thereof, to a subject in need thereof.

In another aspect, the present invention relates to a method of modulating sequestration of a protein to the proteasome comprising administering the composition comprising the compounds having the general formula $(A)_k$-$L_1$ or $(A)_k$-L-Q described herein, or a salt, enantiomer, stereoisomer, polymorph, or N-oxide thereof, to a subject in need thereof.

EXAMPLES

General Synthetic Schemes

Compounds of the present invention generally can be prepared beginning with commercially available starting materials and using synthetic techniques known to those of skill in the art. Outlined below are some reaction schemes suitable for preparing compounds of the present invention. Further exemplification is found in the specific examples provided.

Example 1: Competition Assay

CRBN binding is assessed with a MAPPIT-like assay by determining the ability of test compounds to compete with a trimethoprim-lenalidomide hybrid ligand for binding to CRBN in cells. The traditional MAPPIT assay, as described for example in Lemmens, et al. "MAPPIT, a mammalian two-hybrid method for in-cell detection of protein-protein interactions," *Methods Mol Biol.* 2015; 1278:447-55, has been used to monitor protein-protein interactions. A bait protein (protein A) is expressed as a fusion protein in which it is genetically fused to an engineered intracellular receptor domain of the leptin receptor, which is itself fused to the extracellular domain of the erythropoietin (Epo) receptor. Binding of Epo ligand to the EpoR component results in activation of receptor-associated intracellular JAK2. However, activated JAK2 cannot activate the leptin receptor to trigger STAT3 binding and its phosphorylation because its tyrosine residues, normally phosphorylated by activated JAK2, have been mutated. Reconstitution of a JAK2 phosphorylatable STAT3 docking site is instead created through interaction of a protein B with protein A, whereby protein B is fused to a cytoplasmic domain of the gp130 receptor (which now harbors appropriate tyrosine resides recognized by the activated JAK2 kinase). Thus, physical interaction of protein A with protein B reconstitutes and Epo triggers JAK2-STAT3 signaling pathway activation. Activation of STAT3 can be monitored by introduction of a STAT3-responsive reporter gene, including a luciferase-encoding gene or a gene encoding a fluorescent marker such as GFP or some other type of fluorescent protein (EGF etc.). In this manner, the MAPPIT assay provides a versatile assay to assess such recombinant protein-protein interactions, or compound- or hybrid ligand-induced protein-protein interactions, in intact cells.

Here, we use a similar MAPPIT-like assay to determine the ability of test compounds to compete with the trimethoprim-lenalidomide-induced binding between DHFR and CRBN. Therefore, HEK293 cells transfected with the appropriate cDNAs encoding transgenes (encoding DHFR and CRBN fusion proteins), are used to generate a positive assay signal as a result of ternary protein/compound complex formation, including a DHFR-fusion protein, a trimethoprim(TMP)-lenalidomide hybrid ligand (TMP is a ligand for DHFR), and a CRBN-gp130 fusion protein (CRBN binds the ligand lenalidomide)—thus, a DHFR-TMP-LEN-CRBN complex formation. Formation of the complex results in activation of a STAT-responsive luciferase reporter gene. That signal is set to 100% luciferase activity. In a separate sample set up, cells are prepared in the same manner but, in addition, co-incubated with a test compound whose interaction with CRBN is investigated. Binding to the CRBN fusion protein competes with binding of the hybrid ligand to the same CRBN protein, hence inhibiting the assay signal due to prevention of ternary complex formation, which is required to generate an assay signal. Increasing concentrations of test compound are assessed to determine CRBN binding efficiency as determined in this type of ligand competition experiment in living cells. Specificity of signal inhibition is assessed by a parallel experimental set up in which test compound effect is assessed for inhibition of signal generated by a control gp130 fusion protein (CTRL) that directly binds to the DHFR-fusion protein in the absence of hybrid ligand (i.e. a direct interaction of the proteins).

In more detail, HEK293T cells are cultured in Dulbecco's modified Eagle's medium supplemented with 10% fetal calf serum, incubated at 37° C., 8% $CO_2$. Cells are transfected with a plasmid encoding *E. coli* Dihydrofolate Reductase (DHFR) fused to the tails of the cytoplasmic domain of a mutated leptin receptor (pCLG-eDHFR), a plasmid encoding a CRBN prey fused to gp130 cytoplasmic domain (pMG1-CRBN) or a plasmid encoding a REM2 control prey that can directly interact with the leptin receptor of the DHFR fusion protein (pMG1-REM2), and the STAT3 responsive pXP2d2-rPAPI-luciferase reporter plasmid—using a standard transfection method, as described (Lievens, et al. "Array MAPPIT: high-throughput interactome analysis in mammalian cells." Journal of Proteome Research 8.2

(2009): 877-886). Cells are treated with leptin to activate the leptin receptor fusion protein and supplemented with 300 nM trimethoprim-lenalidomide fusion compound (hybrid ligand, where trimethoprim interacts with DHFR and lenalidomide with CRBN) without or with the indicated dose of test compound at 24 hours after transfection. Luciferase activity, induced by formation of the ternary complex including DHFR-trimethoprim-lenalidomide-CRBN, and consequential activation of STAT3 signaling, is measured 24 hours after compound treatment using the Luciferase Assay System kit (PROMEGA, Madison, WI) with an Ensight plate reader (PERKIN ELMER LIFE SCIENCES, Waltham, MA). Data points represent the average luciferase activity of triplicate samples derived from cells treated with leptin+test compound for the REM2 control (CTRL) or cells treated with leptin+hybrid ligand+test compound (CRBN) relative to leptin (CTRL) or leptin+hybrid ligand (CRBN) only treated samples (the signals obtained in absence of added test compound for both cases is set at 100% of luciferase activity on y-axis). Error bars represent standard deviations. Curves are fit using 4-parameter nonlinear regression in GRAPHPAD PRISM software

Example 2: Recruitment Assays

In this Example 2, a similar MAPPIT-like assay is applied as described in Example 1 to determine test compound-induced binding of a particular substrate protein of interest to CRBN. In this experimental set-up, cells are transfected with a construct encoding a CRBN-fusion protein and another one encoding a substrate-fusion protein. Test compound activity is assessed with increasing concentrations of test compounds (dose-response studies) to monitor the ability to promote CRBN-ligand-induced protein interaction.

Specifically, HEK293T cells are transfected with a plasmid encoding the MAPPIT receptor fusion wherein the protein of interest (CRBN or substrate protein) is genetically linked to a cytoplasmic domain of the leptin receptor, which itself is fused to the extracellular domain of the erythropoietin (Epo) receptor (pSEL-X, where X represents either CRBN or any of the tested substrate proteins of interest) or to the extracellular domain of the leptin receptor (pCLG-X, where X represents either CRBN or any of the tested substrate proteins of interest), a plasmid encoding the MAPPIT gp130 fusion (pMG1-Y, Y being either any of the tested substrate proteins or CRBN) and a STAT3-responsive luciferase-encoding reporter plasmid (pXP2d2-rPAPI-luciferase reporter plasmid), as described (Lievens, et al. "Array MAPPIT: high-throughput interactome analysis in mammalian cells." Journal of Proteome Research 8.2 (2009): 877-886). Full size proteins are fused for each of the target proteins tested, except in the case of IKZF1 where isoform 7 is used, and BRD4, where isoform 3 is applied. For the study, the following construct combinations are used: IKZF1 recruitment: pSEL-CRBN+pMG1-IKZF1(isoform 7); ASS1 recruitment: pSEL-CRBN+pMG1-ASS1; SALL4 recruitment: pSEL-SALL4+pMG1-CRBN; DHFR recruitment: pCLG-DHFR+pMG1-CRBN; ESR1 recruitment: pSEL-CRBN+pMG1-ESR1; BRD4 recruitment: pSEL-CRBN+pMG1-BRD4(isoform 3). Cells are treated with erythropoietin (Epo; where pSEL-type receptor fusions constructs are used) or leptin (in the case pCLG-type receptor fusion constructs are applied) without or with the indicated dose of test compound at 24 hours after transfection. Luciferase activity is measured 24 hours after test compound treatment using the Luciferase Assay System kit (PROMEGA, Madison, WI) with an Ensight plate reader (PERKIN ELMER LIFE SCIENCES, Waltham, MA). Data points depict fold induction of the average luciferase activity of triplicate samples from Epo or leptin+test compound treated cells versus Epo or leptin only treated cells. Error bars represent standard deviations. Curves are fit using 4-parameter nonlinear regression in GRAPHPAD PRISM software.

Example 3: Protein Degradation Bioassays

The following bioassays were performed to evaluate the level of protein degradation observed in various cell types using representative compounds disclosed herein.

In each bioassay, cells were treated with varying amounts of compounds encompassed by the present disclosure. The degradation of the following proteins were evaluated in this study: TANK-binding kinase 1 (TBK1), estrogen receptor α (ERα), bromodomain-containing protein 4 (BRD4), androgen receptor (AR), and c-Myc.

1. TBK1 Western Protocol

Panc02.13 cells were purchased from ATCC and cultured in RPMI-1640 (Gibco), supplemented with 15% FBS (ATCC) and 10 Units/mL human recombinant insulin (Gibco). DMSO control and compound treatments (0.1 μM, 0.3 μM, and 1 μM) were carried out in 12-well plates for 16 h. TLR3 agonist Poly I:C (Invivogen; tlrl-pic) was added for the final 3 h. Cells were harvested, and lysed in RIPA buffer (50 mM Tris pH8, 150 mM NaCl, 1% Tx-100, 0.1% SDS, 0.5% sodium deoxycholate) supplemented with protease and phosphatase inhibitors. Lysates were clarified at 16,000 g for 10 minutes, and supernatants were separated by SDS-PAGE. Immunoblotting was performed using standard protocols. The antibodies used were TBK1 (Cell Signaling #3504), pIRF3 (abcam #ab76493), and GAPDH (Cell Signaling #5174). Bands were quantified using a Biorad ChemiDoc MP imaging system.

2. ERRα Western Protocol

NAMALWA cells (ATCC) were cultured in RPMI-1640 (Life Technologies) supplemented with 15% FBS (Life Technologies). DMSO controls and compound incubations (0.1 μM, 0.3 μM, and 1 μM) were carried out in 24-well plates for 16 h. Cells were harvested and lysed with cell lysis buffer (Cell Signaling Technologies) containing protease inhibitors (Thermo Scientific). Lysates were clarified at 16,000 g for 10 minutes, and supernatants were separated by SDS-PAGE. Immunoblotting was performed using standard protocols. The antibodies used were ERRα (Cell Signaling #8644) and GAPDH (Cell Signaling #5174). Bands were quantified using a Bio-Rad ChemiDoc MP imaging system.

3. BRD4 Western Protocol

VCaP cells were purchased from ATCC and cultured in Dulbecco's Modified Eagle's Medium (ATCC), supplemented with 10% FBS (ATCC) and Penicillin/Streptomycin (Life Technologies). DMSO control and compound treatments (0.003 μM, 0.01 μM, 0.03 μM and 0.1 μM) were performed in 12-well plates for 16 h. Cells were harvested, and lysed in RIPA buffer (50 mM Tris pH8, 150 mM NaCl, 1% Tx-100, 0.1% SDS, 0.5% sodium deoxycholate) supplemented with protease and phosphatase inhibitors. Lysates were clarified at 16,000 g for 10 minutes, and protein concentration was determined. Equal amount of protein (20 μg) was subjected to SDS-PAGE analysis and followed by immunoblotting according to standard protocols. The antibodies used were BRD4 (Cell Signaling #13440), and Actin (Sigma #5441). Detection reagents were Clarity Western ECL substrate (Bio-rad #170-5060).

4. AR ELISA Protocol

VCaP cells were purchased from ATCC and cultured in Dulbecco's Modified Eagle's Medium (ATCC), supplemented with 10% FBS (ATCC) and Penicillin/Streptomycin (Life Technologies). DMSO control and compound treatments (0.0001 μM-1 μM) were performed in 96-well plates for 16 h. Cells were harvested, and lysed with Cell Lysis Buffer (Catalog #9803) (20 mM Tris-HCL (pH 7.5), 150 mM NaCl, 1 mM $Na_2EDTA$, 1 mM EGTA, 1% Triton, 2.5 mM sodium pyrophosphate, 1 mM B-glycerophosphate, 1 mM $Na_3VO_4$, 1 ug/ml leupeptin. Lysates were clarified at 16,000 g for 10 minutes, and loaded into the PathScan AR ELISA (Cell Signaling Catalog #12850). The PathScan® Total Androgen Receptor Sandwich ELISA Kit is a solid phase sandwich enzyme-linked immunosorbent assay (ELISA) that detects endogenous levels of total androgen receptor protein. An Androgen Receptor Rabbit mAb has been coated onto the microwells. After incubation with cell lysates, androgen receptor protein is captured by the coated antibody. Following extensive washing, an Androgen Receptor Mouse Detection mAb is added to detect the captured androgen receptor protein. Anti-mouse IgG, HRP-linked Antibody is then used to recognize the bound detection antibody. HRP substrate, TMB, is added to develop color. The magnitude of absorbance for the developed color is proportional to the quantity of total androgen receptor protein.

5. c-Myc ELISA Assay Protocol

22RV-1 cells were purchased from ATCC and cultured in RPMI+10% FBS media. Cells were harvested using trypsin (Gibco #25200-114), counted and seeded at 30,000 cells/well at a volume of 75 μL/well in RPMI+10% FBS media in 96-well plates. The cells were dosed with compounds diluted in 0.1% DMSO, incubated for 18 h then washed and lysed in 50 uL RIPA buffer (50 mM Tris pH8, 150 mM NaCl, 1% Tx-100, 0.1% SDS, 0.5% sodium deoxycholate) supplemented with protease and phosphatase inhibitors. The lysates were clarified at 4000 rpm at 4° C. for 10 minutes then aliquots were added into a 96-well ELISA plate of Novex Human c-Myc ELISA kit from Life Technologies Catalog #KH02041. 50 ul of c-Myc Detection antibody was added into every well, the plates incubated at room temperature for 3 hrs, then washed with ELISA wash buffer. 100 uL of the anti-rabbit IgG-HRP secondary antibody was added to each well and incubated at room temperature for 30 minutes. The plates were washed with ELISA wash buffer, 100 μL TMB added to each well, and then monitored every 5 minutes for a color change. 100 μL of stop solution is added and the plates read at 450 nm.

Example 4: Preparation of the Compounds

The compounds of the present invention can be prepared by methods well known in the art of organic chemistry. See, for example, J. March, 'Advanced Organic Chemistry' 4th Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' 3rd Edition, John Wiley and Sons, 1999. The protective groups are optionally removed at a convenient subsequent stage using methods well known in the art. The products of the reactions are optionally isolated and purified, if desired, using conventional techniques, but not limited to, filtration, distillation, crystallization, chromatography and the like. Such materials are optionally characterized using conventional means, including physical constants and spectral data.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH3), N-hydroxsuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

HPLC Purification

Purification was performed using HPLC ($H_2O$—MeOH; Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100A, 10 μm, 19 mm×10 mm) The material was dissolved in 0.7 mL DMSO. Flow: 30 mL/min. Purity of the obtained fractions was checked via the analytical LCMS. Spectra were recorded for each fraction as it was obtained straight after chromatography in the solution form. The solvent was evaporated in the flow of $N_2$ at 80° C. On the basis of post-chromatography LCMS analysis fractions were united. Solid fractions were dissolved in 0.5 mL MeOH and transferred into a pre-weighted marked vials. Obtained solutions were again evaporated in the flow of $N_2$ at 80° C. After drying, products were finally characterized by LCMS and $^1H$ NMR.

Analytical Methods

NMR

Instrument specifications:

Bruker AVANCE DRX 500

Varian UNITYplus 400

LC/MS

Instrument specifications:

Agilent 1100 Series LC/MSD system with DAD\ELSD and Agilent LC\MSD VL (G1956A), SL (G1956B) mass-spectrometer.

Agilent 1200 Series LC/MSD system with DAD\ELSD and Agilent LC\MSD SL (G6130A), SL (G6140A) mass-spectrometer.

All the LC/MS data were obtained using positive/negative mode switching.

Column Zorbax SB-C18 1.8 μm 4.6×15 mm Rapid Resolution cartridge (PN 821975-932)

Mobile phase A—acetonitrile, 0.1% formic acid

B—water (0.1% formic acid)

Flow rate 3 ml/min

Gradient 0 min-100% B 0.01 min—100% B 1.5 min—0% B 1.8 min—0% B 1.81 min—100% B

Injection volume 11

Ionization mode atmospheric pressure chemical ionization (APCI)

Scan range m/z 80-1000

Example 5: Activity of Illustrative Bifunctional Compound a. Synthesis of TMP-LEN TMP-LEN was made according to the reaction scheme below.

To a solution of 4-pentynoic acid (51) (3.4 g, 34.5 mmol) in 100 mL benzene, 2 drops of DMF were added, following by addition of oxalyl chloride (17.5 g, 138 mmol). The mixture was stirred at 80° C. for 2 h and evaporated to dryness giving chloroanhydride (52) (3.1 g, 76%) that was used for the next step without additional purification.

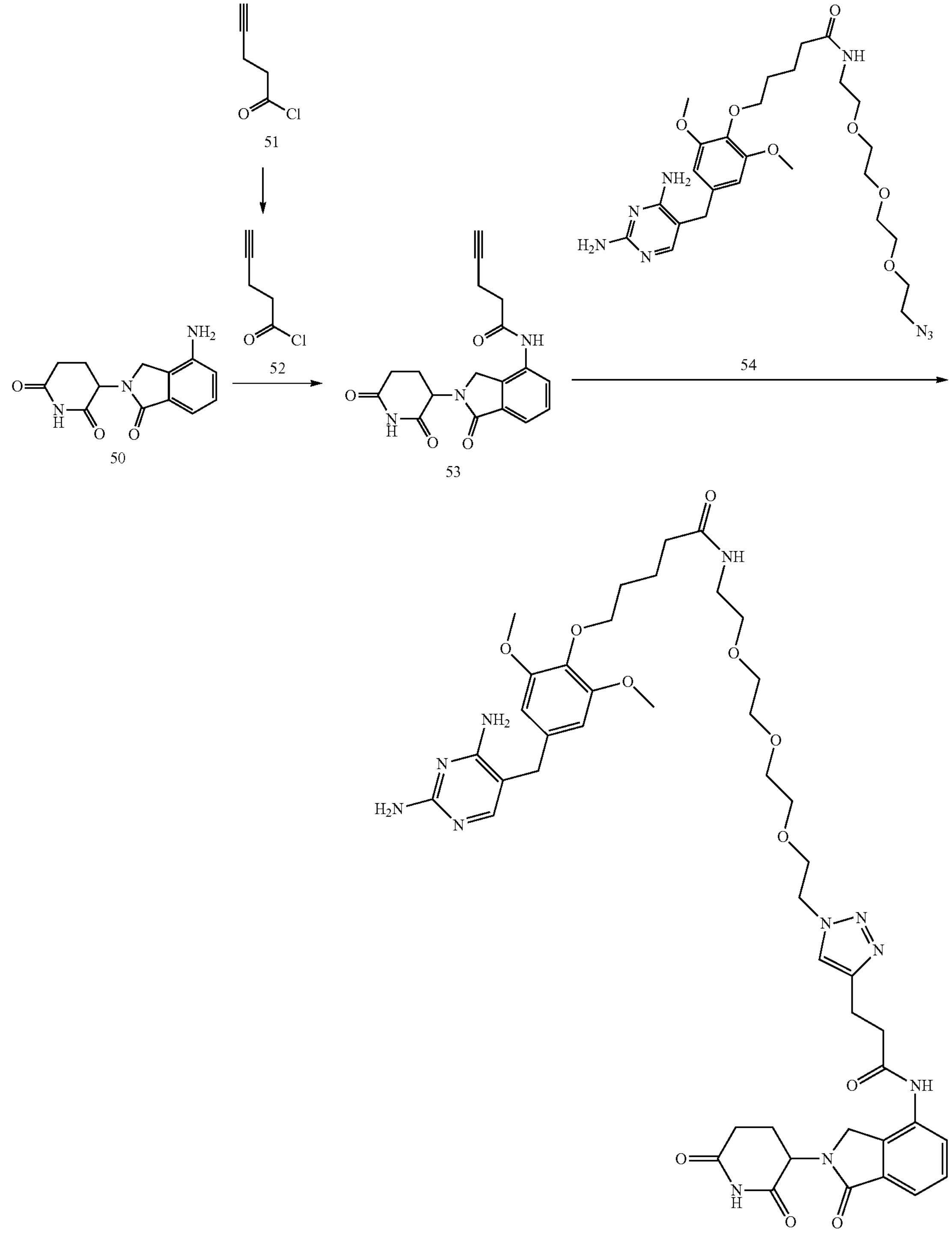

51

52

50

53

54

TMP-LEN

Molecular Weight =916.01

Molecular Formula = C44H57N11O11

To a solution of (50) (345 mg, 1.33 mmol) in 30 mL THF, chloroanhydride (52) (315 mg, 2.70 mmol) in 5 mL THF was added and the mixture was stirred at 75° C. for 7 h. The reaction mixture was quenched with 0.5 mL MeOH, stirred for 1 h and evaporated to dryness. The solid residue was washed with $Et_2O$ and dried giving compound (53) (541 mg, 100%).

Figure 3:
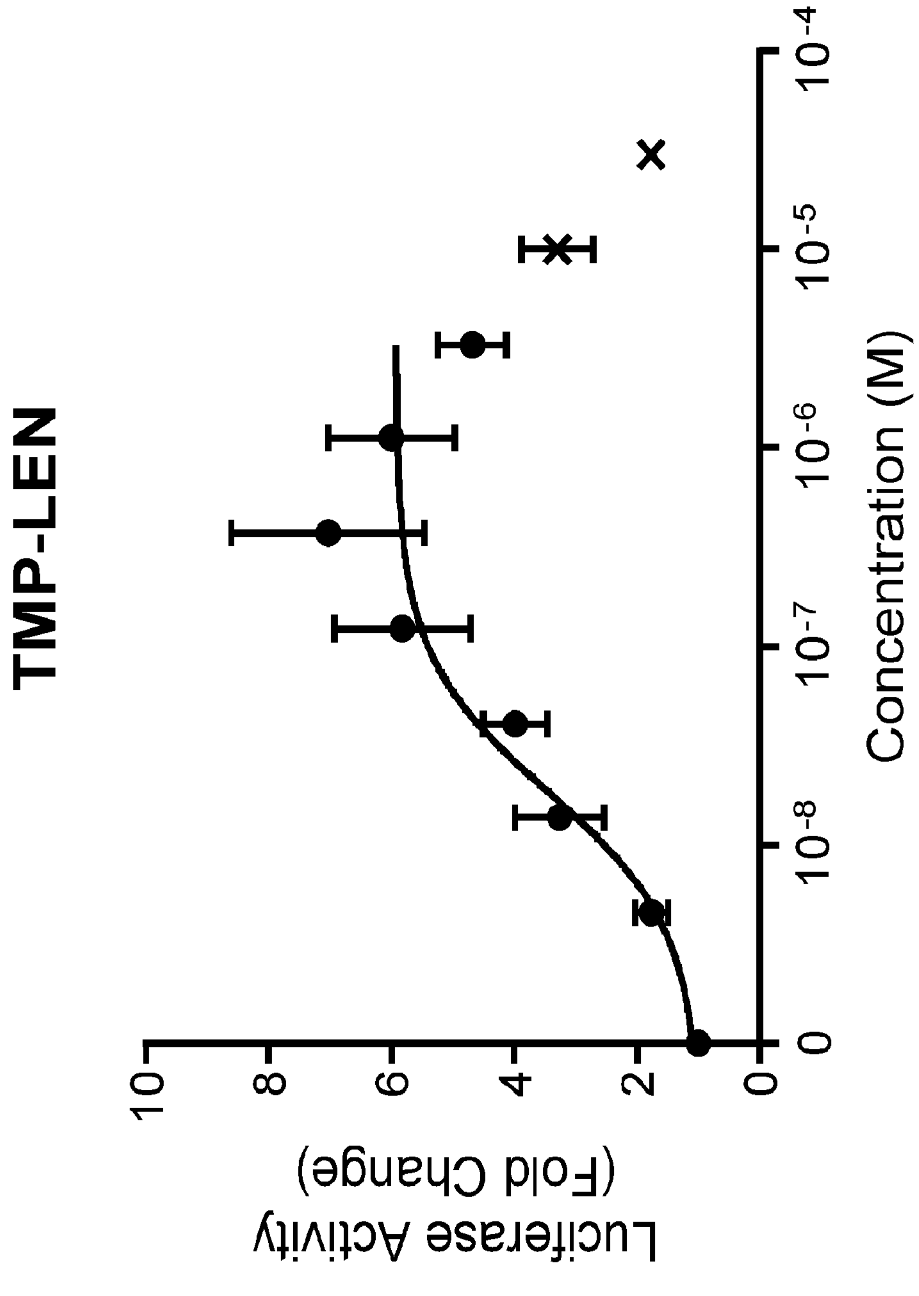
FIG. 3 illustrates TMP-LEN hybrid ligand-induced binding between CRBN and DHFR detected with a MAPPIT-like assay. A hybrid molecule consisting of the DHFR ligand trimethoprim (TMP) fused to the CRBN ligand lenalidomide through a PEG linker was used to induce DHFR recruitment to CRBN bait in the MAPPIT assay. As shown, with CRBN expressed as a gp130 fusion and DHFR linked to the MAPPIT chimeric membrane receptor, a TMP-LEN dose-dependent signal can be observed.

To a solution of Compound (53) (33 mg, 0.112 mmol), and TMP-azide (63 mg, 0.109 mmol) in DMF-$H_2O$, 2:1 (10 mL), sodium ascorbate (24 mg, 0.120 mmol) was added, following by addition of $CuSO_4 \cdot 5H_2O$ (27 mg, 0.109 mmol) and the mixture was stirred for 15 h at ambient temperature. The mixture was diluted with $H_2O$, extracted with $CHCl_3$, and the organic layer was discarded. Aqueous layer was evaporated to dryness, and the target product was purified on a C18 reverse-phase HPLC column, eluting with a gradient MeCN—$H_2O$—0.10% TFA. The fractions containing the target product were evaporated to dryness giving compound TMP-LEN (23 mg, 23%) as a solid.

b. Evaluation of Lenalidomide Hybrid Ligand-Induced Binding Between CRBN and DHFR A similar MAPPIT-like assay as described in Example 1 was applied to evaluate binding between CRBN and DHFR (dihydrofolate reductase) induced by a hybrid molecule consisting of the DHFR ligand trimethoprim (TMP) fused to the CRBN ligand lenalidomide (LEN) through a PEG linker. As in the protocol described in Example 1, HEK293T cells were co-transfected with a plasmid encoding a fusion construct of the (*E. coli*) DHFR anchor protein fused to the chimeric MAPPIT receptor containing the leptin receptor extracellular domain linked to an engineered intracellular domain of the leptin receptor (pCLG-DHFR) and a gp130-CRBN bait fusion construct, together with the STAT3-responsive luciferase-encoding reporter plasmid (pXP2d2-rPAPI-luciferase reporter plasmid), as described (Lievens, et al. "Array MAPPIT: high-throughput interactome analysis in mammalian cells." Journal of Proteome Research 8.2 (2009): 877-886). At 24 h after transfection the cells were treated with leptin without and with the indicated concentration of TMP-LEN hybrid ligand, and another 24 h later luciferase activity was determined using the Luciferase Assay System kit (PROMEGA, Madison, WI) with an Ensight plate reader (PERKIN ELMER LIFE SCIENCES, Waltham, MA). The dose-response curve shown in FIG. 3 represents the fold induction of the average luciferase activity of triplicate samples from leptin+test compound treated cells versus leptin only treated cells. Error bars represent standard deviations and curves were fit using 4-parameter nonlinear regression in GRAPHPAD PRISM software. This example shows that the MAPPIT assay presented here can be applied to assess binding between two proteins induced by a hybrid ligand.

Example 6: Test Results

The following compounds were tested in the Competition Assay and/or Recruitment Assay described herein, and the results are listed below.

TABLE 6

| ID | Structure/Name |
|---|---|
| C80392 | 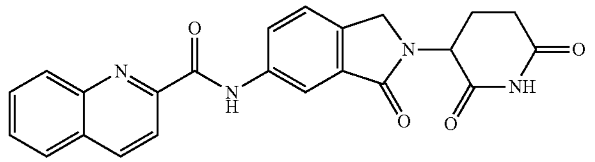 [SMILES: O=C1CCC(N2Cc3ccc(NC(=O)c4ccc5ccccc5n4)cc3C2=O)C(=O)N1] N-[2-(2,6-dioxo-3-piperidyl)-3-oxo-isoindolin-5-yl]quinoline-2-carboxamide |
| C12584 | 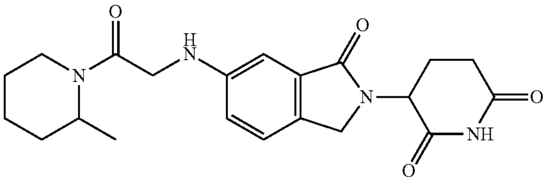 [SMILES: CC1CCCCN1C(=O)CNc1ccc2c(c1)C(=O)N(C1CCC(=O)NC1=O)C2] 3-[6-[[2-(2-methyl-1-piperidyl)-2-oxo-ethyl]amino]-1-oxo-isoindolin-2-yl]piperidine-2,6-dione |
| CC-885 | 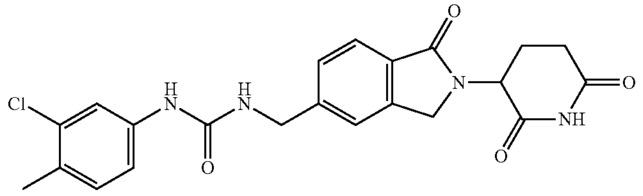 [SMILES: Cc1ccc(NC(=O)NCc2ccc3c(c2)CN(C2CCC(=O)NC2=O)C3=O)cc1Cl] 1-(3-chloro-4-methyl-phenyl)-3-[[2-(2,6-dioxo-3-piperidyl)-1-oxo-isoindolin-5-yl]methyl]urea |

TABLE 6-continued
| | |
|---|---|
| C74668 | 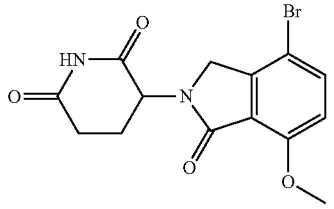 [SMILES: COc1ccc(Br)c2c1C(=O)N(C1CCC(=O)NC1=O)C2]<br>3-(4-bromo-7-methoxy-1-oxo-isoindolin-2-yl)piperidine-2,6-dione |
| CC-220 | 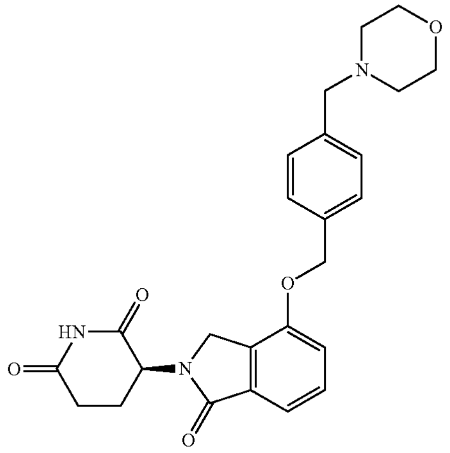 [SMILES: O=C1CC[C@H](N2Cc3c(OCc4ccc(CN5CCOCC5)cc4)cccc3C2=O)C(=O)N1]<br>(3S)-3-[4-[[4-(morpholinomethyl)phenyl]methoxy]-1-oxo-isoindolin-2-yl]piperidine-2,6-dione |
| C80370 | 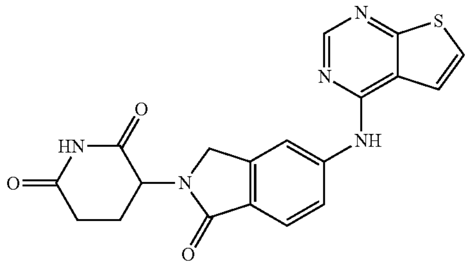 [SMILES: O=C1CCC(N2Cc3cc(Nc4ncnc5sccc45)ccc3C2=O)C(=O)N1]<br>3-[1-oxo-5-(thieno[2,3-d]pyrimidin-4-ylamino)isoindolin-2-yl] piperidine-2,6-dione |
| C24031 | 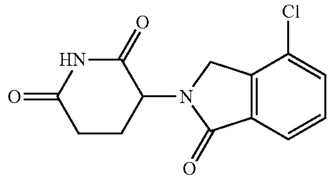 [SMILES: O=C1CCC(N2Cc3c(Cl)cccc3C2=O)C(=O)N1]<br>3-(4-chloro-1-oxo-isoindolin-2-yl)piperidine-2,6-dione |
| C48014 | 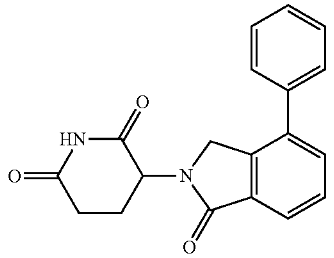 [SMILES: O=C1CCC(N2Cc3c(cccc3-c3ccccc3)C2=O)C(=O)N1]<br>3-(1-oxo-4-phenyl-isoindolin-2-yl)piperidine-2,6-dione |

TABLE 6-continued

C58181

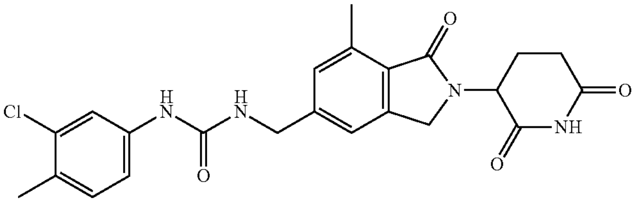 [SMILES: Cc1ccc(NC(=O)NCc2cc(C)c3c(c2)CN(C2CCC(=O)NC2=O)C3=O)cc1Cl]

1-(3-chloro-4-methyl-phenyl)-3-[[2-(2,6-dioxo-3-piperidyl)-7-methyl-1-oxo-isoindolin-5-yl]methyl]urea

C95330

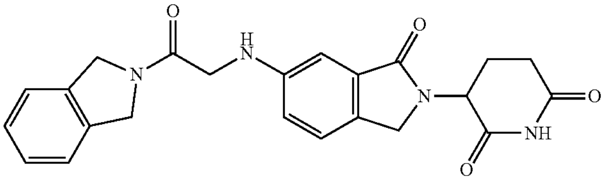 [SMILES: O=C1CCC(N2Cc3ccc(NCC(=O)N4Cc5ccccc5C4)cc3C2=O)C(=O)N1]

3-[6-[(2-isoindolin-2-yl-2-oxo-ethyl)amino]-1-oxo-isoindolin-2-yl]piperidine-2,6-dione

C95338

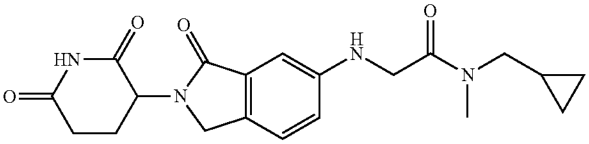 [SMILES: CN(CC1CC1)C(=O)CNc1ccc2c(c1)C(=O)N(C1CCC(=O)NC1=O)C2]

N-(cyclopropylmethyl)-2-[[2-(2,6-dioxo-3-piperidyl)-3-oxo-isoindolin-5-yl]amino]-N-methyl-acetamide C80382
acetic acid
salt

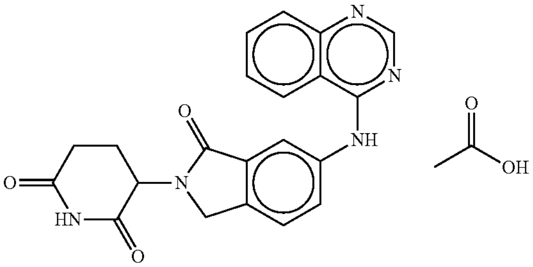

acetic acid; 3-[1-oxo-6-(quinazolin-4-ylamino)isoindolin-2-yl]pipieridine-2,6-dione

C80369

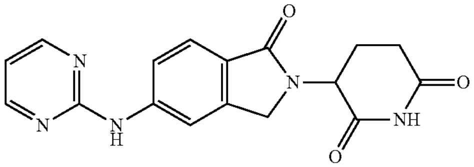 [SMILES: O=C1CCC(N2Cc3cc(Nc4ncccn4)ccc3C2=O)C(=O)N1]

3-[1-oxo-5-(pyrimidin-2-ylamino)isoindolin-2-yl]piperidine-2,6-dione

C47935

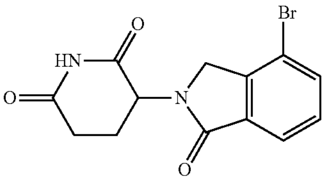

3-(4-bromo-1-oxo-isoindolin-2-yl)piperidine-2,6-dione

TABLE 6-continued

C12583

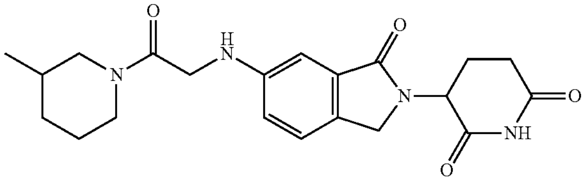 [SMILES: CC1CCCN(C(=O)CNc2ccc3c(c2)C(=O)N(C2CCC(=O)NC2=O)C3)C1]

3-[6-[[2-(3-methyl-1-piperidyl)-2-oxo-ethyl]amino]-1-oxo-isoindolin-2-yl]piperidine-2,6-dione

C28558

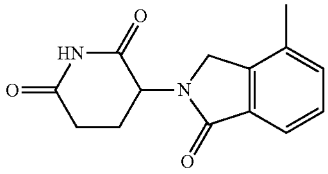 [SMILES: Cc1cccc2c1CN(C1CCC(=O)NC1=O)C2=O]

3-(4-methyl-1-oxo-isoindolin-2-yl)piperidine-2,6-dione

C80387

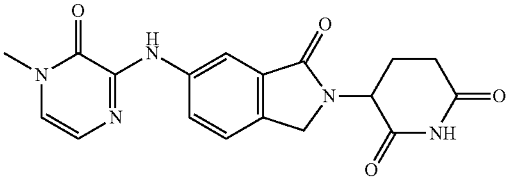 [SMILES: Cn1ccnc(Nc2ccc3c(c2)C(=O)N(C2CCC(=O)NC2=O)C3)c1=O]

3-[6-[(4-methyl-3-oxo-pyrazin-2-yl)amino]-1-oxo-isoindolin-2-yl]
piperidine-2,6-dione

C80386

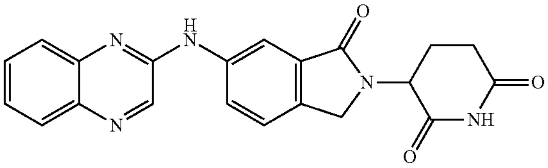 [SMILES: O=C1CCC(N2Cc3ccc(Nc4cnc5ccccc5n4)cc3C2=O)C(=O)N1]

3-[1-oxo-6-(quinoxalin-2-ylamino)isoindolin-2-yl]piperidine-2,6-dione

C67858

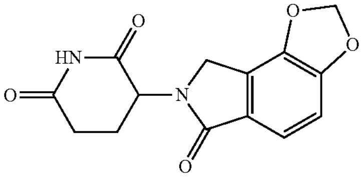 [SMILES: O=C1CCC(N2Cc3c(ccc4c3OCO4)C2=O)C(=O)N1]

3-(6-oxo-8H-[1,3]dioxolo[4,5-e]isoindol-7-yl)piperidine-2,6-dione

C28577

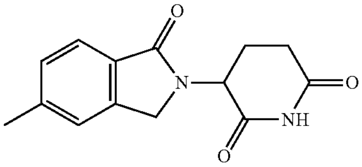 [SMILES: Cc1ccc2c(c1)CN(C1CCC(=O)NC1=O)C2=O]

3-(5-methyl-1-oxo-isoindolin-2-yl)piperidine-2,6-dione

C89676

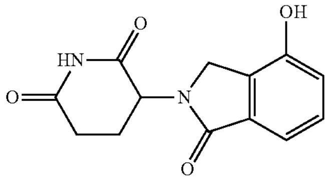

3-(4-hydroxy-1-oxo-isoindolin-2-yl)piperidine-2,6-dione

TABLE 6-continued
C98103
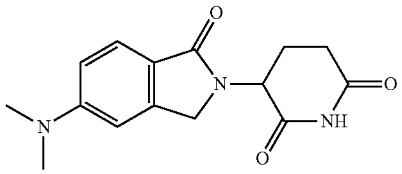 [SMILES: CN(C)c1ccc2c(c1)CN(C1CCC(=O)NC1=O)C2=O]
3-[5-(dimethylamino)-1-oxo-isoindolin-2-yl]piperidine-2,6-dione
C80383
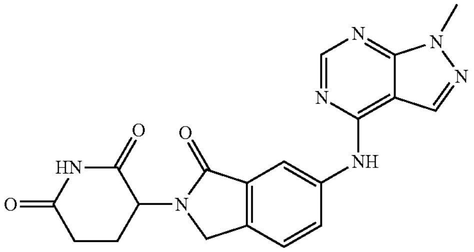 [SMILES: Cn1ncc2c(Nc3ccc4c(c3)C(=O)N(C3CCC(=O)NC3=O)C4)ncnc21]
3-[6-[(1-methylpyrazolo[3,4-d]pyrimidin-4-yl)amino]-1-oxo-isoindolin-2-yl]piperidine-2,6-dione
C80391
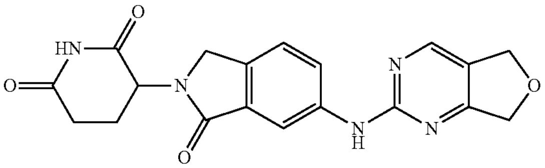 [SMILES: O=C1CCC(N2Cc3ccc(Nc4ncc5c(n4)COC5)cc3C2=O)C(=O)N1]
3-[6-(5,7-dihydrofuro[3,4-d]pyrimidin-2-ylamino)-1-oxo-isoindolin-2-yl]
piperidine-2,6-dione
C48016
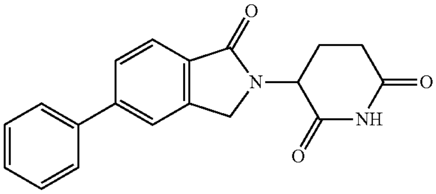 [SMILES: O=C1CCC(N2Cc3cc(-c4ccccc4)ccc3C2=O)C(=O)N1]
3-(1-oxo-5-phenyl-isoindolin-2-yl)piperidine-2,6-dione
C05955
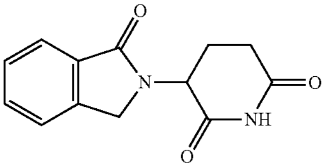 [SMILES: O=C1CCC(N2Cc3ccccc3C2=O)C(=O)N1]
3-(1-oxoisoindolin-2-yl)piperidine-2,6-dione
C28620
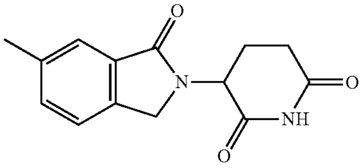 [SMILES: Cc1ccc2c(c1)C(=O)N(C1CCC(=O)NC1=O)C2]
3-(6-methyl-1-oxo-isoindolin-2-yl)piperidine-2,6-dione TABLE 6-continued

C80384

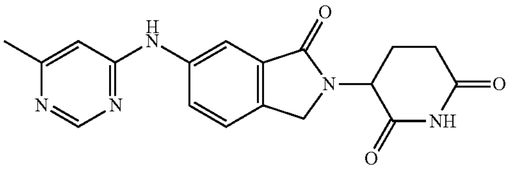 [SMILES: Cc1cc(Nc2ccc3c(c2)C(=O)N(C2CCC(=O)NC2=O)C3)ncn1]

3-[6-[(6-methylpyrimidin-4-yl)amino]-1-oxo-isoindolin-2-yl]
piperidine-2,6-dione

C51383

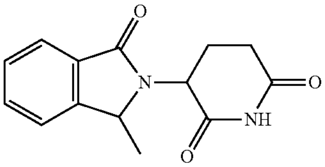 [SMILES: CC1c2ccccc2C(=O)N1C1CCC(=O)NC1=O]

3-(1-methyl-3-oxo-isoindolin-2-yl)piperidine-2,6-dione

C84965

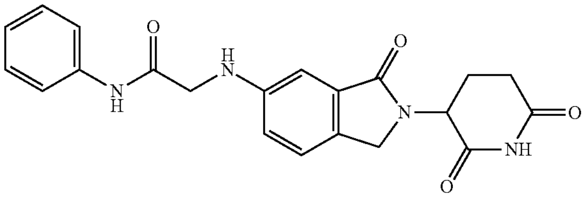 [SMILES: O=C1CCC(N2Cc3ccc(NCC(=O)Nc4ccccc4)cc3C2=O)C(=O)N1]

2-[[2-(2,6-dioxo-3-piperidyl)-3-oxo-isoindolin-5-yl]amino]-N-phenyl-acetamide

C12595

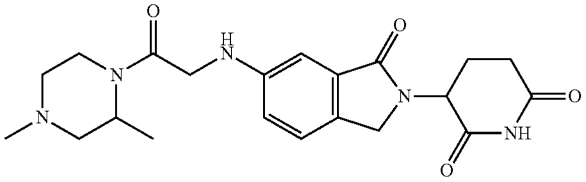 [SMILES: CC1CN(C)CCN1C(=O)CNc1ccc2c(c1)C(=O)N(C1CCC(=O)NC1=O)C2]

3-[6-[[2-(2,4-dimethylpiperazin-1-yl)-2-oxo-ethyl]amino]-1-
oxo-isoindolin-2-yl]piperidine-2,6-dione

C96622

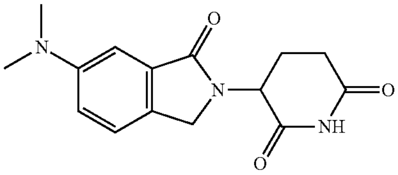 [SMILES: CN(C)c1ccc2c(c1)C(=O)N(C1CCC(=O)NC1=O)C2]

3-[6-(dimethylamino)-1-oxo-isoindolin-2-yl]piperidine-2,6-dione

C22622

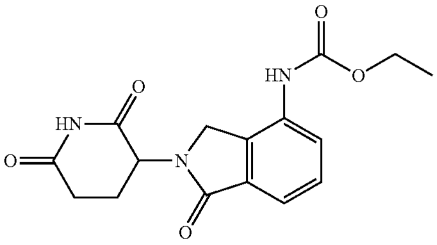 [SMILES: CCOC(=O)Nc1cccc2c1CN(C1CCC(=O)NC1=O)C2=O]

ethyl N-[2-(2,6-dioxo-3-piperidyl)-1-oxo-isoindolin-4-yl]carbamate

TABLE 6-continued
C48018
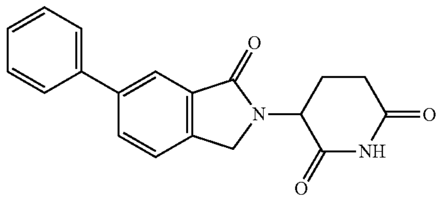 [SMILES: O=C1CCC(N2Cc3ccc(-c4ccccc4)cc3C2=O)C(=O)N1]
3-(1-oxo-6-phenyl-isoindolin-2-yl)piperidine-2,6-dione
LEN
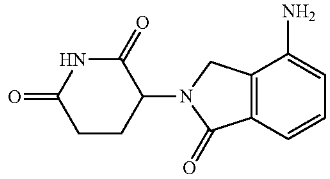 [SMILES: Nc1cccc2c1CN(C1CCC(=O)NC1=O)C2=O]
3-(4-amino-1-oxo-isoindolin-2-yl)piperidine-2,6-dione
C23066
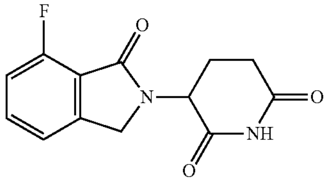 [SMILES: O=C1CCC(N2Cc3cccc(F)c3C2=O)C(=O)N1]
3-(7-fluoro-1-oxo-isoindolin-2-yl)piperidine-2,6-dione
C84964
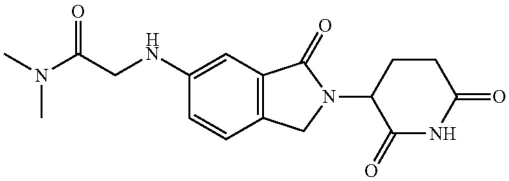 [SMILES: CN(C)C(=O)CNc1ccc2c(c1)C(=O)N(C1CCC(=O)NC1=O)C2]
2-[[2-(2,6-dioxo-3-piperidyl)-3-oxo-isoindolin-5-yl]amino]-N,N-dimethyl-acetamide
C29137
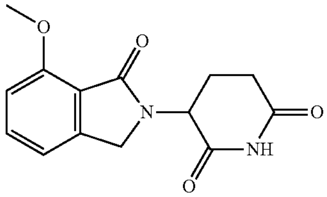 [SMILES: COc1cccc2c1C(=O)N(C1CCC(=O)NC1=O)C2]
3-(7-methoxy-1-oxo-isoindolin-2-yl)piperidine-2,6-dione
C12586
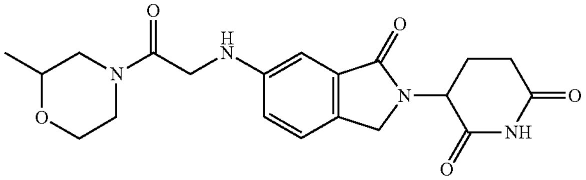 [SMILES: CC1CN(C(=O)CNc2ccc3c(c2)C(=O)N(C2CCC(=O)NC2=O)C3)CCO1]
3-[6-[[2-(2-methylmorpholin-4-yl)-2-oxo-ethyl]amino]-1-oxo-isoindolin-2-yl]piperidine-2,6-dione TABLE 6-continued
C28891
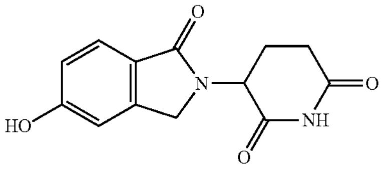 [SMILES: O=C1CCC(N2Cc3cc(O)ccc3C2=O)C(=O)N1]
3-(5-hydroxy-1-oxo-isoindolin-2-yl)piperidine-2,6-dione
C35856
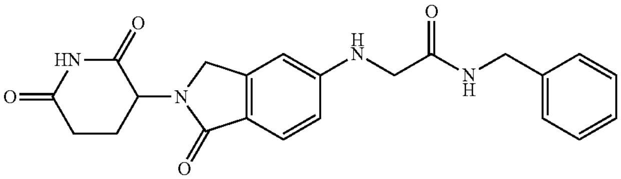 [SMILES: O=C(CNc1ccc2c(c1)CN(C1CCC(=O)NC1=O)C2=O)NCc1ccccc1]
N-benzyl-2-[[2-(2,6-dioxo-3-piperidyl)-1-oxo-isoindolin-5-yl]amino]acetamide
C35751
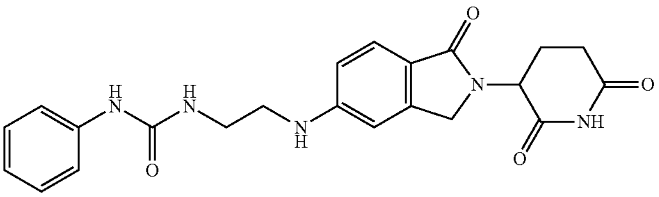 [SMILES: O=C1CCC(N2Cc3cc(NCCNC(=O)Nc4ccccc4)ccc3C2=O)C(=O)N1]
1-[2-[[2-(2,6-dioxo-3-piperidyl)-1-oxo-isoindolin-5-yl]amino]ethyl]-3-phenyl-urea
C28928
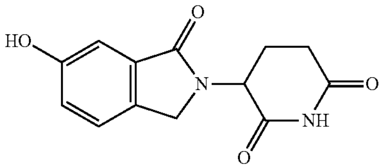 [SMILES: O=C1CCC(N2Cc3ccc(O)cc3C2=O)C(=O)N1]
3-(6-hydroxy-1-oxo-isoindolin-2-yl)piperidine-2,6-dione
C28973
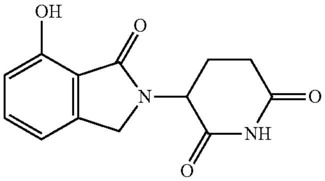 [SMILES: O=C1CCC(N2Cc3cccc(O)c3C2=O)C(=O)N1]
3-(7-hydroxy-1-oxo-isoindolin-2-yl)piperidine-2,6-dione
C48020
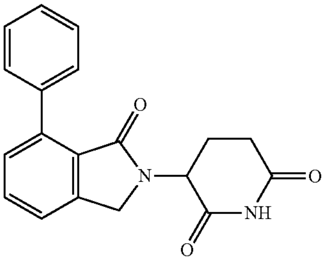 [SMILES: O=C1CCC(N2Cc3cccc(-c4ccccc4)c3C2=O)C(=O)N1]
3-(1-oxo-7-phenyl-isoindolin-2-yl)piperidine-2,6-dione TABLE 6-continued

| | |
|---|---|
| C68126 | 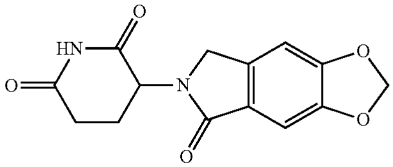 [SMILES: O=C1CCC(N2Cc3cc4c(cc3C2=O)OCO4)C(=O)N1] 3-(7-oxo-5H-[1,3]dioxolo[4,5-f]isoindol-6-yl)piperidine-2,6-dione |
| C07207 | 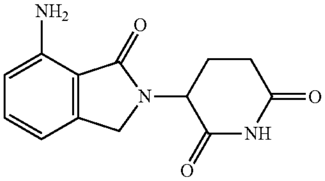 [SMILES: Nc1cccc2c1C(=O)N(C1CCC(=O)NC1=O)C2] 3-(7-amino-1-oxo-isoindolin-2-yl)piperidine-2,6-dione |
| C95333 | 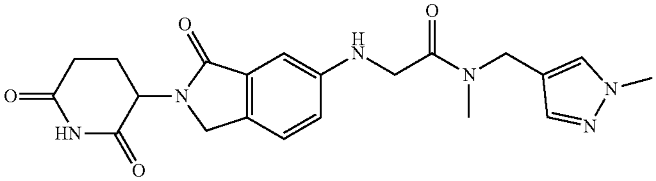 [SMILES: CN(Cc1cnn(C)c1)C(=O)CNc1ccc2c(c1)C(=O)N(C1CCC(=O)NC1=O)C2] 2-[[2-(2,6-dioxo-3-piperidyl)-3-oxo-isoindolin-5-yl]amino]-N-methyl-N-[(1-methyl) methyl]acetamide |
| C84966 | 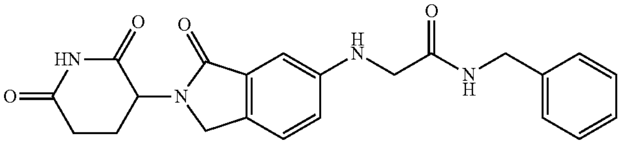 [SMILES: O=C(CNc1ccc2c(c1)C(=O)N(C1CCC(=O)NC1=O)C2)NCc1ccccc1] N-benzyl-2-[[2-(2,6-dioxo-3-piperidyl)-3-oxo-isoindolin-5-yl]amino]acetamide |
| C48003 | 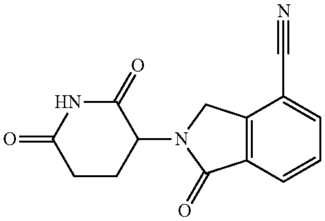 [SMILES: N#Cc1cccc2c1CN(C1CCC(=O)NC1=O)C2=O] 2-(2,6-dioxo-3-piperidyl)-1-oxo-isoindoline-4-carbonitrile |
| C66979 | 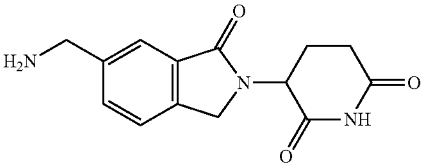 [SMILES: NCc1ccc2c(c1)C(=O)N(C1CCC(=O)NC1=O)C2] 3-[6-(aminomethyl)-1-oxo-isoindolin-2-yl]piperidine-2,6-dione |
| C80389 | 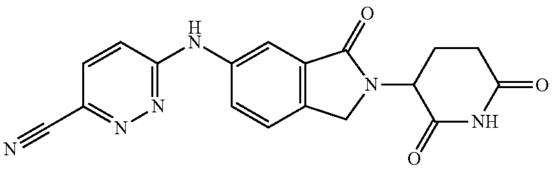 [SMILES: N#Cc1ccc(Nc2ccc3c(c2)C(=O)N(C2CCC(=O)NC2=O)C3)nn1] 6-[[2-(2,6-dioxo-3-piperidyl)-3-oxo-isoindolin-5-yl]amino]pyridazine-3-carbonitrile |

TABLE 6-continued
C28661
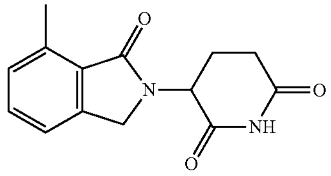 [SMILES: Cc1cccc2c1C(=O)N(C1CCC(=O)NC1=O)C2]
3-(7-methyl-1-oxo-isoindolin-2-yl)piperidine-2,6-dione
C35833
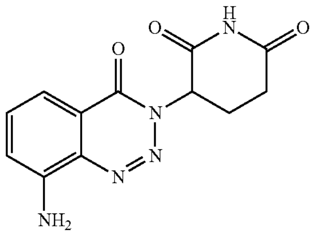 [SMILES: Nc1cccc2c(=O)n(C3CCC(=O)NC3=O)nnc12]
3-(8-amino-4-oxo-1,2,3-benzotriazin-3-yl)piperidine-2,6-dione
C59904
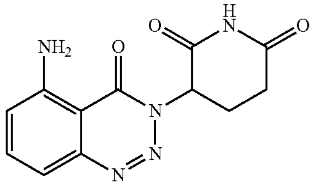 [SMILES: Nc1cccc2nnn(C3CCC(=O)NC3=O)c(=O)c12]
3-(5-amino-4-oxo-1,2,3-benzotriazin-3-yl)piperidine-2,6-dione
C80390
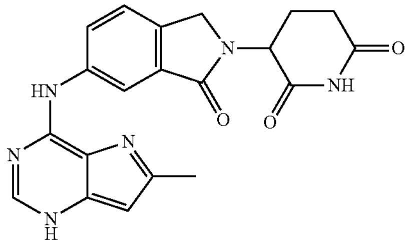 [SMILES: Cc1cc2[nH]cnc(Nc3ccc4c(c3)C(=O)N(C3CCC(=O)NC3=O)C4)c-2n1]
3-[6-[(6-methylpyrrolo[3,2-d]pyrimidin-4-yl)amino]-1-oxo-isoindolin-2-yl]piperidine-2,6-dione
C35754
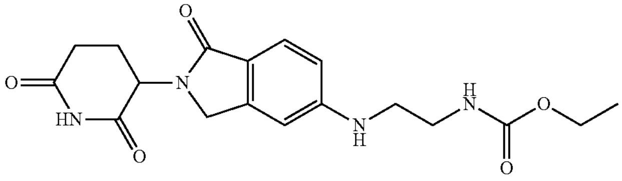 [SMILES: CCOC(=O)NCCNc1ccc2c(c1)CN(C1CCC(=O)NC1=O)C2=O]
ethyl N-[2-[[2-(2,6-dioxo-3-piperidyl)-1-oxo-isoindolin-5-yl]amino]ethyl]carbamate
C49708
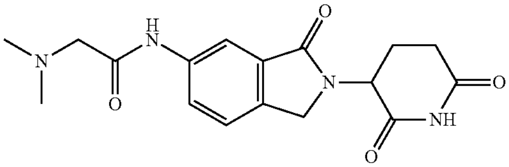 [SMILES: CN(C)CC(=O)Nc1ccc2c(c1)C(=O)N(C1CCC(=O)NC1=O)C2]
2-(dimethylamino)-N-[2-(2,6-dioxo-3-piperidyl)-3-oxo-isoindolin-5-yl]acetamide TABLE 6-continued
C80380
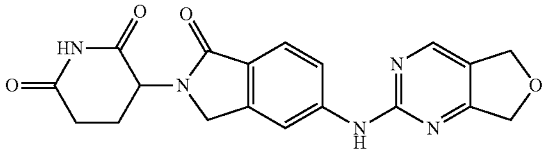 [SMILES: O=C1CCC(N2Cc3cc(Nc4ncc5c(n4)COC5)ccc3C2=O)C(=O)N1]
3-[5-(5,7-dihydrofuro[3,4-d]pyrimidin-2-ylamino)-1-oxo-isoindolin-2-yl]piperidine-2,6-dione
C35797
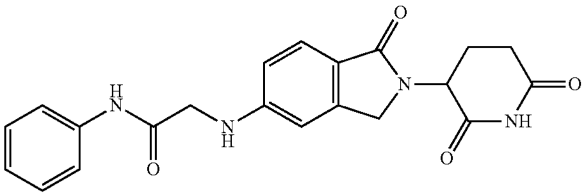 [SMILES: O=C1CCC(N2Cc3cc(NCC(=O)Nc4ccccc4)ccc3C2=O)C(=O)N1]
2-[[2-(2,6-dioxo-3-piperidyl)-1-oxo-isoindolin-5-yl] amino]-N-phenyl-acetamide
C80395
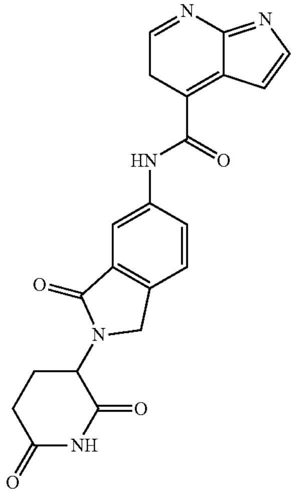 [SMILES: O=C1CCC(N2Cc3ccc(NC(=O)C4=C5C=CN=C5N=CC4)cc3C2=O)C(=O)N1]
N-[2-(2,6-dioxo-3-piperidyl)-3-oxo-isoindolin-5-yl]-5H-pyrrolo [2,3-6]pyridine-4-carboxamide
C80373
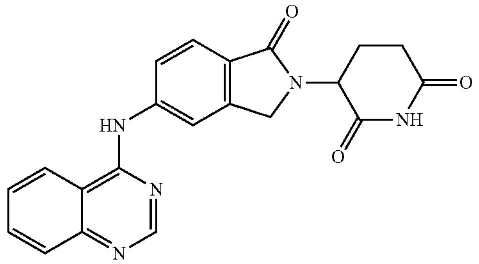 [SMILES: O=C1CCC(N2Cc3cc(Nc4ncnc5ccccc45)ccc3C2=O)C(=O)N1]
3-[1-oxo-5-(quinazolin-4-ylamino)isoindolin-2-yl]piperidine-2,6-dione
CC-122
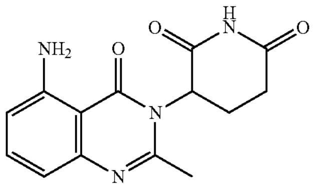 [SMILES: Cc1nc2cccc(N)c2c(=O)n1C1CCC(=O)NC1=O]
3-(5-amino-2-methyl-4-oxo-quinazolin-3-yl)piperidine-2,6-dione TABLE 6-continued

C45748

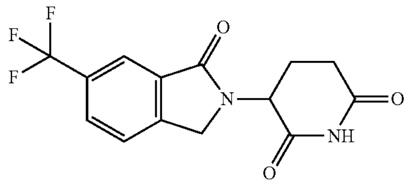 [SMILES: O=C1CCC(N2Cc3ccc(C(F)(F)F)cc3C2=O)C(=O)N1]

3-[1-oxo-6-(trifluoromethyl)isoindolin-2-yl]piperidine-2,6-dione

C80379

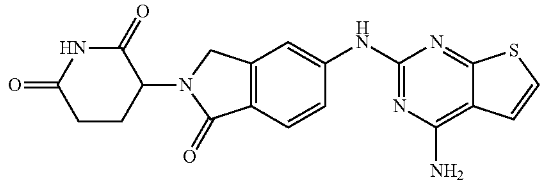 [SMILES: Nc1nc(Nc2ccc3c(c2)CN(C2CCC(=O)NC2=O)C3=O)nc2sccc12]

3-[5-[(4-aminothieno[2,3-d]pyrimidin-2-yl)amino]-1-oxo-isoindolin-2-yl]piperidine-2,6-dione

C47933

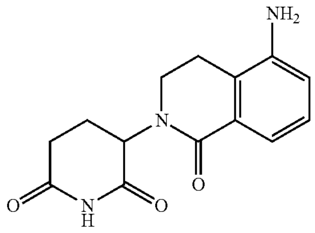 [SMILES: Nc1cccc2c1CCN(C1CCC(=O)NC1=O)C2=O]

3-(5-amino-1-oxo-3,4-dihydroisoquinolin-2-yl)piperidine-2,6-dione

POM

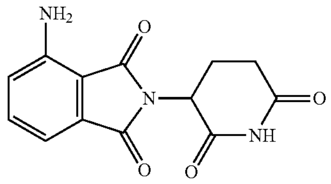 [SMILES: Nc1cccc2c1C(=O)N(C1CCC(=O)NC1=O)C2=O]

4-amino-2-(2,6-dioxo-3-piperidyl)isoindoline-1,3-dione

C22548

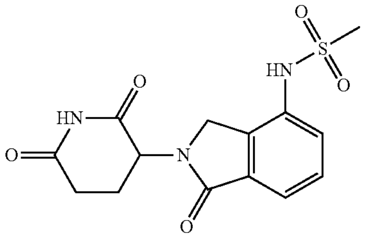 [SMILES: CS(=O)(=O)Nc1cccc2c1CN(C1CCC(=O)NC1=O)C2=O]

N-[2-(2,6-dioxo-3-piperidyl)-1-oxo-isoindolin-4-yl]methanesulfonamide

C84963

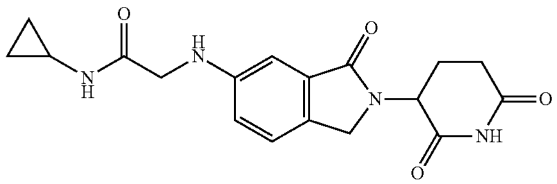 [SMILES: O=C1CCC(N2Cc3ccc(NCC(=O)NC4CC4)cc3C2=O)C(=O)N1]

N-cyclopropyl-2-[[2-(2,6-dioxo-3-piperidyl)-3-oxo-isoindolin-5-yl]amino]acetamide TABLE 6-continued
C22586
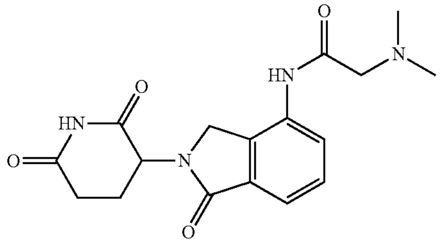 [SMILES: CN(C)CC(=O)Nc1cccc2c1CN(C1CCC(=O)NC1=O)C2=O]
2-(dimethylamino)-N-[2-(2,6-dioxo-3-piperidyl)-1-oxo-isoindolin-4-yl]acetamide
C84971
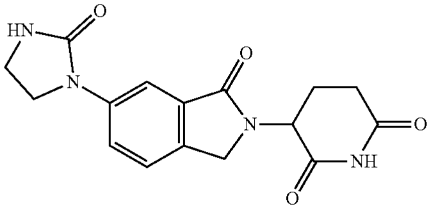 [SMILES: O=C1CCC(N2Cc3ccc(N4CCNC4=O)cc3C2=O)C(=O)N1]
3-[1-oxo-6-(2-oxoimidazolidin-1-yl)isoindolin-2-yl]piperidine-2,6-dione
C48007
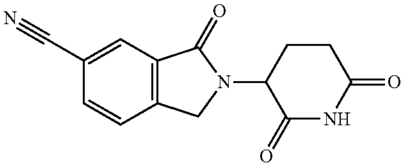 [SMILES: N#Cc1ccc2c(c1)C(=O)N(C1CCC(=O)NC1=O)C2]
2-(2,6-dioxo-3-piperidyl)-3-oxo-isoindoline-5-carbonitrile
C99884
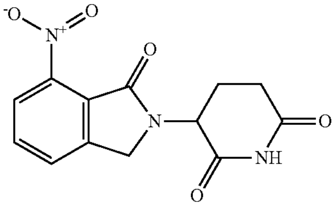
3-(7-nitro-1-oxo-isoindolin-2-yl)piperidine-2,6-dione
C29330
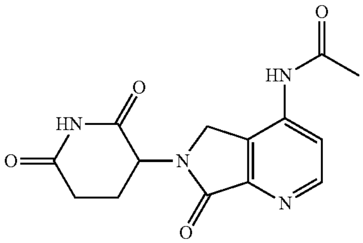 [SMILES: CC(=O)Nc1ccnc2c1CN(C1CCC(=O)NC1=O)C2=O]
N-[2-(2,6-dioxo-3-piperidyl)-1-oxo-isoindolin-4-yl]acetamide
C84970
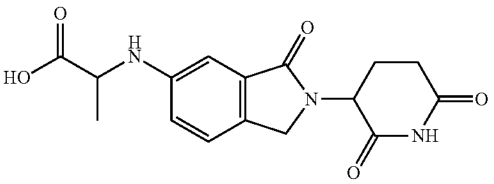 [SMILES: CC(Nc1ccc2c(c1)C(=O)N(C1CCC(=O)NC1=O)C2)C(=O)O]
2-[[2-(2,6-dioxo-3-piperidyl)-3-oxo-isoindolin-5-yl]amino]propanoic acid TABLE 6-continued
C29361
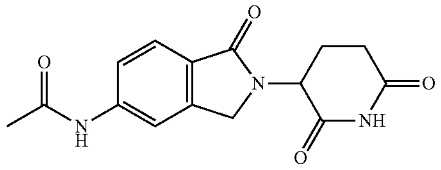 [SMILES: CC(=O)Nc1ccc2c(c1)CN(C1CCC(=O)NC1=O)C2=O]
N-[2-(2,6-dioxo-3-piperidyl)-1-oxo-isoindolin-5-yl]acetamide
C22564
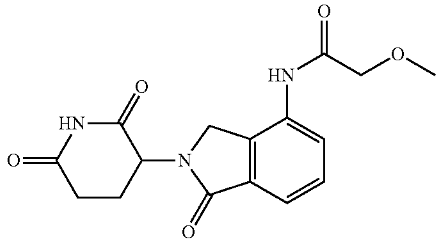
N-[2-(2,6-dioxo-3-piperidyl)-1-oxo-isoindolin-4-yl]-2-methoxy-acetamide
C48005
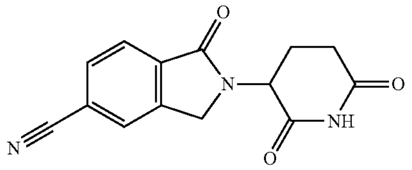 [SMILES: N#Cc1ccc2c(c1)CN(C1CCC(=O)NC1=O)C2=O]
2-(2,6-dioxo-3-piperidyl)-1-oxo-isoindoline-5-carbonitrile
C80375
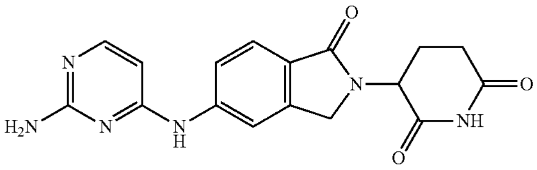 [SMILES: Nc1nccc(Nc2ccc3c(c2)CN(C2CCC(=O)NC2=O)C3=O)n1]
3-[5-[(2-aminopyrimidin-4-yl)amino]-1-oxo-isoindolin-2-yl]
piperidine-2,6-dione
C48009
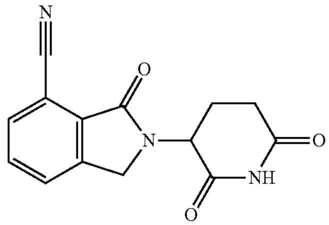 [SMILES: N#Cc1cccc2c1C(=O)N(C1CCC(=O)NC1=O)C2]
2-(2,6-dioxo-3-piperidyl)-3-oxo-isoindoline-4-carbonitrile
C80378
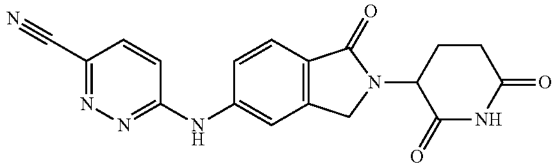 [SMILES: N#Cc1ccc(Nc2ccc3c(c2)CN(C2CCC(=O)NC2=O)C3=O)nn1]
6-[[2-(2,6-dioxo-3-piperidyl)-1-oxo-isoindolin-5-yl]amino]pyridazine-3-carbonitrile TABLE 6-continued
C21223
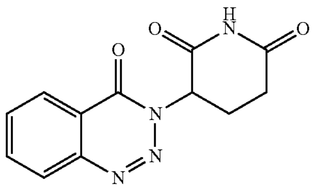 [SMILES: O=C1CCC(n2nnc3ccccc3c2=O)C(=O)N1]
3-(4-oxo-1,2,3-benzotriazin-3-yl)piperidine-2,6-dione
C13247
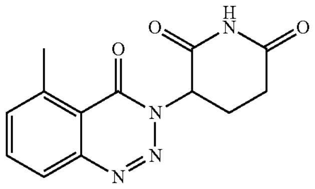 [SMILES: Cc1cccc2nnn(C3CCC(=O)NC3=O)c(=O)c12]
3-(5-methyl-4-oxo-1,2,3-benzotriazin-3-yl)piperidine-2,6-dione
C35811
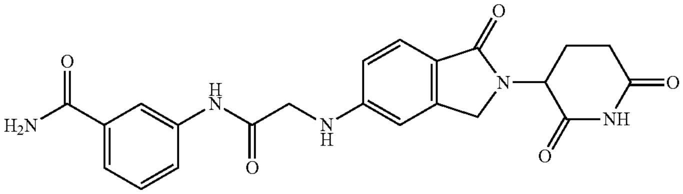 [SMILES: NC(=O)c1cccc(NC(=O)CNc2ccc3c(c2)CN(C2CCC(=O)NC2=O)C3=O)c1]
3-[[2-[[2-(2,6-dioxo-3-piperidyl)-1-oxo-isoindolin-5-yl] amino]acetyl]amino]benzamide
C47959
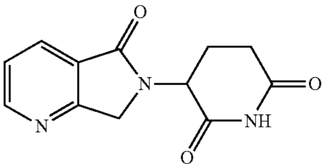 [SMILES: O=C1CCC(N2Cc3ncccc3C2=O)C(=O)N1]
3-(5-oxo-7H-pyrrolo[3,4-b]pyridin-6-yl)piperidine-2,6-dione
C80396
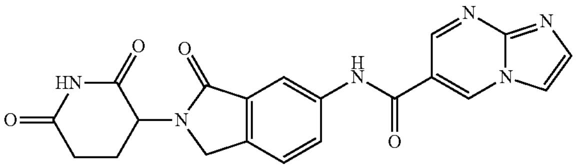 [SMILES: O=C1CCC(N2Cc3ccc(NC(=O)c4cnc5nccn5c4)cc3C2=O)C(=O)N1]
N-[2-(2,6-dioxo-3-piperidyl)-3-oxo-isoindolin-5-yl]imidazo[1,2-a] pyrimidine-6-carboxamide
C16463
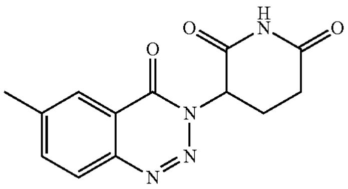 [SMILES: Cc1ccc2nnn(C3CCC(=O)NC3=O)c(=O)c2c1]
3-(6-methyl-4-oxo-1,2,3-benzotriazin-3-yl)piperidine-2,6-dione TABLE 6-continued
C64324
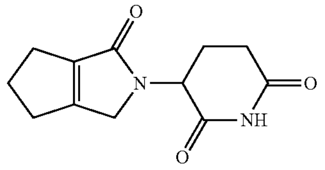 [SMILES: O=C1CCC(N2CC3=C(CCC3)C2=O)C(=O)N1]
2-(2,6-dioxo-3-piperidyl)-5,6-dihydro-4H-cyclopenta[c]pyrrole-1,3-dione
C84967
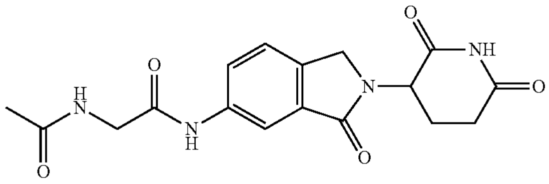 [SMILES: CC(=O)NCC(=O)Nc1ccc2c(c1)C(=O)N(C1CCC(=O)NC1=O)C2]
2-acetamido-N-[2-(2,6-dioxo-3-piperidyl)-3-oxo-isoindolin-5-yl]acetamide
C89940
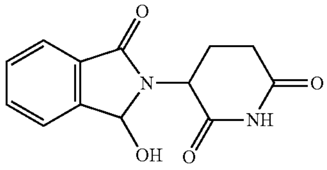 [SMILES: O=C1CCC(N2C(=O)c3ccccc3C2O)C(=O)N1]
3-(1-hydroxy-3-oxo-isoindolin-2-yl)piperidine-2,6-dione
C35830
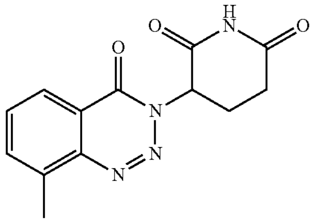 [SMILES: Cc1cccc2c(=O)n(C3CCC(=O)NC3=O)nnc12]
3-(8-methyl-4-oxo-1,2,3-benzotriazin-3-yl)piperidine-2,6-dione
C47995
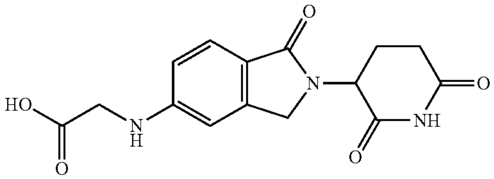 [SMILES: O=C(O)CNc1ccc2c(c1)CN(C1CCC(=O)NC1=O)C2=O]
2-[[2-(2,6-dioxo-3-piperidyl)-1-oxo-isoindolin-5-yl]amino]acetic acid
C64376
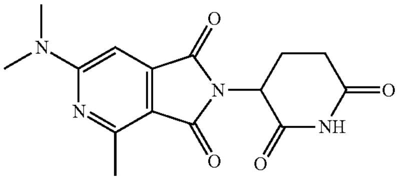 [SMILES: Cc1nc(N(C)C)cc2c1C(=O)N(C1CCC(=O)NC1=O)C2=O]
6-(dimethylamino)-2-(2,6-dioxo-3-piperidyl)-4-methyl-pyrrolo[3,4-c]
pyridine-1,3-dione TABLE 6-continued
C84961
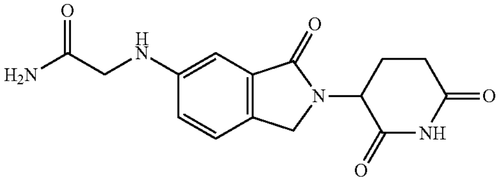 [SMILES: NC(=O)CNc1ccc2c(c1)C(=O)N(C1CCC(=O)NC1=O)C2]
2-[[2-(2,6-dioxo-3-piperidyl)-3-oxo-isoindolin-5-yl]amino]acetamide
C22594
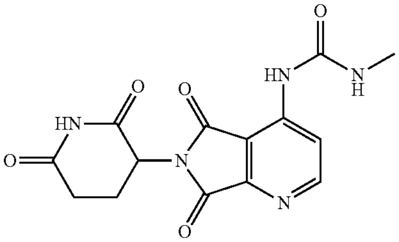 [SMILES: CNC(=O)Nc1ccnc2c1C(=O)N(C1CCC(=O)NC1=O)C2=O]
1-[2-(2,6-dioxo-3-piperidyl)-1-oxo-isoindolin-4-yl]-3-methyl-urea
C12598
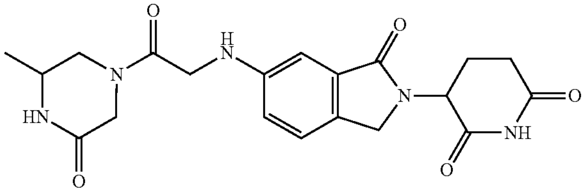 [SMILES: CC1CN(C(=O)CNc2ccc3c(c2)C(=O)N(C2CCC(=O)NC2=O)C3)CC(=O)N1]
3-[6-[[2-(3-methyl-5-oxo-piperazin-1-yl)-2-oxo-ethyl]amino]-1-oxo-isoindolin-2-yl]piperidine-2,6-dione
C29408
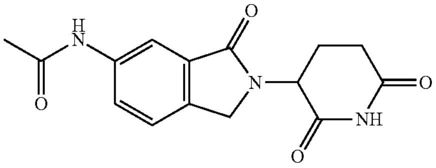 [SMILES: CC(=O)Nc1ccc2c(c1)C(=O)N(C1CCC(=O)NC1=O)C2]
N-[2-(2,6-dioxo-3-piperidyl)-3-oxo-isoindolin-5-yl]acetamide
C73349
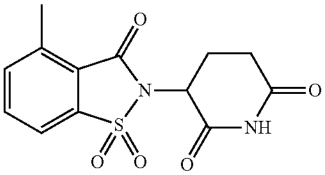 [SMILES: Cc1cccc2c1C(=O)N(C1CCC(=O)NC1=O)S2(=O)=O]
3-(4-methyl-1,1,3-trioxo-1,2-benzothiazol-2-yl)piperidine-2,6-dione
5HPP-33
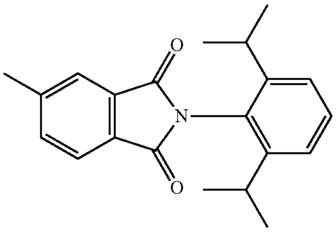 [SMILES: Cc1ccc2c(c1)C(=O)N(c1c(C(C)C)cccc1C(C)C)C2=O]
2-(2,6-diisopropylphenyl)-5-methyl-isoindoline-1,3-dione TABLE 6-continued
C12597
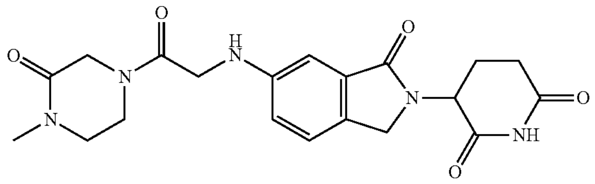 [SMILES: CN1CCN(C(=O)CNc2ccc3c(c2)C(=O)N(C2CCC(=O)NC2=O)C3)CC1=O]
3-[6-[[2-(4-methyl-3-oxo-piperazin-1-yl)-2-oxo-ethyl]amino]-1-oxo-isoindolin-2-yl]piperidine-2,6-dione
ZE26-0001
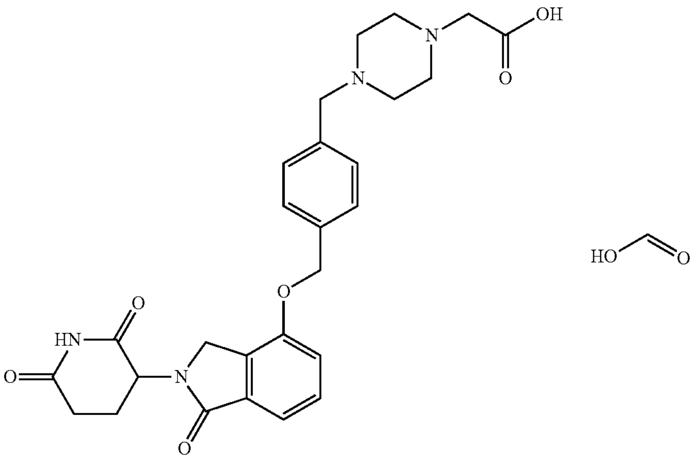 [SMILES: O=C(O)CN1CCN(Cc2ccc(COc3cccc4c3CN(C3CCC(=O)NC3=O)C4=O)cc2)CC1 ; O=CO]
2-[4-[[4-[[2-(2,6-dioxo-3-piperidyl)-1-oxo-isoindolin-4-yl]oxomethyl]phenyl]methyl]piperazin-1-yl]acetic acid; formic acid
C98053
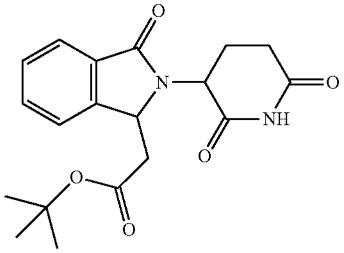 [SMILES: CC(C)(C)OC(=O)CC1c2ccccc2C(=O)N1C1CCC(=O)NC1=O]
t-butyl 2-[2-(2,6-dioxo-3-piperidyl)-3-oxo-isoindolin-1-yl]acetate
C51830
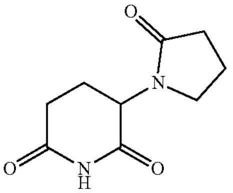 [SMILES: O=C1CCC(N2CCCC2=O)C(=O)N1]
3-(2-oxopyrrolidin-1-yl)piperidine-2,6-dione
C97402
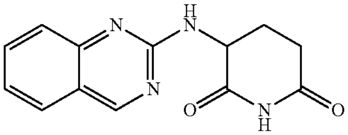 [SMILES: O=C1CCC(Nc2ncc3ccccc3n2)C(=O)N1]
3-(quinazolin-2-ylamino)piperidine-2,6-dione TABLE 6-continued
C68121
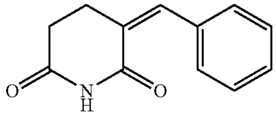 [SMILES: O=C1CC/C(=C/c2ccccc2)C(=O)N1]
(3Z)-3-benzylidenepiperidine-2,6-dione
C47998
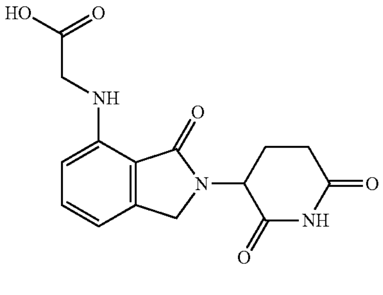 [SMILES: O=C(O)CNc1cccc2c1C(=O)N(C1CCC(=O)NC1=O)C2]
2-[[2-(2,6-dioxo-3-piperidyl)-3-oxo-isoindolin-4-yl]amino]acetic acid
C49713
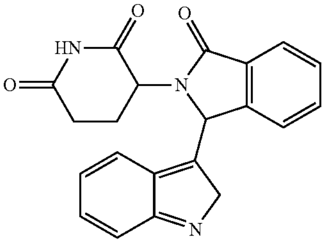 [SMILES: O=C1CCC(N2C(=O)c3ccccc3C2C2=c3ccccc3=NC2)C(=O)N1]
3-[1-(2H-indol-3-yl)-3-oxo-isoindolin-2-yl]piperidine-2,6-dione
C36126
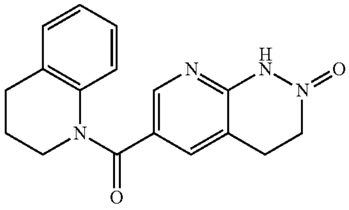
6-(3,4-dihydro-2H-quinoline-1-carbonyl)-3,4-dihydro-1H-1,8-naphthyridin-2-one
C39453
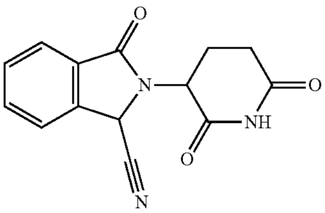 [SMILES: N#CC1c2ccccc2C(=O)N1C1CCC(=O)NC1=O]
2-(2,6-dioxo-3-piperidyl)-3-oxo-isoindoline-1-carbonitrile
C10981
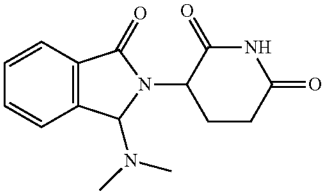 [SMILES: CN(C)C1c2ccccc2C(=O)N1C1CCC(=O)NC1=O]
3-[1-(dimethylamino)-3-oxo-isoindolin-2-yl]piperidine-2,6-dione TABLE 6-continued
C80394
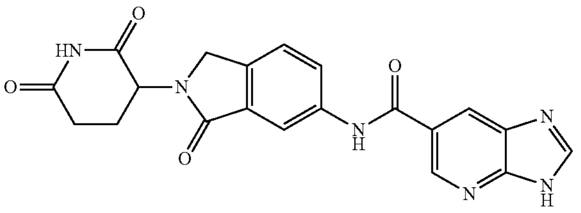 [SMILES: O=C1CCC(N2Cc3ccc(NC(=O)c4cnc5[nH]cnc5c4)cc3C2=O)C(=O)N1]
N-[2-(2,6-dioxo-3-piperidyl)-3-oxo-isoindolin-5-yl]-3H-imidazo[4,5-b]pyridine-6-carboxamide
C11892
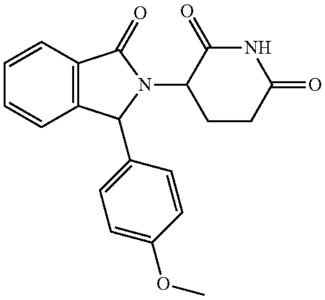 [SMILES: COc1ccc(C2c3ccccc3C(=O)N2C2CCC(=O)NC2=O)cc1]
3-[1-(4-methoxyphenyl)-3-oxo-isoindolin-2-yl]piperidine-2,6-dione
C44292
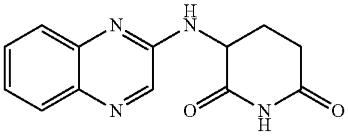 [SMILES: O=C1CCC(Nc2cnc3ccccc3n2)C(=O)N1]
3-(quinoxalin-2-ylamino)piperidine-2,6-dione
C12693
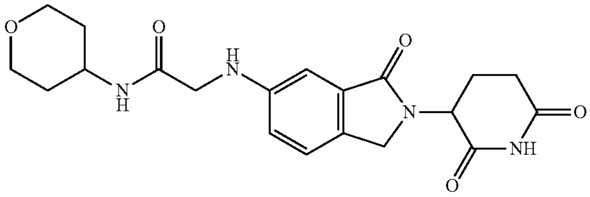 [SMILES: O=C1CCC(N2Cc3ccc(NCC(=O)NC4CCOCC4)cc3C2=O)C(=O)N1]
2-[[2-(2,6-dioxo-3-piperidyl)-3-oxo-isoindolin-5-yl]amino]-N-tetrahydropyran-4-yl-acetamide
C56572
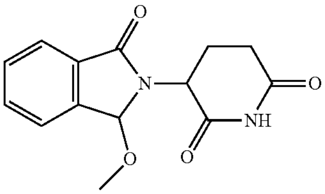 [SMILES: COC1c2ccccc2C(=O)N1C1CCC(=O)NC1=O]
3-(1-methoxy-3-oxo-isoindolin-2-yl)piperidine-2,6-dione
C55468
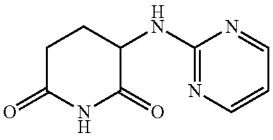 [SMILES: O=C1CCC(Nc2ncccn2)C(=O)N1]
3-(pyrimidin-2-ylamino)piperidine-2,6-dione TABLE 6-continued
C29490
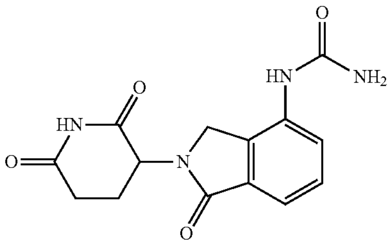 [SMILES: NC(=O)Nc1cccc2c1CN(C1CCC(=O)NC1=O)C2=O]
[2-(2,6-dioxo-3-piperidyl)-1-oxo-isoindolin-4-yl]urea
C47997
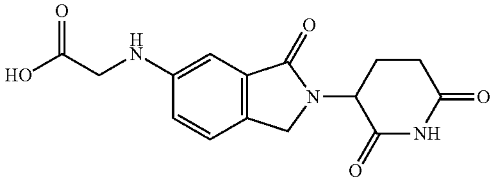 [SMILES: O=C(O)CNc1ccc2c(c1)C(=O)N(C1CCC(=O)NC1=O)C2]
2-[[2-(2,6-dioxo-3-piperidyl)-3-oxo-isoindolin-5-yl]amino]acetic acid
C98696
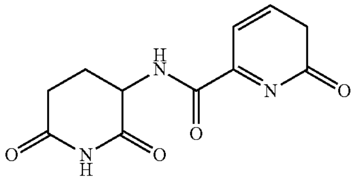 [SMILES: O=C1CC=CC(C(=O)NC2CCC(=O)NC2=O)=N1]
N-(2,6-dioxo-3-piperidyl)-2-oxo-3H-pyridine-6-carboxamide
C12581
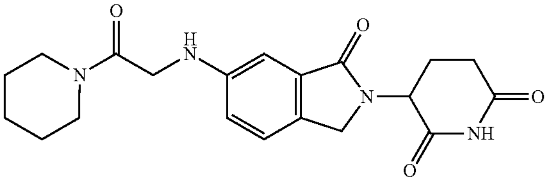 [SMILES: O=C1CCC(N2Cc3ccc(NCC(=O)N4CCCCC4)cc3C2=O)C(=O)N1]
3-[1-oxo-6-][2-oxo-2-(1-piperidyl)ethyl]amino]isoindolin-2-yl]piperidine-2,6-dione
C12589
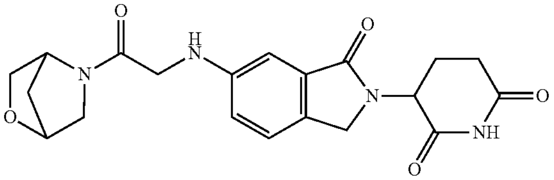 [SMILES: O=C1CCC(N2Cc3ccc(NCC(=O)N4CC5CC4CO5)cc3C2=O)C(=O)N1]
3-[6-[[2-(2-oxa-5-azabicyclo[2.2.1]heptan-5-yl)-2-oxo-ethyl]amino]-1-oxo-isoindolin
dione
C15352
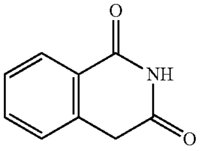 [SMILES: O=C1Cc2ccccc2C(=O)N1]
4H-isoquinoline-1,3-dione TABLE 6-continued
C95329
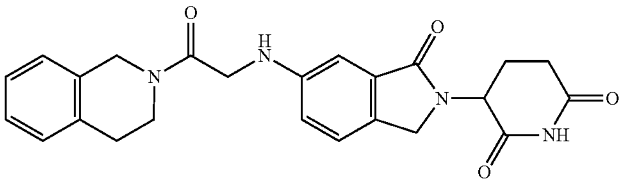 [SMILES: O=C1CCC(N2Cc3ccc(NCC(=O)N4CCc5ccccc5C4)cc3C2=O)C(=O)N1]
3-[6-[[2-(3,4-dihydro-1H-isoquinolin-2-yl)-2-oxo-ethyl]amino]-1-oxo-isoindolin
C29457
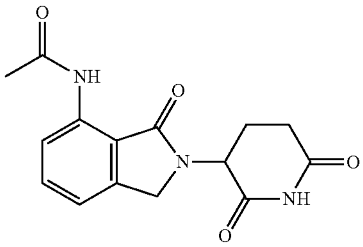 [SMILES: CC(=O)Nc1cccc2c1C(=O)N(C1CCC(=O)NC1=O)C2]
N-[2-(2,6-dioxo-3-piperidyl)-3-oxo-isoindolin-4-yl]acetamide
C16899
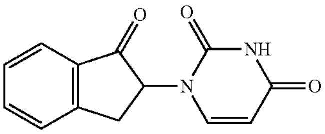 [SMILES: O=C1c2ccccc2CC1n1ccc(=O)[nH]c1=O]
1-(1-oxoindan-2-yl)pyrimidine-2,4-dione
C96413
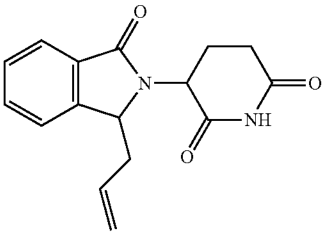 [SMILES: C=CCC1c2ccccc2C(=O)N1C1CCC(=O)NC1=O]
3-(1-allyl-3-oxo-isoindolin-2-yl)piperidine-2,6-dione
C40531
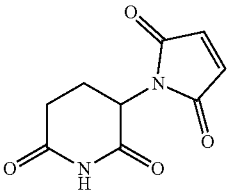 [SMILES: O=C1CCC(N2C(=O)C=CC2=O)C(=O)N1]
3-(2,5-dioxopyrrol-1-yl)piperidine-2,6-dione
C75987
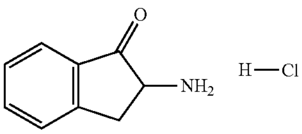 [SMILES: NC1Cc2ccccc2C1=O ; Cl]
2-aminoindan-1-one; hydrochloride TABLE 6-continued
C35745
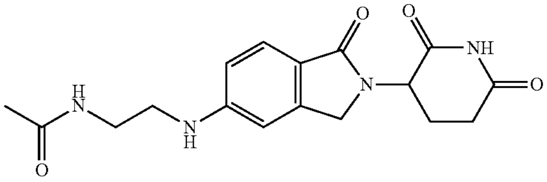 [SMILES: CC(=O)NCCNc1ccc2c(c1)CN(C1CCC(=O)NC1=O)C2=O]
N-[2-[[2-(2,6-dioxo-3-piperidyl)-1-oxo-isoindolin-5-yl]amino]ethyl]acetamide
C95336
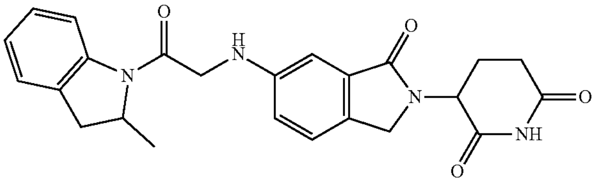 [SMILES: CC1Cc2ccccc2N1C(=O)CNc1ccc2c(c1)C(=O)N(C1CCC(=O)NC1=O)C2]
3-[6-[[2-(2-methylindolin-1-yl)-2-oxo-ethyl]amino]-1-oxo-isoindolin-2-yl]piperidine-2,6-dione
C64348
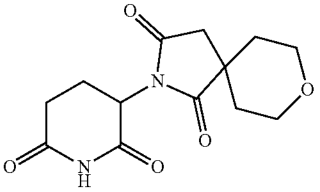 [SMILES: O=C1CCC(N2C(=O)CC3(CCOCC3)C2=O)C(=O)N1]
2-(2,6-dioxo-3-piperidyl)-8-oxa-2-azaspiro[4.5]decane-1,3-dione
C02896
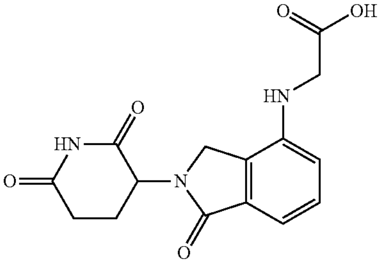 [SMILES: O=C(O)CNc1cccc2c1CN(C1CCC(=O)NC1=O)C2=O]
2-[[2-(2,6-dioxo-3-piperidyl)-1-oxo-isoindolin-4-yl]amino]acetic acid
C39772
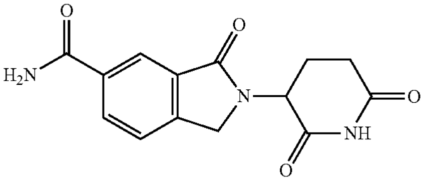 [SMILES: NC(=O)c1ccc2c(c1)C(=O)N(C1CCC(=O)NC1=O)C2]
2-(2,6-dioxo-3-piperidyl)-3-oxo-isoindoline-5-carboxamide
C75688
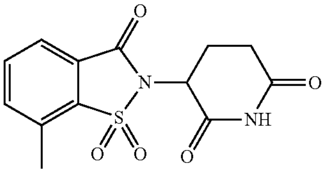 [SMILES: Cc1cccc2c1S(=O)(=O)N(C1CCC(=O)NC1=O)C2=O]
3-(7-methyl-1,1,3-trioxo-1,2-benzothiazol-2-yl)piperidine-2,6-dione TABLE 6-continued
| | |
|---|---|
| C64329 | 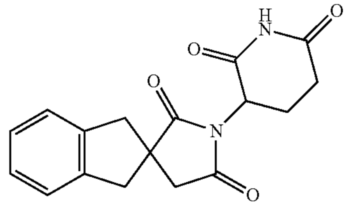 [SMILES: O=C1CCC(N2C(=O)CC3(Cc4ccccc4C3)C2=O)C(=O)N1]<br>1'-(2,6-dioxo-3-piperidyl)spiro[indane-2,3'-pyrrolidine]-2',5'-dione |
| C34491 | 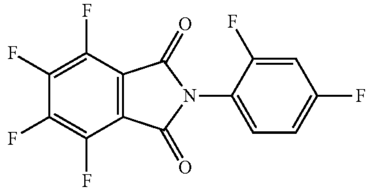 [SMILES: O=C1c2c(F)c(F)c(F)c(F)c2C(=O)N1c1ccc(F)cc1F]<br>2-(2,4-difluorophenyl)-4,5,6,7-tetrafluoro-isoindoline-1,3-dione |
| 5'-OH-THL | 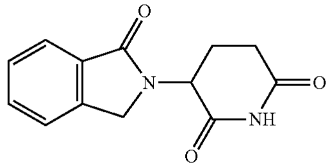 [SMILES: O=C1CCC(N2Cc3ccccc3C2=O)C(=O)N1]<br>3-(1-oxoisoindolin-2-yl)piperidine-2,6-dione |
| C80374 | 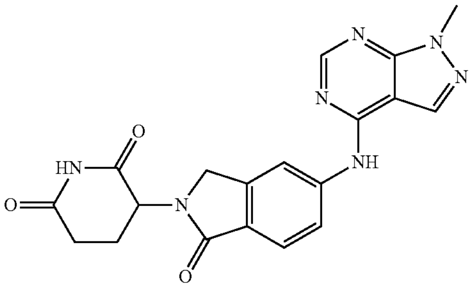 [SMILES: Cn1ncc2c(Nc3ccc4c(c3)CN(C3CCC(=O)NC3=O)C4=O)ncnc21]<br>3-[5-[(1-methylpyrazolo[3,4-d]pyrimidin-4-yl)amino]-1-oxo-isoindolin-2-yl]piperidine-2,6-dione |
| C24191 | 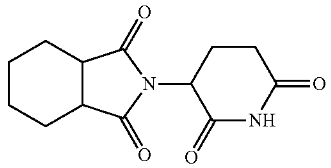<br>2-(2,6-dioxo-3-piperidyl)-3a,4,5,6,7,7a-hexahydroisoindole-1,3-dione |
| C87699 | 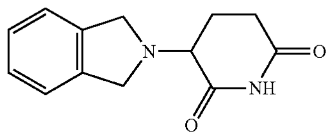 [SMILES: O=C1CCC(N2Cc3ccccc3C2)C(=O)N1]<br>3-isoindolin-2-ylpiperidine-2,6-dione |

TABLE 6-continued
C36128
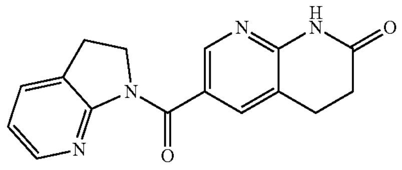 [SMILES: O=C1CCc2cc(C(=O)N3CCc4cccnc43)cnc2N1]
6-(2,3-dihydropyrrolo[2,3-b]pyridine-1-carbonyl)-3,4-dihydro-1H-1,8-naphthyridin-2-obe
C17800
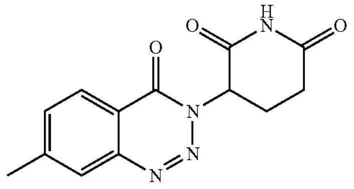 [SMILES: Cc1ccc2c(=O)n(C3CCC(=O)NC3=O)nnc2c1]
3-(7-methyl-4-oxo-1,2,3-benzotriazin-3-yl)piperidine-2,6-dione
C08493
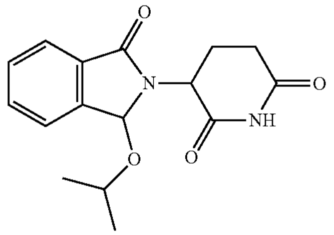 [SMILES: CC(C)OC1c2ccccc2C(=O)N1C1CCC(=O)NC1=O]
3-(1-isopropoxy-3-oxo-isoindolin-2-yl)piperidine-2,6-dione
C07128
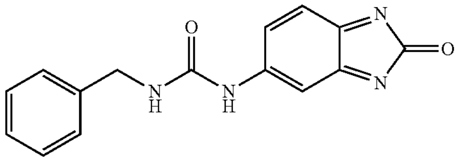 [SMILES: O=C1N=c2ccc(NC(=O)NCc3ccccc3)cc2=N1]
1-benzyl-3-(2-oxobenzimidazol-5-yl)urea
C64319
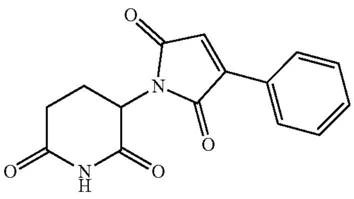 [SMILES: O=C1CCC(N2C(=O)C=C(c3ccccc3)C2=O)C(=O)N1]
3-(2,5-dioxo-3-phenyl-pyrrol-1-yl)piperidine-2,6-dione
C49278
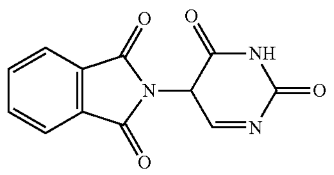 [SMILES: O=C1N=CC(N2C(=O)c3ccccc3C2=O)C(=O)N1]
2-(2,6-dioxo-5H-pyrimidin-5-yl)isoindoline-1,3-dione TABLE 6-continued
| | | |
|---|---|---|
| C33779 | 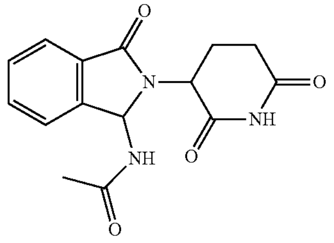 [SMILES: CC(=O)NC1c2ccccc2C(=O)N1C1CCC(=O)NC1=O] N-[2-(2,6-dioxo-3-piperidyl)-3-oxo-isoindolin-1-yl]acetamide | |
| C12695 | 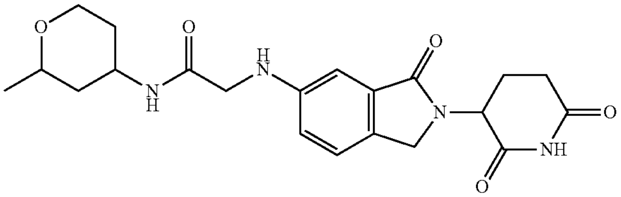 [SMILES: CC1CC(NC(=O)CNc2ccc3c(c2)C(=O)N(C2CCC(=O)NC2=O)C3)CCO1] 2-[[2-(2,6-dioxo-3-piperidyl)-3-oxo-isoindolin-5-yl]amino]-N-(2-methyltetrahydropyran-4-yl)acetamide | |
| C09563 | 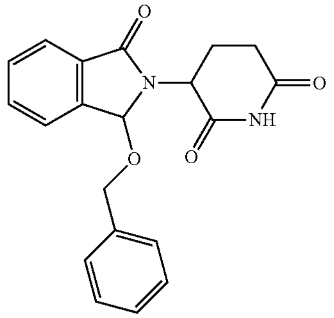 3-(1-benzyloxy-3-oxo-isoindolin-2-yl)piperidine-2,6-dione | |
| glutarimide | 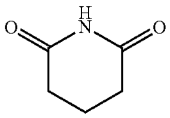 piperidine-2,6-dione | |
| C38935 | 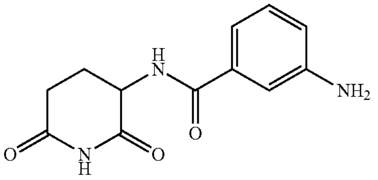 [SMILES: Nc1cccc(C(=O)NC2CCC(=O)NC2=O)c1] 3-amino-N-(2,6-dioxo-3-piperidyl)benzamide | |

TABLE 6-continued
C30231
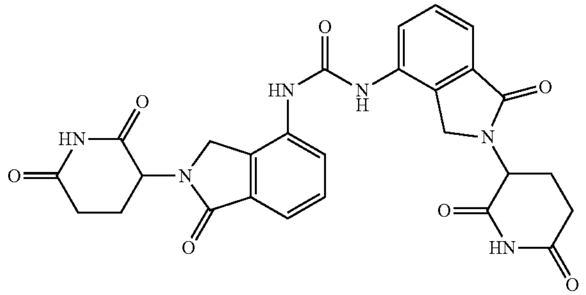 [SMILES: O=C1CCC(N2Cc3c(NC(=O)Nc4cccc5c4CN(C4CCC(=O)NC4=O)C5=O)cccc3C2=O)C(=O)N1]
1,3-bis[2-(2,6-dioxo-3-piperidyl)-1-oxo-isoindolin-4-yl]urea
C64340
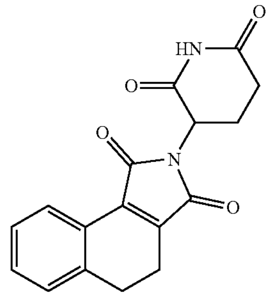 [SMILES: O=C1CCC(N2C(=O)C3=C(C2=O)c2ccccc2CC3)C(=O)N1]
2-(2,6-dioxo-3-piperidyl)-4,5-dihydrobenzo[e]isoindole-1,3-dione
C23258
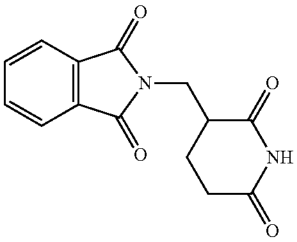 [SMILES: O=C1CCC(CN2C(=O)c3ccccc3C2=O)C(=O)N1]
2-[(2,6-dioxo-3-piperidyl)methyl]isoindoline-1,3-dione
C12582
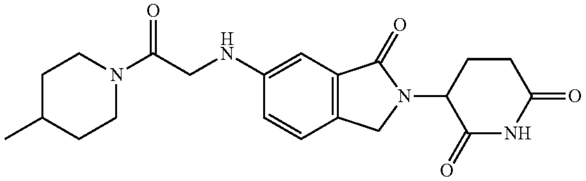 [SMILES: CC1CCN(C(=O)CNc2ccc3c(c2)C(=O)N(C2CCC(=O)NC2=O)C3)CC1]
3-[6-[[2-(4-methyl-1-piperidyl)-2-oxo-ethyl]amino]-1-oxo-isoindolin-2-yl] piperidine-2,6-dione
C60651
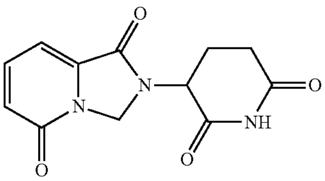 [SMILES: O=C1CCC(N2Cn3c(cccc3=O)C2=O)C(=O)N1]
2-(2,6-dioxo-3-piperidyl)-3H-imidazo[1,5-a]pyridine-1,5-dione TABLE 6-continued
C29737
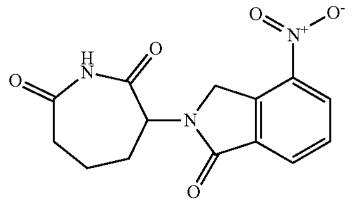 [SMILES: O=C1CCCC(N2Cc3c(cccc3[N+](=O)[O-])C2=O)C(=O)N1]
3-(4-nitro-1-oxo-isoindolin-2-yl)azepane-2,7-dione
C64372
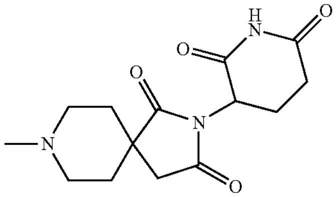 [SMILES: CN1CCC2(CC1)CC(=O)N(C1CCC(=O)NC1=O)C2=O]
2-(2,6-dioxo-3-piperidyl)-8-methyl-2,8-diazaspiro[4.5]decane-1,3-dione
C09063
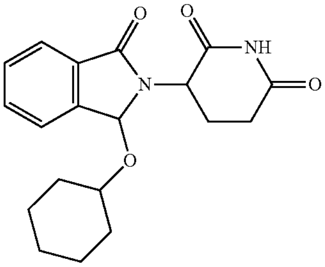 [SMILES: O=C1CCC(N2C(=O)c3ccccc3C2OC2CCCCC2)C(=O)N1]
3-[1-(cyclohexoxy)-3-oxo-isoindolin-2-yl]piperidine-2,6-dione
C95334
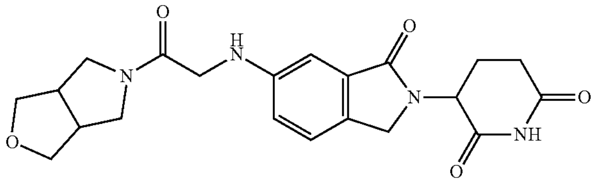 [SMILES: O=C1CCC(N2Cc3ccc(NCC(=O)N4CC5COCC5C4)cc3C2=O)C(=O)N1]
3-[6-[[2-(1,3,3a,4,6,6a-hexahydrofuro[3,4-c]pyrrol-5-yl)-2-oxo-ethyl]amino]-1-oxo-isoindolin-2-yl]piperidine-2,6-dione TABLE 6-continued
| | |
|---|---|
| C14950 | 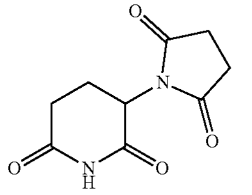 [SMILES: O=C1CCC(N2C(=O)CCC2=O)C(=O)N1]<br>3-(2,5-dioxopyrrolidin-1-yl)piperidine-2,6-dione |
| C46003 | 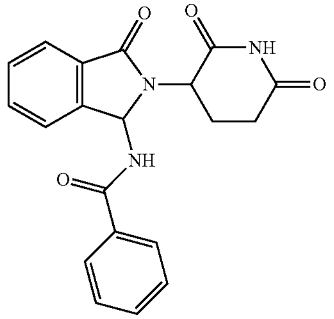 [SMILES: O=C1CCC(N2C(=O)c3ccccc3C2NC(=O)c2ccccc2)C(=O)N1]<br>N-[2-(2,6-dioxo-3-piperidyl)-3-oxo-isoindolin-1-yl]benzamide |
| C51647 | 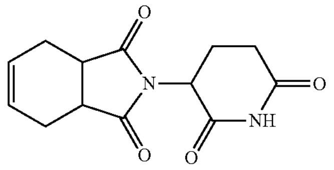 [SMILES: O=C1CCC(N2C(=O)C3CC=CCC3C2=O)C(=O)N1]<br>2-(2,6-dioxo-3-piperidyl)-3a,4,7,7a-tetrahydroisoindole-1,3-dione |
| C12697 | 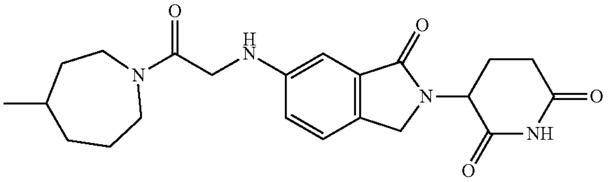 [SMILES: CC1CCCN(C(=O)CNc2ccc3c(c2)C(=O)N(C2CCC(=O)NC2=O)C3)CC1]<br>3-[6-[[2-(4-methylazepan-1-yl)-2-oxo-ethyl]amino]-1-oxo-isoindolin-2-yl]piperidine-2,6-dione |
| C64344 | 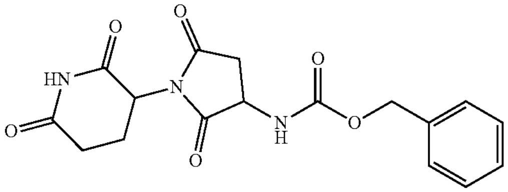 [SMILES: O=C1CCC(N2C(=O)CC(NC(=O)OCc3ccccc3)C2=O)C(=O)N1]<br>benzyl N-[1-(2,6-dioxo-3-piperidyl)-2,5-dioxo-pyrrolidin-3-yl]carbamate |
| C10537 | 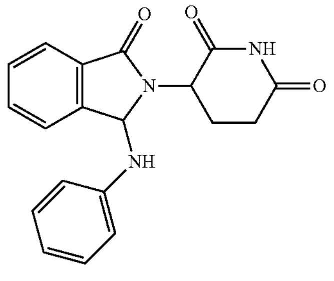 [SMILES: O=C1CCC(N2C(=O)c3ccccc3C2Nc2ccccc2)C(=O)N1]<br>3-(1-anilino-3-oxo-isoindolin-2-yl)piperidine-2,6-dione |

TABLE 6-continued
C12694
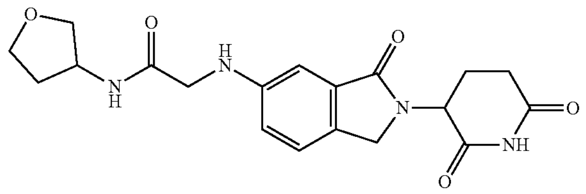 [SMILES: O=C1CCC(N2Cc3ccc(NCC(=O)NC4CCOC4)cc3C2=O)C(=O)N1]
2-[[2-(2,6-dioxo-3-piperidyl)-3-oxo-isoindolin-5-yl]amino]-N-tetrahydrofuran-3-yl-acetamide
C38930
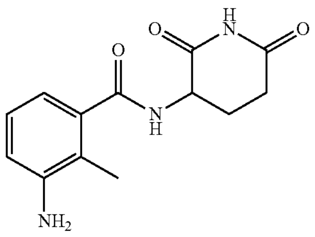 [SMILES: Cc1c(N)cccc1C(=O)NC1CCC(=O)NC1=O]
3-amino-N-(2,6-dioxo-3-piperidyl)-2-methyl-benzamide
C80385
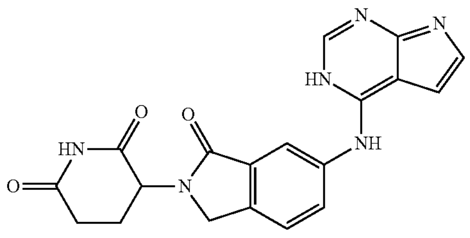 [SMILES: O=C1CCC(N2Cc3ccc(Nc4[nH]cnc5nccc4-5)cc3C2=O)C(=O)N1]
3-[1-oxo-6-(3H-pyrrolo[2,3-d]pyrimidin-4-ylamino)isoindolin-2-yl]piperidine-2,6-dione
C80393
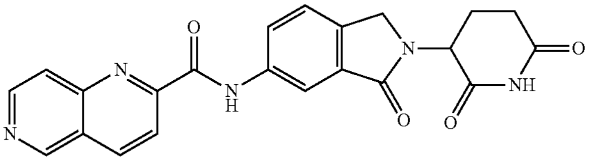 [SMILES: O=C1CCC(N2Cc3ccc(NC(=O)c4ccc5cnccc5n4)cc3C2=O)C(=O)N1]
N-[2-(2,6-dioxo-3-piperidyl)-3-oxo-isoindolin-5-yl]-1,6-naphthyridine-2-carboxamide
C47930
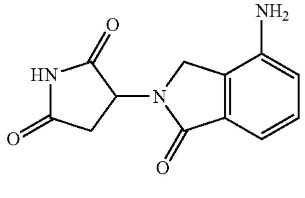 [SMILES: Nc1cccc2c1CN(C1CC(=O)NC1=O)C2=O]
3-(4-amino-1-oxo-isoindolin-2-yl)pyrrolidine-2,5-dione
C47927
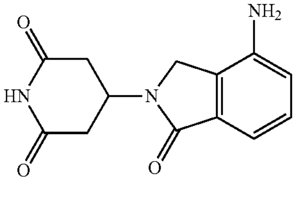 [SMILES: Nc1cccc2c1CN(C1CC(=O)NC(=O)C1)C2=O]
4-(4-amino-1-oxo-isoindolin-2-yl)piperidine-2,6-dione TABLE 6-continued
C47932
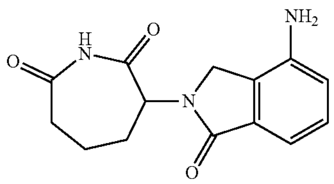 [SMILES: Nc1cccc2c1CN(C1CCCC(=O)NC1=O)C2=O]
3-(4-amino-1-oxo-isoindolin-2-yl)azepane-2,7-dione
C47928
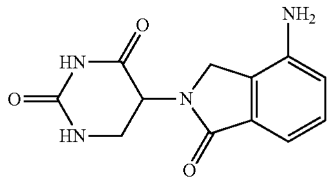 [SMILES: Nc1cccc2c1CN(C1CNC(=O)NC1=O)C2=O]
5-(4-amino-1-oxo-isoindolin-2-yl)hexahydropyrimidine-2,4-dione
C10239
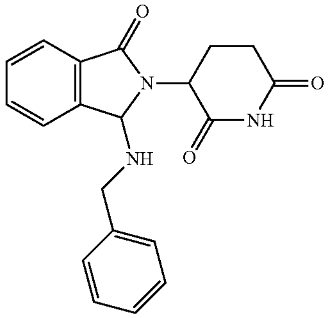 [SMILES: O=C1CCC(N2C(=O)c3ccccc3C2NCc2ccccc2)C(=O)N1]
3-[1-(benzylamino)-3-oxo-isoindolin-2-yl]piperidine-2,6-dione
C36124
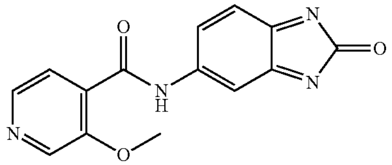 [SMILES: COc1cnccc1C(=O)Nc1ccc2c(c1)=NC(=O)N=2]
3-methoxy-N-(2-oxobenzimidazol-5-yl)pyridine-4-carboxamide
C80376
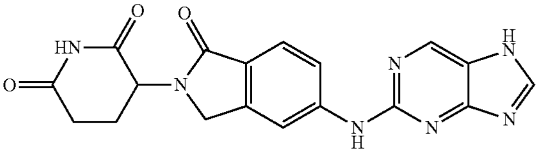 [SMILES: O=C1CCC(N2Cc3cc(Nc4ncc5[nH]cnc5n4)ccc3C2=O)C(=O)N1]
3-[1-oxo-5-(7H-purin-2-ylamino)isoindolin-2-yl]piperidine-2,6-dione
C10001
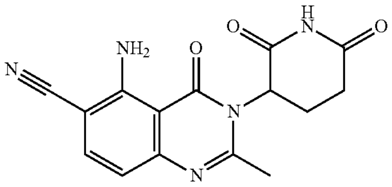 [SMILES: Cc1nc2ccc(C#N)c(N)c2c(=O)n1C1CCC(=O)NC1=O]
5-amino-3-(2,6-dioxo-3-piperidyl)-2-methyl-4-oxo-quinazoline-6-carbonitrile TABLE 6-continued

| | |
|---|---|
| C55859 | 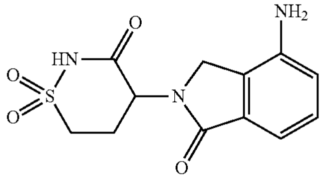 [SMILES: Nc1cccc2c1CN(C1CCS(=O)(=O)NC1=O)C2=O]<br>4-(4-Amino-1-oxoisoindolin-2yl)-1,2-thiazinan-3-one 1,1-dioxide |
| THL | 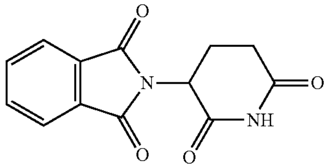 [SMILES: O=C1CCC(N2C(=O)c3ccccc3C2=O)C(=O)N1]<br>2-(2,6-dioxo-3-piperidyl)isoindoline-1,3-dione |

| ID | IC50 Competition(M) | EC50_IKZF1 (M) | EC50_ASS1 (M) | EC50_SALL4 (M) | Recruitment Assessment |
|---|---|---|---|---|---|
| C80392 | 2.05303E−11 | NA | NA | NA | FALSE |
| C12584 | 7.91364E−11 | NA | NA | NA | FALSE |
| CC-885 | 4.65169E−10 | << | 8.01E−08 | NA | TRUE |
| C74668 | 1.88601E−09 | NA | NA | NA | FALSE |
| CC-220 | 1.00796E−08 | << | 6.24E−08 | << | TRUE |
| C80370 | 1.09103E−08 | NA | NA | NA | FALSE |
| C24031 | 1.14592E−08 | 5.87E−08 | 2.59E−07 | << | TRUE |
| C48014 | 2.43314E−08 | 1.24E−06 | 9.21E−07 | 6.21E−08 | TRUE |
| C58181 | 2.91268E−08 | NA | >> | NA | TRUE |
| C95330 | 3.0027E−08 | NA | NA | NA | FALSE |
| C95338 | 3.20528E−08 | NA | NA | NA | FALSE |
| C80382 acetic acid salt | 3.34174E−08 | NA | NA | NA | FALSE |
| C80369 | 4.15416E−08 | >> | 1.29E−06 | NA | TRUE |
| C47935 | 4.53754E−08 | 1.62E−07 | 6.77E−07 | 2.70E−08 | TRUE |
| C12583 | 4.9194E−08 | NA | NA | NA | FALSE |
| C28558 | 5.04383E−08 | 7.74E−08 | 3.68E−07 | << | TRUE |
| C80387 | 5.41939E−08 | NA | NA | NA | FALSE |
| C80386 | 6.73708E−08 | NA | NA | NA | FALSE |
| C67858 | 1.06453E−07 | 5.69E−07 | 8.84E−07 | 2.93E−08 | TRUE |
| C28577 | 1.12883E−07 | 1.61E−06 | 6.53E−07 | << | TRUE |
| C89676 | 1.26858E−07 | 1.13E−07 | 8.32E−07 | << | TRUE |
| C98103 | 1.44886E−07 | 1.29E−06 | >> | << | TRUE |
| C80383 | 1.47987E−07 | NA | NA | NA | FALSE |
| C80391 | 1.62797E−07 | >> | NA | 1.52E−07 | TRUE |
| C48016 | 1.73495E−07 | >> | NA | 1.22E−07 | TRUE |
| C05955 | 1.7519E−07 | 5.21E−07 | 1.55E−06 | << | TRUE |
| C28620 | 1.78223E−07 | >> | NA | 2.70E−07 | TRUE |
| C80384 | 1.78827E−07 | NA | NA | NA | FALSE |
| C51383 | 1.90194E−07 | 1.52E−06 | 1.70E−06 | 5.93E−08 | TRUE |
| C84965 | 1.99835E−07 | >> | NA | NA | TRUE |
| C12595 | 2.07712E−07 | NA | NA | NA | FALSE |
| C96622 | 2.13914E−07 | NA | NA | NA | FALSE |
| C22622 | 2.25027E−07 | >> | >> | 1.21E−07 | TRUE |
| C48018 | 2.28101E−07 | >> | NA | 3.95E−07 | TRUE |
| LEN | 2.43162E−07 | 6.22E−07 | 1.05E−06 | 1.33E−07 | TRUE |
| C23066 | 2.48406E−07 | >> | >> | 8.82E−08 | TRUE |
| C84964 | 2.65591E−07 | NA | NA | NA | FALSE |
| C29137 | 3.04218E−07 | NA | NA | NA | FALSE |
| C12586 | 3.82684E−07 | NA | NA | NA | FALSE |
| C28891 | 4.79112E−07 | 1.04E−07 | 4.23E−06 | 1.05E−07 | TRUE |
| C35856 | 4.84125E−07 | 1.15E−06 | >> | 1.88E−07 | TRUE |
| C35751 | 4.85851E−07 | >> | 1.45E−06 | 2.32E−07 | TRUE |
| C28928 | 4.88558E−07 | >> | >> | 2.26E−07 | TRUE |
| C28973 | 5.26297E−07 | >> | NA | 1.50E−07 | TRUE |
| C48020 | 5.4615E−07 | NA | NA | NA | FALSE |
| C68126 | 5.64062E−07 | >> | >> | 3.19E−07 | TRUE |
| C07207 | 5.86861E−07 | >> | NA | 3.07E−07 | TRUE |
| C95333 | 5.90522E−07 | NA | NA | NA | FALSE |
| C84966 | 5.99373E−07 | NA | NA | NA | FALSE |
| C48003 | 6.21907E−07 | >> | >> | 5.81E−07 | TRUE |
| C66979 | 6.33015E−07 | NA | NA | NA | FALSE |
| C80389 | 6.45036E−07 | NA | NA | NA | FALSE |
| C28661 | 6.54317E−07 | NA | NA | NA | FALSE |

TABLE 6-continued

| | | | | | |
|---|---|---|---|---|---|
| C35833 | 6.83558E−07 | NA | NA | NA | FALSE |
| C59904 | 7.03899E−07 | 1.22E−07 | 6.98E−07 | 3.30E−08 | TRUE |
| C80390 | 7.28895E−07 | >> | NA | NA | TRUE |
| C35754 | 7.36821E−07 | >> | >> | 2.78E−07 | TRUE |
| C49708 | 7.5179E−07 | NA | NA | NA | FALSE |
| C80380 | 7.6043E−07 | 1.78E−06 | NA | 9.89E−09 | TRUE |
| C35797 | 8.50894E−07 | 1.33E−06 | >> | 1.08E−06 | TRUE |
| C80395 | 8.80494E−07 | >> | NA | NA | TRUE |
| C80373 | 8.92014E−07 | >> | >> | NA | TRUE |
| CC-122 | 9.46128E−07 | 2.01E−07 | 1.39E−06 | 1.99E−07 | TRUE |
| C45748 | 9.52933E−07 | NA | NA | NA | FALSE |
| C80379 | 9.70979E−07 | >> | NA | NA | TRUE |
| C47933 | 1.0938E−06 | >> | NA | NA | TRUE |
| POM | 1.10121E−06 | 7.27E−07 | 2.07E−06 | 6.77E−08 | TRUE |
| C22548 | 1.10968E−06 | 4.94E−07 | >> | 6.31E−07 | TRUE |
| C84963 | 1.21084E−06 | NA | NA | NA | FALSE |
| C22586 | 1.29799E−06 | >> | NA | 1.14E−06 | TRUE |
| C84971 | 1.31113E−06 | NA | NA | NA | FALSE |
| C48007 | 1.34315E−06 | 1.62E−06 | >> | 4.30E−07 | TRUE |
| C99884 | 1.36829E−06 | NA | NA | NA | FALSE |
| C29330 | 1.41494E−06 | >> | >> | 2.50E−07 | TRUE |
| C84970 | 1.42322E−06 | NA | NA | 1.01E−06 | TRUE |
| C29361 | 1.43168E−06 | >> | >> | 1.86E−07 | TRUE |
| C22564 | 1.67347E−06 | >> | >> | 8.73E−07 | TRUE |
| C48005 | 1.73199E−06 | >> | NA | 5.95E−07 | TRUE |
| C80375 | 2.05608E−06 | NA | NA | NA | FALSE |
| C48009 | 2.18134E−06 | NA | NA | NA | FALSE |
| C80378 | 2.20805E−06 | >> | 9.42E−06 | 3.87E−07 | TRUE |
| C21223 | 2.29375E−06 | >> | >> | 5.17E−07 | TRUE |
| C13247 | 2.29444E−06 | 2.88E−06 | 8.55E−06 | 4.02E−07 | TRUE |
| C35811 | 2.44321E−06 | >> | >> | 6.41E−07 | TRUE |
| C47959 | 2.5664E−06 | >> | >> | 4.41E−07 | TRUE |
| C80396 | 2.62647E−06 | >> | NA | 1.38E−06 | TRUE |
| C16463 | 2.67093E−06 | >> | NA | 7.72E−07 | TRUE |
| C64324 | 2.74862E−06 | NA | NA | NA | FALSE |
| C84967 | 3.15182E−06 | NA | NA | >> | TRUE |
| C89940 | 3.28532E−06 | >> | >> | 4.38E−07 | TRUE |
| C35830 | 3.45963E−06 | >> | 5.56E−06 | 5.88E−07 | TRUE |
| C47995 | 3.70808E−06 | >> | >> | 5.18E−07 | TRUE |
| C64376 | 3.94892E−06 | NA | NA | NA | FALSE |
| C84961 | 4.00542E−06 | NA | NA | NA | FALSE |
| C22594 | 4.49003E−06 | 2.76E−06 | >> | 7.71E−07 | TRUE |
| C12598 | 4.88466E−06 | NA | NA | NA | FALSE |
| C29408 | 4.92017E−06 | NA | NA | NA | FALSE |
| C73349 | 4.94642E−06 | NA | NA | NA | FALSE |
| 5HPP-33 | 5.1107E−06 | NA | NA | NA | FALSE |
| C12597 | 5.50144E−06 | NA | NA | NA | FALSE |
| ZE26-0001 | 5.76168E−06 | 4.68E−06 | >> | 8.01E−07 | TRUE |
| C98053 | 5.76611E−06 | NA | NA | NA | FALSE |
| C51830 | 6.03878E−06 | NA | NA | NA | FALSE |
| C97402 | 6.3212E−06 | NA | NA | NA | FALSE |
| C68121 | 6.5036E−06 | NA | NA | NA | FALSE |
| C47998 | 6.58948E−06 | NA | NA | 2.17E−06 | TRUE |
| C49713 | 6.73708E−06 | NA | NA | NA | FALSE |
| C36126 | 7.23164E−06 | NA | NA | NA | FALSE |
| C39453 | 7.51549E−06 | 1.71E−05 | NA | 8.75E−07 | TRUE |
| C10981 | 7.80566E−06 | >> | >> | 1.46E−06 | TRUE |
| C80394 | 7.99132E−06 | >> | NA | NA | TRUE |
| C11892 | 8.15508E−06 | NA | NA | NA | FALSE |
| C44292 | 8.32122E−06 | NA | NA | NA | FALSE |
| C12693 | 8.32631E−06 | >> | NA | 2.62E−06 | TRUE |
| C56572 | 8.60508E−06 | NA | NA | NA | FALSE |
| C55468 | 8.68221E−06 | NA | NA | NA | FALSE |
| C29490 | 8.86373E−06 | >> | NA | NA | TRUE |
| C47997 | 9.09859E−06 | NA | NA | NA | FALSE |
| C98696 | 9.3409E−06 | NA | NA | NA | FALSE |
| C12581 | 9.99653E−06 | NA | NA | NA | FALSE |
| C12589 | 1.02777E−05 | NA | NA | NA | FALSE |
| C15352 | 1.031E−05 | NA | NA | NA | FALSE |
| C95329 | 1.03261E−05 | NA | NA | NA | FALSE |
| C29457 | 1.03599E−05 | >> | NA | >> | TRUE |
| C16899 | 1.03816E−05 | NA | NA | NA | FALSE |
| C96413 | 1.03991E−05 | NA | NA | NA | FALSE |
| C40531 | 1.10435E−05 | NA | NA | NA | FALSE |
| C75987 | 1.12251E−05 | NA | NA | NA | FALSE |
| C35745 | 1.12483E−05 | >> | NA | 2.63E−06 | TRUE |
| C95336 | 1.19471E−05 | NA | NA | NA | FALSE |
| C64348 | 1.29256E−05 | NA | NA | NA | FALSE |
| C02896 | 1.38151E−05 | NA | NA | NA | FALSE |
| C39772 | 1.38404E−05 | NA | NA | NA | FALSE |

TABLE 6-continued

| | | | | | |
|---|---|---|---|---|---|
| C75688 | 1.47323E−05 | NA | NA | NA | FALSE |
| C64329 | 1.51214E−05 | NA | NA | NA | FALSE |
| C34491 | 1.61223E−05 | NA | NA | NA | FALSE |
| 5'-OH-THL | 1.61621E−05 | NA | NA | NA | FALSE |
| C80374 | 1.65805E−05 | >> | NA | NA | TRUE |
| C24191 | 1.7708E−05 | NA | NA | NA | FALSE |
| C87699 | 1.96334E−05 | NA | NA | 4.82E−06 | TRUE |
| C36128 | 2.02561E−05 | NA | NA | NA | FALSE |
| C17800 | 2.18924E−05 | >> | NA | 9.04E−07 | TRUE |
| C08493 | 2.28752E−05 | >> | NA | 2.70E−06 | TRUE |
| C07128 | 2.3835E−05 | NA | NA | NA | FALSE |
| C64319 | 4.28801E−05 | NA | NA | NA | FALSE |
| C49278 | 4.53958E−05 | NA | NA | NA | FALSE |
| C33779 | 4.94369E−05 | NA | NA | 3.03E−06 | TRUE |
| C12695 | 5.79759E−05 | NA | NA | NA | FALSE |
| C09563 | 5.82854E−05 | NA | NA | NA | FALSE |
| glutarimide | 9.53602E−05 | NA | NA | NA | FALSE |
| C38935 | 9.92946E−05 | >> | NA | NA | TRUE |
| C30231 | 0.000247103 | 2.73E−06 | >> | 1.78E−06 | TRUE |
| C64340 | 0.002503261 | >> | NA | 1.49E−06 | TRUE |
| C23258 | 0.014526546 | NA | NA | NA | FALSE |
| C12582 | 0.037396754 | NA | NA | NA | FALSE |
| C60651 | 0.113371238 | NA | NA | NA | FALSE |
| C29737 | 0.122564012 | 1.41E−06 | NA | NA | TRUE |
| C64372 | 0.223963175 | NA | NA | NA | FALSE |
| C09063 | 0.453327822 | NA | NA | NA | FALSE |
| C95334 | 1.594934429 | NA | NA | NA | FALSE |
| C14950 | 3.958295874 | NA | NA | NA | FALSE |
| C46003 | 32.56223026 | NA | NA | NA | FALSE |
| C51647 | 51.17761807 | NA | NA | NA | FALSE |
| C12697 | 51.67955472 | NA | NA | NA | FALSE |
| C64344 | 112.7097496 | NA | NA | NA | FALSE |
| C10537 | | NA | NA | NA | FALSE |
| C12694 | | >> | NA | 3.43E−06 | TRUE |
| C38930 | | NA | NA | NA | FALSE |
| C80385 | | NA | NA | NA | FALSE |
| C80393 | 7.00E−09 | NA | NA | NA | FALSE |
| C47930 | | 7.84E−07 | NA | NA | TRUE |
| C47927 | | >> | NA | NA | TRUE |
| C47932 | | >> | NA | NA | TRUE |
| C47928 | | NA | NA | NA | FALSE |
| C10239 | | >> | NA | 1.16E−06 | TRUE |
| C36124 | | NA | NA | NA | FALSE |
| C80376 | | >> | NA | 5.59E−07 | TRUE |
| C10001 | | >> | >> | 1.25E−06 | TRUE |
| C55859 | | NA | NA | NA | FALSE |
| THL | | >> | >> | NA | TRUE |

IC50 Competition values were determined using the protocol and reagents described in Example 1. EC50 values for recruitment of IKZF1, ASS1 and SALL4 were determined using the protocols and reagents descrbied in Example 2. Recruitment assessment was made for each compound, where TRUE = observation of recruitment of any tested substrate at any tested compound concentration from among IKZF1, ASS1 and SALL4, and FALSE = no observed recruitment of any tested substrate at any tested compound concentration from among IKF1, ASS1 and SALL4. NA represents instances where no substrate recruitment was observed at any tested concentration, >> represents instances were an EC50 curve could not be calculated as values did not reach a plateau over the measured concentration range, and << represents instances where an EC50 could not be calculate because a value was read above 50% of control at the first concentration tested for the compound (13.7 nM).

TABLE 7

IC50 Competition values were determined using the protocol and reagents described in Example 1. EC50 values for recruitment of the indicated target proteins were determined using the protocols and reagents described in Example 2. NA represents instances where no substrate recruitment was observed at any tested concentration , >> represents instances were an EC50 curve could not be calculated as values did not reach a plateau over the measured concentration range, and << represents instances where an EC50 could not be calculated because a value was read above 50% of control at the first concentration tested for the compound (13.7 nM).

| Compound ID | Competition IC50 (M) | Recruitment Target protein | Recruitment EC50 (M) | Functional Activity Type | Functional Activity Result |
|---|---|---|---|---|---|
| LEN-TMP | NA | DHFR | 1.44E−07 | | |
| 5.53 | 1.39E−06 | ESR1 | | | |
| 5.54 | 8.38E−07 | ESR1 | | | |
| 5.55 | 1.05E−06 | ESR1 | | | |
| 5.56 | 5.80E−06 | ESR1 | | | |

TABLE 7-continued

IC50 Competition values were determined using the protocol and reagents described in Example 1. EC50 values for recruitment of the indicated target proteins were determined using the protocols and reagents described in Example 2. NA represents instances where no substrate recruitment was observed at any tested concentration , >> represents instances were an EC50 curve could not be calculated as values did not reach a plateau over the measured concentration range, and << represents instances where an EC50 could not be calculated because a value was read above 50% of control at the first concentration tested for the compound (13.7 nM).

| Compound ID | Competition IC50 (M) | Recruitment Target protein | Recruitment EC50 (M) | Functional Activity Type | Functional Activity Result |
|---|---|---|---|---|---|
| 5.57 | 1.09E−07 | BRD4 | | | |
| 5.58 | 9.98E−08 | BRD4 | | | |
| 5.59 | 6.80E−08 | BRD4 | | | |
| 5.60 | 1.16E−07 | BRD4 | | | |

Example 7: Evaluation of CRBN Binding and/or Substrate Recruitment of Bifunctional Compounds For selected bifunctional compounds, the Competition Assay and/or Recruitment Assay described in Example 1 and Example 2, respectively, are applied to evaluate CRBN binding and/or substrate recruitment. The resulting dose-response curves are shown in FIG. 3.

Example 8: Synthesis Intermediates and Final Compounds

Intermediates Synthesis

Synthesis of Intermediate 1:

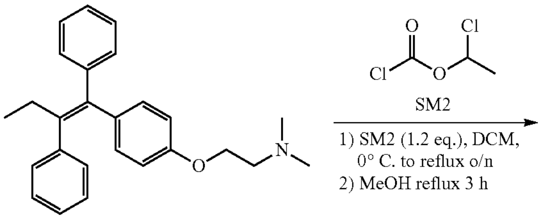

SM1

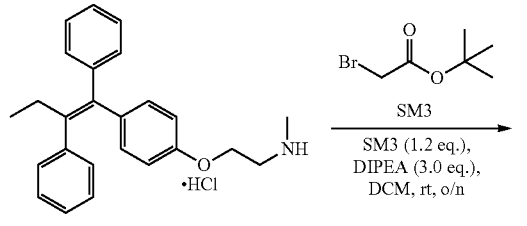

1.

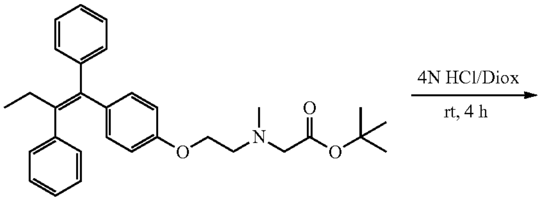

1.

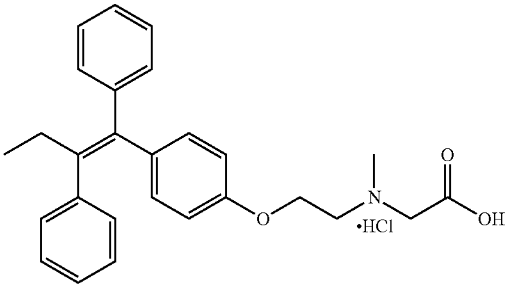

Intermediate 1

To a solution of SM1 (5.0 g, 13.5 mmol) in DCM (50 mL) at 0° C. under $N_2$ atmosphere was added SM2 (3.8 g, 27.0 mmol) and mixture was then heated at 60° C. overnight.

The reaction was cooled to RT, concentrated and the residue dissolved in MeOH (50 mL). The mixture was heated at reflux for 3 hours then concentrated to afford target 1.1 (4.5 g, yield 94%) as a white solid. TLC: $R_f$=0.15 (DMC/MeOH=10:1, v/v, 254 nm). LCMS: (Method P0-POS): m/z 358.2 $[M+H]^+$, 2.109 min.

To a solution of compound 1.1 (4.5 g, 12.6 mmol) in DCM (50 mL) was added SM3 (2.9 g, 15.1 mmol) and DIPEA (4.9 g, 37.8 mmol) and the resulting mixture was stirred at RT overnight.

The mixture was diluted with water (100 mL), extracted with DCM (50 mL×3) and the combined organic extracts washed with brine, dried over $Na_2SO_4$, filtered and concentrated. The residue was purified by column (eluent Petroleum DCM:MeOH=40:1, v:v) to give the product 1.2 (4.9 g, yield 83%) as a white solid.

To a solution of compound 1.2 (4.9 g, 10.4 mmol) in 1-4 dioxane (20 mL) was added 4N HCl/Dioxane (30 mL) and the mixture was stirred at RT for 4 h.

The mixture was concentrated and the residue was triturated with ether to afford Intermediate 1 (4 g, 93%) as a white solid. TLC: $R_f$ 0.1 (DCM/MeOH=10:1, v/v, 254 nm) LCMS: (P0(-1)-POS): m/z 416.2 $[M+H]^+$, 3.457 min. $^1H$ NMR (400 MHz, DMSO-$d_6$) (FID No:CJP-0147-084-HNMR) δ 7.40-7.37 (m, 2H), 7.31-7.27 (m, 1H), 7.22-7.19 (m, 4H), 7.14-7.11 (m, 3H), 6.79-6.77 (m, 2H), 6.66-6.64 (m, 2H), 4.25 (t, J=4.4 Hz, 2H), 4.13 (s, 2H), 3.54-3.53 (m, 2H), 2.89 (s, 3H), 2.40-2.34 (m, 2H), 0.85 (t, J=7.2 Hz, 3H).

Synthesis of Intermediate 2

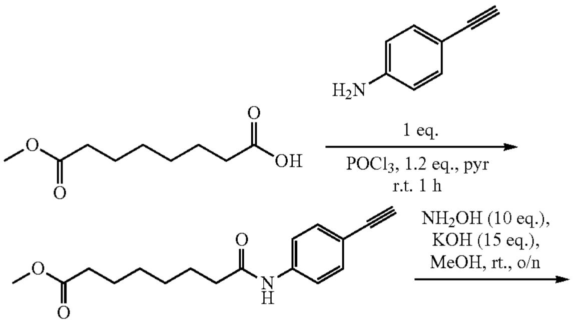

2.1

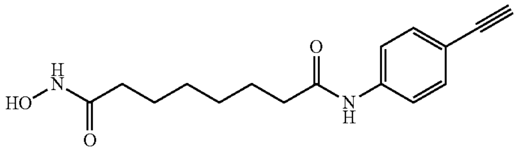

Intermediate 2

To the solution of the acid (21 g, 111.57 mmol) and the amine (20.53 g, 111.57 mmol) in pyridine (300 mL) was added $POCl_3$ (13.07 g, 133.89 mmol) at 0° C. and the mixture stirred at room temperature for 30 min.

The mixture was diluted with water (600 mL) and extracted with EtOAc (200 mL×3). The combined organic layers were washed with brine (200 mL), dried over $Na_2SO_4$ and concentrated under reduced pressure. The residue was purified by column chromatography (Petroleum ether:EtOAc, 1:1, v/v) to afford 2.1 (10 g, 31%) as a yellow solid. TLC: $R_f$=0.49 (Petroleum Ether:EtOAc=1:1, v/v, 254 nm). LCMS: (LCMS Method P2-POS): m/z 288.20 $[M+H]^+$, 3.598 min.

To a solution of $NH_2OH$ HCl (11.49 g, 348 mmol) in MeOH (100 mL) at 0° C. was added KOH (29.29 g, 522 mmol) and the mixture was stirred for 1 h. The resulting precipitate was filtered off and the solution of free $NH_2OH$ was placed in a round bottom flask and cooled in an ice bath. Compound 2.1 (10 g, 34.8 mmol) was added to the solution and the mixture was stirred at RT overnight.

The mixture was diluted with water (200 mL) and acidified with AcOH to pH ~5, then kept in a refrigerator+4° C. for 3 h. The precipitate was collected by filtration, washed with water and crystallized from acetone/THF (1:1, v/v) to afford Intermediate 2 (7 g, 70%) as a white solid. TLC: $R_f$=0 (EtOAc/Petroleum Ether=1/1, v/v). LCMS: (Method P2-POS): m/z 289.20 $[M+H]^+$, 2.820 min. $^1H$ NMR: $^1H$ NMR (400 MHz, DMSO-$d_6$) (FID No:YJ-0489-075-HNMR) 10.32 (s, 1H), 10.03 (s, 1H), 8.65 (s, 1H), 7.61-7.59 (m, 2H), 7.40-7.38 (m, 2H), 4.06 (s, 1H), 2.32-2.28 (m, 2H), 1.95-1.91 (m, 2H), 1.58-1.47 (m, 4H), 1.28-1.27 (m, 4H).

Synthesis of Intermediate 3

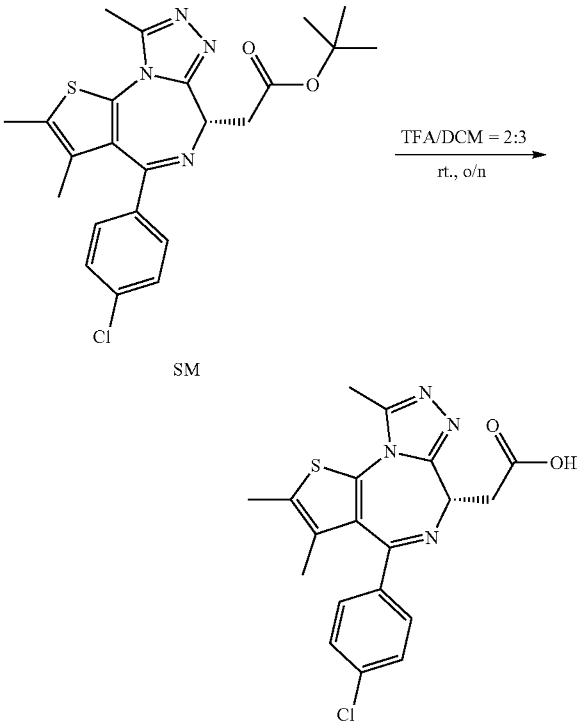

SM

Intermediate 3

To a solution of SM (2.4 g, 5.25 mmol) in DCM (15 mL) was added TFA (10 mL) and the mixture was stirred at RT overnight. TLC showed SM was consumed. The solvent was removed under vacuum. The residue was triturated with water (25 mL*2) to afford Intermediate 3 (2.00 g, 95%) as a light yellow solid. LCMS: (Method P2-POS): m/z 401.10 $[M+H]^+$, 3.209 min. $^1H$ NMR: (400 MHz, DMSO-$d_6$, FID No: WFL-0259-100-1-20190227-HNMR) δ 12.43 (s, 1H), 7.50 (d, J=8.8 Hz, 2H), 7.47-7.41 (m, 2H), 4.45 (t, J=7.2 Hz, 1H), 3.43 (dd, J=16.8, 6.8 Hz, 1H), 3.32 (dd, J=16.8, 7.4 Hz, 1H), 2.60 (s, 3H), 2.41 (s, 3H), 1.63 (s, 3H).

Synthesis of Intermediate 9

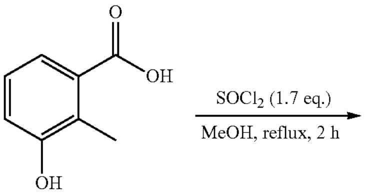

SM1

-continued

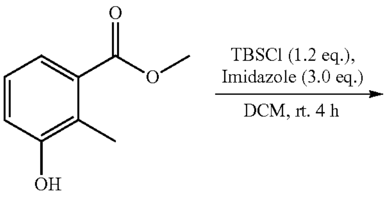

9.1

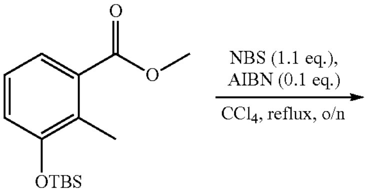

9.2

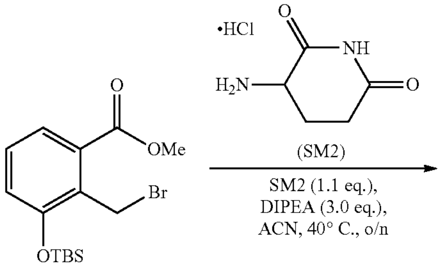

9.3

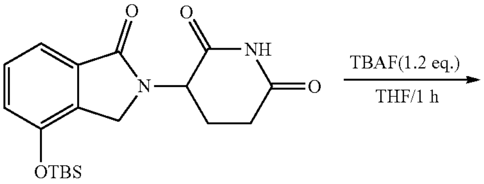

9.4

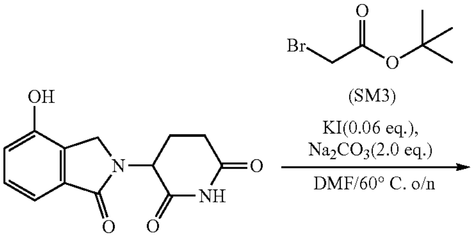

9.5

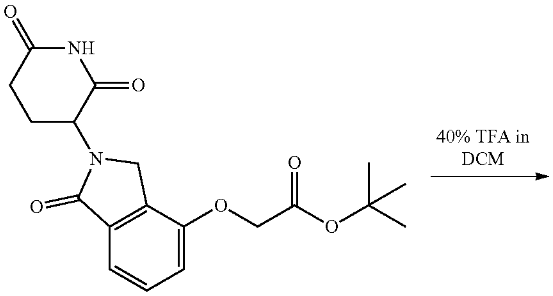

9.6

-continued

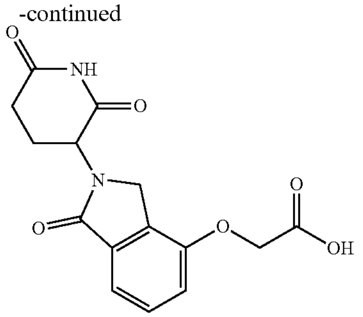

Intermediate 9

To a solution of SM1 (46 g, 0.3 mol) in MeOH (300 mL) at 0° C. was added $SOCl_2$ (59 g, 0.5 mol) and the mixture was heated at 70° C. for 2 h. The mixture was then concentrated to afford product 9.1 (42 g, 84%) as a brown solid. TLC: $R_f$=0.65 (DCM:MeOH=20:1, v/v, 254 nm). $^1$H NMR: $^1$H NMR (400 MHz, DMSO-$d_6$) (FID No:CJP-0147-055-HNMR) δ 9.69 (m, 1H), 7.18-7.16 (m, 1H), 7.07 (t, J=8 Hz, 1H), 7.00-6.98 (m, 1H), 3.79 (s, 3H), 2.27 (s, 3H).

To a solution of 9.1 (65 g, 0.39 mol) in DCM (500 mL) was added imidazole (91.4 g, 1.17 mol) and TBSCl (70.5 g, 0.47 mol) and the mixture was stirred at RT for 2 h.

The mixture was diluted with water (800 mL) and extracted with DCM (300 mL×3). The combined organic layers was washed with brine (400 mL), dried over $Na_2SO_4$, filtered and concentrated to afford product 9.2 (100 g, 91%) as a brown oil. TLC: $R_f$=0.8 (DCM:MeOH=20:1, v/v, 254 nm). $^1$H NMR: $^1$H NMR (400 MHz, DMSO-$d_6$) (FID No:FGX41-013-HNMR) δ 7.35-7.33 (m, 1H), 7.18 (t, J=8.4 Hz, 1H), 7.04-7.01 (m, 1H), 3.80 (s, 3H), 2.31 (s, 3H), 0.98 (s, 9H), 0.21 (s, 6H).

To a solution of compound 9.2 (100 g, 0.36 mol) in $CCl_4$ (500 mL) was added NBS (71.2 g, 0.40 mol) and AIBN (5.9 g, 0.036 mol) and the mixture was heated at reflux for 3 h.

The mixture was concentrated and the residue diluted with water (500 mL) and extracted with DCM (200 mL×3). The combined organic layers were washed with brine (300 mL), dried over $Na_2SO_4$, filtered and concentrated to afford product 9.3 (120 g, 94%) as a brown oil. TLC: $R_f$=0.3 (DCM:MeOH=40:1, v/v, 254 nm)$^1$H NMR: $^1$H NMR (400 MHz, DMSO-$d_6$) (FID No:FGX41-025-HNMR) δ7.47-7.45 (m, 1H), 7.37 (t, J=8 Hz, 1H), 7.16-7.14 (m, 1H), 4.95 (s, 2H), 3.86 (s, 3H), 1.03 (s, 9H), 0.29 (s, 6H).

To a solution of compound 9.3 (90 g, 0.25 mol) in ACN (600 mL) was added SM2 (45.1 g, 0.28 mol) and DIPEA (96.9 g, 0.75 mol) and the mixture was heated at 40° C. overnight.

The mixture was concentrated and the residue was triturated with EtOAc (150 mL×2) to afford compound 9.4 (60 g, 63%) as a white solid. TLC: $R_f$=0.28 (DCM:MeOH=10:1, v/v, 254 nm). LCMS: (LCMS Method P1-POS): m/z 375.1 $[M+H]^+$, 2.117 min.

To a solution of compound 9.4 (50 g, 0.13 mol) in THF (400 mL) was added TBAF (1 M solution in THF, 160 mL, 0.16 mol) and the mixture was stirred at RT for 3 h.

The mixture was concentrated under reduce pressure and the residue was triturated with EtOAc (150 mL×2) to afford product 9.5 (28 g, 80%) as a white solid. TLC: $R_f$=0.5 (DCM:MeOH=10:1, v/v, 254 nm). LCMS: (LCMS Method P2-POS): m/z 261.0 $[M+H]^+$, 1.611 min.

To a solution of compound 9.5 (16.0 g, 61.5 mmol) in DMF (100 mL) was added SM3 (8.4 g, 43.1 mmol), $Na_2CO_3$ (13.0 g, 123 mmol) and KI (2.0 g, 12.3 mmol) and the mixture was heated at 60° C. for 6 hours.

The mixture diluted with water (800 mL), extracted with EtOAc (200 mL×3) and the combined organic layers washed with brine (300 mL), dried over $Na_2SO_4$, filtered and concentrated. The residue was purified by silica gel column (DCM/MeOH=200:1 to 40:1, v/v) to afford product 9.6 (6.0 g, 26%) as a white solid. TLC: $R_f$=0.6 (DCM:MeOH=10:1, v/v, 254 nm). LCMS: (LCMS Method S12): m/z 373.1 $[M-H]^-$, 3.779 min.

To a solution of compound 9.6 (14 g, 37.4 mmol) in DCM (100 mL) at 0° C. was added TFA (40 mL) and the mixture was stirred at RT for 6 h.

The mixture was concentrated and the residue rinsed with ether (100 mL) to afford Intermediate 9 (11 g, 92%) as a white solid. TLC: Rt=0.2 (DCM:MeOH=10:1, v/v, 254 nm). LCMS: (LCMS Method P1-POS): m/z 319.1 $[M+H]^+$, 1.774 min. $^1$H NMR: $^1$H NMR (400 MHz, DMSO-$d_6$) (FID No:CJP-0147-102) δ10.97 (s, 1H), 7.46 (t, J=8 Hz, 1H), 7.34-7.32 (m, 1H), 7.17-7.15 (m, 1H), 5.13-5.08 (m, 1H), 4.84 (s, 2H), 4.42-4.24 (m, 2H), 2.91-2.86 (m, 1H), 2.61-2.56 (m, 1H), 2.49-2.40 (m, 1H), 2.02-1.98 (m, 2H).

Synthesis of Intermediates 10-13

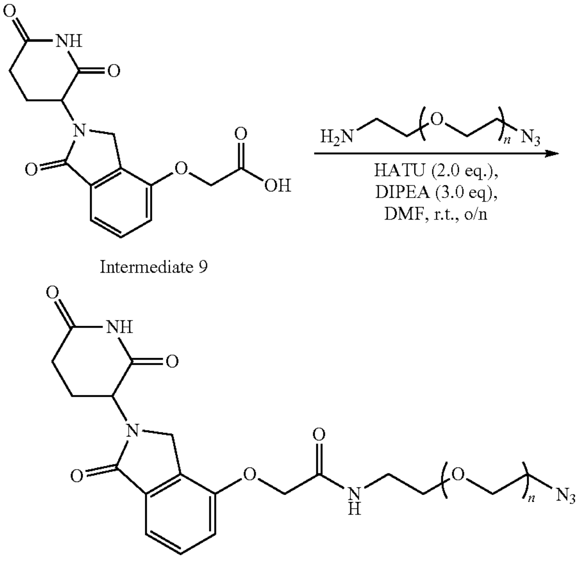

Intermediate 10: n = 4
Intermediate 11: n = 3
Intermediate 12: n = 2
Intermediate 13: n = 0

To a solution of Intermediate 9 in DMF (0.25 M) was added HATU (2.0 eq.) and DIPEA (3.0 eq.) and the mixture was stirred at RT for 30 min. The amino-azide (1.2 eq.) was then added and stirring was continued at RT for 16 h. The mixture was diluted with water, extracted by DCM/MeOH (15/1) and the combined organic layers were washed with brine, dried over $Na_2SO_4$, filtrated, concentrated. The residue was purified by Biotage $C_{18}$ column or p-TLC to afford Intermediate 10-13.

Intermediate 10 was purified by Biotage $C_{18}$ Column (40% ACN in water) to afford Intermediate 10 (yield: 43%) as a colorless oil. LCMS: (Method S12): m/z 563.3 $[M+H]^+$, 1.233 min. $^1$H NMR: (400 MHz, DMSO-$d_6$, FID No: CJP-0147-104-HNMR) δ 11.00 (s, 1H), 8.11 (t, J=5.6 Hz, 1H), 7.47 (t, J=8.0 Hz, 1H), 7.34 (d, J=6.4 Hz 1H), 7.13 (d, J=8.0 Hz 1H), 5.16-5.11 (m, 1H), 4.64 (s, 2H), 4.48-4.32 (m, 2H), 3.60-3.58 (m, 2H), 3.50-3.48 (m, 4H), 3.43-3.38 (m, 8H), 3.39-3.28 (m, 6H), 2.97-2.90 (m, 1H), 2.63-2.61 (m, 1H), 2.44-2.37 (m, 1H), 2.04-2.00 (m, 1H)

Intermediate 11 was purified by Biotage C18 Column (40% ACN in water) to afford Int 11 (yield: 25%) as a semi-solid. LCMS: (LCMS Method S12): m/z 519.3 $[M+H]^+$, 2.333 min. $^1H$ NMR: (400 MHz, DMSO-$d_6$, FID No: CJP-0147-099-HNMR) δ 11.00 (s, 1H), 8.11 (t, J=5.6 Hz, 1H), 7.47 (t, J=8.0 Hz, 1H), 7.34 (d, J=6.4 Hz 1H), 7.13 (d, J=8.0 Hz 1H), 5.16-5.11 (m, 1H), 4.64 (s, 2H), 4.48-4.32 (m, 2H), 3.59-3.57 (m, 2H), 3.50-3.44 (m, 8H), 3.38-3.31 (m, 6H), 2.96-2.90 (m, 1H), 2.62-2.59 (m, 1H), 2.43-2.36 (m, 1H), 2.03-1.99 (m, 1H).

Intermediate 12 was purified by prep-TLC (DCM: MeOH=10:1, v/v) to afford Intermediate 12 (yield: 63%) as a yellow oil. TLC: $R_f$=0.18 (DCM:MeOH=20:1, v/v, 254 nm). LCMS: (LCMS Method P2):m/z=475.30 $[M+H]^+$, 2.516 min. $^1H$ NMR: $^1H$ NMR (400 MHz, Chloroform-d) (FID NO:ZJ-0523-016-HNMR) δ 8.14 (s, 1H), 7.57 (d, J=7.6 Hz, 1H), 7.47 (t, J=7.8 Hz, 1H), 7.02 (d, J=8.2 Hz, 1H), 6.85 (s, 1H), 5.23 (dd, J=13.4, 5.2 Hz, 1H), 4.61 (s, 2H), 4.52 (d, J=16.4 Hz, 1H), 4.38 (d, J=16.6 Hz, 1H), 3.64-3.61 (m, 2H), 3.60-3.55 (m, 6H), 3.33 (dd, J=5.6, 4.4 Hz, 2H), 3.03-2.89 (m, 1H), 2.84 (ddd, J=17.8, 13.0, 5.2 Hz, 1H), 2.40 (qd, J=13.0, 5.0 Hz, 1H), 2.24 (ddd, J=10.2, 5.2, 2.8 Hz, 1H), 1.58-1.36 (m, 2H).

Intermediate 13 was purified by Biotage C18 Column (40% ACN in water) to afford Int-13 (yield: 27%) as a white solid. LCMS: (LCMS Method P0-POS): m/z 387.1 $[M+H]^+$, 2.165 min. $^1H$ NMR:$^1H$ NMR (400 MHz, DMSO-$d_6$, FID No: LL-0450-112-HNMR) δ 11.00 (s, 1H), 8.30 (t, J=5.4 Hz, 1H), 7.47 (t, J=7.8 Hz, 1H), 7.35 (d, J=7.2 Hz, 1H), 7.15 (d, J=7.8 Hz, 1H), 5.14 (dd, J=13.4, 5.1 Hz, 1H), 4.66 (d, J=2.2 Hz, 2H), 4.46 (d, J=17.4 Hz, 1H), 4.35 (d, J=17.4 Hz, 1H), 3.43-3.37 (m, 2H), 3.37-3.33 (m, 2H), 2.99-2.86 (m, 1H), 2.61 (d, J=16.8 Hz, 1H), 2.41 (m, 1H), 2.02 (m, 1H).

Synthesis of Compounds 5.49-5.52 Listed in Table 5

General Procedures

To a solution of azide (1.0 eq.) in tert-butanol/$H_2O$ (1/1, v/v) (0.03 M) was added Intermediate 2 (1.0 eq.), followed by CuSO4·5$H_2O$ (0.2 eq.) and sodium ascorbate (1.0 eq.) and the mixture was heated at 80° C., for 5 h under a $N_2$ atmosphere. The mixture was diluted with water, extracted with DCM/MeOH (15/1) and the combined organic layers were washed with brine, dried over $Na_2SO_4$, filtrated, concentrated and purified by prep-TLC or prep-HPLC to afford compounds 5.49-5.52.

Compound 5.49 was purified by prep-HPLC (5-60% ACN in water containing 0.1% TFA) to afford the compound 5.49 (yield 5%) as a white solid. LCMS: (LCMS Method S12-5MIN): m/z 851.5 $[M+H]^+$, 1.047 min. $^1H$ NMR: (400 MHz, DMSO-$d_6$) (FID No:CJP-0147-115-HNMR) δ11.00 (s, 1H), 10.32 (s, 1H), 9.94 (s, 1H), 8.42 (s, 1H), 8.11 (t, J=6.0 Hz, 1H), 7.76-7.50 (m, 4H), 7.46 (t, J=8.0 Hz, 1H), 7.35-7.33 (m, 1H), 7.14-1.12 (m, 1H), 5.16-5.11 (m, 1H), 4.64 (s, 2H), 4.54 (t, J=5.2 Hz, 2H), 4.47-4.31 (m, 2H), 3.84 (t, J=5.2 Hz, 2H), 3.53-3.47 (m, 3H), 3.46-3.44 (m, 3H), 3.44-3.41 (m, 8H), 3.40-3.26 (m, 3H), 2.95-2.89 (m, 1H), 2.63-2.58 (m, 1H), 2.443-2.40 (m, 1H), 2.33-2.28 (m, 2H), 2.02-1.94 (m, 3H), 1.59-1.51 (m, 4H), 1.49-1.21 (m, 4H)

Compound 5.50 was purified by prep-HPLC (5-60% ACN in water containing 0.1% TFA) to afford the compound 5.50 (yield 8%) as a colorless oil. LCMS: (LCMS Method S12-5MIN): m/z 807.4 $[M+H]^+$, 2.165 min. $^1H$ NMR: (400 MHz, DMSO-$d_6$) (FID No:CJP-0147-116-HNMR) δ11.00 (s, 1H), 10.33 (s, 1H), 9.95 (s, 1H), 8.64 (s, 1H), 8.42 (s, 1H), 8.10 (t, J=5.6 Hz, 1H), 7.75-7.65 (m, 4H), 7.46 (t, J=4.8 Hz, 1H), 7.35-7.33 (m, 1H), 7.14-1.11 (m, 1H), 5.15-5.10 (m, 1H), 4.63 (s, 2H), 4.54 (t, J=5.2 Hz, 2H), 4.46-4.30 (m, 2H), 3.84 (t, J=5.2 Hz, 2H), 3.84-3.44 (m, 2H), 3.42-3.40 (m, 2H), 3.40 (s, 4H), 3.33-3.28 (m, 2H), 3.25-3.16 (m, 2H), 2.95-2.92 (m, 1H), 2.86-2.58 (m, 1H), 2.50-2.42 (m, 1H), 2.39-2.30 (m, 2H), 2.00-1.94 (m, 3H), 1.59-1.49 (m, 5H), 1.39-1.21 (m, 2H)

Compound 5.51 was purified by prep-TLC (DCM/MeOH=10/1, v/v) to afford compound 5.51 (yield: 12%) as a yellow solid. TLC: $R_f$=0.29 (Petroleum Ether:EtOAc=5:1, v/v, 254 nm). LCMS: (LCMS Method P2): m/z 763.45 $[M+H]^+$, 2.421 min. $^1H$ NMR: $^1H$ NMR (400 MHz, DMSO-$d_6$) (FID NO:ZJ-0523-018-HNMR) δ 11.00 (s, 1H), 10.33 (s, 1H), 9.95 (s, 1H), 8.65 (s, 1H), 8.42 (s, 1H), 8.09 (s, 1H), 7.73 (s, 2H), 7.66 (s, 2H), 7.44 (d, J=7.9 Hz, 1H), 7.34 (d, J=7.6 Hz, 1H), 7.12 (d, J=8.2 Hz, 1H), 4.58 (d, J=37.0 Hz, 4H), 4.41 (s, 1H), 4.34 (s, 1H), 3.84 (d, J=6.6 Hz, 2H), 3.55-3.45 (m, 4H), 3.40 (d, J=6.0 Hz, 2H), 3.25 (d, J=5.6 Hz, 2H), 3.17 (d, J=5.0 Hz, 2H), 2.60 (d, J=17.2 Hz, 1H), 2.40 (d, J=12.6 Hz, 1H), 2.30 (t, J=7.6 Hz, 2H), 1.94 (t, J=7.4 Hz, 3H), 1.53 (d, J=35.6 Hz, 4H), 1.28 (s, 4H), 1.09 (t, J=7.0 Hz, 1H).

Compound 5.52 was purified by prep-HPLC (5-60% ACN in water containing 0.1% TFA) to afford compound 5.52 (yield: 34%) as a brown solid. LCMS: (LCMS Method S12): m/z 675.3 $[M+H]^+$, 2.170 min. $^1H$ NMR: (400 MHz, DMSO-$d_6$, FID No: LL-0450-115-HNMR) δ10.99 (s, 1H), 10.32 (s, 1H), 9.94 (s, 1H), 8.42 (s, 1H), 8.30 (s, 1H), 7.72 (s, 2H), 7.67 (s, 2H), 7.43 (t, J=7.8 Hz, 1H), 7.33 (s, 1H), 7.10 (d, J=7.8 Hz, 1H), 5.11 (dd, J=13.2, 5.2 Hz, 1H), 4.64 (d, J=2.2 Hz, 2H), 4.51 (s, 2H), 4.39 (s, 1H), 4.34 (s, 1H), 3.66-3.58 (m, 2H), 2.91 (ddd, J=17.4, 13.6, 5.2 Hz, 1H), 2.58 (d, J=17.2 Hz, 1H), 2.40 (td, J=13.0, 4.4 Hz, 1H), 2.31 (s, 2H), 2.07 (s, 4H), 1.94 (s, 3H), 1.58 (d, J=7.2 Hz, 2H), 1.54-1.45 (m, 2H), 1.35-1.23 (m, 4H).

Synthesis of Compounds 5.53 and 5.56 Listed in Table 5

To a solution of the azide (1.0 eq.) in THF (0.08 M) was added $PPh_3$ (2.0 eq.) and 2 M HCl (4.0 eq.) and the mixture was stirred at RT overnight. More $PPh_3$ (1.0 eq.) was added and stirring was continued for a further 8 h. The solvent was removed under vacuum and the residue was triturated with diethyl ether to afford the title amine intermediates, which were used directly in the next step without any further purification.

To a solution of Intermediate 1 in DMF (0.045 M) was added the amine intermediate (1.2 eq.) followed by TBTU (1.5 eq.) and DIPEA (3.0 eq.) and the mixture was stirred at RT for 16 h under a N2 atmosphere. The mixture was diluted with water, extracted with DCM/MeOH (15/1) and the combined organic layers were washed with brine, dried over $Na_2SO_4$, filtrated, concentrated. The residue was purified by prep-TLC or prep-HPLC to afford compounds 5.53 and 5.56.

Compound 5.53 was purified by prep-HPLC (5-80% ACN in water containing 0.1% TFA) to afford the compound 5.53 (yield 6%) as a white solid. LCMS: (LCMS Method S12-5MIN): m/z 934.4 $[M+H]^+$, 2.356 min. $^1H$ NMR: (400 MHz, DMSO-$d_6$) (FID No:CJP-0147-132-HNMR) δ8 (t, J=5.2 Hz, 1H). 12, 7.73-7.62 (m, 2H), 7.46 (t, J=8.0 Hz, 1H), 7.39-7.33 (m, 3H), 7.29-7.26 (m, 1H), 7.21-7.11 (m, 8H), 6.74-6.59 (m, 4H), 5.15-5.12 (m, 1H), 4.64 (s, 2H), 4.48-4.34 (m, 4H), 4.22 (t, J=5.6 Hz, 1H), 3.91 (t, J=5.2 Hz, 1H), 3.43-3.32 (m, 14H), 3.19-3.18 (m, 2H), 2.97-2.90 (m, 3H), 2.68-2.58 (m, 3H), 2.39-2.37 (m, 3H), 2.25 (s, 3H), 2.02-1.99 (m, 1H), 1.66-1.62 (m, 1H), 1.40-1.32 (m, 1H), 0.91 (t, J=7.6 Hz, 1H), 0.86-080 (m, 3H).

Compound 5.56 was purified by prep-HPLC (5-80% ACN in water containing 0.1% TFA) to afford compound 5.56 (yield: 10%) as a white solid. LCMS: (LCMS Method S12): m/z 758.3 $[M+H]^+$, 3.088 min. $^1H$ NMR: (400 MHz, DMSO-$d_6$, FID No: LL-0450-120-HNMR) δ 9.80 (s, 1H), 8.59 (s, 1H), 8.15 (d, J=5.8 Hz, 1H), 7.63 (s, 1H), 7.44 (t, J=7.8 Hz, 1H), 7.38 (dd, J=8.0, 6.8 Hz, 2H), 7.34-7.26 (m, 2H), 7.22-7.17 (m, 4H), 7.15-7.09 (m, 4H), 6.77 (d, J=8.8 Hz, 2H), 6.64 (d, J=8.8 Hz, 2H), 4.77 (dd, J=10.2, 4.7 Hz, 1H), 4.62 (d, J=17.6 Hz, 3H), 4.43 (d, J=18.0 Hz, 2H), 4.18 (s, 2H), 3.92 (d, J=33.0 Hz, 3H), 3.21 (d, J=19.4 Hz, 4H), 2.85 (s, 3H), 2.37 (d, J=7.4 Hz, 2H), 2.26 (s, 2H), 2.23-2.18 (m, 1H), 2.10-2.00 (m, 1H), 0.84 (t, J=7.4 Hz, 3H).

Synthesis of Compounds 5.54 and 5.55 Listed in Table 5

To a solution of the bis-amine (1.0 eq.) in DCM (0.47 M) was added $(Boc)_2O$ (1.0 eq.) and TEA (2.5 eq.) and the mixture was stirred at RT for 2 h. The solvent was removed under vacuum and the residue was diluted with water and extracted with EtOAc. The organic layer was washed with brine, dried over $Na_2SO_4$, filtered and concentrated to afford the mono-boc-amine, which was used directly in the next step without any further purification.

To a solution of acid intermediate 1, 4 or 9 (1.0 eq.) in DMF (0.15 M) was added the mono-boc-amine (1.2 eq.) followed by TBTU (1.5 eq.) and DIPEA (3.0 eq.) and the mixture was stirred at RT for 16 h under a N2 atmosphere. The mixture was diluted with water and extracted by DCM/MeOH (30/1). The combined organic layers were washed with brine, dried over $Na_2SO_4$, filtered, concentrated and the residue was purified by column chromatography on silica gel to afford the boc-protected intermediates.

To a solution of boc-protected intermediates in dioxane was added 4 M HCl in dioxane (8 eq.) and the mixture was stirred at RT for 2-4 h. The solvent was removed under vacuum to afford title HCl salt, which were used directly in the next step.

To a solution of Intermediate 1 (1.0 eq.) in DMF (0.045 M) was added the amine HCl salt (1.2 eq.) followed by TBTU (1.5 eq.) and DIPEA (3.0 eq.) and the mixture was stirred at RT for 16 h under a N2 atmosphere. The mixture was diluted with water and extracted by DCM/MeOH (15/1). The combined organic layers were washed with brine, dried over $Na_2SO_4$, filtrated, concentrated and the residue purified by prep-TLC or prep-HPLC to afford the final compounds.

Compound 5.54 was purified by prep-TLC (DCM/MeOH=10/1, v/v) to afford compound 5.54 (yield: 13%) as an off-white solid. TLC: $R_f$=0.15 (DCM:MeOH=10:1, v/v, 254 nm). LCMS: (LCMS Method P2): m/z 846.50 $[M+H]^+$, 0.490 min. $^1H$ NMR (400 MHz, DMSO-$d_6$) (FID NO:ZJ-0523-039-HNMR) δ 11.00 (s, 1H), 8.11 (t, J=5.8 Hz, 1H), 7.69 (s, 1H), 7.46 (t, J=7.8 Hz, 1H), 7.35 (t, J=8.0 Hz, 3H), 7.30-7.25 (m, 1H), 7.22-7.17 (m, 4H), 7.14-7.10 (m, 4H), 5.13 (dd, J=13.2, 5.2 Hz, 1H), 4.63 (d, J=1.6 Hz, 2H), 4.44 (d, J=17.6 Hz, 1H), 4.33 (d, J=17.6 Hz, 1H), 3.93 (t, J=5.6 Hz, 2H), 3.43 (s, 3H), 3.41-3.34 (m, 4H), 3.27 (q, J=6.2 Hz, 3H), 3.18 (d, J=5.8 Hz, 2H), 3.02 (s, 2H), 2.72 (s, 2H), 2.44-2.32 (m, 4H), 2.29 (s, 1H), 2.03-1.97 (m, 1H), 1.24 (d, J=2.8 Hz, 3H), 0.86-0.84 (m, 3H).

Compound 5.55 was purified by prep-TLC (DCM/MeOH=10/1, v/v) to afford compound 5.55 (yield: 11%) as an off-white solid. LCMS: (LCMS Method P2): m/z 890.4 $[M+H]^+$, 3.172 min. $^1H$ NMR (400 MHz, DMSO-$d_6$) (FID NO:CJP-0147-137-HNMR) δ 11.00 (s, 1H), 8.12 (t, J=5.6 Hz, 1H), 7.68 (s, 1H), 7.46 (t, J=7.6 Hz, 1H), 7.39-7.28 (m, 4H), 7.21-7.11 (m, 8H), 6.74-6.59 (m, 4H), 5.16-5.11 (m, 1H), 4.64 (s, 2H), 4.72-4.31 (m, 2H), 3.92 (t, J=5.6 Hz, 2H), 3.46-3.41 (m, 10H), 3.36-3.32 (m, 2H), 3.29-3.26 (m, 2H), 3.19-3.16 (m, 2H), 2.99-2.88 (m, 3H), 2.70-2.58 (m, 3H), 2.39-2.34 (m, 2H), 2.27 (s, 3H), 2.02-1.98 (m, 1H), 1.26-1.24 (m, 1H), 0.84 (t, J=7.2 Hz, 3H).

Synthesis of Compounds 5.57-5.60 Listed in Table 5

To a solution of Intermediate 3 (1.0 eq.) in DMF (0.05 M) was added the amine HCl salt (1.2 eq.) followed by TBTU (1.5 eq.) and DIPEA (3.0 eq.) and The mixture was stirred at RT for 16 h under a N2 atmosphere. The mixture was diluted with water and extracted by DCM/MeOH (15/1). The combined organic layers were washed with brine, dried over $Na_2SO_4$, filtrated, concentrated and the residue purified by prep-TLC or prep HPLC to afford compounds 5.57-5.60.

Compound 5.57 was purified by prep-TLC (DCM/MeOH=8/1, v/v) to afford compound 5.57 (yield 4%) as a yellow solid. LCMS: (LCMS Method S12-5MIN): m/z 919.5 $[M+H]^+$, 3.033 min. $^1H$ NMR: (400 MHz, DMSO-$d_6$) (FID No:CJP-0147-135-HNMR) δ11.00 (s, 1H), 8.27 (t, J=5.6 Hz, 1H), 8.12 (t, J=5.6 Hz, 1H), 7.49-7.47 (m, 3H), 7.43-7.35 (m, 2H), 7.35-7.33 (m, 1H), 7.13 (d, J=8 Hz, 1H), 5.14-5.11 (m, 1H), 4.64 (s, 2H), 4.52-4.48 (m, 1H), 4.43-4.30 (m, 2H), 3.52-3.43 (m, 13H), 3.33-3.25 (m, 4H), 3.22-3.21 (m, 5H), 2.92-2.82 (m, 1H), 2.62-2.59 (m, 4H), 2.50-2.40 (m, 4H), 2.03-1.99 (m, 1H), 1.62 (s, 3H).

Compound 5.58 was purified by prep-TLC (DCM/MeOH=10/1, v/v) to afford compound 5.58 (yield 4%) as a white solid. LCMS: (LCMS Method S12-5MIN): m/z 875.2 $[M+H]^+$, 2.898 min. $^1H$ NMR: (400 MHz, DMSO-$d_6$) (FID No:CJP-0147-138-HNMR) δ11.00 (s, 1H), 8.27 (t, J=5.6 Hz, 1H), 8.13 (t, J=5.6 Hz, 1H), 7.49-7.43 (m, 5H), 7.40 (d, J=7.6 Hz, 1H), 7.13 (d, J=8.0 Hz, 1H), 5.14-5.11 (m, 1H), 4.64 (s, 2H), 4.52-4.47 (m, 2H), 4.43-4.31 (m, 1H), 3.51 (d, J=9.2 Hz, 8H), 3.46-3.43 (m, 4H), 3.32-3.21 (m, 6H), 2.96-2.88 (m, 1H), 2.62-2.59 (m, 4H), 2.50-2.40 (m, 4H), 2.02-1.99 (m, 1H), 1.62 (s, 3H)

Compound 5.59 was purified by Pre-HPLC (5-50% ACN in water containing 0.1% TFA) to afford compound 5.59 (yield: 7%) as an off-white solid. LCMS: (LCMS Method P2): m/z 831.30 $[M+H]^+$, 1.678 min. $^1H$ NMR (400 MHz, DMSO-$d_6$) (FID NO:ZJ-0523-038-HNMR) δ 11.00 (s, 1H), 8.27 (t, J=5.8 Hz, 1H), 8.13 (t, J=5.8 Hz, 1H), 7.49-7.42 (m, 5H), 7.34 (d, J=7.6 Hz, 1H), 7.12 (d, J=8.2 Hz, 1H), 5.13 (d, J=8.4 Hz, 1H), 4.64 (s, 2H), 4.52-4.42 (m, 3H), 4.33 (d, J=17.6 Hz, 2H), 3.52 (s, 3H), 3.45 (q, J=3.2 Hz, 4H), 3.27 (d, J=10.8 Hz, 4H), 2.97-2.85 (m, 2H), 2.59 (s, 3H), 2.40 (s, 3H), 1.99 (d, J=7.0 Hz, 1H), 1.61 (s, 2H), 1.47 (s, 1H), 1.28-1.23 (m, 3H).

Compound 5.60 was purified Purified by prep-HPLC (5-50% ACN in water containing 0.1% TFA) to afford compound 5.60 (yield: 30%) as a white solid. LCMS: (LCMS Method S12): m/z 743.2 $[M+H]^+$, 2.842 min. $^1H$ NMR: (400 MHz, DMSO-$d_6$, FID No: LL-0450-145-HNMR) δ 10.96 (d, J=2.8 Hz, 1H), 8.34 (d, J=5.6 Hz, 1H), 7.66-7.54 (m, 1H), 7.52-7.43 (m, 3H), 7.41 (s, 2H), 7.34 (dd, J=7.6, 3.2 Hz, 1H), 7.15 (s, 1H), 5.10 (s, 1H), 4.61 (d, J=3.0 Hz, 2H), 4.49 (tt, J=9.6, 4.8 Hz, 1H), 4.45-4.38 (m, 1H), 4.32 (dd, J=17.6, 14.8 Hz, 1H), 3.44 (d, J=6.8 Hz, 1H), 3.23 (q, J=5.6 Hz, 5H), 2.95-2.81 (m, 1H), 2.59 (d, J=11.8 Hz, 2H), 2.44-2.35 (m, 3H), 2.34-2.26 (m, 1H), 1.95-1.87 (m, 1H), 1.85-1.77 (m, 1H), 1.57 (d, J=15.2 Hz, 3H), 1.06 (t, J=6.8 Hz, 1H).

Example 9: Competition and Recruitment Activity

The competition and recruitment activities of the compounds described herein were measured according to the assays illustrated in Example 1 and Example 2. The strength of IC50 or EC50 is reported from strongest to weakest (i.e. +++ to +), while "NA" being Not Applicable.

| | | Recruitment | |
|---|---|---|---|
| Compound ID | Competition IC50 (M) | Target protein | EC50 (M) |
| 5.01 | +++ | NA | NA |
| 5.02 | +++ | NA | NA |
| 5.03 | +++ | NA | NA |
| 5.04 | +++ | NA | NA |
| 5.05 | +++ | NA | NA |
| 5.06 | ++ | NA | NA |
| 5.07 | ++ | NA | NA |
| 5.08 | ++ | NA | NA |
| 5.10 | NA | DHFR | +++ |
| 5.12 | NA | DHFR | +++ |
| 5.13 | NA | DHFR | +++ |
| 5.14 | ++ | NA | NA |
| 5.19 | NA | DHFR | +++ |
| 5.20 | NA | DHFR | +++ |
| 5.21 | + | NA | NA |
| 5.23 | NA | DHFR | +++ |
| 5.24 | ++ | NA | NA |
| 5.26 | NA | DHFR | +++ |
| 5.28 | ++ | NA | NA |
| 5.29 | ++ | NA | NA |
| 5.31 | ++ | NA | NA |
| 5.32 | +++ | NA | NA |
| 5.46 | NA | DHFR | +++ |
| 5.49 | ++ | HDAC6 | + |
| 5.50 | + | HDAC6 | ++ |
| 5.51 | + | HDAC6 | ++ |
| 5.52 | + | HDAC6 | + |
| 5.53 | ++ | ESR1 | +++ |
| 5.54 | +++ | ESR1 | +++ |
| 5.55 | ++ | ESR1 | +++ |
| 5.56 | ++ | ESR1 | ++ |
| 5.60 | +++ | BRD4 | +++ |
| 5.64 | ++ | NA | NA |
| TMP-LEN | NA | DHFR | +++ |
| LEN | +++ | NA | NA |
| 5.01 | 4.35E−07 | NA | NA |
| 5.02 | 3.76E−07 | NA | NA |
| 5.03 | 8.73E−07 | NA | NA |
| 5.04 | 1.89E−07 | NA | NA |
| 5.05 | 1.94E−07 | NA | NA |
| 5.08 | 5.25E−06 | NA | NA |
| 5.10 | NA | DHFR | 7.95E−08 |
| 5.12 | NA | DHFR | 3.55E−08 |
| 5.13 | NA | DHFR | 4.69E−07 |
| 5.19 | NA | DHFR | 4.20E−09 |
| 5.20 | NA | DHFR | 1.01E−08 |
| 5.23 | NA | DHFR | 1.19E−07 |
| 5.26 | NA | DHFR | 4.50E−07 |
| 5.46 | NA | DHFR | 1.44E−08 |
| 5.53 | 1.39E−06 | ESR1 | 7.35E−07 |
| 5.54 | 8.38E−07 | ESR1 | 1.35E−07 |
| 5.55 | 1.05E−06 | ESR1 | 4.42E−07 |
| 5.64 | 9.06E−06 | NA | NA |
| TMP-LEN | NA | DHFR | 1.86E−08 |
| LEN | 2.12E−07 | NA | NA |

The invention claimed is:

1. A compound of the general formula (A) K-L-Q, or a salt, enantiomer, stereoisomer, polymorph, or N-oxide thereof, wherein:

A is a compound that binds to an E3 ubiquitin ligase and has a structure of Formula III

III

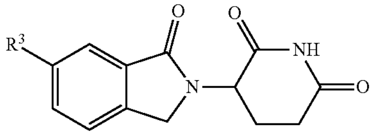

Q is a moiety that binds to a target protein which is sequestered to the E3 ubiquitin ligase and/or degraded upon interaction with the E3 ubiquitin ligase, wherein Q is selected from the group consisting of trimethoprim, vorinostat, tamoxifen, JQ1, Nutlin 3, afatinib, chloroalkane, dasatinib, BIRB796, FK-506, simvastatin, rapamycin, and sorafenib;

L is a linker;

each A is covalently linked to the L as allowed by valence;

$R^3$ is cyano, aryl, —NH—($C_3$-$C_{10}$)heteroaryl, or —N($R^5$)—$(CH_2)_m$—X—$(CH_2)_n$—$R^6$, any of which may be optionally substituted with 1 or more $R^w$ groups as allowed by valence;

$R^5$ at each occurrence is independently H, ($C_1$-$C_3$)alkyl, ($C_3$-$C_{10}$)heterocyclo, ($C_3$-$C_{10}$)cycloalkyl, —$(CH_2)_n$—($C_3$-$C_{10}$) cycloalkyl, —$(CH_2)_n$—($C_3$-$C_{10}$)heterocyclo, —$(CH_2)_n$-aryl, —$(CH_2)_n$-heteroaryl, aryl, or heteroaryl, any of which may be optionally substituted with 1 or more $R^w$ groups as allowed by valence;

$R^6$ at each occurrence is independently OH, ($C_1$-$C_3$)alkyl, —($C_1$-$C_3$)alkoxy, ($C_3$-$C_{10}$)heterocyclo, ($C_3$-$C_{10}$)cycloalkyl, —$(CH_2)_n$—($C_3$-$C_{10}$)cycloalkyl, —$(CH_2)_n$—($C_3$-$C_{10}$)heterocyclo, —$(CH_2)_n$-aryl, —$(CH_2)_n$-heteroaryl, aryl, heteroaryl, or $R^5$ and $R^6$ taken together with the atoms they are attached to forming a nitrogen containing ($C_3$-$C_{10}$)heterocyclic ring, any of which may be optionally substituted with 1 or more $R^w$ groups as allowed by valence;

$R^w$ at each occurrence is independently H, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, wherein said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more groups selected from the group consisting of halo, cyano, oxo($C_3$-$C_{10}$)heterocyclo, ($C_3$-$C_{10}$)cycloalkyl, —$(CH_2)_n$—($C_3$-$C_{10}$)cycloalkyl, —$(CH_2)_n$—($C_3$-$C_{10}$)heterocyclo, —$(CH_2)_n$-aryl, —$(CH_2)_n$-heteroaryl, aryl, and heteroaryl;

X is a bond, —$SO_2$—, —$(CH_2)_n$C(O)$(CH_2)_m$—, —C(O)NH—, —C(O)N($R^w$)—, —NHC (O)NH—, or —$(CH_2)_n$—;

m is 0, 1, 2, 3, or 4;

k is 1, 2, 3, 4, 5, 6, 7, 8, 9, or 10; and n is 0, 1, 2, 3, or 4.

2. The compound of claim 1, wherein L is -$L_b$-$(La)_t$-; wherein La at each occurrence is independently selected from the group consisting of a bond, $CR^5R^6$, C($R^5R^6$)O, C($R^5R^6$) C($R^5R^6$)O, $SO_2$, $NR^5$, C($R^5R^6$) $NR^5$, $SO_2NR^5$, $SONR^5$, $CONR^5$, $NR^5CONR^6$, $NR^5SO_2NR^6$, CO, $CR^5$═$CR^6$, C≡C, $SiR^5R^6$, P(O)$R^5$, P(O)$OR^5$, $NR^5$C(═NCN) $NR^6$, $NR^5$C(═NCN), and $NR^5$C(═C$NO_2$)$NR^6$, any of which may be optionally substituted with 1 or more $R^w$ groups as allowed by valence;

$L_b$ is selected from the group consisting of:

a bond,

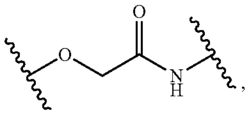,

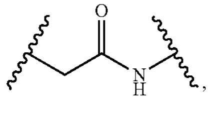,

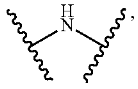,

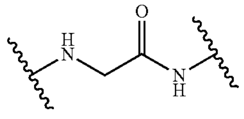,

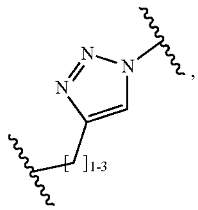,

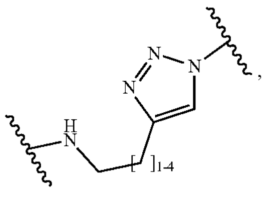,

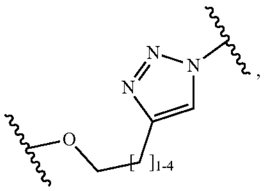,

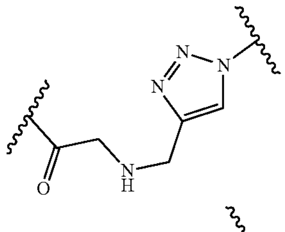,

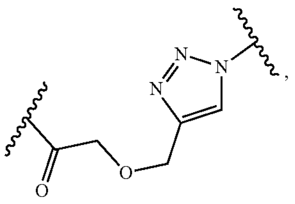,

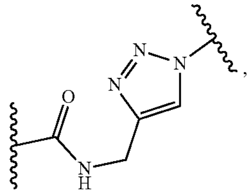,

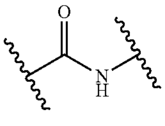,

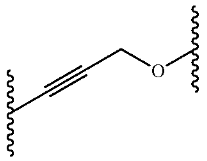

and

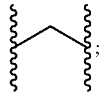;

t is 0, 1, 2, 3, 4, 5, 6, 7, 8, 9, 10, 11, 12, 13, 14, 15, 16, 17, 18, 19, or 20.

3. The compound of claim 1, wherein L is $-(CH_2CH_2)_t-$, $-(CH_2O)_t-$ or $-(CH_2CH_2O)_t-$.

4. The compound of claim 1, wherein Q is a moiety selected from the group consisting of trimethoprim, vorinostat, tamoxifen, and JQ1.

5. The compound of claim 1, wherein the compound is capable of simultaneously binding to the target protein and the E3 ubiquitin ligase, and wherein the binding causes ubiquitination of the target protein by the E3 ubiquitin ligase or the binding causes degradation of the target protein by the proteasome.

6. A pharmaceutical composition comprising the compound of claim 1 and a pharmaceutically acceptable carrier, additive, and/or excipient.

7. A method for treating a disease in a subject wherein dysregulated protein activity is responsible for said disease, said method comprising administering an effective amount of the pharmaceutical composition of claim 6, wherein the disease is (i) a cancer selected from squamous-cell carcinoma, basal cell carcinoma, adenocarcinoma, hepatocellular carcinoma, renal cell carcinoma, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, uterine cancer, leukemia, lymphoma, Burkitt's lymphoma, Non-Hodgkin's lymphoma, melanoma, a myeloproliferative disease, multiple myeloma, sarcoma glioma, astrocytoma, oligodendroglioma, ependymoma, glioblastoma, neuroblastoma, ganglioneuroma, ganglioglioma, medulloblastoma, pineal cell tumor, meningioma, meningeal sarcoma, neurofibroma, Schwannoma, testicular cancer, thyroid cancer, Hodkin's disease, Wilms' tumor, and teratocarcinoma; or (ii) an autoimmune disease or disorder selected from multiple sclerosis, diabetes mellitus, lupus, celiac disease, Crohn's disease, ulcerative colitis, Guillain-Barre syndrome, scleroderma, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome, transplantation rejection, rheumatoid arthritis, systemic lupus erythematosus, dermatomyositis, Sjogren's syndrome, lupus erythematosus, myasthenia gravis, Reiter's syndrome, and Grave's disease.

8. The method of claim 7, wherein the disease is a cancer selected from squamous-cell carcinoma, basal cell carcinoma, adenocarcinoma, hepatocellular carcinoma, renal cell carcinoma, bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, uterine cancer, leukemia, lymphoma, Burkitt's lymphoma, Non-Hodgkin's lymphoma, melanoma, a myeloproliferative disease, multiple myeloma, sarcoma, glioma, astrocytoma, oligodendroglioma, ependymoma, glioblastoma, neuroblastoma, ganglioneuroma, ganglioglioma, medulloblastoma, pineal cell tumor, meningioma, meningeal sarcomas, neurofibroma, Schwannoma, testicular cancer, thyroid cancer, Hodgkin's disease, Wilms' tumor, and teratocarcinoma.

9. The method of claim 7, wherein the disease is an autoimmune disease or disorder selected from multiple sclerosis, diabetes mellitus, lupus, celiac disease, Crohn's disease, ulcerative colitis, Guillain-Barre syndrome, scleroderma, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome, transplantation rejection, rheumatoid arthritis, systemic lupus erythematosus, dermatomyositis, Sjogren's syndrome, lupus erythematosus, myasthenia gravis, Reiter's syndrome, and Grave's disease.

10. A method of modulating cereblon, or modulating proteasomal degradation of a protein, or modulating sequestration of a protein to the proteasome, comprising administering the pharmaceutical composition of claim 6 to a subject in need thereof.

* * * * *